US012668814B2

(12) United States Patent
Sabeti et al.

(10) Patent No.: US 12,668,814 B2
(45) Date of Patent: *Jun. 30, 2026

(54) ENGINEERED MUSCLE TARGETING COMPOSITIONS

(71) Applicants: THE BROAD INSTITUTE, INC., Cambridge, MA (US); PRESIDENT AND FELLOWS OF HARVARD COLLEGE, Cambridge, MA (US); MASSACHUSETTS INSTITUTE OF TECHNOLOGY, Cambridge, MA (US)

(72) Inventors: Pardis Sabeti, Cambridge, MA (US); Mohammadsharif Tabebordbar, Cambridge, MA (US); Simon Ye, Cambridge, MA (US); Kim Lagerborg, Cambridge, MA (US); Alexandra Stanton, Cambridge, MA (US); Amy Wagers, Cambridge, MA (US)

(73) Assignees: The Broad Institute, Inc., Cambridge, MA (US); President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 877 days.

This patent is subject to a terminal disclaimer.

(21) Appl. No.: 17/614,327

(22) PCT Filed: Jul. 22, 2021

(86) PCT No.: PCT/US2021/042812
§ 371 (c)(1),
(2) Date: Nov. 24, 2021

(87) PCT Pub. No.: WO2022/020616
PCT Pub. Date: Jan. 27, 2022

(65) Prior Publication Data
US 2023/0159949 A1 May 25, 2023

Related U.S. Application Data

(60) Provisional application No. 63/183,038, filed on May 2, 2021, provisional application No. 63/107,394, filed on Oct. 29, 2020, provisional application No. 63/055,265, filed on Jul. 22, 2020.

(51) Int. Cl.
*C12N 15/864* (2006.01)
*A61K 48/00* (2006.01)
*A61P 21/00* (2006.01)
*C12N 15/86* (2006.01)

(52) U.S. Cl.
CPC .............. *C12N 15/86* (2013.01); *A61P 21/00* (2018.01); *A61K 48/00* (2013.01); *C12N 2750/14122* (2013.01); *C12N 2750/14142* (2013.01); *C12N 2750/14143* (2013.01); *C12N*

*2750/14145* (2013.01); *C12N 2750/14171* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 5,173,414 A | 12/1992 | Lebkowski et al. | |
| 5,846,946 A | 12/1998 | Huebner et al. | |
| 6,911,199 B2 | 6/2005 | Vigne et al. | |
| 6,962,815 B2 | 11/2005 | Bartlett | |
| 7,285,381 B1 | 10/2007 | Hallek et al. | |
| 7,745,391 B2 | 6/2010 | Mintz et al. | |
| 7,749,492 B2 | 7/2010 | Bartlett | |
| 8,404,658 B2 | 3/2013 | Hajjar et al. | |
| 8,454,972 B2 | 6/2013 | Nabel et al. | |
| 8,476,418 B2 | 7/2013 | Mueller et al. | |
| 8,703,735 B2 | 4/2014 | Iversen et al. | |
| 8,771,945 B1 | 7/2014 | Zhang | |
| 8,895,308 B1 | 11/2014 | Zhang et al. | |
| 10,066,228 B2 | 9/2018 | Linsley et al. | |
| 10,076,536 B2 | 9/2018 | Kole et al. | |
| 2003/0166593 A1* | 9/2003 | Chien .................... | C12N 15/86 435/320.1 |
| 2003/0233675 A1 | 12/2003 | Cao et al. | |
| 2005/0287122 A1 | 12/2005 | Bartlett et al. | |

(Continued)

FOREIGN PATENT DOCUMENTS

| | | |
|---|---|---|
| CN | 103561774 A | 2/2014 |
| CN | 107532177 A | 1/2018 |

(Continued)

OTHER PUBLICATIONS

WO 2010114143 english transaltion, 2010, pp. 1-18.*
Alba, R., et al., "Gutless adenovirus: last-generation adenovirus for gee therapy." Gene Therapy, vol. 12, 2005, pp. S18-S27.
Flotte, et al. "A Phase I Study of an Adeno-Associated Virus-CFTR Gene Vector in Adult CF Patients with Mild Lung Disease." Human Gene Therapy. vol. 7, Jun. 10, 1996, pp. 1145-1159.
Kay, M.A., et al. "Evidence of gene transfer and expression of factor IX in haemophilia B patients treated with an AAV vector." Nature. vol. 24, Mar. 2000, pp. 257-261.
Thrasher, A.J., et al. "X-SCID transgene leukaemogenicity." Nature. vol. 44, Sep. 21, 2006, pp. E5-E6.
Woods, N., et al. "Woods et al., Reply." Nature. vol. 44, Sep. 21, 2006, pp. E6-E7.

(Continued)

*Primary Examiner* — Maria Marvich
(74) *Attorney, Agent, or Firm* — F. Brent Nix, Esq.; Johnson, Marcou, Isaacs & Nix, LLC; Ming Zhang

(57) ABSTRACT

Described herein are muscle-specific targeting moieties and compositions including the muscle specific targeting motifs. Also described herein are uses of the muscle-specific targeting motifs and compositions including the muscle specific targeting moieties. In some embodiments, the muscle-specific targeting moieties and compositions including the muscle specific targeting moieties can be used to direct delivery of a cargo to a muscle cell.

13 Claims, 77 Drawing Sheets

Specification includes a Sequence Listing.

(56) References Cited

U.S. PATENT DOCUMENTS

| | | | |
|---|---|---|---|
| 2009/0222937 A1 | 9/2009 | Arnould et al. | |
| 2009/0271881 A1 | 10/2009 | Arnould et al. | |
| 2010/0229252 A1 | 9/2010 | Perez-Michaut | |
| 2011/0016540 A1 | 1/2011 | Weinstein et al. | |
| 2011/0023145 A1 | 1/2011 | Weinstein et al. | |
| 2011/0091441 A1 | 4/2011 | Gouble et al. | |
| 2011/0182867 A1 | 7/2011 | Orkin et al. | |
| 2011/0225664 A1 | 9/2011 | Smith | |
| 2012/0204282 A1 | 8/2012 | Zhang | |
| 2013/0145487 A1 | 6/2013 | Cedrone | |
| 2014/0287983 A1 | 9/2014 | Mourich et al. | |
| 2014/0315977 A1 | 10/2014 | Bestwick et al. | |
| 2015/0079038 A1 | 3/2015 | Deverman et al. | |
| 2015/0267202 A1 | 9/2015 | Iversen et al. | |
| 2016/0251398 A1 | 9/2016 | Weller et al. | |
| 2017/0051278 A1 | 2/2017 | Kole et al. | |
| 2017/0130245 A1 | 5/2017 | Kotin et al. | |
| 2017/0360960 A1* | 12/2017 | Gray | A61K 9/0014 |
| 2018/0161359 A1 | 6/2018 | Mourich et al. | |
| 2018/0169130 A1 | 6/2018 | Lorain et al. | |
| 2018/0216111 A1 | 8/2018 | Wilton et al. | |
| 2018/0271893 A1 | 9/2018 | Kole et al. | |
| 2019/0015440 A1 | 1/2019 | Passini et al. | |
| 2019/0054113 A1 | 2/2019 | Kaye | |
| 2019/0100755 A1 | 4/2019 | Linsley et al. | |
| 2019/0127424 A1 | 5/2019 | Srivastava et al. | |
| 2019/0177723 A1 | 6/2019 | Dickson | |
| 2019/0284555 A1 | 9/2019 | Schnell | |
| 2021/0380969 A1 | 12/2021 | Nonnenmacher et al. | |
| 2022/0186256 A1* | 6/2022 | Danos | C07K 14/005 |

FOREIGN PATENT DOCUMENTS

| | | | |
|---|---|---|---|
| CN | 109476707 A | 3/2019 | |
| CN | 109897831 A | 6/2019 | |
| CN | 114729384 A | 7/2022 | |
| CN | 114787179 A | 7/2022 | |
| WO | WO 93/24641 A2 | 12/1993 | |
| WO | WO 00/12738 A1 | 3/2000 | |
| WO | 200170955 A2 | 9/2001 | |
| WO | WO 0170955 A2 | 9/2001 | |
| WO | WO 2010114143 | * 10/2010 | |
| WO | WO 2013/126794 A1 | 7/2013 | |
| WO | WO 2013130824 A1 | 9/2013 | |
| WO | WO 2013163628 A2 | 10/2013 | |
| WO | WO 2015/048577 A2 | 4/2014 | |
| WO | WO 2014/093622 A2 | 6/2014 | |
| WO | 2014/139182 A1 | 9/2014 | |
| WO | WO 2015/089354 A1 | 6/2015 | |
| WO | WO 2015/116568 A2 | 7/2015 | |
| WO | WO 2015/134812 A1 | 9/2015 | |
| WO | WO 2015/148670 A1 | 10/2015 | |
| WO | WO 2015/148860 A1 | 10/2015 | |
| WO | WO 2015/148863 A2 | 10/2015 | |
| WO | WO 2015/153789 A1 | 10/2015 | |
| WO | WO 2015153791 A1 | 10/2015 | |
| WO | WO2016/115543 A2 | 7/2016 | |
| WO | WO 2017/06283 A1 | 1/2017 | |
| WO | WO 2017/096164 A1 | 6/2017 | |
| WO | WO 2017/106304 A1 | 6/2017 | |
| WO | WO 2017165862 A1 | 9/2017 | |
| WO | WO 2018119330 A2 | 6/2018 | |
| WO | 2018189244 A1 | 10/2018 | |
| WO | 2019060454 A2 | 3/2019 | |
| WO | WO 2019/059973 A1 | 3/2019 | |
| WO | WO 2019118806 A1 | 6/2019 | |
| WO | 2019193119 A1 | 10/2019 | |
| WO | WO 2019/207132 A1 | 10/2019 | |
| WO | 20190217911 A1 | 11/2019 | |
| WO | WO 2019/217911 A1 | 11/2019 | |
| WO | 2020023462 A1 | 1/2020 | |
| WO | 20200160183 A1 | 8/2020 | |
| WO | WO 2020160183 A1 | 8/2020 | |
| WO | 2021/050974 A1 | 3/2021 | |
| WO | 2021/072197 A1 | 4/2021 | |
| WO | 2022/226374 A1 | 1/2022 | |

OTHER PUBLICATIONS

Crane, B., et al. "Rescue administration of a helper-dependent adenovirus vector with long-term efficacy in dogs with glycogen storage disease type la." Gene Therapy, vol. 19, 2012, pp. 443-452.

West, M. H. P., et al. "Gene Expression in Adeno-Associated Virus Vectors: The Effects of Chimeric mRNA Structure, Helper Virus, and Adenovirus VAI, RNA." Virology. vol. 160, 1987, pp. 38-47.

Wang, M., et al. "Evaluation of Amphiphilic Peptide Modified Antisense Morpholino Oligonucleotides In Vitro and in Dystrophic mdx Mice." Polymers, vol. 9, 2017, pp. 1-14.

Geisler, A., and H. Fechner. "MicroRNA-regulated viral vectors for gene therapy." World J Exp Med, vol. 6, No. 2, May 20, 2016, pp. 37-54.

Morral, N., et al., "High Doses of a Helper-Dependent Adenoviral Vector Yield Supraphysiological Levels of alpha1-Antitrypsin with Negligible Toxicity." Human Gene Therapy, vol. 9, Dec. 10, 1998, pp. 2709-2716.

Afione, S. A., et al., "In vivo Model of Adeno-Associated Virus Vector Persistence and Rescue." Journal of Virology, vo. 70, No. 5, May 1996, pp. 3235-3241.

Mendell, J. R., et al., "Single-Dose Gene-Replacement Therapy for Spinal Muscular Atrophy." New England Journal of Medicine, vol. 377, No. 18, Nov. 2, 2017, pp. 1713-1722.

Naso, M. F., et al., "Adeno-Associated Virus (AAV) as a Vector for Gene Therapy." BioDrugs, vol. 31 (2017), pp. 317-334.

Wu, Z., et al., "Adeno-associated Virus Serotypes: Vector Toolkit for Human Gene Therapy." Molecular Therapy, vol. 14, No. 3, Sep. 2006, pp. 316-327.

Faust, S. M., et al., "CpG-depleted adeno-associated virus vectors evade immune detection." Journal of Clinical Investigation, vol. 123, Jul. 2013, pp. 2994-3001.

Hocquemiller, M., et al., "Adeno-Associated Virus-Based Gene Therapy for CNS Diseases." Human Gene Therapy, vol. 27, No. 7, pp. 478-496.

Qiao, C., et al., "Liver-specific microRNA-122 target sequences incorporated in AAV vectors efficiently inhibits transgene expression in the liver." Gene Therapy, vol. 18, No. 4, Apr. 2011, pp. 1-19.

Xiang, Z., et al., "The Effect of CpG Sequences on Capsid-Specific CD8+TCellResponses to AAV VectorGene Transfer." Molecular Therapy, vol. 28, No. 3 Mar. 2020, pp. 771-783.

Xie, J., et al., "MicroRNA-regulated, Systemically Delivered rAAV9: A Step Closer to CNS-restricted Transgene Expression." Molecular Therapy, vol. 19, No. 3, Mar. 2011, pp. 526-535.

Domenger and Grimm "Next-generation AAV vectors—do not judge a virus (only) by its cover." Human Molecular genetics, vo. 28, No. R1, Oct. 1, 2019, pp. R3-R14.

Yu, et al., "A muscle-targeting peptide displayed on AAV2 improves muscle tropism on systemic delivery", Gene Therapy, vol. 16, pp. 953-962, May 28, 2009.

Lee et al., "Adeno-Associated Virus (AAV) Vectors: Rational Design Strategies for Capsid Engineering", Curr Opin Biomed Eng. 7, pp. 58-63, 2018.

Börner, et al., "Pre-arrayed Pan-AAV Peptide Display Libraries for Rapid Single-Round Screening", Mol. Ther. Apr. 8, 2020;28(4):1016-1032.

Büning, et al., "Capsid Modifications for Targeting and Improving the Efficacy of AAV Vectors", Mol. Ther. Methods Clin Dev. Jan. 26, 2019;12:248-265.

Vigne, et al., "RGD inclusion in the hexon monomer provides adenovirus type 5-based vectors with a fiber knob-independent pathway for infection", J Virol., vol. 73, No. 6, pp. 5156-5161, Accepted: Feb. 1, 1999.

K. Varadi et al. "Novel random peptide libraries displayed on AAV serotype 9 for selection of endothelial cell-directed gene transfer vectors", Gene Therapy. vol. 19, No. 8, Aug. 1, 2012, pp. 800-809.

Yu C. Y. et al.: "A muscle-targeting peptide displayed on AAV2 improves muscle tropism upon systemic delivery", Gene Ther. vol 16, No. 8. May 28, 2009, pp. 953-962.

(56)           References Cited

OTHER PUBLICATIONS

Dan Wang et al. "The potential of adeno-associated viral vectors for gene delivery to muscle tissue", Expert Opinion on Drug Delivery, vol. 11, No. 3., Mar. 1, 2014, pp. 345-364.
Sourav R. Choudhury et al. "In Vivo Selection Yields AAV-B1 Capsid for Central Nervous System and Muscle Gene Therapy", Molecular Therapy, vol. 24, No. 7, Jun. 7, 2016, pp. 1247-1257.
L. Yang et al., "A myocardium tropic adeno-associated virus (AAV) evolved by DNA shuffling and in vivo selection", Proceeding sof the National Academy of Sciences, vol. 106, No. 10, Mar. 10, 2009, pp. 3946-3951.
Perabo L. et al., "In vitro selection of viral vectors with modified tropism: The Adeno-Associated virus display", Mol. Ther. vol. 8, No. 1, Jul. 2003, pp. 151-157.
Stefan Michelfelder et al., Successful Expansion but Not Complete Restriction of Tropism of Adeno-Associated Virus by In vivo Biopanning of Random Virus Display Peptide Libraries. PLOS ONE, vol. 4, No. 4, Apr. 9, 2009, e5122, pp. 1-13.
Adachi K. et al. "Creation of a liver-detargeting AAV2-derived mutant based on the knowledge of AAV9 capsid function." Mol. Ther., vol. 21, No. S1, abstract No. 124 May 2013, p. 1.
Tang Ying et al. "AAV-directed muscular dystrophy gene therapy", Expert Opinion on Biological Therapy vol. 10, No. 3. Mar. 1, 2010 pp. 395-408.
Dimattia et al. Structural Insight into the Unique Properties of Adeno-Associated Virus Serotype 9. J. Virology. vol. 86, No. 12, Apr. 11, 2012. pp. 6947-6958.
M. D. Weitzman and R. M. Linden. "Adeno-Associated Virus Biology". Chapter in Methods in Molecular Biology. R. O. Snyder and P. Moullier (eds.) Humana Press. Totowa NJ, USA. Jan. 1, 2011. pp. 1-23.
K. Adachi et al. "Drawing a high-resolution functional map of adeno-associated virus capsid by massively parallel sequencing". Nature Communications, vol. 5. No. 3075. Jan. 17, 2014, pp. 1-14.
S. Teramato et al. "Crisis of adenoviruses in human gene therapy." The Lancet, vol. 355, May 27, 2000 pp. 1911-1912.
C. M. Lai et al. "Adenovirus and Adeno-Associated Virus Vectors". DNA Cell Biol.vol. 21, No. 12, Jul. 6, 2004, pp. 895-913.
A.V. Cideciyan. "Vision 1 Year after Gene Therapy for Leber's Congenital Amaurosis" N. Engl J Med. Aug. 13, 2009, pp. 725-727.
F. Simonelli et al. "Gene Therapy for Leber's Congenital Amaurosis is Safe and Effective Through 1.5 Years After Vector Administration", Molecular Therapy, vol. 18, No. 3, Mar. 2010 pp. 643-650.
M.A. Croyle et al. "PEGylated helper-dependent adenoviral vectors: highly efficient vectors with an enhanced safety profile", Gene Therapy vol. 12, Jan. 13, 2005, pp. 579-587.
A. Amalfitano et al. "Production and Characterization of Improved Adenovirus Vectors with the E1, E2b, and E3 Genes Deleted", Gene Therapy, vol. 72, No. 2, Feb. 1, 1998, pp. 923-933.
N. Morral et al. "Administration of helper-dependent adenoviral vectors and sequential delivery of different vector serotype for long-term liver-directed gene transfer in baboons", PNAS, vol. 26, No. 22, Oct. 26, 1999, pp. 12816-12821.
A. Rosewell et al. "Helper-Dependent Adenoviral Vectors", J Genet Syndr Gene Ther., Suppl. 5, No., 001, Oct. 29, 2011, pp. 1-34.
Balague, C. et al. "Sustained high-level expression of full-length human factor VIII and restoration of clotting activity in hemophilic mice using a minimal adenovirus vector". Blood, vol. 95, No. 3, Feb. 1, 2000, pp. 820-828.
S. Kubo and K. Mitani et al. "A New Hybrid System Capable of Efficient Lentiviral Vector Production and Stable Gene Transfer Mediated by a Single Helper-Dependent Adenoviral Vector", Journal of Virology, vol. 77, Mar. 2003, pp. 2964-2971.
W. Zhang et al. "Hybrid Adeno-Associated Viral Vectors Utilizing Transposase-Mediated Somatic Integration for Stable Transgene Expression in Human Cells", PLOS ONE, vol. 8, No. 10, e76771, Oct. 2013, pp. 1-17.
A. L. Cooney et al. "Hybrid Nonviral/Viral Vector Systems for Improved piggyBac DNA Transposon In Vivo Delivery", Molecular Therapy, vol. 23, No. 4, Apr. 2015, pp. 667-674.

Kubo, S. et al."Adenovirus-retrovirus hybrid vectors achieve highly enhanced tumor transduction and antitumor efficacy in vivo". Mol Ther, vol. 19., No. 1, Jan. 2011. pp. 76-82.
A. Ehrhardt et al. "Somatic integration from an adenoviral hybrid vector into a hot spot in mouse liver results in persistent transgene expression levels in vivo", Mol. Ther. vol. 15, No., 1, Jan. 2007, pp. 146-156.
W. Liu et al. "Recombinant Human Foamy VirMus, a Novel Vector for Neurological Disorders Gene Therapy, Drives Production of GAD in Cultured Astrocytes", Mol. Ther. vol., 15, No. 10, Oct. 2007, pp. 1834-1841.
R. M. Kotin. "Prosepects for the Use of Adeon-Associated Virus as a Vector for Human Gene Therapy", Human Gene Therapy, vol. 5, No. 7, Jul. 1994, pp. 793-801.
N. Muzyczka. "Adeno-associated Virus (AAV) Vectors: Will they work?" J. Clin Invest. vol. 94, Oct. 1994, p. 1351.
A. Srivastava. "In vivo tissue-tropism of adeno-associated viral vectors". Curr Opin Virol. vol. 21., Dec. 2016, pp. 1-12.
D. Grimm et al. "In Vitro and In Vivo Gene Therapy Vector Evolution via Multispecies Interbreeding and Retargeting of Adeno-Associated Viruses", J. Virololgy. vol. 82, No. 12, Jun. 2008, pp. 5887-5911.
J. Tratschin et al. "Adeno-Associated Virus Vector for High-Frequency Integration, Expression, and Rescue of Genes in Mammalian Cells", Molecular and Cellular Biology, vol. 5, No. 11, Nov. 1985, pp. 3251-3260.
J. Tratschin et al. "A human parvovirus, adeno-associated virus, as a eucaryotic vector: transient expression and encapsidation of the procaryotic gene for chloramphenicol acetyltransferase.", Mol Cell Biol. vol. 4, No. 10, Oct. 1984, pp. 2072-2081.
P. L. Hermonat et al. Use of adeno-associated virus as a mammalian DNA cloning vector: Transduction of neomycin resistance into mammalian tissue culture cells Proc. Natl. Acad. Sci. USA, vol. 81, Oct. 1984, pp. 6466-6470.
R. J. Samulski et al. "Helper-free stocks of recombinant adeno-associated viruses: normal integration does not require viral gene expression", J. Virology, vol. 63, No. 9, Sep. 1989, pp. 3822-3828.
S. Q. Harper, et al. "Modular flexibility of dystrophin: Implications for gene therapy of Duchenne muscular dystrophy" Nat. Medicine. vol. 8, No. 3, Mar. 2002, pp. 253-261.
S.B. England et al. "Very mild muscular dystrophy associated with the deletion of 46% of dystrophin", Nature. vol. 343, Jan. 11, 1990, pp. 180-182.
D. J. Wells et al., "Expression of human full-length and minidystrophin in transgenic mdx mice: implications for gene therapy of Duchenne muscular dystrophy", Human Molecular Genetics, vol. 4, No. 8, Aug. 1995, pp. 1245-1250.
Salva, M.Z., et al. "Design of Tissue-specific Regulatory Cassettes for High-Level rAAV-mediated Expression in Skeletal and Cardiac Muscle" Molecular Therapy, vol. 15, No. 2, Feb. 2007, pp. 320-329.
J.R. Mendell, et al. "Gene therapy for muscular dystrophy: Lessons learned and path forward", Neuorscience Letters, vol. 527, No. 2, Oct. 11, 2012, pp. 90-99.
L. R. Rodino-Klapac et al. "Micro-dystrophin and follistatin co-delivery restores muscle function in aged DMD model" Human Molecular Genetics, vol. 22, No. 24, Dec. 15, 2013, pp. 4929-4937.
V. M. Velazquez, et al. "Effective Depletion of Pre-existing Anti-AAV Antibodies Requires Broad Immune Targeting" Molecular Therapy: Methods & Clinical Development. vol. 4, Mar. 2017, pp. 159-168.
D. M. Nelson et al. "Variable rescue of microtubule and physiological phenotypes in mdx muscle expressing different miniaturized dystrophins", Human Molecular Genetics, vol. 27, No. 12, Jun. 15, 2018, pp. 2090-2100.
Asokan, A. et al. Adeno-associated virus type 2 contains an integrin alpha5beta1 binding domain essential for viral cell entry. J Virol, vol. 80, Sep. 2006, pp. 8961-8969.
Bengtsson, N. E., et al. "Muscle-specific CRISPR/Cas9 dystrophin gene editing ameliorates pathophysiology in a mouse model for Duchenne muscular dystrophy", Nat Commun vol. 8, 14454 Feb. 14, 2017, pp. 1-10.

(56) References Cited

OTHER PUBLICATIONS

G. Berry and A. Asokan, "Cellular transduction mechanisms of adeno-associated viral vectors", Curr Opin Virol vol. 21, Dec. 2016 pp. 1-12.

C.L. Bell et al. "The AAV9 receptor and its modification to improve in vivo lung gene transfer in mice", J Clin Invest vol. 121, No. 6 Jun. 2011 pp. 2427-2435.

M. Cerletti et al. "Highly efficient, functional engraftment of skeletal muscle stem cells in dystrophic muscles". Cell vol. 134 No. 1, Jul. 11, 2008, pp. 37-47.

K. Y. Chan et al. "Engineered AAVs for efficient noninvasive gene delivery to the central and peripheral nervous systems". Nat Neurosci vol. 20, No. 8, Jun. 26, 2017, pp. 1172-1179.

Jin et al., An Engineered Serum Albumin-binging AAV9 Capsid Achieves Improved Liver Transduction after Intravenous Delivery in Mice, 2019, bioRxiv, pp. 1-24.

"Third-Party Pre-issuance Submission under 37 C.F.R. §1.290", filed in U.S. Appl. No. 17/707,944, on Nov. 6, 2022. pp. 1-29.

The Broad Institute, Inc., "Chapter I International Preliminary Report on Patentability", mailed by the International Bureau for PCT/US2021/042812 on Feb. 2, 2023, 8 pages.

Chan et al., "Engineered AAVs for Efficient Noninvasive Gene Delivery to the Central and Pheripheral Nervous Systems", Nature Neuroscience, vol. 20, No. 8, Aug. 2017, pp. 1172-1179.

Boucas et al.: "Engineering adeno-associated virus serotype 2-based targeting vectors using a new insertion site-position 453—and single point mutations", The Journal of Gene Medicine, vol. 11, No. 12, Dec. 1, 2009, pp. 1103-1113.

Chan, S., et al. "Branched fibers in dystrophic mdx muscle are associated with a loss of force following lengthening contractions". Am J Physiol Cell Physiol vol. 293,Jun. 13, 2007, pp. C985-992.

S. Childers et al. "Gene therapy prolongs survival and restores function in murine and canine models of myotubular myopathy". Sci Transl Med vol. 6, No. 220ra210. Jan. 1, 2014, pp. 1-31.

D. Dalkara et al. "In vivo-directed evolution of a new adeno-associated virus for therapeutic outer retinal gene delivery from the vitreous". Sci Transl Med vol. 5, No. 189, 189ra176, Jun. 12, 2013, pp. 1-12.

R. C. Challis et al. "Widespread and targeted gene expression by systemic AAV vectors: Production, purification, and administration" bioRxiv, Jan. 19, 2018. doi: https://doi.org/10.1101/246405, pp. 1-66.

M. Davidsson et al. "A systematic capsid evolution approach performed in vivo for the design of AAV vectors with tailored properties and tropism". Proc Natl Acad Sci U S A, vol. 116, No. 52, Dec. 26, 2019, pp. 27053-27062.

B.E. Deverman Cre-dependent selection yields AAV variants for widespread gene transfer to the adult brain. Nat Biotechnol vol. 34, No. 2, Feb. 2016, pp. 1-21.

W. Ding et al. "Intracellular trafficking of adeno-associated viral vectors". Gene Ther vo. 12, No. 11, Jun. 2005, pp. 873-880.

Duan,, D. "Micro-Dystrophin Gene Therapy Goes Systemic in Duchenne Muscular Dystrophy Patients". Hum Gene Ther vol. 29, No. 7, Apr. 5, 2018, pp. 733-736.

Duan, D., "Systemic AAV Micro-dystrophin Gene Therapy for Duchenne Muscular Dystrophy". Mol Ther vol. 26, No. 10 Oct. 2018, pp. 2337-2356.

A.M. Dudek et al. An Alternate Route for Adeno-associated Virus (AAV) Entry Independent of AAV Receptor. J Virol vol. 92, No. 7, e02213-17, Apr. 1, 2018, pp. 1-15.

M. Elverman et al. "Long-term effects of systemic gene therapy in a canine model of myotubular myopathy". Muscle Nerve vol. 56, No. 5, May 22, 2017, pp. 943-953.

K.D. Farris et al. "Improved splicing of adeno-associated viral (AAV) capsid protein-supplying pre-mRNAs leads to increased recombinant AAV vector production". Hum Gene Ther vol. 19, No. 12, Dec. 19, 2008, pp. 1421-1427.

G. Gao et al. "Biology of AAV serotype vectors in liver-directed gene transfer to nonhuman primates". Mol Ther vol. 13, No. 1, Oct. 10, 2005, pp. 77-87.

J.M. Goldstein, et al. "In Situ Modification of Tissue Stem and Progenitor Cell Genomes". Cell Rep vo. 27, No. 4, Apr. 23, 2019, pp. 1254-1264 e1257.

C.H. Hakim et al. "A Five-Repeat Micro-Dystrophin Gene Ameliorated Dystrophic Phenotype in the Severe DBA/2J-mdx Model of Duchenne Muscular Dystrophy". Mol Ther Methods Clin Dev, vol. 27, No. 3, Mar. 6, 2019, pp. 216-230.

K.S. Hanlon et al. "Selection of an Efficient AAV Vector for Robust CNS Transgene Expression". Mol Ther Methods Clin Dev, vol. 15, Oct. 23, 2019, pp. 320-332.

C. Hinderer et al. "Severe Toxicity in Nonhuman Primates and Piglets Following High-Dose Intravenous Administration of an Adeno-Associated Virus Vector Expressing Human SMN". Hum Gene Ther. vol. 29, No. 3 Feb. 12, 2018, pp. 285-298.

J. Hordeaux et al. "The Neurotropic Properties of AAV-PHP.B Are Limited to C57BL/6J Mice". Mol Ther, vol. 26, No. 3, Mar. 7, 2018, pp. 664-668.

Hynes R.O. "Integrins: bidirectional, allosteric signaling machines". Cell, vol. 110, No. 6, Sep. 20, 2002, pp. 673-687.

Korbelin, J., et al. Pulmonary Targeting of Adeno-associated Viral Vectors by Next-generation Sequencing-guided Screening of Random Capsid Displayed Peptide Libraries. Mol Ther vol. 24, No. 6, Jun. 2016, pp. 1050-1061.

N. Levitt et al. "Definition of an efficient synthetic poly(A) site". Genes Dev, vol. 3, Jul. 1989, 1019-1025.

C. Li and R. J. Samulski. Engineering adeno-associated virus vectors for gene therapy. Nat Rev Genet, vol. 21, No. 4, Feb. 10, 2020, pp. 255-272.

C. Li et al. "Development of Patient-specific AAV Vectors After Neutralizing Antibody Selection for Enhanced Muscle Gene Transfer", Mol. Ther. vol. 24, No. 6, Jan. 2016, pp. 53-65.

D. L. Mack, "Systemic AAV8-Mediated Gene Therapy Drives Whole-Body Correction of Myotubular Myopathy in Dogs". Mol Ther, vol. 25, No. 4, Apr. 5, 2017, pp. 839-854.

J.R. Mendell et al. "Assessment of Systemic Delivery of rAAVrh74. MHCK7.micro-dystrophin in Children With Duchenne Muscular Dystrophy", JAMA Neurology, vo. 77 No. 9, Jun. 15, 2020, pp. 1-10.

L. Morales et al. "Broader Implications of Progressive Liver Dysfunction and Lethal Sepsis in Two Boys following Systemic High-Dose AAV". Mol Ther, vol. 28, No. 8, Aug. 5, 2020, pp. 1753-1755.

D.A. Murrey et al, "Feasibility and safety of systemic rAAV9-hNAGLU delivery for treating mucopolysaccharidosis IIIB: toxicology, biodistribution, and immunological assessments in primates". Hum Gene Ther Clin Dev, vol. 25, No. 2, Jun. 2014, pp. 72-84.

C.E. Nelson et al. "In vivo genome editing improves muscle function in a mouse model of Duchenne muscular dystrophy". Science vol. 351, No. 6271, Jan. 22, 2016, pp. 403-407 (included as pp. 1-12).

M.D. Pierschbacher and E. Ruoslahti, "Cell attachment activity of fibronectin can be duplicated by small synthetic fragments of the molecule". Nature 309, 30-33.

S. Pillay et al. "An essential receptor for adeno-associated virus infection". Nature vol. 530, No. 7588, Feb. 4, 2016, pp. 108-112.

N. Pulicherla et al. Engineering liver-detargeted AAV9 vectors for cardiac and musculoskeletal gene transfer. Mol Ther, vol. 19,No. 6, Jun. 2011, pp. 1070-1078.

E. Ruoslahti. "RGD and other recognition sequences for integrins" Annu Rev Cell Dev Biol, vol. 12, 1996, pp. 697-715.

C. Summerford et al. "AlphaVbeta5 integrin: a co-receptor for adeno-associated virus type 2 infection". Nat Med vol. 5, No. 1, Jan. 1999, pp. 78-82.

M. Tabebordbar et al. "In vivo gene editing in dystrophic mouse muscle and muscle stem cells". Science vol. 351, No. 6271, Jan. 26, 2016, pp. 407-411.

L. V. Tse et al. "Structure-guided evolution of antigenically distinct adeno-associated virus variants for immune evasion". Proc Natl Acad Sci U S A vol. 114, May 30, 2017, pp. E4812-E4821.

J. Weinmann et al. "Identification of a myotropic AAV by massively parallel in vivo evaluation of barcoded capsid variants". Nat Commun vol. 11, No. 1, article 5432, Oct. 28, 2020, pp. 1-12.

(56)                    References Cited

OTHER PUBLICATIONS

Z. Wu et al. Single amino acid changes can influence titer, heparin binding, and tissue tropism in different adeno-associated virus serotypes. J Virol, vol. 80, No. 22, Nov. 2006, pp. 11393-11397.

L. Yang et al. "A myocardium tropic adeno-associated virus (AAV)evolved by DNA shuffling and in vivo selection", Proc Natl Acad Sci U S A vol. 106, No. 10, Mar. 10, 2009, pp. 3946-3951.

L. Yang and X. Xiao. "Creation of a cardiotropic adeno-associated virus: the story of viral directed evolution" Virology Journal. vol. 10, article 50, 2013, pp. 1-8.

C. Zincarelli et al. "Analysis of AAV serotypes 1-9 mediated gene expression and tropism in mice after systemic Injection". Mol Ther, vol. 16, No. 6, Jun. 2008, pp. 1073-1080.

D. Wang, et al. "A Rationally Engineered Capsid Variant of AAV9 for Systemic CNS-Directed and Peripheral Tissue-Detargeted Gene Delivery in Neonates", Mo. Ther. vol 9., Jun. 2018. pp. 234-246.

H. Zhang et al. "Addition of Six-His-Tagged Peptide to the C Terminus of Adeno-Associated Virus VP3 Does not Affect Viral Tropism or Production", Journal of Virology, vol. 76, No. 23, Dec. 2002, pp. 12023-12031.

K. Adachi et al. "A new recombinant adeno-associated virus (AAV)-Based Random Peptide Display Library System: Infection-Defective AAV1.9-3 as a Novel detargeted platform for vector evolution". Gene Therapy and Regulation. vol 5, No. 1, 2010, pp. 31-55.

J. Jang et al. "An evolved Adeno-associated viral variant enhances gene delivery and gene targeting in neural stem cells", Molecular Therapy. vol. 19, No. 4, Apr. 2011, pp. 667-675.

R. Sayroo et al. "Development of novel AAV serotype 6 based vectors with selective tropism for human cancer cells", Gene Therapy. vol 23, Oct. 8, 2015, pp. 18-25.

Pytela, et al. "Identification and isolation of a 140 kd cell surface glycoprotein with properties expected of a fibronectin receptor", Cell 40, 191-198 , 1985.

"UniProt Accession No. A0A1P8U1E3", A0A1P8U1E3_9ACTN, Apr. 12, 2017.

The Broad Institute, Inc., Opposition filed by Laboratorios Legrand S.A. for Colombian Patent Application No. NC2023/0000866, 19 pages, Jun. 5, 2023.

The Broad Institute, Inc., Extended European Search report for EP 21846426.1, Jul. 30, 2024, 13 pages.

The Broad Institute, Inc., "Office Action and Search Report for Chilean Patent Appln. No. 202300204", Jul. 12, 2024, 22 pages.

Krupovic and Koonin, Multiple origins of viral capsid proteins from cellular ancestors, PNAS, 2017, pp. 2401-2410.

Mattenberger et al., Globally defining the effects of mutations in a picornavirus capsid, elife 2021 pp. 1-26.

Zdechlik et al, Programmable Assembly of Adena-Associated Virus-Antibody Composites for Receptor-Mediated Gene Delivery, Bioconjugate Chem. 2020, 31, 1093-1106.

The Broad Institute, Inc., International Preliminary Report on Patentability for PCT/US2020/056133, issued by The International Bureau of WIPO on Apr. 28, 2022, 12 pages.

Unknown et al., "Third-Party Submission filed under 37 § C.F.R. 1.290 in U.S. Appl. No. 17/764,509", filed Jun. 27, 2023, pp. 1-133.

Tabebordbar et al., "Directed evolution of a family of AAV capsid variants enabling potent muscle-directed gene delivery across species," Cell, vol. 184, No. 19, pp. 4919-4938, Sep. 2021.

The Broad Institute, Inc., "Extended European Search Report for EP 20877004.0", Oct. 19, 2023, 10 pages.

The Broad Institute, Inc., "third Office Action and Search Report for Chinese Patent Application No. 2020800849233", Sep. 5, 2024, 58 pages.

The Broad Institute, Inc., "Office Action for Canadian Patent Application No. 3,153,902", Dec. 23, 2024, 4 pages.

Eichoff et al., "Nanobody-Enhanced Targeting of AAV Gene Therapy Vectors", 2019, Mol. Ther. Methods Clin. Devl. 15, 211-220.

Zedechlik et al., "Programmable Assembly of Adeno-Associated Virus-Antibody Composites for Receptor-Mediated Gene Delivery", 2020, Bioconjugate Chem. 31, 1093-1106.

Michels et al., "Lentiviral and adeno-associated vectors efficiently transduce mouse T lymphocytes when targeted to murine CD8", Mol. Ther. Methods Clin. Dev. 23, 334-347, 2021.

Judd et al., "Random Insertion of mCherry Into VP3 Domain of Adeno-associated Virus Yields Fluorescent Capsids With no Loss of Infectivity", Mol. Ther. Nucleic Acids 1, e54, 10 pages, 2012.

Wagner et al., "Synthetic Biology: Emerging Concepts to Design and Advance Adeno-Associated Viral Vectors for Gene Therapy", 2021, Adv. Sci. 8, 2004018, 22 pages.

Stutika et al., "A Comprehensive RNA Sequencing Analysis of the Adeno-Associated Virus (AAV) Type 2 Transcriptome Reveals Novel AAV Transcripts, Splice Variants, and Derived Proteins", 2016 J. Viral., vol. 90(3), 1278-1289.

Farris et al., "Improved splicing of adeno-associated viral (AAV) capsid protein-supplying pre-mRNAs leads to increased recombinant AAV vector production", 2008, Human Gene Ther., vol. 19, 14221-1427.

Michelfelder et al., "Peptide ligands incorporated into the threefold spike capsid domain to re-direct gene transduction of AAV8 and AAV9 in vivo", 2011, PLoS ONE, vol. 6(8), e23101.doi:10.1371/journal.pone.002310, 11 pages.

Wu et al., "Mutational analysis of the adeno-associated virus type 2 (AAV2) capsid gene and construction of AAV2 vectors with altered tropism", Journal of Virology (2000) vol. 7 4, No. 18, pp. 8635-8647.

Nguyen et al, Retargeted and detargeted adenovirus for gene delivery to the muscle, Virology. Jan. 15, 2018; 514: 118-123.

* cited by examiner

Variable region VIII

10^6 -10^7
capsid variants

Random
*n-mer*
*inserted*

AAV9 helper adenovirus
plasmid

AAV Rep
plasmid

AAV capsid
plasmid library
(10 ng)

HEK293

AAV capsid
virus library

Each capsid variant encapsulates it own
coding sequence as the vector genome

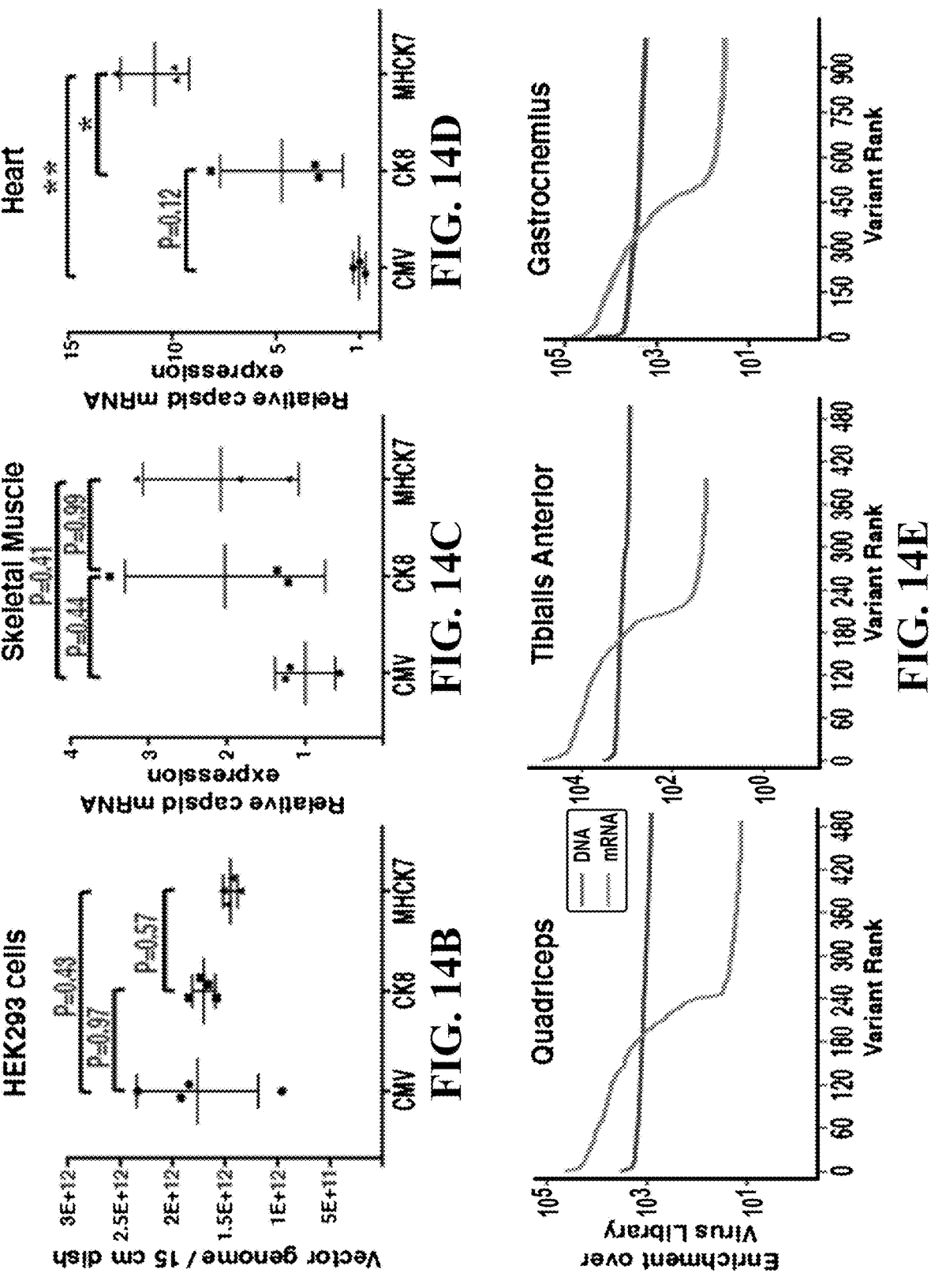

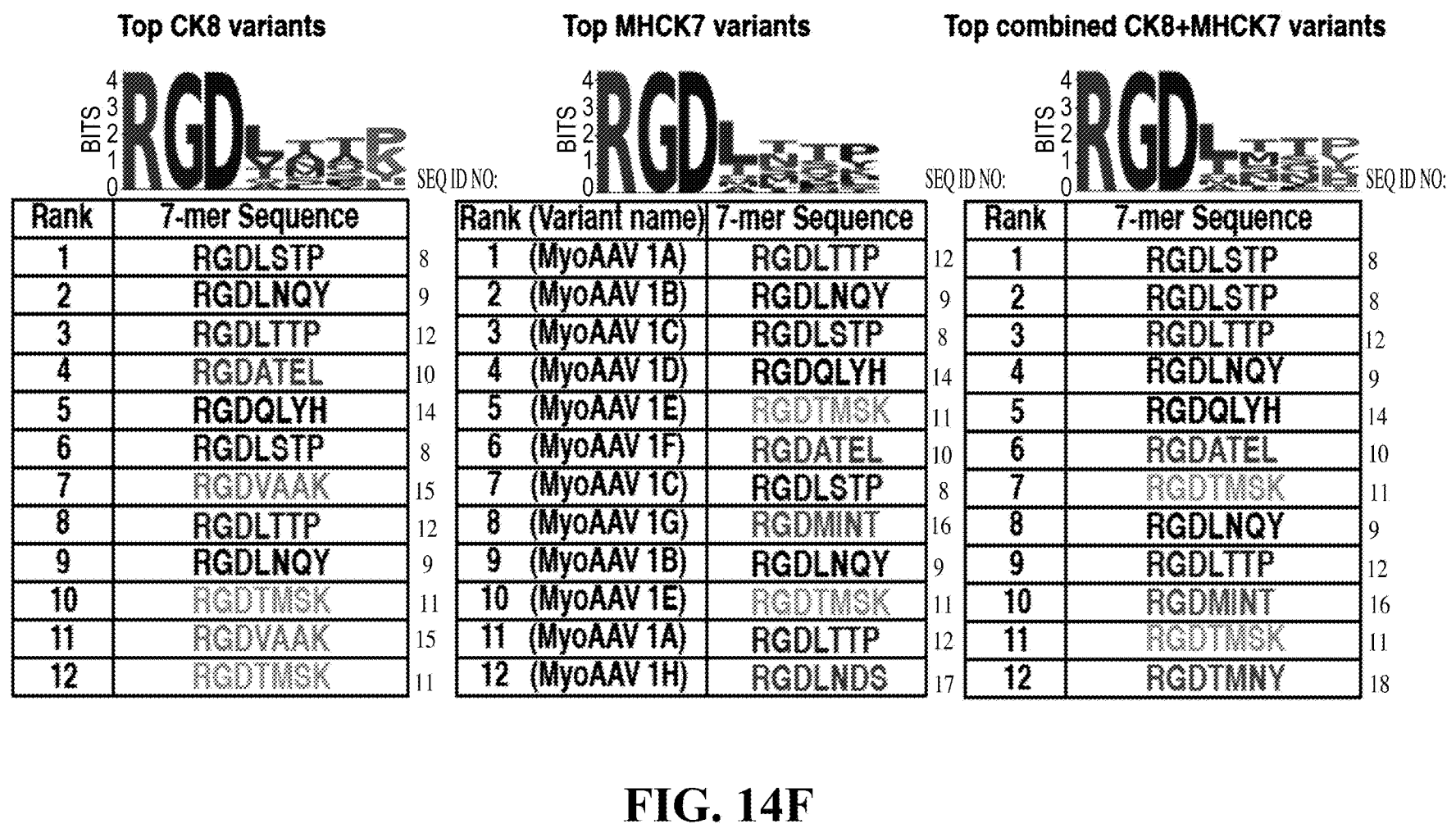

Top CK8 variants

| Rank | 7-mer Sequence | SEQ ID NO: |
|---|---|---|
| 1 | RGDLSTP | 8 |
| 2 | RGDLNQY | 9 |
| 3 | RGDLTTP | 12 |
| 4 | RGDATEL | 10 |
| 5 | RGDQLYH | 14 |
| 6 | RGDLSTP | 8 |
| 7 | RGDVAAK | 15 |
| 8 | RGDLTTP | 12 |
| 9 | RGDLNQY | 9 |
| 10 | RGDTMSK | 11 |
| 11 | RGDVAAK | 15 |
| 12 | RGDTMSK | 11 |

Top MHCK7 variants

| Rank (Variant name) | 7-mer Sequence | SEQ ID NO: |
|---|---|---|
| 1 (MyoAAV 1A) | RGDLTTP | 12 |
| 2 (MyoAAV 1B) | RGDLNQY | 9 |
| 3 (MyoAAV 1C) | RGDLSTP | 8 |
| 4 (MyoAAV 1D) | RGDQLYH | 14 |
| 5 (MyoAAV 1E) | RGDTMSK | 11 |
| 6 (MyoAAV 1F) | RGDATEL | 10 |
| 7 (MyoAAV 1C) | RGDLSTP | 8 |
| 8 (MyoAAV 1G) | RGDMINT | 16 |
| 9 (MyoAAV 1B) | RGDLNQY | 9 |
| 10 (MyoAAV 1E) | RGDTMSK | 11 |
| 11 (MyoAAV 1A) | RGDLTTP | 12 |
| 12 (MyoAAV 1H) | RGDLNDS | 17 |

Top combined CK8+MHCK7 variants

| Rank | 7-mer Sequence | SEQ ID NO: |
|---|---|---|
| 1 | RGDLSTP | 8 |
| 2 | RGDLSTP | 8 |
| 3 | RGDLTTP | 12 |
| 4 | RGDLNQY | 9 |
| 5 | RGDQLYH | 14 |
| 6 | RGDATEL | 10 |
| 7 | RGDTMSK | 11 |
| 8 | RGDLNQY | 9 |
| 9 | RGDLTTP | 12 |
| 10 | RGDMINT | 16 |
| 11 | RGDTMSK | 11 |
| 12 | RGDTMNY | 18 |

FIG. 14F

Systemic injection of

2E+12 vg/kg
AAV9-MHCK7-
human *MTM1*

*or*

2E+12 vg/kg
MyoAAV 1A-MHCK7-
human *MTM1*

4 weeks-old
*Mtm1* Knockout mice

Body weight, activity, and survival
measurement over 8 months

MyoAAV 1A-
hMTM1

AAV9-
hMTM1

MyoAAV 1A-
hMTM1

AAV9-
hMTM1

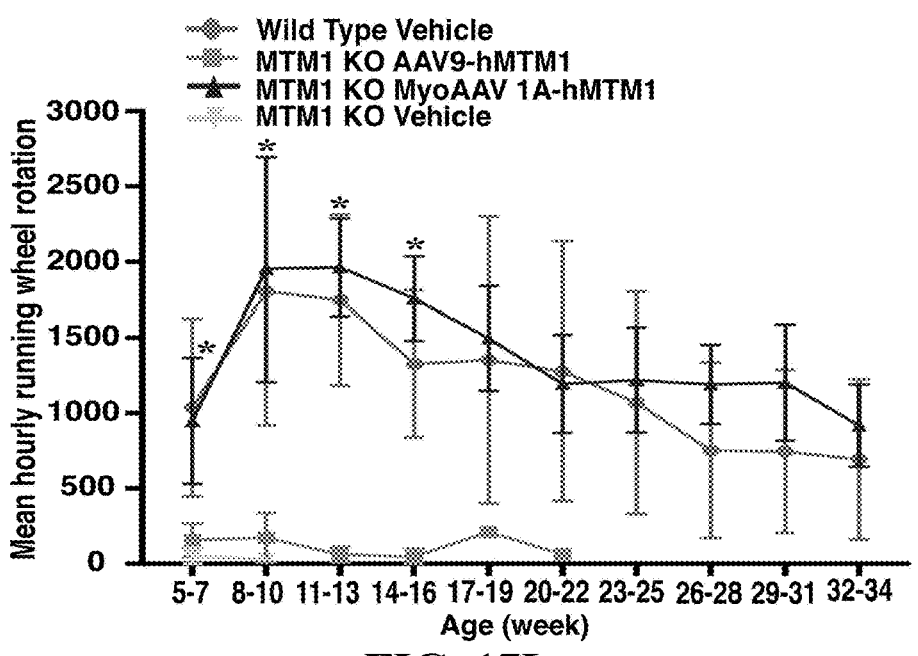
FIG. 17I
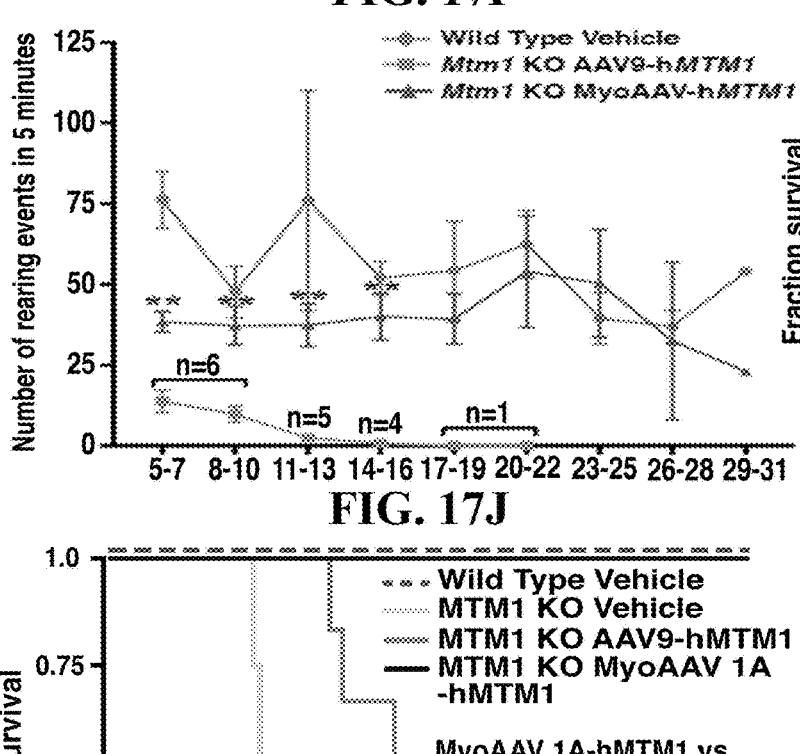
FIG. 17J
FIG. 17K

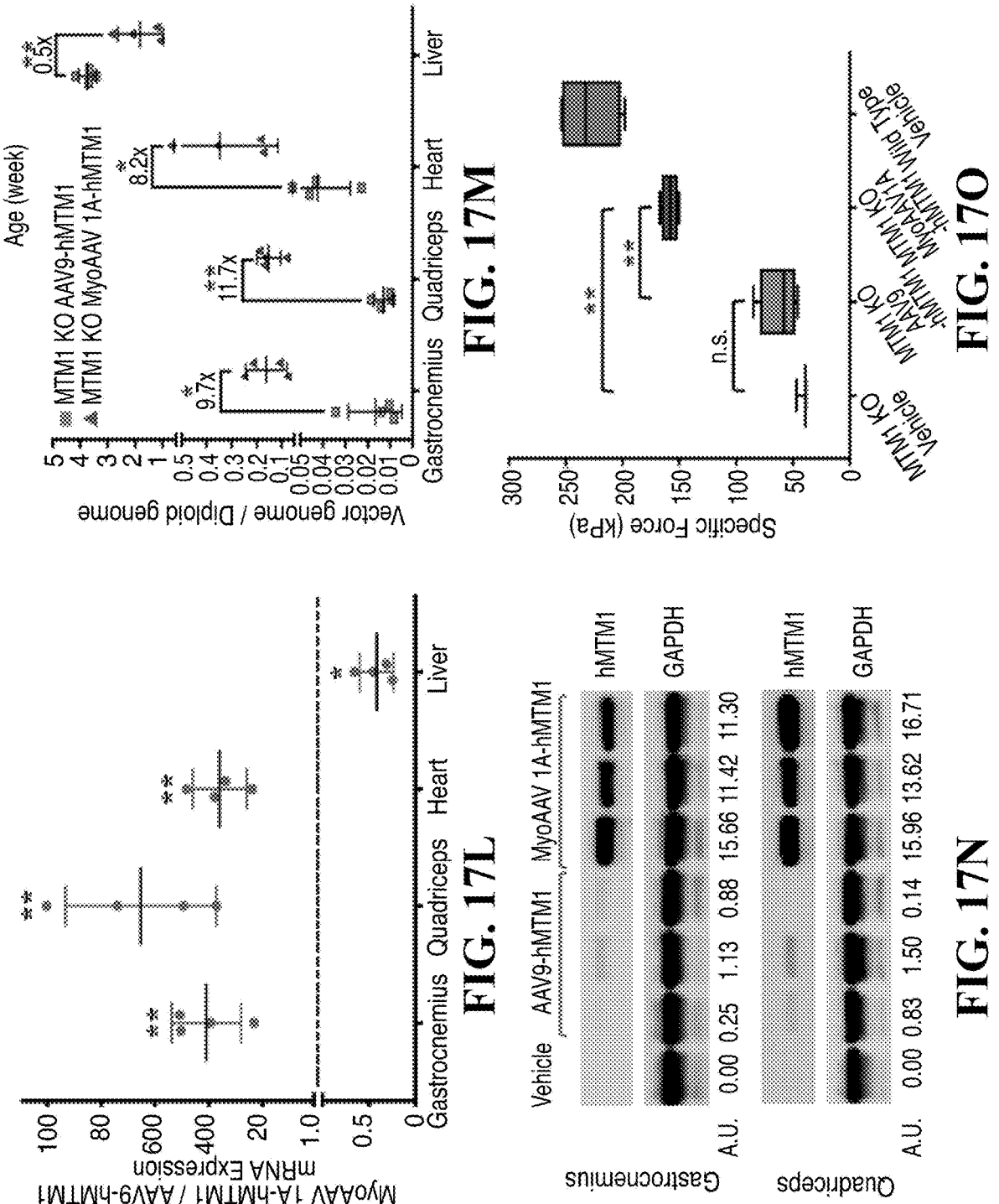

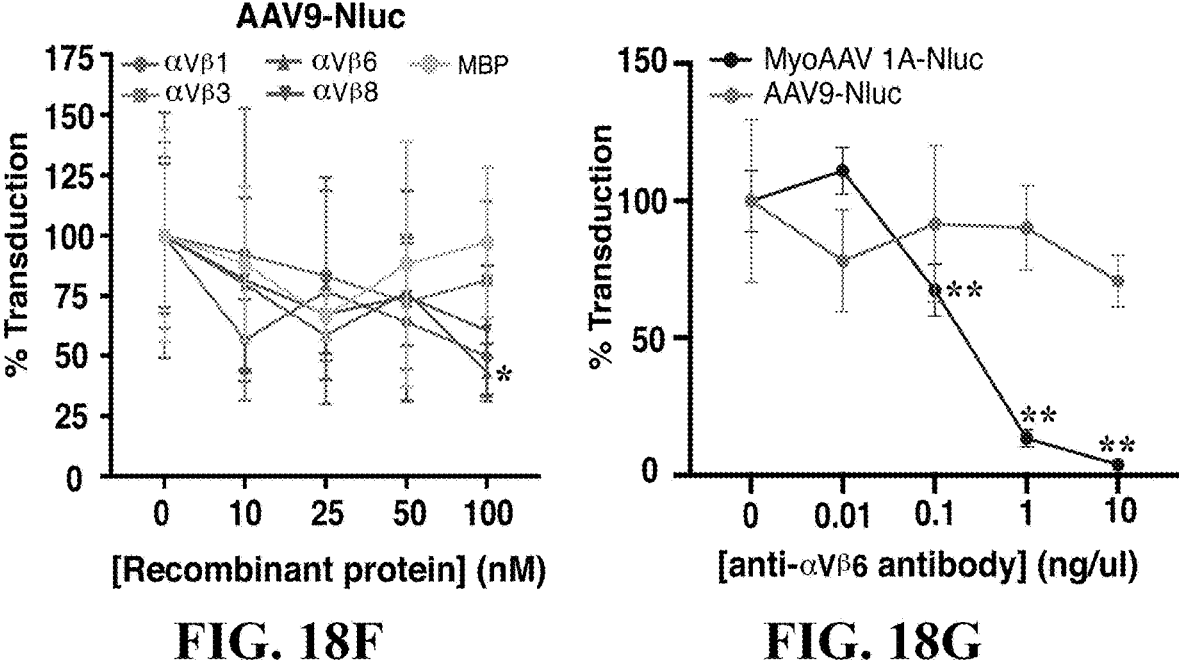
FIG. 18F
FIG. 18G
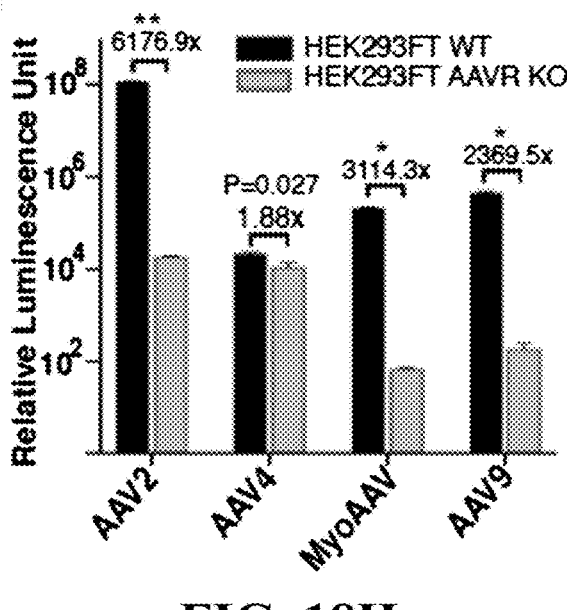
FIG. 18H

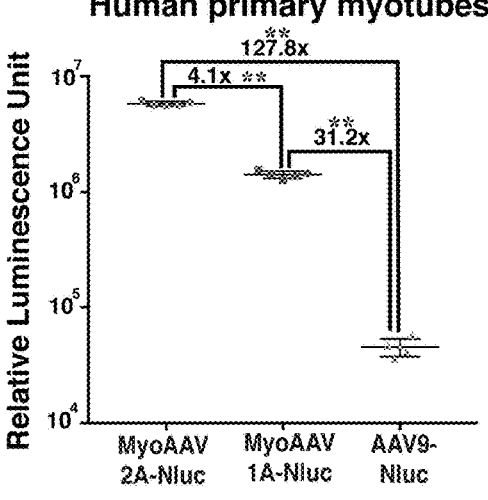
FIG. 19F
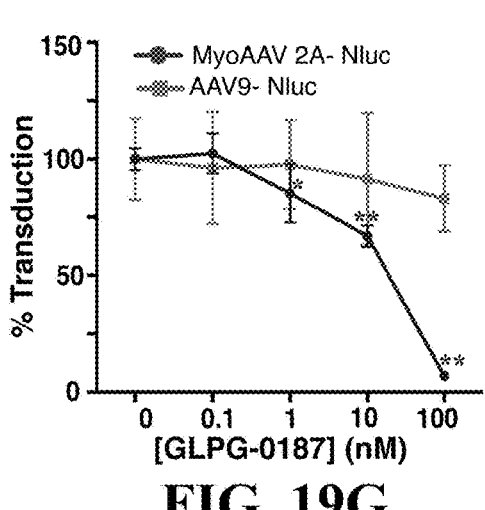
FIG. 19G
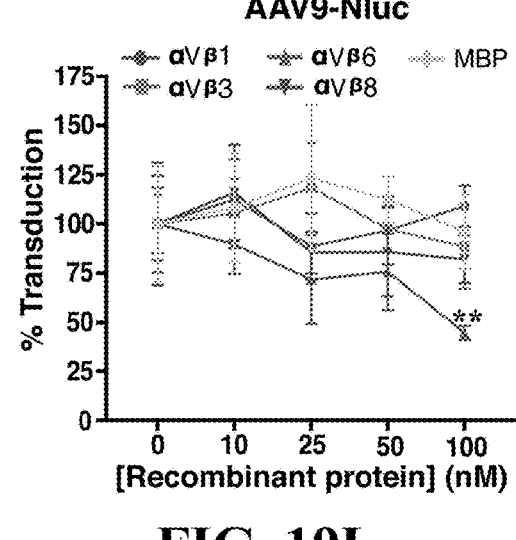
FIG. 19H
FIG. 19I

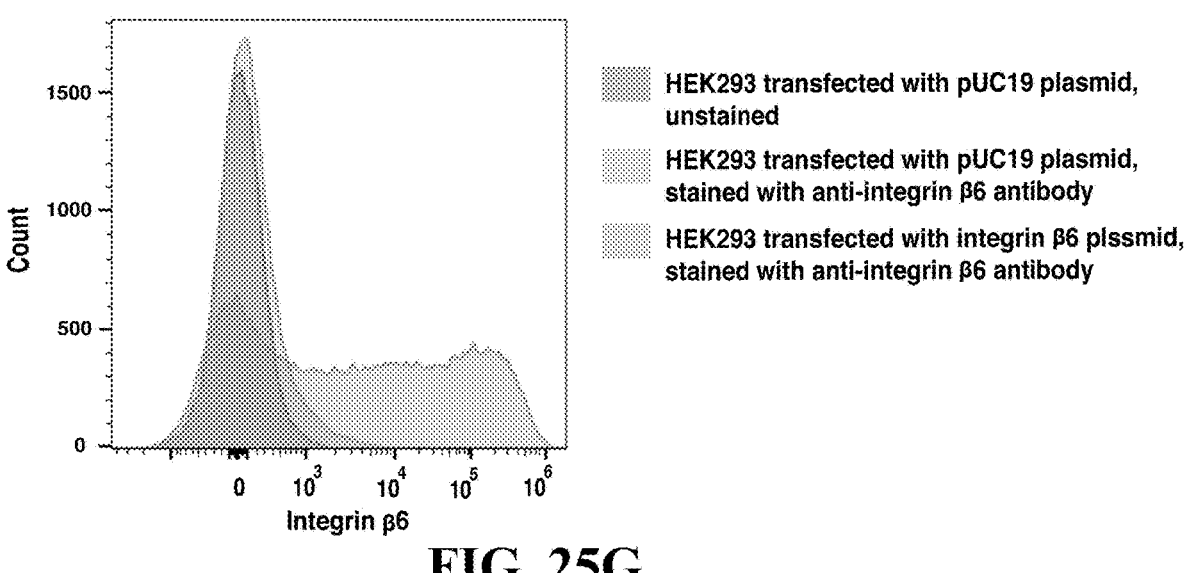
HEK293 transfected with pUC19 plasmid, unstained
HEK293 transfected with pUC19 plasmid, stained with anti-integrin β6 antibody
HEK293 transfected with integrin β6 plssmid, stained with anti-integrin β6 antibody
FIG. 25G
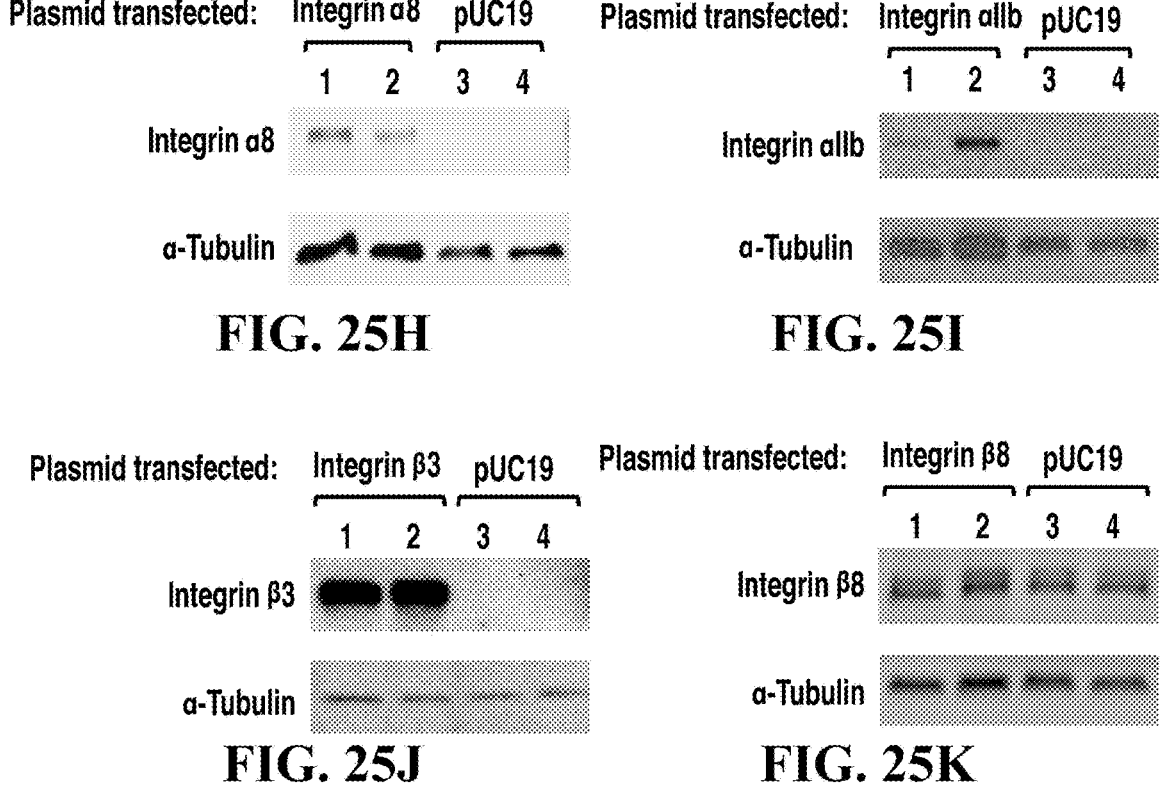
FIG. 25H
FIG. 25I
FIG. 25J
FIG. 25K

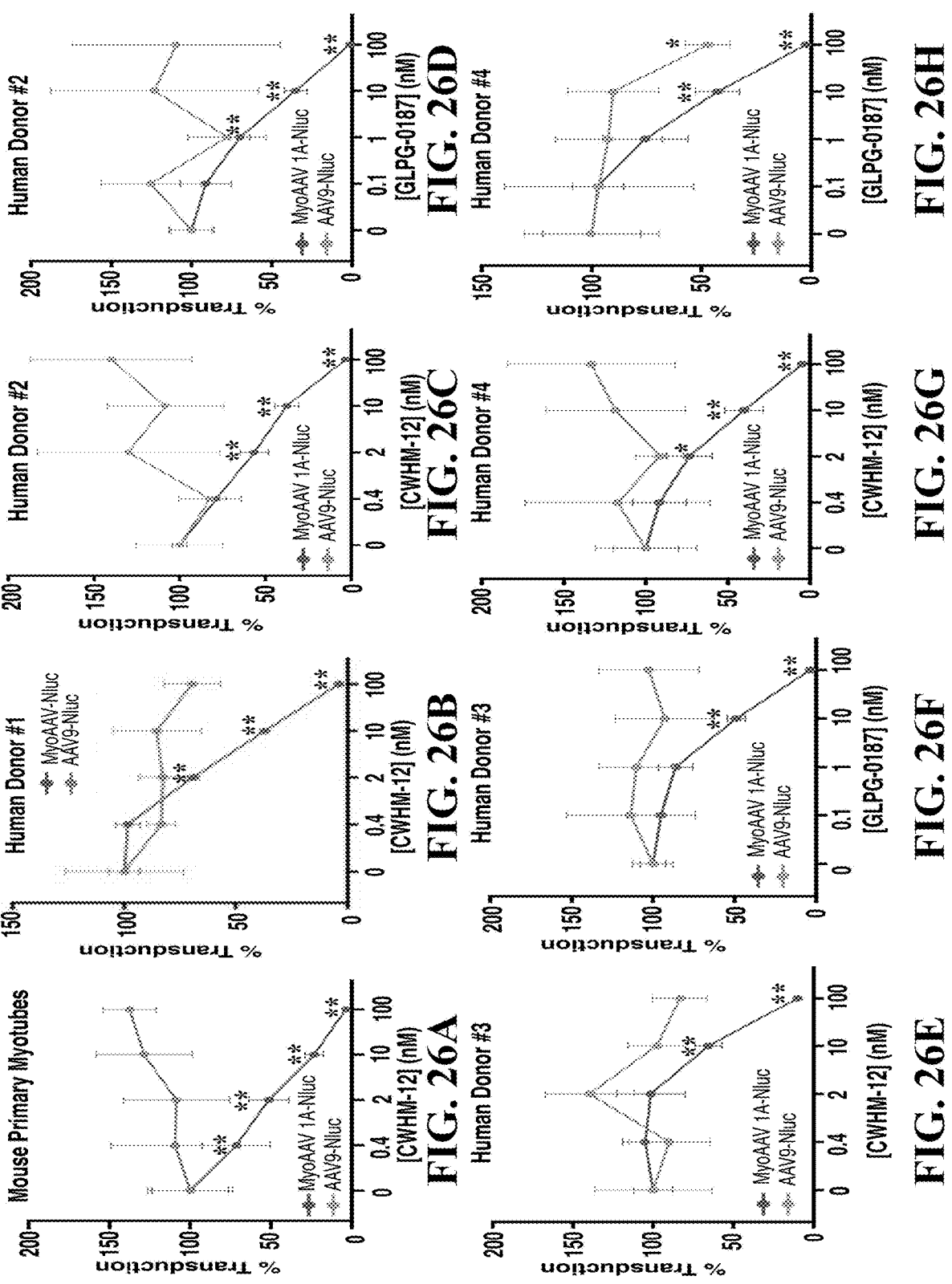

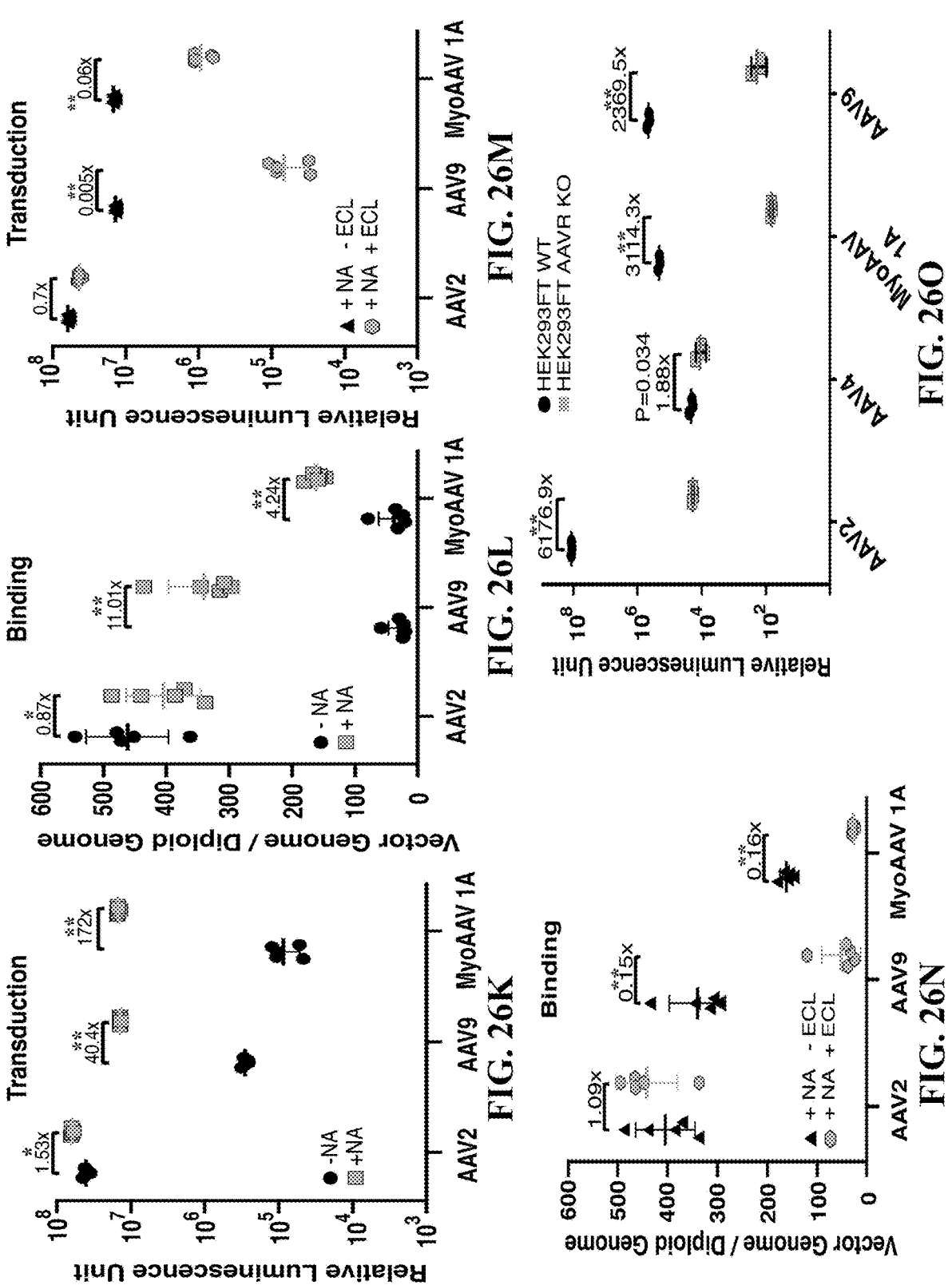

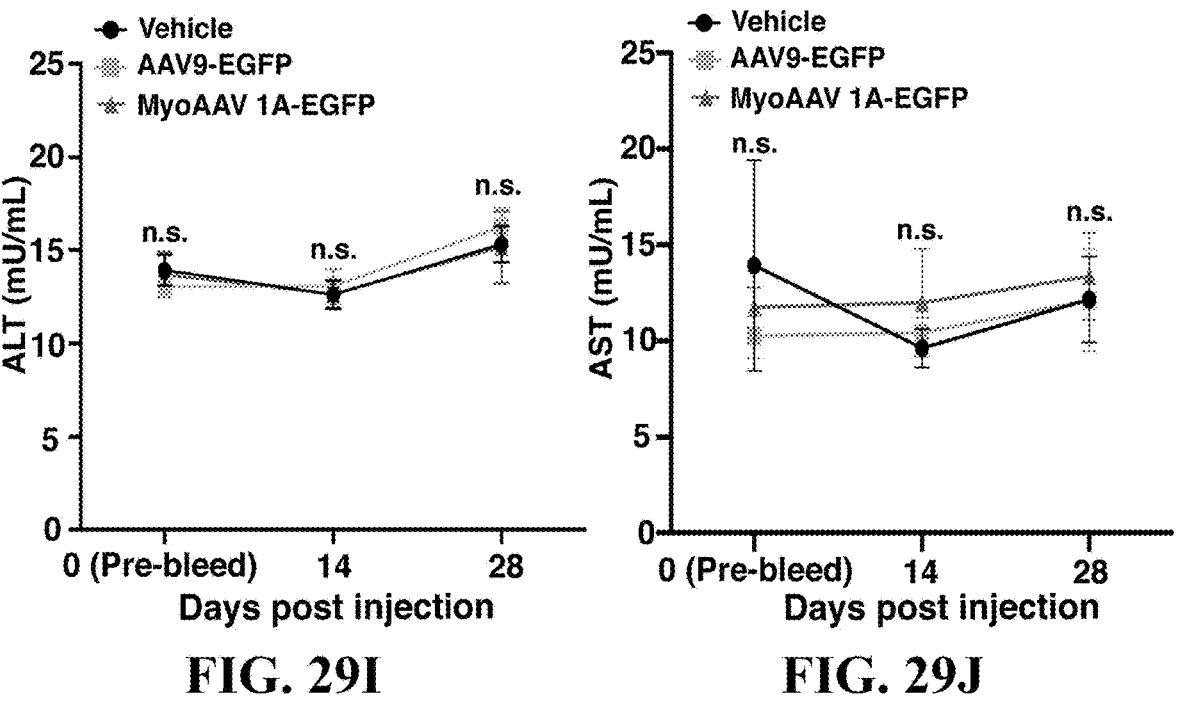
FIG. 29I          FIG. 29J
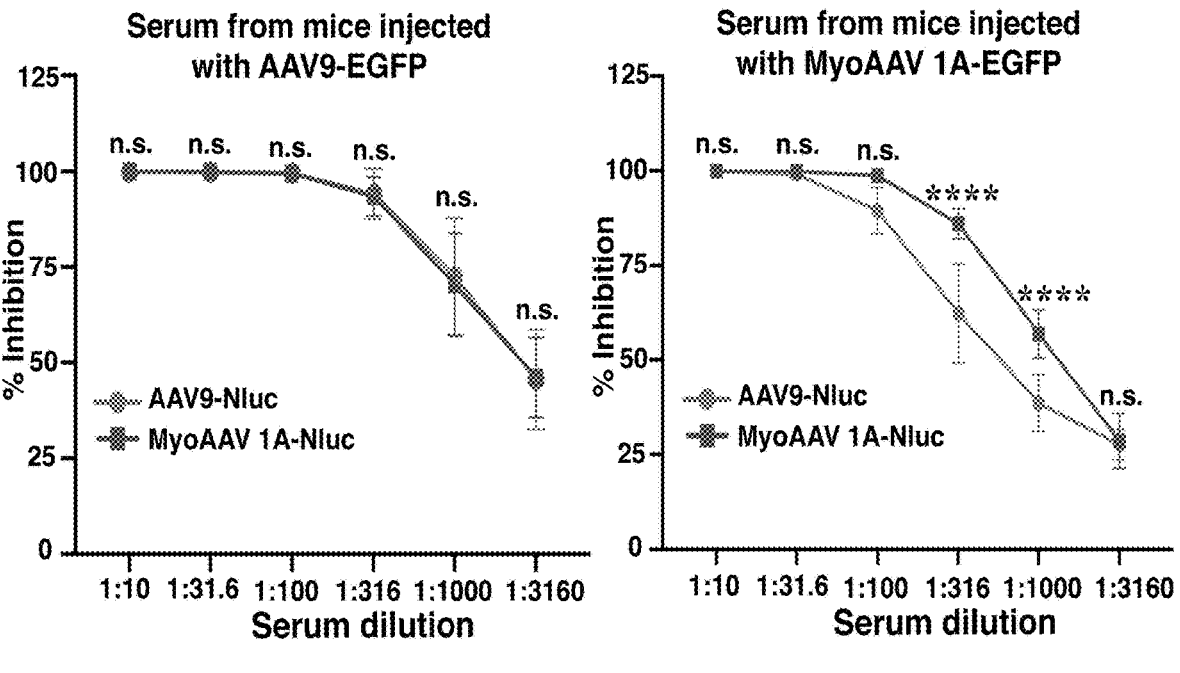
FIG. 29K          FIG. 29L

C57BL/6J Mouse Tissues

ENGINEERED MUSCLE TARGETING COMPOSITIONS

CROSS-REFERENCE TO RELATED APPLICATIONS

This application is National Stage application of International Application No. PCT/US2021/042812, filed Jul. 22, 201, which claims the benefit of and priority to U.S. Provisional Patent Application No. 63/055,265, filed on Jul. 22, 2020 entitled "Engineered Muscle Targeting Compositions", U.S. Provisional Patent Application No. 63/107,394, filed on Oct. 29, 2020 entitled "Engineered Muscle Targeting Compositions", and U.S. Provisional Patent Application No. 63/183,038, filed on May 2, 2021 entitled "Engineered Muscle Targeting Compositions", the contents of which are incorporated by reference in their entireties herein.

SEQUENCE LISTING

This application contains a sequence listing filed in electronic form as an ASCII.txt file entitled BROD-5215WP_ST25.txt, created on Jul. 13, 2021 and having a size of 186,097 bytes (188 KB on disk). The content of the sequence listing is incorporated herein in its entirety.

TECHNICAL FIELD

The subject matter disclosed herein is generally directed to muscle targeting compositions, including, recombinant adeno-associated virus (AAV) vectors and systems thereof, compositions, and uses thereof.

BACKGROUND

Recombinant AAVs (rAAVs) are the most commonly used delivery vehicles for gene therapy and gene editing. Nonetheless, rAAVs that contain natural capsid variants have limited cell tropism. Indeed, rAAVs used today mainly infect the liver after systemic delivery. Further, the transduction efficiency of conventional rAAVs in other cell-types, tissues, and organs by these conventional rAAVs with natural capsid variants is limited. Therefore, AAV-mediated polynucleotide delivery for diseased that affect cells, tissues, and organs other than the liver (e.g., nervous system, skeletal muscle, and cardiac muscle) typically requires an injection of a large dose of virus (typically about $1 \times 10^{14}$ vg/kg), which often results in liver toxicity. Furthermore, because large doses are required when using conventional rAAVs, manufacturing sufficient amounts of a therapeutic rAAV needed to dose adult patients is extremely challenging. Additionally, due to differences in gene expression and physiology, mouse and primate models respond differently to viral capsids. Transduction efficiency of different virus particles varies between different species, and as a result, preclinical studies in mice often do not accurately reflect results in primates, including humans. As such there exists a need for improved rAAVs for use in the treatment of various genetic diseases.

SUMMARY

In certain example embodiments, described herein are compositions comprising: a targeting moiety effective to target a muscle cell, wherein the targeting moiety comprises one or more n-mer motif, wherein at least one n-mer motif of the one or more n-mer motifs comprises or consists of $X_m RGDX_n$, wherein $X_m$ and $X_n$ are each independently selected from any amino acid, wherein n is 1, 2, 3, 4, 5, 6, 7, 8, or 9, and wherein m is 1-4; and optionally a cargo, wherein the cargo is coupled to or is otherwise associated with the targeting moiety.

In certain example embodiments, the at least one n-mer motif is as in any one of Table 2, Table 3, FIG. 14, or any combination thereof.

In certain example embodiments, the targeting moiety comprises a polypeptide, a polynucleotide, a lipid, a polymer, a sugar, or a combination thereof.

In certain example embodiments, the targeting moiety comprises a viral protein.

In certain example embodiments, the viral protein is a capsid protein.

In certain example embodiments, the viral protein is an adeno associated virus (AAV) protein.

In certain example embodiments, the n-mer motif is located between two amino acids of the viral protein such that the n-mer motif is external to a viral capsid.

In certain example embodiments, the n-mer motif is inserted between any two contiguous amino acids between amino acids 262-269, 327-332, 382-386, 452-460, 488-505, 527-539, 545-558, 581-593, 704-714, or any combination thereof in an AAV9 capsid polypeptide or in an analogous position in an AAV1, AAV2, AAV3, AAV4, AAV5, AAV6, AAV7, AAV8, AAV rh.74, or AAV rh.10 capsid polypeptide.

In certain example embodiments, the n-mer motif is inserted between amino acids 588 and 589 in an AAV9 capsid polypeptide or in an analogous position in an AAV1, AAV2, AAV3, AAV4, AAV5, AAV6, AAV7, AAV8, AAV rh.74, or AAV rh.10 capsid polypeptide.

In certain example embodiments, the composition is an engineered viral particle.

In certain example embodiments, the engineered viral particle is an engineered AAV viral particle.

In certain example embodiments, the AAV viral particle is an engineered AAV1, AAV2, AAV3, AAV4, AAV5, AAV6, AAV7, AAV8, AAV9, AAV rh.74, or AAV rh.10 viral particle.

In certain example embodiments, the n-mer motif is 3-15 amino acids.

In certain example embodiments, the optional cargo is capable of treating or preventing a muscle disease or disorder.

In certain example embodiments, the muscle disease or disorder is (a) an auto immune disease;

(b) a cancer;

(c) a muscular dystrophy;

(d) a neuro-muscular disease;

(e) a sugar or glycogen storage disease;

(f) an expanded repeat disease;

(g) a dominant negative disease;

(h) a cardiomyopathy;

(i) a viral disease;

(j) a progeroid disease; or (k) any combination thereof.

In certain example embodiments, the cargo is a morpholino, a peptide-linked morpholino, an antisense oligonucleotide, a PMO, a therapeutic transgene, a polynucleotide encoding a therapeutic polypeptide or peptide, a PPMO, one or more peptides, one or more polynucleotides encoding a CRISPR-Cas protein, a guide RNA, or both, a ribonucleoprotein, wherein the ribonucleoprotein comprises a CRISPR-Cas system molecule, a therapeutic transgene RNA, or other gene modifying or therapeutic RNA and/or protein, or any combination thereof.

In certain example embodiments, the cargo is capable of inducing exon skipping in a gene.

In certain example embodiments, the cargo is capable of inducing exon skipping in a dystrophin gene.

In certain example embodiments, the cargo is a mini- or micro-dystrophin gene.

In certain example embodiments, the mini- or micro-dystrophin gene comprises spectrin-like repeats 1, 2, 3, and 24, and optionally an nNOS domain.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is Type 1 or Type 2.

In certain example embodiments, the cardiomyopathy is dilated cardiomyopathy, hypertrophic cardiomyopathy, DMD-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

In certain example embodiments, the composition has increased muscle cell potency, muscle cell specificity, reduced immunogenicity, or any combination thereof.

Described in certain example embodiments herein are vector systems comprising: a vector comprising: one or more polynucleotides each encoding all or part of one or more targeting moieties effective to target a muscle cell, wherein each targeting moiety comprises one or more n-mer motifs, wherein at least one n-mer motif of the one or more n-mer motifs comprises or consists of $X_m RGDX_n$, wherein $X_m$ and $X_n$ are each independently selected from any amino acid, wherein n is 1, 2, 3, 4, 5, 6, 7, 8, or 9, and wherein m is 1-4, and wherein at least one of the one or more poly-nucleotides at least encodes the at least one n-mer motif, and optionally, a regulatory element operatively coupled to one or more of the polynucleotide(s).

In certain example embodiments, at least one n-mer motif is as in any one of Table 2, Table 3, FIG. 14F, or any combination thereof.

In certain example embodiments, the vector system further comprises a cargo.

In certain example embodiments, the cargo is a cargo polynucleotide and is optionally coupled to one or more of the one or more polynucleotides encoding the targeting moiety.

In certain example embodiments, the cargo polynucle-otide is present on the same vector or a different vector than the one or more polynucleotides encoding the targeting moiety.

In certain example embodiments, the vector system is capable of producing virus particles that contain the cargo when present.

In certain example embodiments, the vector system is capable of producing a capsid polypeptide comprising one or more of the targeting moieties.

In certain example embodiments, the vector system is capable of producing AAV virus particles.

In certain example embodiments, the AAV viral particles are engineered AAV1, AAV2, AAV3, AAV4, AAV5, AAV6, AAV7, AAV8, AAV9, AAV rh.74, or AAV rh.10 viral particle.

In certain example embodiments, the capsid polypeptide is an engineered AAV1, AAV2, AAV3, AAV4, AAV5, AAV6, AAV7, AAV8, AAV9, AAV rh.74, AAV rh.10 capsid poly-peptide.

In certain example embodiments of the vector system, the one or more polynucleotides encoding one n-mer motifs is inserted between two codons corresponding to two amino acids of the viral protein such that the n-mer motif(s) is external to the viral capsid.

In certain example embodiments, the one or more poly-nucleotides encoding one or more n-mer motifs is/are inserted between two codons corresponding to any two contiguous amino acids between amino acids 262-269, 327-332, 382-386, 452-460, 488-505, 527-539, 545-558, 581-593, 704-714, or any combination thereof in an AAV9 capsid polypeptide or in an analogous position in an AAV1, AAV2, AAV3, AAV4, AAV5, AAV6, AAV7, AAV8, AAV rh.74, AAV rh.10 capsid polypeptide.

In certain example embodiments, the one or more poly-nucleotides encoding one or more n-mer motifs is/are inserted between the codons corresponding to amino acid 588 and 589 in the AAV9 capsid polynucleotide or in an analogous position in an AAV1, AAV2, AAV3, AAV4, AAV5, AAV6, AAV7, AAV8, AAV rh.74, AAV rh.10 capsid polypeptide.

In certain example embodiments, the vector comprising the one or more polynucleotides each encoding all or part of one or more targeting moieties does not comprise splice regulatory elements.

In certain example embodiments, the vector system further comprises a viral rep protein encoding polynucleotide.

In certain example embodiments, the viral rep protein encoding polynucleotide is an AAV rep protein encoding polynucleotide.

In certain example embodiments, the viral rep protein encoding polynucleotide is on the same vector or different vector as the one or more polynucleotides each encoding all or part of one or more targeting moieties.

In certain example embodiments, the viral rep protein is operatively coupled to a regulatory element.

Described in certain example embodiments herein are polynucleotides encoded by and/or produced by a vector system as in any of the preceding paragraphs or as described elsewhere herein.

In certain example embodiments, the polypeptide is a viral polypeptide.

In certain example embodiments, the viral polypeptide is an AAV polypeptide.

In certain example embodiments, described herein are particles produced by a vector system and/or including a polypeptide as described in any of the preceding paragraphs or as described elsewhere herein.

In certain example embodiments, the particle is a viral particle.

In certain example embodiments, the viral particle is an adeno-associated virus (AAV) particle, lentiviral particle, or a retroviral particle.

In certain example embodiments, the viral particle has a muscle-specific tropism.

In certain example embodiments, the cargo is capable of treating or preventing a muscle disease or disorder.

In certain example embodiments, the muscle disease or disorder is a. an auto immune disease;

b. a cancer;

c. a muscular dystrophy;

d. a neuro-muscular disease;

e. a sugar or glycogen storage disease;

f. an expanded repeat disease;

g. a dominant negative disease;

h. a cardiomyopathy;

i. a viral disease;

j. a progeroid disease; or k. any combination thereof.

In certain example embodiments, the cargo is a morpholino, a peptide-linked morpholino, an antisense oligonucleotide, a PMO, a therapeutic transgene, a polynucleotide encoding a therapeutic polypeptide or peptide, a PPMO, one or more peptides, one or more polynucleotides encoding a CRISPR-Cas protein, a guide RNA, or both, a ribonucleoprotein, wherein the ribonucleoprotein comprises a CRISPR-Cas system molecule, a therapeutic transgene RNA, or other gene modifying or therapeutic RNA and/or protein, or any combination thereof.

In certain example embodiments, the cargo is capable of inducing exon skipping in a gene.

In certain example embodiments, the cargo is capable of inducing exon skipping in a dystrophin gene.

In certain example embodiments, the cargo is a mini- or micro-dystrophin gene.

In certain example embodiments, the mini- or micro-dystrophin gene comprises spectrin-like repeats 1, 2, 3, and 24, and optionally an nNOS domain.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is Type 1 or Type 2.

In certain example embodiments, the cardiomyopathy is dilated cardiomyopathy, hypertrophic cardiomyopathy, DMD-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

In certain example embodiments, the polypeptide, the particle, or both have increased muscle cell potency, muscle cell specificity, reduced immunogenicity, or any combination thereof.

In certain example embodiments, described herein are cells comprising:

a. a composition as in any of the preceding paragraphs or described elsewhere herein;

b. a vector system as in of the preceding paragraphs or described elsewhere herein;

c. a polypeptide as in of the preceding paragraphs or described elsewhere herein;

d. a particle as in any of the preceding paragraphs or described elsewhere herein; or e. a combination thereof.

In certain example embodiments, the cell is prokaryotic.

In certain example embodiments, the cell is eukaryotic.

In certain example embodiments, described herein are pharmaceutical formulations comprising:

a. a composition as in any of the preceding paragraphs or described elsewhere herein;

b. a vector system as in any of the preceding paragraphs or described elsewhere herein;

c. a polypeptide as in any of the preceding paragraphs or described elsewhere herein;

d. a particle as in any of the preceding paragraphs or described elsewhere herein;

e. a cell as in any of the preceding paragraphs or described elsewhere herein; or f. a combination thereof; and a pharmaceutically acceptable carrier.

In certain example embodiments, described herein are methods comprising:

administering, to a subject in need thereof, a a. composition as in any of the preceding paragraphs or described elsewhere herein;

b. vector system as in any of the preceding paragraphs or described elsewhere herein;

c. polypeptide as in any of the preceding paragraphs or described elsewhere herein;

d. particle as in any of the preceding paragraphs or described elsewhere herein;

e. cell as in any of the preceding paragraphs or described elsewhere herein;

f. pharmaceutical formulation as of the preceding paragraphs or described elsewhere herein; or g. combination thereof In certain example embodiments, the subject has a muscle disease or disorder.

In certain example embodiments, the muscle disease or disorder is a. an auto immune disease;

b. a cancer;

c. a muscular dystrophy;

d. a neuro-muscular disease;

e. a sugar or glycogen storage disease;

f. an expanded repeat disease;

g. a dominant negative disease;

h. a cardiomyopathy;

i. a viral disease;

j. a progeroid disease; or k. any combination thereof.

In certain example embodiments, the expanded repeat disease is Huntington's disease, a Myotonic Dystrophy, or Facioscapulohumeral muscular dystrophy (FSHD).

In certain example embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD.

In certain example embodiments, the myotonic dystrophy is Type 1 or Type 2.

In certain example embodiments, the cardiomyopathy is dilated cardiomyopathy, hypertrophic cardiomyopathy, DMD-associated cardiomyopathy, or Dannon disease.

In certain example embodiments, the sugar or glycogen storage disease is a MPS type III disease or Pompe disease.

In certain example embodiments, the MPS type III disease, is MPS Type IIIA, IIIB, IIIC, or IIID.

In certain example embodiments, the neuro-muscular disease is Charcot-Marie-Tooth disease or Friedreich's Ataxia.

In certain example embodiments, the compositions have reduced or eliminated targeting or specificity for a non-muscle cell. In certain example embodiments, the non-muscle cells is a liver cell.

These and other embodiments, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 14A-14F—DELIVER identifies a class of muscle-tropic AAV capsid variants containing an RGD motif. FIG. 14A) Schematic of virus library production and capsid variant selection using DELIVER (SEQ ID NO: 13). FIG. 14B) Comparison of rAAV titers produced using ITR-containing constructs that express the AAV9 capsid coding sequence under the control of CMV, CK8, or MHCK7 promoters. Data are presented as mean±SD (n=4). P-value calculated by one-way analysis of variance (ANOVA) with Tukey's multiple comparisons test (MCT). FIGS. 14C-14D) In vivo expression of the AAV9 capsid library mRNA expressed under the control of CMV, CK8, or MHCK7 promoters in mouse skeletal muscle (FIG. 14C) and heart (FIG. 14D) after systemic injection. Data are presented as mean±SD (n=3). P-value calculated by one-way ANOVA with Tukey's MCT. *: P<0.05, **: P<0.01. FIG. 14E) Graphs showing enrichment of capsid variants expressed under MHCK7 promoter over virus library at the DNA and mRNA level in different mouse skeletal muscles. FIG. 14F) Sequence of the 7-mer insertion in the top highly expressed capsid variants in mouse muscles after the second round of transcript-based selection. Variants with the same color in each group are encoded by synonymous DNA codons (SEQ ID NO: 8-12, 14-18). See also FIGS. 21A-21I.

FIGS. 15A-15B) Whole mount fluorescent (FIG. 15A) and cross section (FIG. 15B) images of skeletal muscles, heart and liver from C57BL/6J mice systemically injected with 1E+12 vg of AAV9- or MyoAAV 1A-CMV-EGFP. Green: EGFP, Red: laminin for muscles, Lectin for Liver, Blue: Hoechst. Scale bar in cross sections: 100 μm. FIG. 15C) Quantification of fold difference in EGFP mRNA expression in various tissues of injected male and female C57BL/6J mice. Dashed red line indicates relative expression from AAV9-CMV-EGFP. Data are presented as mean±SD (n=3-4); *: P<0.05, : P<0.01 (Student t test between AAV9 and MyoAAV 1A injected mice for each group). FIG. 15D) Quantification of in vitro transduction in mouse (left) and human (right) primary myotubes transduced with vehicle, AAV9- or Myo-AAV 1A-CK8-Nluc. Data are presented as mean±SD (n=5); : P<0.01 (Student t test). Donor 1: 29 year old male, donor 2: 19 year old female, donor 3: 20 year old male, donor 4: 34 year old female. See also FIGS. 22A-22K and 29A-29O.

FIG. 16A) Whole body in vivo bioluminescence images of BALB/cJ mice systemically injected with 4E+11 vg of AAV8-, AAV9-, or MyoAAV 1A-CMV-Fluc, taken over 120 days. FIG. 16B) Quantification of total luminescence from forelimbs and hindlimbs of animals injected with AAV8-, AAV9-, or MyoAAV 1A-CMV-Fluc, assessed over 120 days. P-value calculated between AAV8, AAV9, and MyoAAV 1A groups by two-way ANOVA with Tukey's MCT; Data are presented as mean±SD (n=5). **: P<0.01 for both MyoAAV 1A vs AAV8 and MyoAAV 1A vs AAV9. Difference between AAV8 and AAV9 groups is not statistically significant at any of the time points. FIG. 16C) Whole organ luminescence images of TA, Triceps, Gastrocnemius, Quadriceps, and Abdominal muscles from mice injected with 4E+11 vg of AAV8-, AAV9-, or MyoAAV-CMV-Fluc harvested 4 months after injection. Color scale: 1E+7-1E+8.

FIG. 16D) Quantification of total luminescence from different muscles of animals injected with AAV8-, AAV9-, or MyoAAV-CMV-Fluc harvested 120 days after injection. Data are presented as mean±SEM (n=5). *: P<0.01 (Mann-Whitney test between MyoAAV and AAV9 groups). See also FIGS. 22A-22K, 23A-23B, and 29A-29O.

FIG. 17A) Representative immunofluorescence images for dystrophin (red) in mdx muscles injected with AAV9- or MyoAAV 1A-Dmd CRISPR. Scale bar: 400 µm. FIG. 17K) Survival curve for Mtm1 KO animals injected with vehicle, AAV9-hMTM1, or MyoAAV 1A-hMTM1, as well as wild type littermates injected with vehicle. (n=6 for KO AAV9, n=6 for KO MyoAAV 1A, n=3 for wild type vehicle, n=4 for KO vehicle). Data points for the Mtm1 KO mice injected with vehicle are from a previous experiment. P-value calculated between MyoAAV 1A and AAV9 groups; : P<0.01 (Mantel-Cox test). FIG. 17**M) Quantification of vector genome per diploid genome in various tissues of Mtm1 KO mice injected with AAV9- or MyoAAV 1A-hMTM1 analyzed 4 weeks after injection. Data are presented as mean±SD (n=4). *: P<0.05, : P<0.01 (Student t test). FIG. 17O) Extensor digitorum longus (EDL) muscle specific force for wild-type C57BL/6J mice injected with vehicle (n=4), and Mtm1 KO mice injected with vehicle (n=2), AAV9-hMTM1 (n=4), or MyoAAV 1A-hMTM1 (n=4). : P<0.01 (ANOVA with Tukey's MCT). See also FIGS. 24A-24G.

FIGS. 18A-18L—MyoAAV transduction is dependent on both integrin heterodimers and AAVR. FIGS. 18A-18B) Quantification of in vitro transduction (FIG. 18A) and viruses bound to cell surface (FIG. 18B) in HEK293 cells transfected with plasmids encoding for RGD-binding integrin heterodimers or with pUC19, and transduced with AAV9- or MyoAAV-CMV-Nluc. Data are presented as mean±SEM (n=3). P-value calculated compared to the pUC19 transfected cell in each group. *:P<0.05, : P<0.01 (ANOVA with Dunnett's multiple comparisons test). FIG. 18C In vitro transduction efficiency in mouse primary myotubes treated with different concentrations of GLPG-0187 pan-integrin αV antagonists and transduced with AAV9- or MyoAAV-CK8-Nluc. Data are presented as mean±SEM (n=5). P-value calculated compared to the 0 nM small molecule condition in each group. : P<0.01 (ANOVA with Dunnett's multiple comparisons test). FIG. 18D) In vitro transduction efficiency in human primary myotubes treated with different concentrations of GLPG-0187 pan-integrin αV antagonists and transduced with AAV9- or MyoAAV 1A-CK8-Nluc. Data are presented as mean±SD (n=5). P-value calculated compared to the 0 nM small molecule condition in each group. *: P<0.01 (ANOVA with Dunnett's MCT). FIGS. 18E-18F) In vitro transduction efficiency in human primary myotubes transduced with MyoAAV 1A-CK8-Nluc (FIG. 18E) or AAV9-CK8-Nluc (FIG. 18F) incubated with different concentrations of αVb1, αVb3, αVb6, αVb8, or MBP recombinant proteins. Data are presented as mean±SD (n=5). *: P<0.01, : P<0.001 (ANOVA with Dunnett's MCT with the 0 nM recombinant protein set as the control for each group). FIG. 18G) In vitro transduction efficiency in human primary myotubes treated with different concentrations of anti-αVb6 antibody and transduced with AAV9- or MyoAAV-CK8-Nluc. Data are presented as mean±SEM (n=5). P-value calculated compared to the 0 ng/ul antibody condition in each group. : P<0.001 (ANOVA with Dunnett's multiple comparisons test). FIGS. 18G-18H) In vitro transduction efficiency in human primary myotubes treated with different concentrations of anti-αVb6 (FIG. 18G) or isotype control (FIG. 18H) antibody and transduced with AAV9- or MyoAAV 1A-CK8-Nluc. Data are presented as mean±SD (n=5). P-value calculated compared to the 0 ng/ul antibody condition in each group; *: P<0.01, **: P<0.001 (ANOVA with Dunnett's MCT). FIGS. 18I-18J) Quantification of in vitro transduction (FIG. 18I) and viruses bound to cell surface (FIG. 18J) in HEK293 cells transfected with plasmids encoding for RGD-binding integrin heterodimers or with pUC19 and transduced with MyoAAV 1A-CMV-Nluc. Data are presented as mean±SD (n=3); *: P<0.01 (one-way ANOVA with Dunnett's MCT with the pUC19 transfected cells set as the control). FIG. 18K shows in vitro transduction efficiency in human primary myotubes treated with different concentrations of CWHM-12 pan-integrin αV antagonists and transduced with AAV9- or MyoAAV 1A-CK8-Nluc. Data are presented as mean±SD (n=5). P-value calculated compared to the 0 nM small molecule condition in each group. *: P<0.01 (ANOVA with Dunnett's MCT. FIG. 18L shows in vitro transduction efficiency in human primary myotubes treated with different concentrations of an isotype control antibody and transduced with AAV9- or MyoAAV 1A-CK8-Nluc. Data are presented as mean SD (n=5). P-value calculated compared to the 0 ng/ul antibody condition in each group; *: P<0.01, **: P<0.001 (ANOVA with Dunnett's MCT). See also FIGS. 25A-25K and 26A-26O.

FIGS. 19A-19M—Further evolution of MyoAAV using DELIVER generates more enhanced muscle-tropic capsid variants. FIG. 19A) Structure of the AAV9 VR-VIII surface loop and the predicted structure of the MyoAAV 1A VR-VIII surface loop with the amino acids annotated. FIG. 19B) Schematic of virus library design and sequence of the top hits identified from mouse muscles after injection of the second-round virus library at two different doses (SEQ ID NO: 2-7, 19-21). FIG. 19C) Different tissues of C57BL/6J mice systemically injected with 2E+11 vg of MyoAAV 1A-CMV-EGFP (left) or MyoAAV 2A-CMV-EGFP (right) illuminated by blue light. FIG. 19D) Whole mount fluorescent images of gastrocnemius, triceps, TA, and quadriceps of mice systemically injected with 2E+11 vg of AAV9-, Myo-AAV 1A-, or MyoAAV 2A-CMV-EGFP. FIG. 19E) Quantification of fold difference in EGFP mRNA expression in various tissues of C57BL/6J mice systemically injected with 2E+11 vg of MyoAAV 1A-, or MyoAAV 2A-CMV-EGFP compared to mice injected with the same dose of AAV9-CMV-EGFP. Dashed red line indicates relative expression from AAV9-CMV-EGFP. Data are presented as mean±SD (n=11 for MyoAAV 1A and MyoAAV 2A, n=8 for AAV9). P-value calculated compared to the AAV9 group. *: P<0.05, **: P<0.01 (ANOVA with Dunnett's MCT). FIG. 19F) Quantification of in vitro transduction in human primary myotubes transduced with AAV9-, MyoAAV 1A-, or Myo-AAV 2A-CK8-Nluc. Data are presented as mean±SD (n=5). *: P<0.01 (ANOVA with Tukey's MCT). FIG. 19G) In vitro transduction efficiency in human primary myotubes treated with different concentrations of GLPG-0187 integrin αV antagonists and transduced with AAV9- or MyoAAV 2A-CK8-Nluc. Data are presented as mean±SD (n=5). P-value calculated compared to the 0 nM small molecule condition in each group. *: P<0.05, : P<0.01 (ANOVA with Dunnett's MCT). FIGS. 19H-19I) In vitro transduction efficiency in human primary myotubes transduced with MyoAAV 2A-CK8-Nluc (FIG. 19H) or AAV9-CK8-Nluc (FIG. 19I) incubated with different concentrations of αVb1, αVb3, αVb6, αVb8, or MBP recombinant proteins. Data are presented as mean±SD (n=5). : P<0.01, *: P<0.001 (one-way ANOVA with Dunnett's MCT with the 0 nM recombinant protein condition in each group as the control). FIG. 19J) Whole body in vivo bioluminescence images of BALB/cJ mice systemically injected with 2E+11 vg of AAVrh74-, AAV9-, or MyoAAV 2A-CMV-Fluc, taken over 21 days. Color scale: 6E+6-1E+9. FIG. 19K) Quantification of total luminescence from hindlimbs of animals injected with AAVrh74-, AAV9-, or MyoAAV 2A-CMV-Fluc, assessed over 21 days. P-value calculated between AAVrh74, AAV9, and MyoAAV 2A groups by two-way ANOVA with Tukey's MCT; : P<0.01 for both MyoAAV 2A vs AAVrh74 and MyoAAV 2A vs AAV9. Difference between AAVrh74 and AAV9 groups is not statistically significant at any of the time points. FIG. 19L) Quantification of vector genome per diploid genome in various tissues of C57BL/6J mice injected with 2E+11 vg of AAV9-, MyoAAV 1A-, or MyoAAV 2A-CMV-EGFP. Data are presented as mean±SD (n=11 for MyoAAV 1A and MyoAAV 2A, n=8 for AAV9). P-value calculated between MyoAAV 2A and AAV9 groups; *: P<0.05, **: P<0.01 (Student t test). FIG. 19M) In vitro transduction efficiency in human primary myotubes treated with different concentrations of anti-αVb6 antibody (left) or 10 ng/ul isotype control antibody (right) and transduced with AAV9- or first or second-generation RGD-containing capsid variants encoding for Nluc under the control of CK8 promoter. Data are presented as mean±SD (n=5). P-value for the anti-αVb6 antibody data calculated between the first-generation and second-generation groups. *: P<0.05, : P<0.01 (Two-way ANOVA with Tukey's MCT). P-value for the isotype control data calculated between the isotype control and 10 ng/ul anti-αVb6 antibody condition for each group; : P<0.01 (Student t test). See also FIGS. 27A-27B.

FIG. 20A) Representative immunofluorescence images for microdystrophin-FLAG (red) in muscles of DBA/2J-mdx mice injected with 2E+13 vg/kg AAV9- or MyoAAV 2A-CK8-microdystrophin. Scale bar: 400 μm. FIG. 20B) Western blots detecting microdystrophin-FLAG and GAPDH in muscles of mice injected with 2E+13 vg/kg AAV9- or MyoAAV 2A-CK8-microdystrophin, with relative signal intensity determined by densitometry at the bottom. A.U.: arbitrary unit, normalized to GAPDH. FIG. 20C) Quantification of fold difference in microdystrophin mRNA expression in various muscles and liver of DBA/2J-mdx mice systemically injected with 2E+13 vg/kg of MyoAAV 2A-CK8-microdystrophin compared to mice injected with the same dose of AAV9-CK8-microdystrophin. Dashed red line indicates relative expression from AAV9-CK8-microdystrophin. Data are presented as mean±SD (n=9-10); *: P<0.05, : P<0.01 (Student t test). FIG. 20D) Quantification of vector genome per diploid genome in various muscles and liver of DBA/2J-mdx mice injected with 2E+13 vg/kg of AAV9- or MyoAAV 2A-CK8-microdystrophin. Data are presented as mean±SD (n=9-10). : P<0.01 (Student t test). FIGS. 20E-20F) Muscle specific force (FIG. 20E) and decrease in force after eccentric contractions (FIG. 20F) for DBA2/J mice injected with vehicle (n=10), and DBA/2J-mdx mice injected with vehicle (n=10), AAV9-CK8-microdystrophin (n=10), or MyoAAV 2A-CK8-microdystrophin (n=10). *: P<0.05, : P<0.01, *: P<0.001 (ANOVA with Tukey's MCT).

FIG. 21A) Schematic representation of different steps in AAV transduction. FIGS. 21B-21G) Graphs showing enrichment of capsid variants expressed under the ubiquitous CMV promoter over virus library at the DNA and mRNA level in Brain (FIG. 21B), Kidney (FIG. 21C), Lung (FIG. 21D), Skeletal Muscle (FIG. 21E), Heart (FIG. 21F), and Liver (FIG. 21G) of injected mice. Transcript-based selection as used in DELIVER enables more stringent identification of functional capsid variants compared to DNA-based selections. Enrichment over the virus library is calculated by dividing reads per million (RPM) for each variant identified in the tissue by RPM of the same variant in the virus library. FIGS. 21H-21I) Correlation between abundance of each capsid variant in the virus library with abundance of vector genome DNA (FIG. 21H) or expressed mRNA (under the control of CMV promoter, FIG. 21I) from that variant identified in the liver of mice injected with the virus library. While the relative amount of the vector genome DNA from each variant is correlated with the abundance of that variant in the virus library, there is almost no correlation between the levels of capsid mRNA expression from each variant and quantity of that variant in the virus library based on the linear regression between the two sample types. RPM: Reads Per Million.

FIGS. 22A-22B) Whole mount fluorescent (FIG. 22A) and cross section (FIG. 22B) images of Triceps, Gastrocnemius, and Abdominal muscles from C57BL/6J mice systemically injected with 1E+12 vg of AAV9- or MyoAAV 1A-CMV-EGFP. Green: EGFP, Red: laminin, Blue: Hoechst. Scale bar in cross sections: 100 μm. FIG. 22C) Whole mount fluorescent images of Lung, Kidney, Spleen, and Brain from C57BL/6J mice systemically injected with 1E+12 vg of AAV9- or MyoAAV 1A-CMV-EGFP. FIG. 22D) Quantification of vector genome per diploid genome in various tissues of C57BL/6J mice injected with 1E+12 vg of AAV9 or MyoAAV 1A-CMV-EGFP. Data are presented as mean±SD (n=4); *: P<0.05, : P<0.01 (Student t test). FIG. 22E) Comparison of recombinant AAV titers produced by the top RGD-containing capsid variants with wild type AAV9. Data are presented as mean±SD (n=3). P-value calculated by ANOVA with Dunnett's MCT with AAV9 as the control. FIG. 22F) Schematic of the satellite cell transduction analysis experiment. Delivery of Cre recombinase to cells containing the Ai9 locus results in removal of the STOP cassette from the genome and expression of tdTomato. FIG. 22G) Percent tdTomato+transduced muscle stem cells isolated from 6 months old mdx-Ai9 mice, 2 weeks after systemic injection with 4E+11 vg of AAV8-, AAV9-, or MyoAAV 1A-CMV-Cre. Data are presented as mean±SD (n=4); : P<0.01 (one-way ANOVA with Tukey's MCT). FIG. 22H) Representative FACS plots from muscle stem cells isolated from the injected mdx-Ai9 mice. FIG. 22I) Representative immunofluorescence images of myotubes differentiated from FACS sorted muscle stem cells isolated from mdx-Ai9 mice injected systemically with AAV8-, AAV9-, or MyoAAV 1A-CMV-Cre. Green, myosin heavy chain (MHC); red, tdTomato; blue, Hoechst. Scale bar: 400 μm. FIG. 22J) Western blots detecting EGFP and Vinculin in muscles of mice injected with vehicle, or 1E+12 vg of AAV9- or MyoAAV 1A-CMV-EGFP. FIG. 22K) Gating strategy for isolating skeletal muscle precursors from the mononuclear cells in the muscle.

FIG. 23A) Whole body in vivo bioluminescence images of BALB/cJ mice injected with 4E+11 vg of AAV8-, AAV9-, or MyoAAV-CMV-Fluc over 120 days. This image shows the luminescence signal from the same mice shown in FIG. 16A with a different color scale (5E+6-5E+7) to enable detection of the signal in muscles of mice injected with AAV8- and AAV9-CMV-Fluc. FIG. 23B) Whole organ luminescence images of TA, Triceps, Gastrocnemius, Quadriceps, and Abdominal muscles from mice injected with 4E+11 vg of AAV8-, AAV9-, or MyoAAV-CMV-Fluc harvested 4 months after injection. This image shows the luminescence signal from the same mice shown in FIG. 16C with a different color scale (5E+5-5E+7) to enable detection of the signal in muscles of mice injected with AAV8- and AAV9-CMV-Fluc.

FIGS. 24A-24G—MyoAAV-Dmd CRISPR systemic administration results in higher levels of SaCas9 and gRNA expression compared to AAV9-Dmd CRISPR in multiple muscles throughout the body. FIG. 24A) Schematic of the AAV constructs used to generate the AAV9- and MyoAAV 1A-Dmd CRISPR viruses. FIG. 24B) Schematic of dystrophin restoration after AAV-Dmd CRISPR administration to mdx mice. Mice were injected with 4.5E+12 vg of SaCas9 and 9E+12 vg of gRNA AAV. FIGS. 24C-24D Quantification of fold difference in SaCas9 mRNA (FIG. 24C) or gRNA (FIG. 24D) expression in different muscles of 8 weeks old mdx mice systemically injected with 4.5E+12 vg of AAV9- or MyoAAV 1A-CMV-SaCas9 and 9E+12 vg of AAV9- or MyoAAV 1A-gRNA. Dashed red line indicates relative expression from AAV9-CMV-SaCas9 (FIG. 24F) and AAV9-gRNA (FIG. 24F). Data are presented as mean±SD (n=5-6); *: P<0.05, : P<0.01, *: P<0.001, **: P<0.0001 (Student t test). FIG. 24E) Schematic of the AAV construct used to generate the AAV9- and MyoAAV 1A-MHCK7 human MTM1 viruses. FIG. 24F) Schematic of the AAV construct used to generate the AAV9- and Myo-AAV 1A-MHCK7 human MTM1 viruses. FIG. 24G) Number of rearing events in 5 minutes by wild type mice injected with vehicle, or Mtm1 KO mice injected with vehicle, AAV9-hMTM1, or MyoAAV 1A-hMTM1, both at 2E+12 vg/kg. Data are presented as mean SD (n=6 for KO AAV9, n=6 for KO MyoAAV 1A, n=3 for wild type vehicle, n=4 for KO vehicle) for weekly measurements averaged across three-week time periods. Data points for the Mtm1 KO mice injected with vehicle are from a previous experiment. P-value calculated between MyoAAV 1A and AAV9 groups; : P<0.01 (Multiple t tests with Holm-Sidak MCT).

FIGS. 25A-25K—Flow cytometry and western blot confirms overexpression of Integrin alpha and beta proteins after plasmid transfection in HEK293 cells. FIGS. 25A-25G) Representative histograms from flow cytometry analysis of HEK293 cells transfected with pUC19 or plasmids expressing integrin αV (FIG. 25A), β1 (FIG. 25B), α5 (FIG. 25C), β8 (FIG. 25D), β5 (FIG. 25E), β3 (FIG. 25F), or β6 (FIG. 25G) under the control of EF1α promoter and stained with antibodies against the overexpressed protein. FIGS. 2511-25I) Western blots showing overexpression of integrin α8 (FIG. 25H), αIIb (FIG. 25I), β3 (FIG. 25J), and β8 (FIG. 25K) in HEK293 cells transfected with the corresponding integrin plasmid (lanes 1 and 2) compared to the cells transfected with pUC19 (lanes 3 and 4).

FIGS. 26A-26O—Integrin αV antagonists suppress Myo-AAV, but not AAV9 transduction in primary mouse myotubes, as well as primary human myotubes from different donors. FIGS. 26A-26B) In vitro transduction efficiency in mouse primary myotubes treated with different concentrations of CWHM-12 (FIG. 26A) or GLPG-0187 (FIG. 26B and FIG. 26J) integrin αV antagonists and transduced with AAV9- or MyoAAV-CK8-Nluc (MyoAAV 1A-CK8-Nluc). Data are presented as mean±SEM (n=5). *: P<0.05, **:

P<0.01 (ANOVA with Dunnett's MCT with the 0 nM condition for each group as the control). FIGS. 26C-26H) In vitro transduction efficiency in human primary myotubes from three different donors treated with different concentrations of CWHM-12 (FIGS. 26C, 26E, and 26G) or GLPG-0187 (FIGS. 26D, 26F, and 26H) integrin αV antagonists and transduced with AAV9- or MyoAAV 1A-CK8-Nluc. Data are presented as mean±SD (n=5). *: P<0.05, : P<0.01 (ANOVA with Dunnett's MCT with the 0 nM condition for each group as the control). FIGS. 26J-26K) Quantification of in vitro transduction (FIG. 26J) and binding (FIG. 26K) of untreated HEK293 cells or cells pre-treated with NA and transduced with AAV2-, AAV9-, or MyoAAV 1A-CMV-Nluc. Data are presented as mean±SD (n=5); *: P<0.01, **: P<0.0001 (Student t test using log transformed data). FIG. 26L) Quantification of in vitro transduction (K) and binding (L) of HEK293 cells pre-treated with NA and ECL or NA alone with AAV2-, AAV9-, or MyoAAV 1A-CMV-Nluc. Data are presented as mean±SD (n=5); *: P<0.01, : P<0.0001 (Student t test using log transformed data). FIG. 26M) Comparison of in vitro transduction between HEK293FT and HEK293FT AAVR KO cells transduced with AAV2-, AAV4-, AAV9-, or MyoAAV 1A-CMV-Nluc. Data are presented as mean±SD (n=3). : P<0.0001 (Student t test using the log transformed data). FIG. 26N) Quantification of in vitro binding of HEK293 cells pre-treated with NA and ECL or NA alone with AAV2-, AAV9-, or MyoAAV 1A-CMV-Nluc. Data are presented as mean±SD (n=5); *: P<0.01, : P<0.0001 (Student t test using log transformed data). FIG. 26O) Comparison of in vitro transduction between HEK293FT and HEK293FT AAVR KO cells transduced with AAV2-, AAV4-, AAV9-, or MyoAAV 1A-CMV-Nluc. Data are presented as mean±SD (n=3). : P<0.0001 (Student t test using the log transformed data).

FIG. 27A) Quantification of vector genome per diploid genome in various tissues of C57BL/6J mice injected with 2E+11 vg of AAV9-, MyoAAV-, or EMyo-AAV-CMV-EGFP. Data are presented as mean±SEM (n=11 for MyoAAV and EMyoAAV, n=8 for AAV9). *: P<0.05 (Mann-Whitney test). FIG. 27B) In vitro transduction efficiency in human primary myotubes treated with different concentrations of anti-αVβ6 antibody and transduced with AAV9- or first or second-generation RGD-containing capsid variants encoding for Nluc under the control of CK8 promoter. Data are presented as mean±SEM (n=5). The graph on the left demonstrates the transduction efficiency for each individual variant. In the graph on the right, results from the first-generation variants (RGDLTTP (SEQ ID NO: 12), RGDLSTP (SEQ ID NO: 8), RGDLNQY (SEQ ID NO: 9), RGDATEL (SEQ ID NO: 10), and RGDTMSK (SEQ ID NO: 11)) and second-generation variants (GPGRGDQTTL (SEQ ID NO: 2), AEGRGDQYTR (SEQ ID NO: 3), ATGRGDLGQA (SEQ ID NO: 4), AVARGDQGLI (SEQ ID NO: 5), NISRGDQGYQ (SEQ ID NO: 6), APARGDQGSQ (SEQ ID NO: 7)) are plotted as two groups. *: P<0.01

(two-stage Benjamini, Krieger, & Yekutieli test between the first-generation and second-generation groups) (SEQ ID NO: 2-12).

Figures 28A, 28B:
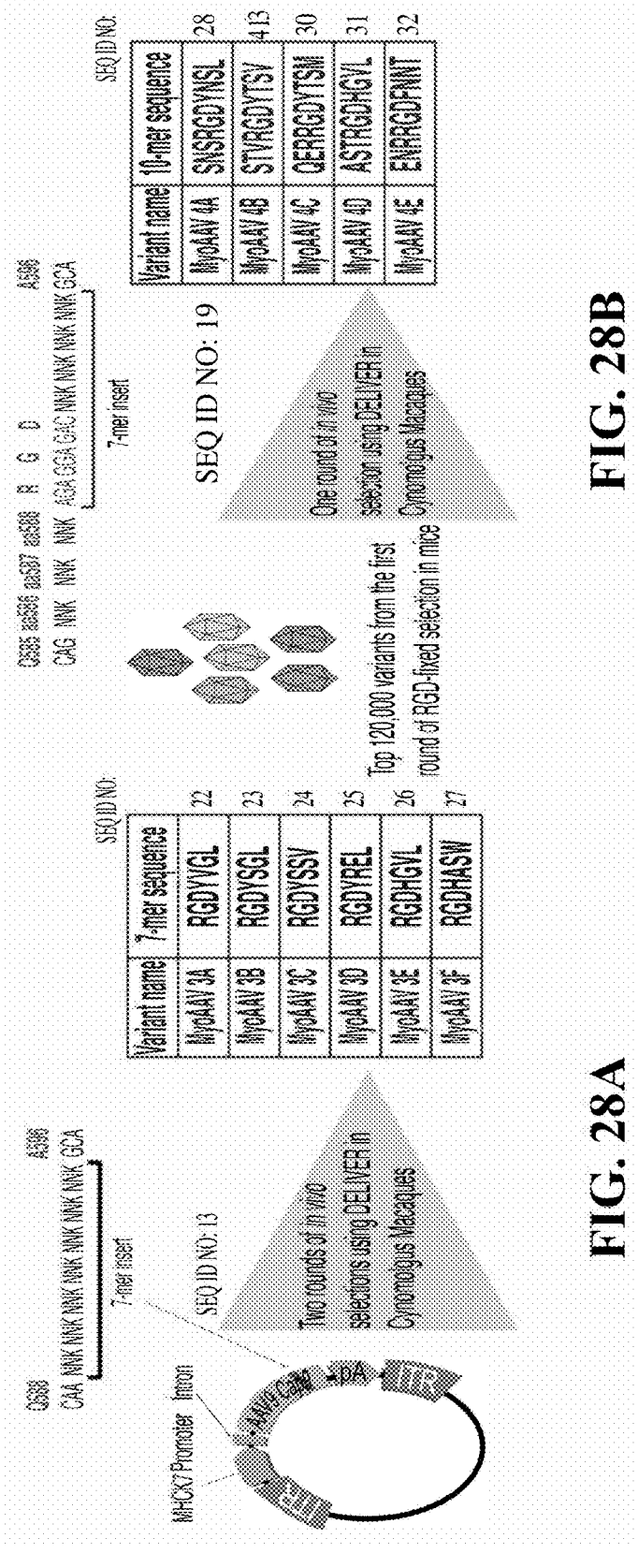
Figures 28C, 28D:
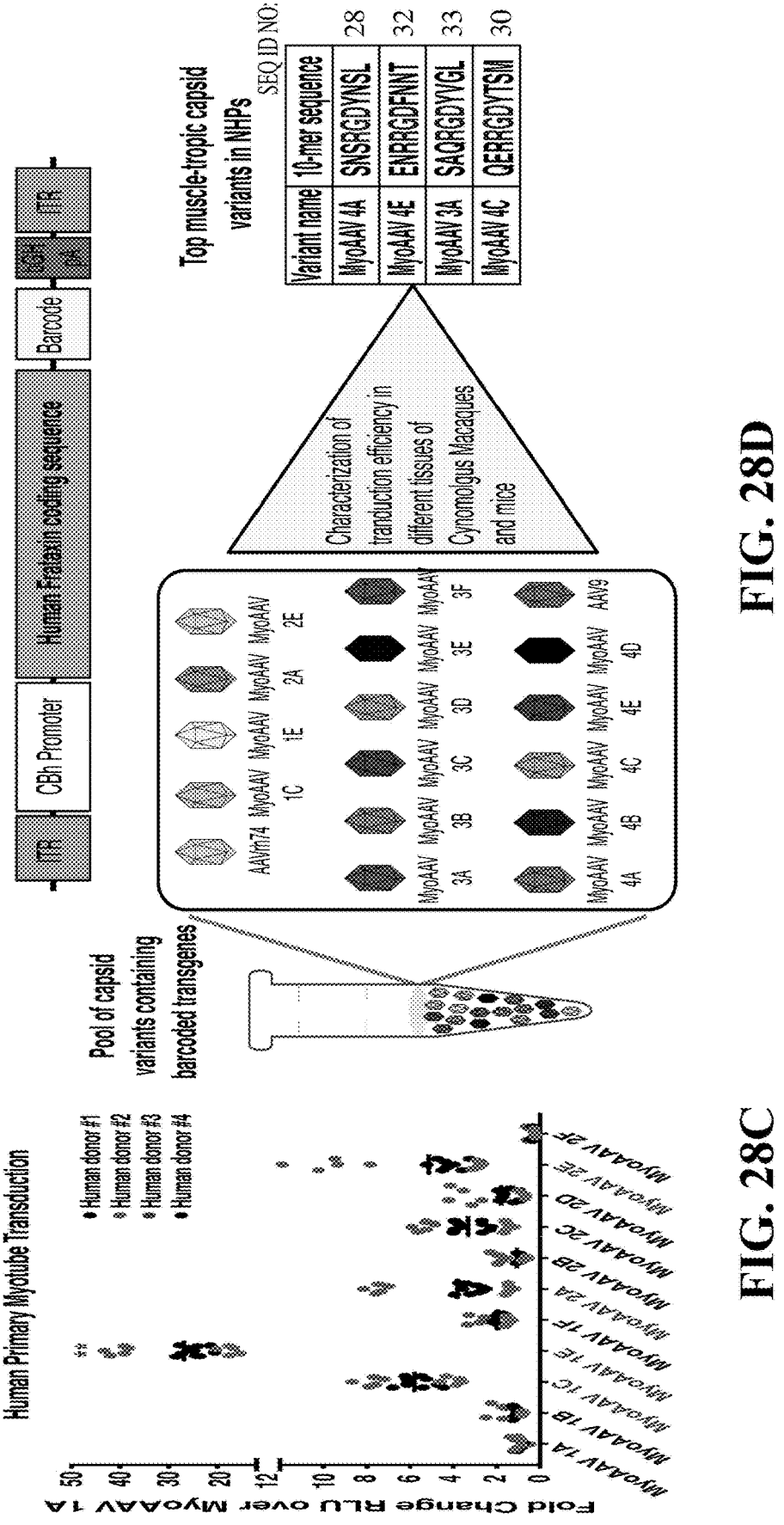
Figure 28E:
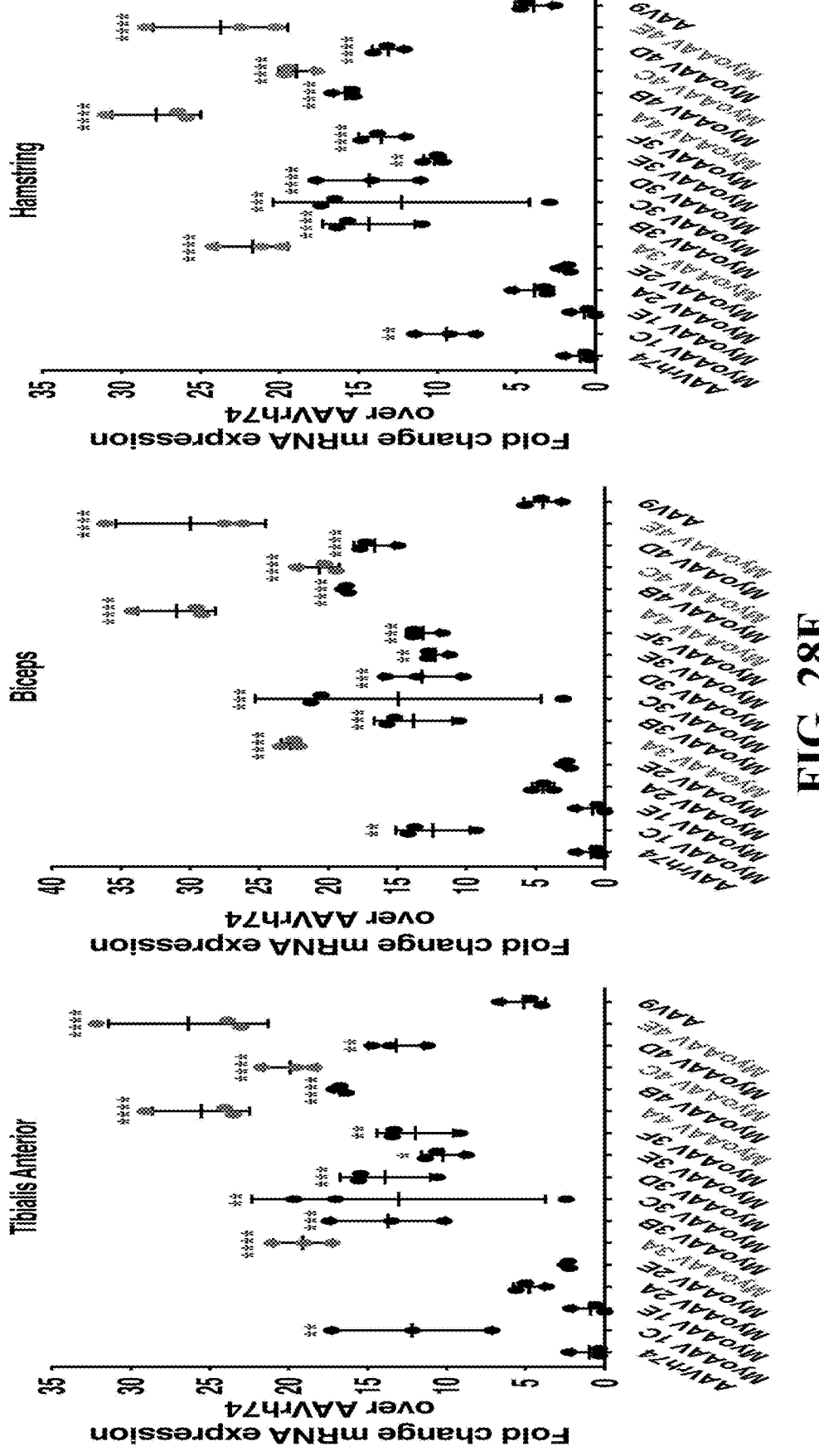
Figure 28E:
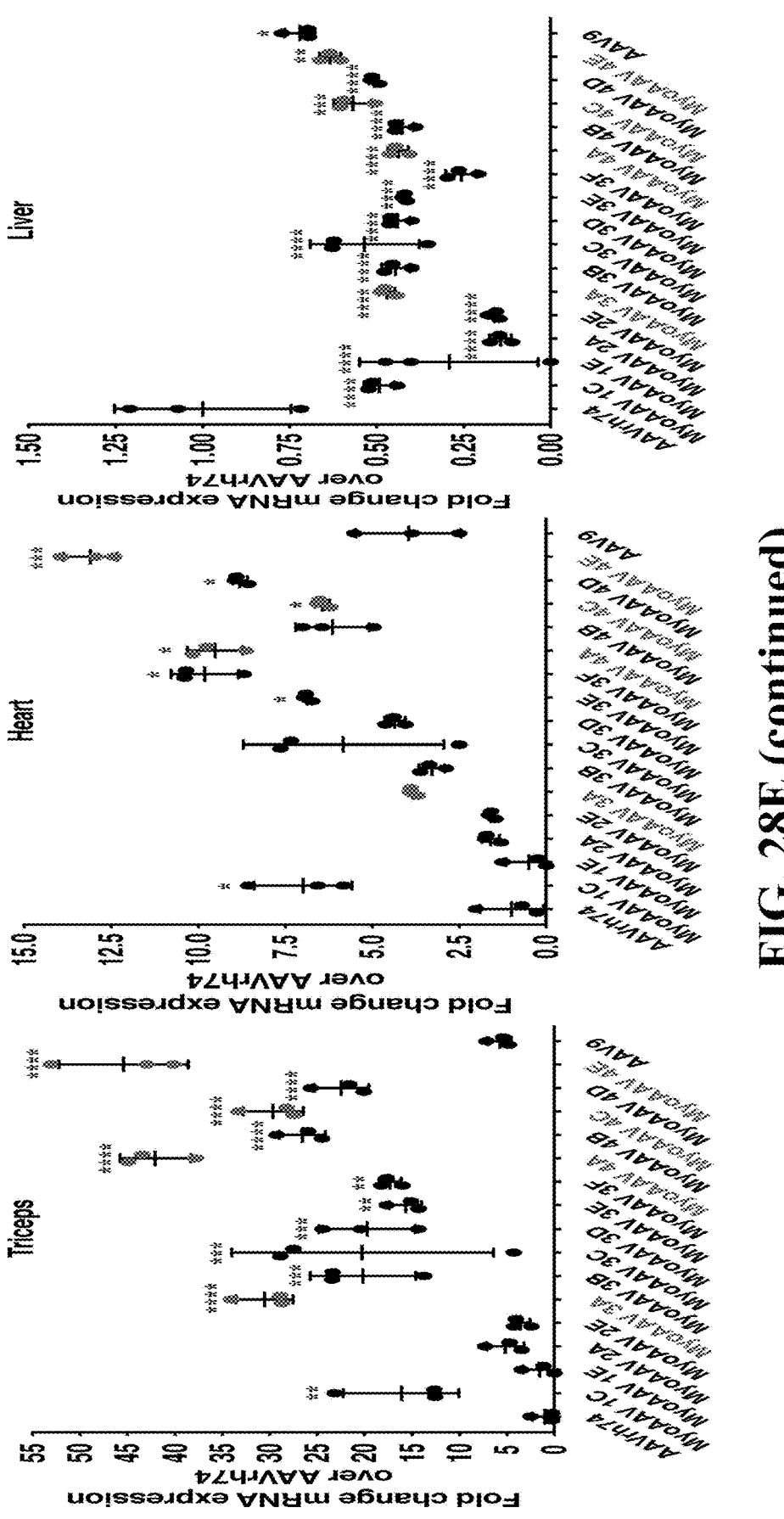
Figures 28F, 28G, 28H:
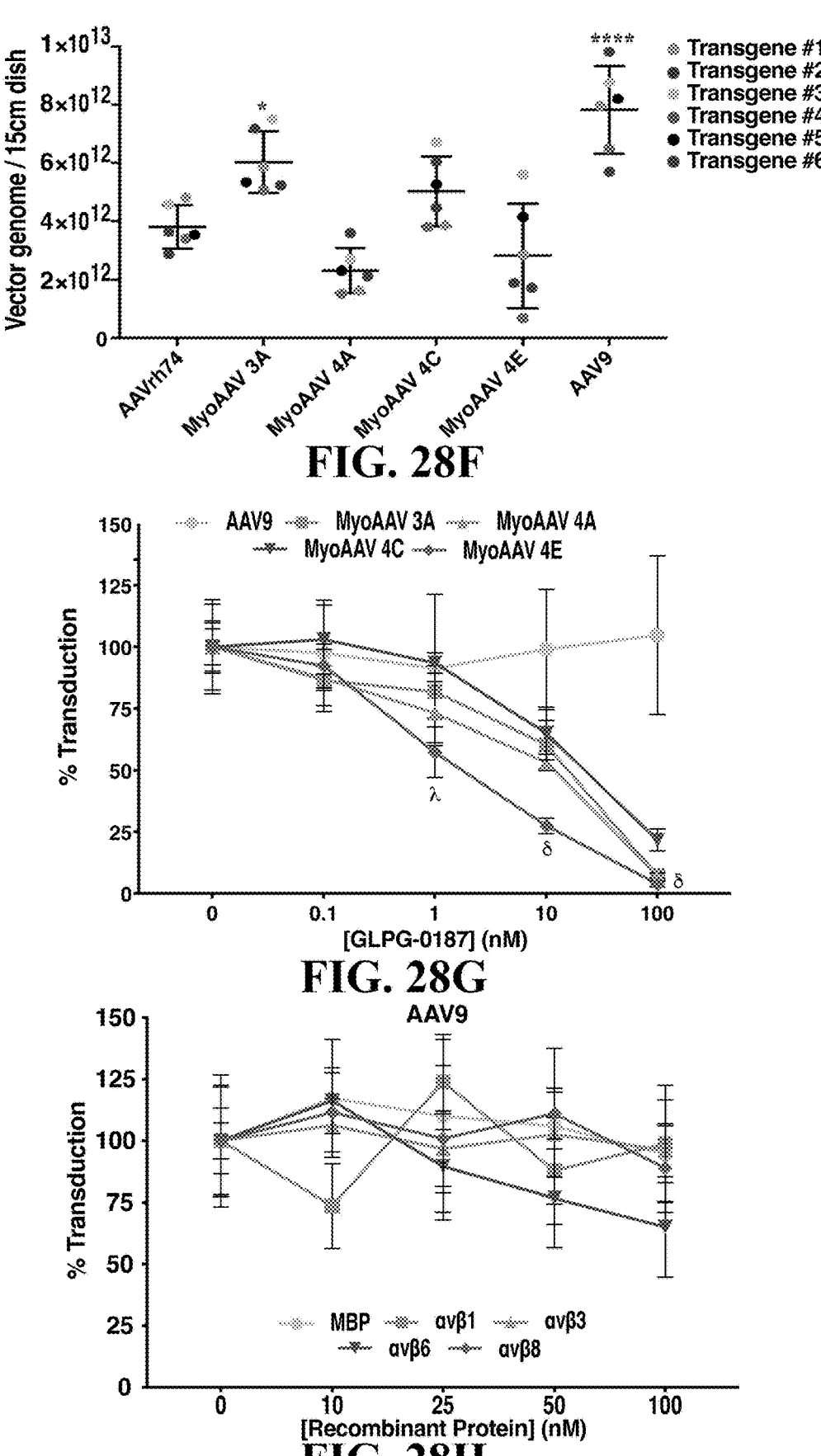
Figure 28I:
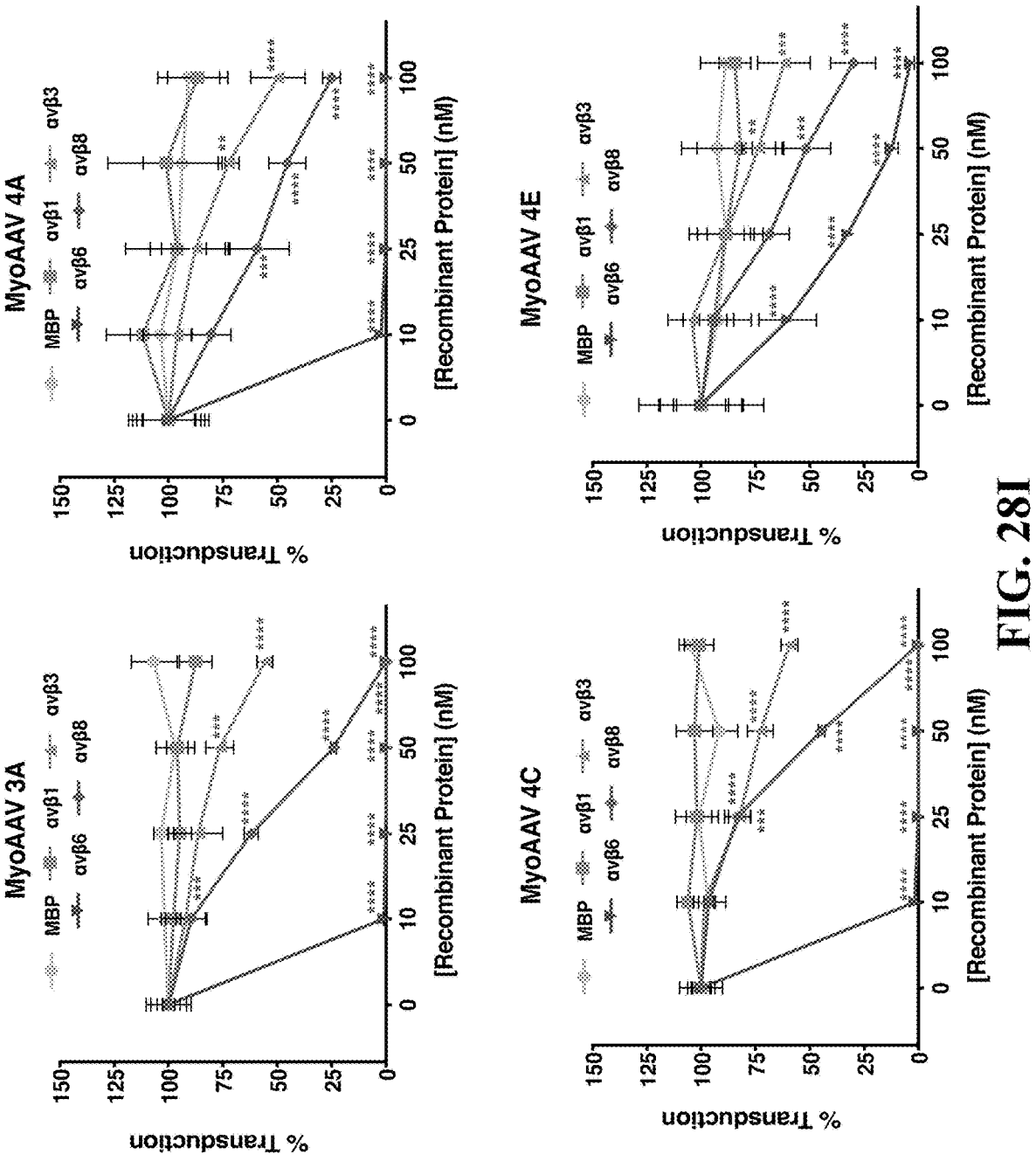
Figures 28J, 28K:
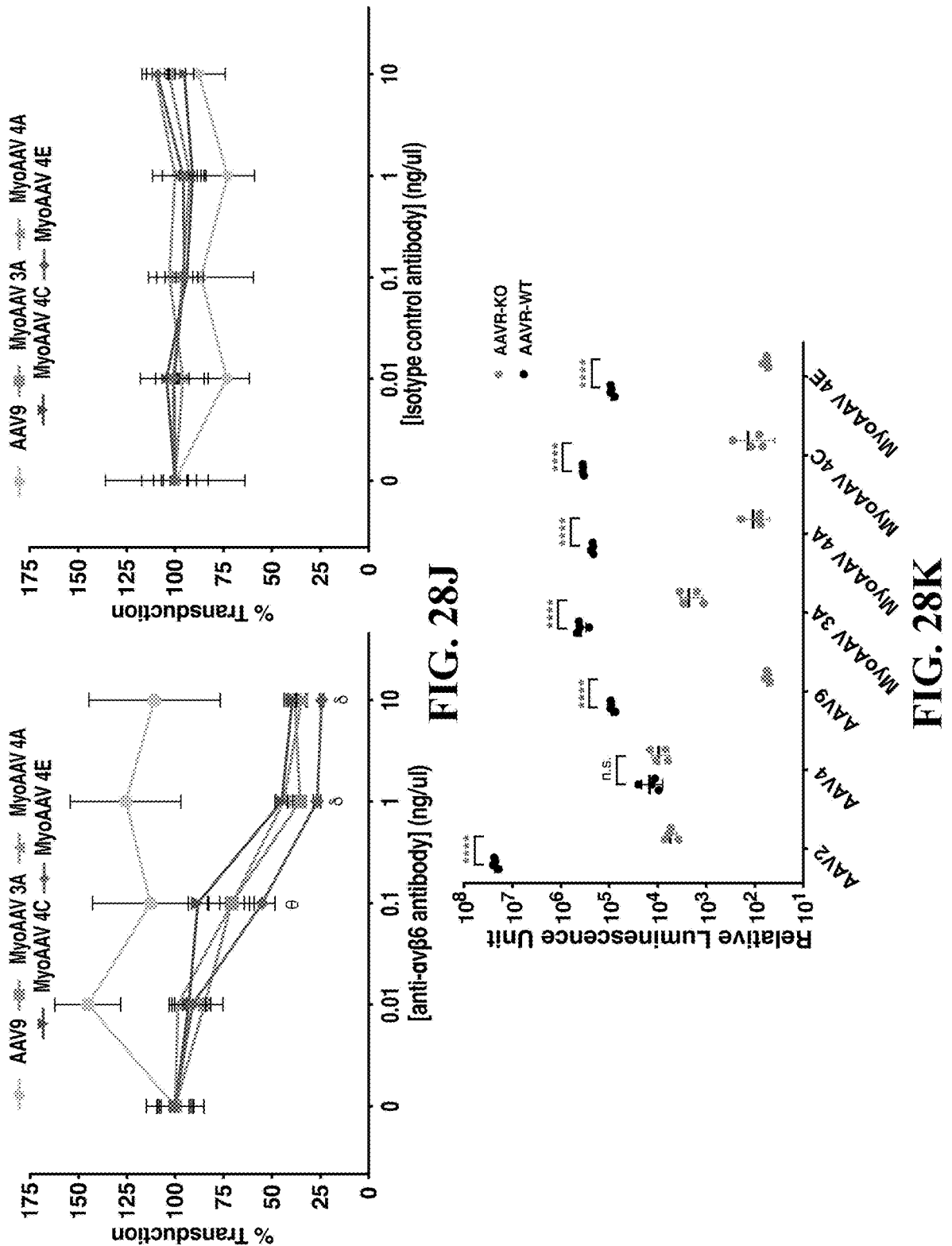

FIGS. 28A-28K—MyoAAV class of capsid variants evolved in NHPs transduce different muscles of Cynomolgus Macaques with high efficiency. FIGS. 28A-28B) Schematic of virus library design and sequence of the top hits identified from NHP muscles after two rounds of in vivo selections in macaques from capsid variants containing a random 7-mer insert (FIG. 28A) (SEQ ID NO: 13, 22-27), or from one round of in vivo selection in macaques using the top 120,000 variants identified from the first round of RGD-fixed selection in mice (FIG. 28B) (SEQ ID NO: 19, 28-32). FIG. 28C) Comparison of in vitro transduction between the 11 muscle-tropic capsid variants selected in mice in human primary myotubes from four different donors. Data are presented as individual data points with mean; **: P<0.01 (one-way ANOVA with Dunnett MCT with MyoAAV 1A as the control). FIG. 28D) Schematic of the barcoded human Frataxin transgene and the pool of capsid variants used for characterization of the top muscle-tropic variants in NHPs (SEQ ID NO: 28, 30, 32-33). FIG. 28E) Fold change mRNA expression over AAVrh74 in different skeletal muscles, heart, and liver of 3 Cynomolgus Macaques. mRNA expression quantified by deep sequencing of the barcodes associated with each capsid variant. Data are presented as mean±SD (n=3). *: P<0.05, : P<0.01, *: P<0.001, ****: P<0.0001 (one-way ANOVA with Dunnett's MCT with AAVrh74 as the control). FIG. 28F) Comparison of AAVrh74, MyoAAV 3A, MyoAAV 4A, MyoAAV 4C, and MyoAAV 4E, and AAV9 titers with α different transgenes. Data are presented as mean±SD (n=6). *: P<0.05; **: P<0.0001 (one-way ANOVA with Dunnett's MCT with AAVrh74 as the control). FIG. 28G) In vitro transduction efficiency in human primary myotubes treated with different concentrations of GLPG-0187 integrin αV antagonist and transduced with AAV9-, MyoAAV 3A-, MyoAAV 4A-, MyoAAV 4C-, or MyoAAV 4E-CK8-Nluc. Data are presented as mean±SD (n=5). P-value calculated with a one-way ANOVA with Dunnett's MCT with the 0 nM condition for each group set as the control.: P<0.0001 for MyoAAV 3A, MyoAAV 4A, MyoAAV 4C, and MyoAAV 4E: P<0.0001 for MyoAAV 4A and MyoAAV 4E. FIGS. 28H-28I) In vitro transduction efficiency in human primary myotubes transduced with AAV9-CK8-Nluc (FIG. 28H) or MyoAAV 3A-, MyoAAV 4A-, MyoAAV 4C-, or MyoAAV 4E-CK8-Nluc (FIG. 28I) incubated with different concentrations of αVb1, αVb3, αVb6, αVb8, or MBP recombinant proteins. Data are presented as mean±SD (n=5). : P<0.01, *: P<0.001, **: P<0.0001 (one-way ANOVA with Dunnett's MCT with the 0 nM recombinant protein condition in each group as the control). FIG. 28J) In vitro transduction efficiency in human primary myotubes treated with different concentrations of anti-αVb6 antibody or mouse isotype control and transduced with AAV9-, MyoAAV 3A-, MyoAAV 4A-MyoAAV 4C-, or MyoAAV 4E-CK8-Nluc. Data are presented as mean±SD (n=5). P<0.0001 for MyoAAV 3A, MyoAAV 4A, MyoAAV 4C, and MyoAAV 4E: P<0.0001 for MyoAAV 3 A, MyoAAV 4A, and MyoAAV 4E (one-way ANOVA with Dunnett's MCT with the 0 nM condition for each group as the control). FIG. 28K) Comparison of in vitro transduction between HEK293FT and HEK293FT AAVR KO cells transduced with AAV2-, AAV4-, AAV9-, MyoAAV 3A-, MyoAAV 4A-, MyoAAV 4C-, or MyoAAV 4E-CMV-Nluc. Data are presented as mean±SD (n=4): P<0.0001 (Student t test on log transformed data).

Figures 29A, 29B, 29C, 29D:
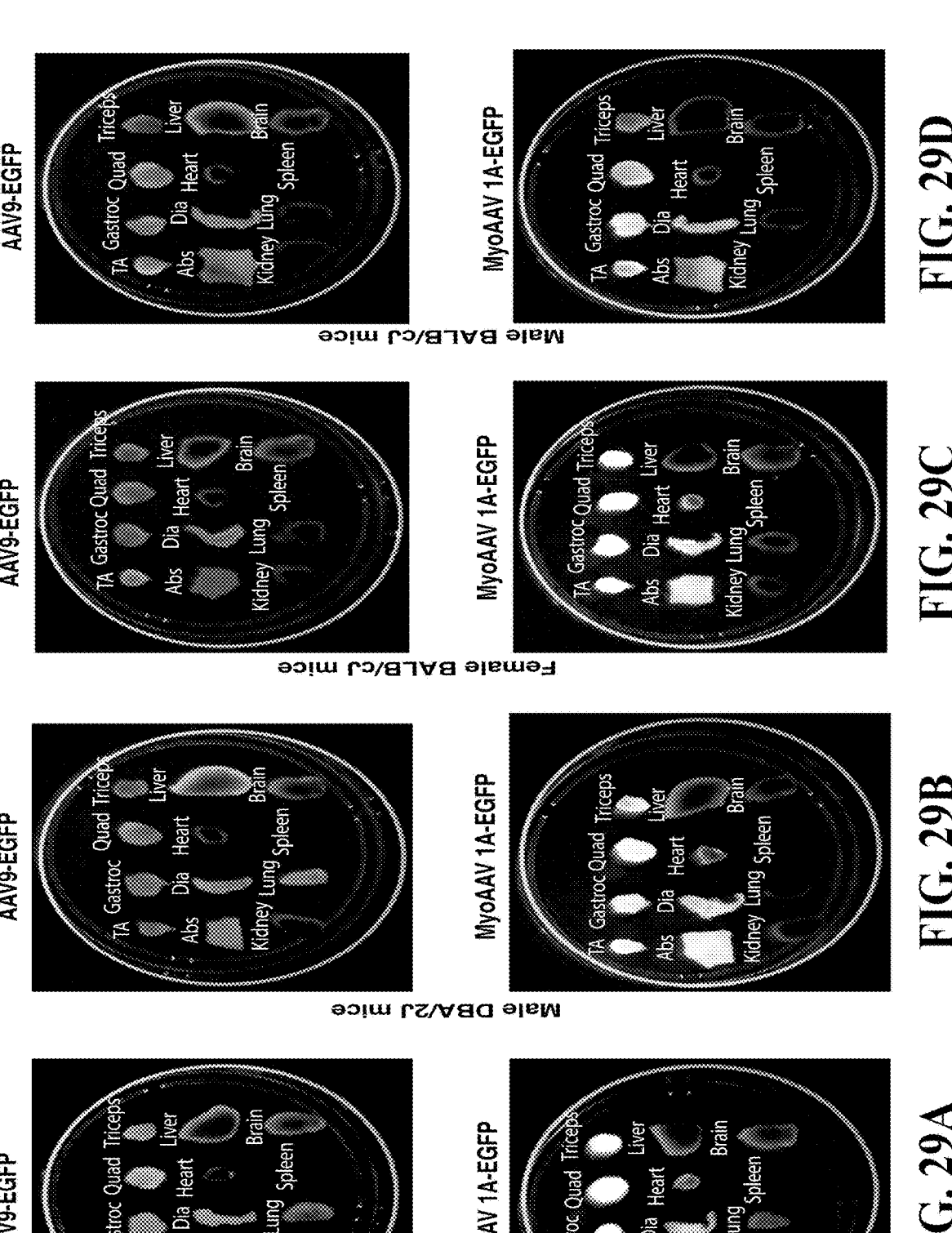
Figure 29E:
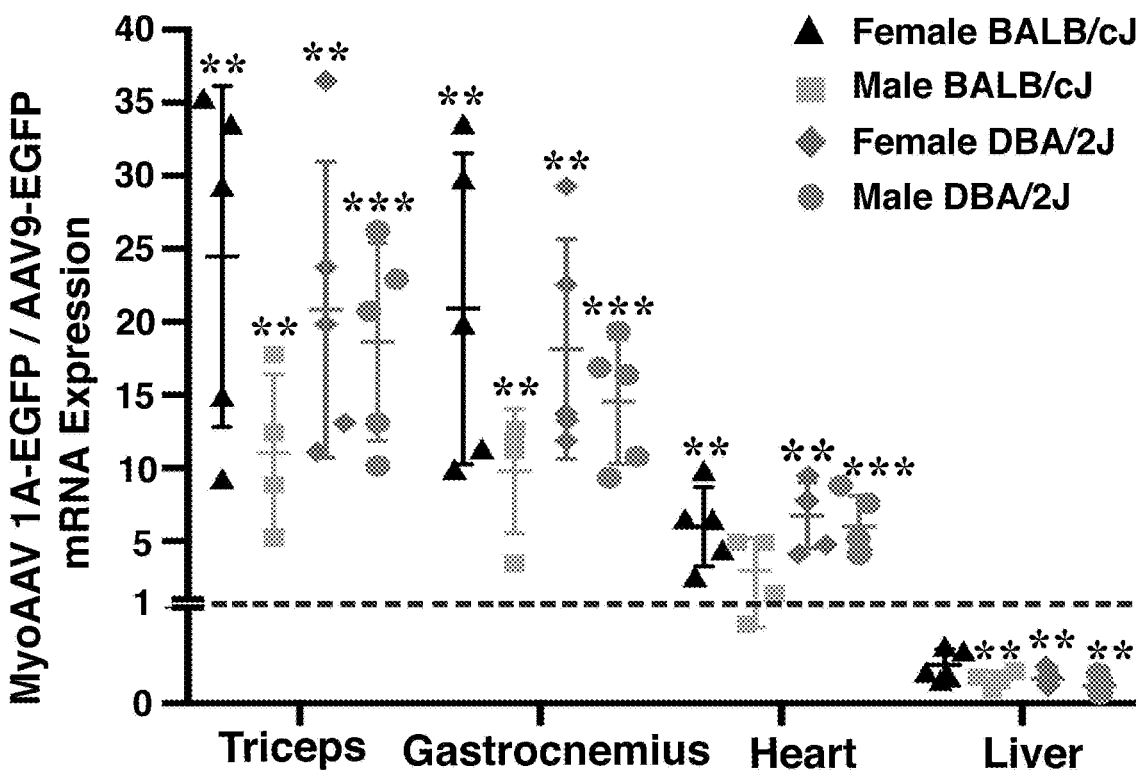
Figure 29F:
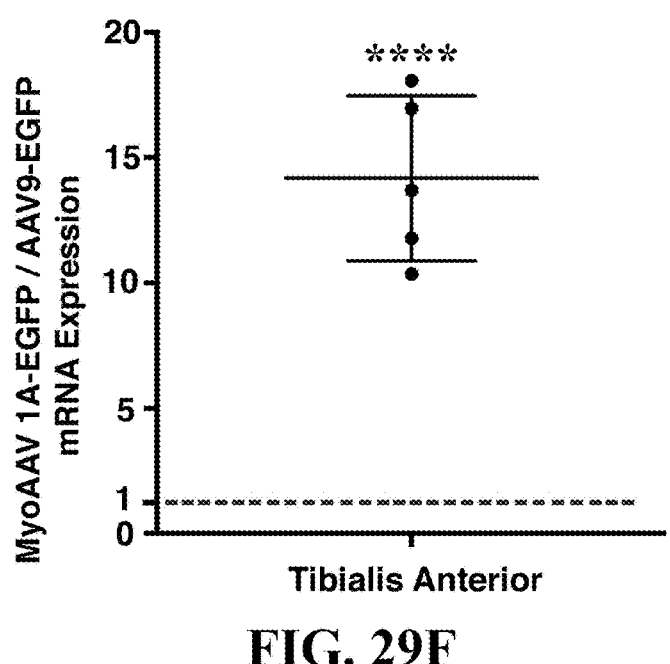
Figure 29G:
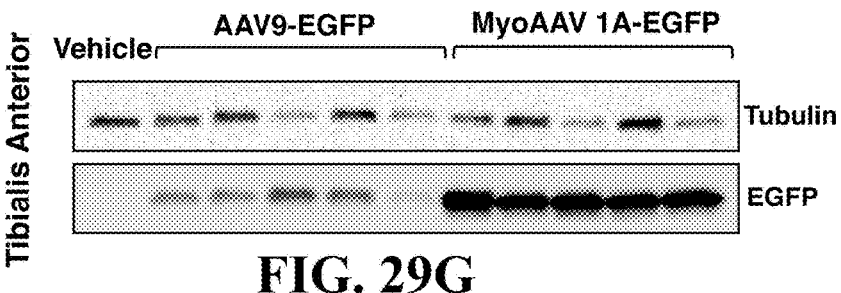
Figure 29H:
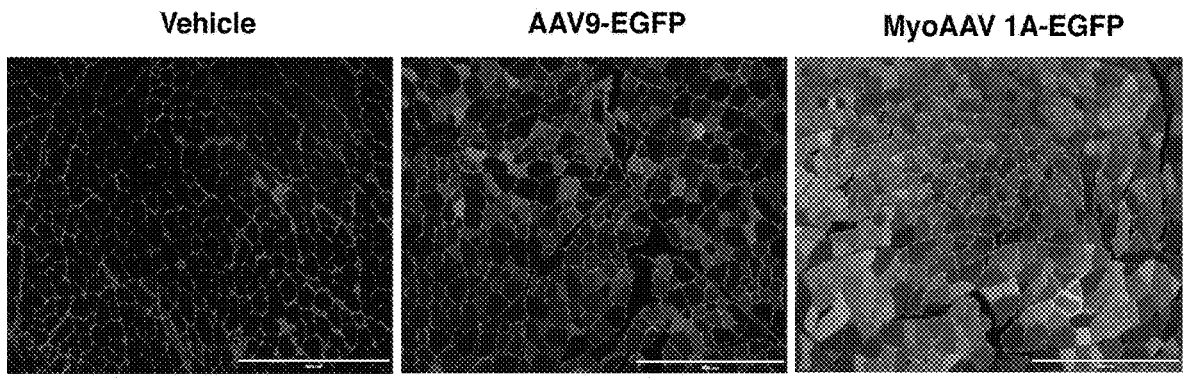
Figure 29M:
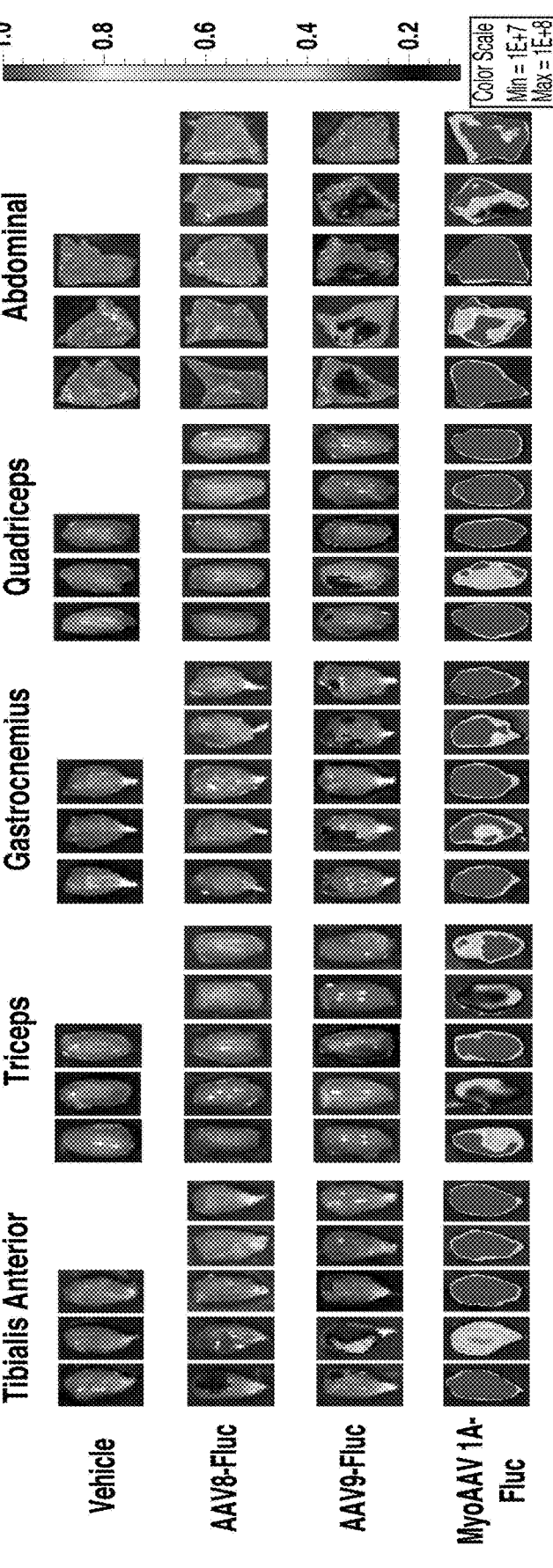
Figure 29N:
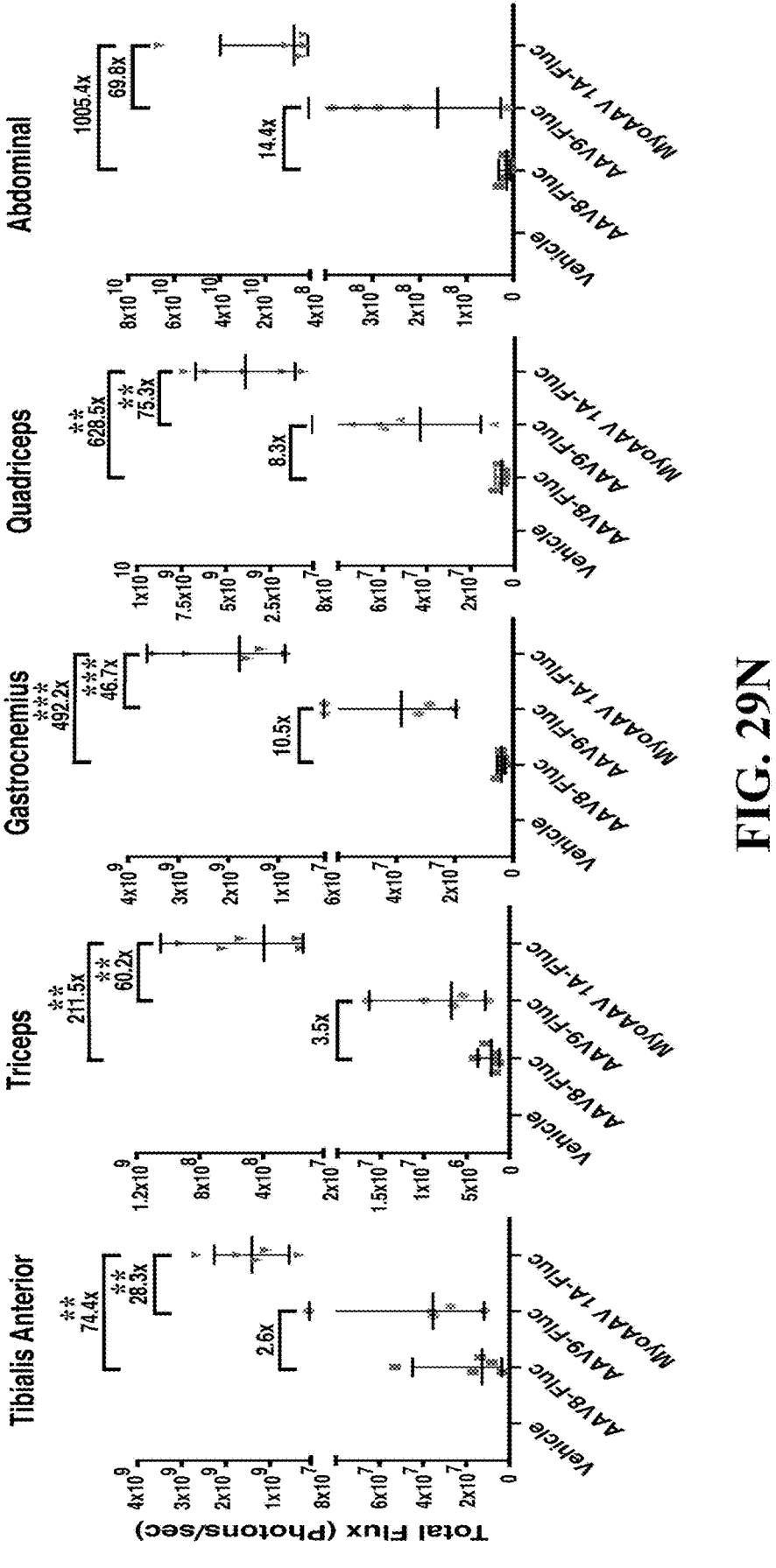
Figure 29O:
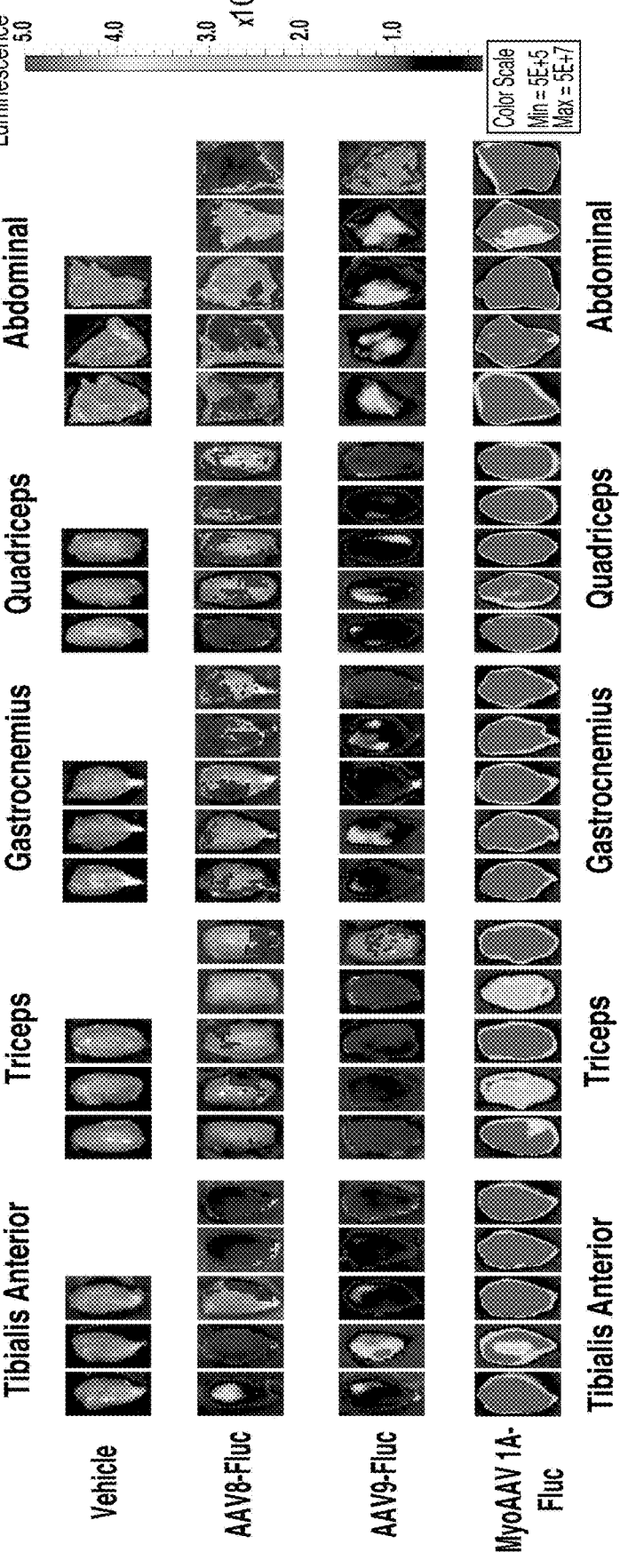

FIGS. 29A-29O—MyoAAV 1A effectively transduces different skeletal muscles after systemic administration in mice from DBA/2J and BALB/cJ backgrounds, and is highly potent in muscle transduction after intramuscular delivery. FIGS. 29A-29D) Different tissues of female DBA/ 2J (FIG. 29A), male DBA/2J (FIG. 29B), female BALB/cJ (FIG. 29C), and male BALB/cJ (FIG. 29D) mice systemically injected with 1E+12 vg of AAV9-CMV-EGFP (top) or MyoAAV 1A-CMV-EGFP (bottom) illuminated by blue light. FIG. 29E) Quantification of fold difference in EGFP mRNA expression in Triceps, Gastrocnemius, Heart, and Liver of male and female DBA/2J and BALB/cJ mice systemically injected with 1E+12 vg of AAV9- or MyoAAV 1A-CMV-EGFP. Dashed grey line indicates relative expression from AAV9-CMV-EGFP. Data are presented as mean±SD (n=4-5); : P<0.01, *: P<0.001 (Student t test between AAV9 and MyoAAV 1A injected mice for each group). FIG. 29F) Quantification of fold difference in EGFP mRNA expression in TA of C57BL/6J mice intramuscularly injected with 2E+10 vg of AAV9- or MyoAAV 1A-CMV-EGFP. Dashed grey line indicates relative expression from AAV9-CMV-EGFP. Data are presented as mean±SD (n=5); **: P<0.0001 (Student t test). FIG. 29G) Western blots detecting EGFP and Tubulin in TA muscles of C57BL/6J mice injected intramuscularly with vehicle, or 2E+10 vg of AAV9- or MyoAAV 1A-CMV-EGFP. FIG. 29H) Immuno-fluorescence images of the TA from C57BL/6J mice intra-muscularly injected with vehicle, or 2E+10 vg of AAV9- or MyoAAV 1A-CMV-EGFP. Greyscale: EGFP, Red: laminin, Blue: Hoechst. Scale bar in cross sections: 400 μm. FIGS. 29I-29J) Quantification of ALT (FIG. 29I) and AST (FIG. 29J) enzyme levels in serums of C57BL/6J mice before injection, as well as 14 and 28 days after systemic injection of vehicle, or 1E+12 vg AAV9- or MyoAAV 1A-CMV-EGFP. Data are presented as mean±SD (n=5). P-value calculated by two-way ANOVA with Tukey's MCT. Signifi-cance threshold: P<0.05. Difference between any two groups at each time point is not significant. FIGS. 29K-29L) Inhi-bition of AAV9- or MyoAAV 1A-CMV-Nluc transduction in HEK293 cells by serum from mice injected with AAV9-CMV-EGFP (FIG. 29K) or MyoAAV 1A-CMV EGFP (FIG. 29L); Data are presented as mean±SD (n=5); : P<0.0001 (two-way ANOVA with Sidak's MCT). FIG. 29M) Whole organ luminescence images of TA, Triceps, Gastrocnemius, Quadriceps, and Abdominal muscles from mice injected with 4E+11 vg of AAV8-, AAV9-, or Myo-AAV 1A-CMV-Fluc harvested 4 months after injection. Grey scale: 1E+7-1E+8. FIG. 29N) Quantification of total luminescence from different muscles of animals injected with AAV8-, AAV9-, or MyoAAV 1A-CMV-Fluc harvested 120 days after injection. Data are presented as mean±SD (n=5); : P<0.01, *: P<0.001 (one-way ANOVA with Tukey's MCT). FIG. 29O) Whole organ luminescence images of TA, Triceps, Gastrocnemius, Quadriceps, and Abdominal muscles from mice injected with 4E+11 vg of AAV8-, AAV9-, or MyoAAV 1A-CMV-Fluc harvested 4 months after injection. This image shows the luminescence signal from the same mice shown in FIG. 17C** with a greyscale (5E+5-5E+7) to enable detection of the signal in muscles of mice injected with AAV8- and AAV9-CMV-Fluc.

Figure 30A:
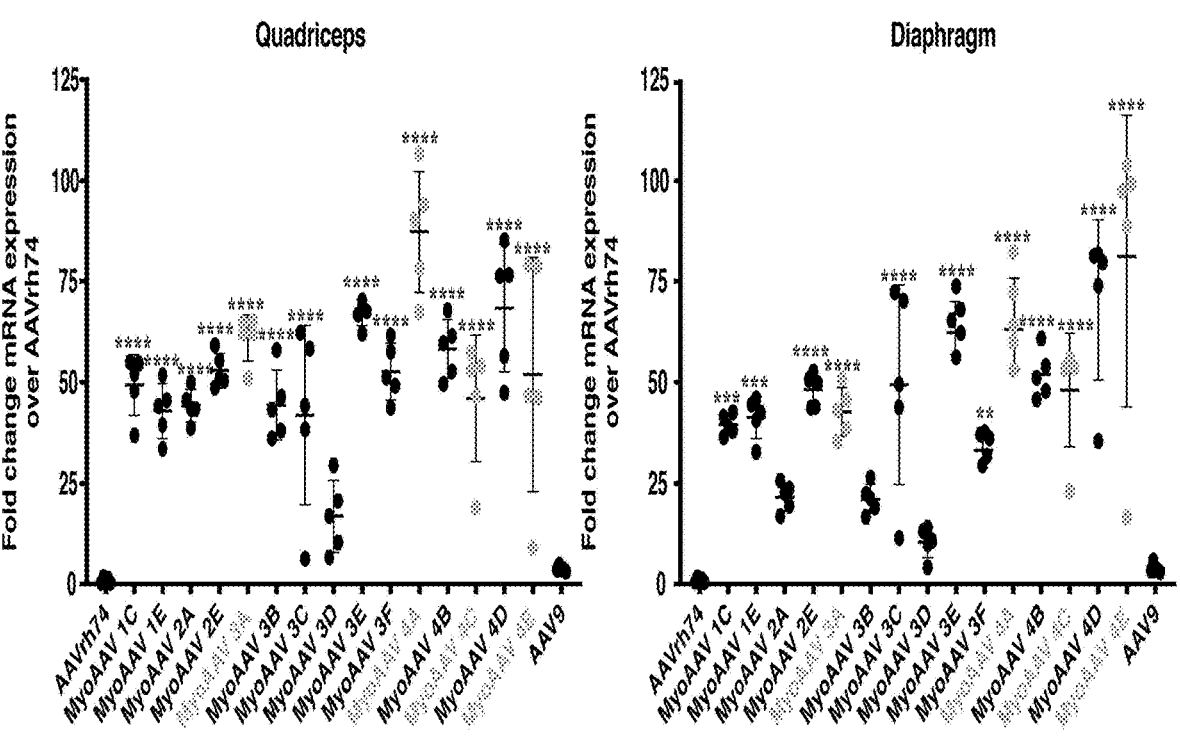
Figure 30A:
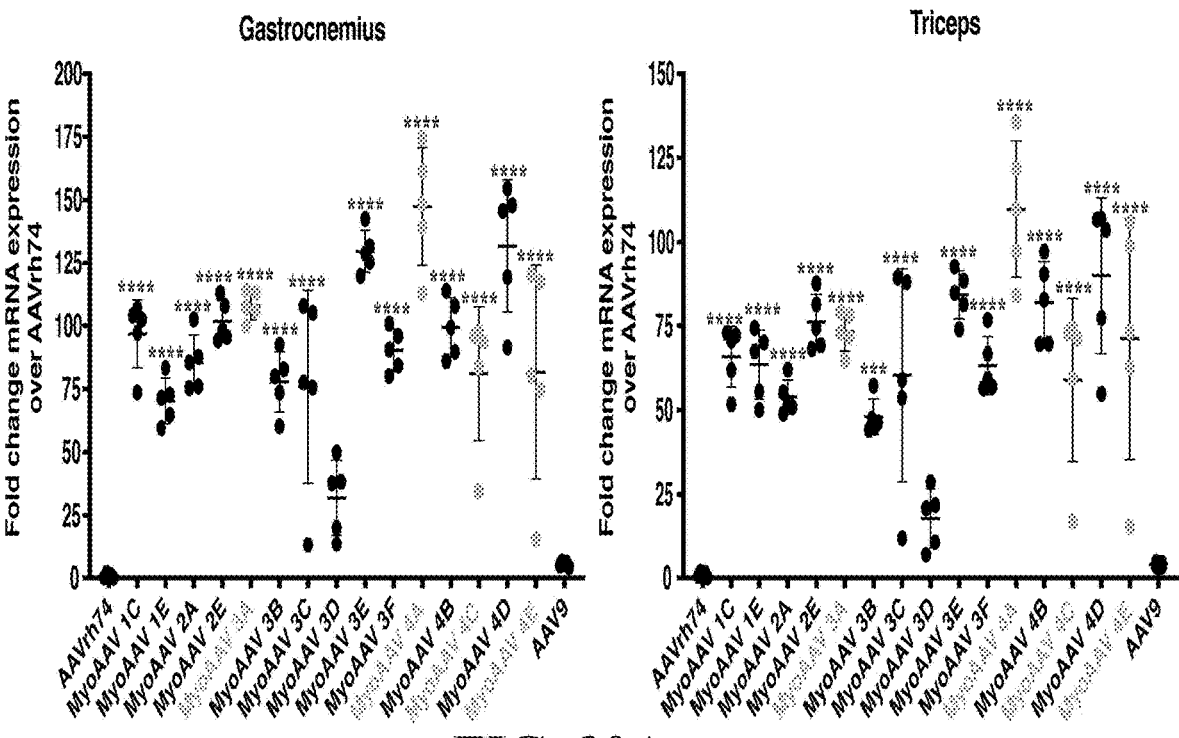
Figure 30A:
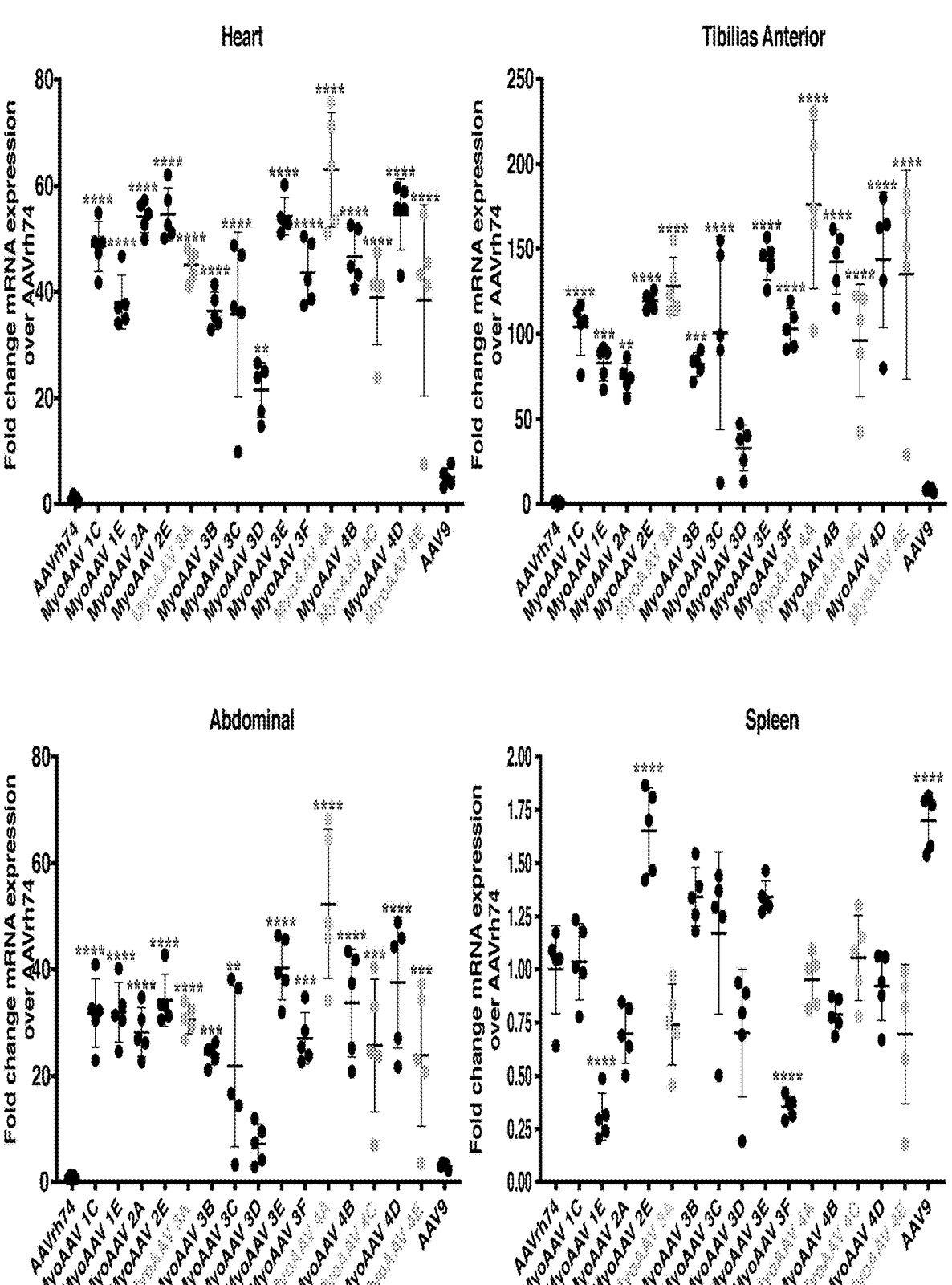
Figure 30A:
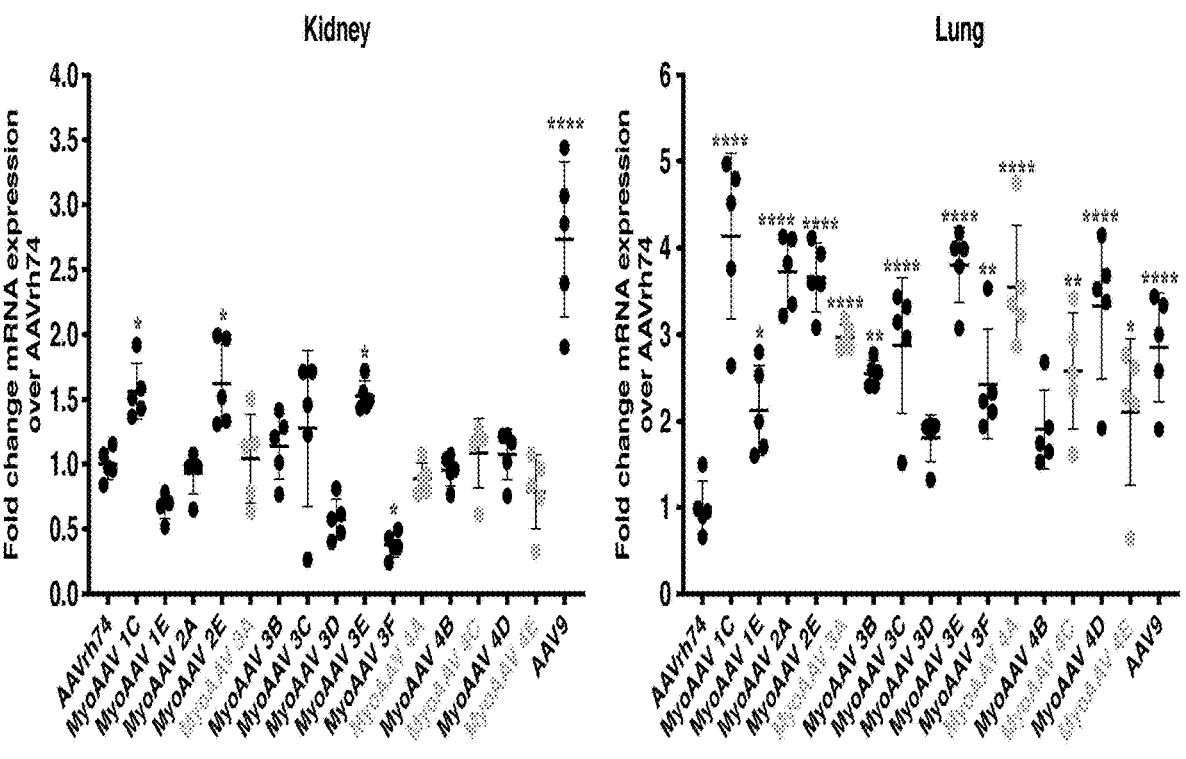
Figure 30A:
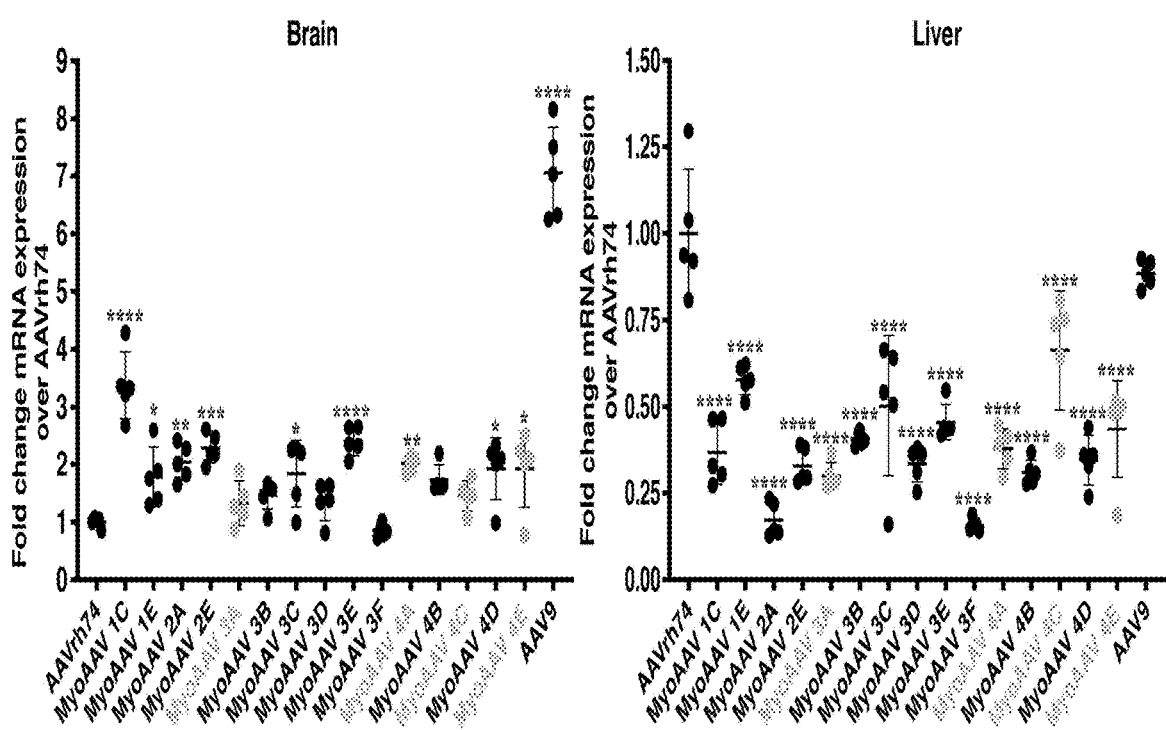
Figure 30B:
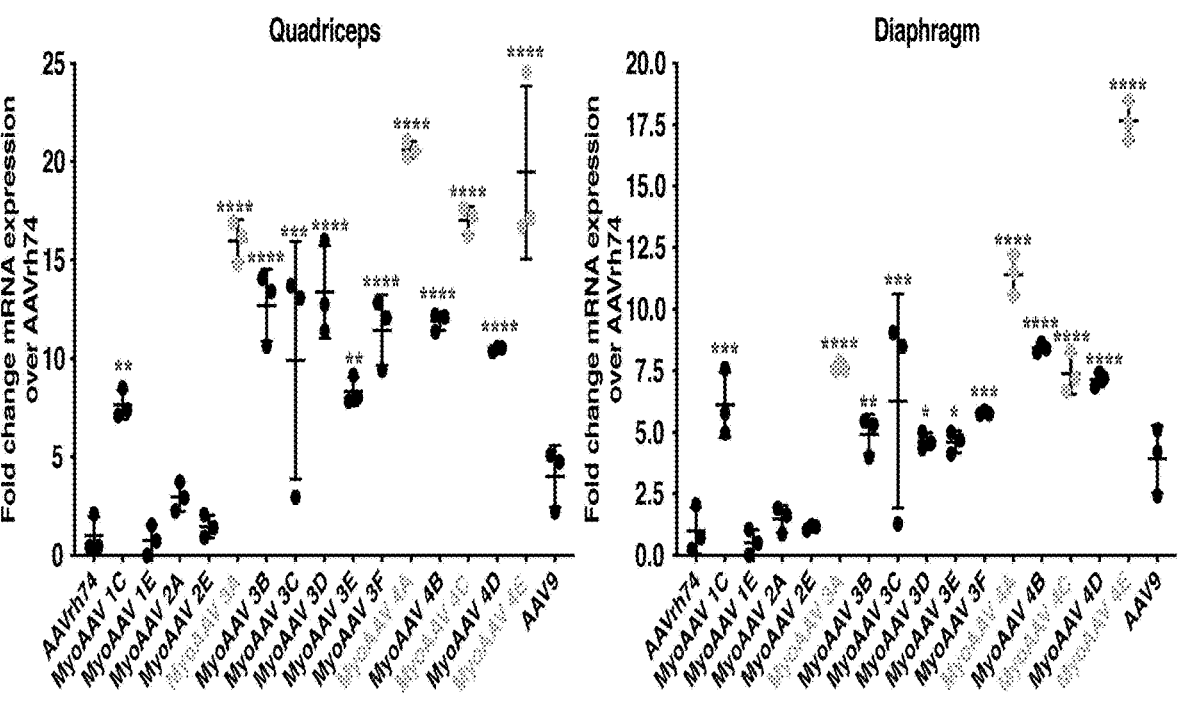
Figure 30B:
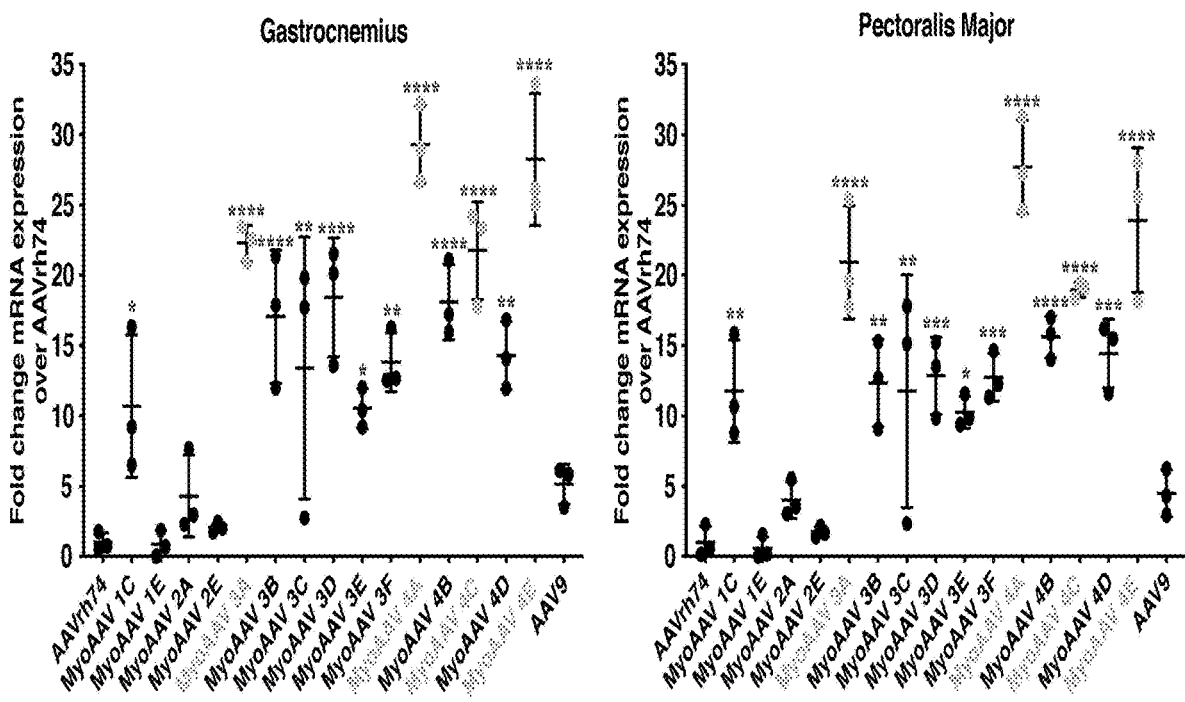
Figure 30B:
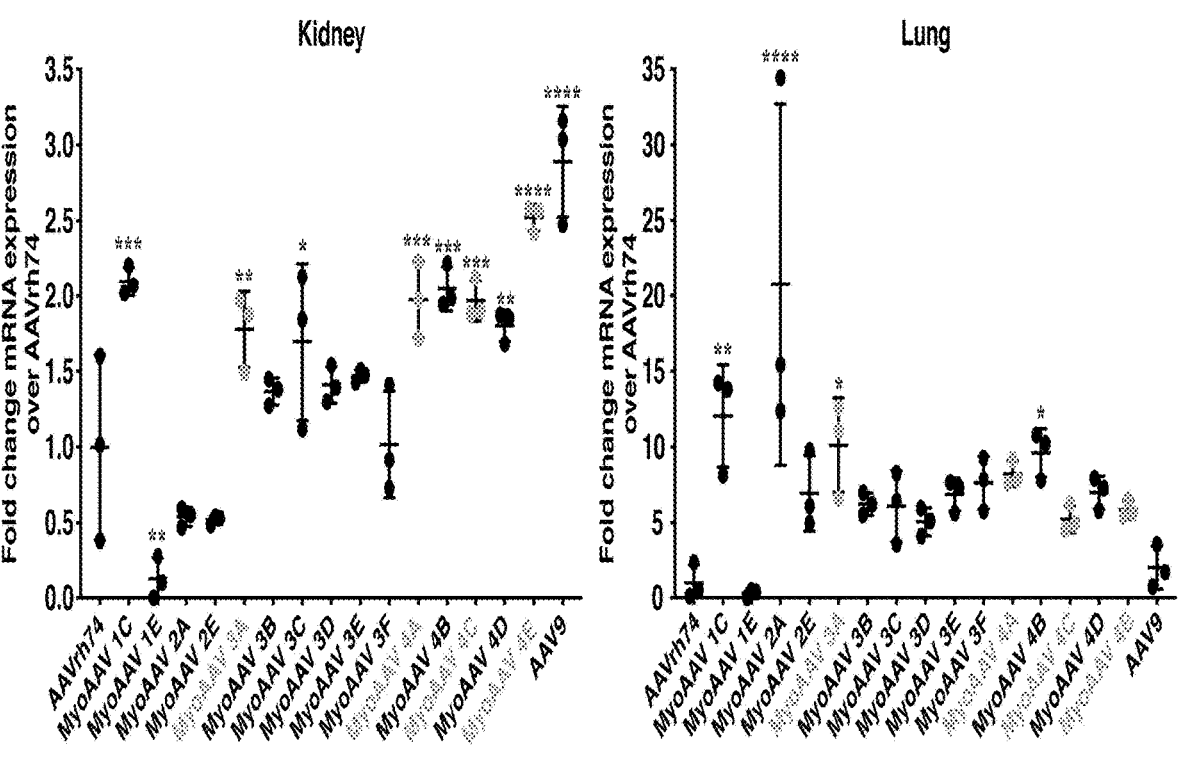
Figure 30B:
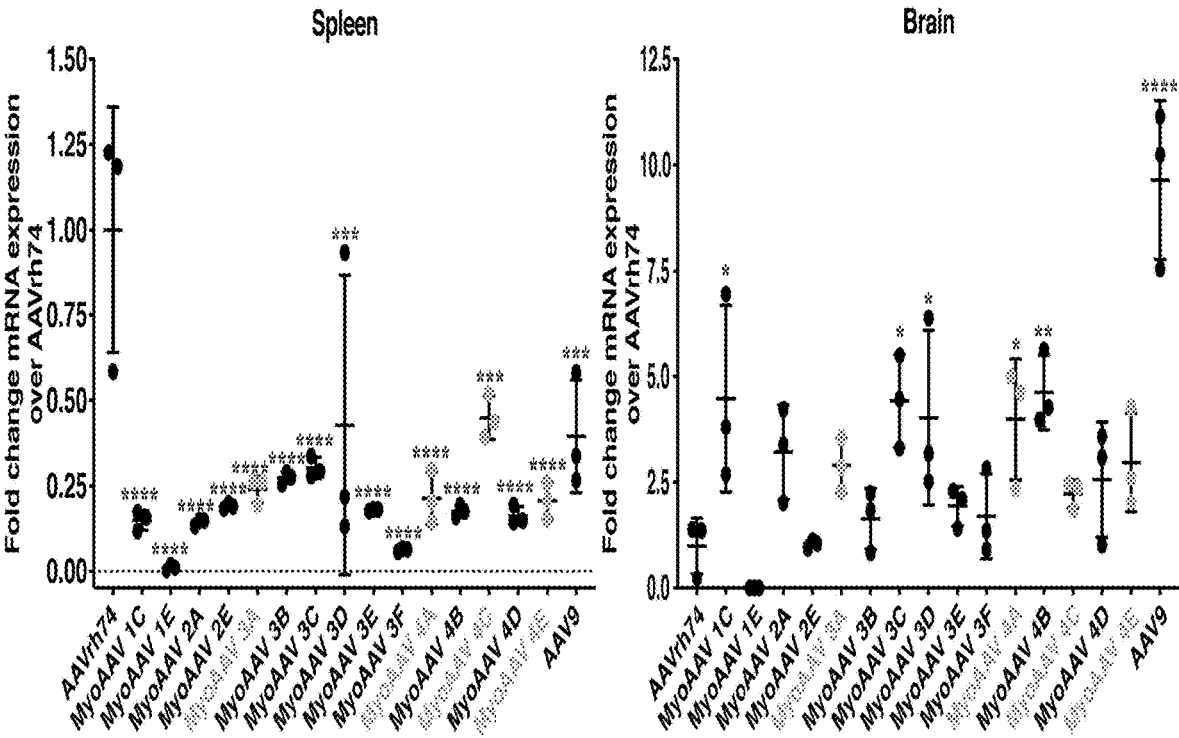
Figure 30B:
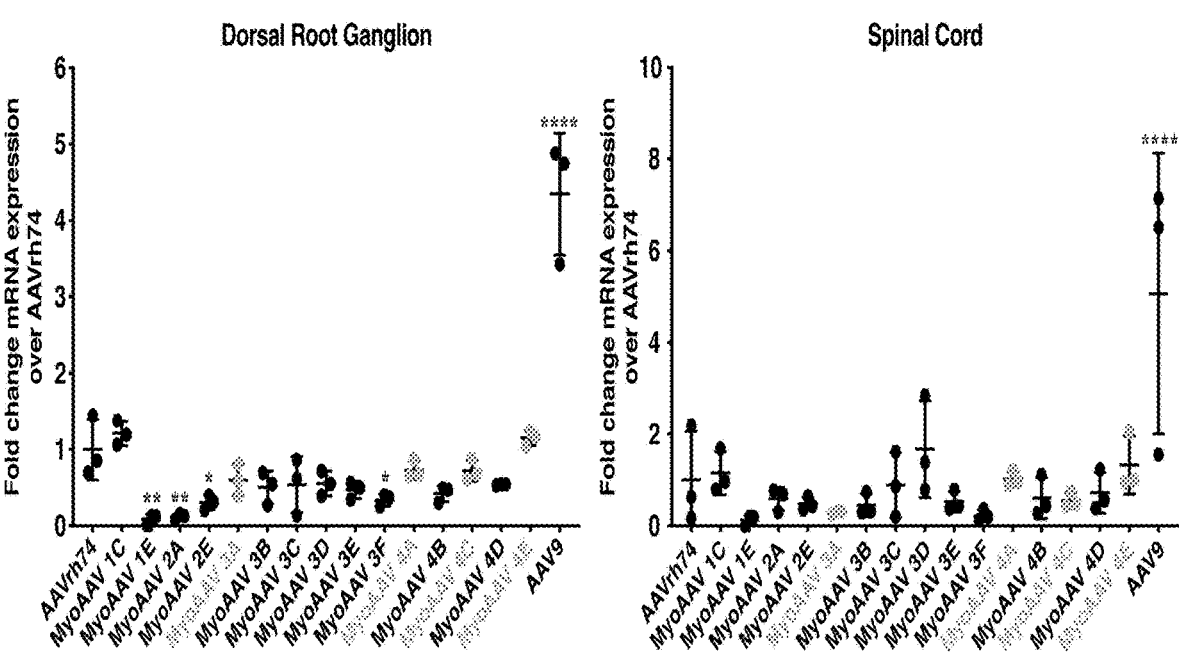
Figure 30C:
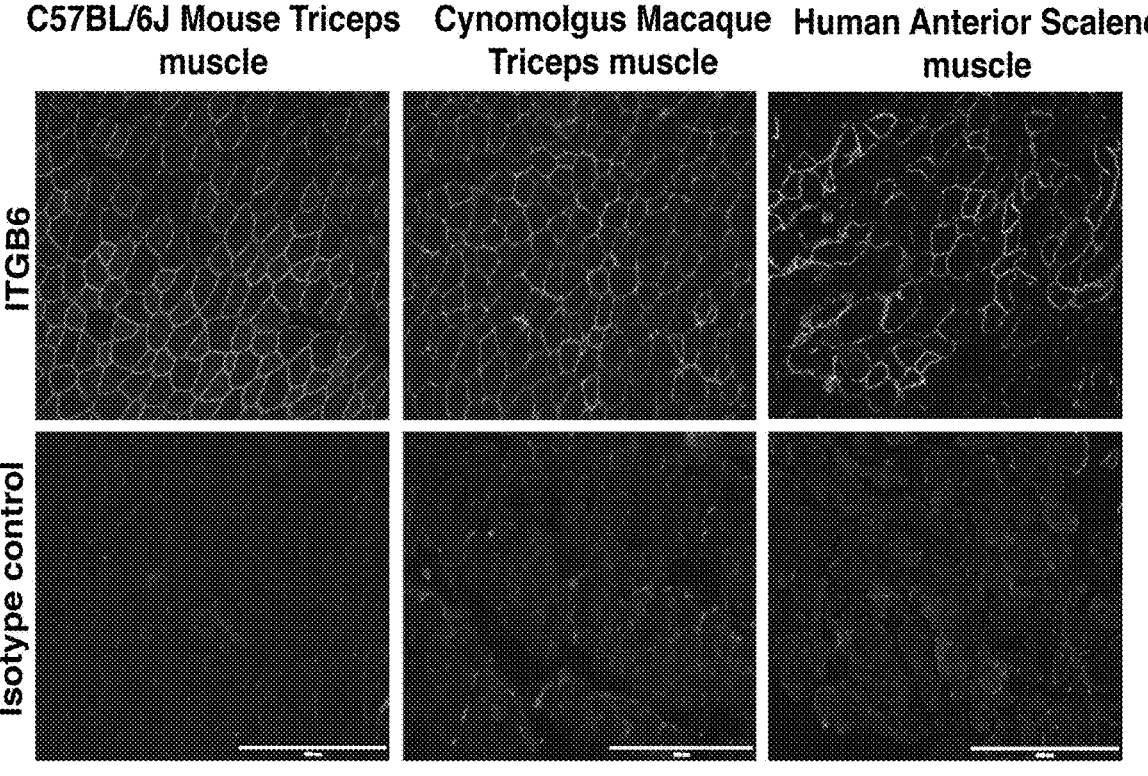

FIGS. 30A-30C—Characterization of muscle-tropic capsid variants evolved in Cynomolgus Macaque. FIGS. 30A-30B) Fold change mRNA expression over AAVrh74 in different tissues of C57BL/6J mice (FIG. 30A) or Cynomol-gus Macaques (FIG. 30B). mRNA expression was quantified by deep sequencing of the barcodes associated with each capsid variant. Data are presented as mean±SD (n=5 for mice and n=3 for macaques). *: P<0.05, : P<0.01, *: P<0.001, **: P<0.0001 (one-way ANOVA with Dunnett's MCT with AAVrh74 as the control). FIG. 30C**) Represen-tative immunofluorescence images for (ITGB6) integrin beta-6 (greyscale) and an isotype control (greyscale) in C57BL/6J Mouse Triceps muscle, Cynomolgus Macaque Triceps muscle, and Human Anterior Scalene muscle. Scale bar: 400 μm.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly under-stood by one of ordinary skill in the art to which this disclosure pertains. Definitions of common terms and tech-niques in molecular biology may be found in Molecular Cloning: A Laboratory Manual, $2^{nd}$ edition (1989) (Sam-brook, Fritsch, and Maniatis); Molecular Cloning: A Labo-ratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Fresh-ney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Rob-ert A. Meyers (ed.), Molecular Biology and Biotechnology: a Comprehensive Desk Reference, published by VCH Pub-lishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011)

As used herein, the singular forms "a" "an", and "the" include both singular and plural referents unless the context clearly dictates otherwise.

The term "optional" or "optionally" means that the sub-sequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints. It will be further understood that the endpoints of each of the ranges are significant both in relation to the other endpoint, and inde-pendently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further embodiment. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range. Where a range is expressed, a further embodiment includes from the one particular value and/or to the other particular value.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide muscle-specific targeting moieties that can be coupled to or otherwise associated with a cargo. Embodiments disclosed herein provide polypeptides and particles that can incorporate one or more of the muscle-specific targeting moieties. The polypeptides and/or particles can be coupled to, attached to, encapsulate, or otherwise incorporate a cargo, thereby associating the cargo with the targeting moiety(ies).

Embodiments disclosed herein provide muscle-specific targeting moieties that can contain one or more of an n-mer motif as further described herein. In some embodiments, the n-mer motif is an enhanced myoAAV motif. In some embodiments, the n-mer motif can confer muscle-specificity of the targeting moiety.

In some embodiments, the n-mer motif does not contain R-G-D as the first three amino acids of the motif. In some embodiments, the n-mer motif is a second generation RGD motif. In some embodiments, the n-mer motif containing a second generation RGD motif has greater muscle specificity, targeting, and/or efficacy than an n-mer motif not containing a second generation RGD motif.

Embodiments disclosed herein provide engineered adeno-associated virus (AAV) capsids that can be engineered to confer cell-specific and/or species-specific tropism to an engineered AAV particle.

Embodiments disclosed herein also provide methods of generating the rAAVs having engineered capsids that can involve systematically directing the generation of diverse libraries of variants of modified surface structures, such as variant capsid proteins. Embodiments of the method of generating rAAVs having engineered capsids can also include stringent selection of capsid variants capable of targeting a specific cell, tissue, and/or organ type. Embodiments of the method of generating rAAVs having engineered capsids can include stringent selection of capsid variants capable of efficient and/or homogenous transduction in at least two or more species.

Embodiments disclosed herein provide vectors and systems thereof capable of producing an engineered AAV described herein.

Embodiments disclosed herein provide cells that can be capable of producing the engineered AAV particles described herein. In some embodiments, the cells include one or more vectors or system thereof described herein.

Embodiments disclosed herein provide engineered AAVs that can include an engineered capsid described herein. In some embodiments, the engineered AAV can include a cargo polynucleotide to be delivered to a cell. In some embodiments, the cargo polynucleotide is a gene modification polynucleotide.

Embodiments disclosed herein provide formulations that can contain an engineered AAV vector or system thereof, an engineered AAV capsid, engineered AAV particles including an engineered AAV capsid described herein, and/or an engineered cell described herein that contains an engineered AAV capsid, and/or an engineered AAV vector or system thereof. In some embodiments, the formulation can also include a pharmaceutically acceptable carrier. The formulations described herein can be delivered to a subject in need thereof or a cell.

Embodiments disclosed herein also provide kits that contain one or more of the one or more of the polypeptides, polynucleotides, vectors, engineered AAV capsids, engineered AAV particles, cells, or other components described herein and combinations thereof and pharmaceutical formulations described herein. In embodiments, one or more of the polypeptides, polynucleotides, vectors, engineered AAV capsids, engineered AAV particles cells, and combinations thereof described herein can be presented as a combination kit Embodiments disclosed herein provide methods of using the engineered AAVs having a cell-specific tropism described herein to deliver, for example, a therapeutic poly-nucleotide to a cell. In this way, the engineered AAVs described herein can be used to treat and/or prevent a disease in a subject in need thereof. Embodiments disclosed herein also provide methods of delivering the engineered AAV capsids, engineered AAV virus particles, engineered AAV vectors or systems thereof and/or formulations thereof to a cell. Also provided herein are methods of treating a subject in need thereof by delivering an engineered AAV particle, engineered AAV capsid, engineered AAV capsid vector or system thereof, an engineered cell, and/or formulation thereof to the subject.

Additional features and advantages of the embodiments engineered AAVs and methods of making and using the engineered AAVs are further described herein.

Muscle-Specific Targeting Moieties and Compositions Thereof.

Described herein are targeting moieties that can be capable of specifically targeting, binding, associating with, or otherwise interact specifically with a muscle cell. In some embodiments, the targeting moiety can be or include an n-mer motif.

In some embodiments, then-mer motif contains a second generation RGD motif. The term "second generation RGD motif" refers to n-mer motifs that include the presence of the amino acid motif R-G-D, and has the general formula consists of $X_m RGDX_n$, wherein $X_m$ and $X_n$ are each independently selected from any amino acid, wherein n is 1, 2, 3, 4, 5, 6, 7, 8, or 9, and wherein m is 1-4. Exemplary n-mer motifs and methods of generating and identifying suitable n-mer motifs capable of muscle targeting are described in greater detail elsewhere herein.

In some embodiments, the targeting moiety can include more than one n-mer motifs. In some embodiments, the targeting moiety can include 1, 2, 3, 4, 5, 6, 7, 8, 9, 10 or more n-mer motifs. In some embodiments, all the n-motifs included in the targeting moiety can be the same. In some embodiments where more than one n-mer motif is included, at least two of the n-mer motifs are different from each other. In some embodiments where more than one n-mer motif is included, all the n-mer motifs are different from each other. In some embodiments, each n-mer motif included in the targeting moiety can be any one of those set forth in any of Tables 2-3, FIG. 14F or any of those provided in the Figures and Working Examples set forth elsewhere herein. In some embodiments, an n-mer motif containing a second generation RGD motif confers greater muscle specificity, targeting, and/or efficacy than an n-mer motif not containing a second generation RGD motif. In some embodiments, an n-mer motif containing a second generation RGD motif confers greater muscle specificity, targeting, and/or efficacy than an n-mer motif having R-G-D as the first three amino acids of the motif.

In some embodiments, the first 1, 2, 3, or 4 amino acids of an n-mer motif can replace 1, 2, 3, or 4 amino acids of a polypeptide into which it is inserted and preceding the insertion site. In some embodiments, the amino acids of the n-mer motif that replace 1 or more amino acids of the polypeptide into which the n-mer motif is inserted come before or immediately before an "RGD" in an n-mer motif. For example, in one or more of the 10-mer inserts shown in e.g., Tables 2-3, the first three amino acids shown can replace 1-3 amino acids into a polypeptide to which they may be inserted. Using an AAV as another non-limiting example, one or more of the n-mer motifs can be inserted into e.g., and AAV9 capsid prolylpeptide between amino acids 588 and 589 and the insert can replace amino acids 586, 587, and 588 such that the amino acid immediately preceding the n-mer motif after insertion is residue 585. It will be appreciated that this principle can apply in any other insertion context and is not necessarily limited to insertion between residues 588 and 589 of an AAV9 capsid or equivalent position in another AAV capsid. It will further be appreciated that in some embodiments, no amino acids in the polypeptide into which the n-mer motif is inserted are replaced by the n-mer motif.

The muscle-specific targeting moiety can be coupled to or otherwise associated with a cargo. In some embodiments, one or more muscle-specific targeting moieties described herein is directly attached to the cargo. In some embodiments, one or more muscle-specific targeting moieties described herein is indirectly coupled to the cargo, such as via a linker molecule. In some embodiments, one or more one or more muscle-specific targeting moieties described herein is coupled to associated with a polypeptide or other particle that is coupled to, attached to, encapsulates, and/or contains a cargo.

Exemplary particles include, without limitation, viral particles (e.g., viral capsids, which is inclusive of bacteriophage capsids), polysomes, liposomes, nanoparticles, microparticles, exosomes, micelles, and the like. The term "nanoparticle" as used herein includes a nanoscale deposit of a homogenous or heterogeneous material. Nanoparticles may be regular or irregular in shape and may be formed from a plurality of co-deposited particles that form a composite nanoscale particle. Nanoparticles may be generally spherical in shape or have a composite shape formed from a plurality of co-deposited generally spherical particles. Exemplary shapes for the nanoparticles include, but are not limited to, spherical, rod, elliptical, cylindrical, disc, and the like. In some embodiments, the nanoparticles have a substantially spherical shape.

As used herein, the term "specific" when used in relation to described an interaction between two moieties, refers to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

In some embodiments, in addition to the n-mer motif(s) the targeting moiety can include a polypeptide, a polynucleotide, a lipid, a polymer, a sugar, or a combination thereof.

In some embodiments, the targeting moiety is incorporated into a viral protein, such as a capsid protein, including but not limited to lentiviral, adenoviral, AAV, bacteriophage, retroviral proteins. In some embodiments, n-mer motif is located between two amino acids of the viral protein such that the n-mer motif is external (i.e., is presented on the surface of) to a viral capsid.

In some embodiments, the composition containing one or more of the muscle-specific targeting moieties described herein has increased muscle cell potency, muscle cell specificity, reduced immunogenicity, or any combination thereof. As used herein the terms "muscle-specific", "muscle cell specificity", "muscle cell potency" and the like, refer to the increased specificity, selectivity, or potency, of the muscle-specific targeting moieties and compositions incorporating said muscle-specific targeting moieties of the present invention for muscle cells relative to non-muscle cells. In some embodiments, the cell specificity, or selectivity, or potency, or a combination thereof of a muscle-specific targeting moiety or composition incorporating a muscle-specific targeting moiety described herein is at least 2 to at least 500 times more specific, selective, and/or potent for/in a muscle cell relative to a non-muscle cell. In some embodiments, the specificity, or selectivity, or potency of/in a muscle-specific targeting moiety described herein is at least 2, to/or 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 times more specific or selective for a muscle cell relative to a non-muscle cell.

Stated in the alternative, the in some embodiments, the muscle-specific targeting moieties and/or compositions containing one or more of the muscle-specific targeting moieties described herein has decreased non-muscle cell potency, non-muscle cell specificity, reduced immunogenicity, or any combination thereof. In some embodiments, the muscle-specific targeting moieties and/or compositions containing one or more of the muscle-specific targeting moieties described herein is at least 2 to at least 500 times less specific, less selective, and/or less potent for/in a non-muscle cell relative to a muscle cell. In some embodiments, the specificity, or selectivity, or potency of/in a muscle-specific targeting moiety described herein is at least 2, to/or 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 times less specific or selective for a non-muscle cell relative to a muscle cell.

Immunogenicity of the compositions incorporating a muscle-specific targeting moiety can be reduced, for example, 1-100 or more fold. In some embodiments, immunogenicity is reduced 1 to/or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more fold.

Cargos can include any molecule that is capable of being coupled to or associated with the muscle-specific targeting moieties described herein. Cargos can include, without limitation, nucleotides, oligonucleotides, polynucleotides, amino acids, peptides, polypeptides, riboproteins, lipids, sugars, pharmaceutically active agents (e.g., drugs, imaging and other diagnostic agents, and the like), chemical compounds, and combinations thereof. In some embodiments, the cargo is DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, radiation sensitizers, chemotherapeutics, radioactive compounds, imaging agents, and combinations thereof.

In some embodiments, the cargo is capable of treating or preventing a muscle disease or disorder. In some embodiments, the muscle disease or disorder is (a) an auto immune disease; (b) a cancer; (c) a muscular dystrophy; (d) a neuro-muscular disease; (e) a sugar or glycogen storage disease; (f) an expanded repeat disease; (g) a dominant negative disease; (h) a cardiomyopathy; (i) a viral disease; (j) a progeroid disease; or (k) any combination thereof. In some embodiments, the expanded repeat disease is Huntington's disease, a Myotonic Dystrophy, or Facioscapulohumeral muscular dystrophy (FSHD). In some embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD. In some embodiments, the myotonic dystrophy is Type 1 or Type 2. In some embodiments, the sugar or glycogen storage disease is a MPS type III disease or Pompe disease. In some embodiments, the MPS type III disease, is MPS Type IIIA, IIIB, IIIC, or IIID. In some embodiments, the neuro-muscular disease is Charcot-Marie-Tooth disease or Friedreich's Ataxia.

In some embodiments, the cargo is a morpholino, a peptide-linked morpholino, an antisense oligonucleotide, a PMO, a therapeutic transgene, a polynucleotide encoding a therapeutic polypeptide or peptide, a PPMO, one or more peptides, one or more polynucleotides encoding a CRISPR-Cas protein, a guide RNA, or both, a ribonucleoprotein, wherein the ribonucleoprotein comprises a CRISPR-Cas system molecule, a therapeutic transgene RNA, or other gene modifying or therapeutic RNA and/or protein, or any combination thereof.

In some embodiments, the cargo is capable of inducing exon skipping in a gene.

In some embodiments, the cargo is capable of inducing exon skipping in a dystrophin gene.

In some embodiments, the cargo is a mini- or micro-dystrophin gene. In some embodiments, the mini- or micro-dystrophin gene comprises spectrin-like repeats 1, 2, 3, and 24, or a combination thereof, and optionally an nNOS domain.

Engineered Viral Capsids and Encoding Polynucleotides

Described herein are various embodiments of engineered viral capsids, such as adeno-associated virus (AAV) capsids, that can be engineered to confer cell-specific tropism, such as muscle specific tropism, to an engineered viral particle. Engineered viral capsids can be lentiviral, retroviral, adenoviral, or AAV capsids. The engineered capsids can be included in an engineered virus particle (e.g., an engineered lentiviral, retroviral, adenoviral, or AAV virus particle), and can confer cell-specific tropism, reduced immunogenicity, or both to the engineered viral particle. The engineered viral capsids described herein can include one or more engineered viral capsid proteins described herein. The engineered viral capsids described herein can include one or more engineered viral capsid proteins described herein that can contain a muscle-specific targeting moiety containing or composed of an n-mer motif described elsewhere herein.

The engineered viral capsid and/or capsid proteins can be encoded by one or more engineered viral capsid polynucle- otides. In some embodiments, the engineered viral capsid polynucleotide is an engineered AAV capsid polynucleotide, engineered lentiviral capsid polynucleotide, engineered ret- roviral capsid polynucleotide, or engineered adenovirus capsid polynucleotide. In some embodiments, an engineered viral capsid polynucleotide (e.g., an engineered AAV capsid polynucleotide, engineered lentiviral capsid polynucleotide, engineered retroviral capsid polynucleotide, or engineered adenovirus capsid polynucleotide) can include a 3' polyade- nylation signal. The polyadenylation signal can be an SV40 polyadenylation signal.

The engineered viral capsids can be variants of wild-type viral capsid. For example, in some embodiments, the engi- neered AAV capsids can be variants of wild-type AAV capsids. In some embodiments, the wild-type AAV capsids can be composed of VP1, VP2, VP3 capsid proteins or a combination thereof. In other words, the engineered AAV capsids can include one or more variants of a wild-type VP1, wild-type VP2, and/or wild-type VP3 capsid proteins. In some embodiments, the serotype of the reference wild-type AAV capsid can be AAV-1, AAV-2, AAV-3, AAV-4, AAV-5, AAV-6, AAV-8, AAV-9 or any combination thereof. In some embodiments, the serotype of the wild-type AAV capsid can be AAV-9. The engineered AAV capsids can have a different tropism than that of the reference wild-type AAV capsid.

The engineered viral capsid can contain 1-60 engineered capsid proteins. In some embodiments, the engineered viral capsids can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 engineered capsid proteins. In some embodiments, the engi- neered viral capsid can contain 0-59 wild-type viral capsid proteins. In some embodiments, the engineered viral capsid can contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 wild-type viral capsid proteins.

In some embodiments, the engineered AAV capsid can contain 1-60 engineered capsid proteins. In some embodi- ments, the engineered AAV capsids can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 engineered capsid proteins. In some embodiments, the engineered AAV capsid can contain 0-59 wild-type AAV capsid proteins. In some embodiments, the engineered AAV capsid can contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 wild-type AAV capsid proteins.

In some embodiments, the engineered viral capsid protein can have an n-mer amino acid motif, where n can be at least 3 amino acids. In some embodiments, n can be 3, 4, 5, 6, 7, 8, 9, 10, 11, 12, 13, 14, or 15 amino acids. In some embodiments, an engineered AAV capsid can have a 6-mer or 7-mer amino acid motif. In some embodiments, the n-mer amino acid motif can be inserted between two amino acids in the wild-type viral protein (VP) (or capsid protein). In some embodiments, the n-mer motif can be inserted between two amino acids in a variable amino acid region in a viral capsid protein.

In some embodiments, the n-mer motif can be inserted between two amino acids in a variable amino acid region in an AAV capsid protein. The core of each wild-type AAV viral protein contains an eight-stranded beta-barrel motif (betaB to betaI) and an alpha-helix (alphaA) that are con- served in autonomous parvovirus capsids (see e.g., DiMattia et al. 2012. J. Virol. 86(12):6947-6958). Structural variable regions (VRs) occur in the surface loops that connect the beta-strands, which cluster to produce local variations in the capsid surface. AAVs have 12 variable regions (also referred to as hypervariable regions) (see e.g., Weitzman and Linden. 2011. "Adeno-Associated Virus Biology." In Snyder, R. O., Moullier, P. (eds.) Totowa, NJ: Humana Press). In some embodiments, one or more n-mer motifs can be inserted between two amino acids in one or more of the 12 variable regions in the wild-type AVV capsid proteins. In some embodiments, the one or more n-mer motifs can be each be inserted between two amino acids in VR-I, VR-II, VR-III, VR-IV, VR-V, VR-VI, VR-VII, VR-III, VR-IX, VR-X, VR-XI, VR-XII, or a combination thereof. In some embodi- ments, the n-mer can be inserted between two amino acids in the VR-III of a capsid protein. In some embodiments, the engineered capsid can have an n-mer inserted between any two contiguous amino acids between amino acids 262 and 269, between any two contiguous amino acids between amino acids 327 and 332, between any two contiguous amino acids between amino acids 382 and 386, between any two contiguous amino acids between amino acids 452 and 460, between any two contiguous amino acids between amino acids 488 and 505, between any two contiguous amino acids between amino acids 545 and 558, between any two contiguous amino acids between amino acids 581 and 593, between any two contiguous amino acids between amino acids 704 and 714 of an AAV9 viral protein. In some embodiments, the engineered capsid can have an n-mer inserted between amino acids 588 and 589 of an AAV9 viral protein. In some embodiments, the engineered capsid can have a 7-mer motif inserted between amino acids 588 and 589 of an AAV9 viral protein. SEQ ID NO: 1 is a reference AAV9 capsid sequence for at least referencing the insertion sites discussed above. It will be appreciated that n-mers can be inserted in analogous positions in AAV viral proteins of other serotypes. In some embodiments as previously dis- cussed, the n-mer(s) can be inserted between any two contiguous amino acids within the AAV viral protein and in some embodiments the insertion is made in a variable region.

In some embodiments, the first 1, 2, 3, or 4 amino acids of an n-mer motif can replace 1, 2, 3, or 4 amino acids of a polypeptide into which it is inserted and preceding the insertion site. In some embodiments, the amino acids of the n-mer motif that replace 1 or more amino acids of the polypeptide into which the n-mer motif is inserted come before or immediately before an "RGD" in an n-mer motif. For example, in one or more of the 10-mer inserts shown in e.g., Tables 2-3, the first three amino acids shown can replace 1-3 amino acids into a polypeptide to which they may be inserted. Using an AAV as another non-limiting example, one or more of the n-mer motifs can be inserted into e.g., and AAV9 capsid prolylpeptide between amino acids 588 and 589 and the insert can replace amino acids 586, 587, and 588 such that the amino acid immediately preceding the n-mer motif after insertion is residue 585. It will be appreciated that this principle can apply in any other insertion context and is not necessarily limited to insertion between residues 588 and 589 of an AAV9 capsid or equivalent position in another AAV capsid. It will further be appreciated that in some embodiments, no amino acids in the polypeptide into which the n-mer motif is inserted are replaced by the n-mer motif.

```
AAV9 capsid reference Sequence.
                                  SEQ ID NO: 1
MAADGYLPDWLEDNLSEGIREWWALKPGAPQPKANQ

QHQDNARGLVLPGYKYLGPGNGLDKGEPVNAADAA

ALEHDKAYDQQLKAGDNPYLKYNHADAEFQERLKE

DTSFGGNLGRAVFQAKKRLLEPLGLVEEAAKTAPG

KKRPVEQSPQEPDSSAGIGKSGAQPAKKRLNFGQT

GDTESVPDPQPIGEPPAAPSGVGSLTMASGGGAPV

ADNNEGADGVGSSSGNWHCDSQWLGDRVITTSTRT

WALPTYNNHLYKQISNSTSGGSSNDNAYFGYSTPW

GYFDFNRFHCHFSPRDWQRLINNNWGFRPKRLNFK

LFNIQVKEVTDNNGVKTIANNLTSTVQVFTDSDYQ

LPYVLGSAHEGCLPPFPADVFMIPQYGYLTLNDGS

QAVGRSSFYCLEYFPSQMLRTGNNFQFSYEFENVP

FHSSYAHSQSLDRLMNPLIDQYLYYLSKTINGSGQ

NQQTLKFSVAGPSNMAVQGRNYIPGPSYRQQRVST

TVTQNNNSEFAWPGASSWALNGRNSLMNPGPAMAS

HKEGEDRFFPLSGSLIFGKQGTGRDNVDADKVMIT

NEEEIKTTNPVATESYGQVATNHQSAQAQAQTGWV

QNQGILPGMVWQDRDVYLQGPIWAKIPHTDGNFHP

SPLMGGFGMKHPPPQILIKNTPVPADPPTAFNKDK

LNSFITQYSTGQVSVEIEWELQKENSKRWNPEIQY

TSNYYKSNNVEFAVNTEGVYSEPRPIGTRYLTRNL
```

In some embodiments, the n-mer can be an amino acid can be any amino acid motif as shown or encoded by a nucleic acid as shown in Tables 2-3, FIG. 14F, and/or in the Working Examples herein. In some embodiments, insertion of the n-mer in an AAV or other viral capsid can result in cell, tissue, organ, specific engineered AAV or other viral capsids or other composition that includes the n-mer motif or capsid proteins of the present invention. In some embodiments, the engineered capsid or other composition containing an n-mer motif has a specificity for bone tissue and/or cells, lung tissue and/or cells, liver tissues and/or cells, bladder tissue and/or cells, kidney tissue and/or cells, cardiac tissue and/or cells, skeletal muscle tissue and/or cells, smooth muscle and/or cells, neuronal tissue and/or cells, intestinal tissue and/or cells, pancreases tissue and/or cells, adrenal gland tissue and/or cells, brain tissue and/or cells, tendon tissues or cells, skin tissues and/or cells, spleen tissue and/or cells, eye tissue and/or cells, blood cells, synovial fluid cells, immune cells (including specificity for particular types of immune cells), and combinations thereof. In some embodiments, the engineered capsid or other composition containing an n-mer motif has a specificity for muscles cells, including but not limited to, skeletal muscle tissue and/or cells and smooth muscle tissue and/or cells.

In some embodiments, the AAV capsids or other viral capsids or compositions can be muscle-specific. In some embodiments, muscle-specificity of the engineered AAV or other viral capsid or other composition is conferred by a muscle specific n-mer motif incorporated in the engineered AAV or other viral capsid or other composition described herein. While not intending to be bound by theory, it is believed that the n-mer motif confers a 3D structure to or within a domain or region of the engineered AAV capsid or other viral capsid or other composition such that the interaction of the viral particle or other composition containing the engineered AAV capsid or other viral capsid or other composition described herein has increased or improved interactions (e.g., increased affinity) with a cell surface receptor and/or other molecule on the surface of a muscle cell. In some embodiments, the cell surface receptor is AAV receptor (AAVR). In some embodiments, the cell surface receptor is a muscle cell specific AAV receptor. In some embodiments, the cell surface receptor or other molecule is a cell surface receptor or other molecule selectively expressed on the surface of a muscle cell. In some embodiments, the cell surface receptor or molecule is an integrin or dimer thereof. In some embodiments, the cell surface receptor or molecule is an Vb6 integrin heterodimer.

In some embodiments, a muscle specific engineered viral particle or other composition described herein containing the muscle-specific capsid, n-mer motif, or muscle-specific targeting moiety described herein can have an increased uptake, delivery rate, transduction rate, efficiency, amount, or a combination thereof in a muscle cell as compared to other cells types and/or other virus particles (including but not limited to AAVs) and other compositions that do not contain the muscle-specific n-mer motif of the present invention.

Also described herein are polynucleotides that encode the engineered muscle-specific targeting moieties and other compositions described herein (including, but not limited to, the engineered AAV capsids) described herein.

In some embodiments, the engineered polynucleotide can be included in a polynucleotide that is configured to be a viral genome donor in a viral vector system that can be used to generate engineered viral particles described elsewhere herein.

In some embodiments, the engineered AAV capsid encoding polynucleotide can be included in a polynucleotide that is configured to be an AAV genome donor in an AAV vector system that can be used to generate engineered AAV particles described elsewhere herein. In some embodiments, the engineered AAV capsid encoding polynucleotide can be operably coupled to a poly adenylation tail. In some embodiments, the poly adenylation tail can be an SV40 poly adenylation tail. In some embodiments, the AAV capsid encoding polynucleotide can be operably coupled to a promoter. In some embodiments, the promoter can be a tissue specific promoter. In some embodiments, the tissue specific promoter is specific for muscle (e.g., cardiac, skeletal, and/or smooth muscle), neurons and supporting cells (e.g., astrocytes, glial cells, Schwann cells, etc.), fat, spleen, liver, kidney, immune cells, spinal fluid cells, synovial fluid cells, skin cells, cartilage, tendons, connective tissue, bone, pancreas, adrenal gland, blood cell, bone marrow cells, placenta, endothelial cells, and combinations thereof. In some embodiments, the promoter can be a constitutive promoter. Suitable tissue specific promoters and constitutive promoters are discussed elsewhere herein and are generally known in the art and can be commercially available.

Suitable muscle specific promoters include, but are not limited to CK8, MHCK7, Myoglobin promoter (Mb), Desmin promoter, muscle creatine kinase promoter (MCK) and variants thereof, and SPc5-12 synthetic promoter.

Suitable immune cell specific promoters include, but are not limited to, B29 promoter (B cells), CD14 promoter (monocytic cells), CD43 promoter (leukocytes and platelets), CD68 (macrophages), and SV40/CD43 promoter (leukocytes and platelets).

Suitable blood cell specific promoters include, but are not limited to, CD43 promoter (leukocytes and platelets), CD45 promoter (hematopoietic cells), INF-beta (hematopoietic cells), WASP promoter (hematopoietic cells), SV40/CD43 promoter (leukocytes and platelets), and SV40/CD45 promoter (hematopoietic cells).

Suitable pancreatic specific promoters include, but are not limited to, the Elastase-1 promoter.

Suitable endothelial cell specific promoters include, but are not limited to, Fit-1 promoter and ICAM-2 promoter.

Suitable neuronal tissue/cell specific promoters include, but are not limited to, GFAP promoter (astrocytes), SYN1 promoter (neurons), and NSE/RU5' (mature neurons).

Suitable kidney specific promoters include, but are not limited to, NphsI promoter (podocytes).

Suitable bone specific promoters include, but are not limited to, OG-2 promoter (osteoblasts, odontoblasts).

Suitable lung specific promoters include, but are not limited to, SP-B prompter (lung).

Suitable liver specific promoters include, but are not limited to, SV40/Alb promoter.

Suitable heart specific promoters include, but are not limited to, alpha-MHC.

Suitable constitutive promoters include, but are not limited to CMV, RSV, SV40, EF1alpha, CAG, and beta-actin.

AAVs with Reduced Non-Muscle Cell Specificity

In some embodiments, the n-mer motif(s) described herein are inserted into an AAV protein (e.g., an AAV capsid protein) that has reduced specificity (or no detectable, measurable, or clinically relevant interaction ) for one or more non-muscle cell types. Exemplary non-muscle cell types include, but are not limited to, liver, kidney, lung, heart, spleen, central or peripheral nervous system cells, bone, immune, stomach, intestine, eye, skin cells and the like. In some embodiments, the non-muscle cells are liver cells.

In certain example embodiments, the AAV capsid protein is an engineered AAV capsid protein having reduced or eliminated uptake in a non-muscle cell as compared to a corresponding wild-type AAV capsid polypeptide.

In certain example embodiments, the non-muscle cell is a liver cell.

In certain example embodiments, the wild-type capsid polypeptide is an AAV1, AAV2, AAV3, AAV4, AAV5, AAV6, AAV7, AAV8, AAV9, AAV rh.74, or AAV rh.10 capsid polypeptide.

In certain example embodiments, the engineered AAV capsid protein comprises one or more mutations that result in reduced or eliminated uptake in a non-muscle cell.

In certain example embodiments, the one or more mutations are a. in position 267, b. in position 269, c. in position 504, d. in position 505, e. in position 590, f. or any combination thereof in the AAV9 capsid protein (SEQ ID NO: 1) or in one or more positions corresponding thereto in a non-AAV9 capsid polypeptide.

In certain example embodiments, the non-AAV9 capsid protein is an AAV1, AAV2, AAV3, AAV4, AAV5, AAV6, AAV7, AAV8, AAV rh.74, or AAV rh.10 capsid polypeptide.

In certain example embodiments, the mutation in position 267 in the AAV9 capsid protein (SEQ ID NO: 1) or position corresponding thereto in a non-AAV9 capsid polypeptide is a G or X mutation to A, wherein X is any amino acid.

In certain example embodiments, the mutation in position 269 in the AAV9 capsid protein (SEQ ID NO: 1) or position corresponding thereto in a non-AAV9 capsid polypeptide is an S or X to T mutation, wherein X is any amino acid.

In certain example embodiments, the mutation in position 504 in the AAV9 capsid protein (SEQ ID NO: 1) or position corresponding thereto in a non-AAV9 capsid polypeptide is a G or X to A mutation, wherein X is any amino acid.

In certain example embodiments, the mutation in position 505 in the AAV9 capsid protein (SEQ ID NO: 1) or position corresponding thereto in a non-AAV9 capsid polypeptide is a P or X to A mutation, wherein X is any amino acid.

In certain example embodiments, the mutation in position 590 in the AAV9 capsid protein (SEQ ID NO: 1) or position corresponding thereto in a non-AAV9 capsid polypeptide is a Q or X to A mutation, wherein X is any amino acid.

In certain example embodiments, the engineered AAV capsid protein is an engineered AAV9 capsid polypeptide comprising a mutation at position 267, position 269 or both of a wild-type AAV9 capsid protein (SEQ ID NO: 1), wherein the mutation at position 267 is a G to A mutation and wherein the mutation at position 269 is an S to T mutation.

In certain example embodiments, the engineered AAV capsid protein is an engineered AAV9 capsid polypeptide comprising a mutation at position 590 of a wild-type AAV9 capsid protein (SEQ ID NO: 1), wherein the mutation at position 509 is a Q to A mutation.

In certain example embodiments, the engineered AAV capsid protein is an engineered AAV9 capsid polypeptide comprising a mutation at position 504, position 505, or both of a wild-type AAV9 capsid protein (SEQ ID NO: 1), wherein the mutation at position 504 is a G to A mutation and wherein the mutation at position 505 is a P to A mutation.

In some embodiments, the AAV capsid protein in which the n-mer motif(s) can be inserted can be 80-100 (e.g., 80, 81, 82, 83, 84, 85, 86, 87, 88, 89, 90, 91, 92, 93, 94, 95, 96, 97, 98, 99, to/or 100) percent identical to SEQ ID NO: 4 or SEQ ID NO: 5 of International Patent Application Publication WO 2019/217911, which is incorporated by reference as if expressed in its entirety herein. These sequences are also incorporated herein as SEQ ID NOS: 330 and 331 respectively. It will be appreciated that when considering variants of these AAV9 capsid proteins with reduced liver specificity, that residues 267 and/or 269 must contain the relevant mutations or equivalents.

SEQ ID 330:

Met Ala Ala Asp Gly Tyr Leu Pro Asp Trp Leu Glu Asp Asn Leu Ser

Glu Gly Ile Arg Glu Trp Trp Ala Leu Lys Pro Gly Ala Pro Gln Pro

Lys Ala Asn Gln Gln His Gln Asp Asn Ala Arg Gly Leu Val Leu Pro

Gly Tyr Lys Val Leu Gly Pro Gly Asn Gly Leu Asp Lys Gly Glu Pro

Val Asn Ala Ala Asp Ala Ala Ala Leu Glu His Asp Lys Ala Tyr Asp

Gln Gln Leu Lys Ala Gly Asp Asn Pro Tyr Leu Lys Tyr Asn His Ala

Asp Ala Glu Phe Gln Glu Arg Leu Lys Glu Asp Thr Ser Phe Gly Gly

Asn Leu Gly Arg Ala Val Phe Gln Ala Lys Lys Arg Leu Leu Glu Pro

Leu Gly Leu Val Glu Glu Ala Ala Lys Thr Ala Pro Gly Lys Lys Arg

Pro Val Glu Gln Ser Pro Gln Glu Pro Asp Ser Ser Ala Gly Ile Gly

Lys Ser Gly Ala Gln Pro Ala Lys Lys Arg Leu Asn Phe Gly Gln Thr

Gly Asp Thr Glu Ser Val Pro Asp Pro Gln Pro Ile Gly Glu Pro Pro

Ala Ala Pro Ser Gly Val Gly Ser Leu Thr Met Ala Ser Gly Gly Gly

Ala Pro Val Ala Asp Asn Asn Glu Gly Ala Asp Gly Val Gly Ser Ser

Ser Gly Asn Trp His Cys Asp Ser Gln Trp Leu Gly Asp Arg Val Ile

Thr Thr Ser Thr Arg Thr Trp Ala Leu Pro Thr Tyr Asn Asn His Leu

Tyr Lys Gln Ile Ser Asn Ser Thr Ser Gly Ala Ser Ser Asn Asp Asn

Ala Tyr Phe Gly Tyr Ser Thr Pro Trp Gly Tyr Phe Asp Phe Asn Arg

Phe His Cys His Phe Ser Pro Arg Asp Trp Gln Arg Leu Ile Asn Asn

Asn Trp Gly Phe Arg Pro Lys Arg Leu Asn Phe Lys Leu Phe Asn Ile

Gln Val Lys Glu Val Thr Asp Asn Asn Gly Val Lys Thr Ile Ala Asn

Asn Leu Thr Ser Thr Val Gln Val Phe Thr Asp Ser Asp Tyr Gln Leu

Pro Tyr Val Leu Gly Ser Ala His Glu Gly Cys Leu Pro Pro Phe Pro

Ala Asp Val Phe Met Ile Pro Gln Tyr Gly Tyr Leu Thr Leu Asn Asp

Gly Ser Gln Ala Val Gly Arg Ser Ser Phe Tyr Cys Leu Glu Tyr Phe

Pro Ser Gln Met Leu Arg Thr Gly Asn Asn Phe Gln Phe Ser Tyr Glu

Phe Glu Asn Val Pro Phe His Ser Ser Tyr Ala His Ser Gln Ser Leu

Asp Arg Leu Met Asn Pro Leu Ile Asp Gln Tyr Leu Tyr Tyr Leu Ser

Lys Thr Ile Asn Gly Ser Gly Gln Asn Gln Gln Thr Leu Lys Phe Ser

Val Ala Gly Pro Ser Asn Met Ala Val Gln Gly Arg Asn Tyr Ile Pro

Gly Pro Ser Tyr Arg Gln Gln Arg Val Ser Thr Thr Val Thr Gln Asn

Asn Asn Ser Glu Phe Ala Trp Pro Gly Ala Ser Ser Trp Ala Leu Asn

Gly Arg Asn Ser Leu Met Asn Pro Gly Pro Ala Met Ala Ser His Lys

Glu Gly Glu Asp Arg Phe Phe Pro Leu Ser Gly Ser Leu Ile Phe Gly

Lys Gln Gly Thr Gly Arg Asp Asn Val Asp Ala Asp Lys Val Met Ile

Thr Asn Glu Glu Glu Ile Lys Thr Thr Asn Pro Val Ala Thr Glu Ser

Tyr Gly Gln Val Ala Thr Asn His Gln Ser Ala Gln Ala Gln Ala Gln

Thr Gly Trp Val Gln Asn Gln Gly Ile Leu Pro Gly Met Val Trp Gln

Asp Arg Asp Val Tyr Leu Gln Gly Pro Ile Trp Ala Lys Ile Pro His

Thr Asp Gly Asn Phe His Pro Ser Pro Leu Met Gly Gly Phe Gly Met

Lys His Pro Pro Pro Gln Ile Leu Ile Lys Asn Thr Pro Val Pro Ala

Asp Pro Pro Thr Ala Phe Asn Lys Asp Lys Leu Asn Ser Phe Ile Thr

-continued

Gln Tyr Ser Thr Gly Gln Val Ser Val Glu Ile Glu Trp Glu Leu Gln

Lys Glu Asn Ser Lys Arg Trp Asn Pro Glu Ile Gln Tyr Thr Ser Asn

Tyr Tyr Lys Ser Asn Asn Val Glu Phe Ala Val Asn Thr Glu Gly Val

Tyr Ser Glu Pro Arg Pro Ile Gly Thr Arg Tyr Leu Thr Arg Asn Leu

SEQ ID NO: 331
Met Ala Ala Asp Gly Tyr Leu Pro Asp Trp Leu Glu Asp Asn Leu Ser

Glu Gly Ile Arg Glu Trp Trp Ala Leu Lys Pro Gly Ala Pro Gln Pro

Lys Ala Asn Gln Gln His Gln Asp Asn Ala Arg Gly Leu Val Leu Pro

Gly Tyr Lys Val Leu Gly Pro Gly Asn Gly Leu Asp Lys Gly Glu Pro

Val Asn Ala Ala Asp Ala Ala Ala Leu Glu His Asp Lys Ala Tyr Asp

Gln Gln Leu Lys Ala Gly Asp Asn Pro Tyr Leu Lys Tyr Asn His Ala

Asp Ala Glu Phe Gln Glu Arg Leu Lys Glu Asp Thr Ser Phe Gly Gly

Asn Leu Gly Arg Ala Val Phe Gln Ala Lys Lys Arg Leu Leu Glu Pro

Leu Gly Leu Val Glu Glu Ala Ala Lys Thr Ala Pro Gly Lys Lys Arg

Pro Val Glu Gln Ser Pro Gln Glu Pro Asp Ser Ser Ala Gly Ile Gly

Lys Ser Gly Ala Gln Pro Ala Lys Lys Arg Leu Asn Phe Gly Gln Thr

Gly Asp Thr Glu Ser Val Pro Asp Pro Gln Pro Ile Gly Glu Pro Pro

Ala Ala Pro Ser Gly Val Gly Ser Leu Thr Met Ala Ser Gly Gly Gly

Ala Pro Val Ala Asp Asn Asn Glu Gly Ala Asp Gly Val Gly Ser Ser

Ser Gly Asn Trp His Cys Asp Ser Gln Trp Leu Gly Asp Arg Val Ile

Thr Thr Ser Thr Arg Thr Trp Ala Leu Pro Thr Tyr Asn Asn His Leu

Tyr Lys Gln Ile Ser Asn Ser Thr Ser Gly Ala Ser Thr Asn Asp Asn

Ala Tyr Phe Gly Tyr Ser Thr Pro Trp Gly Tyr Phe Asp Phe Asn Arg

Phe His Cys His Phe Ser Pro Arg Asp Trp Gln Arg Leu Ile Asn Asn

Asn Trp Gly Phe Arg Pro Lys Arg Leu Asn Phe Lys Leu Phe Asn Ile

Gln Val Lys Glu Val Thr Asp Asn Asn Gly Val Lys Thr Ile Ala Asn

Asn Leu Thr Ser Thr Val Gln Val Phe Thr Asp Ser Asp Tyr Gln Leu

Pro Tyr Val Leu Gly Ser Ala His Glu Gly Cys Leu Pro Pro Phe Pro

Ala Asp Val Phe Met Ile Pro Gln Tyr Gly Tyr Leu Thr Leu Asn Asp

Gly Ser Gln Ala Val Gly Arg Ser Ser Phe Tyr Cys Leu Glu Tyr Phe

Pro Ser Gln Met Leu Arg Thr Gly Asn Asn Phe Gln Phe Ser Tyr Glu

Phe Glu Asn Val Pro Phe His Ser Ser Tyr Ala His Ser Gln Ser Leu

Asp Arg Leu Met Asn Pro Leu Ile Asp Gln Tyr Leu Tyr Tyr Leu Ser

Lys Thr Ile Asn Gly Ser Gly Gln Asn Gln Gln Thr Leu Lys Phe Ser

Val Ala Gly Pro Ser Asn Met Ala Val Gln Gly Arg Asn Tyr Ile Pro

Gly Pro Ser Tyr Arg Gln Gln Arg Val Ser Thr Thr Val Thr Gln Asn

Asn Asn Ser Glu Phe Ala Trp Pro Gly Ala Ser Ser Trp Ala Leu Asn

Gly Arg Asn Ser Leu Met Asn Pro Gly Pro Ala Met Ala Ser His Lys

Glu Gly Glu Asp Arg Phe Phe Pro Leu Ser Gly Ser Leu Ile Phe Gly

Lys Gln Gly Thr Gly Arg Asp Asn Val Asp Ala Asp Lys Val Met Ile

Thr Asn Glu Glu Glu Ile Lys Thr Thr Asn Pro Val Ala Thr Glu Ser

-continued

```
Tyr Gly Gln Val Ala Thr Asn His Gln Ser Ala Gln Ala Gln Ala Gln

Thr Gly Trp Val Gln Asn Gln Gly Ile Leu Pro Gly Met Val Trp Gln

Asp Arg Asp Val Tyr Leu Gln Gly Pro Ile Trp Ala Lys Ile Pro His

Thr Asp Gly Asn Phe His Pro Ser Pro Leu Met Gly Gly Phe Gly Met

Lys His Pro Pro Pro Gln Ile Leu Ile Lys Asn Thr Pro Val Pro Ala

Asp Pro Pro Thr Ala Phe Asn Lys Asp Lys Leu Asn Ser Phe Ile Thr

Gln Tyr Ser Thr Gly Gln Val Ser Val Glu Ile Glu Trp Glu Leu Gln

Lys Glu Asn Ser Lys Arg Trp Asn Pro Glu Ile Gln Tyr Thr Ser Asn

Tyr Tyr Lys Ser Asn Asn Val Glu Phe Ala Val Asn Thr Glu Gly Val

Tyr Ser Glu Pro Arg Pro Ile Gly Thr Arg Tyr Leu Thr Arg Asn Leu
```

In some embodiments, the AAV capsid protein in which the in which the n-mer motif(s) can be inserted can be 80-100 (e.g., 80, 81, 82, 83, 84, 85, 86, 87, 88, 89, 90, 91, 92, 93, 94, 95, 96, 97, 98, 99, to/or 100) percent identical to any of those described in Adachi et al., (Nat. Comm. 2014. 5:3075, DOI: 10.1038/ncomms4075) that have reduced specificity for a non-CNS cell, particularly a liver cell. Adachi et al., (Nat. Comm. 2014. 5:3075, DOI: 10.1038/ncomms4075) is incorporated by reference herein as if expressed in its entirety.

In some embodiments, the modified AAV can have about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent or fold reduction in specificity for a non-muscle as compared to a wild-type AAV or control. In some embodiments, the modified AAV can have no measurable or detectable uptake and/or expression in one or more non-muscle cells.

Methods of Generating Engineered AAV Capsids

Figure 1:
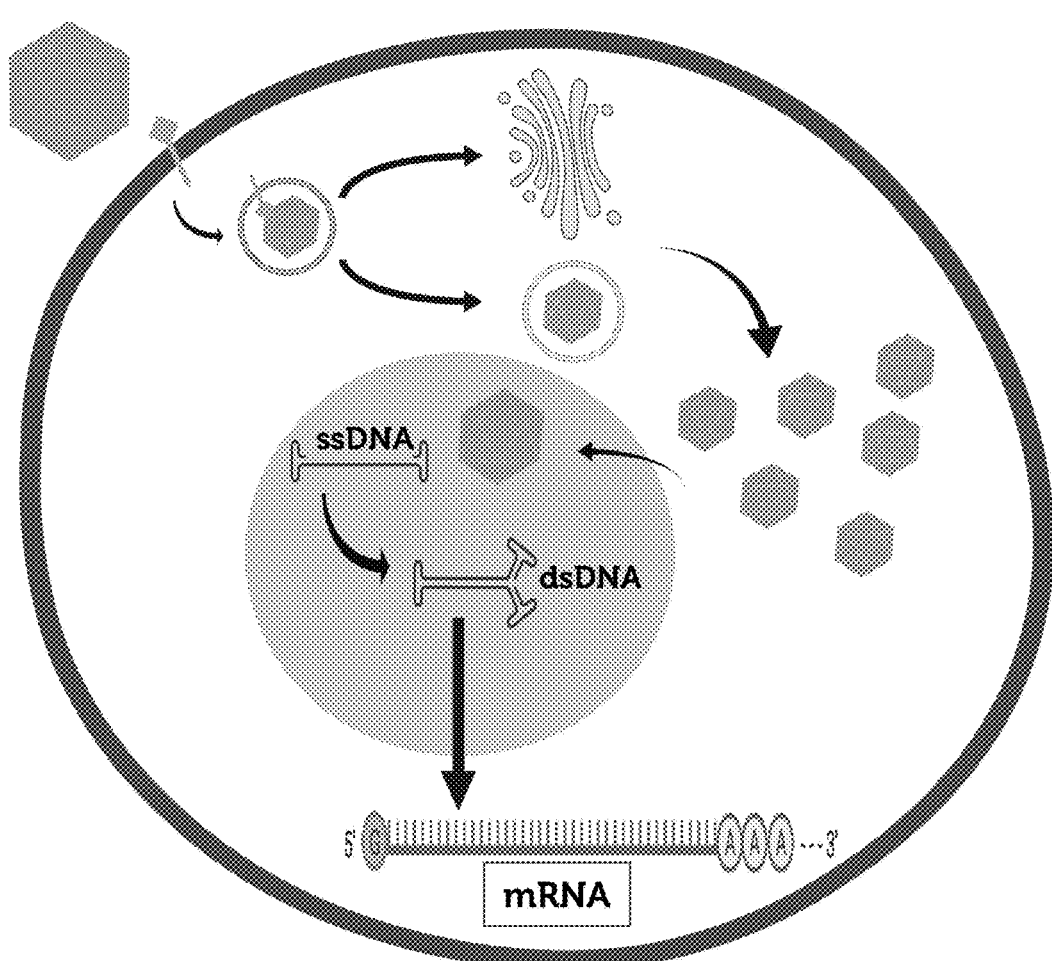
FIG. 1—The adeno-associated virus (AAV) transduction mechanism, which results in production of mRNA from the transgene.
Figure 6:
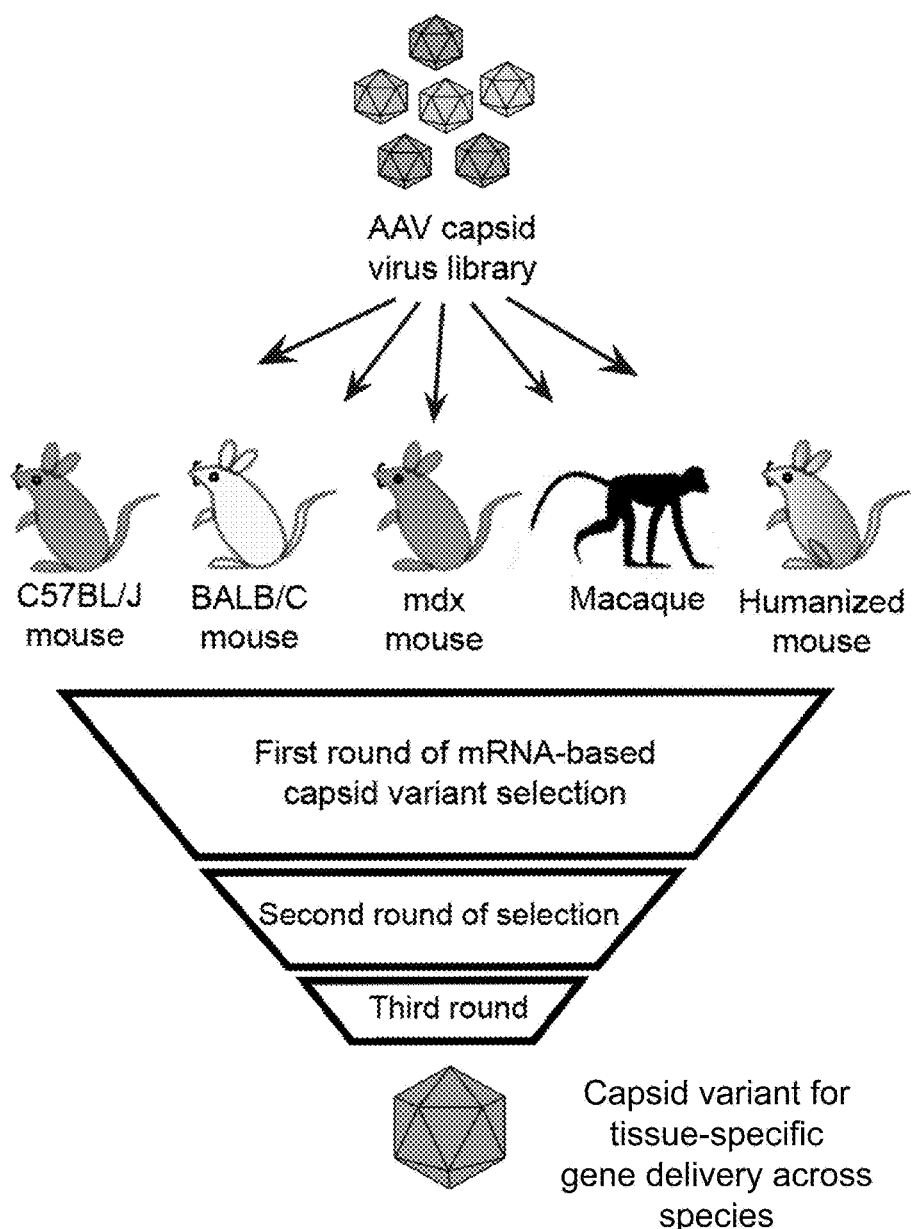
FIG. 6—A schematic demonstrating embodiments of a method of producing and selecting capsid variants for tissue-specific gene delivery across species.
Figures 7, 8:
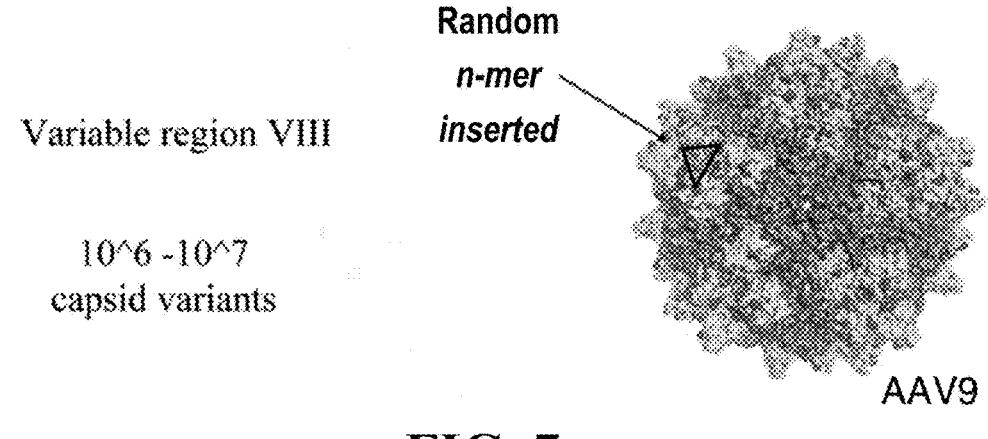
FIG. 7—A schematic demonstrating embodiments of generating an AAV capsid variant library, particularly insertion of a random n-mer (n=3-15 amino acids) into a wild-type AAV, e.g., AAV9.
FIG. 8—A schematic demonstrating embodiments of generating an AAV capsid variant library, particularly variant AAV particle production. Each capsid variant encapsulates its own coding sequence as the vector genome.

Also provided herein are methods of generating engineered AAV capsids. The engineered AAV capsid variants can be variants of wild-type AAV capsids. FIGS. 6-8 can illustrate various embodiments of methods capable of generating engineered AAV capsids with variant motifs described herein. Generally, an AAV capsid library can be generated by expressing engineered capsid vectors each containing an engineered AAV capsid polynucleotide previously described in an appropriate AAV producer cell line. See e.g., FIG. 8. It will be appreciated that although FIG. 8 shows a helper-dependent method of AAV particle production, it will be appreciated that this can be done via a helper-free method as well. This can generate an AAV capsid library that can contain one more desired cell-specific engineered AAV capsid variant. As shown in FIG. 6 the AAV capsid library can be administered to various non-human animals for a first round of mRNA-based selection. As shown in FIG. 1, the transduction process by AAVs and related vectors can result in the production of an mRNA molecule that is reflective of the genome of the virus that transduced the cell. As is at least demonstrated in the Examples herein, mRNA based-selection can be more specific and effective to determine a virus particle capable of functionally transducing a cell because it is based on the functional product produced as opposed to just detecting the presence of a virus particle in the cell by measuring the presence of viral DNA.

After first-round administration, one or more engineered AAV virus particles having a desired capsid variant can then be used to form a filtered AAV capsid library. Desirable AAV virus particles can be identified by measuring the mRNA expression of the capsid variants and determining which variants are highly expressed in the desired cell type(s) as compared to non-desired cells type(s). Those that are highly expressed in the desired cell, tissue, and/or organ type are the desired AAV capsid variant particles. In some embodiments, the AAV capsid variant encoding polynucleotide is under control of a tissue-specific promoter that has selective activity in the desired cell, tissue, or organ.

The engineered AAV capsid variant particles identified from the first round can then be administered to various non-human animals. In some embodiments, the animals used in the second round of selection and identification are not the same as those animals used for first round selection and identification. Similar to round 1, after administration the top expressing variants in the desired cell, tissue, and/or organ type(s) can be identified by measuring viral mRNA expression in the cells. The top variants identified after round two can then be optionally barcoded and optionally pooled. In some embodiments, top variants from the second round can then be administered to a non-human primate to identify the top cell-specific variant(s), particularly if the end use for the top variant is in humans. Administration at each round can be systemic.

In some embodiments, the method of generating an AAV capsid variant can include the steps of: (a) expressing a vector system described herein that contains an engineered AAV capsid polynucleotide in a cell to produce engineered AAV virus particle capsid variants; (b) harvesting the engineered AAV virus particle capsid variants produced in step (a); (c) administering engineered AAV virus particle capsid variants to one or more first subjects, wherein the engineered AAV virus particle capsid variants are produced by expressing an engineered AAV capsid variant vector or system thereof in a cell and harvesting the engineered AAV virus particle capsid variants produced by the cell; and (d) identifying one or more engineered AAV capsid variants produced at a significantly high level by one or more specific cells or specific cell types in the one or more first subjects. In this context, "significantly high" can refer to a titer that can range from between about $2 \times 10^{11}$ to about $6 \times 10^{12}$ vector genomes per 15 cm dish.

The method can further include the steps of: (e) administering some or all engineered AAV virus particle capsid variants identified in step (d) to one or more second subjects; and (f) identifying one or more engineered AAV virus particle capsid variants produced at a significantly high level in one or more specific cells or specific cell types in the one or more second subjects. The cell in step (a) can be a prokaryotic cell or a eukaryotic cell. In some embodiments, the administration in step (c), step (e), or both is systemic. In some embodiments, one or more first subjects, one or more second subjects, or both, are non-human mammals. In some embodiments, one or more first subjects, one or more second subjects, or both, are each independently selected from the group consisting of: a wild-type non-human mammal, a humanized non-human mammal, a disease-specific non-human mammal model, and a non-human primate.

Figure 11:
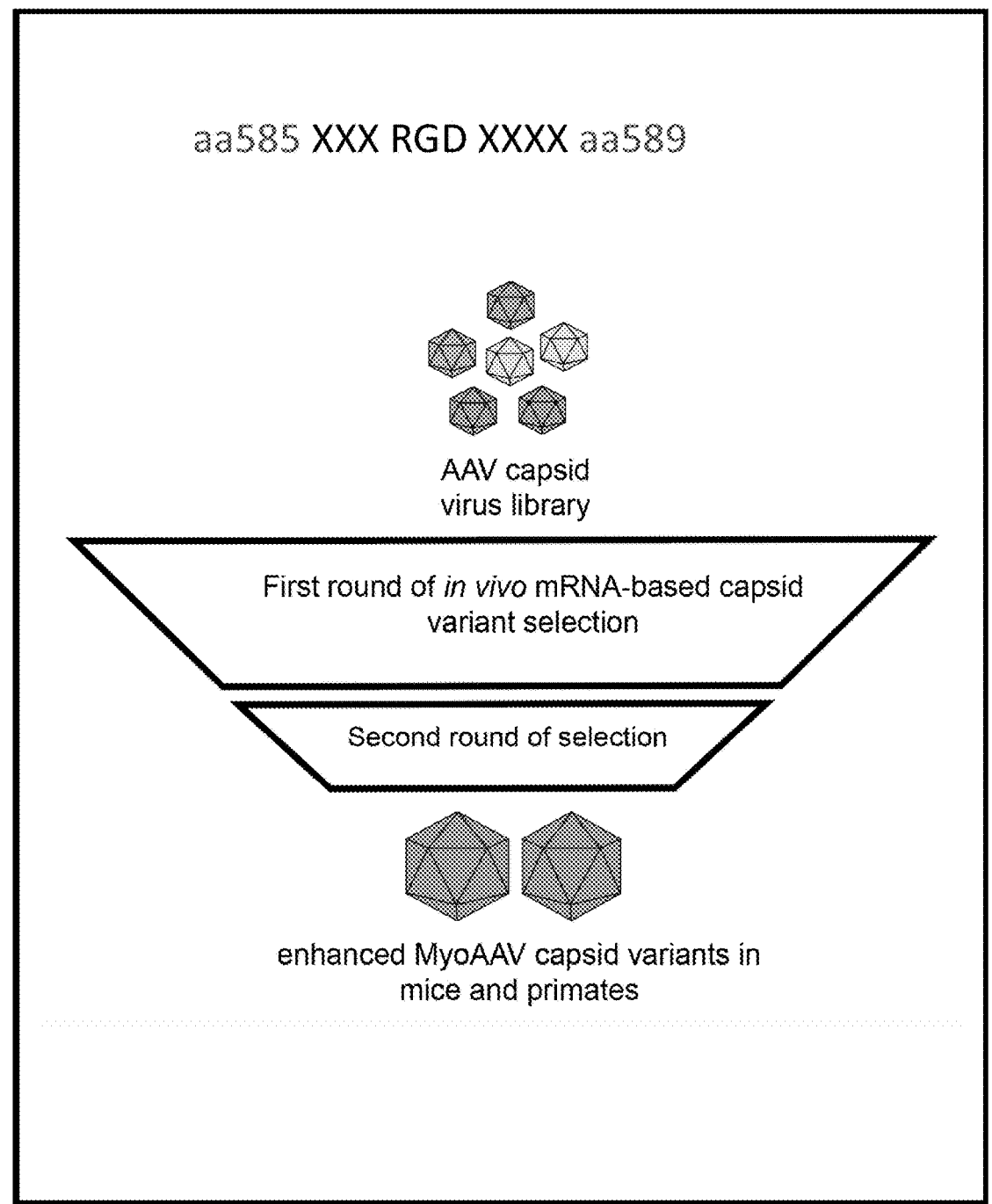
FIG. 11—A schematic of selection of further optimized myoAAV capsid variants (also referred to herein as enhanced MyoAAV capsid variants).

In some embodiments, further optimization of the variant motifs can be performed. In some embodiments, the first and/or second generation motifs, (including capsids RGD containing motifs) can be further used to optimize capsid variants as shown e.g., in FIG. 11 and as further discussed in the Working Examples herein.

The polynucleotides and vector systems described herein can also be used to generate viral particles and other compositions that can be generated to contain a cargo molecule that can be delivered to a cell.

Engineered Vectors and Vector Systems

Also provided herein are vectors and vector systems that can contain one or more of the engineered polynucleotides described herein that can encode one or more of the n-mer motifs of the present invention, including but not limited to engineered viral polynucleotides (e.g., engineered AAV polynucleotides). In some embodiments, the polynucleotide(s) that can encode an n-mer motif of the present invention can be any as described in Tables 2-3, FIG. 14, and/or as described elsewhere herein. In some embodiments, the polynucleotide can encode any n-mer motif as set forth in any of Tables 2-3, FIG. 14, and/or as described elsewhere herein. As used in this context, engineered viral capsid polynucleotides refers to any one or more of the polynucleotides described herein capable of encoding an engineered viral capsid as described elsewhere herein and/or polynucleotide(s) capable of encoding one or more engineered viral capsid proteins described elsewhere herein. Further, where the vector includes an engineered viral capsid polynucleotide described herein, the vector can also be referred to and considered an engineered vector or system thereof although not specifically noted as such. In embodiments, the vector can contain one or more polynucleotides encoding one or more elements of an engineered viral capsid described herein. The vectors and systems thereof can be useful in producing bacterial, fungal, yeast, plant cells, animal cells, and transgenic animals that can express one or more components of the engineered viral capsid, particle, or other compositions described herein. Within the scope of this disclosure are vectors containing one or more of the polynucleotide sequences described herein. One or more of the polynucleotides that are part of the engineered viral capsid and system thereof described herein can be included in a vector or vector system.

In some embodiments, the vector can include an engineered viral (e.g., AAV) capsid polynucleotide having a 3' polyadenylation signal. In some embodiments, the 3' polyadenylation is an SV40 polyadenylation signal. In some embodiments the vector does not have splice regulatory elements. In some embodiments, the vector includes one or more minimal splice regulatory elements. In some embodiments, the vector can further include a modified splice regulatory element, wherein the modification inactivates the splice regulatory element. In some embodiments, the modified splice regulatory element is a polynucleotide sequence sufficient to induce splicing, between a rep protein polynucleotide and the engineered viral (e.g., AAV) capsid protein variant polynucleotide. In some embodiments, the polynucleotide sequence can be sufficient to induce splicing is a splice acceptor or a splice donor. In some embodiments, the viral (e.g., AAV) capsid polynucleotide is an engineered viral (e.g., AAV) capsid polynucleotide as described elsewhere herein. It some embodiments, the vector does not include one or more minimal splice regulatory elements, modified splice regulatory agent, splice acceptor, and/or splice donor.

The vectors and/or vector systems can be used, for example, to express one or more of the engineered viral (e.g., AAV) capsid and/or other polynucleotides in a cell, such as a producer cell, to produce engineered viral (e.g., AAV) particles and/or other compositions (e.g., polypeptides, particles, etc.) containing an engineered viral (e.g., AAV) capsid or other composition containing an n-mer motif of the present invention described elsewhere herein. Other uses for the vectors and vector systems described herein are also within the scope of this disclosure. In general, and throughout this specification, the term is a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g., a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include adeno-associated viruses, and types of such vectors can also be selected for targeting particular types of cells, such as those engineered viral (e.g., AAV) vectors containing an engineered viral (e.g., AAV) capsid polynucleotide with a desired cell-specific tropism. These and other embodiments of the vectors and vector systems are described elsewhere herein.

In some embodiments, the vector can be a bicistronic vector. In some embodiments, a bicistronic vector can be used for one or more elements of the engineered viral (e.g., AAV) capsid system described herein. In some embodiments, expression of elements of the engineered viral (e.g., AAV) capsid system described herein can be driven by a suitable constitutive or tissue specific promoter. Where the element of the engineered viral (e.g., AAV) capsid system is an RNA, its expression can be driven by a Pol III promoter, such as a U6 promoter. In some embodiments, the two are combined.

Cell-Based Vector Amplification and Expression

Vectors can be designed for expression of one or more elements of the engineered viral (e.g., AAV) capsid system or other compositions containing an n-mer motif of the present invention described herein (e.g., nucleic acid transcripts, proteins, enzymes, and combinations thereof) in a suitable host cell. In some embodiments, the suitable host cell is a prokaryotic cell. Suitable host cells include, but are not limited to, bacterial cells, yeast cells, insect cells, and mammalian cells. The vectors can be viral-based or non-viral based. In some embodiments, the suitable host cell is a eukaryotic cell. In some embodiments, the suitable host cell is a suitable bacterial cell. Suitable bacterial cells include, but are not limited to, bacterial cells from the bacteria of the species *Escherichia coli*. Many suitable strains of *E. coli* are known in the art for expression of vectors. These include, but are not limited to Pir1, Stbl2, Stbl3, Stbl4, TOP10, XL1 Blue, and XL10 Gold. In some embodiments, the host cell is a suitable insect cell. Suitable insect cells include those from *Spodoptera frugiperda*. Suitable strains of *S. frugiperda* cells include, but are not limited to, Sf9 and Sf21. In some embodiments, the host cell is a suitable yeast cell. In some embodiments, the yeast cell can be from *Saccharomyces cerevisiae*. In some embodiments, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U20S, A549, HT1080, CAD, P19, NIH 3T3, L929, N2a, MCF-7, Y79, SO-Rb50, HepG 2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insect cells. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092, 085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of an engineered AAV capsid system so as to drive expression of the one or more elements of the engineered AAV capsid system described herein.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988.

*Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of an engineered viral (e.g., AAV) capsid system or other composition containing an n-mer motif described herein are introduced into a host cell such that expression of the elements of the engineered delivery system described herein direct formation of an engineered viral (e.g., AAV) capsid system or other composition containing an n-mer motif described herein (including but not limited to an engineered gene transfer agent particle, which is described in greater detail elsewhere herein). For example, different elements of the engineered viral (e.g., AAV) capsid system or other composition containing an n-mer motif described herein can each be operably linked to separate regulatory elements on separate vectors. RNA(s) of different elements of the engineered delivery system described herein can be delivered to an animal or mammal or cell thereof to produce an animal or mammal or cell thereof that constitutively or inducibly or conditionally expresses different elements of the engineered viral (e.g., AAV) capsid system or other composition containing an n-mer motif described herein that incorporates one or more elements of the engineered viral (e.g., AAV) capsid system or other composition containing an n-mer motif described herein or contains one or more cells that incorporates and/or expresses one or more elements of the engineered viral (e.g., AAV) capsid system or other composition containing an n-mer motif described herein.

In some embodiments, two or more of the elements expressed from the same or different regulatory element(s), can be combined in a single vector, with one or more additional vectors providing any components of the system not included in the first vector. Engineered polynucleotides of the present invention that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding one or more engineered viral (e.g., AAV) capsid proteins or other composition containing an n-mer motif described herein, embedded within one or more intron sequences (e.g., each in a different intron, two or more in at least one intron, or all in a single intron). In some embodiments, the engineered polynucleotides of the present invention (including but not limited to engineered viral polynucleotides) can be operably linked to and expressed from the same promoter.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g., molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In embodiments, the polynucleotides and/or vectors thereof described herein (including, but not limited to, the engineered AAV capsid polynucleotides of the present invention) can include one or more regulatory elements that can be operatively linked to the polynucleotide. The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOL-OGY: METHODS IN ENZYMOLOGY 185, Academic Press, San Diego, Calif. (1990). Regulatory elements include those that direct constitutive expression of a nucleo-tide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (op-tionally with the CMV enhancer) (see, e.g., Boshart et al, Cell, 41:521-530 (1985)), the SV40 promoter, the dihydro-folate reductase promoter, the β-actin promoter, the phos-phoglycerol kinase (PGK) promoter, and the EF1α pro-moter. Also encompassed by the term "regulatory element" are enhancers elements, such as WPRE; CMV enhancers; the R-U5′ segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981).

In some embodiments, the regulatory sequence can be a regulatory sequence described in U.S. Pat. No. 7,776,321, U.S. Pat. Pub. No. 2011/0027239, and PCT publication WO 2011/028929, the contents of which are incorporated by reference herein in their entirety. In some embodiments, the vector can contain a minimal promoter. In some embodi-ments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4 Kb.

To express a polynucleotide, the vector can include one or more transcriptional and/or translational initiation regula-tory sequences, e.g., promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some embodiments, the regulatory element can be a regulated promoter. "Regulated promoter" refers to promot-ers that direct gene expression not constitutively, but in a temporally- and/or spatially-regulated manner, and includes tissue-specific, tissue-preferred and inducible promoters. In some embodiments, the regulated promoter is a tissue spe-cific promoter as previously discussed elsewhere herein. Regulated promoters include conditional promoters and inducible promoters. In some embodiments, conditional promoters can be employed to direct expression of a poly-nucleotide in a specific cell type, under certain environmen-tal conditions, and/or during a specific state of development. Suitable tissue specific promoters can include, but are not limited to, liver specific promoters (e.g. APOA2, SERPIN A1 (hAAT), CYP3A4, and MIR122), pancreatic cell pro-moters (e.g. INS, IRS2, Pdx1, Alx3, Ppy), cardiac specific promoters (e.g. Myh6 (alpha MHC), MYL2 (MLC-2v), TNI3 (cTnl), NPPA (ANF), Slc8a1 (Ncx1)), central nervous system cell promoters (SYN1, GFAP, INA, NES, MOBP, MBP, TH, FOXA2 (HNF3 beta)), skin cell specific promot-ers (e.g. FLG, K14, TGM3), immune cell specific promot-ers, (e.g. ITGAM, CD43 promoter, CD14 promoter, CD45 promoter, CD68 promoter), urogenital cell specific promot-ers (e.g. Pbsn, Upk2, Sbp, Ferl14), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are discussed elsewhere herein and can be generally known in the art and are within the scope of this disclosure.

Inducible/conditional promoters can be positively induc-ible/conditional promoters (e.g. a promoter that activates transcription of the polynucleotide upon appropriate inter-action with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repres-sor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Where expression in a plant cell is desired, the compo-nents of the engineered AAV capsid system described herein are typically placed under control of a plant promoter, i.e., a promoter operable in plant cells. The use of different types of promoters is envisaged. In some embodiments, inclusion of an engineered viral (e.g., AAV) capsid system vector in a plant can be for viral vector production purposes.

A constitutive plant promoter is a promoter that is able to express the open reading frame (ORF) that it controls in all or nearly all of the plant tissues during all or nearly all developmental stages of the plant (referred to as "constitu-tive expression"). One non-limiting example of a constitu-tive promoter is the cauliflower mosaic virus 35S promoter.

Different promoters may direct the expression of a gene in different tissues or cell types, or at different stages of development, or in response to different environmental conditions. In particular embodiments, one or more of the engineered AAV capsid system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the engineered AAV capsid system and other compositions of the present invention are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome), such as a Light Inducible Transcriptional Effector (LITE) that direct changes in transcriptional activity in a sequence-specific manner. The components of a light inducible system may include one or more elements of the engineered AAV capsid system or other compositions of the present invention described herein, a light-responsive cytochrome heterodimer (e.g., from *Arabidopsis thaliana*), and a transcriptional activation/repression domain. In some embodiments, the vector can include one or more of the inducible DNA binding proteins provided in PCT publication WO 2014/018423 and US Publications, 2015/0291966, 2017/0166903, 2019/0203212, which describe e.g., embodiments of inducible DNA binding proteins and methods of use and can be adapted for use with the present invention.

In some embodiments, transient or inducible expression can be achieved by including, for example, chemical-regulated promotors, i.e., whereby the application of an exogenous chemical induces gene expression. Modulation of gene expression can also be obtained by including a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which, are regulated by antibiotics, such as tetracycline-inducible and tetracycline-repressible promoters (Gatz et al., (1991) Mol Gen Genet 227:229-37; U.S. Pat. Nos. 5,814,618 and 5,789,156) can also be used herein.

In some embodiments, the vector or system thereof can include one or more elements capable of translocating and/or expressing an engineered polynucleotide of the present invention (e.g., an engineered viral (e.g., AAV) capsid polynucleotide) to/in a specific cell component or organelle. Such organelles can include, but are not limited to, nucleus, ribosome, endoplasmic reticulum, Golgi apparatus, chloro-plast, mitochondria, vacuole, lysosome, cytoskeleton, plasma membrane, cell wall, peroxisome, centrioles, etc.

Selectable Markers and Tags

One or more of the engineered polynucleotides of the present invention (e.g., an engineered viral (e.g., AAV) capsid polynucleotide) can be operably linked, fused to, or otherwise modified to include a polynucleotide that encodes or is a selectable marker or tag, which can be a polynucleotide or polypeptide. In some embodiments, the polypeptide encoding a polypeptide selectable marker can be incorporated in the engineered polynucleotide of the present invention (e.g., an engineered viral (e.g., AAV) capsid polynucleotide) such that the selectable marker polypeptide, when translated, is inserted between two amino acids between the N- and C-terminus of an engineered polypeptide (e.g., the engineered AAV capsid polypeptide) or at the N- and/or C-terminus of the engineered polypeptide (e.g., an engineered AAV capsid polypeptide). In some embodiments, the selectable marker or tag is a polynucleotide barcode or unique molecular identifier (UMI).

It will be appreciated that the polynucleotide encoding such selectable markers or tags can be incorporated into a polynucleotide encoding one or more components of the engineered AAV capsid system described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Suitable selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly(NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FlAsH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

Selectable markers and tags can be operably linked to one or more components of the engineered AAV capsid system or other compositions and/or systems described herein via suitable linker, such as a glycine or glycine serine linkers as short as GS or GG up to (GGGGG)₃ (SEQ ID NO: 34) or (GGGGS)₃ (SEQ ID NO: 35). Other suitable linkers are described elsewhere herein.

The vector or vector system can include one or more polynucleotides encoding one or more targeting moieties. In some embodiments, the targeting moiety encoding poly-nucleotides can be included in the vector or vector system, such as a viral vector system, such that they are expressed within and/or on the virus particle(s) produced such that the virus particles can be targeted to specific cells, tissues, organs, etc. In some embodiments, the targeting moiety encoding polynucleotides can be included in the vector or vector system such that the engineered polynucleotide(s) of the present invention (e.g., an engineered viral (e.g., AAV) capsid polynucleotide(s)) and/or products expressed there-from include the targeting moiety and can be targeted to specific cells, tissues, organs, etc. In some embodiments, such as non-viral carriers, the targeting moiety can be attached to the carrier (e.g., polymer, lipid, inorganic mol-ecule etc.) and can be capable of targeting the carrier and any attached or associated engineered polynucleotide(s) of the present invention, the engineered polypeptides, or other compositions of the present invention described herein, to specific cells, tissues, organs, etc. In some embodiments, the specific cells are muscle cells.

Cell-free Vector and Polynucleotide Expression

In some embodiments, the polynucleotide(s) encoding an n-mer motif of the present invention can be expressed from a vector or suitable polynucleotide in a cell-free in vitro system. In some embodiments, the polynucleotide encoding one or more features of the engineered AAV capsid system can be expressed from a vector or suitable polynucleotide in a cell-free in vitro system. In other words, the polynucle-otide can be transcribed and optionally translated in vitro. In vitro transcription/translation systems and appropriate vec-tors are generally known in the art and commercially avail-able. Generally, in vitro transcription and in vitro translation systems replicate the processes of RNA and protein synthe-sis, respectively, outside of the cellular environment. Vectors and suitable polynucleotides for in vitro transcription can include T7, SP6, T3, promoter regulatory sequences that can be recognized and acted upon by an appropriate polymerase to transcribe the polynucleotide or vector.

In vitro translation can be stand-alone (e.g., translation of a purified polyribonucleotide) or linked/coupled to tran-scription. In some embodiments, the cell-free (or in vitro) translation system can include extracts from rabbit reticu-locytes, wheat germ, and/or E. coli. The extracts can include various macromolecular components that are needed for translation of exogenous RNA (e.g., 70S or 80S ribosomes, tRNAs, aminoacyl-tRNA, synthetases, initiation, elongation factors, termination factors, etc.). Other components can be included or added during the translation reaction, including but not limited to, amino acids, energy sources (ATP, GTP), energy regenerating systems (creatine phosphate and cre-atine phosphokinase (eukaryotic systems)) (phosphoenol pyruvate and pyruvate kinase for bacterial systems), and other co-factors (Mg2+, K+, etc.). As previously mentioned, in vitro translation can be based on RNA or DNA starting material. Some translation systems can utilize an RNA template as starting material (e.g., reticulocyte lysates and wheat germ extracts). Some translation systems can utilize a DNA template as a starting material (e.g., E coli-based systems). In these systems transcription and translation are coupled and DNA is first transcribed into RNA, which is subsequently translated. Suitable standard and coupled cell-free translation systems are generally known in the art and are commercially available.

Codon Optimization of Vector Polynucleotides

As described elsewhere herein, the polynucleotide encod-ing an n-mer motif of the present invention and/or other polynucleotides described herein can be codon optimized. In some embodiments, polynucleotides of the engineered AAV capsid system described herein can be codon optimized. In some embodiments, one or more polynucleotides contained in a vector ("vector polynucleotides") described herein that are in addition to an optionally codon optimized polynucle-otide encoding an n-mer motif, including but not limited to, embodiments of the engineered AAV capsid system described herein, can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accord-ingly, genes can be tailored for optimal gene expression in a given organism based on codon optimization. Codon usage tables are readily available, for example, at the "Codon Usage Database" available at. kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particu-lar host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-target-ing Cas protein corresponds to the most frequently used codon for a particular amino acid. As to codon usage in yeast, reference is made to the online Yeast Genome data-base available at yeastgenome.org/community/codon_us-age.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

The vector polynucleotide can be codon optimized for expression in a specific cell-type, tissue type, organ type, and/or subject type. In some embodiments, a codon opti-mized sequence is a sequence optimized for expression in a eukaryote, e.g., humans (i.e., being optimized for expression in a human or human cell), or for another eukaryote, such as another animal (e.g., a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g., astrocytes, glial cells, Schwann cells etc.), muscle cells (e.g., cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Non-Viral Vectors and Carriers

In some embodiments, the vector is a non-viral vector or carrier. In some embodiments, non-viral vectors can have the advantage(s) of reduced toxicity and/or immunogenicity and/or increased bio-safety as compared to viral vectors The terms of art "Non-viral vectors and carriers" and as used herein in this context refers to molecules and/or compositions that are not based on one or more component of a virus or virus genome (excluding any nucleotide to be delivered and/or expressed by the non-viral vector) that can be capable of attaching to, incorporating, coupling, and/or otherwise interacting with an engineered capsid polynucleotide (e.g., an engineered AAV capsid polynucleotide) or other composition of the present invention described herein and can be capable of ferrying the polynucleotide to a cell and/or expressing the polynucleotide. It will be appreciated that this does not exclude the inclusion of a virus-based polynucleotide that is to be delivered. For example, if a gRNA to be delivered is directed against a virus component and it is inserted or otherwise coupled to an otherwise non-viral vector or carrier, this would not make said vector a "viral vector". Non-viral vectors and carriers include naked polynucleotides, chemical-based carriers, polynucleotide (non-viral) based vectors, and particle-based carriers. It will be appreciated that the term "vector" as used in the context of non-viral vectors and carriers refers to polynucleotide vectors and "carriers" used in this context refers to a non-nucleic acid or polynucleotide molecule or composition that be attached to or otherwise interact with a polynucleotide to be delivered, such as an engineered AAV capsid polynucleotide of the present invention.

Naked Polynucleotides

In some embodiments one or more engineered AAV capsid polynucleotides or other polynucleotides of the present invention described elsewhere herein can be included in a naked polynucleotide. The term of art "naked polynucleotide" as used herein refers to polynucleotides that are not associated with another molecule (e.g., proteins, lipids, and/or other molecules) that can often help protect it from environmental factors and/or degradation. As used herein, associated with includes, but is not limited to, linked to, adhered to, adsorbed to, enclosed in, enclosed in or within, mixed with, and the like. Naked polynucleotides that include one or more of the engineered AAV capsid polynucleotides or other polynucleotides of the present invention described herein can be delivered directly to a host cell and optionally expressed therein. The naked polynucleotides can have any suitable two- and three-dimensional configurations. By way of non-limiting examples, naked polynucleotides can be single-stranded molecules, double stranded molecules, circular molecules (e.g., plasmids and artificial chromosomes), molecules that contain portions that are single stranded and portions that are double stranded (e.g., ribozymes), and the like. In some embodiments, the naked polynucleotide contains only the engineered AAV capsid polynucleotide(s) or other polynucleotides of the present invention. In some embodiments, the naked polynucleotide can contain other nucleic acids and/or polynucleotides in addition to the engineered AAV capsid polynucleotide(s) or other polynucleotides of the present invention described elsewhere herein. The naked polynucleotides can include one or more elements of a transposon system. Transposons and system thereof are described in greater detail elsewhere herein.

Non-Viral Polynucleotide Vectors

In some embodiments, one or more of the engineered AAV capsid polynucleotides or other polynucleotides of the present invention can be included in a non-viral polynucleotide vector. Suitable non-viral polynucleotide vectors include, but are not limited to, transposon vectors and vector systems, plasmids, bacterial artificial chromosomes, yeast artificial chromosomes, AR (antibiotic resistance)-free plasmids and miniplasmids, circular covalently closed vectors (e.g., minicircles, minivectors, miniknots), linear covalently closed vectors ("dumbbell shaped"), MIDGE (minimalistic immunologically defined gene expression) vectors, MiLV (micro-linear vector) vectors, Ministrings, mini-intronic plasmids, PSK systems (post-segregationally killing systems), ORT (operator repressor titration) plasmids, and the like. See e.g., Hardee et al. 2017. Genes. 8(2):65.

In some embodiments, the non-viral polynucleotide vector can have a conditional origin of replication. In some embodiments, the non-viral polynucleotide vector can be an ORT plasmid. In some embodiments, the non-viral polynucleotide vector can have a minimalistic immunologically defined gene expression. In some embodiments, the non-viral polynucleotide vector can have one or more post-segregationally killing system genes. In some embodiments, the non-viral polynucleotide vector is AR-free. In some embodiments, the non-viral polynucleotide vector is a minivector. In some embodiments, the non-viral polynucleotide vector includes a nuclear localization signal. In some embodiments, the non-viral polynucleotide vector can include one or more CpG motifs. In some embodiments, the non-viral polynucleotide vectors can include one or more scaffold/matrix attachment regions (S/MARs). See e.g., Mirkovitch et al. 1984. Cell. 39:223-232, Wong et al. 2015. Adv. Genet. 89:113-152, whose techniques and vectors can be adapted for use in the present invention. S/MARs are AT-rich sequences that play a role in the spatial organization of chromosomes through DNA loop base attachment to the nuclear matrix. S/MARs are often found close to regulatory elements such as promoters, enhancers, and origins of DNA replication. Inclusion of one or S/MARs can facilitate a once-per-cell-cycle replication to maintain the non-viral polynucleotide vector as an episome in daughter cells. In embodiments, the S/MAR sequence is located downstream of an actively transcribed polynucleotide (e.g., one or more engineered AAV capsid polynucleotides or other polynucleotides or molecules of the present invention) included in the non-viral polynucleotide vector. In some embodiments, the S/MAR can be a S/MAR from the beta-interferon gene cluster. See e.g., Verghese et al. 2014. Nucleic Acid Res. 42:e53; Xu et al. 2016. Sci. China Life Sci. 59:1024-1033; Jin et al. 2016. 8:702-711; Koirala et al. 2014. Adv. Exp. Med. Biol. 801:703-709; and Nehlsen et al. 2006. Gene Ther. Mol. Biol. 10:233-244, whose techniques and vectors can be adapted for use in the present invention.

In some embodiments, the non-viral vector is a transposon vector or system thereof. As used herein, "transposon" (also referred to as transposable element) refers to a polynucleotide sequence that is capable of moving form location in a genome to another. There are several classes of transposons. Transposons include retrotransposons and DNA transposons. Retrotransposons require the transcription of the polynucleotide that is moved (or transposed) in order to transpose the polynucleotide to a new genome or polynucleotide. DNA transposons are those that do not require reverse transcription of the polynucleotide that is moved (or transposed) in order to transpose the polynucleotide to a new genome or polynucleotide. In some embodiments, the non-viral polynucleotide vector can be a retrotransposon vector. In some embodiments, the retrotransposon vector includes long terminal repeats. In some embodiments, the retrotransposon vector does not include long terminal repeats. In some embodiments, the non-viral polynucleotide vector can be a DNA transposon vector. DNA transposon vectors can include a polynucleotide sequence encoding a transposase. In some embodiments, the transposon vector is configured as a non-autonomous transposon vector, meaning that the transposition does not occur spontaneously on its own. In some of these embodiments, the transposon vector lacks one or more polynucleotide sequences encoding proteins required for transposition. In some embodiments, the non-autonomous transposon vectors lack one or more Ac elements.

In some embodiments a non-viral polynucleotide transposon vector system can include a first polynucleotide vector that contains the engineered AAV capsid polynucleotide(s) or other polynucleotides, or molecules of the present invention described herein flanked on the 5' and 3' ends by transposon terminal inverted repeats (TIRs) and a second polynucleotide vector that includes a polynucleotide capable of encoding a transposase coupled to a promoter to drive expression of the transposase. When both are expressed in the same cell the transposase can be expressed from the second vector and can transpose the material between the TIRs on the first vector (e.g., the engineered AAV capsid polynucleotide(s) or other polynucleotides or molecules of the present invention) and integrate it into one or more positions in the host cell's genome. In some embodiments the transposon vector or system thereof can be configured as a gene trap. In some embodiments, the TIRs can be configured to flank a strong splice acceptor site followed by a reporter and/or other gene (e.g., one or more of the engineered AAV capsid polynucleotide(s) or other polynucleotides or molecules of the present invention) and a strong poly A tail. When transposition occurs while using this vector or system thereof, the transposon can insert into an intron of a gene and the inserted reporter or other gene can provoke a mis-splicing process and as a result it in activates the trapped gene.

Any suitable transposon system can be used. Suitable transposon and systems thereof can include Sleeping Beauty transposon system (Tc1/mariner superfamily) (see e.g., Ivics et al. 1997. Cell. 91(4): 501-510), piggyBac (piggyBac superfamily) (see e.g., Li et al. 2013 110 (25): E2279-E2287 and Yusa et al. 2011. PNAS. 108(4): 1531-1536), Tol2 (superfamily hAT), Frog Prince (Tc1/mariner superfamily) (see e.g., Miskey et al. 2003 Nucleic Acid Res. 31(23):6873-6881) and variants thereof.

Chemical Carriers

In some embodiments the engineered AAV capsid polynucleotide(s) or other polynucleotides or other molecules of the present invention described herein can be coupled to a chemical carrier. Chemical carriers that can be suitable for delivery of polynucleotides can be broadly classified into the following classes: (i) inorganic particles, (ii) lipid-based, (iii) polymer-based, and (iv) peptide based. They can be categorized as (1) those that can form condensed complexes with a polynucleotide (such as the engineered AAV capsid polynucleotide(s) of the present invention), (2) those capable of targeting specific cells, (3) those capable of increasing delivery of the polynucleotide or other molecules (such as the engineered AAV capsid polynucleotide(s)) of the present invention to the nucleus or cytosol of a host cell, (4) those capable of disintegrating from DNA/RNA in the cytosol of a host cell, and (5) those capable of sustained or controlled release. It will be appreciated that any one given chemical carrier can include features from multiple categories. The term "particle" as used herein, refers to any suitable sized particles for delivery of the compositions (including particles, polypeptides, polynucleotides, and other compositions described herein) present invention described herein. Suitable sizes include macro-, micro-, and nano-sized particles.

In some embodiments, the non-viral carrier can be an inorganic particle. In some embodiments, the inorganic particle, can be a nanoparticle. The inorganic particles can be configured and optimized by varying size, shape, and/or porosity. In some embodiments, the inorganic particles are optimized to escape from the reticulo endothelial system. In some embodiments, the inorganic particles can be optimized to protect an entrapped molecule from degradation. The suitable inorganic particles that can be used as non-viral carriers in this context can include, but are not limited to, calcium phosphate, silica, metals (e.g., gold, platinum, silver, palladium, rhodium, osmium, iridium, ruthenium, mercury, copper, rhenium, titanium, niobium, tantalum, and combinations thereof), magnetic compounds, particles, and materials, (e.g., supermagnetic iron oxide and magnetite), quantum dots, fullerenes (e.g., carbon nanoparticles, nanotubes, nanostrings, and the like), and combinations thereof. Other suitable inorganic non-viral carriers are discussed elsewhere herein.

In some embodiments, the non-viral carrier can be lipid-based. Suitable lipid-based carriers are also described in greater detail herein. In some embodiments, the lipid-based carrier includes a cationic lipid or an amphiphilic lipid that is capable of binding or otherwise interacting with a negative charge on the polynucleotide to be delivered (e.g., such as an engineered AAV capsid polynucleotide of the present invention). In some embodiments, chemical non-viral carrier systems can include a polynucleotide (such as the engineered AAV capsid polynucleotide(s)) or other composition or molecule of the present invention) and a lipid (such as a cationic lipid). These are also referred to in the art as lipoplexes. Other embodiments of lipoplexes are described elsewhere herein. In some embodiments, the non-viral lipid-based carrier can be a lipid nano emulsion. Lipid nano emulsions can be formed by the dispersion of an immiscible liquid in another stabilized emulsifying agent and can have particles of about 200 nm that are composed of the lipid, water, and surfactant that can contain the polynucleotide to be delivered (e.g., the engineered AAV capsid polynucleotide(s) of the present invention). In some embodiments, the lipid-based non-viral carrier can be a solid lipid particle or nanoparticle.

In some embodiments, the non-viral carrier can be peptide-based. In some embodiments, the peptide-based non-viral carrier can include one or more cationic amino acids. In some embodiments, 35 to 40, 45, 50, 55, 60, 65, 70, 75, 80, 85, 90, 95, 99 or 100% of the amino acids are cationic. In some embodiments, peptide carriers can be used in conjunction with other types of carriers (e.g., polymer-based carriers and lipid-based carriers to functionalize these carriers). In some embodiments, the functionalization is targeting a host cell. Suitable polymers that can be included in the polymer-based non-viral carrier can include, but are not limited to, polyethylenimine (PEI), chitosan, poly (DL-lactide) (PLA), poly (DL-Lactide-co-glycoside) (PLGA), dendrimers (see e.g., US Pat. Pub. 2017/0079916 whose techniques and compositions can be adapted for use with the engineered AAV capsid polynucleotides of the present invention), polymethacrylate, and combinations thereof.

In some embodiments, the non-viral carrier can be configured to release an engineered delivery system polynucleotide that is associated with or attached to the non-viral carrier in response to an external stimulus, such as pH, temperature, osmolarity, concentration of a specific molecule or composition (e.g., calcium, NaCl, and the like), pressure and the like. In some embodiments, the non-viral carrier can be a particle that is configured includes one or more of the engineered AAV capsid polynucleotides or other compositions of the present invention describe herein and an environmental triggering agent response element, and optionally a triggering agent. In some embodiments, the particle can include a polymer that can be selected from the group of polymethacrylates and polyacrylates. In some embodiments, the non-viral particle can include one or more embodiments of the compositions microparticles described in US Pat. Pubs. 20150232883 and 20050123596, whose techniques and compositions can be adapted for use in the present invention.

In some embodiments, the non-viral carrier can be a polymer-based carrier. In some embodiments, the polymer is cationic or is predominantly cationic such that it can interact in a charge-dependent manner with the negatively charged polynucleotide to be delivered (such as the engineered AAV capsid polynucleotide(s) of the present invention). Polymer-based systems are described in greater detail elsewhere herein.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as an engineered AAV capsid polynucleotide, cargo, or other composition or molecule of the present invention, into a virus particle and producing said virus particle when used alone or with one or more other viral vectors (such as in a viral vector system). Viral vectors and systems thereof can be used for producing viral particles for delivery of and/or expression and/or generation of one or more compositions of the present invention described herein (including, but not limited to, any viral particle and associated cargo). The viral vector can be part of a viral vector system involving multiple vectors. In some embodiments, systems incorporating multiple viral vectors can increase the safety of these systems. Suitable viral vectors can include adenoviral-based vectors, adeno associated vectors, helper-dependent adenoviral (HdAd) vectors, hybrid adenoviral vectors, and the like. Other embodiments of viral vectors and viral particles produce therefrom are described elsewhere herein. In some embodiments, the viral vectors are configured to produce replication incompetent viral particles for improved safety of these systems.

Adenoviral Vectors, Helper-Dependent Adenoviral Vectors, and Hybrid Adenoviral Vectors In some embodiments, the vector can be an adenoviral vector. In some embodiments, the adenoviral vector can include elements such that the virus particle produced using the vector or system thereof can be serotype 2, 5, or 9. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g., Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261. The engineered AAV capsids can be included in an adenoviral vector to produce adenoviral particles containing said engineered AAV capsids.

In some embodiments the vector can be a helper-dependent adenoviral vector or system thereof. These are also referred to in the field as "gutless" or "gutted" vectors and are a modified generation of adenoviral vectors (see e.g., Thrasher et al. 2006. Nature. 443:E5-7). In embodiments of the helper-dependent adenoviral vector system one vector (the helper) can contain all the viral genes required for replication but contains a conditional gene defect in the packaging domain. The second vector of the system can contain only the ends of the viral genome, one or more engineered AAV capsid polynucleotides, and the native packaging recognition signal, which can allow selective packaged release from the cells (see e.g., Cideciyan et al. 2009. N Engl J Med. 361:725-727). Helper-dependent Adenoviral vector systems have been successful for gene delivery in several contexts (see e.g., Simonelli et al. 2010. J Am Soc Gene Ther. 18:643-650; Cideciyan et al. 2009. N Engl J Med. 361:725-727; Crane et al. 2012. Gene Ther. 19(4):443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the engineered AAV capsid polynucleotides described herein. In some embodiments, the polynucleotide to be delivered via the viral particle produced from a helper-dependent adenoviral vector or system thereof can be up to about 38 kb. Thus, in some embodiments, a adenoviral vector can include a DNA polynucleotide to be delivered that can range in size from about 0.001 kb to about 37 kb (see e.g., Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g., Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4):667-674), whose techniques and vectors described therein can be modified and adapted for use in the engineered AAV capsid system of the present invention. In some embodiments, a hybrid-adenoviral vector can include one or more features of a retrovirus and/or an adeno-associated virus. In some embodiments the hybrid-adenoviral vector can include one or more features of a spuma retrovirus or foamy virus (FV). See e.g., Ehrhardt et al. 2007. Mol. Ther. 15:146-156 and Liu et al. 2007. Mol. Ther. 15:1834-1841, whose techniques and vectors described therein can be modified and adapted for use in the engineered AAV capsid system of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g., Ehrhardt et al. 2007. Mol. Ther. 156:146-156 and Shuji et al. 2011. Mol. Ther. 19:76-82, whose techniques and vectors described therein can be modified and adapted for use in the engineered AAV capsid system of the present invention.

Adeno Associated Vectors

In an embodiment, the engineered vector or system thereof can be an adeno-associated vector (AAV). See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb. The AAV vector or system thereof can include one or more engineered capsid polynucleotides described herein.

The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof. In some embodiments, the promoter can be a tissue specific promoter as previously discussed. In some embodiments, the tissue specific promoter can drive expression of an engineered capsid AAV capsid polynucleotide described herein.

The AAV vector or system thereof can include one or more polynucleotides that can encode one or more capsid proteins, such as the engineered AAV capsid proteins described elsewhere herein. The engineered capsid proteins can be capable of assembling into a protein shell (an engineered capsid) of the AAV virus particle. The engineered capsid can have a cell-, tissue-, and/or organ-specific tropism.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E40RF6, and VA RNAs. In some embodiments, a producing host cell line expresses one or more of the adenovirus helper factors.

The AAV vector or system thereof can be configured to produce AAV particles having a specific serotype. In some embodiments, the serotype can be AAV-1, AAV-2, AAV-3, AAV-4, AAV-5, AAV-6, AAV-8, AAV-9 or any combinations thereof. In some embodiments, the AAV can be AAV1, AAV-2, AAV-5, AAV-9 or any combination thereof. One can select the AAV of the AAV with regard to the cells to be targeted; e.g., one can select AAV serotypes 1, 2, 5, 9 or a hybrid capsid AAV-1, AAV-2, AAV-5, AAV-9 or any combination thereof for targeting brain and/or neuronal cells; and one can select AAV-4 for targeting cardiac tissue; and one can select AAV-8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. See also Srivastava. 2017. Curr. Opin. Virol. 21:75-80.

It will be appreciated that while the different serotypes can provide some level of cell, tissue, and/or organ specificity, each serotype still is multi-tropic and thus can result in tissue-toxicity if using that serotype to target a tissue that the serotype is less efficient in transducing. Thus, in addition to achieving some tissue targeting capacity via selecting an AAV of a particular serotype, it will be appreciated that the tropism of the AAV serotype can be modified by an engineered AAV capsid described herein. As described elsewhere herein, variants of wild-type AAV of any serotype can be generated via a method described herein and determined to have a particular cell-specific tropism, which can be the same or different as that of the reference wild-type AAV serotype. In some embodiments, the cell, tissue, and/or specificity of the wild-type serotype can be enhanced (e.g., made more selective or specific for a particular cell type that the serotype is already biased towards). For example, wild-type AAV-9 is biased towards muscle and brain in humans (see e.g., Srivastava. 2017. Curr. Opin. Virol. 21:75-80.) By including an engineered AAV capsid and/or capsid protein variant of wild-type AAV-9 as described herein, the bias for e.g., brain can be reduced or eliminated and/or the muscle septicity increased such that the brain specificity appears reduced in comparison, thus enhancing the specificity for the muscle as compared to the wild-type AAV-9. As previously mentioned, inclusion of an engineered capsid and/or capsid protein variant of a wild-type AAV serotype can have a different tropism than the wild-type reference AAV serotype. For example, an engineered AAV capsid and/or capsid protein variant of AAV-9 can have specificity for a tissue other than muscle or brain in humans.

In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the 2nd plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5. It will be appreciated that wild-type hybrid AAV particles suffer the same specificity issues as with the non-hybrid wild-type serotypes previously discussed.

Advantages achieved by the wild-type based hybrid AAV systems can be combined with the increased and customizable cell-specificity that can be achieved with the engineered AAV capsids can be combined by generating a hybrid AAV that can include an engineered AAV capsid described elsewhere herein. It will be appreciated that hybrid AAVs can contain an engineered AAV capsid containing a genome with elements from a different serotype than the reference wild-type serotype that the engineered AAV capsid is a variant of. For example, a hybrid AAV can be produced that includes an engineered AAV capsid that is a variant of an AAV-9 serotype that is used to package a genome that contains components (e.g., rep elements) from an AAV-2 serotype. As with wild-type based hybrid AAVs previously discussed, the tropism of the resulting AAV particle will be that of the engineered AAV capsid.

A tabulation of certain wild-type AAV serotypes as to these cells can be found in Grimm, D. et al, J. Virol. 82: 5887-5911 (2008) reproduced below as Table 1. Further tropism details can be found in Srivastava. 2017. Curr. Opin. Virol. 21:75-80 as previously discussed.

fication and packaging in linkage with the heterologous sequences of interest (e.g., the engineered AAV capsid polynucleotide(s)).

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Application publication No. US 2004-0171156 A1. Other suitable methods and techniques are described elsewhere herein.

Construction of recombinant AAV vectors are described in a number of publications, including U.S. Pat. No. 5,173, 414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. AAV vectors are discussed elsewhere herein.

In some embodiments, the vector can have one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors.

Delivery vehicles, vectors, particles, nanoparticles, formulations and components thereof for expression of one or more elements of a engineered AAV capsid system described herein are as used in the foregoing documents, such as International Patent Application Publication WO 2014/ 093622 (PCT/US2013/074667) and are discussed in greater detail herein.

Virus Particle Production from Viral Vectors

AAV Particle Production

There are two main strategies for producing AAV particles from AAV vectors and systems thereof, such as those described herein, which depend on how the adenovirus helper factors are provided (helper v. helper free). In some

TABLE 1

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In some embodiments, the AAV vector or system thereof is AAV rh.74 or AAV rh.10.

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome ampliembodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g., the engineered AAV capsid polynucleotide(s)). In some embodiments, a method of producing AAV particles from AAV vectors and systems thereof can be a "helper free" method, which includes co-transfection of an appropriate producing cell line with three vectors (e.g., plasmid vectors): (1) an AAV vector that contains a polynucleotide of interest (e.g., the engineered AAV capsid polynucleotide(s)) between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

The engineered AAV vectors and systems thereof described herein can be produced by any of these methods.

Vector and Virus Particle Delivery

A vector (including non-viral carriers) described herein can be introduced into host cells to thereby produce transcripts, proteins, or peptides, including fusion proteins or peptides encoded by nucleic acids as described herein (e.g., engineered AAV capsid system transcripts, proteins, enzymes, mutant forms thereof, fusion proteins thereof, etc.), and virus particles (such as from viral vectors and systems thereof).

One or more engineered AAV capsid polynucleotides can be delivered using adeno associated virus (AAV), adenovirus or other plasmid or viral vector types as previously described, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus.

For plasmid delivery, the route of administration, formulation and dose can be as in U.S. Pat. No. 5,846,946 and as in clinical studies involving plasmids. In some embodiments, doses can be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into or otherwise delivered to the tissue or cell of interest.

In terms of in vivo delivery, AAV is advantageous over other viral vectors for a couple of reasons such as low toxicity (this may be due to the purification method not requiring ultra-centrifugation of cell particles that can activate the immune response) and a low probability of causing insertional mutagenesis because it doesn't integrate into the host genome.

The vector(s) and virus particles described herein can be delivered into a host cell in vitro, in vivo, and or ex vivo. Delivery can occur by any suitable method including, but not limited to, physical methods, chemical methods, and biological methods. Physical delivery methods are those methods that employ physical force to counteract the membrane barrier of the cells to facilitate intracellular delivery of the vector. Suitable physical methods include, but are not limited to, needles (e.g., injections), ballistic polynucleotides (e.g., particle bombardment, micro projectile gene transfer, and gene gun), electroporation, sonoporation, photoporation, magnetofection, hydroporation, and mechanical massage. Chemical methods are those methods that employ a chemical to elicit a change in the cells membrane permeability or other characteristic(s) to facilitate entry of the vector into the cell. For example, the environmental pH can be altered which can elicit a change in the permeability of the cell membrane. Biological methods are those that rely and capitalize on the host cell's biological processes or biological characteristics to facilitate transport of the vector (with or without a carrier) into a cell. For example, the vector and/or its carrier can stimulate an endocytosis or similar process in the cell to facilitate uptake of the vector into the cell.

Delivery of engineered AAV capsid system components (e.g., polynucleotides encoding engineered AAV capsid and/or capsid proteins) to cells via particles. The term "particle" as used herein, refers to any suitable sized particles for delivery of the engineered AAV capsid system components described herein. Suitable sizes include macro-, micro-, and nano-sized particles. In some embodiments, any of the of the engineered AAV capsid system components (e.g., polypeptides, polynucleotides, vectors and combinations thereof described herein) can be attached to, coupled to, integrated with, otherwise associated with one or more particles or component thereof as described herein. The particles described herein can then be administered to a cell or organism by an appropriate route and/or technique. In some embodiments, particle delivery can be selected and be advantageous for delivery of the polynucleotide or vector components. It will be appreciated that in embodiments, particle delivery can also be advantageous for other engineered capsid system molecules and formulations described elsewhere herein.

Engineered Virus Particles Including an Engineered Viral (e.g., AAV) Capsid

Also described herein are engineered virus particles (also referred to here and elsewhere herein as "engineered viral particles" that can contain an engineered viral capsid (e.g., AAV capsid, referred to as "engineered AAV particles") as described in detail elsewhere herein. It will be appreciated that the engineered AAV particles can be adenovirus-based particles, helper adenovirus-based particles, AAV-based particles, or hybrid adenovirus-based particles that contain at least one engineered AAV capsid proteins as previously described. An engineered AAV capsid is one that that contains one or more engineered AAV capsid proteins as are described elsewhere herein. In some embodiments, the engineered AAV particles can include 1-60 engineered AAV capsid proteins described herein. In some embodiments, the engineered AAV particles can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 engineered capsid proteins. In some embodiments, the engineered AAV particles can contain 0-59 wild-type AAV capsid proteins. In some embodiments, the engineered AAV particles can contain 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 wild-type AAV capsid proteins. The engineered AAV particles can thus include one or more n-mer motifs as is previously described.

The engineered AAV particle can include one or more cargo polynucleotides. Cargo polynucleotides are discussed in greater detail elsewhere herein. Methods of making the engineered AAV particles from viral and non-viral vectors are described elsewhere herein. Formulations containing the engineered virus particles are described elsewhere herein.

Cargo Polynucleotides

Cargos are also described elsewhere herein. In some embodiments, the cargo is a cargo polynucleotide that can be packaged into an engineered viral particle and subsequently delivered to a cell. In some embodiments, delivery is muscle specific. The engineered viral (e.g., AAV) capsid polynucleotides, other viral (e.g., AAV) polynucleotide(s), and/or vector polynucleotides can contain one or more cargo polynucleotides. In some embodiments, the one or more cargo polynucleotides can be operably linked to the engineered viral (e.g., AAV) capsid polynucleotide(s) and can be part of the engineered viral (e.g., AAV) genome of the viral (e.g., AAV) system of the present invention. The cargo polynucleotides can be packaged into an engineered viral (e.g., AAV) particle, which can be delivered to, e.g., a cell. In some embodiments, the cargo polynucleotide can be capable of modifying a polynucleotide (e.g., gene or transcript) of a cell to which it is delivered. As used herein, "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA. Polynucleotide, gene, transcript, etc. modification includes all genetic engineering techniques including, but not limited to, gene editing as well as conventional recombinational gene modification techniques (e.g., whole or partial gene insertion, deletion, and mutagenesis (e.g. insertional and deletional mutagenesis) techniques.

In some embodiments, the cargo molecule is a polynucleotide that is or can encode a vaccine. In some embodiments, the vaccine can stimulate an immune response against a cancer. In some embodiments, the vaccine can stimulate an immune response against colorectal or pancreatic cancer. In some embodiments, the vaccine can create an unstable environment for hCG-producing cells, such as hCG producing cancer cells.

Gene Modification Cargo Polynucleotides

In some embodiments, the cargo molecule can be a polynucleotide or polypeptide that can alone or when delivered as part of a system, whether or not delivered with other components of the system, operate to modify the genome, epigenome, and/or transcriptome of a cell to which it is delivered. Such systems include, but are not limited to, CRISPR-Cas systems. Other gene modification systems, e.g., TALENs, Zinc Finger nucleases, Cre-Lox, morpholinos, etc. are other non-limiting examples of gene modification systems whose one or more components can be delivered by the engineered viral (e.g., AAV) particles described herein.

In some embodiments, the cargo molecule is a gene editing system or component thereof. In some embodiments, the cargo molecule is a CRISPR-Cas system molecule or a component thereof. In some embodiments, the cargo molecule is a polynucleotide that encodes one or more components of a gene modification system (such as a CRISPR-Cas system). In some embodiments the cargo molecule is a gRNA.

In some embodiments, the cargo molecule can be a polynucleotide or polypeptide that can alone or when delivered as part of a system, whether or not delivered with other components of the system, operate to modify the genome, epigenome, and/or transcriptome of a cell to which it is delivered, is such that it treats or prevents a disease, a disorder, or a symptom thereof of a muscle or skeletal disorder, a neurologic disease or disorder, and/or viruses (such as single stranded RNA viruses). In some embodiments, the cargo molecule, whether or not delivered with other components of the system, operate to modify the genome, epigenome, and/or transcriptome of a cell to which it is delivered, is such that it treats or prevents, a progeroid disease (e.g. progeroid laminopathy) a glycogen storage disease an immune disorder (such as an autoimmune disease), a cancer, Duchenne muscular dystrophy (DMD), 6 Limb-girdle muscular dystrophy diseases (LGMD), Charcot-Marie-Tooth (CMT), MPS IIIA, Pompe disease, or other CNS-related diseases such as Huntington's and other expanded repeat diseases.

In some embodiments, the cargo molecule, whether or not delivered with other components of the system, operate to modify the genome, epigenome, and/or transcriptome of a cell to which it is delivered, is such that can modify the GAA gene, such as any of those described in US Pat. App. Pub. 20190284555, the contents of which are incorporated by reference as if expressed in their entirety herein and can be adapted for use with the present invention.

In some embodiments, the cargo molecule includes an oligonucleotide coupled to a MHCK7, CK8, or other muscle specific promoter.

In some embodiments, the cargo molecule is a micro-dystrophin oligonucleotide that contains only selected regions of the dystrophin gene optimized for protein functionality. In some embodiments, the selected regions include spectrin-like repeats 1, 2, 3, and 24. See e.g., Harper S Q, Hauser M A, DelloRusso C, et al. Modular flexibility of dystrophin: implications for gene therapy of Duchenne muscular dystrophy. Nat Med. 2002; 8(3):253-261. In some embodiments, the micro-dystrophin oligonucleotide is that is delivered by the rAAV agent known as AAVrh74. MHCK7 microdystrophin gene or SRP-9001, which is subject to the clinical trials NCT03375164 and NCT03769116. This microdystrophin gene construct includes NT-H1-R1-R2-R3-H2-R24-H4-CR-CT. In some embodiments, the microdystrophin gene includes ABD-H1-R1-R2-R3-H2-R24-H4-CR-CT. In some embodiments, the microdystrophin gene includes H stands for hinge region. England S B, et al. Nature. 1990; 343(6254):180-182; Wells D J, et al. Hum Mol Genet. 1995; 4(8):1245-1250, Salva M Z, et al. Mol Ther. 2007; 15(2):320-329; Mendell J R, et al. Neurosci Lett. 2012; 527(2):90-99; Rodino-Klapac L R, et al. Hum Mol Genet. 2013; 22(24):4929-4937; Velazquez V M, et al. Mol Ther Methods Clin Dev. 2017; 4:159-168; Harper S Q, et al. Nat Med. 2002; 8(3):253-261; Nelson D M, et al. Hum Mol Genet. 2018; 27(12):2090-2100. In some embodiments, the selected regions at least include spectrin-like repeats 2 and 3. In some embodiments, the micro-dystrophin gene contains a nNOS domain. In some embodiments, the nNOS domain is composed of spectrin-like repeats 16 and/or 17. In some embodiments, the micro-dystrophin gene includes spectrin-like repeats 16 and 17. In some embodiments, the nNOS domain is composed of spectrin-like repeats R1, R16, R17, R23, and R24. In some embodiments, the micro-dystrophin gene is coupled to a muscle specific promoter. In some embodiments, the micro-dystrophin oligonucleotide is coupled to a MHCK7, CK8, SNP18, SP0033, SP0051, SP0173, tmCK, or another muscle specific promoter.

In some embodiments, the cargo micro-dystrophin includes an ABD (actin binding domain), one or more hinge regions (e.g., H1, H2, H3, H4), and one or more spectrin-like repeats (e.g. R1, R1' R2, R3, R16, R17, R20, R21, R22, R23, R24, R24' and optionally a dystroglycan binding domain (DBD). In some embodiments, the micro-dystrophin is composed of ABD-H1-R1-R16-R17-R23-R24-H4-DBD. In some embodiments, the micro-dystrophin is composed of ABD-H1-R1-R2-R3-H2-R24-H4-CR. In some embodiments, the micro-dystrophin gene includes ABD-H1-R1-R2-R3-H2-R24-H4-CR-CT. In some embodiments, the micro-dystrophin gene includes ABD-H1-R1'-R24'-H4-CR-CT.

In some embodiments, the cargo molecule is a polynucleotide that can encode a micro-dystrophin gene, where the micro-dystrophin gene contains spectrin-like repeats, R1, R16, R17, R23 and R24. In some embodiments, the micro-dystrophin gene contains hinge region (H) 4 and/or H1. In some embodiments, the micro-dystrophin gene contains the N-terminal actin binding domain. In some embodiments, the micro-dystrophin gene contains the C-terminal dystroglycan binding domain of the human full-length dystrophin protein. The micro-dystrophin gene can contain an nNOS domain. In some embodiments, the nNOS domain is composed of spectrin-like repeats 16 and/or 17. In some embodiments, the micro-dystrophin gene includes spectrin-like repeats 16 and 17. The micro-dystrophin gene can be as described in WO2019118806A1 and WO2016/115543, which are incorporated by reference as if expressed in their entirety herein and can be adapted for use with the present invention. In some embodiments, the cargo polynucleotide can encode a 5-repeat micro-dystrophin protein that contains, from N- to C— terminus, the N-terminal actin binding domain, Hinge region 1 (H1), spectrin-like repeats R1, R16, R17, R23, and R24, Hinge region 4 (H4), and the C-terminal dystroglycan binding domain of the human full-length dystrophin protein. The protein sequence of this 5-repeat micro-dystrophin and the related dystrophin minigene are described in WO2016/115543. In some embodiments, the cargo polynucleotide can correspond to a micro-dystrophin gene that is part of the agent known as SGT001 as currently in clinical trial having the identifier number NCT03368742.

In some embodiments, the cargo molecule is a minidys gene or vector. In some embodiments, the minidys gene or vector can be composed of ABD-H1-R1-R2-R3-R16-R17-H3-R20-R21; ABD-H1-R1-R2-R3-R16-R17-H3-R20-R21-R22-R23-R24-H4-CR; or H3-R20-R21-R22-R23-R24-H4-CR-CT.

In some embodiments, the cargo molecule is an SCGB cDNA. In some embodiments, the SGCB cDNA is coupled to a MHCK7, CK8 promoter, SNP18 promoter, SP0033 promoter, SP0051, SP0173 promoter, tmCK promoter or another muscle specific promoter. In some embodiments, the cargo molecule is a beta-sarcoglycan cDNA, an alpha-sarcoglycan cDNA, a dysferlin cDNA, a gamma-sarcoglycan cDNA, a Calpin-3 cDNA, a SGSH cDNA (e.g., LYS-SAF302), a neurtropin 3 cDNA, an anoctamin-5 cDNA, or any combination thereof.

In some embodiments, the cargo molecule, whether or not delivered with other components of the system, operate to modify the genome, epigenome, and/or transcriptome of a cell to which it is delivered, is such that treat, prevent, and/or modify a gene or gene product associated with an expanded repeat disease, such as Huntington's disease, such as those described in U.S. Pat. App. Pub. 20190100755, U.S. patent Ser. No. 10/066,228, the contents of which are incorporated by reference as if expressed in their entirety herein and can be adapted for use with the present invention.

In some embodiments, the cargo molecule is an antisense oligomer or RNA molecule, such as those described in U.S. Pat. App. Pub. US20160251398, US20150267202, US20190015440, US20140287983, US20180216111, WO/2017/062835, US20190177723, US20170051278, US20180271893, WO/2016/14965, U.S. patent Ser. No. 10/076,536, WO/2018/00580, WO/2018/11866, WO/2019/059973, the contents of which are incorporated by reference as if expressed in their entirety herein and can be adapted for use with the present invention.

In some embodiments, the cargo molecule, whether or not delivered with other components of the system, operate to modify the genome, epigenome, and/or transcriptome of a cell to which it is delivered, is such that it treats or prevents a single stranded RNA virus, such as influenza, West Nile Virus, SARS, Hepatitis C, dengue fever, Ebola, Marburg, and/or Calicivirus. In some embodiments the cargo molecule can be an antisense antiviral compound, such as any of those described in U.S. Pat. No. 8,703,735B2, the contents of which are incorporated by reference as if expressed in their entirety herein and can be adapted for use with the present invention.

Additional, exemplary genetic and gene associated diseases and genes capable of being modified by a cargo molecule described herein are listed elsewhere herein, see e.g., Tables 4-5.

In some embodiments, the cargo molecule can add or modify a GALGT2 gene. Instead of acting to resupply missing dystrophin, GALGT2 gene therapy fortifies the structural integrity of muscle in ways that compensate for the absence of dystrophin, by increasing expression of proteins not mutated or lost in the disease. GALGT2 offers the potential to treat DMD irrespective of specific dystrophin mutation, as well as having utility in other muscular dystrophies.

In some embodiments the cargo molecule is a morpholino, such as in US Patent Application Pub. US2018/0161359 and US2019/0054113 the contents of which are incorporated by reference as if expressed in their entirety herein and can be adapted for use with the present invention. In some embodiments, the morpholino is a morpholino oligomer (PMO) or a peptide linked morpholino PPMO. PMO based platforms can be used to treat genetic diseases by altering mRNA transcription. PMOs are synthetic chemical structures modeled after the natural framework of RNA. While PMOs have the same nucleic acid bases found in RNA, they are bound to six-sided morpholine rings instead of five-sided ribose rings. In addition, the morpholine rings are connected to each other by phosphorodiamidate linkages instead of the phosphodiester linkages found in RNA. PMOs and PPMOs can be used for exon skipping and translation suppression.

In some embodiments, the cargo molecule can be a peptide-oligomer, conjugate as described in e.g., International Patent Application Publication WO2017106304A1, the contents of which are incorporated by reference as if expressed in their entirety herein and can be adapted for use with the present invention.

In some embodiments, the morpholino is the morpholino found in Eteplirsen, which can be effective to target Exon 51 of the dystrophin mRNA. In some embodiments the cargo molecule can generate exon skipping in the context of DMD, such as those described in e.g., US Patent Application Pub. US2014/0315977A1 and US2018/010581, the contents of which are incorporated by reference as if expressed in their entirety herein and can be adapted for use with the present invention.

Exon Skipping

In some embodiments, the nucleotide sequences may encode nucleic acids capable of inducing exon skipping. Such encoded nucleic acids may be antisense oligonucleotides or antisense nucleotide systems. As used herein, the term "exon skipping" refers to the modification of pre-mRNA splicing by the targeting of splice donor and/or acceptor sites within a pre-mRNA with one or more complementary antisense oligonucleotide(s) (AONs). By blocking access of a spliceosome to one or more splice donor or acceptor site, an AON may prevent a splicing reaction thereby causing the deletion of one or more exons from a fully-processed mRNA. Exon skipping may be achieved in the nucleus during the maturation process of pre-mRNAs. In some examples, exon skipping may include the masking of key sequences involved in the splicing of targeted exons by using antisense oligonucleotides (AON) that are complementary to splice donor sequences within a pre-mRNA.

In some embodiments, the nucleotide sequences encode antisense oligonucleotides or antisense nucleotide systems capable of inducing exon skipping in dystrophin mRNA. For example, a non-sense or frameshift mutation within exon x of a dystrophin gene yields a carboxy-terminally truncated, non-functional dystrophin protein. The expression of that mature mRNA transcript may yield a functional dystrophin protein that is deleted in the amino acids encoded by exon x but that includes dystrophin amino acids both N-terminal and C-terminal to those deleted amino acids.

The nucleotide sequences may encode antisense oligonucleotides or antisense nucleotide systems capable of inducing exon skipping at exon 1, 2, 3, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 45, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or any combination thereof. The nucleotide sequences may encode antisense oligonucleotides or antisense nucleotide systems capable of inducing exon skipping at exon 43, 44, 50, 51, 52, 55, or any combination thereof.

CRISPR-Cas System Cargo Molecules

In some embodiments, the engineered viral (e.g., AAV) or other particles described herein can include one or more CRISPR-Cas system molecules, which can be polynucleotides or polypeptides. In some embodiments, the polynucleotides can encode one or more CRISPR-Cas system molecules. In some embodiments, the polynucleotide encodes a Cas protein, a CRISPR Cascade protein, a gRNA, or a combination thereof. Other CRISPR-Cas system molecules are discussed elsewhere herein and can be delivered either as a polypeptide or a polynucleotide.

In general, a CRISPR-Cas or CRISPR system as used in herein and in documents, such as International Patent Application Publication WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target RNA may be an RNA polynucleotide or a part of a RNA polynucleotide to which a part of the gRNA, i.e., the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence is in this instance a sequence optimized for expression in eukaryote, e.g., humans (i.e., being optimized for expression in humans), or for another eukaryote, animal or mammal as herein discussed; see, e.g., SaCas9 human codon optimized sequence in International Patent Application Publication WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also, the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to International Patent Application Publication WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere. Lentiviral and retroviral systems, as well as non-viral systems for delivering CRISPR-Cas system components are generally known in the art. AAV and adenovirus-based systems for CRISPR-Cas system components are generally known in the art as well as described herein (e.g., the engineered AAVs of the present invention).

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain embodiments the invention involves vectors, e.g., for delivering or introducing in a cell Cas and/or RNA capable of guiding Cas to a target locus (i.e., guide RNA), but also for propagating these components (e.g., in prokaryotic cells). This can be in addition to delivery of one or more CRISPR-Cas components or other gene modification system component not already being delivered by an engineered AAV particle described herein. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. Patent Application Publication 2004/0171156, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words, samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see e.g., nar.oxford-journals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cas 12, Cas 12a, Cas 13a, Cas 13b, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium* siraeum DSM 15702 (EsCas13d) or *Ruminococcus* sp. N15. MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

The methods, systems, and tools provided herein may be designed for use with Class 1 CRISPR proteins, which may be Type I, Type III or Type IV Cas proteins as described in Makarova et al., The CRISPR Journal, v. 1, n., 5 (2018); DOI: 10.1089/crispr.2018.0033, incorporated in its entirety herein by reference, and particularly as described in FIG. 1, p. 326. The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g. Cas 4, DNA nuclease), CRISPR associated Rossman fold (CARF) domain containing proteins, and/or RNA transcriptase. Although Class 1 systems have limited sequence similarity, Class 1 system proteins can be identified by their similar architectures, including one or more Repeat Associated Mysterious Protein (RAMP) family subunits, e.g., Cas 5, Cas6, Cas7. RAMP proteins are characterized by having one or more RNA recognition motif domains. Large subunits (for example cas8 or cas10) and small subunits (for example, cas11) are also typical of Class 1 systems. See, e.g., FIGS. 1 and 2. Koonin E V, Makarova K S. 2019 Origins and evolution of CRISPR-Cas systems. Phil. Trans. R. Soc. B 374: 20180087, DOI: 10.1098/rstb.2018.0087. In one embodiment, Class 1 systems are characterized by the signature protein Cas3. The Cascade in particular Class1 proteins can comprise a dedicated complex of multiple Cas proteins that binds pre-crRNA and recruits an additional Cas protein, for example Cas6 or Cas5, which is the nuclease directly responsible for processing pre-crRNA. In one embodiment, the Type I CRISPR protein comprises an effector complex comprises one or more Cas5 subunits and two or more Cas7 subunits. Class 1 subtypes include Type I-A, I-B, I-C, I-U, I-D, I-E, and I-F, Type IV-A and IV-B, and Type III-A, III-D, III-C, and III-B. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al, the CRISPR Journal, v. 1, n5, FIG. 5.

Cas Molecules

In some embodiments, the cargo molecule can be or include a Cas polypeptide and/or a polynucleotide that can encode a Cas polypeptide or a fragment thereof. Any Cas molecule can be a cargo molecule. In some embodiments, the cargo molecule is Class I CRISPR-Cas system Cas polypeptide. In some embodiments, the cargo molecule is a Class II CRISPR-Cas system Cas polypeptide. In some embodiments, the Cas polypeptide is a Type I Cas polypeptides. In some embodiments, the Cas polypeptide is a Type II Cas polypeptides. In some embodiments, the Cas polypeptides is a Type III Cas polypeptide. In some embodiments, the Cas polypeptides is a Type IV Cas polypeptide. In some embodiments, the Cas polypeptides is a Type V Cas polypeptide. In some embodiments, the Cas polypeptides is a Type VI Cas polypeptide. In some embodiments, the Cas polypeptides is a Type VII Cas polypeptide. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cas 12, Cas 12a, Cas 13a, Cas 13b, Cas 13c, Cas 13d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

Guide Sequences

As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. Each gRNA may be designed to include multiple binding recognition sites (e.g., aptamers) specific to the same or different adapter protein. Each gRNA may be designed to bind to the promoter region −1000−+1 nucleic acids upstream of the transcription start site (i.e., TSS), preferably −200 nucleic acids. This positioning improves functional domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 g RNA, at least 50 gRNA) comprised in a composition. Said multiple gRNA sequences can be tandemly arranged and are preferably separated by a direct repeat.

In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that an RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at. novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

As used herein, the term "crRNA" or "guide RNA" or "single guide RNA" or "sgRNA" or "one or more nucleic acid components" of a Type V or Type VI CRISPR-Cas locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In general, the CRISPR-Cas, CRISPR-Cas9 or CRISPR system may be as used in the foregoing documents, such as International Patent Application Publication WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e., RNA capable of guiding Cas to a target genomic locus, are used interchangeably as in foregoing cited documents such as International Patent Application Publication WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an embodiment of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

The methods according to the invention as described herein comprehend inducing one or more mutations in a eukaryotic cell (in vitro, i.e., in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In certain embodiments, guides of the invention comprise non-naturally occurring nucleic acids and/or non-naturally occurring nucleotides and/or nucleotide analogs, and/or chemically modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, peptide nucleic acids (PNA), or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified nucleotides include linkage of chemical moieties at the 2' position, including but not limited to peptides, nuclear localization sequence (NLS), peptide nucleic acid (PNA), polyethylene glycol (PEG), triethylene glycol, or tetraethyleneglycol (TEG). Further examples of modified bases include, but are not limited to, 2-aminopurine, 5-bromo-uridine, pseudouridine ($\Psi$), $N^1$-methylpseudouridine (me$^1\Psi$), 5-methoxyuridine (5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl (cEt), 2'-O-methyl-3'-thioPACE (MSP), or 2'-O-methyl-3'-phosphonoacetate (MP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066; Ryan et al., Nucleic Acids Res. (2018) 46(2): 792-803). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), 2'-O-methyl-3'-thioPACE (MSP), or 2'-O-methyl-3'-phosphonoacetate (MP). Such modification can enhance genome editing efficiency (see Hendel et al., Nat. Biotechnol. (2015) 33(9): 985-989; Ryan et al., Nucleic Acids Res. (2018) 46(2): 792-803). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), Rhodamine, peptides, nuclear localization sequence (NLS), peptide nucleic acid (PNA), polyethylene glycol (PEG), triethylene glycol, or tetraethyleneglycol (TEG). In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554). In some embodiments, 3 nucleotides at each of the 3' and 5' ends are chemically modified. In a specific embodiment, the modifications comprise 2'-O-methyl or phosphorothioate analogs. In a specific embodiment, 12 nucleotides in the tetraloop and 16 nucleotides in the stem-loop region are replaced with 2'-O-methyl analogs. Such chemical modifications improve in vivo editing and stability (see Finn et al., Cell Reports (2018), 22: 2227-2235). In some embodiments, more than 60 or 70 nucleotides of the guide are chemically modified. In some embodiments, this modification comprises replacement of nucleotides with 2'-O-methyl or 2'-fluoro nucleotide analogs or phosphorothioate (PS) modification of phosphodiester bonds. In some embodiments, the chemical modification comprises 2'-O-methyl or 2'-fluoro modification of guide nucleotides extending outside of the nuclease protein when the CRISPR complex is formed or PS modification of 20 to 30 or more nucleotides of the 3'-terminus of the guide. In a particular embodiment, the chemical modification further comprises 2'-O-methyl analogs at the 5' end of the guide or 2'-fluoro analogs in the seed and tail regions. Such chemical modifications improve stability to nuclease degradation and maintain or enhance genome-editing activity or efficiency, but modification of all nucleotides may abolish the function of the guide (see Yin et al., Nat. Biotech. (2018), 35(12): 1179-1187). Such chemical modifications may be guided by knowledge of the structure of the CRISPR complex, including knowledge of the limited number of nuclease and RNA 2'-OH interactions (see Yin et al., Nat. Biotech. (2018), 35(12): 1179-1187). In some embodiments, one or more guide RNA nucleotides may be replaced with DNA nucleotides. In some embodiments, up to 2, 4, 6, 8, 10, or 12 RNA nucleotides of the 5'-end tail/seed guide region are replaced with DNA nucleotides. In certain embodiments, the majority of guide RNA nucleotides at the 3' end are replaced with DNA nucleotides. In particular embodiments, 16 guide RNA nucleotides at the 3' end are replaced with DNA nucleotides. In particular embodiments, 8 guide RNA nucleotides of the 5'-end tail/seed region and 16 RNA nucleotides at the 3' end are replaced with DNA nucleotides. In particular embodiments, guide RNA nucleotides that extend outside of the nuclease protein when the CRISPR complex is formed are replaced with DNA nucleotides. Such replacement of multiple RNA nucleotides with DNA nucleotides leads to decreased off-target activity but similar on-target activity compared to an unmodified guide; however, replacement of all RNA nucleotides at the 3' end may abolish the function of the guide (see Yin et al., Nat. Chem. Biol. (2018) 14, 311-316). Such modifications may be guided by knowledge of the structure of the CRISPR complex, including knowledge of the limited number of nuclease and RNA 2'-OH interactions (see Yin et al., Nat. Chem. Biol. (2018) 14, 311-316).

In one embodiment of the invention, the guide comprises a modified crRNA for Cpf1, having a 5'-handle and a guide segment further comprising a seed region and a 3'-terminus. In some embodiments, the modified guide can be used with a Cpf1 of any one of *Acidaminococcus* sp. BV3L6 Cpf1 (AsCpf1); *Francisella tularensis* subsp. *Novicida* U112 Cpf1 (FnCpf1); *L. bacterium* MC2017 Cpf1 (Lb3Cpf1); *Butyrivibrio proteoclasticus* Cpf1 (BpCpf1); Parcubacteria bacterium GWC2011_GWC2_44_17 Cpf1 (PbCpf1); Peregrinibacteria bacterium GW2011_GWA_33_10 Cpf1 (PeCpf1); *Leptospira inadai* Cpf1 (LiCpf1); *Smithella* sp. SC_K08D17 Cpf1 (SsCpf1); *L. bacterium* MA2020 Cpf1 (Lb2Cpf1); *Porphyromonas crevioricanis* Cpf1 (PcCpf1); *Porphyromonas macacae* Cpf1 (PmCpf1); *Candidatus Methanoplasma termitum* Cpf1 (CMtCpf1); *Eubacterium eligens* Cpf1 (EeCpf1); *Moraxella bovoculi* 237 Cpf1 (MbCpf1); *Prevotella disiens* Cpf1 (PdCpf1); or *L. bacterium* ND2006 Cpf1 (LbCpf1).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromouridine, pseudouridine ($\Psi$), $N^1$-methylpseudouridine (me$^1\Psi$), 5-methoxyuridine (5moU), inosine, 7-methylguanosine, 2'-O-methyl-3'-phosphorothioate (MS), S-constrained ethyl(cEt), phosphorothioate (PS), 2'-O-methyl-3'-thioPACE (MSP), or 2'-O-methyl-3'-phosphonoacetate (MP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In some embodiments, all nucleotides are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., Nature Biomedical Engineering, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs. In some embodiments, 3 nucleotides at each of the 3' and 5' ends are chemically modified. In a specific embodiment, the modifications comprise 2'-O-methyl or phosphorothioate analogs. In a specific embodiment, 12 nucleotides in the tetraloop and 16 nucleotides in the stem-loop region are replaced with 2'-O-methyl analogs. Such chemical modifications improve in vivo editing and stability (see Finn et al., Cell Reports (2018), 22: 2227-2235).

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU. In some embodiments, the guide molecule forms a stemloop with a separate non-covalently linked sequence, which can be DNA or RNA.

Synthetically Linked Guide

In one embodiment, the guide comprises a tracr sequence and a tracr mate sequence that are chemically linked or conjugated via a non-phosphodiester bond. In one embodiment, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in International Patent Application Publication WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in International Patent Application Publication WO2011/008730.

A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain embodiments of guide architecture are retained, certain embodiment of guide architecture cam be modified, for example by addition, subtraction, or substitution of features, whereas certain other embodiments of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2.

In certain embodiments, guides of the invention comprise specific binding sites (e.g., aptamers) for adapter proteins, which may comprise one or more functional domains (e.g., via fusion protein). When such a guides forms a CRISPR complex (i.e., CRISPR enzyme binding to guide and target) the adapter proteins bind and, the functional domain associated with the adapter protein is positioned in a spatial orientation which is advantageous for the attributed function to be effective. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target.

The skilled person will understand that modifications to the guide which allow for binding of the adapter+functional domain but not proper positioning of the adapter+functional domain (e.g., due to steric hindrance within the three-dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and most preferably at both the tetra loop and stem loop 2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one embodiment, the stemloop 2, e.g., "ACTTgtt-tAAGT" (SEQ ID NO: 36) can be replaced by any "XXXXgtttYYYY" (SEQ ID NO: 37), e.g., where XXXX and YYYY represent any complementary sets of nucleotides that together will base pair to each other to create a stem.

In one embodiment, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one embodiment, the stem made of the X and Y nucleotides, together with the "gttt," will form a complete hairpin in the overall secondary structure; and this may be advantageous and the amount of base pairs can be any amount that forms a complete hairpin. In one embodiment, any complementary X:Y base-pairing sequence (e.g., as to length) is tolerated, so long as the secondary structure of the entire sgRNA is preserved. In one embodiment, the stem can be a form of X:Y base-pairing that does not disrupt the secondary structure of the whole sgRNA in that it has a DR:tracr duplex, and 3 stemloops. In one embodiment, the "gttt" tetraloop that connects ACTT and AAGT (or any alternative stem made of X:Y base pairs) can be any sequence of the same length (e.g., 4 base pair) or longer that does not interrupt the overall secondary structure of the sgRNA. In one embodiment, the stemloop can be something that further lengthens stemloop2, e.g., can be MS2 aptamer. In one embodiment, the stemloop3 "GGCACCGagtCGGTGC" (SEQ ID NO: 38) can likewise take on a "XXXXXXXagtYYYYYYY" (SEQ ID NO: 39) form, e.g., wherein X7 and Y7 represent any complementary sets of nucleotides that together will base pair to each other to create a stem. In one embodiment, the stem comprises about 7 bp comprising complementary X and Y sequences, although stems of more or fewer base pairs are also contemplated. In one embodiment, the stem made of the X and Y nucleotides, together with the "agt", will form a complete hairpin in the overall secondary structure. In one embodiment, any complementary X:Y base pairing sequence is tolerated, so long as the secondary structure of the entire sgRNA is preserved. In one embodiment, the stem can be a form of X:Y basepairing that doesn't disrupt the secondary structure of the whole sgRNA in that it has a DR:tracr duplex, and 3 stemloops. In one embodiment, the "agt" sequence of the stemloop 3 can be extended or be replaced by an aptamer, e.g., a MS2 aptamer or sequence that otherwise generally preserves the architecture of stemloop3. In one embodiment for alternative Stemloops 2 and/or 3, each X and Y pair can refer to any base pair. In one embodiment, non-Watson Crick base pairing is contemplated, where such pairing otherwise generally preserves the architecture of the stemloop at that position.

In one embodiment, the DR:tracrRNA duplex can be replaced with the form: gYYYYag(N)NNNNxxxxNNNN (AAN)uuRRRRu (SEQ ID NO: 40) (using standard IUPAC nomenclature for nucleotides), wherein (N) and (AAN) represent part of the bulge in the duplex, and "xxxx" represents a linker sequence. NNNN on the direct repeat can be anything so long as it base-pairs with the corresponding NNNN portion of the tracrRNA. In one embodiment, the DR:tracrRNA duplex can be connected by a linker of any length (xxxx . . . ), any base composition, as long as it doesn't alter the overall structure.

In one embodiment, the sgRNA structural requirement is to have a duplex and 3 stemloops. In most embodiments, the actual sequence requirement for many of the particular base requirements are lax, in that the architecture of the DR:tracrRNA duplex should be preserved, but the sequence that creates the architecture, i.e., the stems, loops, bulges, etc., may be altered.

Aptamers

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer-------MS2 RNA-binding protein------VP64 activator; and

Guide 2—PP7 aptamer-------PP7 RNA-binding protein-------SID4× repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS can be used. They can be used in repeats of 3 ((GGGGS)₃(SEQ ID NO: 35)) or 6, 9 or even 12 or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

Dead Guides

In one embodiment, the invention provides guide sequences which are modified in a manner which allows for formation of the CRISPR complex and successful binding to the target, while at the same time, not allowing for successful nuclease activity (i.e., without nuclease activity/without indel activity). For matters of explanation such modified guide sequences are referred to as "dead guides" or "dead guide sequences". These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity. Briefly, the surveyor assay involves purifying and amplifying a CRISPR target site for a gene and forming heteroduplexes with primers amplifying the CRISPR target site. After re-anneal, the products are treated with SURVEYOR nuclease and SURVEYOR enhancer S (Transgenomics) following the manufacturer's recommended protocols, analyzed on gels, and quantified based upon relative band intensities.

Hence, in a related embodiment, the invention provides a non-naturally occurring or engineered composition Cas9 CRISPR-Cas system comprising a functional Cas9 as described herein, and guide RNA (gRNA) wherein the gRNA comprises a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay. For shorthand purposes, a gRNA comprising a dead guide sequence whereby the gRNA is capable of hybridizing to a target sequence such that the Cas9 CRISPR-Cas system is directed to a genomic locus of interest in a cell without detectable indel activity resultant from nuclease activity of a non-mutant Cas9 enzyme of the system as detected by a SURVEYOR assay is herein termed a "dead gRNA". It is to be understood that any of the gRNAs according to the invention as described herein elsewhere may be used as dead gRNAs/gRNAs comprising a dead guide sequence as described herein below. Any of the methods, products, compositions and uses as described herein elsewhere is equally applicable with the dead gRNAs/gRNAs comprising a dead guide sequence as further detailed below. By means of further guidance, the following particular embodiments and embodiments are provided.

The ability of a dead guide sequence to direct sequence-specific binding of a CRISPR complex to a target sequence may be assessed by any suitable assay. For example, the components of a CRISPR system sufficient to form a CRISPR complex, including the dead guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

As explained further herein, several structural parameters allow for a proper framework to arrive at such dead guides. Dead guide sequences are shorter than respective guide sequences which result in active Cas9-specific indel formation. Dead guides are 5%, 10%, 20%, 30%, 40%, 50%, shorter than respective guides directed to the same Cas9 leading to active Cas9-specific indel formation.

As explained below and known in the art, one embodiment of gRNA-Cas9 specificity is the direct repeat sequence, which is to be appropriately linked to such guides. In particular, this implies that the direct repeat sequences are designed dependent on the origin of the Cas9. Thus, structural data available for validated dead guide sequences may be used for designing Cas9 specific equivalents. Structural similarity between, e.g., the orthologous nuclease domains RuvC of two or more Cas9 effector proteins may be used to transfer design equivalent dead guides. Thus, the dead guide herein may be appropriately modified in length and sequence to reflect such Cas9 specific equivalents, allowing for formation of the CRISPR complex and successful binding to the target, while at the same time, not allowing for successful nuclease activity.

The use of dead guides in the context herein as well as the state of the art provides a surprising and unexpected platform for network biology and/or systems biology in both in vitro, ex vivo, and in vivo applications, allowing for multiplex gene targeting, and in particular bidirectional multiplex gene targeting. Prior to the use of dead guides, addressing multiple targets, for example for activation, repression and/or silencing of gene activity, has been challenging and in some cases not possible. With the use of dead guides, multiple targets, and thus multiple activities, may be addressed, for example, in the same cell, in the same animal, or in the same patient. Such multiplexing may occur at the same time or staggered for a desired timeframe.

For example, the dead guides now allow for the first time to use gRNA as a means for gene targeting, without the consequence of nuclease activity, while at the same time providing directed means for activation or repression. Guide RNA comprising a dead guide may be modified to further include elements in a manner which allow for activation or repression of gene activity, in particular protein adaptors (e.g., aptamers) as described herein elsewhere allowing for functional placement of gene effectors (e.g., activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g., an activator or repressor; dimerized MS2 bacteriophage coat proteins as fusion proteins with an activator or repressor), or a protein which itself binds an effector (e.g., activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

Thus, one embodiment is a gRNA of the invention which comprises a dead guide, wherein the gRNA further comprises modifications which provide for gene activation or repression, as described herein. The dead gRNA may comprise one or more aptamers. The aptamers may be specific to gene effectors, gene activators or gene repressors. Alternatively, the aptamers may be specific to a protein which in turn is specific to and recruits/binds a specific gene effector, gene activator or gene repressor. If there are multiple sites for activator or repressor recruitment, it is preferred that the sites are specific to either activators or repressors. If there are multiple sites for activator or repressor binding, the sites may be specific to the same activators or same repressors. The sites may also be specific to different activators or different repressors. The gene effectors, gene activators, gene repressors may be present in the form of fusion proteins.

In an embodiment, the dead gRNA as described herein or the Cas9 CRISPR-Cas complex as described herein includes a non-naturally occurring or engineered composition comprising two or more adaptor proteins, wherein each protein is associated with one or more functional domains and wherein the adaptor protein binds to the distinct RNA sequence(s) inserted into the at least one loop of the dead gRNA.

Hence, an embodiment provides a non-naturally occurring or engineered composition comprising a guide RNA (gRNA) comprising a dead guide sequence capable of hybridizing to a target sequence in a genomic locus of interest in a cell, wherein the dead guide sequence is as defined herein, a Cas9 comprising at least one or more nuclear localization sequences, wherein the Cas9 optionally comprises at least one mutation wherein at least one loop of the dead gRNA is modified by the insertion of distinct RNA sequence(s) that bind to one or more adaptor proteins, and wherein the adaptor protein is associated with one or more functional domains; or, wherein the dead gRNA is modified to have at least one non-coding functional loop, and wherein the composition comprises two or more adaptor proteins, wherein the each protein is associated with one or more functional domains.

In certain embodiments, the adaptor protein is a fusion protein comprising the functional domain, the fusion protein optionally comprising a linker between the adaptor protein and the functional domain, the linker optionally including a GlySer linker.

In certain embodiments, the at least one loop of the dead gRNA is not modified by the insertion of distinct RNA sequence(s) that bind to the two or more adaptor proteins.

In certain embodiments, the one or more functional domains associated with the adaptor protein is a transcriptional activation domain.

In certain embodiments, the one or more functional domains associated with the adaptor protein is a transcriptional activation domain comprising VP64, p65, MyoD1, HSF1, RTA or SET7/9.

In certain embodiments, the one or more functional domains associated with the adaptor protein is a transcriptional repressor domain.

In certain embodiments, the transcriptional repressor domain is a KRAB domain.

In certain embodiments, the transcriptional repressor domain is a NuE domain, NcoR domain, SID domain or a SID4X domain.

In certain embodiments, at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity.

In certain embodiments, the DNA cleavage activity is due to a Fok1 nuclease.

In certain embodiments, the dead gRNA is modified so that, after dead gRNA binds the adaptor protein and further binds to the Cas9 and target, the functional domain is in a spatial orientation allowing for the functional domain to function in its attributed function.

In certain embodiments, the at least one loop of the dead gRNA is tetra loop and/or loop2. In certain embodiments, the tetra loop and loop 2 of the dead gRNA are modified by the insertion of the distinct RNA sequence(s).

In certain embodiments, the insertion of distinct RNA sequence(s) that bind to one or more adaptor proteins is an aptamer sequence. In certain embodiments, the aptamer sequence is two or more aptamer sequences specific to the same adaptor protein. In certain embodiments, the aptamer sequence is two or more aptamer sequences specific to different adaptor protein.

In certain embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

In certain embodiments, the cell is a eukaryotic cell. In certain embodiments, the eukaryotic cell is a mammalian cell, optionally a mouse cell. In certain embodiments, the mammalian cell is a human cell.

In certain embodiments, a first adaptor protein is associated with a p65 domain and a second adaptor protein is associated with a HSF1 domain.

In certain embodiments, the composition comprises a Cas9 CRISPR-Cas complex having at least three functional domains, at least one of which is associated with the Cas9 and at least two of which are associated with dead gRNA.

In certain embodiments, the composition further comprises a second gRNA, wherein the second gRNA is a live gRNA capable of hybridizing to a second target sequence such that a second Cas9 CRISPR-Cas system is directed to a second genomic locus of interest in a cell with detectable indel activity at the second genomic locus resultant from nuclease activity of the Cas9 enzyme of the system.

In certain embodiments, the composition further comprises a plurality of dead gRNAs and/or a plurality of live gRNAs.

One embodiment of the invention is to take advantage of the modularity and customizability of the gRNA scaffold to establish a series of gRNA scaffolds with different binding sites (in particular aptamers) for recruiting distinct types of effectors in an orthogonal manner. Again, for matters of example and illustration of the broader concept, replacement of the MS2 stem-loops with PP7-interacting stem-loops may be used to bind/recruit repressive elements, enabling multiplexed bidirectional transcriptional control. Thus, in general, gRNA comprising a dead guide may be employed to provide for multiplex transcriptional control and preferred bidirectional transcriptional control. This transcriptional control is most preferred of genes. For example, one or more gRNA comprising dead guide(s) may be employed in targeting the activation of one or more target genes. At the same time, one or more gRNA comprising dead guide(s) may be employed in targeting the repression of one or more target genes. Such a sequence may be applied in a variety of different combinations, for example the target genes are first repressed and then at an appropriate period other targets are activated, or select genes are repressed at the same time as select genes are activated, followed by further activation and/or repression. As a result, multiple components of one or more biological systems may advantageously be addressed together.

In an embodiment, the invention provides nucleic acid molecule(s) encoding dead gRNA or the Cas9 CRISPR-Cas complex or the composition as described herein.

In an embodiment, the invention provides a vector system comprising: a nucleic acid molecule encoding dead guide RNA as defined herein. In certain embodiments, the vector system further comprises a nucleic acid molecule(s) encoding Cas9. In certain embodiments, the vector system further comprises a nucleic acid molecule(s) encoding (live) gRNA. In certain embodiments, the nucleic acid molecule or the vector further comprises regulatory element(s) operable in a eukaryotic cell operably linked to the nucleic acid molecule encoding the guide sequence (gRNA) and/or the nucleic acid molecule encoding Cas9 and/or the optional nuclear localization sequence(s).

In another embodiment, structural analysis may also be used to study interactions between the dead guide and the active Cas9 nuclease that enable DNA binding, but no DNA cutting. In this way amino acids important for nuclease activity of Cas9 are determined. Modification of such amino acids allows for improved Cas9 enzymes used for gene editing.

A further embodiment is combining the use of dead guides as explained herein with other applications of CRISPR, as explained herein as well as known in the art. For example, gRNA comprising dead guide(s) for targeted multiplex gene activation or repression or targeted multiplex bidirectional gene activation/repression may be combined with gRNA comprising guides which maintain nuclease activity, as explained herein. Such gRNA comprising guides which maintain nuclease activity may or may not further include modifications which allow for repression of gene activity (e.g., aptamers). Such gRNA comprising guides which maintain nuclease activity may or may not further include modifications which allow for activation of gene activity (e.g., aptamers). In such a manner, a further means for multiplex gene control is introduced (e.g., multiplex gene targeted activation without nuclease activity/without indel activity may be provided at the same time or in combination with gene targeted repression with nuclease activity).

For example, 1) using one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene activators; 2) may be combined with one or more gRNA (e.g., 1-50, 1-40, 1-30, 1-20, preferably 1-10, more preferably 1-5) comprising dead guide(s) targeted to one or more genes and further modified with appropriate aptamers for the recruitment of gene repressors. 1) and/or 2) may then be combined with 3) one or more gRNA (e.g., 1-50, 1-40, 1-30, 1-20, preferably 1-10, more preferably 1-5) targeted to one or more genes. This combination can then be carried out in turn with 1)+2)+3) with 4) one or more gRNA (e.g., 1-50, 1-40, 1-30, 1-20, preferably 1-10, more preferably 1-5) targeted to one or more genes and further modified with appropriate aptamers for the recruitment of gene activators. This combination can then be carried in turn with 1)+2)+3)+4) with 5) one or more gRNA (e.g., 1-50, 1-40, 1-30, 1-20, preferably 1-10, more preferably 1-5) targeted to one or more genes and further modified with appropriate aptamers for the recruitment of gene repressors. As a result, various uses and combinations are included in the invention. For example, combination 1)+2); combination 1)+3); combination 2)+3); combination 1)+2)+3); combination 1)+2)+3)+4); combination 1)+3)+4); combination 2)+3)+4); combination 1)+2)+4); combination 1)+2)+3)+4)+5); combination 1)+3)+4)+5); combination 2)+3)+4)+5); combination 1)+2)+4)+5); combination 1)+2)+3)+5); combination 1)+3)+5); combination 2)+3)+5); combination 1)+2)+5).

In an embodiment, the invention provides an algorithm for designing, evaluating, or selecting a dead guide RNA targeting sequence (dead guide sequence) for guiding a Cas9 CRISPR-Cas system to a target gene locus. In particular, it has been determined that dead guide RNA specificity relates to and can be optimized by varying i) GC content and ii) targeting sequence length. In an embodiment, the invention provides an algorithm for designing or evaluating a dead guide RNA targeting sequence that minimizes off-target binding or interaction of the dead guide RNA. In an embodiment of the invention, the algorithm for selecting a dead guide RNA targeting sequence for directing a CRISPR system to a gene locus in an organism comprises a) locating one or more CRISPR motifs in the gene locus, analyzing the 20 nucleotide (nt) sequence downstream of each CRISPR motif by i) determining the GC content of the sequence; and ii) determining whether there are off-target matches of the 15 downstream nucleotides nearest to the CRISPR motif in the genome of the organism, and c) selecting the 15 nucleotide sequence for use in a dead guide RNA if the GC content of the sequence is 70% or less and no off-target matches are identified. In an embodiment, the sequence is selected for a targeting sequence if the GC content is 60% or less. In certain embodiments, the sequence is selected for a targeting sequence if the GC content is 55% or less, 50% or less, 45% or less, 40% or less, 35% or less or 30% or less. In an embodiment, two or more sequences of the gene locus are analyzed and the sequence having the lowest GC content, or the next lowest GC content, or the next lowest GC content is selected. In an embodiment, the sequence is selected for a targeting sequence if no off-target matches are identified in the genome of the organism. In an embodiment, the targeting sequence is selected if no off-target matches are identified in regulatory sequences of the genome.

In an embodiment, the invention provides a method of selecting a dead guide RNA targeting sequence for directing a functionalized CRISPR system to a gene locus in an organism, which comprises: a) locating one or more CRISPR motifs in the gene locus; b) analyzing the 20 nt sequence downstream of each CRISPR motif by: i) determining the GC content of the sequence; and ii) determining whether there are off-target matches of the first 15 nt of the sequence in the genome of the organism; c) selecting the sequence for use in a guide RNA if the GC content of the sequence is 70% or less and no off-target matches are identified. In an embodiment, the sequence is selected if the GC content is 50% or less. In an embodiment, the sequence is selected if the GC content is 40% or less. In an embodiment, the sequence is selected if the GC content is 30% or less. In an embodiment, two or more sequences are analyzed and the sequence having the lowest GC content is selected. In an embodiment, off-target matches are determined in regulatory sequences of the organism. In an embodiment, the gene locus is a regulatory region. An embodiment provides a dead guide RNA comprising the targeting sequence selected according to the aforementioned methods.

In an embodiment, the invention provides a dead guide RNA for targeting a functionalized CRISPR system to a gene locus in an organism. In an embodiment of the invention, the dead guide RNA comprises a targeting sequence wherein the CG content of the target sequence is 70% or less, and the first 15 nt of the targeting sequence does not match an off-target sequence downstream from a CRISPR motif in the regulatory sequence of another gene locus in the organism. In certain embodiments, the GC content of the targeting sequence 60% or less, 55% or less, 50% or less, 45% or less, 40% or less, 35% or less or 30% or less. In certain embodiments, the GC content of the targeting sequence is from 70% to 60% or from 60% to 50% or from 50% to 40% or from 40% to 30%. In an embodiment, the targeting sequence has the lowest CG content among potential targeting sequences of the locus.

In an embodiment of the invention, the first 15 nt of the dead guide match the target sequence. In another embodiment, first 14 nt of the dead guide match the target sequence. In another embodiment, the first 13 nt of the dead guide match the target sequence. In another embodiment first 12 nt of the dead guide match the target sequence. In another embodiment, first 11 nt of the dead guide match the target sequence. In another embodiment, the first 10 nt of the dead guide match the target sequence. In an embodiment of the invention the first 15 nt of the dead guide does not match an off-target sequence downstream from a CRISPR motif in the regulatory region of another gene locus. In other embodiments, the first 14 nt, or the first 13 nt of the dead guide, or the first 12 nt of the guide, or the first 11 nt of the dead guide, or the first 10 nt of the dead guide, does not match an off-target sequence downstream from a CRISPR motif in the regulatory region of another gene locus. In other embodiments, the first 15 nt, or 14 nt, or 13 nt, or 12 nt, or 11 nt of the dead guide do not match an off-target sequence downstream from a CRISPR motif in the genome.

In certain embodiments, the dead guide RNA includes additional nucleotides at the 3'-end that do not match the target sequence. Thus, a dead guide RNA that includes the first 15 nt, or 14 nt, or 13 nt, or 12 nt, or 11 nt downstream of a CRISPR motif can be extended in length at the 3' end to 12 nt, 13 nt, 14 nt, 15 nt, 16 nt, 17 nt, 18 nt, 19 nt, 20 nt, or longer.

The invention provides a method for directing a Cas9 CRISPR-Cas system, including but not limited to a dead Cas9 (dCas9) or functionalized Cas9 system (which may comprise a functionalized Cas9 or functionalized guide) to a gene locus. In an embodiment, the invention provides a method for selecting a dead guide RNA targeting sequence and directing a functionalized CRISPR system to a gene locus in an organism. In an embodiment, the invention provides a method for selecting a dead guide RNA targeting sequence and effecting gene regulation of a target gene locus by a functionalized Cas9 CRISPR-Cas system. In certain embodiments, the method is used to effect target gene regulation while minimizing off-target effects. In an embodiment, the invention provides a method for selecting two or more dead guide RNA targeting sequences and effecting gene regulation of two or more target gene loci by a functionalized Cas9 CRISPR-Cas system. In certain embodiments, the method is used to effect regulation of two or more target gene loci while minimizing off-target effects.

In an embodiment, the invention provides a method of selecting a dead guide RNA targeting sequence for directing a functionalized Cas9 to a gene locus in an organism, which comprises: a) locating one or more CRISPR motifs in the gene locus; b) analyzing the sequence downstream of each CRISPR motif by: i) selecting 10 to 15 nt adjacent to the CRISPR motif, ii) determining the GC content of the sequence; and c) selecting the 10 to 15 nt sequence as a targeting sequence for use in a guide RNA if the GC content of the sequence is 40% or more. In an embodiment, the sequence is selected if the GC content is 50% or more. In an embodiment, the sequence is selected if the GC content is 60% or more. In an embodiment, the sequence is selected if the GC content is 70% or more. In an embodiment, two or more sequences are analyzed and the sequence having the highest GC content is selected. In an embodiment, the method further comprises adding nucleotides to the 3' end of the selected sequence which do not match the sequence downstream of the CRISPR motif. An embodiment provides a dead guide RNA comprising the targeting sequence selected according to the aforementioned methods.

In an embodiment, the invention provides a dead guide RNA for directing a functionalized CRISPR system to a gene locus in an organism wherein the targeting sequence of the dead guide RNA consists of 10 to 15 nucleotides adjacent to the CRISPR motif of the gene locus, wherein the CG content of the target sequence is 50% or more. In certain embodiments, the dead guide RNA further comprises nucleotides added to the 3' end of the targeting sequence which do not match the sequence downstream of the CRISPR motif of the gene locus.

In an embodiment, the invention provides for a single effector to be directed to one or more, or two or more gene loci. In certain embodiments, the effector is associated with a Cas9, and one or more, or two or more selected dead guide RNAs are used to direct the Cas9-associated effector to one or more, or two or more selected target gene loci. In certain embodiments, the effector is associated with one or more, or two or more selected dead guide RNAs, each selected dead guide RNA, when complexed with a Cas9 enzyme, causing its associated effector to localize to the dead guide RNA target. One non-limiting example of such CRISPR systems modulates activity of one or more, or two or more gene loci subject to regulation by the same transcription factor.

In an embodiment, the invention provides for two or more effectors to be directed to one or more gene loci. In certain embodiments, two or more dead guide RNAs are employed, each of the two or more effectors being associated with a selected dead guide RNA, with each of the two or more effectors being localized to the selected target of its dead guide RNA. One non-limiting example of such CRISPR systems modulates activity of one or more, or two or more gene loci subject to regulation by different transcription factors. Thus, in one non-limiting embodiment, two or more transcription factors are localized to different regulatory sequences of a single gene. In another non-limiting embodiment, two or more transcription factors are localized to different regulatory sequences of different genes. In certain embodiments, one transcription factor is an activator. In certain embodiments, one transcription factor is an inhibitor. In certain embodiments, one transcription factor is an activator and another transcription factor is an inhibitor. In certain embodiments, gene loci expressing different components of the same regulatory pathway are regulated. In certain embodiments, gene loci expressing components of different regulatory pathways are regulated.

In an embodiment, the invention also provides a method and algorithm for designing and selecting dead guide RNAs that are specific for target DNA cleavage or target binding and gene regulation mediated by an active Cas9 CRISPR-Cas system. In certain embodiments, the Cas9 CRISPR-Cas system provides orthogonal gene control using an active Cas9 which cleaves target DNA at one gene locus while at the same time binds to and promotes regulation of another gene locus.

In an embodiment, the invention provides an method of selecting a dead guide RNA targeting sequence for directing a functionalized Cas9 to a gene locus in an organism, without cleavage, which comprises a) locating one or more CRISPR motifs in the gene locus; b) analyzing the sequence downstream of each CRISPR motif by i) selecting 10 to 15 nt adjacent to the CRISPR motif, ii) determining the GC content of the sequence, and c) selecting the 10 to 15 nt sequence as a targeting sequence for use in a dead guide RNA if the GC content of the sequence is 30% more, 40% or more. In certain embodiments, the GC content of the targeting sequence is 35% or more, 40% or more, 45% or more, 50% or more, 55% or more, 60% or more, 65% or more, or 70% or more. In certain embodiments, the GC content of the targeting sequence is from 30% to 40% or from 40% to 50% or from 50% to 60% or from 60% to 70%. In an embodiment of the invention, two or more sequences in a gene locus are analyzed and the sequence having the highest GC content is selected.

In an embodiment of the invention, the portion of the targeting sequence in which GC content is evaluated is 10 to 15 contiguous nucleotides of the 15 target nucleotides nearest to the PAM. In an embodiment of the invention, the portion of the guide in which GC content is considered is the 10 to 11 nucleotides or 11 to 12 nucleotides or 12 to 13 nucleotides or 13, or 14, or 15 contiguous nucleotides of the 15 nucleotides nearest to the PAM.

In an embodiment, the invention further provides an algorithm for identifying dead guide RNAs which promote CRISPR system gene locus cleavage while avoiding functional activation or inhibition. It is observed that increased GC content in dead guide RNAs of 16 to 20 nucleotides coincides with increased DNA cleavage and reduced functional activation.

In some embodiments, the efficiency of functionalized Cas9 can be increased by addition of nucleotides to the 3' end of a guide RNA which do not match a target sequence downstream of the CRISPR motif. For example, of dead guide RNA 11 to 15 nt in length, shorter guides may be less likely to promote target cleavage but are also less efficient at promoting CRISPR system binding and functional control. In certain embodiments, addition of nucleotides that don't match the target sequence to the 3' end of the dead guide RNA increase activation efficiency while not increasing undesired target cleavage. In an embodiment, the invention also provides a method and algorithm for identifying improved dead guide RNAs that effectively promote CRISPRP system function in DNA binding and gene regulation while not promoting DNA cleavage. Thus, in certain embodiments, the invention provides a dead guide RNA that includes the first 15 nt, or 14 nt, or 13 nt, or 12 nt, or 11 nt downstream of a CRISPR motif and is extended in length at the 3' end by nucleotides that mismatch the target to 12 nt, 13 nt, 14 nt, 15 nt, 16 nt, 17 nt, 18 nt, 19 nt, 20 nt, or longer.

In an embodiment, the invention provides a method for effecting selective orthogonal gene control. As will be appreciated from the disclosure herein, dead guide selection according to the invention, taking into account guide length and GC content, provides effective and selective transcription control by a functional Cas9 CRISPR-Cas system, for example to regulate transcription of a gene locus by activation or inhibition and minimize off-target effects. Accordingly, by providing effective regulation of individual target loci, the invention also provides effective orthogonal regulation of two or more target loci.

In certain embodiments, orthogonal gene control is by activation or inhibition of two or more target loci. In certain embodiments, orthogonal gene control is by activation or inhibition of one or more target locus and cleavage of one or more target locus.

In one embodiment, the invention provides a cell comprising a non-naturally occurring Cas9 CRISPR-Cas system comprising one or more dead guide RNAs disclosed or made according to a method or algorithm described herein wherein the expression of one or more gene products has been altered. In an embodiment of the invention, the expression in the cell of two or more gene products has been altered. The invention also provides a cell line from such a cell.

In one embodiment, the invention provides a multicellular organism comprising one or more cells comprising a non-naturally occurring Cas9 CRISPR-Cas system comprising one or more dead guide RNAs disclosed or made according to a method or algorithm described herein. In one embodiment, the invention provides a product from a cell, cell line, or multicellular organism comprising a non-naturally occurring Cas9 CRISPR-Cas system comprising one or more dead guide RNAs disclosed or made according to a method or algorithm described herein.

A further embodiment of this invention is the use of gRNA comprising dead guide(s) as described herein, optionally in combination with gRNA comprising guide(s) as described herein or in the state of the art, in combination with systems e.g., cells, transgenic animals, transgenic mice, inducible transgenic animals, inducible transgenic mice) which are engineered for either overexpression of Cas9 or preferably knock in Cas9. As a result, a single system (e.g., transgenic animal, cell) can serve as a basis for multiplex gene modifications in systems/network biology. On account of the dead guides, this is now possible in both in vitro, ex vivo, and in vivo.

For example, once the Cas9 is provided for, one or more dead gRNAs may be provided to direct multiplex gene regulation, and preferably multiplex bidirectional gene regulation. The one or more dead gRNAs may be provided in a spatially and temporally appropriate manner if necessary or desired (for example tissue specific induction of Cas9 expression). On account that the transgenic/inducible Cas9 is provided for (e.g., expressed) in the cell, tissue, animal of interest, both gRNAs comprising dead guides or gRNAs comprising guides are equally effective. In the same manner, a further embodiment of this invention is the use of gRNA comprising dead guide(s) as described herein, optionally in combination with gRNA comprising guide(s) as described herein or in the state of the art, in combination with systems (e.g., cells, transgenic animals, transgenic mice, inducible transgenic animals, inducible transgenic mice) which are engineered for knockout Cas9 CRISPR-Cas.

As a result, the combination of dead guides as described herein with CRISPR applications described herein and CRISPR applications known in the art results in a highly efficient and accurate means for multiplex screening of systems (e.g., network biology). Such screening allows, for example, identification of specific combinations of gene activities for identifying genes responsible for diseases (e.g., on/off combinations), in particular gene related diseases. A preferred application of such screening is cancer. In the same manner, screening for treatment for such diseases is included in the invention. Cells or animals may be exposed to aberrant conditions resulting in disease or disease like effects. Candidate compositions may be provided and screened for an effect in the desired multiplex environment. For example, a patient's cancer cells may be screened for which gene combinations will cause them to die, and then use this information to establish appropriate therapies.

In one embodiment, the invention provides a kit comprising one or more of the components described herein. The kit may include dead guides as described herein with or without guides as described herein.

The structural information provided herein allows for interrogation of dead gRNA interaction with the target DNA and the Cas9 permitting engineering or alteration of dead gRNA structure to optimize functionality of the entire Cas9 CRISPR-Cas system. For example, loops of the dead gRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g., SID4X). In some embodiments, the functional domain is an epigenetic modifying domain, such that an epigenetic modifying enzyme is provided. In some embodiments, the functional domain is an activation domain, which may be the P65 activation domain.

An embodiment of the invention is that the above elements are comprised in a single composition or comprised in individual compositions. These compositions may advantageously be applied to a host to elicit a functional effect on the genomic level.

In general, the dead gRNA are modified in a manner that provides specific binding sites (e.g., aptamers) for adapter proteins comprising one or more functional domains (e.g., via fusion protein) to bind to. The modified dead gRNA are modified such that once the dead gRNA forms a CRISPR complex (i.e., Cas9 binding to dead gRNA and target) the adapter proteins bind and, the functional domain on the adapter protein is positioned in a spatial orientation which is advantageous for the attributed function to be effective. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target.

The skilled person will understand that modifications to the dead gRNA which allow for binding of the adapter+ functional domain but not proper positioning of the adapter+ functional domain (e.g., due to steric hindrance within the three dimensional structure of the CRISPR complex) are modifications which are not intended. The one or more modified dead gRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases, it is advantageous that additionally at least one NLS is provided. In some instances, it is advantageous to position the NLS at the N terminus. When more than one functional domain is included, the functional domains may be the same or different.

The dead gRNA may be designed to include multiple binding recognition sites (e.g., aptamers) specific to the same or different adapter protein. The dead gRNA may be designed to bind to the promoter region −1000−+1 nucleic acids upstream of the transcription start site (i.e., TSS), preferably −200 nucleic acids. This positioning improves functional domains which affect gene activation (e.g., transcription activators) or gene inhibition (e.g., transcription repressors). The modified dead gRNA may be one or more modified dead gRNAs targeted to one or more target loci (e.g., at least 1 gRNA, at least 2 gRNA, at least 5 gRNA, at least 10 gRNA, at least 20 gRNA, at least 30 gRNA, at least 50 gRNA) comprised in a composition.

The adaptor protein may be any number of proteins that binds to an aptamer or recognition site introduced into the modified dead gRNA and which allows proper positioning of one or more functional domains, once the dead gRNA has been incorporated into the CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified dead gRNA, the (inactivated) Cas9 (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral gRNA selection) and concentration of gRNA (e.g., dependent on whether multiple gRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals, which are not believed prior to the present invention or application. For example, the target cell comprises Cas9 conditionally or inducibly (e.g., in the form of Cre dependent constructs) and/or the adapter protein conditionally or inducibly and, on expression of a vector introduced into the target cell, the vector expresses that which induces or gives rise to the condition of Cas9 expression and/or adaptor expression in the target cell. By applying the teaching and compositions of the current invention with the known method of creating a CRISPR complex, inducible genomic events affected by functional domains are also an embodiment of the current invention. One example of this is the creation of a CRISPR knock-in/conditional transgenic animal (e.g., mouse comprising e.g. a Lox-Stop-polyA-Lox (LSL) cassette) and subsequent delivery of one or more compositions providing one or more modified dead gRNA (e.g., −200 nucleotides to TSS of a target gene of interest for gene activation purposes) as described herein (e.g. modified dead gRNA with one or more aptamers recognized by coat proteins, e.g., MS2), one or more adapter proteins as described herein (MS2 binding protein linked to one or more VP64) and means for inducing the conditional animal (e.g., Cre recombinase for rendering Cas9 expression inducible). Alternatively, the adaptor protein may be provided as a conditional or inducible element with a conditional or inducible Cas9 to provide an effective model for screening purposes, which advantageously only requires minimal design and administration of specific dead gRNAs for a broad number of applications.

In another embodiment the dead guides are further modified to improve specificity. Protected dead guides may be synthesized, whereby secondary structure is introduced into the 3' end of the dead guide to improve its specificity. A protected guide RNA (pgRNA) comprises a guide sequence capable of hybridizing to a target sequence in a genomic locus of interest in a cell and a protector strand, wherein the protector strand is optionally complementary to the guide sequence and wherein the guide sequence may in part be hybridizable to the protector strand. The pgRNA optionally includes an extension sequence. The thermodynamics of the pgRNA-target DNA hybridization is determined by the number of bases complementary between the guide RNA and target DNA. By employing 'thermodynamic protection', specificity of dead gRNA can be improved by adding a complementary protector sequence. For example, one method adds a complementary protector strand of varying lengths to the 3' end of the guide sequence within the dead gRNA. As a result, the protector strand is bound to at least a portion of the dead gRNA and provides for a protected gRNA (pgRNA). In turn, the dead gRNA references herein may be easily protected using the described embodiments, resulting in pgRNA. The protector strand can be either a separate RNA transcript or strand or a chimeric version joined to the 3' end of the dead gRNA guide sequence.

Tandem Guides and Uses in a Multiplex (Tandem) Targeting Approach

The inventors have shown that CRISPR enzymes as defined herein can employ more than one RNA guide without losing activity. This enables the use of the CRISPR enzymes, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity. It is noted that the terms "CRISPR-Cas system", "CRISP-Cas complex" "CRISPR complex" and "CRISPR system" are used interchangeably. Also, the terms "CRISPR enzyme", "Cas enzyme", or "CRISPR-Cas enzyme", can be used interchangeably. In preferred embodiments, said CRISPR enzyme, CRISP-Cas enzyme or Cas enzyme is Cas9, or any one of the modified or mutated variants thereof described herein elsewhere.

In one embodiment, the invention provides a non-naturally occurring or engineered CRISPR enzyme, preferably a class 2 CRISPR enzyme, preferably a Type V or VI CRISPR enzyme as described herein, such as without limitation Cas9 as described herein elsewhere, used for tandem or multiplex targeting. It is to be understood that any of the CRISPR (or CRISPR-Cas or Cas) enzymes, complexes, or systems according to the invention as described herein elsewhere may be used in such an approach. Any of the methods, products, compositions and uses as described herein elsewhere are equally applicable with the multiplex or tandem targeting approach further detailed below. By means of further guidance, the following particular embodiments and embodiments are provided.

In one embodiment, the invention provides for the use of a Cas9 enzyme, complex or system as defined herein for targeting multiple gene loci. In one embodiment, this can be established by using multiple (tandem or multiplex) guide RNA (gRNA) sequences.

In one embodiment, the invention provides methods for using one or more elements of a Cas9 enzyme, complex or system as defined herein for tandem or multiplex targeting, wherein said CRISP system comprises multiple guide RNA sequences. Preferably, said gRNA sequences are separated by a nucleotide sequence, such as a direct repeat as defined herein elsewhere.

The Cas9 enzyme, system or complex as defined herein provides an effective means for modifying multiple target polynucleotides. The Cas9 enzyme, system or complex as defined herein has a wide variety of utility including modifying (e.g., deleting, inserting, translocating, inactivating, activating) one or more target polynucleotides in a multiplicity of cell types. As such the Cas9 enzyme, system or complex as defined herein of the invention has a broad spectrum of applications in, e.g., gene therapy, drug screening, disease diagnosis, and prognosis, including targeting multiple gene loci within a single CRISPR system.

In one embodiment, the invention provides a Cas9 enzyme, system or complex as defined herein, i.e., a Cas9 CRISPR-Cas complex having a Cas9 protein having at least one destabilization domain associated therewith, and multiple guide RNAs that target multiple nucleic acid molecules such as DNA molecules, whereby each of said multiple guide RNAs specifically targets its corresponding nucleic acid molecule, e.g., DNA molecule. Each nucleic acid molecule target, e.g., DNA molecule can encode a gene product or encompass a gene locus. Using multiple guide RNAs hence enables the targeting of multiple gene loci or multiple genes. In some embodiments the Cas9 enzyme may cleave the DNA molecule encoding the gene product. In some embodiments expression of the gene product is altered. The Cas9 protein and the guide RNAs do not naturally occur together. The invention comprehends the guide RNAs comprising tandemly arranged guide sequences. The invention further comprehends coding sequences for the Cas9 protein being codon optimized for expression in a eukaryotic cell. In a preferred embodiment the eukaryotic cell is a mammalian cell, a plant cell or a yeast cell and in a more preferred embodiment the mammalian cell is a human cell. Expression of the gene product may be decreased. The Cas9 enzyme may form part of a CRISPR system or complex, which further comprises tandemly arranged guide RNAs (gRNAs) comprising a series of 2, 3, 4, 5, 6, 7, 8, 9, 10, 15, 25, 25, 30, or more than 30 guide sequences, each capable of specifically hybridizing to a target sequence in a genomic locus of interest in a cell. In some embodiments, the functional Cas9 CRISPR system or complex binds to the multiple target sequences. In some embodiments, the functional CRISPR system or complex may edit the multiple target sequences, e.g., the target sequences may comprise a genomic locus, and in some embodiments, there may be an alteration of gene expression. In some embodiments, the functional CRISPR system or complex may comprise further functional domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences).

In preferred embodiments the CRISPR enzyme used for multiplex targeting is Cas9, or the CRISPR system or complex comprises Cas9. In some embodiments, the CRISPR enzyme used for multiplex targeting is AsCas9, or the CRISPR system or complex used for multiplex targeting comprises an AsCas9. In some embodiments, the CRISPR enzyme is an LbCas9, or the CRISPR system or complex comprises LbCas9. In some embodiments, the Cas9 enzyme used for multiplex targeting cleaves both strands of DNA to produce a double strand break (DSB). In some embodiments, the CRISPR enzyme used for multiplex targeting is a nickase. In some embodiments, the Cas9 enzyme used for multiplex targeting is a dual nickase. In some embodiments, the Cas9 enzyme used for multiplex targeting is a Cas9 enzyme such as a DD Cas9 enzyme as defined herein elsewhere.

In some general embodiments, the Cas9 enzyme used for multiplex targeting is associated with one or more functional domains. In some more specific embodiments, the CRISPR enzyme used for multiplex targeting is a deadCas9 as defined herein elsewhere.

In an embodiment, the present invention provides a means for delivering the Cas9 enzyme, system or complex for use in multiple targeting as defined herein or the polynucleotides defined herein. Non-limiting examples of such delivery means are e.g., particle(s) delivering component(s) of the complex, vector(s) comprising the polynucleotide(s) discussed herein (e.g., encoding the CRISPR enzyme, providing the nucleotides encoding the CRISPR complex). In some embodiments, the vector may be a plasmid or a viral vector such as AAV, or lentivirus. Transient transfection with plasmids, e.g., into HEK cells may be advantageous, especially given the size limitations of AAV and that while Cas9 fits into AAV, one may reach an upper limit with additional guide RNAs.

Also provided is a model that constitutively expresses the Cas9 enzyme, complex or system as used herein for use in multiplex targeting. The organism may be transgenic and may have been transfected with the present vectors or may be the offspring of an organism so transfected. In a further embodiment, the present invention provides compositions comprising the CRISPR enzyme, system and complex as defined herein or the polynucleotides or vectors described herein. Also provides are Cas9 CRISPR systems or complexes comprising multiple guide RNAs, preferably in a tandemly arranged format. Said different guide RNAs may be separated by nucleotide sequences such as direct repeats.

Also provided is a method of treating a subject, e.g., a subject in need thereof, comprising inducing gene editing by transforming the subject with the polynucleotide encoding the Cas9 CRISPR system or complex or any of polynucleotides or vectors described herein and administering them to the subject. A suitable repair template may also be provided, for example delivered by a vector comprising said repair template. Also provided is a method of treating a subject, e.g., a subject in need thereof, comprising inducing transcriptional activation or repression of multiple target gene loci by transforming the subject with the polynucleotides or vectors described herein, wherein said polynucleotide or vector encodes or comprises the Cas9 enzyme, complex or system comprising multiple guide RNAs, preferably tandemly arranged. Where any treatment is occurring ex vivo, for example in a cell culture, then it will be appreciated that the term 'subject' may be replaced by the phrase "cell or cell culture."

Compositions comprising Cas9 enzyme, complex or system comprising multiple guide RNAs, preferably tandemly arranged, or the polynucleotide or vector encoding or comprising said Cas9 enzyme, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas9 CRISPR system in screening is also provided by the present invention, e.g., gain of function screens. Cells which are artificially forced to overexpress a gene are able to down regulate the gene over time (reestablishing equilibrium) e.g., by negative feedback loops. By the time the screen starts the unregulated gene might be reduced again. Using an inducible Cas9 activator allows one to induce transcription right before the screen and therefore minimizes the chance of false negative hits. Accordingly, by use of the instant invention in screening, e.g., gain of function screens, the chance of false negative results may be minimized.

In one embodiment, the invention provides an engineered, non-naturally occurring CRISPR system comprising a Cas9 protein and multiple guide RNAs that each specifically target a DNA molecule encoding a gene product in a cell, whereby the multiple guide RNAs each target their specific DNA molecule encoding the gene product and the Cas9 protein cleaves the target DNA molecule encoding the gene product, whereby expression of the gene product is altered; and, wherein the CRISPR protein and the guide RNAs do not naturally occur together. The invention comprehends the multiple guide RNAs comprising multiple guide sequences, preferably separated by a nucleotide sequence such as a direct repeat and optionally fused to a tracr sequence. In an embodiment of the invention the CRISPR protein is a type V or VI CRISPR-Cas protein and in a more preferred embodiment the CRISPR protein is a Cas9 protein. The invention further comprehends a Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another embodiment, the invention provides an engineered, non-naturally occurring vector system comprising one or more vectors comprising a first regulatory element operably linked to the multiple Cas9 CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is Cas9 protein, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one embodiment, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas9 enzyme complexed with the one or more guide sequence(s) that is hybridized to the one or more target sequence(s); and (b) a second regulatory element operably linked to an enzyme-coding sequence encoding said Cas9 enzyme, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a Cas9 CRISPR complex to a different target sequence in a eukaryotic cell. In some embodiments, the CRISPR complex comprises one or more nuclear localization sequences and/or one or more NES of sufficient strength to drive accumulation of said Cas9 CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas9 enzyme, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

In some embodiments, a host cell is transiently or non-transiently transfected with one or more vectors comprising the polynucleotides encoding the Cas9 enzyme, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas9 enzyme, system or complex for use in multiple targeting as defined herein is used to establish a new cell line comprising one or more vector-derived sequences. In some embodiments, a cell transiently transfected with the components of a Cas9 CRISPR system or complex for use in multiple targeting as described herein (such as by transient transfection of one or more vectors, or transfection with RNA), and modified through the activity of a Cas9 CRISPR system or complex, is used to establish a new cell line comprising cells containing the modification but lacking any other exogenous sequence. In some embodiments, cells transiently or non-transiently transfected with one or more vectors comprising the polynucleotides encoding the Cas9 enzyme, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one embodiment, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the Cas9 CRISPR complex to the respective target sequence(s) in a eukaryotic cell, wherein the Cas9 CRISPR complex comprises a Cas9 enzyme complexed with the one or more guide sequence(s) that is hybridized to the respective target sequence(s); and/or (b) a second regulatory element operably linked to an enzyme-coding sequence encoding said Cas9 enzyme comprising preferably at least one nuclear localization sequence and/or NES. In some embodiments, the host cell comprises components (a) and (b). Where applicable, a tracr sequence may also be provided. In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a Cas9 CRISPR complex to a different target sequence in a eukaryotic cell. In some embodiments, the Cas9 enzyme comprises one or more nuclear localization sequences and/or nuclear export sequences or NES of sufficient strength to drive accumulation of said CRISPR enzyme in a detectable amount in and/or out of the nucleus of a eukaryotic cell.

In some embodiments, the Cas9 enzyme is a type V or VI CRISPR system enzyme. In some embodiments, the Cas9 enzyme is a Cas9 enzyme. In some embodiments, the Cas9 enzyme is derived from *Francisella tularensis* 1, *Francisella tularensis* subsp. *novicida, Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens*, or *Porphyromonas macacae* Cas9, and may include further alterations or mutations of the Cas9 as defined herein elsewhere, and can be a chimeric Cas9. In some embodiments, the Cas9 enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the one or more guide sequence(s) is (are each) at least 16, 17, 18, 19, 20, 25 nucleotides, or between 16-30, or between 16-25, or between 16-20 nucleotides in length. When multiple guide RNAs are used, they are preferably separated by a direct repeat sequence.

In one embodiment, the invention provides a method of modifying multiple target polynucleotides in a host cell such as a eukaryotic cell. In some embodiments, the method comprises allowing a Cas9CRISPR complex to bind to multiple target polynucleotides, e.g., to effect cleavage of said multiple target polynucleotides, thereby modifying multiple target polynucleotides, wherein the Cas9CRISPR complex comprises a Cas9 enzyme complexed with multiple guide sequences each of the being hybridized to a specific target sequence within said target polynucleotide, wherein said multiple guide sequences are linked to a direct repeat sequence. Where applicable, a tracr sequence may also be provided (e.g., to provide a single guide RNA, sgRNA). In some embodiments, said cleavage comprises cleaving one or two strands at the location of each of the target sequence by said Cas9 enzyme. In some embodiments, said cleavage results in decreased transcription of the multiple target genes. In some embodiments, the method further comprises repairing one or more of said cleaved target polynucleotide by homologous recombination with an exogenous template polynucleotide, wherein said repair results in a mutation comprising an insertion, deletion, or substitution of one or more nucleotides of one or more of said target polynucleotides. In some embodiments, said mutation results in one or more amino acid changes in a protein expressed from a gene comprising one or more of the target sequence(s). In some embodiments, the method further comprises delivering one or more vectors to said eukaryotic cell, wherein the one or more vectors drive expression of one or more of: the Cas9 enzyme and the multiple guide RNA sequence linked to a direct repeat sequence. Where applicable, a tracr sequence may also be provided. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one embodiment, the invention provides a method of modifying expression of multiple polynucleotides in a eukaryotic cell. In some embodiments, the method comprises allowing a Cas9 CRISPR complex to bind to multiple polynucleotides such that said binding results in increased or decreased expression of said polynucleotides; wherein the Cas9 CRISPR complex comprises a Cas9 enzyme complexed with multiple guide sequences each specifically hybridized to its own target sequence within said polynucleotide, wherein said guide sequences are linked to a direct repeat sequence. Where applicable, a tracr sequence may also be provided. In some embodiments, the method further comprises delivering one or more vectors to said eukaryotic cells, wherein the one or more vectors drive expression of one or more of: the Cas9 enzyme and the multiple guide sequences linked to the direct repeat sequences. Where applicable, a tracr sequence may also be provided.

In one embodiment, the invention provides a recombinant polynucleotide comprising multiple guide RNA sequences up- or downstream (whichever applicable) of a direct repeat sequence, wherein each of the guide sequences when expressed directs sequence-specific binding of a Cas9CRISPR complex to its corresponding target sequence present in a eukaryotic cell. In some embodiments, the target sequence is a viral sequence present in a eukaryotic cell. Where applicable, a tracr sequence may also be provided. In some embodiments, the target sequence is a proto-oncogene or an oncogene.

Embodiments of the invention encompass a non-naturally occurring or engineered composition that may comprise a guide RNA (gRNA) comprising a guide sequence capable of hybridizing to a target sequence in a genomic locus of interest in a cell and a Cas9 enzyme as defined herein that may comprise at least one or more nuclear localization sequences.

An embodiment of the invention encompasses methods of modifying a genomic locus of interest to change gene expression in a cell by introducing into the cell any of the compositions described herein.

An embodiment of the invention is that the above elements are comprised in a single composition or comprised in individual compositions. These compositions may advantageously be applied to a host to elicit a functional effect on the genomic level.

Engineered Cells and Organisms Expressing Said Engineered AAV Capsids

Described herein are engineered cells that can include one or more of the engineered AAV capsid polynucleotides, polypeptides, vectors, and/or vector systems. In some embodiments, one or more of the engineered AAV capsid polynucleotides can be expressed in the engineered cells. In some embodiments, the engineered cells can be capable of producing engineered AAV capsid proteins and/or engineered AAV capsid particles that are described elsewhere herein. Also described herein are modified or engineered organisms that can include one or more engineered cells described herein. The engineered cells can be engineered to express a cargo molecule (e.g., a cargo polynucleotide) dependently or independently of an engineered AAV capsid polynucleotide as described elsewhere herein.

A wide variety of animals, plants, algae, fungi, yeast, etc. and animal, plant, algae, fungus, yeast cell or tissue systems may be engineered to express one or more nucleic acid constructs of the engineered AAV capsid system described herein using various transformation methods mentioned elsewhere herein. This can produce organisms that can produce engineered AAV capsid particles, such as for production purposes, engineered AAV capsid design and/or generation, and/or model organisms. In some embodiments, the polynucleotide(s) encoding one or more components of the engineered AAV capsid system described herein can be stably or transiently incorporated into one or more cells of a plant, animal, algae, fungus, and/or yeast or tissue system. In some embodiments, one or more of engineered AAV capsid system polynucleotides are genomically incorporated into one or more cells of a plant, animal, algae, fungus, and/or yeast or tissue system. Further embodiments of the modified organisms and systems are described elsewhere herein. In some embodiments, one or more components of the engineered AAV capsid system described herein are expressed in one or more cells of the plant, animal, algae, fungus, yeast, or tissue systems.

Engineered Cells

Described herein are various embodiments of engineered cells that can include one or more of the engineered AAV capsid system polynucleotides, polypeptides, vectors, and/or vector systems described elsewhere herein. In some embodiments, the cells can express one or more of the engineered AAV capsid polynucleotides and can produce one or more engineered AAV capsid particles, which are described in greater detail herein. Such cells are also referred to herein as "producer cells". It will be appreciated that these engineered cells are different from "modified cells" described elsewhere herein in that the modified cells are not necessarily producer cells (i.e., they do not make engineered GTA delivery particles) unless they include one or more of the engineered AAV capsid polynucleotides, engineered AAV capsid vectors or other vectors described herein that render the cells capable of producing an engineered AAV capsid particle. Modified cells can be recipient cells of an engineered AAV capsid particles and can, in some embodiments, be modified by the engineered AAV capsid particle(s) and/or a cargo polynucleotide delivered to the recipient cell. Modified cells are discussed in greater detail elsewhere herein. The term modification can be used in connection with modification of a cell that is not dependent on being a recipient cell. For example, isolated cells can be modified prior to receiving an engineered AAV capsid molecule.

In an embodiment, the invention provides a non-human eukaryotic organism; for example, a multicellular eukaryotic organism, including a eukaryotic host cell containing one or more components of an engineered delivery system described herein according to any of the described embodiments. In other embodiments, the invention provides a eukaryotic organism; preferably a multicellular eukaryotic organism, comprising a eukaryotic host cell containing one or more components of an engineered delivery system described herein according to any of the described embodiments. In some embodiments, the organism is a host of AAV.

In particular embodiments, the plants, algae, fungi, yeast, etc., cells or parts obtained are transgenic plants, comprising an exogenous DNA sequence incorporated into the genome of all or part of the cells.

The engineered cell can be a prokaryotic cell. The prokaryotic cell can be bacterial cell. The prokaryotic cell can be an archaea cell. The bacterial cell can be any suitable bacterial cell. Suitable bacterial cells can be from the genus *Escherichia, Bacillus, Lactobacillus, Rhodococcus, Rhodobacter, Synechococcus, Synechoystis, Pseudomonas, Psedoaltermonas, Stenotrophamonas, and Streptomyces* Suitable bacterial cells include, but are not limited to *Escherichia coli* cells, *Caulobacter crescentus* cells, *Rodhobacter sphaeroides* cells, *Psedoaltermonas haloplanktis* cells. Suitable strains of bacterial include, but are not limited to BL21 (DE3), DL21(DE3)-pLysS, BL21 Star-pLysS, BL21-SI, BL21-AI, Tuner, Tuner pLysS, Origami, Origami B pLysS, Rosetta, Rosetta pLysS, Rosetta-gami-pLysS, BL21 Codon-Plus, AD494, BL2trxB, HMS174, NovaBlue(DE3), BLR, C41(DE3), C43(DE3), Lemo21(DE3), Shuffle T7, Arctic-Express and ArticExpress (DE3).

The engineered cell can be a eukaryotic cell. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments the engineered cell can be a cell line. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CiR, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, the engineered cell is a muscle cell (e.g. cardiac muscle, skeletal muscle, and/or smooth muscle), bone cell, blood cell, immune cell (including but not limited to B cells, macrophages, T-cells, CAR-T cells, and the like), kidney cells, bladder cells, lung cells, heart cells, liver cells, brain cells, neurons, skin cells, stomach cells, neuronal support cells, intestinal cells, epithelial cells, endothelial cells, stem or other progenitor cells, adrenal gland cells, cartilage cells, and combinations thereof.

In some embodiments, the engineered cell can be a fungus cell. As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus,* or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis,* a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains can include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

In some embodiments, the engineered cell is a cell obtained from a subject. In some embodiments, the subject is a healthy or non-diseased subject. In some embodiments, the subject is a subject with a desired physiological and/or biological characteristic such that when a engineered AAV capsid particle is produced it can package one or more cargo polynucleotides that can be related to the desired physiological and/or biological characteristic and/or capable of modifying the desired physiological and/or biological characteristic. Thus, the cargo polynucleotides of the produced engineered AAV capsid particle can be capable of transferring the desired characteristic to a recipient cell. In some embodiments, the cargo polynucleotides are capable of modifying a polynucleotide of the engineered cell such that the engineered cell has a desired physiological and/or biological characteristic.

In some embodiments, a cell transfected with one or more vectors described herein is used to establish a new cell line comprising one or more vector-derived sequences.

The engineered cells can be used to produce engineered viral (e.g., AAV) capsid polynucleotides, vectors, and/or particles. In some embodiments, the engineered viral (e.g., AAV) capsid polynucleotides, vectors, and/or particles are produced, harvested, and/or delivered to a subject in need thereof. In some embodiments, the engineered cells are delivered to a subject. Other uses for the engineered cells are described elsewhere herein. In some embodiments, the engineered cells can be included in formulations and/or kits described elsewhere herein.

The engineered cells can be stored short-term or long-term for use at a later time. Suitable storage methods are generally known in the art. Further, methods of restoring the stored cells for use (such as thawing, reconstitution, and otherwise stimulating metabolism in the engineered cell after storage) at a later time are also generally known in the art.

Formulations

The compositions, polynucleotides, polypeptides, particles, cells, vector systems and combinations thereof described herein can be contained in a formulation, such as a pharmaceutical formulation. In some embodiments, the formulations can be used to generate polypeptides and other particles that include one or more muscle-specific targeting moieties described herein. In some embodiments, the formulations can be delivered to a subject in need thereof. In some embodiments, component(s) of the engineered AAV capsid system, engineered cells, engineered AAV capsid particles, and/or combinations thereof described herein can be included in a formulation that can be delivered to a subject or a cell. In some embodiments, the formulation is a pharmaceutical formulation. One or more of the polypeptides, polynucleotides, vectors, cells, and combinations thereof described herein can be provided to a subject in need thereof or a cell alone or as an active ingredient, such as in a pharmaceutical formulation. As such, also described herein are pharmaceutical formulations containing an amount of one or more of the polypeptides, polynucleotides, vectors, cells, or combinations thereof described herein. In some embodiments, the pharmaceutical formulation can contain an effective amount of the one or more of the polypeptides, polynucleotides, vectors, cells, and combinations thereof described herein. The pharmaceutical formulations described herein can be administered to a subject in need thereof or a cell.

In some embodiments, the amount of the one or more of the polypeptides, polynucleotides, vectors, cells, virus particles, nanoparticles, other delivery particles, and combinations thereof described herein contained in the pharmaceutical formulation can range from about 1 pg/kg to about 10 mg/kg based upon the bodyweight of the subject in need thereof or average bodyweight of the specific patient population to which the pharmaceutical formulation can be administered. The amount of the one or more of the polypeptides, polynucleotides, vectors, cells, and combinations thereof described herein in the pharmaceutical formulation can range from about 1 pg to about 10 g, from about 10 nL to about 10 ml. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells. In embodiments where the pharmaceutical formulation contains one or more cells, the amount can range from about 1 cell to $1\times10^2$, $1\times10^3$, $1\times10^4$, $1\times10^5$, $1\times10^6$, $1\times10^7$, $1\times10^8$, $1\times10^9$, $1\times10^{10}$ or more cells per nL, μL, mL, or L.

In embodiments, were engineered AAV capsid particles are included in the formulation, the formulation can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the engineered AAV capsid particles. In some embodiments, the formulation can be 0.1 to 100 mL in volume and can contain 1 to $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ transducing units (TU)/mL of the engineered AAV capsid particles.

Pharmaceutically Acceptable Carriers and Auxiliary Ingredients and Agents

In embodiments, the pharmaceutical formulation containing an amount of one or more of the polypeptides, polynucleotides, vectors, cells, virus particles, nanoparticles, other delivery particles, and combinations thereof described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to an amount of one or more of the polypeptides, polynucleotides, vectors, cells, engineered AAV capsid particles, nanoparticles, other delivery particles, and combinations thereof described herein, the pharmaceutical formulation can also include an effective amount of an auxiliary active agent, including but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

Suitable hormones include, but are not limited to, amino-acid derived hormones (e.g., melatonin and thyroxine), small peptide hormones and protein hormones (e.g., thyrotropin-releasing hormone, vasopressin, insulin, growth hormone, luteinizing hormone, follicle-stimulating hormone, and thyroid-stimulating hormone), eicosanoids (e.g., arachidonic acid, lipoxins, and prostaglandins), and steroid hormones (e.g., estradiol, testosterone, tetrahydro testosterone Cortisol). Suitable immunomodulators include, but are not limited to, prednisone, azathioprine, 6-MP, cyclosporine, tacrolimus, methotrexate, interleukins (e.g., IL-2, IL-7, and IL-12), cytokines (e.g., interferons (e.g., IFN-a, IFN-β, IFN-ε, IFN-K, IFN-ω, and IFN-γ), granulocyte colony-stimulating factor, and imiquimod), chemokines (e.g., CCL3, CCL26 and CXCL7), cytosine phosphate-guanosine, oligodeoxynucleotides, glucans, antibodies, and aptamers).

Suitable antipyretics include, but are not limited to, non-steroidal anti-inflammatories (e.g., ibuprofen, naproxen, ketoprofen, and nimesulide), aspirin and related salicylates (e.g., choline salicylate, magnesium salicylate, and sodium salicylate), paracetamol/acetaminophen, metamizole, nabumetone, phenazone, and quinine.

Suitable anxiolytics include, but are not limited to, benzodiazepines (e.g., alprazolam, bromazepam, chlordiazepoxide, clonazepam, clorazepate, diazepam, flurazepam, lorazepam, oxazepam, temazepam, triazolam, and tofisopam), serotonergic antidepressants (e.g., selective serotonin reuptake inhibitors, tricyclic antidepressants, and monoamine oxidase inhibitors), mebicar, fabomotizole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipamperone, timiperone, fluspirilene, penfluridol, pimozide, acepromazine, chlorpromazine, cyamemazine, dixyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, thiothixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzapine, paliperidone, perospirone, quetiapine, remoxipride, risperidone, sertindole, trimipramine, ziprasidone, zotepine, alstonie, bifeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, nonsteroidal anti-inflammatories (e.g., ibuprofen, naproxen, ketoprofen, and nimesulide), COX-2 inhibitors (e.g., rofecoxib, celecoxib, and etoricoxib), opioids (e.g., morphine, codeine, oxycodone, hydrocodone, dihydromorphine, pethidine, buprenorphine), tramadol, norepinephrine, flupirtine, nefopam, orphenadrine, pregabalin, gabapentin, cyclobenzaprine, scopolamine, methadone, ketobemidone, piritramide, and aspirin and related salicylates (e.g., choline salicylate, magnesium salicylate, and sodium salicylate).

Suitable antispasmodics include, but are not limited to, mebeverine, papaverine, cyclobenzaprine, carisoprodol, orphenadrine, tizanidine, metaxalone, methocarbamol, chlorzoxazone, baclofen, dantrolene, baclofen, tizanidine, and dantrolene. Suitable anti-inflammatories include, but are not limited to, prednisone, non-steroidal anti-inflammatories (e.g., ibuprofen, naproxen, ketoprofen, and nimesulide), COX-2 inhibitors (e.g., rofecoxib, celecoxib, and etoricoxib), and immune selective anti-inflammatory derivatives (e.g., submandibular gland peptide-T and its derivatives)

Suitable anti-histamines include, but are not limited to, H1-receptor antagonists (e.g., acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, meclizine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g., cimetidine, famotidine, lafutidine, nizatidine, ranitidine, and roxatidine), tritoqualine, catechin, cromoglicate, nedocromil, and p2-adrenergic agonists.

Suitable anti-infectives include, but are not limited to, amebicides (e.g., nitazoxanide, paromomycin, metronidazole, tinidazole, chloroquine, miltefosine, amphotericin b, and iodoquinol), aminoglycosides (e.g., paromomycin, tobramycin, gentamicin, amikacin, kanamycin, and neomycin), anthelmintics (e.g., pyrantel, mebendazole, ivermectin, praziquantel, albendazole, thiabendazole, oxamniquine), antifungals (e.g., azole antifungals (e.g., itraconazole, fluconazole, parconazole, ketoconazole, clotrimazole, miconazole, and voriconazole), echinocandins (e.g., caspofungin, anidulafungin, and micafungin), griseofulvin, terbinafine, flucytosine, and polyenes (e.g., nystatin, and amphotericin b), antimalarial agents (e.g., pyrimethamine/sulfadoxine, artemether/lumefantrine, atovaquone/proguanil, quinine, hydroxychloroquine, mefloquine, chloroquine, doxycycline, pyrimethamine, and halofantrine), antituberculosis agents (e.g., aminosalicylates (e.g., aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g., amantadine, rimantadine, abacavir/lamivudine, emtricitabine/tenofovir, cobicistat/elvitegravir/emtricitabine/tenofovir, efavirenz/emtricitabine/tenofovir, abacavir/lamivudine/zidovudine, lamivudine/zidovudine, emtricitabine/tenofovir, emtricitabine/lopinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delavirdine, nevirapine, entecavir, lamivudine, adefovir, sofosbuvir, didanosine, tenofovir, abacavir, zidovudine, stavudine, emtricitabine, zalcitabine, telbivudine, simeprevir, boceprevir, telaprevir, lopinavir/ritonavir, boceprevir, darunavir, ritonavir, tipranavir, atazanavir, nelfinavir, amprenavir, indinavir, saquinavir, ribavirin, valacyclovir, acyclovir, famciclovir, ganciclovir, and valganciclovir), carbapenems (e.g., doripenem, meropenem, ertapenem, and cilastatin/imipenem), cephalosporins (e.g., cefadroxil, cephradine, cefazolin, cephalexin, cefepime, cefazoline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, ceftizoxime, and ceftazidime), glycopeptide antibiotics (e.g., vancomycin, dalbavancin, oritavancin, and telavancin), glycylcyclines (e.g., tigecycline), leprostatics (e.g., clofazimine and thalidomide), lincomycin and derivatives thereof (e.g., clindamycin and lincomycin ), macrolides and derivatives thereof (e.g., telithromycin, fidaxomicin, erythromycin, azithromycin, clarithromycin, dirithromycin, and troleandomycin), linezolid, sulfamethoxazole/trimethoprim, rifaximin, chloramphenicol, Fosfomycin, metronidazole, aztreonam, bacitracin, penicillin (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, and nafcillin), quinolones (e.g., lomefloxacin, norfloxacin, ofloxacin, gatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g., sulfamethoxazole/trimethoprim, sulfasalazine, and sulfisoxazole), tetracyclines (e.g., doxycycline, demeclocycline, minocycline, doxycycline/salicylic acid, doxycycline/omega-3 polyunsaturated fatty acids, and tetracycline), and urinary anti-infectives (e.g., nitrofurantoin, methenamine, Fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, Cytoxan, cyclophosphamide, decitabine, dexamethasone, docetaxel, hydroxyurea, dacarbazine, leuprolide, epirubicin, oxaliplatin, asparaginase, estramustine, cetuximab, vismodegib, asparaginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylate, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine (tioguanine), dabrafenib, erlotinib, bexarotene, temozolomide, thiotepa, thalidomide, *Bacillus* Calmette-Guerin (BCG), temsirolimus, bendamustine hydrochloride, triptorelin, arsenic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where there is an auxiliary active agent contained in the pharmaceutical formulation in addition to the one or more of the polypeptides, polynucleotides, CRISPR-Cas complexes, vectors, cells, virus particles, nanoparticles, other delivery particles, and combinations thereof described herein, amount, such as an effective amount, of the auxiliary active agent will vary depending on the auxiliary active agent. In some embodiments, the amount of the auxiliary active agent ranges from 0.001 micrograms to about 1 milligram. In other embodiments, the amount of the auxiliary active agent ranges from about 0.01 IU to about 1000 IU. In further embodiments, the amount of the auxiliary active agent ranges from 0.001 mL to about 1 mL. In yet other embodiments, the amount of the auxiliary active agent ranges from about 1% w/w to about 50% w/w of the total pharmaceutical formulation. In additional embodiments, the amount of the auxiliary active agent ranges from about 1% v/v to about 50% v/v of the total pharmaceutical formulation. In still other embodiments, the amount of the auxiliary active agent ranges from about 1% w/v to about 50% w/v of the total pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, gingival, subgingival, intracerebroventricular, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of the targeted effector fusion protein and/or complex thereof or composition containing the one or more of the polypeptides, polynucleotides, vectors, cells, and combinations thereof described herein. The oral dosage form can be administered to a subject in need thereof.

Where appropriate, the dosage forms described herein can be microencapsulated.

The dosage form can also be prepared to prolong or sustain the release of any ingredient. In some embodiments, the one or more of the polypeptides, polynucleotides, vectors, cells, and combinations thereof described herein can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the one or more of the polypeptides, polynucleotides, vectors, cells, and combinations thereof described herein can be formulated with a paraffinic or water-miscible ointment base. In some embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the one or more of the polypeptides, polynucleotides, vectors, cells, and combinations thereof described herein is contained in a dosage form adapted for inhalation is in a particle-size-reduced form that is obtained or obtainable by micronization. In some embodiments, the particle size of the size reduced (e.g., micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient (e.g., the one or more of the polypeptides, polynucleotides, vectors, cells, and combinations thereof described herein and/or auxiliary active agent), which may be generated by various types of metered dose pressurized aerosols, nebulizers, or insufflators.

In some embodiments, the dosage forms can be aerosol formulations suitable for administration by inhalation. In some of these embodiments, the aerosol formulation can contain a solution or fine suspension of the one or more of the polypeptides, polynucleotides, vectors, cells, and combinations thereof described herein and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal, or an aerosol dispenser fitted with a metering valve (e.g., metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of one or more of the polypeptides, polynucleotides, vectors, cells, and combinations thereof described herein. In further embodiments, the aerosol formulation can also contain co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time.

For some dosage forms suitable and/or adapted for inhaled administration, the pharmaceutical formulation is a dry powder inhalable formulation. In addition to the one or more of the polypeptides, polynucleotides, vectors, cells, and combinations thereof described herein, an auxiliary active ingredient, and/or pharmaceutically acceptable salt thereof, such a dosage form can contain a powder base such as lactose, glucose, trehalose, mannitol, and/or starch. In some of these embodiments, the one or more of the polypeptides, polynucleotides, vectors, cells, and combinations thereof described herein is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol dosage forms can be arranged so that each metered dose of aerosol contains a predetermined amount of an active ingredient, such as the one or more of the one or more of the polypeptides, polynucleotides, vectors, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, gingival, subgingival, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or nonaqueous sterile solutions that can optionally be adapted for injection, and which can optionally contain anti-oxidants, buffers, bacteriostats, solutes that render the composition isotonic with the eye or fluid contained therein or around the eye of the subject, and aqueous and nonaqueous sterile suspensions, which can include suspending agents and thickening agents.

For some embodiments, the dosage form contains a predetermined amount of the one or more of the polypeptides, polynucleotides, vectors, cells, and combinations thereof described herein per unit dose. In some embodiments, the predetermined amount of the Such unit doses may therefore be administered once or more than once a day. Such pharmaceutical formulations may be prepared by any of the methods well known in the art.

Kits

Also described herein are kits that contain one or more of the one or more of the compositions, polypeptides, polynucleotides, vectors, cells, or other components described herein and combinations thereof and pharmaceutical formulations described herein. In embodiments, one or more of the polypeptides, polynucleotides, vectors, cells, and combinations thereof described herein can be presented as a combination kit. As used herein, the terms "combination kit" or "kit of parts" refers to the compounds, or formulations and additional components that are used to package, screen, test, sell, market, deliver, and/or administer the combination of elements or a single element, such as the active ingredient, contained therein. Such additional components include but are not limited to, packaging, syringes, blister packages, bottles, and the like. The combination kit can contain one or more of the components (e.g., one or more of the one or more of the polypeptides, polynucleotides, vectors, cells, and combinations thereof) or formulation thereof can be provided in a single formulation (e.g., a liquid, lyophilized powder, etc.), or in separate formulations. The separate components or formulations can be contained in a single package or in separate packages within the kit. The kit can also include instructions in a tangible medium of expression that can contain information and/or directions regarding the content of the components and/or formulations contained therein, safety information regarding the content of the components(s) and/or formulation(s) contained therein, information regarding the amounts, dosages, indications for use, screening methods, component design recommendations and/or information, recommended treatment regimen (s) for the components(s) and/or formulations contained therein. As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory drive or CD-ROM or on a server that can be accessed by a user via, e.g., a web interface.

In one embodiment, the invention provides a kit comprising one or more of the components described herein. In some embodiments, the kit comprises a vector system and instructions for using the kit. In some embodiments, the vector system includes a regulatory element operably linked to one or more engineered polynucleotides, such as those containing a muscle-specific targeting moiety, as described elsewhere herein and, optionally, a cargo molecule, which can optionally be operably linked to a regulatory element. The one or more engineered polynucleotides such as those containing a muscle-specific targeting moiety, as described elsewhere herein and, can be included on the same or different vectors as the cargo molecule in embodiments containing a cargo molecule within the kit.

In some embodiments, the kit comprises a vector system and instructions for using the kit. In some embodiments, the vector system comprises (a) a first regulatory element operably linked to a direct repeat sequence and one or more insertion sites for inserting one or more guide sequences up- or downstream (whichever applicable) of the direct repeat sequence, wherein when expressed, the guide sequence directs sequence-specific binding of a Cas9 CRISPR complex to a target sequence in a eukaryotic cell, wherein the Cas9 CRISPR complex comprises a Cas9 enzyme complexed with the guide sequence that is hybridized to the target sequence; and/or (b) a second regulatory element operably linked to an enzyme-coding sequence encoding said Cas9 enzyme comprising a nuclear localization sequence. Where applicable, a tracr sequence may also be provided. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the Cas9 enzyme comprises one or more nuclear localization sequences of sufficient strength to drive accumulation of said CRISPR enzyme in a detectable amount in the nucleus of a eukaryotic cell. In some embodiments, the CRISPR enzyme is a type V or VI CRISPR system enzyme. In some embodiments, the CRISPR enzyme is a Cas9 enzyme. In some embodiments, the Cas9 enzyme is derived from *Francisella tularensis* 1, *Francisella tularensis* subsp. *novicida, Prevotella albensis,* Lachnospiraceae bacterium MC2017 1, *Butyrivibrio proteoclasticus,* Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai,* Lachnospiraceae bacterium ND2006, *Porphyromonas crevioricanis* 3, *Prevotella disiens,* or *Porphyromonas macacae* Cas9 (e.g., modified to have or be associated with at least one DD), and may include further alteration or mutation of the Cas9, and can be a chimeric Cas9. In some embodiments, the DD-CRISPR enzyme is codon-optimized for expression in a eukaryotic cell. In some embodiments, the DD-CRISPR enzyme directs cleavage of one or two strands at the location of the target sequence In some embodiments, the DD-CRISPR enzyme lacks or substantially DNA strand cleavage activity (e.g., no more than 5% nuclease activity as compared with a wild-type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 16, 17, 18, 19, 20, 25 nucleotides, or between 16-30, or between 16-25, or between 16-20 nucleotides in length.

Methods of Use

General Discussion

The compositions including one or more of the muscle-specific targeting moieties, engineered AAV capsid system polynucleotides, polypeptides, vector(s), engineered cells, engineered AAV capsid particles can be used generally to package and/or deliver one or more cargos to a recipient cell. In some embodiments, delivery is done in cell-specific manner based upon the specificity of the targeting moiety. In some embodiments this is conferred by the tropism of the engineered AAV capsid, which can be influenced at least in part by the inclusion of one or n-mer motifs described elsewhere herein. In some embodiments, compositions including one or more of the muscle-specific targeting moieties, engineered AAV capsid particles, can be administered to a subject or a cell, tissue, and/or organ and facilitate the transfer and/or integration of the cargo to the recipient cell. In other embodiments, engineered cells capable of producing compositions, such as polypeptides and other particles (e.g., engineered AAV capsids and viral particles), containing one or more of the muscle-specific targeting moieties can be generated from the polynucleotides, vectors, and vector systems etc., described herein. This includes without limitation, the engineered AAV capsid system molecules (e.g., polynucleotides, vectors, and vector systems, etc.). In some embodiments, the polynucleotides, vectors, and vector systems etc., described herein capable of generating the compositions, such as polypeptides and other particles (e.g., engineered AAV capsids and viral particles), containing one or more of the muscle-specific targeting moieties can be delivered to a cell or tissue, in vivo, ex vivo, or in vitro. In some embodiments, when delivered to a subject, the composition can transform a subject's cell in vivo or ex vivo to produce an engineered cell that can be capable of making a composition described herein that contains one or more of the muscle-specific targeting moieties described herein, including but not limited to the engineered AAV capsid particles, which can be released from the engineered cell and deliver cargo molecule(s) to a recipient cell in vivo or produce personalized engineered compositions (e.g., AAV capsid particles) for reintroduction into the subject from which the recipient cell was obtained.

In some embodiments, an engineered cell can be delivered to a subject, where it can release produced compositions of the present invention (including but not limited to engineered AAV capsid particles) such that they can then deliver a cargo (e.g., a cargo polynucleotide(s)) to a recipient cell. These general processes can be used in a variety of ways to treat and/or prevent disease or a symptom thereof in a subject, generate model cells, generate modified organisms, provide cell selection and screening assays, in bioproduction, and in other various applications.

In some embodiments, the compositions, such as polypeptides and other particles (e.g., engineered AAV capsids and viral particles), containing one or more of the muscle-specific targeting moieties) can be delivered to a subject or a cell, tissue, and/or organ. In this way they can be used to deliver any cargo they may contain or are associated with to a muscle cell.

In some embodiments, the engineered AAV capsid polynucleotides, vectors, and systems thereof can be used to generate engineered AAV capsid variant libraries that can be mined for variants with a desired cell-specificity. The description provided herein as supported by the various Examples can demonstrate that one having a desired cell-specificity in mind could utilize the present invention as described herein to obtain a capsid with the desired cell-specificity.

The subject invention may be used as part of a research program wherein there is transmission of results or data. A computer system (or digital device) may be used to receive, transmit, display and/or store results, analyze the data and/or results, and/or produce a report of the results and/or data and/or analysis. A computer system may be understood as a logical apparatus that can read instructions from media (e.g., software) and/or network port (e.g., from the internet), which can optionally be connected to a server having fixed media. A computer system may comprise one or more of a CPU, disk drives, input devices such as keyboard and/or mouse, and a display (e.g., a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g., one or more computers, and/or one or more servers). In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users. A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. Accordingly, the invention comprehends performing any method herein-discussed and storing and/or transmitting data and/or results therefrom and/or analysis thereof, as well as products from performing any method herein-discussed, including intermediates.

Therapeutics

In some embodiments, the compositions containing one or more of the muscle-specific targeting moieties described herein, including, but not limited to the engineered AAV capsid particles, engineered cells, and/or formulations thereof described herein can be delivered to a subject in need thereof as a therapy for one or more diseases. In some embodiments, the disease to be treated is a genetic or epigenetic based disease. In some embodiments, the disease to be treated is not a genetic or epigenetic based disease. In some embodiments, one the compositions containing one or more of the muscle-specific targeting moieties described herein, including, but not limited to, the engineered AAV capsid particles, engineered cells, and/or formulations thereof described herein can be delivered to a subject in need thereof as a treatment or prevention (or as a part of a treatment or prevention) of a disease. It will be appreciated that the specific disease to be treated and/or prevented by delivery of a composition, formulation, cell and the like of the present invention, can be dependent on the cargo coupled to, attached to, contained in, or otherwise associated with the composition, formulation, cell and the like of the present invention.

Genetic diseases that can be treated are discussed in greater detail elsewhere herein (see e.g., discussion on Gene-modification based-therapies below). Other diseases include, but are not limited to, any of the following: cancer, Acinetobacter infections, actinomycosis, African sleeping sickness, AIDS/HIV, amoebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, Bacterial meningitis, Bacterial pneumonia, Bacterial vaginosis, *Bacteroides* infection, balantidiasis, Bartonellosis,

*Baylisascaris* infection, BK virus infection, Black Piedra, Blastocytosis, Blastomycosis, Bolivian hemorrhagic fever, Botulism, Brazilian hemorrhagic fever, brucellosis, Bubonic plague, Burkholderia infection, buruli ulcer, calicivirus invention, campylobacteriosis, Candidiasis, Capillariasis, Carrion's disease, Cat-scratch disease, cellulitis, Chagas Disease, Chancroid, Chickenpox, Chikungunya, *Chlamydia, Chlamydia pneumoniae*, Cholera, Chromoblastomycosis, Chytridiomycosis, Clonorchiasis, *Clostridium difficile* colitis, Coccidioidomycosis, Colorado tick fever, rhinovirus/ coronavirus infection (common cold), Creutzfeldt-Jakob disease, Crimean-congo hemorrhagic fever, Cryptococcosis, Cryptosporidiosis, Cutaneous larva migrans (CLM), cyclosporiasis, cysticercosis, cytomegalovirus infection, Dengue fever, Desmodesmus infection, Dientamoebiasis, Diphtheria, Diphyllobothriasis, Dracunculiasis, Ebola, Echinococcosis, Ehrlichiosis, Enterobiasis, *Enterococcus* infection, Enterovirus infection, Epidemic typhus, Erythema Infectiosum, Exanthem subitum, Fascioliasis, Fasciolopsiasis, fatal familial insomnia, filariasis, *Clostridium perfringens* infection, *Fusobacterium* infection, Gas gangrene (clostridial myonecrosis), geotrichosis, Gerstmann-Straussler-Scheinker syndrome, Giardiasis, Glanders, Gnathostomiasis, Gonorrhea, Granuloma inguinale, Group A streptococcal infection, Group B streptococcal infection, *Haemophilus influenzae* infection, Hand, foot, and mouth disease, hantavirus pulmonary syndrome, heartland virus disease, *Helicobacter pylori* infection, hemorrhagic fever with renal syndrome, Hendra virus infection, Hepatitis (all groups A, B, C, D, E), herpes simplex, histoplasmosis, hookworm infection, human bocavirus infection, human ewingii ehrlichiosis, Human granulocytic anaplasmosis, human metapneumovirus infection, human monocytic ehrlichiosis, human papilloma virus, Hymenolepiasis, Epstein-Barr infection, mononucleosis, influenza, isosporiasis, Kawasaki disease, Kingella kingae infection, Kuru, Lassa fever, Legionellosis (Legionnaires disease and Potomac Fever), Leishmaniasis, Leprosy, Leptospirosis, Listeriosis, Lyme disease, lymphatic filariasis, lymphocytic choriomeningitis, Malaria, Marburg hemorrhagic fever, measles, Middle East respiratory syndrome, Melioidosis, meningitis, Meningococcal disease, Metagonimiasis, Microsporidosis, Molluscum contagiosum, Monkeypox, Mumps, Murine typhus, *Mycoplasma* pneumonia, *Mycoplasma genitalium* infection, Mycetoma, Myiasis, Conjunctivitis, Nipah virus infection, Norovirus, Variant Creutzfeldt-Jakob disease, Nocardiosis, Onchocerciasis, Opisthorchiasis, Paracoccidioidomycosis, Paragonimiasis, Pasteurellosis, Pediculosisi capitis, Pediculosis corporis, Pediculosis pubis, pelvic inflammatory disease, pertussis, plague, pneumococcal infection, pneumocystis pneumonia, pneumonia, poliomyelitis, prevotella infection, primary amoebic menigoencephalitis, progressive multifocal leukoencephalopathy, Psittacosis, Q fever, rabies, relapsing fever, respiratory syncytial virus infection, rhinovirus infection, rickettsial infection, Rickettsialpox, Rift Valley Fever, Rocky Mountain Spotted Fever, Rotavirus infection, Rubella, Salmonellosis, SARS, Scabies, Scarlet fever, Schistosomiasis, sepsis, Shigellosis, Shingles, Smallpox, Sporotrichosis, Staphylococcal infection (including MRSA), strongyloidiasis, subacute sclerosing panencephalitis, Syphilis, Taeniasis, tetanus, *Trichophyton* species infection, Toxocariasis, Toxoplasmosis, Trachoma, Trichinosis, Trichiniasis, Tuberculosis, Tularemia, Typhoid Fever, Typhus Fever, *Ureaplasma urealyticum* infection, Valley fever, Venezuelan equine encephalitis, Venezuelan hemorrhagic fever, *Vibrio* species infection, Viral pneumonia, West Nile Fever, White Piedra, *Yersinia*

*pseudotuberculosis*, Yersiniosis, Yellow fever, Zeaspora, Zika fever, Zygomycosis and combinations thereof.

Other diseases and disorders that can be treated using embodiments of the present invention include, but are not limited to, endocrine diseases (e.g., Type I and Type II diabetes, gestational diabetes, hypoglycemia. Glucagonoma, Goiter, Hyperthyroidism, hypothyroidism, thyroiditis, thyroid cancer, thyroid hormone resistance, parathyroid gland disorders, Osteoporosis, osteitis deformans, rickets, osteomalacia, hypopituitarism, pituitary tumors, etc.), skin conditions of infections and non-infectious origin, eye diseases of infectious or non-infectious origin, gastrointestinal disorders of infectious or non-infectious origin, cardiovascular diseases of infectious or non-infectious origin, brain and neuron diseases of infectious or non-infectious origin, nervous system diseases of infectious or non-infectious origin, muscle diseases of infectious or non-infectious origin, bone diseases of infectious or non-infectious origin, reproductive system diseases of infectious or non-infectious origin, renal system diseases of infectious or non-infectious origin, blood diseases of infectious or non-infectious origin, lymphatic system diseases of infectious or non-infectious origin, immune system diseases of infectious or non-infectious origin, mental-illness of infectious or non-infectious origin and the like.

In some embodiments, the disease to be treated is a muscle or muscle related disease or disorder, such as a genetic muscle disease or disorder.

Other diseases and disorders will be appreciated by those of skill in the art.

Adoptive Cell Therapies

Generally speaking, adoptive cell transfer involves the transfer of cells (autologous, allogeneic, and/or xenogeneic) to a subject. The cells may or may not be modified and/or otherwise manipulated prior to delivery to the subject.

In some embodiments, an engineered cell as described herein can be included in an adoptive cell transfer therapy. In some embodiments, an engineered cell as described herein can be delivered to a subject in need thereof. In some embodiments, the cell can be isolated from a subject, manipulated in vitro such that it contains and/or is capable of generating a composition of the present invention containing a muscle-specific targeting moiety described elsewhere herein (including but not limited to an engineered AAV capsid particle) described herein to produce an engineered cell and delivered back to the subject in an autologous manner or to a different subject in an allogeneic or xenogeneic manner. The cell isolated, manipulated, and/or delivered can be a eukaryotic cell. The cell isolated, manipulated, and/or delivered can be a stem cell. The cell isolated, manipulated, and/or delivered can be a differentiated cell. The cell isolated, manipulated, and/or delivered can be an immune cell, a blood cell, an endocrine cell, a renal cell, an exocrine cell, a nervous system cell, a vascular cell, a muscle cell, a urinary system cell, a bone cell, a soft tissue cell, a cardiac cell, a neuron, or an integumentary system cell. Other specific cell types will instantly be appreciated by one of ordinary skill in the art.

In some embodiments, the isolated cell can be manipulated such that it becomes an engineered cell as described elsewhere herein (e.g., contain and/or express one or more engineered delivery system molecules or vectors described elsewhere herein). Methods of making such engineered cells are described in greater detail elsewhere herein.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can be or involve the administration of $10^4$-$10^9$ cells per kg body weight including all integer values of cell numbers within those ranges. In some embodiments, $10^5$ to $10^6$ cells/kg are delivered Dosing in adoptive cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tissue. In some embodiments, the tissue can be a tumor.

To guard against possible adverse reactions, engineered cells can be equipped with a transgenic safety switch, in the form of a transgene that renders the cells vulnerable to exposure to a specific signal. For example, the herpes simplex viral thymidine kinase (TK) gene may be used in this way, for example by introduction into the engineered cell similar to that discussed in Greco, et al., Improving the safety of cell therapy with the TK-suicide gene. Front. Pharmacol. 2015; 6: 95. In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

Methods of modifying isolated cells to obtain the engineered cells with the desired properties are described elsewhere herein. In some embodiments, the methods can include genome modification, including, but not limited to, genome editing using a CRISPR-Cas system to modify the cell. This can be in addition to introduction of an engineered AAV capsid system molecule describe elsewhere herein.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1;112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic cells, such as engineered cells described herein. Therefore, to effectively use an adoptive immunotherapy approach in these conditions, the introduced cells would need to be resistant to the immunosuppressive treatment. Thus, in a particular embodiment, the present invention further comprises a step of modifying the engineered cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to engineered cells for adoptive cell therapy by inactivating the target of the immunosuppressive agent in engineered cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In some embodiments, the gene locus involved in the expression of PD-1 or CTLA-4 genes is targeted. In some embodiments, combinations of genes are targeted, such as but not limited to PD-1 and TIGIT.

In some embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic or other modification of the engineered cells (such as engineered T cells (e.g., the isolated cell is a T cell), the engineered cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. The engineered cells can be expanded in vitro or in vivo.

In some embodiments, the method comprises editing the engineered cells ex vivo by a suitable gene modification method described elsewhere herein (e.g., gene editing via a CRISPR-Cas system) to eliminate potential alloreactive TCRs or other receptors to allow allogeneic adoptive transfer. In some embodiments, T cells are edited ex vivo by a CRISPR-Cas system or other suitable genome modification technique to knock-out or knock-down an endogenous gene encoding a TCR (e.g., an ap TCR) or other relevant receptor to avoid graft-versus-host-disease (GVHTD). In some embodiments, where the engineered cells are T cells, the engineered cells are edited ex vivo by CRISPR or other appropriate gene modification method to mutate the TRAC locus. In some embodiments, T cells are edited ex vivo via a CRISPR-Cas system using one or more guide sequences targeting the first exon of TRAC. See Liu et al., Cell Research 27:154-157 (2017). In some embodiments, the first exon of TRAC is modified using another appropriate gene modification method. In some embodiments, the method comprises use of CRISPR or other appropriate method to knock-in an exogenous gene encoding a CAR or a TCR into the TRAC locus, while simultaneously knocking-out the endogenous TCR (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous TCR promoter.

In some embodiments, the method comprises editing the engineered cell, e.g., engineered T cells, ex vivo via a CRISPR-Cas system to knock-out or knock-down an endogenous gene encoding an HLA-I protein to minimize immunogenicity of the edited cells, e.g. engineered T cells. In some embodiments, engineered T cells can be edited ex vivo via a CRISPR-Cas system to mutate the beta-2 microglobulin (B2M) locus. In some embodiments, engineered cell, e.g., engineered T cells, are edited ex vivo via a CRISPR-Cas system using one or more guide sequences targeting the first exon of B2M. The first exon of B2M can also be modified using another appropriate modification method. See Liu et al., Cell Research 27:154-157 (2017). The first exon of B2M can also be modified using another appropriate modification method, which will be appreciated by those of ordinary skill in the art. In some embodiments, the method comprises use a CRISPR-Cas system to knock-in an exogenous gene encoding a CAR or a TCR into the B2M locus, while simultaneously knocking-out the endogenous B2M (e.g., with a donor sequence encoding a self-cleaving P2A peptide following the CAR cDNA). See Eyquem et al., Nature 543:113-117 (2017). This can also be accomplished using another appropriate modification method, which will be appreciated by those of ordinary skill in the art. In some embodiments, the exogenous gene comprises a promoter-less CAR-encoding or TCR-encoding sequence which is inserted operably downstream of an endogenous B2M promoter.

In some embodiments, the method comprises editing the engineered cell, e.g., engineered T cells, ex vivo via a CRISPR-Cas system to knock-out or knock-down an endogenous gene encoding an antigen targeted by an exogenous CAR or TCR. This can also be accomplished using another appropriate modification method, which will be appreciated by those of ordinary skill in the art. In some embodiments, the engineered cells, such as engineered T cells, are edited ex vivo via a CRISPR-Cas system to knock-out or knock-down the expression of a tumor antigen selected from human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI) (see e.g., International Patent Application Publication WO2016/011210). This can also be accomplished using another appropriate modification method, which will be appreciated by those of ordinary skill in the art. In some embodiments, the engineered cells, such as engineered T cells are edited ex vivo via a CRISPR-Cas system to knock-out or knock-down the expression of an antigen selected from B cell maturation antigen (BCMA), transmembrane activator and CAML Interactor (TACI), or B-cell activating factor receptor (BAFF-R), CD38, CD138, CS-1, CD33, CD26, CD30, CD53, CD92, CD100, CD148, CD150, CD200, CD261, CD262, or CD362 (see e.g., International Patent Application Publication WO2017/011804). This can also be accomplished using another appropriate modification method, which will be appreciated by those of ordinary skill in the art.

Gene Drives

The present invention also contemplates use of the compositions containing a muscle-specific targeting moiety described elsewhere herein, formulations thereof, cells thereof, vector systems, and the like to generate a gene drive via delivery of one or more cargo polynucleotides or production of a composition containing a muscle-specific targeting moiety described elsewhere herein (including but not limited to engineered AAV capsid particles) with one or more cargo polynucleotides capable of producing a gene drive. In some embodiments, the gene drive can be a Cas-mediated RNA-guided gene drive e.g., Cas- to provide RNA-guided gene drives, for example in systems analogous to gene drives described in International Patent Application Publication WO 2015/105928. Systems of this kind may for example provide methods for altering eukaryotic germline cells, by introducing into the germline cell a nucleic acid sequence encoding an RNA-guided DNA nuclease and one or more guide RNAs. The guide RNAs may be designed to be complementary to one or more target locations on genomic DNA of the germline cell. The nucleic acid sequence encoding the RNA guided DNA nuclease and the nucleic acid sequence encoding the guide RNAs may be provided on constructs between flanking sequences, with promoters arranged such that the germline cell may express the RNA guided DNA nuclease and the guide RNAs, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into genomic DNA at a target cut site by mechanisms such as homologous recombination, to render the germline cell homozygous for the foreign nucleic acid sequence. In this way, gene-drive systems are capable of introgressing desired cargo genes throughout a breeding population (see e.g., Gantz et al., 2015, Highly efficient Cas9-mediated gene drive for population modification of the malaria vector mosquito *Anopheles stephensi*, PNAS 2015, published ahead of print Nov. 23, 2015, doi:10.1073/pnas.1521077112; Esvelt et al., 2014, Concerning RNA-guided gene drives for the alteration of wild populations eLife 2014;3:e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs (such as gene drive engineered delivery system constructs) may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in *Caenorhabditis elegans* Using a Small Molecule, PLoS ONE 8(8): e72393. doi:10.1371/journal.pone.0072393).

Transplantation and Xenotransplantation

The compositions containing a muscle-specific targeting moiety described elsewhere herein, formulations thereof, cells thereof, vector systems, and the like, can be used to deliver cargo polynucleotides and/or otherwise be involved in modifying tissues for transplantation between two different persons (transplantation) or between species (xenotransplantation). Such techniques for generation of transgenic animals is described elsewhere herein. Interspecies transplantation techniques are generally known in the art. For example, RNA-guided DNA nucleases can be delivered using via engineered AAV capsid polynucleotides, vectors, engineered cells, and/or engineered AAV capsid particles described herein and can be used to knockout, knockdown or disrupt selected genes in an organ for transplant (e.g. ex vivo (e.g. after harvest but before transplantation) or in vivo (in donor or recipient)), animal, such as a transgenic pig (such as the human heme oxygenase-1 transgenic pig line), for example by disrupting expression of genes that encode epitopes recognized by the human immune system, i.e. xenoantigen genes. Candidate porcine genes for disruption may for example include α(1,3)-galactosyltransferase and cytidine monophosphate-N-acetylneuraminic acid hydroxylase genes (see PCT Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyperacute rejection.

Where it is interspecies transplantation (such as human to human) the composition compositions containing a muscle-specific targeting moiety described elsewhere herein, (e.g., an engineered AAV capsid system molecule, vectors, engineered cells, and/or engineered delivery particles described herein), can be used to deliver cargo polynucleotides and/or otherwise be involved to modify the tissue to be transplanted. In some embodiments, the modification can include modifying one or more HLA antigens or other tissue type determinants, such that the immunogenic profile is more similar or identical to the recipient's immunogenic profile than to the donor's so as to reduce the occurrence of rejection by the recipient. Relevant tissue type determinants are known in the art (such as those used to determine organ matching) and techniques to determine the immunogenic profile (which is made up of the expression signature of the tissue type determinants) are generally known in the art.

In some embodiments, the donor (such as before harvest) or recipient (after transplantation) can receive one or more of the compositions containing a muscle-specific targeting moiety described elsewhere herein, formulations thereof, cells thereof, vector systems, engineered AAV capsid system molecules, vectors, engineered cells, and/or engineered delivery particles described herein that are capable of modifying the immunogenic profile of the transplanted cells, tissue, and/or organ. In some embodiments, the transplanted cells, tissue, and/or organ can be harvested from the donor and the compositions containing a muscle-specific targeting moiety described elsewhere herein, formulations thereof, cells thereof, vector systems, engineered AAV capsid system molecules, vectors, engineered cells, and/or engineered delivery particles described herein capable of modifying the harvested cells, tissue, and/or organ to be, for example, less immunogenic or be modified to have some specific characteristic when transplanted in the recipient can be delivered to the harvested cells, tissue, and/or organ ex vivo. After delivery the cells, tissue, and/or organs can be transplanted into the donor.

Gene Modification and Treatment of Diseases with Genetic or Epigenetic Aspects

The engineered delivery system molecules, vectors, engineered cells, and/or engineered delivery particles described herein containing a muscle-specific targeting moiety can be used to modify genes or other polynucleotides and/or treat diseases with genetic and/or epigenetic aspects. As described elsewhere herein the cargo molecule can be a polynucleotide that can be delivered to a cell and, in some embodiments, be integrated into the genome of the cell. In some embodiments, the cargo molecule(s) can be one or more CRISPR-Cas system components. In some embodiments, the CRISPR-Cas components, when delivered by a composition or formulation thereof of the present invention, such as an engineered AAV capsid particles described herein, can be optionally expressed in the recipient cell and act to modify the genome of the recipient cell in a sequence specific manner. In some embodiments, the cargo molecules that can be packaged and delivered by the engineered AAV capsid particles or other particles and/or compositions described herein can facilitate/mediate genome modification via a method that is not dependent on CRISPR-Cas. Such non-CRISPR-Cas genome modification systems will instantly be appreciated by those of ordinary skill in the art and are also, at least in part, described elsewhere herein. In some embodiments, modification is at a specific target sequence. In other embodiments, modification is at locations that appear to be random throughout the genome.

Examples of disease-associated genes and polynucleotides and disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Any of these can be appropriate to be treated by one or more of the methods described herein. In some embodiments, the disease is a muscle disease or disorder, neuro-muscular disease or disorder, or a cardiomyopathy. In some embodiments, the disease or disorder selected from any one or more of the following:

(a) an auto immune disease;
(b) a cancer;
(c) a muscular dystrophy;
(d) a neuro-muscular disease;
(e) a sugar or glycogen storage disease;
(f) an expanded repeat disease;
(g) a dominant negative disease;
(h) a cardiomyopathy;
(i) a viral disease;
(j) a progeroid disease; or
(k) any combination thereof.

In some embodiments, the expanded repeat disease is Huntington's disease, a Myotonic Dystrophy, or Facioscapulohumeral muscular dystrophy (FSHD). In some embodiments, the muscular dystrophy is Duchene muscular dystrophy, Becker Muscular dystrophy, a Limb-Girdle muscular dystrophy, an Emery Dreifuss muscular dystrophy, a myotonic dystrophy, or FSHD. In some embodiments, the myotonic dystrophy is Type 1 or Type 2. In some embodiments, the cardiomyopathy is dilated cardiomyopathy, hypertrophic cardiomyopathy, DMD-associated cardiomyopathy, or Dannon disease. In some embodiments, the sugar or glycogen storage disease is a MPS type III disease or Pompe disease. In some embodiments, the MIPS type III disease, is MPS Type IIIA, IIIB, IIIC, or HID. In some embodiments, the neuro-muscular disease is Charcot-Marie-Tooth disease or Friedreich's Ataxia.

More specifically, Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex or other method of gene modification of the present invention. Examples of disease-associated and/or cell function-associated genes and polynucleotides are listed in Tables 4 and 5. Additional examples are discussed elsewhere herein.

TABLE 4

| Exemplary Genetic and Other Diseases and Associated Genes | | | |
| --- | --- | --- | --- |
| Disease Name | Primary Tissues or System Affected | Additional Tissues/ Systems Affected | Genes |
| Achondroplasia | Bone and Muscle | | fibroblast growth factor receptor 3 (FGFR3) |
| Achromatopsia | eye | | CNGA3, CNGB3, GNAT2, PDE6C, PDE6H, ACHM2, ACHM3, |
| Acute Renal Injury | kidney | | NFkappaB, AATF, p85alpha, FAS, Apoptosis cascade elements (e.g. FASR, Caspase 2, 3, 4, 6, 7, 8, 9, 10, AKT, TNF alpha, IGF1, IGF1R, RIPK1), p53 |
| Age Related Macular Degeneration | eye | | Abcr; CCL2; CC2; CP (ceruloplasmin); Timp3; cathepsinD; VLDLR, CCR2 |
| AIDS | Immune System | | KIR3DL1, NKAT3, NKB1, AMB11, KIR3DS1, IFNG, CXCL12, SDF1 |
| Albinism (including oculocutaneous albinism (types 1-7) and ocular albinism) | Skin, hair, eyes, | | TYR, OCA2, TYRP1, and SLC45A2, SLC24A5 and C10orf11 |
| Alkaptonuria | Metabolism of amino acids | Tissues/organs where homogentisic acid accumulates, particularly cartilage (joints), heart valves, kidneys | HGD |

TABLE 4-continued

Exemplary Genetic and Other Diseases and Associated Genes

| Disease Name | Primary Tissues or System Affected | Additional Tissues/ Systems Affected | Genes |
|---|---|---|---|
| alpha-1 antitrypsin deficiency (AATD or A1AD) | Lung | Liver, skin, vascular system, kidneys, GI | SERPINA1, those set forth in WO2017165862, PiZ allele |
| ALS | CNS | | SOD1; ALS2; ALS3; ALS5; ALS7; STEX; FUS; TARDBP; VEGF (VEGF-a; VEGF-b; VEGF-c); DPP6; NEFH, PTGS1, SLC1A2, TNFRSF10B, PRPH, HSP90AA1, CRIA2, IFNG, AMPA2 S100B, FGF2, AOX1, CS, TXN, RAPHJ1, MAP3K5, NBEAL1, GPX1, ICA1L, RAC1, MAPT, ITPR2, ALS2CR4, GLS, ALS2CR8, CNTFR, ALS2CR11, FOLH1, FAM117B, P4HB, CNTF, SQSTM1, STRADB, NAIP, NLR, YWHAQ, SLC33A1, TRAK2, SCA1, NIF3L1, NIF3, PARD3B, COX8A, CDK15, HECW1, HECT, C2, WW 15, NOS1, MET, SOD2, HSPB1, NEFL, CTSB, ANG, HSPA8, RNase A, VAPB, VAMP, SNCA, alpha HGF, CAT, ACTB, NEFM, TH, BCL2, FAS, CASP3, CLU, SMN1, G6PD, BAX, HSF1, RNF19A, JUN, ALS2CR12, HSPA5, MAPK14, APEX1, TXNRD1, NOS2, TIMP1, CASP9, XIAP, GLG1, EPO, VEGFA, ELN, GDNF, NFE2L2, SLC6A3, HSPA4, APOE, PSMB8, DCTN2, TIMP3, KIFAP3, SLC1A1, SMN2, CCNC, STUB1, ALS2, PRDX6, SYP, CABIN1, CASP1, GART, CDK5, ATXN3, RTN4, C1QB, VEGFC, HTT, PARK7, XDH, GFAP, MAP2, CYCS, FCGR3B, CCS, UBL5, MMP9m SLC18A3, TRPM7, HSPB2, AKT1, DEERL1, CCL2, NGRN, GSR, TPPP3, APAF1, BTBD10, GLUD1, CXCR4, S:C1A3, FLT1, PON1, AR, LIF, ERBB3, :GA:S1, CD44, TP53, TLR3, GRIA1, GAPDH, AMPA, GRIK1, DES, CHAT, FLT4, CHMP2B, BAG1, CHRNA4, GSS, BAK1, KDR, GSTP1, OGG1, IL6 |
| Alzheimer's Disease | Brain | | E1; CHIP; UCH; UBB; Tau; LRP; PICALM; CLU; PS1; SORL1; CR1; VLDLR; UBA1; UBA3; CHIP28; AQP1; UCHL1; UCHL3; APP, AAA, CVAP, AD1, APOE, AD2, DCP1, ACE1, MPO, PACIP1, PAXIP1L, PTIP, A2M, BLMH, BMH, PSEN1, AD3, ALAS2, ABCA1, BIN1, BDNF, BTNL8, C1ORF49, CDH4, CHRNB2, CKLFSF2, CLEC4E, CR1L, CSF3R, CST3, CYP2C, DAPK1, ESR1, FCAR, FCGR3B, FFA2, FGA, GAB2, GALP, GAPDHS, GMPB, HP, HTR7, IDE, IF127, IFI6, IFIT2, IL1RN, IL-1RA, IL8RA, IL8RB, JAG1, KCNJ15, LRP6, MAPT, MARK4, MPHOSPH1, MTHFR, NBN, NCSTN, NIACR2, NMNAT3, NTM, ORM1, P2RY13, PBEF1, PCK1, PICALM, PLAU, PLXNC1, PRNP, PSEN1, PSEN2, PTPRA, RALGPS2, RGSL2, SELENBP1, SLC25A37, SORL1, Mitoferrin-1, TF, TFAM, TNF, TNFRSF10C, UBE1C |
| Amyloidosis | | | APOA1, APP, AAA, CVAP, AD1, GSN, FGA, LYZ, TTR, PALB |

TABLE 4-continued

| Exemplary Genetic and Other Diseases and Associated Genes | | | |
|---|---|---|---|
| Disease Name | Primary Tissues or System Affected | Additional Tissues/ Systems Affected | Genes |
| Amyloid neuropathy | | | TTR, PALB |
| Anemia | Blood | | CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT |
| Angelman Syndrome | Nervous system, brain | | UBE3A |
| Attention Deficit Hyperactivity Disorder (ADHD) | Brain | | PTCHD1 |
| Autoimmune lymphoproliferative syndrome | Immune system | | TNFRSF6, APT1, FAS, CD95, ALPS1A |
| Autism, Autism spectrum disorders (ASDs), including Asperger's and a general diagnostic category called Pervasive Developmental Disorders (PDDs) | Brain | | PTCHD1; Mecp2; BZRAP1; MDGA2; Sema5A; Neurexin 1; GLO1, RTT, PPMX, MRX16, RX79, NLGN3, NLGN4, KIAA1260, AUTSX2, FMRI, FMR2; FXR1; FXR2; MGLUR5, ATP10C, CDH10, GRM6, MGLUR6, CDH9, CNTN4, NLGN2, CNTNAP2, SEMA5A, DHCR7, NLGN4X, NLGN4Y, DPP6, NLGN5, EN2, NRCAM, MDGA2, NRXN1, FMR2, AFF2, FOXP2, OR4M2, OXTR, FXR1, FXR2, PAH, GABRA1, PTEN, GABRA5, PTPRZ1, GABRB3, GABRG1, HIRIP3, SEZ6L2, HOXA1, SHANK3, IL6, SHBZRAP1, LAMB1, SLC6A4, SERT, MAPK3, TAS2R1, MAZ, TSC1, MDGA2, TSC2, MECP2, UBE3A, WNT2, see also 20110023145 |
| autosomal dominant polycystic kidney disease (ADPKD) - (includes diseases such as von Hippel-Lindau disease and tubreous sclerosis complex disease) | kidney | liver | PKD1, PKD2 |
| Autosomal Recessive Polycystic Kidney Disease (ARPKD) | kidney | liver | PKDH1 |
| Ataxia-Telangiectasia (a.k.a Louis Bar syndrome) | Nervous system, immune system | various | ATM |
| B-Cell Non-Hodgkin Lymphoma | | | BCL7A, BCL7 |
| Bardet-Biedl syndrome | Eye, musculoskeletal system, kidney, reproductive organs | Liver, ear, gastrointestinal system, brain | ARL6, BBS1, BBS2, BBS4, BBS5, BBS7, BBS9, BBS10, BBS12, CEP290, INPP5E, LZTFL1, MKKS, MKS1, SDCCAG8, TRIM32, TTC8 |
| Bare Lymphocyte Syndrome | blood | | TAPBP, TPSN, TAP2, ABCB3, PSF2, RING11, MHC2TA, C2TA, RFX5, RFXAP, RFX5 |
| Bartter's Syndrome (types I, II, III, IVA and B, and V) | kidney | | SLC12A1 (type I), KCNJ1 (type II), CLCNKB (type III), BSND (type IV A), or both the CLCNKA CLCNKB genes (type IV B), CASR (type V). |
| Becker muscular dystrophy | Muscle | | DMD, BMD, MYF6 |
| Best Disease (Vitelliform Macular Dystrophy type 2) | eye | | VMD2 |
| Bleeding Disorders | blood | | TBXA2R, P2RX1, P2X1 |
| Blue Cone Monochromacy | eye | | OPN1LW, OPN1MW, and LCR |
| Breast Cancer | Breast tissue | | BRCA1, BRCA2, COX-2 |
| Bruton's Disease (aka X-linked Agammglobulinemia) | Immune system, specifically B cells | | BTK |
| Cancers (e.g., lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal | Various | | FAS, BID, CTLA4, PDCD1, CBLB, PTPN6, TRAC, TRBC, those described in WO2015048577 |

TABLE 4-continued

| | Exemplary Genetic and Other Diseases and Associated Genes | | |
|---|---|---|---|
| Disease Name | Primary Tissues or System Affected | Additional Tissues/ Systems Affected | Genes |
| cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma | | | |
| Cardiovascular Diseases | heart | Vascular system | IL1B, XDH, TP53, PTGS, MB, IL4, ANGPT1, ABCGu8, CTSK, PTGIR, KCNJ11, INS, CRP, PDGFRB, CCNA2, PDGFB, KCNJ5, KCNN3, CAPN10, ADRA2B, ABCG5, PRDX2, CPAN5, PARP14, MEX3C, ACE, RNF, IL6, TNF, STN, SERPINE1, ALB, ADIPOQ, APOB, APOE, LEP, MTHFR, APOA1, EDN1, NPPB, NOS3, PPARG, PLAT, PTGS2, CETP, AGTR1, HMGCR, IGF1, SELE, REN, PPARA, PON1, KNG1, CCL2, LPL, VWF, F2, ICAM1, TGFB, NPPA, IL10, EPO, SOD1, VCAM1, IFNG, LPA, MPO, ESR1, MAPK, HP, F3, CST3, COG2, MMP9, SERPINC1, F8, HMOX1, APOC3, IL8, PROL1, CBS, NOS2, TLR4, SELP, ABCA1, AGT, LDLR, GPT, VEGFA, NR3C2, IL18, NOS1, NR3C1, FGB, HGF, ILIA, AKT1, LIPC, HSPD1, MAPK14, SPP1, ITGB3, CAT, UTS2, THBD, F10, CP, TNFRSF11B, EGFR, MMP2, PLG, NPY, RHOD, MAPK8, MYC, FN1, CMA1, PLAU, GNB3, ADRB2, SOD2, F5, VDR, ALOX5, HLA-DRB1, PARP1, CD40LG, PON2, AGER, IRS1, PTGS1, ECE1, F7, IRMN, EPHX2, IGFBP1, MAPK10, FAS, ABCB1, JUN, IGFBP3, CD14, PDE5A, AGTR2, CD40, LCAT, CCR5, MMP1, TIMP1, ADM, DYT10, STAT3, MMP3, ELN, USF1, CFH, HSPA4, MMP12, MME, F2R, SELL, CTSB, ANXA5, ADRB1, CYBA, FGA, GGT1, LIPG, HIF1A, CXCR4, PROC, SCARB1, CD79A, PLTP, ADD1, FGG, SAA1, KCNH2, DPP4, NPR1, VTN, KIAA0101, FOS, TLR2, PPIG, IL1R1, AR, CYP1A1, SERPINA1, MTR, RBP4, APOA4, CDKN2A, FGF2, EDNRB, ITGA2, VLA-2, CABIN1, SHBG, HMGB1, HSP90B2P, CYP3A4, GJA1, CAV1, ESR2, LTA, GDF15, BDNF, CYP2D6, NGF, SP1, TGIF1, SRC, EGF, PIK3CG, HLA-A, KCNQ1, CNR1, FBN1, CHKA, BEST1, CTNNB1, IL2, CD36, PRKAB1, TPO, ALDH7A1, CX3CR1, TH, F9, CH1, TF, HFE, IL17A, PTEN, GSTM1, DMD, GATA4, F13A1, TTR, FABP4, PON3, APOC1, INSR, TNFRSF1B, HTR2A, CSF3, CYP2C9, TXN, CYP11B2, PTH, CSF2, KDR, PLA2G2A, THBS1, GCG, RHOA, ALDH2, TCF7L2, NFE2L2, NOTCH1, UGT1A1, IFNA1, PPARD, SIRT1, GNHR1, PAPPA, ARR3, NPPC, AHSP, PTK2, IL13, MTOR, ITGB2, GSTT1, IL6ST, CPB2, CYP1A2, HNF4A, SLC64A, PLA2G6, TNFSF11, SLC8A1, F2RL1, AKR1A1, ALDH9A1, BGLAP, |

TABLE 4-continued

| | | | |
|---|---|---|---|
| Exemplary Genetic and Other Diseases and Associated Genes | | | |
| Disease Name | Primary Tissues or System Affected | Additional Tissues/ Systems Affected | Genes |
| | | | MTTP, MTRR, SULT1A3, RAGE, C4B, P2RY12, RNLS, CREB1, POMC, RAC1, LMNA, CD59, SCM5A, CYP1B1, MIF, MMP13, TIMP2, CYP19A1, CUP21A2, PTPN22, MYH14, MBL2, SELPLG, AOC3, CTSL1, PCNA, IGF2, ITGB1, CAST, CXCL12, IGHE, KCNE1, TFRC, COL1A1, COL1A2, IL2RB, PLA2G10, ANGPT2, PROCR, NOX4, HAMP, PTPN11, SLCA1, IL2RA, CCL5, IRF1, CF:AR, CA:CA, EIF4E, GSTP1, JAK2, CYP3A5, HSPG2, CCL3, MYD88, VIP, SOAT1, ADRBK1, NR4A2, MMP8, NPR2, GCH1, EPRS, PPARGC1A, F12, PECAM1, CCL4, CERPINA34, CASR, FABP2, TTF2, PROS1, CTF1, SGCB, YME1L1, CAMP, ZC3H12A, AKR1B1, MMP7, AHR, CSF1, HDAC9, CTGF, KCNMA1, UGT1A, PRKCA, COMT, S100B, EGR1, PRL, IL15, DRD4, CAMK2G, SLC22A2, CCL11, PGF, THPO, GP6, TACR1, NTS, HNF1A, SST, KCDN1, LOC646627, TBXAS1, CUP2J2, TBXA2R, ADH1C, ALOX12, AHSG, BHMT, GJA4, SLC25A4, ACLY, ALOX5AP, NUMA1, CYP27B1, CYSLTR2, SOD3, LTC4S, UCN, GHRL, APOC2, CLEC4A, KBTBD10, TNC, TYMS, SHC1, LRP1, SOCS3, ADH1B, KLK3, HSD11B1, VKORC1, SERPINB2, TNS1, RNF19A, EPOR, ITGAM, PITX2, MAPK7, FCGR3A, LEEPR, ENG, GPX1, GOT2, HRH1, NR1I2, CRH, HTR1A, VDAC1, HPSE, SFTPD, TAP2, RMF123, PTK2Bm NTRK2, IL6R, ACHE, GLP1R, GHR, GSR, NQO1, NR5A1, GJB2, SLC9A1, MAOA, PCSK9, FCGR2A, SERPINF1, EDN3, UCP2, TFAP2A, C4BPA, SERPINF2, TYMP, ALPP, CXCR2, SLC3A3, ABCG2, ADA, JAK3, HSPA1A, FASN, FGF1, F11, ATP7A, CR1, GFPA, ROCK1, MECP2, MYLK, BCHE, LIPE, ADORA1, WRN, CXCR3, CD81, SMAD7, LAMC2, MAP3K5, CHGA, IAPP, RHO, ENPP1, PTHLH, NRG1, VEGFC, ENPEP, CEBPB, NAGLU,. F2RL3, CX3CL1, BDKRB1, ADAMTS13, ELANE, ENPP2, CISH, GAST, MYOC, ATP1A2, NF1, GJB1, MEF2A, VCL, BMPR2, TUBB, CDC42, KRT18, HSF1, MYB, PRKAA2, ROCK2, TFP1, PRKG1, BMP2, CTNND1, CTH, CTSS, VAV2, NPY2R, IGFBP2, CD28, GSTA1, PPIA, APOH, S100A8, IL11, ALOX15, FBLN1, NR1H3, SCD, GIP, CHGB, PRKCB, SRD5A1, HSD11B2, CALCRL, GALNT2, ANGPTL4, KCNN4, PIK3C2A, HBEGF, CYP7A1, HLA-DRB5, BNIP3, GCKR, S100A12, PADI4, HSPA14, CXCR1, H19, KRTAP19-3, IDDM2, RAC2, YRY1, CLOCK, NGFR, DBH, CHRNA4, CACNA1C, PRKAG2, CHAT, PTGDS, NR1H2, TEK, VEGFB, MEF2C, MAPKAPK2, TNFRSF11A, HSPA9, CYSLTR1, |

TABLE 4-continued

| Exemplary Genetic and Other Diseases and Associated Genes | | | |
| --- | --- | --- | --- |
| Disease Name | Primary Tissues or System Affected | Additional Tissues/ Systems Affected | Genes |
| | | | MATIA, OPRL1, IMPA1, CLCN2, DLD, PSMA6, PSMB8, CHI3L1, ALDH1B1, PARP2, STAR, LBP, ABCC6, RGS2, EFNB2, GJB6, APOA2, AMPD1, DYSF, FDFT1, EMD2, CCR6, GJB3, IL1RL1, ENTPD1, BBS4, CELSR2, F11R, RAPGEF3, HYAL1, ZNF259, ATOX1, ATF6, KHK, SAT1, GGH, TIMP4, SLC4A4, PDE2A, PDE3B, FADS1, FADS2, TMSB4X, TXNIP, LIMS1, RHOB, LY96, FOXO1, PNPLA2, TRH, GJC1, S:C17A5, FTO, GJD2, PRSC1, CASP12, GPBAR1, PXK, IL33, TRIB1, PBX4, NUPR1, 15-SEP, CILP2, TERC, GGT2, MTCO1, UOX, AVP |
| Cataract | eye | | CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1 |
| CDKL-5 Deficiencies or Mediated Diseases | Brain, CNS | | CDKL5 |
| Charcot-Marie-Tooth (CMT) disease (Types 1, 2, 3, 4,) | Nervous system | Muscles (dystrophy) | PMP22 (CMT1A and E), MPZ (CMT1B), LITAF (CMT1C), EGR2 (CMT1D), NEFL (CMT1F), GJB1 (CMT1X), MFN2 (CMT2A), KIF1B (CMT2A2B), RAB7A (CMT2B), TRPV4 (CMT2C), GARS (CMT2D), NEFL (CMT2E), GAPD1 (CMT2K), HSPB8 (CMT2L), DYNC1H1, CMT2O), LRSAM1 (CMT2P), IGHMBP2 (CMT2S), MORC2 (CMT2Z), GDAP1 (CMT4A), MTMR2 or SBF2/MTMR13 (CMT4B), SH3TC2 (CMT4C), NDRG1 (CMT4D), PRX (CMT4F), FIG4 (CMT4J), NT-3 |
| Chédiak-Higashi Syndrome | Immune system | Skin, hair, eyes, neurons | LYST |
| Choroidermia | | | CHM, REP1, |
| Chorioretinal atrophy | eye | | PRDM13, RGR, TEAD1 |
| Chronic Granulomatous Disease | Immune system | | CYBA, CYBB, NCF1, NCF2, NCF4 |
| Chronic Mucocutaneous Candidiasis | Immune system | | AIRE, CARD9, CLEC7A IL12B, IL12B1, IL1F, IL17RA, IL17RC, RORC, STAT1, STAT3, TRAF31P2 |
| Cirrhosis | liver | | KRT18, KRT8, CIRH1A, NAIC, TEX292, KIAA1988 |
| Colon cancer (Familial adenomatous polyposis (FAP) and hereditary nonpolyposis colon cancer (HNPCC)) | Gastrointestinal | | FAP: APC HNPCC: MSH2, MLH1, PMS2, SH6, PMS1 |
| Combined Immunodeficiency | Immune System | | IL2RG, SCIDX1, SCIDX, IMD4); HIV-1 (CCL5, SCYA5, D17S136E, TCP228 |
| Cone(-rod) dystrophy | eye | | AIPL1, CRX, GUA1A, GUCY2D, PITPM3, PROM1, PRPH2, RIMS1, SEMA4A, ABCA4, ADAM9, ATF6, C21ORF2, C8ORF37, CACNA2D4, CDHR1, CERKL, CNGA3, CNGB3, CNNM4, CNAT2, IFT81, KCNV2, PDE6C, PDE6H, POC1B, RAX2, RDH5, RPGRIP1, TTLL5, RetCG1, GUCY2E |

TABLE 4-continued

| | | | |
|---|---|---|---|
| Exemplary Genetic and Other Diseases and Associated Genes | | | |
| Disease Name | Primary Tissues or System Affected | Additional Tissues/ Systems Affected | Genes |
| Congenital Stationary Night Blindness | eye | | CABP4, CACNA1F, CACNA2D4, GNAT1, CPR179, GRK1, GRM6, LRIT3, NYX, PDE6B, RDH5, RHO, RLBP1, RPE65, SAG, SLC24A1, TRPM1, |
| Congenital Fructose Intolerance | Metabolism | | ALDOB |
| Cori's Disease (Glycogen Storage Disease Type III) | Various-wherever glycogen accumulates, particularly liver, heart, skeletal muscle | | AGL |
| Corneal clouding and dystrophy | eye | | APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD |
| Cornea plana congenital | | | KERA, CNA2 |
| Cri du chat Syndrome, also known as 5p syndrome and cat cry syndrome | | | Deletions involving only band 5p15.2 to the entire short arm of chromosome 5, e.g. CTNND2, TERT, |
| Cystic Fibrosis (CF) | Lungs and respiratory system | Pancreas, liver, digestive system, reproductive system, exocrine, glands, | CTFR, ABCC7, CF, MRP7, SCNN1A, those described in WO2015157070 |
| Diabetic nephropathy | kidney | | Gremlin, 12/15- lipoxygenase, TIM44, |
| Dent Disease (Types 1 and 2) | Kidney | | Type 1: CLCN5, Type 2: ORCL |
| Dentatorubro-Pallidoluysian Atrophy (DRPLA) (aka Haw River and Naito-Oyanagi Disease) | CNS, brain, muscle | | Atrophin-1 and Atn1 |
| Down Syndrome | various | | Chromosome 21 trisomy |
| Drug Addiction | Brain | | Prkce; Drd2; Drd4; ABAT; GRIA2; Grm5; Grin1; Htr1b; Grin2a; Drd3; Pdyn; Gria1 |
| Duane syndrome (Types 1, 2, and 3, including subgroups A, B and C). Other names for this condition include: Duane's Retraction Syndrome (or DR syndrome), Eye Retraction Syndrome, Retraction Syndrome, Congenital retraction syndrome and Stilling-Turk-Duane Syndrome | eye | | CHN1, indels on chromosomes 4 and 8 |
| Duchenne muscular dystrophy (DMD) | muscle | Cardiovascular, respiratory | DMD, BMD, dystrophin gene, intron flanking exon 51 of DMD gene, exon 51 mutations in DMD gene, see also WO2013163628 and US Pat. Pub. 20130145487 |
| Edward's Syndrome (Trisomy 18) | | | Complete or partial trisomy of chromosome 18 |
| Ehlers-Danlos Syndrome (Types I-VI) | Various depending on type: including musculoskeletal, eye, vasculature, immune, and skin | | COL5A1, COL5A2, COL1A1, COL3A1, TNXB, PLOD1, COL1A2, FKBP14 and ADAMTS2 |
| Emery-Dreifuss muscular dystrophy | muscle | | LMNA, LMN1, EMD2, FPLD, CMD1A, HGPS, LGMD1B, LMNA, LMN1, EMD2, FPLD, CMD1A |
| Enhanced S-Cone Syndrome | eye | | NR2E3, NRL |
| Fabry's Disease | Various - including skin, eyes, and gastrointestinal system, kidney, heart, brain, nervous system | | GLA |

TABLE 4-continued

Exemplary Genetic and Other Diseases and Associated Genes

| Disease Name | Primary Tissues or System Affected | Additional Tissues/ Systems Affected | Genes |
|---|---|---|---|
| Facioscapulohumeral muscular dystrophy | muscles | | FSHMD1A, FSHD1A, FRG1, |
| Factor H and Factor H-like 1 | blood | | HF1, CFH, HUS |
| Factor V Leiden thrombophilia and Factor V deficiency | blood | | Factor V (F5) |
| Factor V and Factor VII deficiency | blood | | MCFD2 |
| Factor VII deficiency | blood | | F7 |
| Factor X deficiency | blood | | F10 |
| Factor XI deficiency | blood | | F11 |
| Factor XII deficiency | blood | | F12, HAF |
| Factor XIIIA deficiency | blood | | F13A1, F13A |
| Factor XIIIB deficiency | blood | | F13B |
| Familial Hypercholestereolemia | Cardiovascular system | | APOB, LDLR, PCSK9 |
| Familial Mediterranean Fever (FMF) also called recurrent polyserositis or familial paroxysmal polyserositis | Various-organs/tissues with serous or synovial membranes, skin, joints | Heart, kidney, brain/CNS, reproductive organs | MEFV |
| Fanconi Anemia | Various - blood (anemia), immune system, cognitive, kidneys, eyes, musculoskeletal | | FANCA, FACA, FA1, FA, FAA, FAAP95, FAAP90, FLJ34064, FANCC, FANCG, RAD51, BRCA1, BRCA2, BRIP1, BACH1, FANCJ, FANCB, FANCD1, FANCD2, FANCD, FAD, FANCE, FACE, FANCF, FANCI, ERCC4, FANCL, FANCM, PALB2, RAD51C, SLX4, UBE2T, FANCB, XRCC9, PHF9, KIAA1596 |
| Fanconi Syndrome Types I (Childhood onset) and II (Adult Onset) | kidneys | | FRTS1, GATM |
| Fragile X syndrome and related disorders | brain | | FMR1, FMR2; FXR1; FXR2; mGLUR5 |
| Fragile XE Mental Retardation (aka Martin Bell syndrome) | Brain, nervous system | | FMR1 |
| Friedreich Ataxia (FRDA) | Brain, nervous system | heart | FXN/X25 |
| Fuchs endothelial corneal dystrophy | Eye | | TCF4; COL8A2 |
| Galactosemia | Carbohydrate metabolism disorder | Various-where galactose accumulates - liver, brain, eyes | GALT, GALK1, and GALE |
| Gastrointestinal Epithelial Cancer, GI cancer | | | CISH |
| Gaucher Disease (Types 1, 2, and 3, as well as other unusual forms that may not fit into these types) | Fat metabolism disorder | Various-liver, spleen, blood, CNS, skeletal system | GBA |
| Griscelli syndrome | | | |
| Glaucoma | eye | | MYOC, TIGR, GLC1A, JOAG, GPOA, OPTN, GLC1E, FIP2, HYPL, NRP, CYP1B1, GLC3A, OPA1, NTG, NPG, CYP1B1, GLC3A, those described in WO2015153780 |
| Glomerulo sclerosis | kidney | | CC chemokine ligand 2 |
| Glycogen Storage Diseases Types I-VI -See also Cori's Disease, Pompe's Disease, McArdle's disease, Hers Disease, and Von Gierke's disease | Metabolism Diseases | | SLC2A2, GLUT2, G6PC, G6PT, G6PT1, GAA, LAMP2, LAMPB, AGL, GDE, GBE1, GYS2, PYGL, PFKM, see also Cori's Disease, Pompe's Disease, McArdle's disease, Hers Disease, and Von Gierke's disease |
| RBC Glycolytic enzyme deficiency | blood | | any mutations in a gene for an enzyme in the glycolysis pathway including mutations in genes for hexokinases I and II, glucokinase, phosphoglucose isomerase, phosphofructokinase, aldolase Bm triosephosphate isomerease, glyceraldehydee-3- |

TABLE 4-continued

Exemplary Genetic and Other Diseases and Associated Genes

| Disease Name | Primary Tissues or System Affected | Additional Tissues/ Systems Affected | Genes |
|---|---|---|---|
| | | | phosphate dehydrogenase, phosphoglycerokinase, phosphoglycerate mutase, enolase I, pyruvate kinase |
| Hartnup's disease | Malabsorption disease | Various- brain, gastrointestinal, skin, | SLC6A19 |
| Hearing Loss | ear | | NOX3, Hes5, BDNF, |
| Hemochromatosis (HH) | Iron absorption regulation disease | Various- wherever iron accumulates, liver, heart, pancreas, joints, pituitary gland | HFE and H63D |
| Hemophagocytic lymphohistiocytosis disorders | blood | | PRF1, HPLH2, UNC13D, MUNC13-4, HPLH3, HLH3, FHL3 |
| Hemorrhagic disorders | blood | | PI, ATT, F5 |
| Hers disease (Glycogen storage disease Type VI) | liver | muscle | PYGL |
| Hereditary angioedema (HAE) | | | kalikrein B1 |
| Hereditary Hemorrhagic Telangiectasia (Osler-Weber-Rendu Syndrome) | Skin and mucous membranes | | ACVRL1, ENG and SMAD4 |
| Hereditary Spherocytosis | blood | | NK1, EPB42, SLC4A1, SPTA1, and SPTB |
| Hereditary Persistence of Fetal Hemoglobin | blood | | HBG1, HBG2, BCL11A, promoter region of HBG 1 and/or 2 (in the CCAAT box) |
| Hemophilia (hemophilia A (Classic) a B (aka Christmas disease) and C) | blood | | A: FVIII, F8C, HEMA B: FVIX, HEMB C: F9, F11 |
| Hepatic adenoma | liver | | TCF1, HNF1A, MODY3 |
| Hepatic failure, early onset, and neurologic disorder | liver | | SCOD1, SCO1 |
| Hepatic lipase deficiency | liver | | LIPC |
| Hepatoblastoma, cancer and carcinomas | liver | | CTNNB1, PDGFRL, PDGRL, PRLTS, AXIN1, AXIN, CTNNB1, TP53, P53, LFS1, IGF2R, MPRI, MET, CASP8, MCH5 |
| Hermansky-Pudlak syndrome | Skin, eyes, blood, lung, kidneys, intestine | | HPS1, HPS3, HPS4, HPS5, HPS6, HPS7, DTNBP1, BLOC1, BLOC1S2, BLOC3 |
| HIV susceptibility or infection | Immune system | | IL10, CSIF, CMKBR2, CCR2, CMKBR5, CCCKR5 (CCR5), those in WO2015148670A1 |
| Holoprosencephaly (HPE) (Alobar, Semilobar, and Lobar) | brain | | ACVRL1, ENG, SMAD4 |
| Homocystinuria | Metabolic disease | Various- connective tissue, muscles, CNS, cardiovascular system | CBS, MTHFR, MTR, MTRR, and MMADHC |
| HPV | | | HPV16 and HPV18 E6/E7 |
| HSV1, HSV2, and related keratitis | eye | | HSV1 genes (immediate early and late HSV-1 genes (UL1, 1.5, 5, 6, 8, 9, 12, 15, 16, 18, 19, 22, 23, 26, 26.5, 27, 28, 29, 30, 31, 32, 33, 34, 35, 36, 37, 38, 42, 48, 49.5, 50, 52, 54, S6, RL2, RS1, those described in WO2015153789, WO2015153791 |
| Hunter's Syndrome (aka Mucopolysaccharidosis type II) | Lysosomal storage disease | Various- liver, spleen, eye, joint, heart, brain, skeletal | IDS |
| Huntington's disease (HD) and HD-like disorders | Brain, nervous system | | HD, HTT, IT15, PRNP, PRIP, JPH3, JP3, HDL2, TBP, SCA17, PRKCE; IGF1; EP300; RCOR1; PRKCZ; HDAC4; and TGM2, and those described in WO2013130824, WO2015089354 |

TABLE 4-continued

Exemplary Genetic and Other Diseases and Associated Genes

| Disease Name | Primary Tissues or System Affected | Additional Tissues/ Systems Affected | Genes |
|---|---|---|---|
| Hurler's Syndrome (aka mucopolysaccharidosis type I H, MPS IH) | Lysosomal storage disease | Various- liver, spleen, eye, joint, heart, brain, skeletal | IDUA, α-L-iduronidase |
| Hurler-Scheie syndrome (aka mucopolysaccharidosis type I H-S, MPS I H-S) | Lysosomal storage disease | Various- liver, spleen, eye, joint, heart, brain, skeletal | IDUA, α-L-iduronidase |
| hyaluronidase deficiency (aka MPS IX) | Soft and connective tissues | | HYAL1 |
| Hyper IgM syndrome | Immune system | | CD40L |
| Hyper- tension caused renal damage | kidney | | Mineral corticoid receptor |
| Immunodeficiencies | Immune System | | CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI |
| Inborn errors of metabolism: including urea cycle disorders, organic acidemias), fatty acid oxidation defects, amino acidopathies, carbohydrate disorders, mitochondrial disorders | Metabolism diseases, liver | Various organs and cells | See also: Carbohydrate metabolism disorders (e.g. galactosemia), Amino acid Metabolism disorders (e.g. phenylketonuria), Fatty acid metabolism (e.g. MCAD deficiency), Urea Cycle disorders (e.g. Citrullinemia), Organic acidemias (e.g. Maple Syrup Urine disease), Mitochondrial disorders (e.g. MELAS), peroxisomal disorders (e.g. Zellweger syndrome) |
| Inflammation | Various | | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Inflammatory Bowel Diseases (e.g. Ulcerative Colitis and Chron's Disease) | Gastrointestinal | Joints, skin | NOD2, IRGM, LRRK2, ATG5, ATG16L1, IRGM, GATM, ECM1, CDH1, LAMB1, HNF4A, GNA12, IL10, CARD9/15. CCR6, IL2RA, MST1, TNFSF15, REL, STAT3, IL23R, IL12B, FUT2 |
| Interstitial renal fibrosis | kidney | | TGF-β type II receptor |
| Job's Syndrome (aka Hyper IgE Syndrome) | Immune System | | STAT3, DOCK8 |
| Juvenile Retinoschisis | eye | | RS1, XLRS1 |
| Kabuki Syndrome 1 | | | MLL4, KMT2D |
| Kennedy Disease (aka Spinobulbar Muscular Atrophy) | Muscles, brain, nervous system | | SBMA/SMAX1/AR |
| Klinefelter syndrome | Various- particularly those involved in development of male characteristics | | Extra X chromosome in males |
| Lafora Disease | Brain, CNS | | EMP2A and EMP2B |
| Leber Congenital Amaurosis | eye | | CRB1, RP12, CORD2, CRD, CRX, IMPDH1, OTX2, AIPL1, CABP4, CCT2, CEP290, CLUAP1, CRB1, CRX, DTHD1, GDF6, GUCY2D, IFT140, IQCB1, KCNJ13, LCA5, LRAT, NMNAT1, PRPH2, RD3, RDH12, RPE65, RP20, RPGRIP1, SPATA7, TULP1, LCA1, LCA4, GUC2D, CORD6, LCA3, |
| Lesch-Nyhan Syndrome | Metabolism disease | Various - joints, cognitive, brain, nervous system | HPRT1 |
| Leukocyte deficiencies and disorders | blood | | ITGB2, CD18, LCAMB, LAD, EIF2B1, EIF2BA, EIF2B2, EIF2B3, EIF2B5, LVWM, CACH, CLE, EIF2B4 |

TABLE 4-continued

Exemplary Genetic and Other Diseases and Associated Genes

| Disease Name | Primary Tissues or System Affected | Additional Tissues/ Systems Affected | Genes |
|---|---|---|---|
| Leukemia | Blood | | TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN |
| Limb-girdle muscular dystrophy diseases | muscle | | LGMD |
| Lowe syndrome | brain, eyes, kidneys | | OCRL |
| Lupus glomerulo- nephritis | kidney | | MAPK1 |
| Machado- Joseph's Disease (also known as Spinocerebellar ataxia Type 3) | Brain, CNS, muscle | | ATX3 |
| Macular degeneration | eye | | ABC4, CBC1, CHM1, APOE, C1QTNF5, C2, C3, CCL2, CCR2, CD36, CFB, CFH, CFHR1, CFHR3, CNGB3, CP, CRP, CST3, CTSD, CX3CR1, ELOVL4, ERCC6, FBLN5, FBLN6, FSCN2, HMCN1, HTRA1, IL6, IL8, PLEKHA1, PROM1, PRPH2, RPGR, SERPING1, TCOF1, TIMP3, TLR3 |
| Macular Dystrophy | eye | | BEST1, C1QTNF5, CTNNA1, EFEMP1, ELOVL4, FSCN2, GUCA1B, HMCN1, IMPG1, OTX2, PRDM13, PROM1, PRPH2, RP1L1, TIMP3, ABCA4, CFH, DRAM2, IMG1, MFSD8, ADMD, STGD2, STGD3, RDS, RP7, PRPH, AVMD, AOFMD, VMD2 |
| Malattia Leventinesse | eye | | EFEMP1, FBLN3 |
| Maple Syrup Urine Disease | Metabolism disease | | BCKDHA, BCKDHB, and DBT |
| Marfan syndrome | Connective tissue | Musculoskeletal | FBN1 |
| Maroteaux-Lamy Syndrome (aka MPS VI) | Musculoskeletal system, nervous system | Liver, spleen | ARSB |
| McArdle's Disease (Glycogen Storage Disease Type V) | Glycogen storage disease | muscle | PYGM |
| Medullary cystic kidney disease | kidney | | UMOD, HNFJ, FJHN, MCKD2, ADMCKD2 |
| Metachromatic leukodystrophy | Lysosomal storage disease | Nervous system | ARSA |
| Methylmalonic acidemia (MMA) | Metabolism disease | | MMAA, MMAB, MUT, MMACHC, MMADHC, LMBRD1 |
| Morquio Syndrome (aka MPS IV A and B) | Connective tissue, skin, bone, eyes | heart | GALNS |
| Mucopolysaccharidosis diseases (Types I H/S, I H, II, III A B and C, I S, IVA and B, IX, VII, and VI) | Lysosomal storage disease - affects various organs/tissues | | See also Hurler/Scheie syndrome, Hurler disease, Sanfilippo syndrome, Scheie syndrome, Morquio syndrome, hyaluronidase deficiency, Sly syndrome, and Maroteaux-Lamy syndrome |
| Muscular Atrophy | muscle | | VAPB, VAPC, ALS8, SMN1, SMA1, SMA2, SMA3, SMA4, BSCL2, SPG17, GARS, SMAD1, CMT2D, |

TABLE 4-continued

| Disease Name | Primary Tissues or System Affected | Additional Tissues/ Systems Affected | Genes |
|---|---|---|---|
| Muscular dystrophy | muscle | | HEXB, IGHMBP2, SMUBP2, CATF1, SMARD1 FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1 |
| Myotonic dystrophy (Type 1 and Type 2) | Muscles | Eyes, heart, endocrine | CNBP (Type 2) and DMPK (Type 1) |
| Neoplasia | | | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Neurofibromatosis (NF) (NF1, formerly Recklinghausen's NF, and NF2) | brain, spinal cord, nerves, and skin | | NF1, NF2 |
| Niemann-Pick Lipidosis (Types A, B, and C) | Lysosomal Storage Disease | Various- where sphingomyelin accumulates, particularly spleen, liver, blood, CNS | Types A and B: SMPD1; Type C: NPC1 or NPC2 |
| Noonan Syndrome | Various - musculoskeletal, heart, eyes, reproductive organs, blood | | PTPN11, SOS1, RAF1 and KRAS |
| Norrie Disease or X-linked Familial Exudative Vitreoretinopathy | eye | | NDP |
| North Carolina Macular Dystrophy | eye | | MCDR1 |
| Osteogenesis imperfecta (OI) (Types I, II, III, IV, V, VI, VII) | bones, musculoskeletal | | COL1A1, COL1A2, CRTAP, P3H |
| Osteopetrosis | bones | | LRP5, BMND1, LRP7, LR3, OPPG, VBCH2, CLCN7, CLC7, OPTA2, OSTM1, GL, TCIRG1, TIRC7, OC116, OPTB1 |
| Patau's Syndrome (Trisomy 13) | Brain, heart, skeletal system | | Additional copy of chromosome 13 |
| Parkinson's disease (PD) | Brain, nervous system | | SNCA (PARK1), UCHL1 (PARK 5), and LRRK2 (PARK8), (PARK3), PARK2, PARK4, PARK7 (PARK7), PINK1 (PARK6); x-Synuclein, DJ-1, Parkin, NR4A2, NURR1, NOT, TINUR, SNCAIP, TBP, SCA17, NCAP, PRKN, PDJ, DBH, NDUFV2 |
| Pattern Dystrophy of the RPE | eye | | RDS/peripherin |
| Phenylketonuria (PKU) | Metabolism disorder | Various due to build-up of | PAH, PKU1, QDPR, DHPR, PTS |

TABLE 4-continued

Exemplary Genetic and Other Diseases and Associated Genes

| Disease Name | Primary Tissues or System Affected | Additional Tissues/ Systems Affected | Genes |
|---|---|---|---|
| | | phenylalanine, phenyl ketones in tissues and CNS | |
| Polycystic kidney and hepatic disease | Kidney, liver | | FCYT, PKHD1, ARPKD, PKD1, PKD2, PKD4, PKDTS, PRKCSH, G19P1, PCLD, SEC63 |
| Pompe's Disease | Glycogen storage disease | Various - heart, liver, spleen | GAA |
| Porphyria (actually refers to a group of different diseases all having a specific heme production process abnormality) | Various- wherever heme precursors accumulate | | ALAD, ALAS2, CPOX, FECH, HMBS, PPOX, UROD, or UROS |
| posterior polymorphous corneal dystrophy | eyes | | TCF4; COL8A2 |
| Primary Hyperoxaluria (e.g. type 1) | Various - eyes, heart, kidneys, skeletal system | | LDHA (lactate dehydrogenase A) and hydroxyacid oxidase 1 (HAO1) |
| Primary Open Angle Glaucoma (POAG) | eyes | | MYOC |
| Primary sclerosing cholangitis | Liver, gallbladder | | TCF4; COL8A2 |
| Progeria (also called Hutchinson-Gilford progeria syndrome) | All | | LMNA |
| Prader-Willi Syndrome | Musculoskeletal system, brain, reproductive and endocrine system | | Deletion of region of short arm of chromosome 15, including UBE3A |
| Prostate Cancer | prostate | | HOXB13, MSMB, GPRC6A, TP53 |
| Pyruvate Dehydrogenase Deficiency | Brain, nervous system | | PDHA1 |
| Kidney/Renal carcinoma | kidney | | RLIP76, VEGF |
| Rett Syndrome | Brain | | MECP2, RTT, PPMX, MRX16, MRX79, CDKL5, STK9, MECP2, RTT, PPMX, MRX16, MRX79, x-Synuclein, DJ-1 |
| Retinitis pigmentosa (RP) | eye | | ADIPOR1, ABCA4, AGBL5, ARHGEF18, ARL2BP, ARL3, ARL6, BEST1, BBS1, BBS2, C2ORF71, C8ORF37, CA4, CERKL, CLRN1, CNGA1, CMGB1, CRB1, CRX, CYP4V2, DHDDS, DHX38, EMC1, EYS, FAM161A, FSCN2, GPR125, GUCA1B, HK1, HPRPF3, HGSNAT, IDH3B, IMPDH1, IMPG2, IFT140, IFT172, KLHL7, KIAA1549, KIZ, LRAT, MAK, MERTK, MVK, NEK2, NUROD1, NR2E3, NRL, OFD1, PDE6A, PDE6B, PDE6G, POMGNT1, PRCD, PROM1, PRPF3, PRPF4, PRPF6, PRPF8, PRPF31, PRPH2, RPB3, RDH12, REEP6, RP39, RGR, RHO, RLBP1, ROM1, RP1, RP1L1, RPY, RP2, RP9, RPE65, RPGR, SAMD11, SAG, SEMA4A, SLC7A14, SNRNP200, SPP2, SPATA7, TRNT1, TOPORS, TTC8, TULP1, USH2A, ZFN408, ZNF513, see also 20120204282 |
| Scheie syndrome (also known as mucopolysaccharidosis type I S(MPS I-S)) | Various- liver, spleen, eye, joint, heart, brain, skeletal | | IDUA, α-L-iduronidase |
| Schizophrenia | Brain | | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b; 5-HTT (Slc6a4); COMT; DRD (Drd1a); SLC6A3; DAOA; |

TABLE 4-continued

| | Exemplary Genetic and Other Diseases and Associated Genes | | |
| --- | --- | --- | --- |
| Disease Name | Primary Tissues or System Affected | Additional Tissues/ Systems Affected | Genes |
| | | | DTNBP1; Dao (Dao1); TCF4; COL8A2 |
| Secretase Related Disorders | Various | | APH-1 (alpha and beta); PSEN1; NCSTN; PEN-2; Nos1, Parp1, Nat1, Nat2, CTSB, APP, APH1B, PSEN2, PSENEN, BACE1, ITM2B, CTSD, NOTCH1, TNF, INS, DYT10, ADAM17, APOE, ACE, STN, TP53, IL6, NGFR, IL1B, ACHE, CTNNB1, IGF1, IFNG, NRG1, CASP3, MAPK1, CDH1, APBB1, HMGCR, CREB1, PTGS2, HES1, CAT, TGFB1, ENO2, ERBB4, TRAPPC10, MAOB, NGF, MMP12, JAG1, CD40LG, PPARG, FGF2, LRP1, NOTCH4, MAPK8, PREP, NOTCH3, PRNP, CTSG, EGF, REN, CD44, SELP, GHR, ADCYAP1, INSR, GFAP, MMP3, MAPK10, SP1, MYC, CTSE, PPARA, JUN, TIMP1, IL5, IL1A, MMP9, HTR4, HSPG2, KRAS, CYCS, SMG1, IL1R1, PROK1, MAPK3, NTRK1, IL13, MME, TKT, CXCR2, CHRM1, ATXN1, PAWR, NOTCJ2, M6PR, CYP46A1, CSNK1D, MAPK14, PRG2, PRKCA, L1 CAM, CD40, NR1I2, JAG2, CTNND1, CMA1, SORT1, DLK1, THEM4, JUP, CD46, CCL11, CAV3, RNASE3, HSPA8, CASP9, CYP3A4, CCR3, TFAP2A, SCP2, CDK4, JOF1A, TCF7L2, B3GALTL, MDM2, RELA, CASP7, IDE, FANP4, CASK, ADCYAP1R1, ATF4, PDGFA, C21ORF33, SCG5, RMF123, NKFB1, ERBB2, CAV1, MMP7, TGFA, RXRA, STX1A, PSMC4, P2RY2, TNFRSF21, DLG1, NUMBL, SPN, PLSCR1, UBQLN2, UBQLN1, PCSK7, SPON1, SILV, QPCT, HESS, GCC1 |
| Selective IgA Deficiency | Immune system | | Type 1: MSH5; Type 2: TNFRSF13B |
| Severe Combined Immunodeficiency (SCID) and SCID-XI, and ADA-SCID | Immune system | | JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4, those identified in US Pat. App. Pub. 20110225664, 20110091441, 20100229252, 20090271881 and 20090222937; |
| Sickle cell disease | blood | | HBB, BCL11A, BCL11Ae, cis-regulatory elements of the B-globin locus, HBG 1/2 promoter, HBG distal CCAAT box region between -92 and -130 of the HBG Transcription Start Site, those described in WO2015148863, WO 2013/126794, US Pat. Pub. 20110182867 |
| Sly Syndrome (aka MPS VII) | | | GUSB |
| Spinocerebellar Ataxias (SCA types 1, 2, 3, 6, 7, 8, 12 and 17) | | | ATXN1, ATXN2, ATX3 |
| Sorsby Fundus Dystrophy | eye | | TIMP3 |
| Stargardt disease | eye | | ABCR, ELOVL4, ABCA4, PROM1 |
| Tay-Sachs Disease | Lysosomal Storage disease | Various - CNS, brain, eye | HEX-A |
| Thalassemia (Alpha, Beta, Delta) | blood | | HBA1, HBA2 (Alpha), HBB (Beta), HBB and HBD (delta), LCRB, BCL11A, BCL11Ae, cis-regulatory elements of the B-globin locus, HBG 1/2 promoter, those described in WO2015148860, US Pat. Pub. 20110182867, 2015/148860 |
| Thymic Aplasia (DiGeorge Syndrome; 22q11.2 deletion | Immune system, thymus | | deletion of 30 to 40 genes in the middle of chromosome 22 at |

TABLE 4-continued

Exemplary Genetic and Other Diseases and Associated Genes

| Disease Name | Primary Tissues or System Affected | Additional Tissues/ Systems Affected | Genes |
|---|---|---|---|
| syndrome) | | | a location known as 22q11.2, including TBX1, DGCR8 |
| Transthyretin amyloidosis (ATTR) | liver | | TTR (transthyretin) |
| trimethylaminuria | Metabolism disease | | FMO3 |
| Trinucleotide Repeat Disorders (generally) | Various | | HTT; SBMA/SMAX1/AR; FXN/X25 ATX3; ATXN1; ATXN2; DMPK; Atrophin-1 and Atn1 (DRPLA Dx); CBP (Creb-BP - global instability); VLDLR; Atxn7; Atxn10; FEN1, TNRC6A, PABPN1, JPH3, MED15, ATXN1, ATXN3, TBP, CACNA1A, ATXN80S, PPP2R2B, ATXN7, TNRC6B, TNRC6C, CELF3, MAB21L1, MSH2, TMEM185A, SIX5, CNPY3, RAXE, GNB2, RPL14, ATXN8, ISR, TTR, EP400, GIGYF2, OGG1, STC1, CNDP1, C10ORF2, MAML3, DKC1, PAXIP1, CASK, MAPT, SP1, POLG, AFF2, THBS1, TP53, ESR1, CGGBP1, ABT1, KLK3, PRNP, JUN, KCNN3, BAX, FRAXA, KBTBD10, MBNL1, RAD51, NCOA3, ERDA1, TSC1, COMP, GGLC, RRAD, MSH3, DRD2, CD44, CTCF, CCND1, CLSPN, MEF2A, PTPRU, GAPDH, TRIM22, WT1, AHR, GPX1, TPMT, NDP, ARX, TYR, EGR1, UNG, NUMBL, FABP2, EN2, CRYGC, SRP14, CRYGB, PDCD1, HOXA1, ATXN2L, PMS2, GLA, CBL, FTH1, IL12RB2, OTX2, HOXA5, POLG2, DLX2, AHRR, MANF, RMEM158, see also 20110016540 |
| Turner's Syndrome (XO) | Various - reproductive organs, and sex characteristics, vasculature | | Monosomy X |
| Tuberous Sclerosis | CNS, heart, kidneys | | TSC1, TSC2 |
| Usher syndrome (Types I, II, and III) | Ears, eyes | | ABHD12, CDH23, CIB2, CLRN1, DFNB31, GPR98, HARS, MYO7A, PCDH15, USH1C, USH1G, USH2A, USH11A, those described in WO2015134812A1 |
| Velocardiofacial syndrome (aka 22q11.2 deletion syndrome, DiGeorge syndrome, conotruncal anomaly face syndrome (CTAF), autosomal dominant Opitz G/BB syndrome or Cayler cardiofacial syndrome) | Various - skeletal, heart, kidney, immune system, brain | | Many genes are deleted, COM, TBX1, and other are associated with symptoms |
| Von Gierke's Disease (Glycogen Storage Disease type I) | Glycogen Storage disease | Various - liver, kidney | G6PC and SLC37A4 |
| Von Hippel-Lindau Syndrome | Various - cell growth regulation disorder | CNS, Kidney, Eye, visceral organs | VHL |
| Von Willebrand Disease (Types I, II and III) | blood | | VWF |
| Wilson Disease | Various - Copper Storage Disease | Liver, brains, eyes, other tissues where copper builds up | ATP7B |
| Wiskott-Aldrich Syndrome | Immune System | | WAS |
| Xeroderma Pigmentosum | Skin | Nervous system | POLH |
| XXX Syndrome | Endocrine, brain | | X chromosome trisomy |

TABLE 5

| CELLULAR FUNCTION | GENES |
| --- | --- |
| | Exemplary Genes controlling Cellular Functions |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling Actin Cytoskeleton Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |

TABLE 5-continued

| Exemplary Genes controlling Cellular Functions | |
| --- | --- |
| CELLULAR FUNCTION | GENES |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; |

TABLE 5-continued

Exemplary Genes controlling Cellular Functions

| CELLULAR FUNCTION | GENES |
| --- | --- |
| | FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; |

TABLE 5-continued

| Exemplary Genes controlling Cellular Functions | |
| --- | --- |
| CELLULAR FUNCTION | GENES |
| | RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |

TABLE 5-continued

Exemplary Genes controlling Cellular Functions

| CELLULAR FUNCTION | GENES |
| --- | --- |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARMI; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |

TABLE 5-continued

Exemplary Genes controlling Cellular Functions

| CELLULAR FUNCTION | GENES |
|---|---|
| Purine Metabolism | NME2; SMARCA4; MYH9; RRM2; ADAR; EIF2AK4; PKM2; ENTPD1; RAD51; RRM2B; TJP2; RAD51C; NT5E; POLDI; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | EROIL; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |

TABLE 5-continued

| Exemplary Genes controlling Cellular Functions | |
| --- | --- |
| CELLULAR FUNCTION | GENES |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; crn2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 orBm3a); Numb; Reln |

Thus, also described herein are methods of inducing one or more mutations in a eukaryotic or prokaryotic cell (in vitro, i.e., in an isolated eukaryotic cell) as herein discussed comprising delivering to cell a vector as described herein. The mutation(s) can include the introduction, deletion, or substitution of one or more nucleotides at a target sequence of cell(s). In some embodiments, the mutations can include the introduction, deletion, or substitution of 1-75 nucleotides at each target sequence of said cell(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence. The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s). The mutations can include the introduction, deletion, or substitution of 20, 21, 22, 23, 24, 25, 26, 27, 28, 29, 30, 35, 40, 45, 50, or 75 nucleotides at each target sequence of said cell(s). The mutations can include the introduction, deletion, or substitution of 40, 45, 50, 75, 100, 200, 300, 400 or 500 nucleotides at each target sequence of said cell(s). The mutations can include the introduction, deletion, or substitution of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, or 9900 to 10000 nucleotides at each target sequence of said cell(s).

In some embodiments, the modifications can include the introduction, deletion, or substitution of nucleotides at each target sequence of said cell(s) via nucleic acid components (e.g., guide(s) RNA(s) or sgRNA(s)), such as those mediated by a CRISPR-Cas system.

In some embodiments, the modifications can include the introduction, deletion, or substitution of nucleotides at a target or random sequence of said cell(s) via a non CRISPR-Cas system or technique. Such techniques are discussed elsewhere herein, such as where engineered cells and methods of generating the engineered cells and organisms are discussed.

For minimization of toxicity and off-target effect when using a CRISPR-Cas system, it may be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9-like with the D10A mutation) can be delivered with a pair of guide RNAs targeting a site of interest. Guide sequences and strategies to minimize toxicity and off-target effects can be as in International Patent Application Publication WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. Without wishing to be bound by theory, a tracr sequence, which may comprise or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to a guide sequence.

In one embodiment, the invention provides a method of modifying a target polynucleotide in a eukaryotic cell. In some embodiments, the method includes delivering an engineered cell described herein and/or an engineered AAV capsid particle described herein having a CRISPR-Cas molecule as a cargo molecule to a subject and/or cell. The CRISPR-Cas system molecule(s) delivered can complex to bind to the target polynucleotide, e.g., to effect cleavage of said target polynucleotide, thereby modifying the target polynucleotide, wherein the CRISPR complex comprises a CRISPR enzyme complexed with a guide sequence hybridized to a target sequence within said target polynucleotide, wherein said guide sequence can be linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the CRISPR enzyme and one or more vectors drive expression of one or more of: the guide sequence linked to the tracr mate sequence, and the tracr sequence. In some embodiments, said CRISPR enzyme drive expression of one or more of: the guide sequence linked to the tracr mate sequence, and the tracr sequence. In some embodiments such CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject. In some embodiments, the isolated cells can be returned to the subject after delivery of one or more engineered AAV capsid particles to the isolated cell. In some embodiments, the isolated cells can be returned to the subject after delivering one or more molecules of the engineered delivery system described herein to the isolated cell, thus making the isolated cells engineered cells as previously described.

Screening and Cell Selection

The engineered AAV capsid system vectors, engineered cells, and/or engineered AAV capsid particles described herein can be used in a screening assay and/or cell selection assay. The engineered delivery system vectors, engineered cells, and/or engineered AAV capsid particles can be delivered to a subject and/or cell. In some embodiments, the cell is a eukaryotic cell. The cell can be in vitro, ex vivo, in situ, or in vivo. The engineered AAV capsid system molecules, vectors, engineered cells, and/or engineered AAV capsid particles described herein can introduce an exogenous molecule or compound to subject or cell to which they are delivered. The presence of an exogenous molecule or compound can be detected which can allow for identification of a cell and/or attribute thereof. In some embodiments, the delivered molecules or particles can impart a gene or other nucleotide modification (e.g., mutations, gene or polynucleotide insertion and/or deletion, etc.). In some embodiments the nucleotide modification can be detected in a cell by sequencing. In some embodiments, the nucleotide modification can result in a physiological and/or biological modification to the cell that results in a detectable phenotypic change in the cell, which can allow for detection, identification, and/or selection of the cell. In some embodiments, the phenotypic change can be cell death, such as embodiments where binding of a CRISPR complex to a target polynucleotide results in cell death. Embodiments of the invention allow for selection of specific cells without requiring a selection marker or a two-step process that may include a counter-selection system. The cell(s) may be prokaryotic or eukaryotic cells.

In one embodiment the invention provides for a method of selecting one or more cell(s) by introducing one or more mutations in a gene in the one or more cell (s), the method comprising: introducing one or more vectors, which can include one or more engineered delivery system molecules or vectors described elsewhere herein, into the cell (s), wherein the one or more vectors can include a CRISPR enzyme and/or drive expression of one or more of: a guide sequence linked to a tracr mate sequence, a tracr sequence, and an editing template; or other polynucleotide to be inserted into the cell and/or genome thereof, wherein, for example that which is being expressed is within and expressed in vivo by the CRISPR enzyme and/or the editing template, when included, comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is a Cas protein. In another embodiment of the invention the cell to be selected may be a eukaryotic cell.

The screening methods involving the engineered AAV capsid system molecules, vectors, engineered cells, and/or engineered AAV capsid particles, including but not limited to those that deliver one more CRISPR-Cas system molecules to cell, can be used in detection methods such as fluorescence in situ hybridization (FISH). In some embodiments, one or more components of an engineered CRISPR-Cas system that includes a catalytically inactive Cas protein, can be delivered by an engineered AAV capsid system molecule, engineered cell, and/or engineered AAV capsid particle described elsewhere herein to a cell and used in a FISH method. The CRISPR-Cas system can include an inactivated Cas protein (dCas) (e.g., a dCas9), which lacks the ability to produce DNA double-strand breaks may be fused with a marker, such as fluorescent protein, such as the enhanced green fluorescent protein (eEGFP) and co-expressed with small guide RNAs to target pericentric, centric and teleomeric repeats in vivo. The dCas system can be used to visualize both repetitive sequences and individual genes in the human genome. Such new applications of labelled dCas, dCas CRISPR-Cas systems, engineered AAV capsid system molecules, engineered cells, and/or engineered AAV capsid particles can be used in imaging cells and studying the functional nuclear architecture, especially in cases with a small nucleus volume or complex 3-D structures. (Chen B, Gilbert L A, Cimini B A, Schnitzbauer J, Zhang W, Li G W, Park J, Blackburn E H, Weissman J S, Qi L S, Huang B. 2013. Dynamic imaging of genomic loci in living human cells by an optimized CRISPR/Cas system. Cell 155(7): 1479-91. doi: 10.1016/j.cell.2013.12.001., the teachings of which can be applied and/or adapted to the CRISPR systems described herein. A similar approach involving a polynucleotide fused to a marker (e.g., a fluorescent marker) can be delivered to a cell via an engineered AAV capsid system molecule, vector, engineered cell, and/or engineered AAV capsid particle described herein and integrated into the genome of the cell and/or otherwise interact with a region of the genome of a cell for FISH analysis.

Similar approaches for studying other cell organelles and other cell structures can be accomplished by delivering to the cell (e.g., via an engineered delivery AAV capsid molecule, engineered cell, and/or engineered AAV capsid particle described herein) one or more molecules fused to a marker (such as a fluorescent marker), wherein the molecules fused to the marker are capable of targeting one or more cell structures. By analyzing the presence of the markers, one can identify and/or image specific cell structures.

In some embodiments, the engineered AAV capsid system molecules and/or engineered AAV capsid particles can be used in a screening assay inside or outside of a cell. In some embodiments, the screening assay can include delivering a CRISPR-Cas cargo molecule(s) via an engineered AAV capsid particle.

Use of the present system in screening is also provided by the present invention, e.g., gain of function screens. Cells which are artificially forced to overexpress a gene are able to down regulate the gene over time (re-establishing equilibrium) e.g., by negative feedback loops. By the time the screen starts the unregulated gene might be reduced again. Other screening assays are discussed elsewhere herein.

In an embodiment, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results.

In an embodiment, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting. In an embodiment, the cell product is non-human or animal. In some embodiments, the cell product is human.

In some embodiments, a host cell is transiently or non-transiently transfected with one or more vectors described herein. In some embodiments, a cell is transfected as it naturally occurs in a subject optionally to be reintroduced therein. In some embodiments, a cell that is transfected is taken from a subject. In some embodiments, the cell obtained from or is derived from cells taken from a subject, such as a cell line. Delivery mechanisms and techniques of the engineered AAV capsid system, engineered AAV capsid particles are described elsewhere herein.

In some embodiments it is envisaged to introduce the engineered AAV capsid system molecule(s) and/or engineered AAV capsid particle(s) directly to the host cell. For instance, the engineered AAV capsid system molecule(s) can be delivered together with one or more cargo molecules to be packaged into an engineered AAV capsid particle.

In some embodiments, the invention provides a method of expressing an engineered delivery molecule and cargo molecule to be packaged in an engineered GTA particle in a cell that can include the step of introducing the vector according any of the vector delivery systems disclosed herein.

The invention is further described in the following examples, which do not limit the scope of the invention described in the claims.

EXAMPLES

Figure 2:
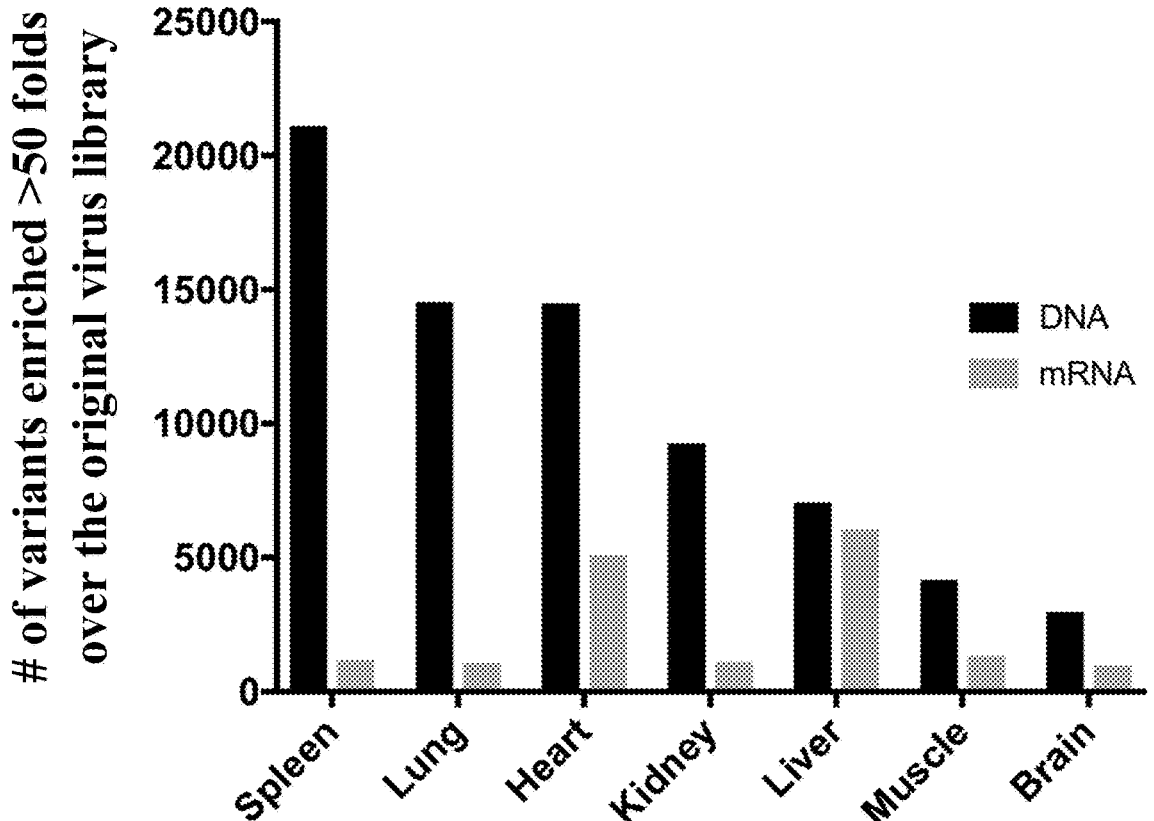
FIG. 2—mRNA-based selection of AAV variants can be more stringent than DNA-based selection. The virus library was expressed under the control of a CMV promoter.

Example 1—mRNA Based Detection Methods are More Stringent for Selection of AAV Variants FIG. 1 demonstrates the adeno-associated virus (AAV) transduction mechanism, which results in production of mRNA. As is demonstrated in FIG. 1, functional transduction of a cell by an AAV particle can result in the production of an mRNA strand. Non-functional transduction would not produce such a product despite the viral genome being detectable using a DNA-based assay. Thus, mRNA-based detection assays to detect transduction by e.g., an AAV can be more stringent and provide feedback as to the functionality of a virus particle that is able to functionally transduce a cell. FIG. 2 shows a graph that can demonstrate that mRNA-based selection of AAV variants can be more stringent than DNA-based selection. The virus library was expressed under the control of a CMV promoter.

Figure 3A:
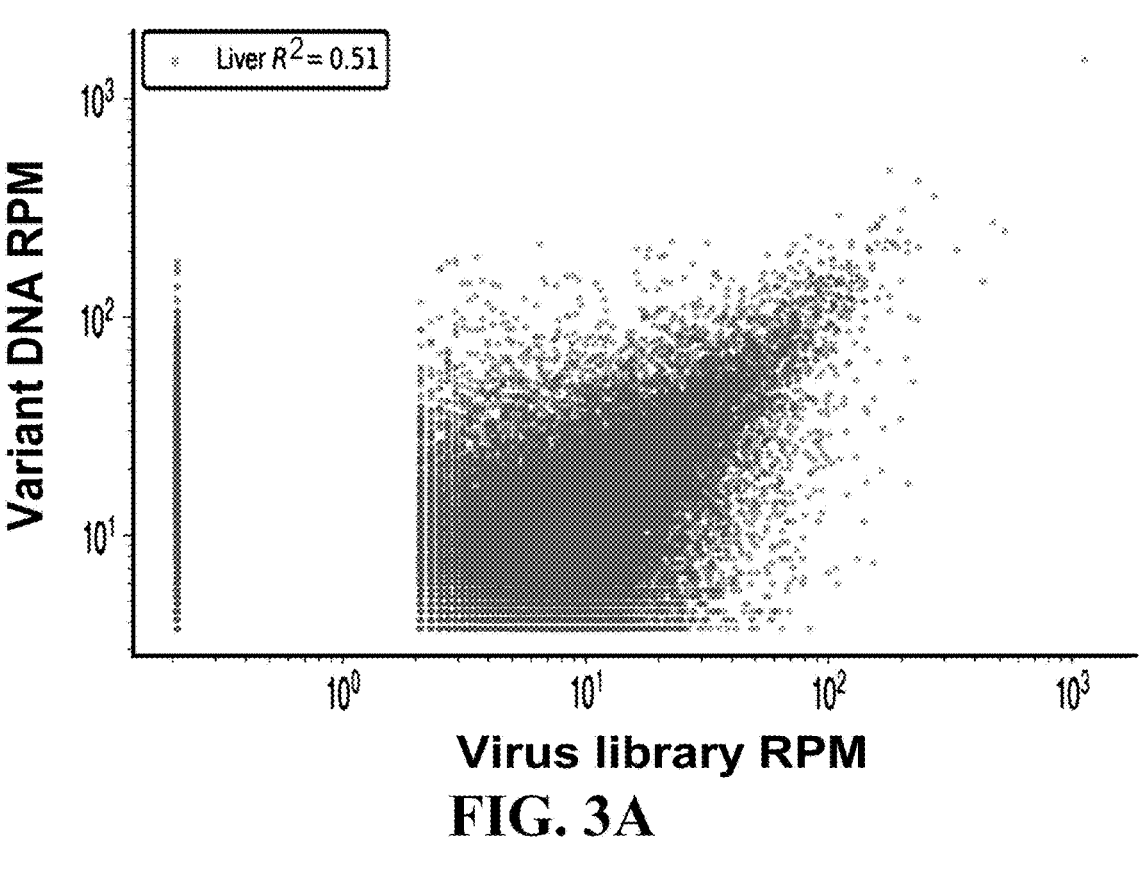
FIGS. 3A-3B—A correlation between the virus library and vector genome DNA (FIG. 3A) and mRNA (FIG. 3B) in the liver.
Figure 3B:
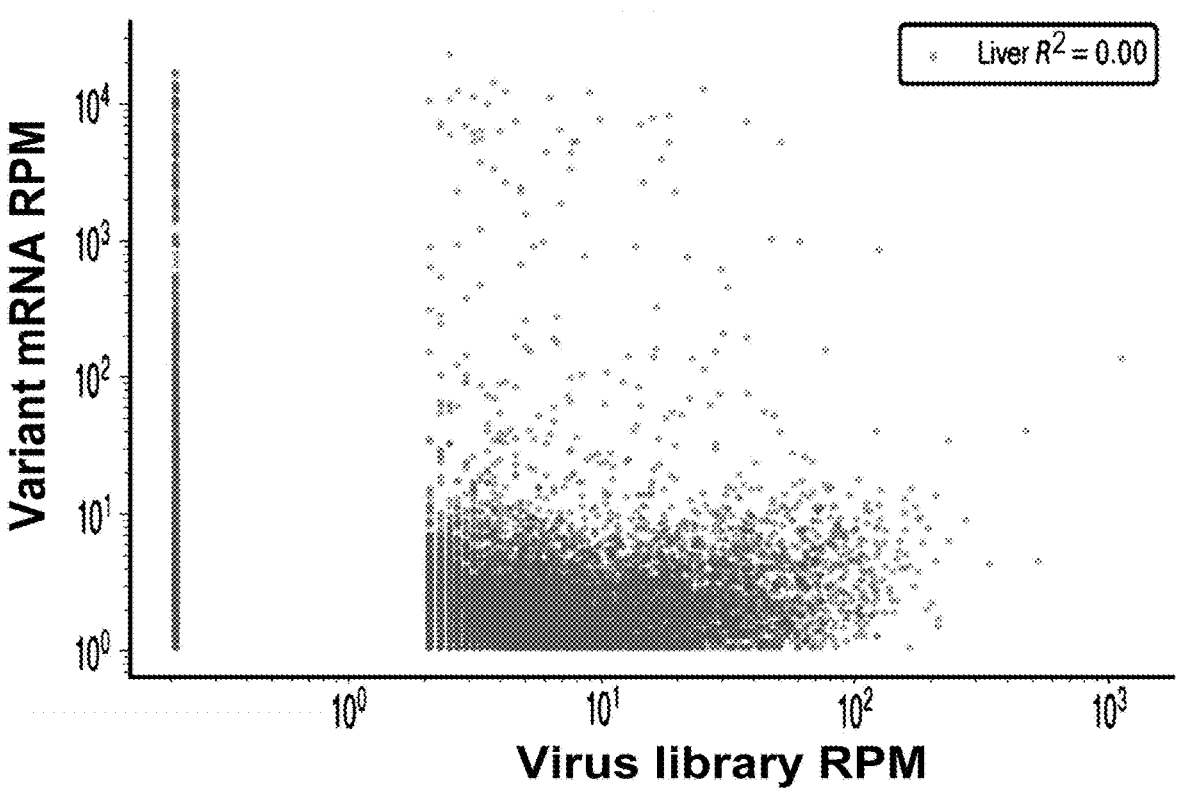

Example 2—mRNA Based Detection Methods can be Used to Detect AAV Capsid Variants from a Capsid Variant Library FIGS. 3A-3B show graphs that can demonstrate a correlation between the virus library and vector genome DNA (FIG. 3A) and mRNA (FIG. 3B) in the liver. FIGS. 4A-4F show graphs that can demonstrate capsid variants expressed at the mRNA level identified in different tissues.

Example 3—Capsid mRNA Expression can be Driven by Tissue Specific Promoters

Figure 5A:
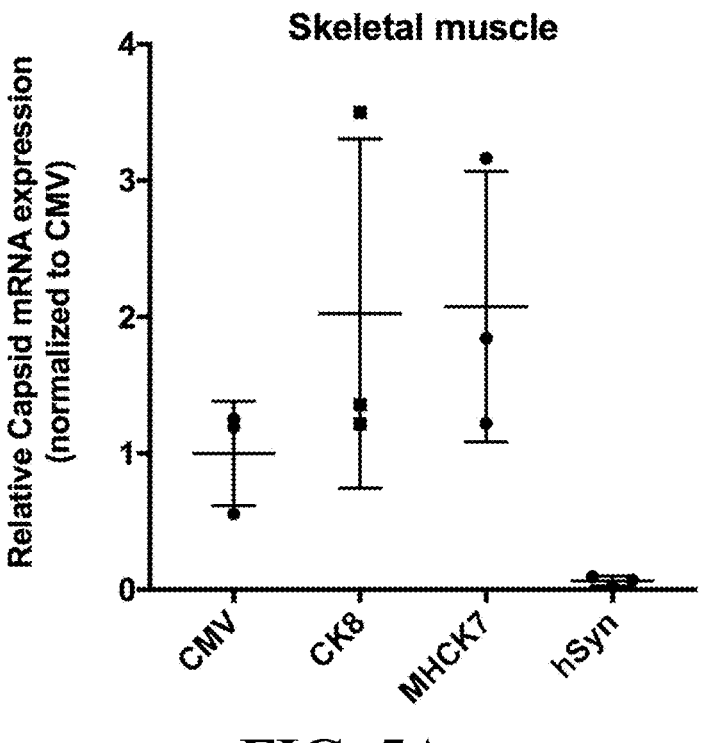
FIGS. 5A-5C—Capsid mRNA expression in different tissues under the control of cell-type specific promoters (as noted on x-axis). CMV was included as an exemplary constitutive promoter. CK8 is a muscle-specific promoter. MHCK7 is a muscle-specific promoter. hSyn is a neuron specific promoter. Expression levels from the cell type-specific promoters have been normalized based on expression levels from the constitutive CMV promoter in each tissue.
Figure 5B:
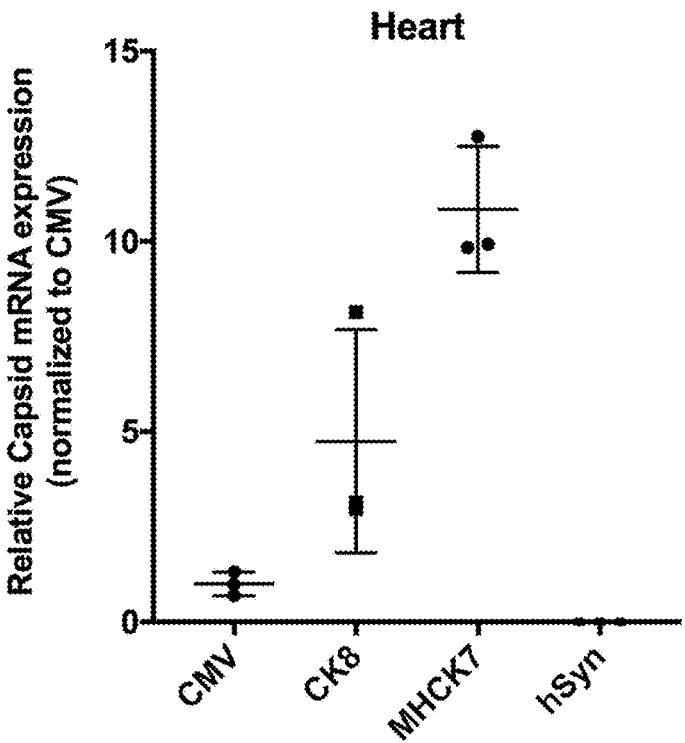
Figure 5C:
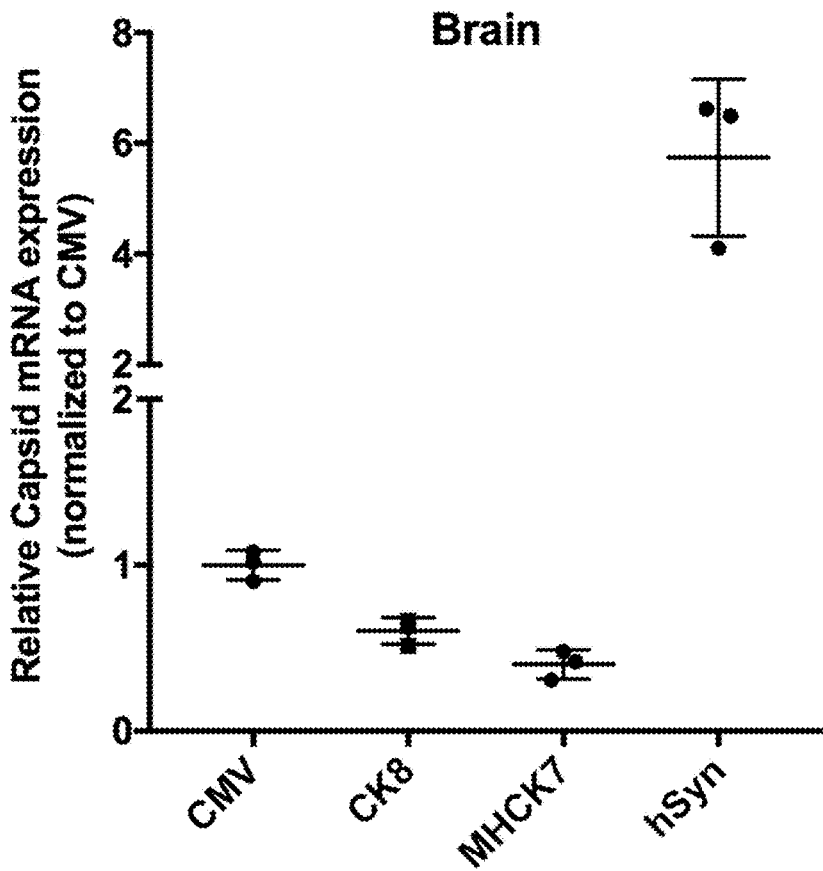

FIGS. 5A-5C show graphs that can demonstrate capsid mRNA expression in different tissues under the control of cell-type specific promoters (as noted on x-axis). CMV was included as an exemplary constitutive promoter. CK8 is a muscle-specific promoter. MHCK7 is a muscle-specific promoter. hSyn is a neuron specific promoter.

Figure 9:
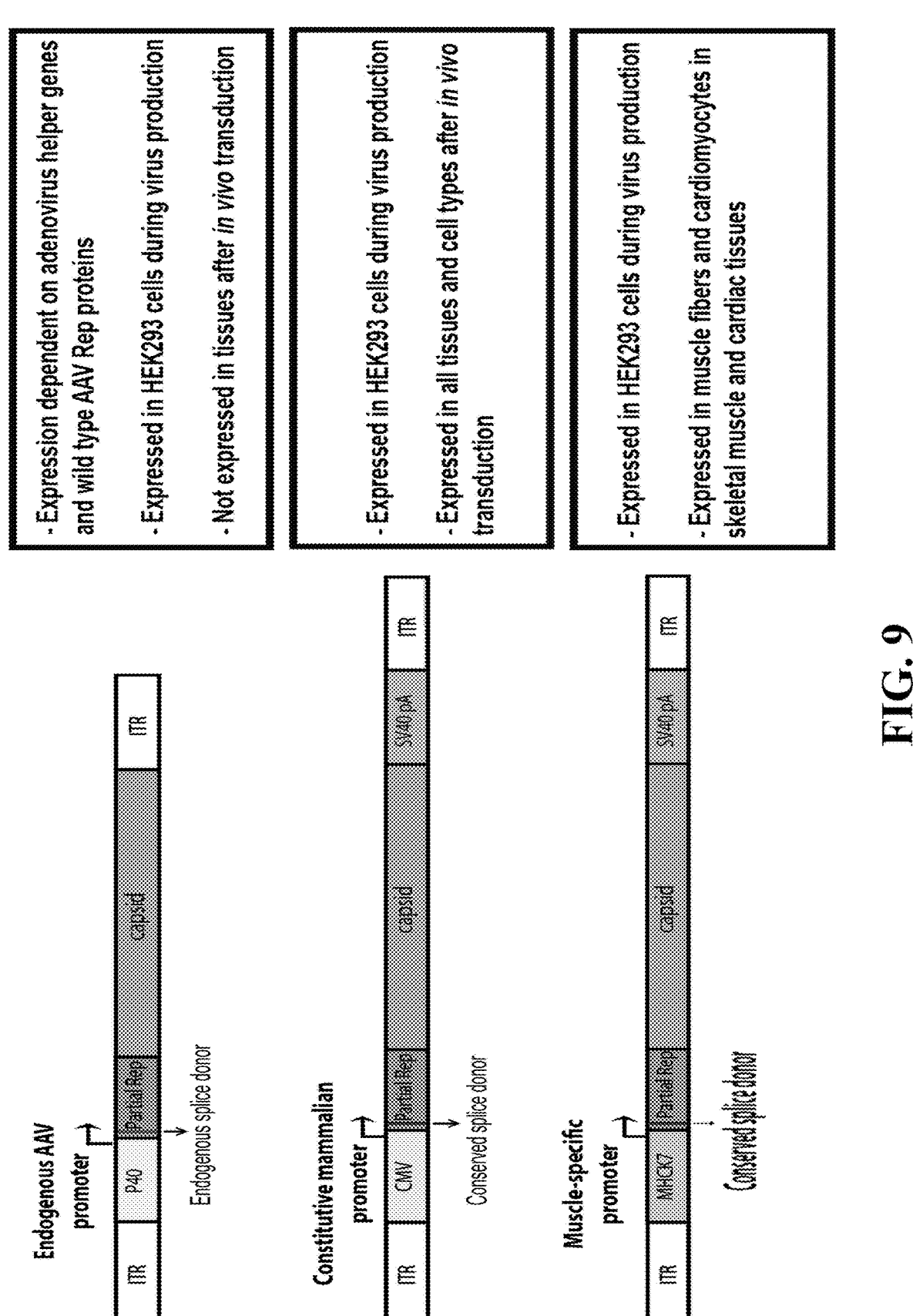
FIG. 9—Exemplary vector maps of representative AAV capsid plasmid library vectors (see e.g., FIG. 8) that can be used in an AAV vector system to generate an AAV capsid variant library.

Example 4—Capsid Variant Library Generation, Variant Screening, and Variant Identification Generally, an AAV capsid library can be generated by expressing engineered capsid vectors each containing an engineered AAV capsid polynucleotide previously described in an appropriate AAV producer cell line. See e.g., FIG. 8. This can generate an AAV capsid library that can contain one more desired cell-specific engineered AAV capsid variant. FIG. 7 shows a schematic demonstrating embodiments of generating an AAV capsid variant library, particularly insertion of a random n-mer (n=3-15 amino acids) into a wild-type AAV, e.g., AAV9. In this example, random 7-mers were inserted between aa588-589 of variable region VIII of AAV9 viral protein and used to form the viral genome containing vectors with one variant per vector. As shown in FIG. 8, the capsid variant vector library was used to generate AAV particles where each capsid variant encapsulated its coding sequence as the vector genome. FIG. 9 shows vector maps of representative AAV capsid plasmid library vectors (see e.g., FIG. 8) that can be used in an AAV vector system to generate an AAV capsid variant library. The library can be generated with the capsid variant polynucleotide under the control of a tissue specific promoter or constitutive promoter. The library was also made with capsid variant polynucleotide that included a polyadenylation signal.

As shown in FIG. 6 the AAV capsid library can be administered to various non-human animals for a first round of mRNA-based selection. As shown in FIG. 1, the transduction process by AAVs and related vectors can result in the production of an mRNA molecule that is reflective of the genome of the virus that transduced the cell. As is at least demonstrated in the Examples herein, mRNA based-selection can be more specific and effective to determine a virus particle capable of functionally transducing a cell because it is based on the functional product produced as opposed to just detecting the presence of a virus particle in the cell by measuring the presence of viral DNA.

After first-round administration, one or more engineered AAV virus particles having a desired capsid variant can then be used to form a filtered AAV capsid library. Desirable AAV virus particles can be identified by measuring the mRNA expression of the capsid variants and determining which variants are highly expressed in the desired cell type(s) as compared to non-desired cells type(s). Those that are highly expressed in the desired cell, tissue, and/or organ type are the desired AAV capsid variant particles. In some embodiments, the AAV capsid variant encoding polynucleotide is under control of a tissue-specific promoter that has selective activity in the desired cell, tissue, or organ.

The engineered AAV capsid variant particles identified from the first round can then be administered to various non-human animals. In some embodiments, the animals used in the second round of selection and identification are not the same as those animals used for first round selection and identification. Similar to round 1, after administration the top expressing variants in the desired cell, tissue, and/or organ type(s) can be identified by measuring viral mRNA expression in the cells. The top variants identified after round two can then be optionally barcoded and optionally pooled. In some embodiments, top variants from the second round can then be administered to a non-human primate to identify the top cell-specific variant(s), particularly if the end use for the top variant is in humans. Administration at each round can be systemic.

Figure 10:
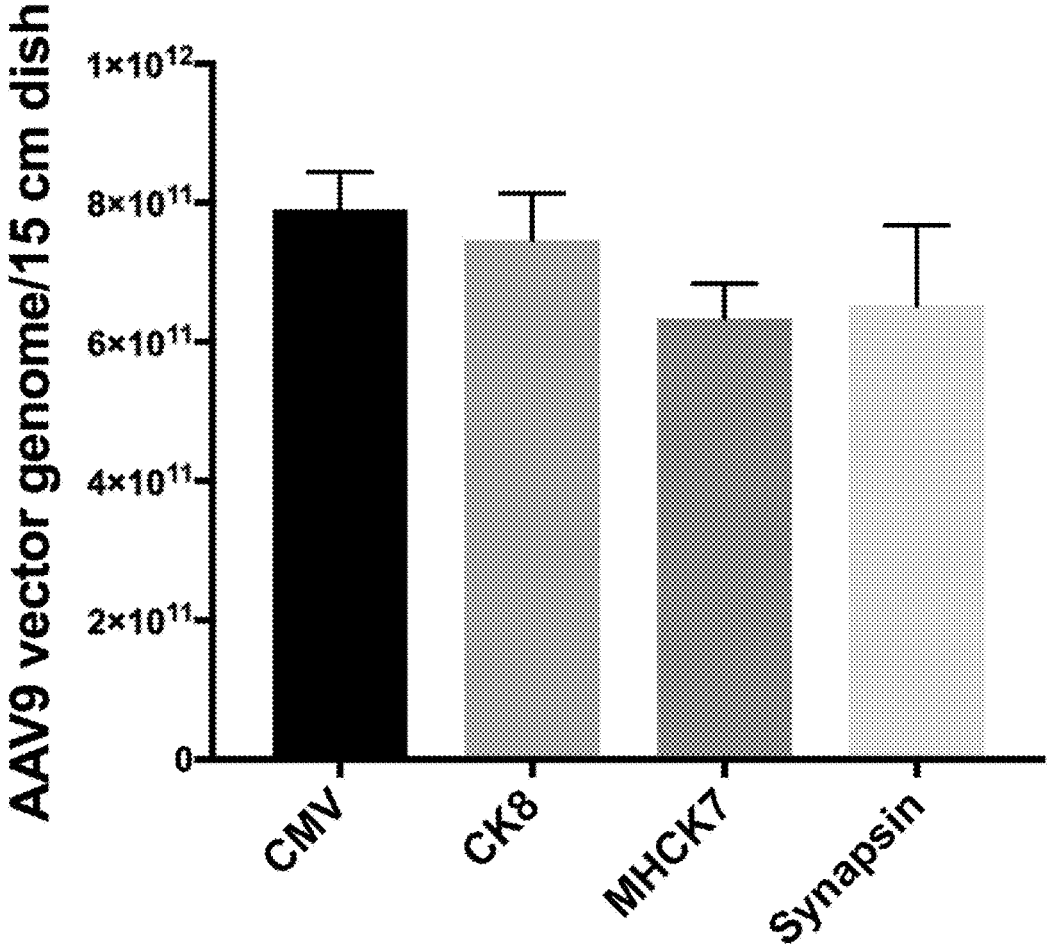
FIG. 10—Viral titer (calculated as AAV9 vector genome/15 cm dish) produced by constructs containing different constitutive and cell-type specific mammalian promoters.

FIG. 10 shows a graph that can demonstrate the viral titer (calculated as AAV9 vector genome/15 cm dish) produced by libraries generated using different promoters. As demonstrated in FIG. 10, virus titer was not affected significantly be the use of different promoters.

Example 5—Muscle-Tropic Enhanced myoAAV Capsids

Figure 12:
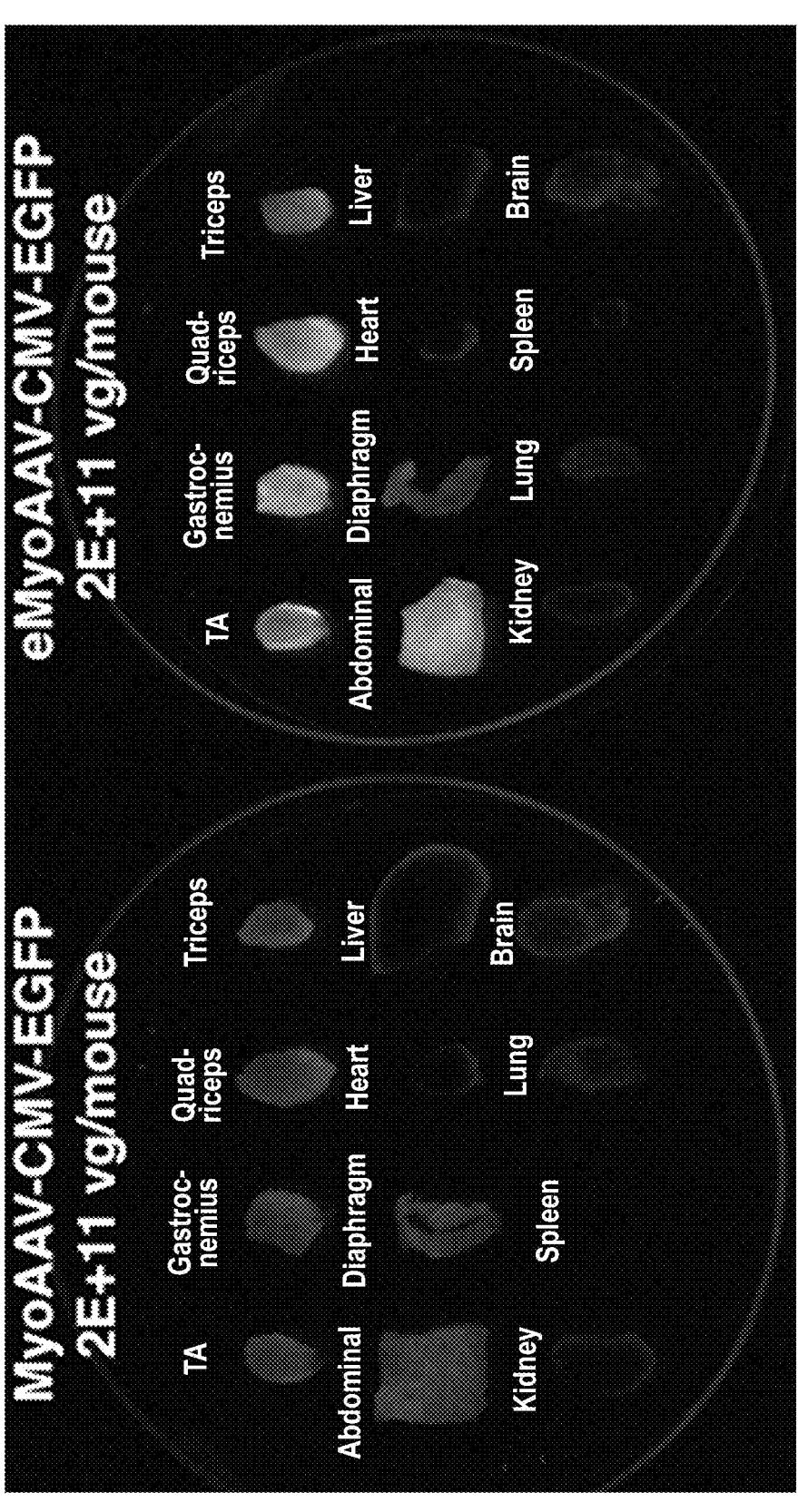
FIG. 12—Enhanced MyoAAV (eMyoAAV) capsid variants can transduce mouse muscle more effectively as compared to the first generation MyoAAV after systemic delivery.

First and second generation muscle specific AAV capsids were developed using a muscle specific promoter and the resulting capsid libraries were screened in mice and non-human primates as described elsewhere herein and/or in e.g., U.S. Provisional Application Serial Nos. 62/899,453, 62/916,207, and 63/018,454. First and second generation myoAAV capsids were further optimized in mice and non-human primates as previously described to generate enhanced myoAAV capsids (see e.g., FIG. 11). Tables 2 and 3 shows the top hits of enhanced muscle specific n-mer motifs and their encoding sequence in rank order within each table. FIG. 12 can demonstrate that enhanced MyoAAV (eMyoAAV) capsid variants can transduce mouse muscle more effectively as compared to the first generation Myo-AAV after systemic delivery.

Figure 13:
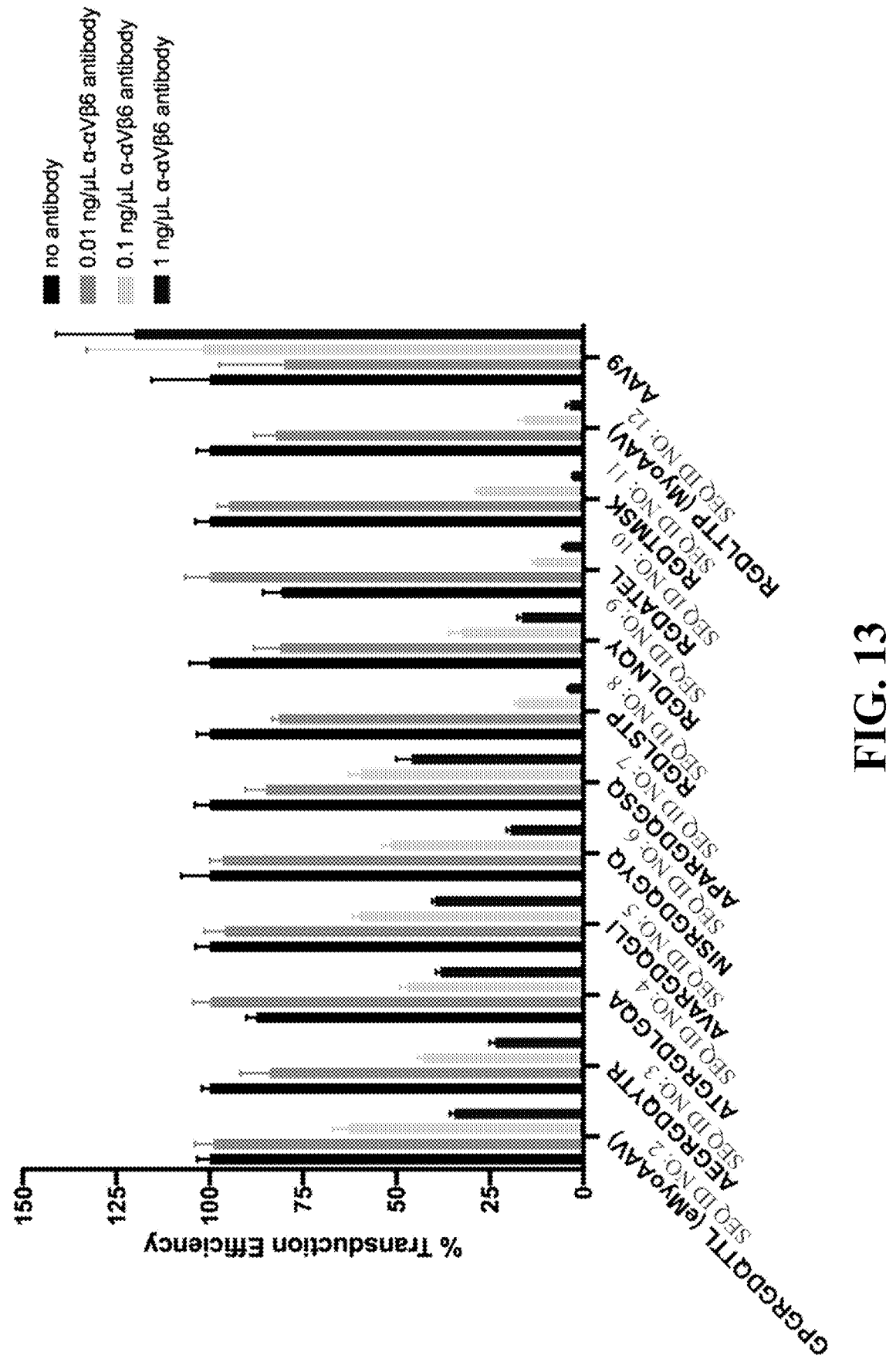
FIG. 13—First and second generation myoAAV capsid variants are dependent on the aVb6 integrin heterodimer for transduction of human primary myotubes (SEQ ID NO: 2-12).

FIG. 13 can demonstrate that first and second generation myoAAV capsid variants are dependent on the αVb6 integrin heterodimer for transduction of human primary myotubes.

TABLE 2

| | | | Mouse enhanced MyoAAV (eMyoAAV) Capsid Variants | |
|---|---|---|---|---|
| Rank | N-mer motif | SEQ ID NO: | Encoding sequence | SEQ ID NO: |
| 1 | AEGRGDQYTR | 3 | GCTGAGGGTAGAGGAGACCAGTATACTCGT | 41 |
| 2 | GPGRGDQTTL | 2 | GGGCCGGGTAGAGGAGACCAGACTACGTTG | 42 |
| 3 | AEGRGDQYTR | 3 | GCGGAAGGCAGAGGAGACCAATACACAAGG | 43 |
| 4 | ATGRGDLGQA | 4 | GCGACTGGTAGAGGAGACCTGGGTCAGGCT | 44 |
| 5 | AVARGDQGLI | 5 | GCGGTGGCGAGAGGAGACCAGGGTCTTATT | 45 |
| 6 | NISRGDQGYQ | 6 | AACATCTCCAGAGGAGACCAAGGTTACCAA | 46 |
| 7 | APARGDQGSQ | 7 | GCGCCGGCTAGAGGAGACCAGGGGAGTCAG | 47 |
| 8 | AVSRGDRMEF | 20 | GCCGTTAGCAGAGGAGACCGGATGGAATTC | 48 |
| 9 | QMGRGDMGIK | 49 | CAGATGGGTAGAGGAGACATGGGGATTAAG | 50 |
| 10 | EYRRGDKADI | 51 | GAGTATCGGAGAGGAGACAAGGCGGATATT | 52 |
| 11 | ESRRGDKEPL | 53 | GAGAGTCGGAGAGGAGACAAGGAGCCGCTG | 54 |

TABLE 2-continued

| | | Mouse enhanced MyoAAV (eMyoAAV) Capsid Variants | | |
|---|---|---|---|---|
| Rank | N-mer motif | SEQ ID NO: | Encoding sequence | SEQ ID NO: |
| 12 | AHMRGDLGGT | 55 | GCACACATGAGAGGAGACCTAGGCGGCACG | 56 |
| 13 | VWQRGDKMDM | 57 | GTGTGGCAAAGAGGAGACAAAATGGACATG | 58 |
| 14 | SIGRGDTGHM | 59 | TCTATTGGGAGAGGAGACACGGGTCATATG | 60 |
| 15 | NIARGDAGQY | 61 | AATATTGCTAGAGGAGACGCTGGTCAGTAT | 62 |
| 16 | AVARGDQGLI | 5 | GCAGTAGCAAGAGGAGACCAAGGCTTAATC | 63 |
| 17 | SVSRGDQGLH | 64 | TCGGTCTCGAGAGGAGACCAAGGATTGCAC | 65 |
| 18 | EYRRGDKADI | 51 | GAATACAGGAGAGGAGACAAAGCAGACATC | 66 |
| 19 | AHMRGDLGGT | 55 | GCGCATATGAGAGGAGACTTGGGGGGGACT | 67 |
| 20 | QIGRGDITHG | 68 | CAGATTGGTAGAGGAGACATTACTCATGGG | 69 |
| 21 | EVRRGDLHGT | 70 | GAAGTCAGAAGAGGAGACTTGCACGGGACA | 71 |
| 22 | SVSRGDVHTM | 72 | AGTGTCTCAAGAGGAGACGTGCACACGATG | 73 |
| 23 | MVTRGDLGTR | 74 | ATGGTGACTAGAGGAGACCTTGGTACGCGG | 75 |
| 24 | NGGRGDTTHF | 76 | AACGGCGGGAGAGGAGACACGACGCACTTC | 77 |
| 25 | TMGRGDMNSL | 78 | ACGATGGGGAGAGGAGACATGAATTCGCTT | 79 |
| 26 | AISRGDQGLS | 80 | GCGATTAGTAGAGGAGACCAGGGTCTTTCT | 81 |
| 27 | NDARGDKSTY | 82 | AACGACGCAAGAGGAGACAAATCCACATAC | 83 |
| 28 | VGLRGDLTGS | 84 | GTGGGGCTGAGAGGAGACTTGACGGGTTCG | 85 |
| 29 | EMRRGDLGTS | 86 | GAGATGAGGAGAGGAGACCTGGGGACGAGT | 87 |
| 30 | AMSRGDMGMA | 88 | GCGATGAGTAGAGGAGACATGGGGATGGCG | 89 |
| 31 | ATGRGDLGQA | 4 | GCAACGGGCAGAGGAGACTTAGGCCAAGCA | 90 |
| 32 | NVARGDQVNY | 91 | AACGTAGCAAGAGGAGACCAAGTTAACTAC | 92 |
| 33 | SIGRGDTGHM | 59 | AGCATCGGAAGAGGAGACACCGGCCACATG | 93 |
| 34 | ASVRGDLSGS | 94 | GCATCCGTAAGAGGAGACCTATCAGGCTCA | 95 |
| 35 | SAARGDTERL | 96 | AGCGCCGCGAGAGGAGACACTGAACGGCTA | 97 |
| 36 | AMSRGDMGMA | 88 | GCCATGTCAAGAGGAGACATGGGTATGGCT | 98 |
| 37 | SPSRGDQGRT | 21 | AGTCCATCGAGAGGAGACCAAGGACGCACT | 99 |
| 38 | VPGRGDLNTM | 100 | GTGCCTGGGAGAGGAGACCTTAATACTATG | 101 |
| 39 | GPGRGDQTTL | 2 | GGTCCTGGGAGAGGAGACCAAACGACCCTT | 102 |
| 40 | TSVRGDHGTL | 103 | ACATCGGTCAGAGGAGACCACGGAACATTG | 104 |
| 41 | TPSRGDLGQT | 105 | ACGCCTTCGAGAGGAGACCTTGGGCAGACT | 106 |
| 42 | AGHRGDTGVI | 107 | GCTGGACACAGAGGAGACACAGGAGTCATC | 108 |
| 43 | APARGDQGSM | 109 | GCGCCGGCGAGAGGAGACCAGGGTAGTATG | 110 |
| 44 | MSLRGDLNGS | 111 | ATGTCGTTGAGAGGAGACTTGAATGGGTCG | 112 |
| 45 | EAKRGDVHSI | 113 | GAGGCTAAGAGAGGAGACGTGCATTCTATT | 114 |
| 46 | SAQRGDVQAV | 115 | AGTGCTCAGAGAGGAGACGTGCAGGCGGTG | 116 |
| 47 | STARGDQGDR | 117 | AGTACGGCGAGAGGAGACCAGGGGGATAGG | 118 |
| 48 | QISRGDLGIN | 119 | CAGATTAGTAGAGGAGACCTGGGGATTAAT | 120 |
| 49 | TFTRGDMTMN | 121 | ACGTTCACAAGAGGAGACATGACGATGAAC | 122 |

TABLE 2-continued

Mouse enhanced MyoAAV (eMyoAAV) Capsid Variants

| Rank | N-mer motif | SEQ ID NO: | Encoding sequence | SEQ ID NO: |
|------|-------------|------------|-------------------|------------|
| 50 | QEGRGDLNMR | 123 | CAAGAAGGAAGAGGAGACCTGAACATGAGG | 124 |
| 51 | AHARGDTSSL | 125 | GCACACGCAAGAGGAGACACCAGCTCCCTG | 126 |
| 52 | TNGRGDAGTL | 127 | ACGAATGGGAGAGGAGACGCTGGGACTCTG | 128 |
| 53 | AFGRGDQGQL | 129 | GCTTTCGGCAGAGGAGACCAAGGGCAACTA | 130 |
| 54 | ADGRGDRSSL | 131 | GCTGATGGGAGAGGAGACCGTTCGTCTCTG | 132 |
| 55 | DGRRGDGHSL | 133 | GACGGACGCAGAGGAGACGGACACAGCCTT | 134 |
| 56 | EKLRGDLHST | 135 | GAGAAGTTGAGAGGAGACCTTCATTCGACT | 136 |
| 57 | EARRGDASAM | 137 | GAGGCGCGTAGAGGAGACGCTTCGGCGATG | 138 |
| 58 | MGTRGDKMDF | 139 | ATGGGAACGAGAGGAGACAAAATGGACTTC | 140 |
| 59 | STSRGDRESY | 141 | TCGACTTCGAGAGGAGACCGGGAGTCGTAT | 142 |
| 60 | CQPRGDTTRC | 143 | TGTCAGCCGAGAGGAGACACGACTCGGTGT | 144 |
| 61 | MHTRGDKMDF | 145 | ATGCACACGAGAGGAGACAAAATGGACTTC | 146 |
| 62 | YSARGDTSGL | 147 | TACAGTGCCAGAGGAGACACAAGTGGCCTG | 148 |
| 63 | STMRGDHEKL | 149 | TCGACGATGAGAGGAGACCATGAGAAGTTG | 150 |
| 64 | TQMRGDGVTL | 151 | ACCCAAATGAGAGGAGACGGGGTCACACTA | 152 |
| 65 | TTRRGDMGDN | 153 | ACTACTCGTAGAGGAGACATGGGGGATAAT | 154 |
| 66 | ANGRGDRLEL | 155 | GCGAATGGTAGAGGAGACAGGCTGGAGTTG | 156 |
| 67 | AVSRGDRMEF | 20 | GCTGTGTCTAGAGGAGACAGGATGGAGTTT | 157 |
| 68 | ENQRGDLSGR | 158 | GAGAATCAGAGAGGAGACTTGTCGGGTCGG | 159 |
| 69 | STGRGDLGQA | 160 | TCGACTGGTAGAGGAGACCTGGGGCAGGCT | 161 |
| 70 | MHTRGDKMDF | 145 | ATGCATACTAGAGGAGACAAGATGGATTTT | 162 |
| 71 | SSARGDYSEV | 163 | AGTAGTGCGAGAGGAGACTATAGTGAGGTG | 164 |
| 72 | AFGRGDQGQL | 129 | GCGTTTGGGAGAGGAGACCAGGGTCAGCTT | 165 |
| 73 | STARGDAATY | 166 | AGTACGGCGAGAGGAGACGCGGCGACTTAT | 167 |
| 74 | VNTRGDTQKL | 168 | GTCAACACAAGAGGAGACACTCAAAAACTT | 169 |
| 75 | AMSRGDHASL | 170 | GCGATGAGTAGAGGAGACCATGCGTCGCTT | 171 |
| 76 | QAARGDVNKL | 172 | CAGGCTGCTAGAGGAGACGTTAATAAGCTG | 173 |
| 77 | RGTRGDTVEL | 174 | AGGGGTACGAGAGGAGACACGGTTGAGTTG | 175 |
| 78 | TTRRGDMGDN | 153 | ACCACCCGGAGAGGAGACATGGGAGACAAC | 176 |
| 79 | ASTRGDYAGV | 177 | GCTAGTACGAGAGGAGACTATGCGGGTGTT | 178 |
| 80 | DDRRGDKLPL | 179 | GACGACAGGAGAGGAGACAAACTGCCCCTT | 180 |
| 81 | SGSRGDLNAV | 181 | TCGGGGTCGAGAGGAGACCTGAATGCGGTG | 182 |
| 82 | EYRRGDQQIQ | 183 | GAGTATAGGAGAGGAGACCAGCAGATTCAG | 184 |
| 83 | TYVRGDRAEV | 185 | ACGTACGTCAGAGGAGACAGAGCAGAAGTG | 186 |
| 84 | QSLRGDLNGS | 187 | CAATCACTAAGAGGAGACTTGAACGGATCC | 188 |
| 85 | EGRRGDTTSL | 189 | GAGGGTCGGAGAGGAGACACGACGTCGTTG | 190 |
| 86 | AENRGDRSSL | 191 | GCGGAGAATAGAGGAGACCGGTCGAGTTTG | 192 |

TABLE 2-continued

Mouse enhanced MyoAAV (eMyoAAV) Capsid Variants

| Rank | N-mer motif | SEQ ID NO: | Encoding sequence | SEQ ID NO: |
|------|-------------|------------|-------------------|------------|
| 87 | VAGRGDRSEL | 193 | GTGGCTGGGAGAGGAGACCGTAGTGAGCTG | 194 |
| 88 | DPARGDIGAR | 195 | GATCCGGCGAGAGGAGACATTGGTGCGCGT | 196 |
| 89 | EMRRGDLGTS | 86 | GAAATGCGCAGAGGAGACTTGGGAACTTCA | 197 |
| 90 | VWQRGDKMDM | 57 | GTTTGGCAGAGAGGAGACAAGATGGATATG | 198 |
| 91 | VIGRGDKALQ | 199 | GTGATTGGGAGAGGAGACAAGGCGCTTCAG | 200 |
| 92 | SFERGDKNSL | 201 | AGCTTCGAAAGAGGAGACAAAAACTCTCTT | 202 |
| 93 | QIARGDIASV | 203 | CAGATTGCTAGAGGAGACATTGCTAGTGTG | 204 |
| 94 | TISRGDLGGA | 205 | ACGATTAGTAGAGGAGACCTGGGTGGGGCT | 206 |
| 95 | AMIRGDMTHS | 207 | GCGATGATTAGAGGAGACATGACGCATAGT | 208 |
| 96 | TSVRGDHGTL | 103 | ACGAGTGTGAGAGGAGACCATGGGACGCTG | 209 |
| 97 | TMRRGDLNDS | 210 | ACGATGCGGAGAGGAGACCTGAATGATAGT | 211 |
| 98 | AYSRGDLGNH | 212 | GCCTACTCCAGAGGAGACCTAGGCAACCAC | 213 |
| 99 | EERRGDTHRL | 214 | GAGGAGCGGAGAGGAGACACTCATCGGCTG | 215 |
| 100 | SQLRGDAGTI | 216 | TCACAACTAAGAGGAGACGCGGGGACAATC | 217 |
| 101 | AMVRGDAHQL | 218 | GCGATGGTGAGAGGAGACGCGCATCAGCTG | 219 |
| 102 | TTSRGDLNSV | 220 | ACGACTAGTAGAGGAGACTTGAATTCGGTT | 221 |
| 103 | WEQRGDMIGK | 222 | TGGGAGCAGAGAGGAGACATGATTGGGAAG | 223 |
| 104 | YTTRGDLQSN | 224 | TACACCACCAGAGGAGACCTCCAATCAAAC | 225 |
| 105 | MSQRGDLSHQ | 226 | ATGTCGCAGAGAGGAGACCTTTCGCATCAG | 227 |
| 106 | ASTRGDTTHM | 228 | GCGAGTACTAGAGGAGACACGACGCATATG | 229 |
| 107 | SDTRGDTHRL | 230 | TCAGACACCAGAGGAGACACCCACAGACTG | 231 |
| 108 | TLGRGDQYTS | 232 | ACGCTGGGTAGAGGAGACCAGTATACGAGT | 233 |
| 109 | SYARGDVREV | 234 | TCGTATGCGAGAGGAGACGTTAGGGAGGTT | 235 |
| 110 | ETRRGDLSQN | 236 | GAGACTCGTAGAGGAGACCTGAGTCAGAAT | 237 |
| ill | TIGRGDLMDK | 238 | ACAATCGGGAGAGGAGACCTGATGGACAAA | 239 |
| 112 | SYTRGDLSQN | 240 | AGTTACACCAGAGGAGACCTTAGCCAAAAC | 241 |
| 113 | SKLRGDASEI | 242 | TCGAAGCTGAGAGGAGACGCTAGTGAGATT | 243 |
| 114 | SMARGDKAEI | 244 | TCGATGGCGAGAGGAGACAAGGCGGAGATT | 245 |
| 115 | GAVRGDHSSL | 246 | GGAGCCGTCAGAGGAGACCACTCATCGTTA | 247 |
| 116 | METRGDMSNR | 248 | ATGGAGACGAGAGGAGACATGAGTAATCGT | 249 |
| 117 | AYTRGDKDAL | 250 | GCGTACACAAGAGGAGACAAAGACGCACTA | 251 |
| 118 | ENRRGDITQS | 252 | GAGAATCGGAGAGGAGACATTACGCAGTCG | 253 |
| 119 | STGRGDLGQA | 160 | TCCACGGGCAGAGGAGACCTTGGACAAGCA | 254 |
| 120 | GAVRGDHSSL | 246 | GGTGCTGTTAGAGGAGACCATAGTAGTCTT | 255 |
| 121 | SQLRGDAGTI | 216 | TCTCAGCTTAGAGGAGACGCTGGTACGATT | 256 |
| 122 | MLLRGDKNDF | 257 | ATGCTCCTAAGAGGAGACAAAAACGACTTC | 258 |
| 123 | KVQRGDASDW | 259 | AAGGTGCAGAGAGGAGACGCGAGTGATTGG | 260 |
| 124 | AFTRGDMQTA | 261 | GCGTTTACGAGAGGAGACATGCAGACTGCT | 262 |

TABLE 2-continued

| | | | | |
|---|---|---|---|---|
| | | Mouse enhanced MyoAAV (eMyoAAV) Capsid Variants | | |
| Rank | N-mer motif | SEQ ID NO: | Encoding sequence | SEQ ID NO: |
| 125 | QPKRGDVQAQ | 263 | CAGCCTAAGAGAGGAGACGTTCAGGCTCAG | 264 |
| 126 | ASLRGDMGVS | 265 | GCTAGTCTGAGAGGAGACATGGGGGTGAGT | 266 |
| 127 | AYSRGDKESF | 267 | GCCTACTCCAGAGGAGACAAAGAATCGTTC | 268 |
| 128 | RFQRGDLTDA | 269 | CGGTTCCAAAGAGGAGACTTGACCGACGCT | 270 |
| 129 | SDARGDTMKL | 271 | TCTGATGCTAGAGGAGACACGATGAAGCTG | 272 |
| 130 | SGARGDTVSL | 273 | AGCGGGGCCAGAGGAGACACAGTAAGTCTC | 274 |
| 131 | DEKRGDQKHL | 275 | GATGAGAAGAGAGGAGACCAGAAGCATCTT | 276 |
| 132 | NGVRGDVQNF | 277 | AACGGAGTAAGAGGAGACGTCCAAAACTTC | 278 |
| 133 | MTLRGDLGGS | 279 | ATGACGTTGAGAGGAGACCTGGGTGGGTCG | 280 |
| 134 | EARRGDASAM | 137 | GAGGCTAGGAGAGGAGACGCTAGTGCGATG | 281 |
| 135 | GQERGDLGTR | 282 | GGGCAGGAGAGAGGAGACCTGGGGACTCGG | 283 |
| 136 | RGARGDLVDA | 284 | AGAGGCGCCAGAGGAGACCTAGTCGACGCT | 285 |
| 137 | QYSRGDHTDL | 286 | CAATACTCCAGAGGAGACCACACCGACCTT | 287 |
| 138 | MNTRGDVHAM | 288 | ATGAACACCAGAGGAGACGTGCACGCTATG | 289 |
| 139 | TVRRGDLATE | 290 | ACGGTACGGAGAGGAGACCTAGCAACCGAA | 291 |
| 140 | NIARGDAGQY | 61 | AATATTGCGAGAGGAGACGCTGGTCAGTAT | 292 |
| 141 | SVGRGDKADI | 293 | TCTGTTGGGAGAGGAGACAAGGCTGATATT | 294 |
| 142 | SHNRGDTGTM | 295 | TCACACAACAGAGGAGACACCGGAACCATG | 296 |
| 143 | TNTRGDKESV | 297 | ACGAACACCAGAGGAGACAAAGAATCAGTA | 298 |
| 144 | SIGRGDQYTI | 299 | TCGATTGGTAGAGGAGACCAGTATACGATT | 300 |
| 145 | QTSRGDAGSW | 301 | CAGACGAGTAGAGGAGACGCGGGGTCTTGG | 302 |
| 146 | AENRGDRSSL | 191 | GCTGAAAACAGAGGAGACCGAAGCAGCCTA | 303 |
| 147 | AISRGDVQSL | 304 | GCGATTTCGAGAGGAGACGTTCAGTCGTTG | 305 |
| 148 | NAQRGDHGQL | 306 | AACGCACAAAGAGGAGACCACGGGCAACTG | 307 |
| 149 | LNSRGDQASV | 308 | CTCAACTCGAGAGGAGACCAAGCCTCCGTC | 309 |
| 150 | SGNRGDIGTF | 310 | TCGGGAAACAGAGGAGACATAGGTACATTC | 311 |
| 151 | NVGRGDQATM | 312 | AACGTGGGAAGAGGAGACCAAGCCACAATG | 313 |
| 152 | SYSRGDTGRL | 314 | TCGTATTCTAGAGGAGACACTGGTCGGCTT | 315 |
| 153 | SHLRGDQALA | 316 | AGCCACTTAAGAGGAGACCAAGCGTTGGCC | 317 |
| 154 | YFARGDMTMN | 318 | TACTTCGCCAGAGGAGACATGACTATGAAC | 319 |
| 155 | QSQRGDLNPM | 320 | CAGTCGCAGAGAGGAGACCTTAATCCTATG | 321 |
| 156 | EQRRGDKTEL | 322 | GAGCAGAGGAGAGGAGACAAGACGGAGCTG | 323 |
| 157 | VSARGDAGQL | 324 | GTGTCTGCGAGAGGAGACGCGGGTCAGTTG | 325 |
| 158 | SPSRGDQGRT | 21 | TCTCCGTCTAGAGGAGACCAGGGGCGGACG | 326 |
| 159 | EASRGDKGTH | 327 | GAGGCTAGTAGAGGAGACAAGGGTACGCAT | 328 |
| 160 | LSTRGDMGMQ | 329 | CTGTCTACTAGAGGAGACATGGGTATGCAG | 332 |
| 161 | ANMRGDQLHT | 333 | GCGAATATGAGAGGAGACCAGCTGCATACT | 334 |

TABLE 2-continued

| | | Mouse enhanced MyoAAV (eMyoAAV) Capsid Variants | | |
|---|---|---|---|---|
| Rank | N-mer motif | SEQ ID NO: | Encoding sequence | SEQ ID NO: |
| 162 | ENTRGDLTHA | 335 | GAGAATACGAGAGGAGACCTTACTCATGCG | 336 |
| 163 | IERRGDSAGL | 337 | ATTGAGCGTAGAGGAGACTCGGCGGGGCTG | 338 |
| 164 | SAMRGDGVSL | 339 | AGTGCGATGAGAGGAGACGGAGTGAGCTTG | 340 |
| 165 | TVSRGDQGLS | 341 | ACGGTTTCGAGAGGAGACCAGGGGTTGTCT | 342 |
| 166 | SIVRGDLNST | 343 | TCGATCGTCAGAGGAGACCTGAACTCCACG | 344 |
| 167 | DVARGDKTNF | 345 | GACGTAGCGAGAGGAGACAAAACAAACTTC | 346 |
| 168 | WSQRGDLSGT | 347 | TGGAGCCAAAGAGGAGACCTGAGTGGAACC | 348 |
| 169 | LNQRGDVSNM | 349 | CTGAACCAAAGAGGAGACGTTTCCAACATG | 350 |
| 170 | AALRGDLSGS | 351 | GCCGCCCTAAGAGGAGACCTATCCGGCTCA | 352 |
| 171 | RVARGDITDI | 353 | AGGGTTGCGAGAGGAGACATTACGGATATT | 354 |
| 172 | STNRGDLNQV | 355 | TCGACGAACAGAGGAGACCTCAACCAAGTT | 356 |
| 173 | DSRRGDSVSL | 357 | GATTCGCGGGAGAGGAGACTCTGTGAGTCTT | 358 |
| 174 | SVGRGDQSQM | 359 | AGTGTTGGGAGAGGAGACCAGTCTCAGATG | 360 |
| 175 | SNTRGDTNSL | 361 | TCCAACACGAGAGGAGACACAAACTCCCTA | 362 |
| 176 | DNRRGDGTTM | 363 | GATAATCGGAGAGGAGACGGTACGACTATG | 364 |
| 177 | TPSRGDQGRL | 365 | ACGCCTTCGAGAGGAGACCAAGGAAGACTA | 366 |
| 178 | NYSRGDSMTL | 367 | AACTACAGCAGAGGAGACTCAATGACGCTT | 368 |
| 179 | MQARGDAGTL | 369 | ATGCAGGCTAGAGGAGACGCTGGGACTCTG | 370 |
| 180 | TQSRGDLSGA | 371 | ACGCAGTCGAGAGGAGACTTGTCTGGTGCG | 372 |
| 181 | FAQRGDLTGV | 373 | TTTGCGCAGAGAGGAGACTTGACTGGGGTT | 374 |
| 182 | APVRGDLIGT | 375 | GCGCCGGTGAGAGGAGACCTGATTGGTACG | 376 |
| 183 | SNTRGDTNSL | 361 | TCGAATACTAGAGGAGACACGAATAGTTTG | 377 |
| 184 | EPKRGDLSNT | 378 | GAGCCGAAGAGAGGAGACTTGAGTAATACG | 379 |
| 185 | SVGRGDTYPL | 380 | TCGGTTGGGAGAGGAGACACTTATCCTCTG | 381 |
| 186 | QTARGDMTGH | 382 | CAAACAGCCAGAGGAGACATGACTGGCCAC | 383 |
| 187 | AGARGDLENR | 384 | GCTGGTGCGAGAGGAGACTTGGAGAATCGG | 385 |
| 188 | MSTRGDLNNV | 386 | ATGAGCACTAGAGGAGACCTAAACAACGTC | 387 |
| 189 | EKQRGDLNSM | 388 | GAAAAACAAAGAGGAGACCTCAACAGCATG | 389 |
| 190 | IKTRGDLGHE | 390 | ATTAAGACGAGAGGAGACCTTGGTCATGAG | 391 |
| 191 | IGRRGDMELS | 392 | ATTGGGAGGAGAGGAGACATGGAGTTGTCT | 393 |
| 192 | TTGRGDLKEV | 394 | ACTACGGGTAGAGGAGACTTGAAGGAGGTT | 395 |
| 193 | TDKRGDQNTV | 396 | ACGGATAAGAGAGGAGACCAGAATACTGTG | 397 |
| 194 | SNVRGDREAV | 398 | TCGAATGTTAGAGGAGACCGGGAGGCGGTT | 399 |
| 195 | SVGRGDQSQM | 359 | TCAGTCGGCAGAGGAGACCAAAGTCAAATG | 400 |
| 196 | YANRGDLSHQ | 401 | TACGCCAACAGAGGAGACCTGAGTCACCAA | 402 |
| 197 | QISRGDLGIN | 119 | CAAATATCGAGAGGAGACCTAGGTATCAAC | 403 |
| 198 | SMMRGDAGQL | 404 | TCGATGATGAGAGGAGACGCTGGGCAGTTG | 405 |

TABLE 2-continued

Mouse enhanced MyoAAV (eMyoAAV) Capsid Variants

| Rank | N-mer motif | SEQ ID NO: | Encoding sequence | SEQ ID NO: |
|---|---|---|---|---|
| 199 | EARRGDSQGL | 406 | GAGGCGCGGAGAGGAGACAGTCAGGGGCTG | 407 |
| 200 | MPTRGDQTKF | 408 | ATGCCCACAAGAGGAGACCAAACCAAATTC | 409 |

TABLE 3

Non-Human Primate enhanced MyoAAV (eMyoAAV) Capsid Variants

| Rank | N-mer insert | SEQ ID NO: | Encoding sequence | SEQ ID NO: |
|---|---|---|---|---|
| 1 | SNSRGDYNSL | 28 | TCAAACTCCAGAGGAGACTACAACTCCTTG | 410 |
| 2 | SSARGDRDYL | 411 | TCGTCGGCTAGAGGAGACCGTGATTATCTG | 412 |
| 3 | STVRGDYTSV | 413 | AGCACGGTCAGAGGAGACTACACGTCCGTG | 414 |
| 4 | QERRGDYTSM | 30 | CAGGAGCGGAGAGGAGACTATACGAGTATG | 415 |
| 5 | NGGRGDTTHF | 76 | AACGGCGGGAGAGGAGACACGACGCACTTC | 416 |
| 6 | ASTRGDHGVL | 31 | GCGAGTACTAGAGGAGACCATGGTGTGTTG | 417 |
| 7 | SYQRGDQHNM | 418 | TCGTACCAAAGAGGAGACCAACACAACATG | 419 |
| 8 | NDTRGDRSYM | 420 | AACGACACAAGAGGAGACCGATCTTACATG | 421 |
| 9 | ENRRGDFNNT | 32 | GAAAACAGGAGAGGAGACTTCAACAACACT | 422 |
| 10 | SGSRGDLSGH | 423 | TCCGGCTCGAGAGGAGACTTGTCAGGACAC | 424 |
| 11 | ENRRGDITQS | 252 | GAGAATCGGAGAGGAGACATTACGCAGTCG | 425 |
| 12 | DKPRGDRQLL | 426 | GATAAGCCGAGAGGAGACCGGCAGTTGTTG | 427 |
| 13 | EERRGDTHRL | 214 | GAGGAGCGGAGAGGAGACACTCATCGGCTG | 428 |
| 14 | AMIRGDMTHS | 207 | GCGATGATTAGAGGAGACATGACGCATAGT | 429 |
| 15 | SNNRGDYTTM | 430 | TCAAACAACAGAGGAGACTACACGACAATG | 431 |
| 16 | QGGRGDLSTL | 432 | CAGGGTGGGAGAGGAGACTTGTCGACGTTG | 433 |
| 17 | SKDRGDYQTL | 434 | TCGAAGGATAGAGGAGACTATCAGACTCTT | 435 |
| 18 | ATARGDQMKL | 436 | GCTACGGCGAGAGGAGACCAGATGAAGCTG | 437 |
| 19 | QHMRGDLTGA | 438 | CAGCATATGAGAGGAGACTTGACTGGTGCG | 439 |
| 20 | DGTRGDLGRY | 440 | GACGGCACGAGAGGAGACCTTGGAAGGTAC | 441 |
| 21 | DSRRGDYANL | 442 | GACTCTCGGAGAGGAGACTACGCAAACCTC | 443 |
| 22 | SAMRGDYTST | 444 | TCGGCGATGAGAGGAGACTATACTAGTACT | 445 |
| 23 | ENRRGDAQLL | 446 | GAGAATCGGAGAGGAGACGCGCAGCTGCTG | 447 |
| 24 | TTLRGDHSQL | 448 | ACGACGCTGAGAGGAGACCATAGTCAGCTT | 449 |
| 25 | DAGRGDMHRM | 450 | GACGCAGGGAGAGGAGACATGCACCGTATG | 451 |
| 26 | QHTRGDLSST | 452 | CAGCATACGAGAGGAGACTTGAGTTCTACT | 453 |
| 27 | QVYRGDRESV | 454 | CAAGTTTACAGAGGAGACAGGGAATCCGTG | 455 |
| 28 | SSQRGDLAGT | 456 | TCGAGTCAGAGAGGAGACTTGGCTGGTACT | 457 |
| 29 | TDVRGDRGTF | 458 | ACGGATGTTAGAGGAGACAGGGGGACGTTT | 459 |
| 30 | SSVRGDREVT | 460 | TCGTCTGTGAGAGGAGACCGGGAGGTGACG | 461 |

TABLE 3-continued

Non-Human Primate enhanced MyoAAV (eMyoAAV) Capsid Variants

| Rank | N-mer insert | SEQ ID NO: | Encoding sequence | SEQ ID NO: |
|------|--------------|------------|-------------------|------------|
| 31 | ENRRGDLTNA | 462 | GAGAATAGGAGAGGAGACCTGACTAATGCG | 463 |
| 32 | SYARGDVHSI | 464 | TCGTATGCGAGAGGAGACGTTCATTCTATT | 465 |
| 33 | DSSRGDLNLR | 466 | GACAGCTCAAGAGGAGACCTCAACCTCCGG | 467 |
| 34 | SNARGDYSNM | 468 | TCGAACGCGAGAGGAGACTACTCAAACATG | 469 |
| 35 | SSVRGDHSVL | 470 | TCGTCTGTGAGAGGAGACCATTCGGTGCTT | 471 |
| 36 | SAFRGDLHAT | 472 | TCGGCTTTTAGAGGAGACCTGCATGCTACT | 473 |
| 37 | SAMRGDYTST | 444 | TCCGCCATGAGAGGAGACTACACAAGCACG | 474 |
| 38 | NAQRGDHGQL | 306 | AACGCACAAAGAGGAGACCACGGGCAACTG | 475 |
| 39 | SDRRGDQLLY | 476 | TCGGATCGGAGAGGAGACCAGCTGTTGTAT | 477 |
| 40 | SGVRGDRLAV | 478 | AGCGGCGTAAGAGGAGACCGCCTAGCCGTA | 479 |
| 41 | ASLRGDLSST | 480 | GCCAGCCTAAGAGGAGACCTCAGCTCAACG | 481 |
| 42 | TNGRGDLHGM | 482 | ACGAACGGAAGAGGAGACCTTCACGGAATG | 483 |
| 43 | TNTRGDHGML | 484 | ACGAATACGAGAGGAGACCATGGGATGCTG | 485 |
| 44 | SSARGDRDYL | 411 | AGTTCCGCCAGAGGAGACCGGGACTACCTC | 486 |
| 45 | EDRRGDLLRT | 487 | GAGGATCGGAGAGGAGACCTTTTGAGGACT | 488 |
| 46 | SSLRGDLLHS | 489 | TCGTCGCTGAGAGGAGACCTGTTGCATTCT | 490 |
| 47 | ENRRGDLTNA | 462 | GAAAACCGTAGAGGAGACCTCACGAACGCT | 491 |
| 48 | DGRRGDRESI | 492 | GACGGCAGGAGAGGAGACCGGGAATCGATC | 493 |
| 49 | TGTRGDTMTW | 494 | ACTGGAACCAGAGGAGACACAATGACATGG | 495 |
| 50 | STVRGDYTSV | 413 | TCGACTGTTAGAGGAGACTATACTTCTGTT | 496 |
| 51 | SATRGDHNVL | 497 | TCGGCAACGAGAGGAGACCACAACGTACTG | 498 |
| 52 | TDRRGDSGTL | 499 | ACGGATCGGAGAGGAGACAGTGGTACTCTG | 500 |
| 53 | TSARGDLIHT | 501 | ACGAGTGCTAGAGGAGACCTGATTCATACG | 502 |
| 54 | SGVRGDRLAV | 478 | AGTGGGGTGAGAGGAGACCGGCTGGCGGTG | 503 |
| 55 | AVERGDRLML | 504 | GCGGTTGAGAGAGGAGACCGTCTTATGCTG | 505 |
| 56 | DRSRGDTHVL | 506 | GACAGGTCGAGAGGAGACACGCACGTACTC | 507 |
| 57 | ESTRGDLRW | 508 | GAGTCGACGAGAGGAGACCTTCGTGTTGTG | 509 |
| 58 | TTIRGDYREL | 510 | ACGACGATTAGAGGAGACTATCGTGAGTTG | 511 |
| 59 | TFIRGDLAGA | 512 | ACGTTCATCAGAGGAGACCTGGCAGGTGCG | 513 |
| 60 | MTSRGDLTTY | 514 | ATGACGAGCAGAGGAGACTTGACAACATAC | 515 |
| 61 | ADRRGDQLYS | 516 | GCGGATCGTAGAGGAGACCAGCTTTATTCG | 517 |
| 62 | AHMRGDLGGT | 55 | GCACACATGAGAGGAGACCTAGGCGGCACG | 518 |
| 63 | GYVRGDLGQH | 519 | GGGTACGTCAGAGGAGACCTGGGGCAACAC | 520 |
| 64 | DASRGDRTSL | 521 | GATGCGAGTAGAGGAGACAGGACTAGTTTG | 522 |
| 65 | TEVRGDRSQV | 523 | ACGGAGGTGAGAGGAGACAGGTCGCAGGTT | 524 |
| 66 | SHLRGDQALA | 316 | TCGCATCTGAGAGGAGACCAGGCTCTTGCG | 525 |
| 67 | SEVRGDRLSI | 526 | TCGGAGGTGAGAGGAGACCGGTTGAGTATT | 527 |
| 68 | SAARGDTERL | 96 | AGCGCCGCGAGAGGAGACACTGAACGGCTA | 528 |

TABLE 3-continued

Non-Human Primate enhanced MyoAAV (eMyoAAV) Capsid Variants

| Rank | N-mer insert | SEQ ID NO: | Encoding sequence | SEQ ID NO: |
|------|-------------|-----------|-------------------|-----------|
| 69 | SDRRGDLSGA | 529 | TCAGACCGTAGAGGAGACCTGTCGGGCGCT | 530 |
| 70 | SVTRGDRVVI | 531 | AGCGTCACAAGAGGAGACAGAGTAGTCATC | 532 |
| 71 | SEGRGDRMAL | 533 | TCGGAGGGGAGAGGAGACAGGATGGCTCTT | 534 |
| 72 | SSTRGDHLSL | 535 | TCGTCTACTAGAGGAGACCATCTTTCGCTG | 536 |
| 73 | AMIRGDMTHS | 207 | GCTATGATCAGAGGAGACATGACCCACTCC | 537 |
| 74 | SSTRGDQIYV | 538 | TCGTCGACGAGAGGAGACCAGATTTATGTG | 539 |
| 75 | EERRGDTHRL | 214 | GAGGAGCGGAGAGGAGACACTCATCGGTTG | 540 |
| 76 | SNSRGDYNSL | 28 | TCGAATTCGAGAGGAGACTATAATAGTCTT | 541 |
| 77 | SAQRDRMGSP | 542 | TCCGCACAAAGGGATCGTATGGGTTCTCCG | 543 |
| 78 | TGTRGDIATF | 544 | ACGGGTACGAGAGGAGACATTGCGACTTTT | 545 |
| 79 | SMQRGDLLST | 546 | TCGATGCAGAGAGGAGACCTGCTTTCTACT | 547 |
| 80 | EDVRGDRSKL | 548 | GAGGATGTGAGAGGAGACAGGAGTAAGCTT | 549 |
| 81 | AHMRGDLGGT | 55 | GCGCATATGAGAGGAGACTTGGGGGGGACT | 550 |
| 82 | TSVRGDQSQY | 551 | ACGAGTGTGAGAGGAGACCAGAGTCAGTAT | 552 |
| 83 | ADRRGDTGLF | 553 | GCGGATCGGAGAGGAGACACGGGGTTGTTT | 554 |
| 84 | NTYRGDRDSL | 555 | AACACTTACAGAGGAGACCGAGACAGCCTG | 556 |
| 85 | TDVRGDRGTF | 458 | ACGGATGTTAGAGGAGACCGGGGGACGTTT | 557 |
| 86 | SRGRGDLNDL | 558 | TCTCGTGGGAGAGGAGACCTGAATGATTTG | 559 |
| 87 | SNVRGDREAV | 398 | AGCAACGTAAGAGGAGACAGGGAAGCCGTC | 560 |
| 88 | MDRRGDASIL | 561 | ATGGACAGGAGAGGAGACGCCTCCATACTG | 562 |
| 89 | SIWRGDRTEV | 563 | TCGATATGGAGAGGAGACCGTACAGAAGTC | 564 |
| 90 | NSQRGDYSGM | 565 | AACTCACAAAGAGGAGACTACAGTGGAATG | 566 |
| 91 | SSVRGDIGGI | 567 | TCTAGCGTAAGAGGAGACATCGGGGGGATC | 568 |
| 92 | ENQRGDLSGR | 158 | GAGAATCAGAGAGGAGACTTGTCGGGTCGG | 569 |
| 93 | EIRRGDLLAQ | 570 | GAGATTCGGAGAGGAGACCTTCTGGCTCAG | 571 |
| 94 | SNIRGDHAVM | 572 | TCGAACATCAGAGGAGACCACGCAGTCATG | 573 |
| 95 | LDTRGDRSQV | 574 | CTGGATACGAGAGGAGACCGGAGTCAGGTT | 575 |
| 96 | ANTRGDHQNF | 576 | GCGAATACGAGAGGAGACCATCAGAATTTT | 577 |
| 97 | QVYRGDRESV | 454 | CAGGTGTATAGAGGAGACCGTGAGTCTGTT | 578 |
| 98 | TSVRGDLSMN | 579 | ACGTCGGTGAGAGGAGACCTTTCGATGAAT | 580 |
| 99 | ASTRGDHGVL | 31 | GCCTCAACGAGAGGAGACCACGGAGTTCTC | 581 |
| 100 | TTTRGDYLNT | 582 | ACGACGACGAGAGGAGACTATCTTAATACG | 583 |
| 101 | AERRGDIKEY | 584 | GCGGAGAGGAGAGGAGACATTAAGGAGTAT | 585 |
| 102 | SHARGDLGST | 586 | TCGCATGCTAGAGGAGACTTGGGTTCGACT | 587 |
| 103 | TSQRGDYVSL | 588 | ACGTCTCAGAGAGGAGACTATGTTTCTCTT | 589 |
| 104 | GPGRGDQTTL | 2 | GGGCCGGGTAGAGGAGACCAGACTACGTTG | 590 |
| 105 | VNVRGDRGEV | 591 | GTGAATGTGAGAGGAGACCGTGGTGAGGTG | 592 |

TABLE 3-continued

Non-Human Primate enhanced MyoAAV (eMyoAAV) Capsid Variants

| Rank | N-mer insert | SEQ ID NO: | Encoding sequence | SEQ ID NO: |
|------|--------------|------------|-------------------|------------|
| 106 | SYRRGDHDQL | 593 | TCGTATCGTAGAGGAGACCATGATCAGCTT | 594 |
| 107 | SGTRGDRVDL | 595 | AGCGGCACAAGAGGAGACAGGGTAGACCTC | 596 |
| 108 | SHFRGDLHTS | 597 | TCCCACTTCAGAGGAGACTTGCACACGTCC | 598 |
| 109 | SDRRGDLSVP | 599 | TCGGATCGTAGAGGAGACCTTTCGGTGCCT | 600 |
| 110 | SGTRGDTLIL | 601 | AGCGGCACCAGAGGAGACACCCTTATACTC | 602 |
| ill | ENTRGDLHGK | 603 | GAAAACACCAGAGGAGACCTCCACGGCAAA | 604 |
| 112 | DRARGDTHVL | 605 | GATCGGGCGAGAGGAGACACGCATGTGCTG | 606 |
| 113 | ASGRGDIAGL | 607 | GCGTCTGGTAGAGGAGACATTGCGGGGCTT | 608 |
| 114 | EGRRGDLFQA | 609 | GAGGGTCGTAGAGGAGACCTGTTTCAGGCG | 610 |
| 115 | RSERGDRLEI | 611 | AGATCCGAAAGAGGAGACAGGCTAGAAATC | 612 |
| 116 | AAYRGDAHVL | 613 | GCGGCCTACAGAGGAGACGCACACGTGCTC | 614 |
| 117 | NDSRGDQHRL | 615 | AACGACTCGAGAGGAGACCAACACCGATTG | 616 |
| 118 | SSARGDHSQL | 617 | TCATCGGCAAGAGGAGACCACTCTCAACTG | 618 |
| 119 | TNERGDRLSI | 619 | ACGAATGAGAGAGGAGACCGTCTTTCGATT | 620 |
| 120 | SNSRGDYTSV | 621 | AGCAACTCCAGAGGAGACTACACCAGTGTC | 622 |
| 121 | NVTRGDHTVM | 623 | AACGTCACAAGAGGAGACCACACCGTTATG | 624 |
| 122 | TMVRGDVKGL | 625 | ACGATGGTGAGAGGAGACGTTAAGGGGCTT | 626 |
| 123 | TGTRGDIATF | 544 | ACCGGGACAAGAGGAGACATAGCCACGTTC | 627 |
| 124 | VQLRGDLAST | 628 | GTGCAGCTGAGAGGAGACTTGGCTTCTACT | 629 |
| 125 | MNRRGDYSEQ | 630 | ATGAACCGGAGAGGAGACTACTCGGAACAA | 631 |
| 126 | ANTRGDLSPV | 632 | GCGAATACTAGAGGAGACCTGAGTCCGGTT | 633 |
| 127 | TGMRGDAGSL | 634 | ACGGGTATGAGAGGAGACGCTGGGAGTCTT | 635 |
| 128 | LDRRGDFSSA | 636 | CTAGACCGCAGAGGAGACTTCAGCTCCGCG | 637 |
| 129 | MYHRGDMTSV | 638 | ATGTACCACAGAGGAGACATGACTTCGGTG | 639 |
| 130 | GSMRGDLHST | 640 | GGGTCGATGAGAGGAGACTTGCATTCGACG | 641 |
| 131 | SSSRGDFSSV | 642 | TCGTCGTCCAGAGGAGACTTCAGCTCTGTT | 643 |
| 132 | TGTRGDLHTY | 644 | ACGGGTACGAGAGGAGACTTGCATACTTAT | 645 |
| 133 | YTQRGDLATV | 646 | TACACCCAAAGAGGAGACCTTGCCACCGTC | 647 |
| 134 | TDVRGDRMYV | 648 | ACGGATGTTAGAGGAGACCGGATGTATGTG | 649 |
| 135 | TSVRGDHGTL | 103 | ACATCGGTCAGAGGAGACCACGGAACATTG | 650 |
| 136 | SNSRGDLSVN | 651 | TCGAACTCCAGAGGAGACCTATCGGTAAAC | 652 |
| 137 | QSGRGDQMTL | 653 | CAGTCTGGGAGAGGAGACCAGATGACGTTG | 654 |
| 138 | MNTRGDLQQS | 655 | ATGAACACCAGAGGAGACTTGCAACAATCG | 656 |
| 139 | AGSRGDLQTV | 657 | GCGGGATCAAGAGGAGACCTACAAACGGTG | 658 |
| 140 | SNMRGDQTYV | 659 | TCGAACATGAGAGGAGACCAAACTTACGTC | 660 |
| 141 | TPSRGDMSNV | 661 | ACGCCAAGTAGAGGAGACATGTCCAACGTC | 662 |
| 142 | NSTRGDLHMA | 663 | AACAGCACAAGAGGAGACCTACACATGGCA | 664 |
| 143 | ANTRGDLSVS | 665 | GCTAACACCAGAGGAGACCTCTCAGTCAGT | 666 |

TABLE 3-continued

Non-Human Primate enhanced MyoAAV (eMyoAAV) Capsid Variants

| Rank | N-mer insert | SEQ ID NO: | Encoding sequence | SEQ ID NO: |
|------|--------------|------------|-------------------|------------|
| 144 | TDRRGDTGLL | 667 | ACCGACCGAAGAGGAGACACCGGCTTACTG | 668 |
| 145 | DGVRGDRATW | 669 | GACGGCGTAAGAGGAGACCGTGCAACATGG | 670 |
| 146 | ENRRGDFNNT | 32 | GAGAATCGTAGAGGAGACTTTAATAATACG | 671 |
| 147 | EPSRGDRMVL | 672 | GAGCCTAGTAGAGGAGACAGGATGGTGTTG | 673 |
| 148 | SGVRGDRIII | 674 | AGCGGCGTTAGAGGAGACCGGATCATAATC | 675 |
| 149 | TSMRGDYTHV | 676 | ACGTCGATGAGAGGAGACTATACGCATGTT | 677 |
| 150 | ASSRGDLTVI | 678 | GCGTCGAGTAGAGGAGACTTGACTGTTATT | 679 |
| 151 | ETRRGDLSLQ | 680 | GAGACGCGTAGAGGAGACCTGTCGCTTCAG | 681 |
| 152 | NNARGDQSMH | 682 | AACAACGCAAGAGGAGACCAATCAATGCAC | 683 |
| 153 | TDRRGDSSAL | 684 | ACGGATAGGAGAGGAGACTCTAGTGCGCTT | 685 |
| 154 | SSQRGDLTGV | 686 | TCAAGCCAAAGAGGAGACTTGACAGGTGTG | 687 |
| 155 | QTARGDVMVH | 688 | CAGACGGCTAGAGGAGACGTTATGGTTCAT | 689 |
| 156 | VSQRGDLNAV | 690 | GTGTCGCAGAGAGGAGACCTGAATGCTGTT | 691 |
| 157 | TMTRGDLAAN | 692 | ACGATGACCAGAGGAGACCTCGCTGCTAAC | 693 |
| 158 | NASRGDHSSL | 694 | AATGCTTCGAGAGGAGACCATTCGTCGTTG | 695 |
| 159 | SNTRGDMGLT | 696 | TCAAACACCAGAGGAGACATGGGCCTCACG | 697 |
| 160 | MYSRGDTHSL | 698 | ATGTATTCGAGAGGAGACACTCATAGTCTG | 699 |
| 161 | ADQRGDRAPL | 700 | GCGGATCAGAGAGGAGACAGGGCTCCGCTT | 701 |
| 162 | QERRGDYTSM | 30 | CAAGAAAGGAGAGGAGACTACACCTCTATG | 702 |
| 163 | SQNRGDLANT | 703 | TCCCAAAACAGAGGAGACCTAGCCAACACG | 704 |
| 164 | EKLRGDLHST | 135 | GAGAAGTTGAGAGGAGACCTTCATTCGACT | 705 |
| 165 | QGGRGDLSTL | 432 | CAAGGCGGAAGAGGAGACCTGAGTACACTG | 706 |
| 166 | SNRRGDTEMQ | 707 | TCGAATAGGAGAGGAGACACTGAGATGCAG | 708 |
| 167 | SGSRGDVSAL | 709 | TCGGGTAGTAGAGGAGACGTGAGTGCTTTG | 710 |
| 168 | ESTRGDRGTL | 711 | GAGTCGACGAGAGGAGACCGTGGTACGCTG | 712 |
| 169 | SAVRGDAALH | 713 | TCGGCGGTGAGAGGAGACGCGGCGCTTCAT | 714 |
| 170 | LSSRGDVNRL | 715 | CTGAGCAGCAGAGGAGACGTTAACCGCCTT | 716 |
| 171 | EQRRGDIQTI | 717 | GAGCAGAGGAGAGGAGACATTCAGACTATT | 718 |
| 172 | AAYRGDAHVL | 613 | GCTGCGTATAGAGGAGACGCGCATGTTCTT | 719 |
| 173 | SPVRGDHGAL | 720 | TCGCCGGTGAGAGGAGACCATGGGGCTTTG | 721 |
| 174 | DSRRGDYANL | 442 | GATTCGAGGAGAGGAGACTATGCGAATCTG | 722 |
| 175 | LSRRGDYQEL | 723 | TTGAGTCGGAGAGGAGACTATCAGGAGTTG | 724 |
| 176 | SYARGDVHSI | 464 | TCCTACGCAAGAGGAGACGTCCACTCCATC | 725 |
| 177 | DSRRGDASYH | 726 | GACTCACGCAGAGGAGACGCGTCGTACCAC | 727 |
| 178 | NHQRGDLSSS | 728 | AACCACCAAAGAGGAGACCTGAGCTCGAGT | 729 |
| 179 | SSTRGDHLSL | 535 | TCCTCAACGAGAGGAGACCACCTGTCTTTG | 730 |
| 180 | SWNRGDISGL | 731 | TCGTGGAACAGAGGAGACATATCTGGCCTT | 732 |

TABLE 3-continued

| | | SEQ ID | | SEQ ID |
|---|---|---|---|---|
| Rank | N-mer insert | NO: | Encoding sequence | NO: |
| 181 | TGTRGDLGTM | 733 | ACGGGTACTAGAGGAGACCTGGGGACGATG | 734 |
| 182 | QQLRGDTHTL | 735 | CAGCAGCTTAGAGGAGACACGCATACTCTT | 736 |
| 183 | AGLRGDRDSL | 737 | GCGGGGTTGAGAGGAGACCGTGATTCGCTT | 738 |
| 184 | QVYRGDRDQL | 739 | CAGGTTTATAGAGGAGACCGGGATCAGTTG | 740 |
| 185 | AGVRGDRVTI | 741 | GCAGGAGTAAGAGGAGACAGAGTGACCATC | 742 |
| 186 | NSARGDLLHS | 743 | AACTCAGCCAGAGGAGACCTTCTGCACTCC | 744 |
| 187 | NHSRGDLTGV | 745 | AACCACAGTAGAGGAGACCTGACAGGCGTT | 746 |
| 188 | NAYRGDTSAF | 747 | AACGCTTACAGAGGAGACACATCCGCGTTC | 748 |
| 189 | SANRGDIMHT | 749 | TCGGCTAACAGAGGAGACATAATGCACACG | 750 |
| 190 | QSARGDLVSY | 751 | CAATCCGCCAGAGGAGACCTCGTCAGTTAC | 752 |
| 191 | DSRRGDASYH | 726 | GATAGTAGGAGAGGAGACGCTAGTTATCAT | 753 |
| 192 | SFVRGDVRTL | 754 | TCGTTTGTGAGAGGAGACGTTCGTACGCTG | 755 |
| 193 | SDMRGDRSVY | 756 | AGCGACATGAGAGGAGACCGATCTGTGTAC | 757 |
| 194 | SGIRGDRYPI | 758 | TCCGGAATCAGAGGAGACCGCTACCCAATA | 759 |
| 195 | SNVRGDMAHS | 760 | TCCAACGTCAGAGGAGACATGGCTCACAGC | 761 |
| 196 | TEVRGDRSQV | 523 | ACTGAGGTTAGAGGAGACCGTTCGCAGGTT | 762 |
| 197 | ASSRGDLQQT | 763 | GCGAGCAGCAGAGGAGACCTGCAACAAACG | 764 |
| 198 | QSARGDLVSY | 751 | CAGTCTGCTAGAGGAGACCTTGTGTCTTAT | 765 |
| 199 | DASRGDRTSL | 521 | GACGCATCTAGAGGAGACCGAACATCCCTC | 766 |
| 200 | NSVRGDLNQT | 767 | AACAGTGTCAGAGGAGACCTCAACCAAACT | 768 |

Example 6—Directed Evolution of Engineered AAV Capsids and Muscle Capsid Variants Recombinant adeno-associated viruses (rAAVs) are the most commonly used vehicles for in vivo gene replacement therapy and gene editing in preclinical and clinical studies, yet selective transduction of specific tissues after systemic delivery remains a challenge. Recombinant AAVs generated using naturally occurring capsids are predominantly seques- tered in the liver after systemic injection. This sequestration limits the efficiency of transduction in other organs (Gao et al., 2006; Murrey et al., 2014; Zincarelli et al., 2008) and poses a particular challenge for gene delivery to skeletal muscle. Because muscle comprises up to 40% of total body mass, achieving therapeutic thresholds in muscle with natu- ral capsid variants requires extremely high virus doses (about 2E+14 vg/kg) (Duan, 2018a, b), which creates a formidable hurdle for vector manufacturing and can result in therapy-limiting toxicity, as observed in some recent clinical trials (Morales et al., 2020).

AAV capsid protein engineering coupled with in vivo selection is a promising approach to enable potent gene delivery to a variety of tissues. AAV capsids are assembled from 5 VP1, 5 VP2, and 50 VP3 subunits that unite to form a complex 3D structure that defines tissue tropism after systemic delivery. Even a single amino acid change in the VP3 subunits located on the capsid surface can alter tropism for different tissues (Pulicherla et al., 2011; Wu et al., 2006). Therefore, AAV capsid engineering strategies typically involve generating diverse capsid libraries, by various meth- ods, followed by selection of variants with desired tropism in animal models. This approach has generated optimized vectors for delivery to a number of tissues, including mouse retina (Dalkara et al., 2013) and central and peripheral nervous systems (Chan et al., 2017; Deverman et al., 2016).

Figure 21A:
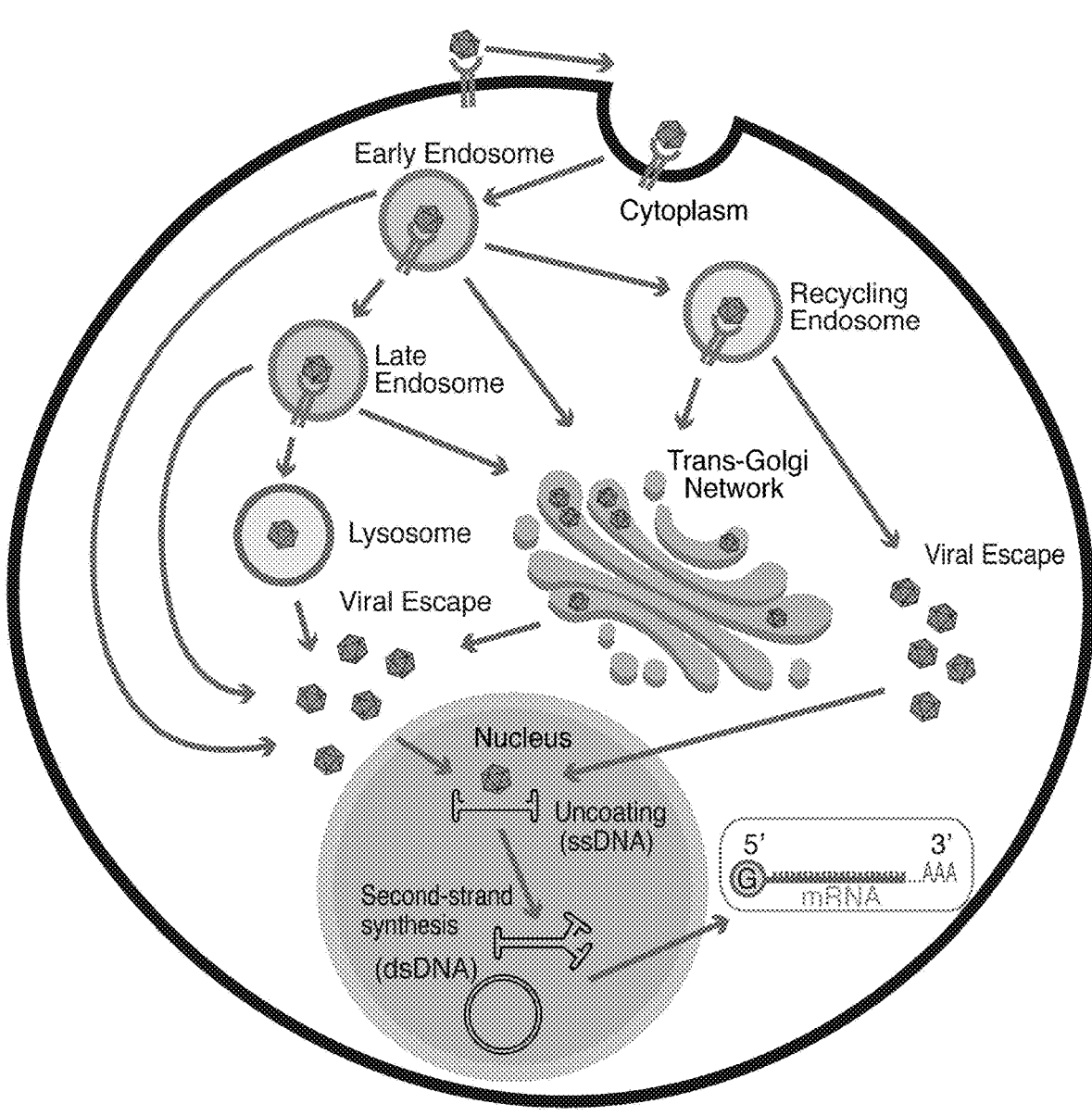
FIGS. 21A-21I—DELIVER allows selection of capsid variants capable of functional transduction in various tissues.
Figure 21B:
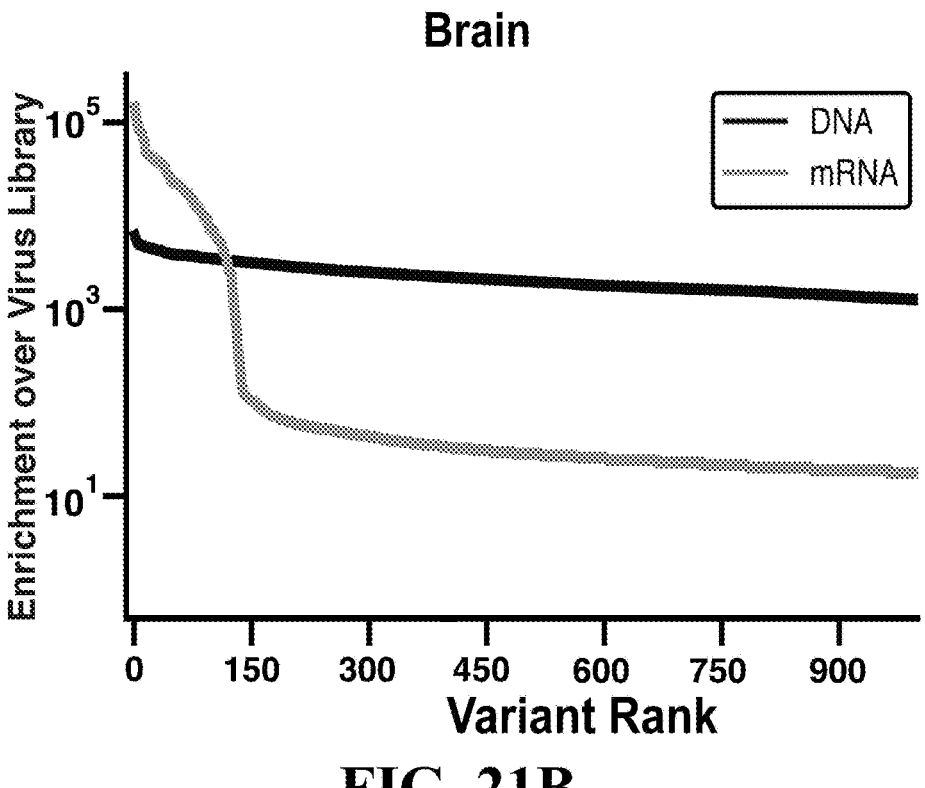
Figure 21C:
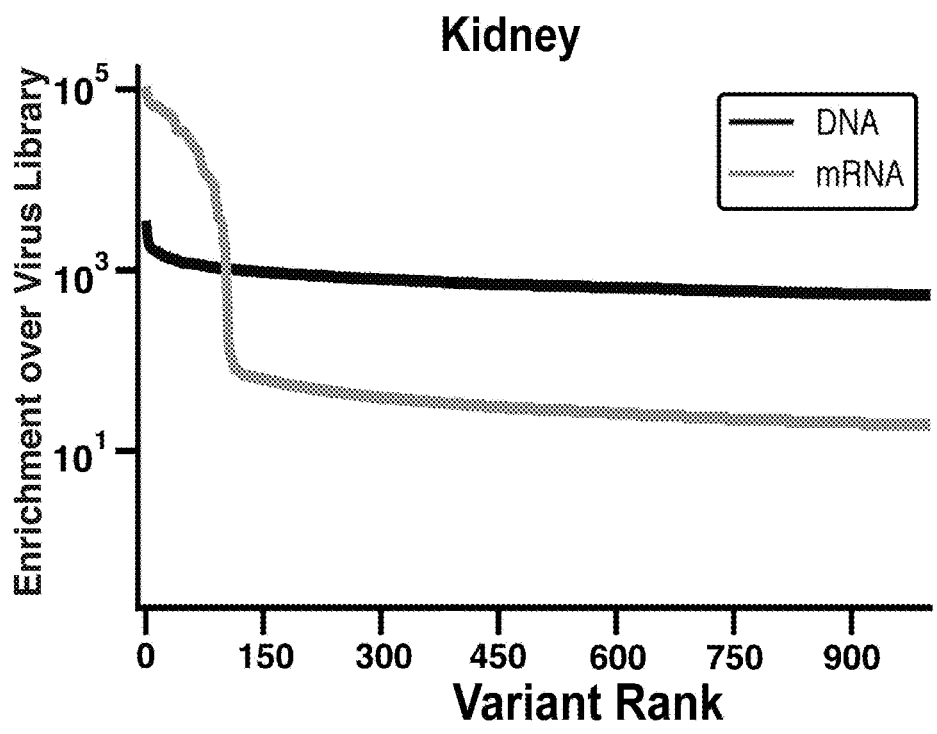

Nevertheless, current capsid engineering approaches have key limitations in terms of their selection methods, the animal models they can use, and the diversity of the libraries they can screen. AAV transduction is a multi-step process including binding to receptors on the cell surface, intracel- lular trafficking, endosomal escape, nuclear entry, vector genome second strand DNA synthesis, and transgene expression ((Berry and Asokan, 2016; Ding et al., 2005), FIG. 21A), and inefficiency in any of these steps can limit vector potency. Therefore, successful identification of potent capsids requires selecting variants that proceed effectively through all stages of transduction. Species- and strain- specific differences in the coding sequence and expression of genes involved in AAV transduction presents yet another challenge, as capsid variants selected in specific mouse strains may not yield potent transduction in other strains or other species (Hordeaux et al., 2018). Thus, an engineering approach that enables selection of potent capsid variants across different strains and species is highly desirable.

This Example describes DELIVER (Directed Evolution of AAV capsids Leveraging In Vivo Expression of transgene RNA) strategy to address these challenges. DELIVER combines diverse capsid library generation with stringent transcript-based in vivo selection and enables directed evolution followed by identification of potent capsid variants in any tissue of interest and any animal model. Here, DELIVER's utility for developing muscle-tropic capsids in mice is demonstrated and the results are compared throughout to AAV9, a naturally occurring AAV capsid currently used clinically in gene replacement trials for Duchenne Muscular Dystrophy (DMD) (clinical trials.gov identifiers: NCT03362502 and NCT03368742). Overall, the muscle-directed vectors demonstrate superior potency and selectivity for transduction of both skeletal muscle and cardiac tissue, providing therapeutic efficacy at substantially reduced dosage when compared to AAV9, and with conserved infectivity for both mouse and human muscle cells. Cross-comparison of muscle-enriched variant capsid sequences furthermore identified a common RGD motif among the top variants, and additional analyses uncovered a strong interaction with, and dependence on, target cell expression of RGD-binding integrin heterodimers. Taken together, this Example demonstrates, among other things, new class of capsid variants with particular utility for therapeutics development and testing in striated muscle, as well as an experimental framework for future evolution of additional families of AAVs with alternative tissue tropism.

Results

Figure 14A:
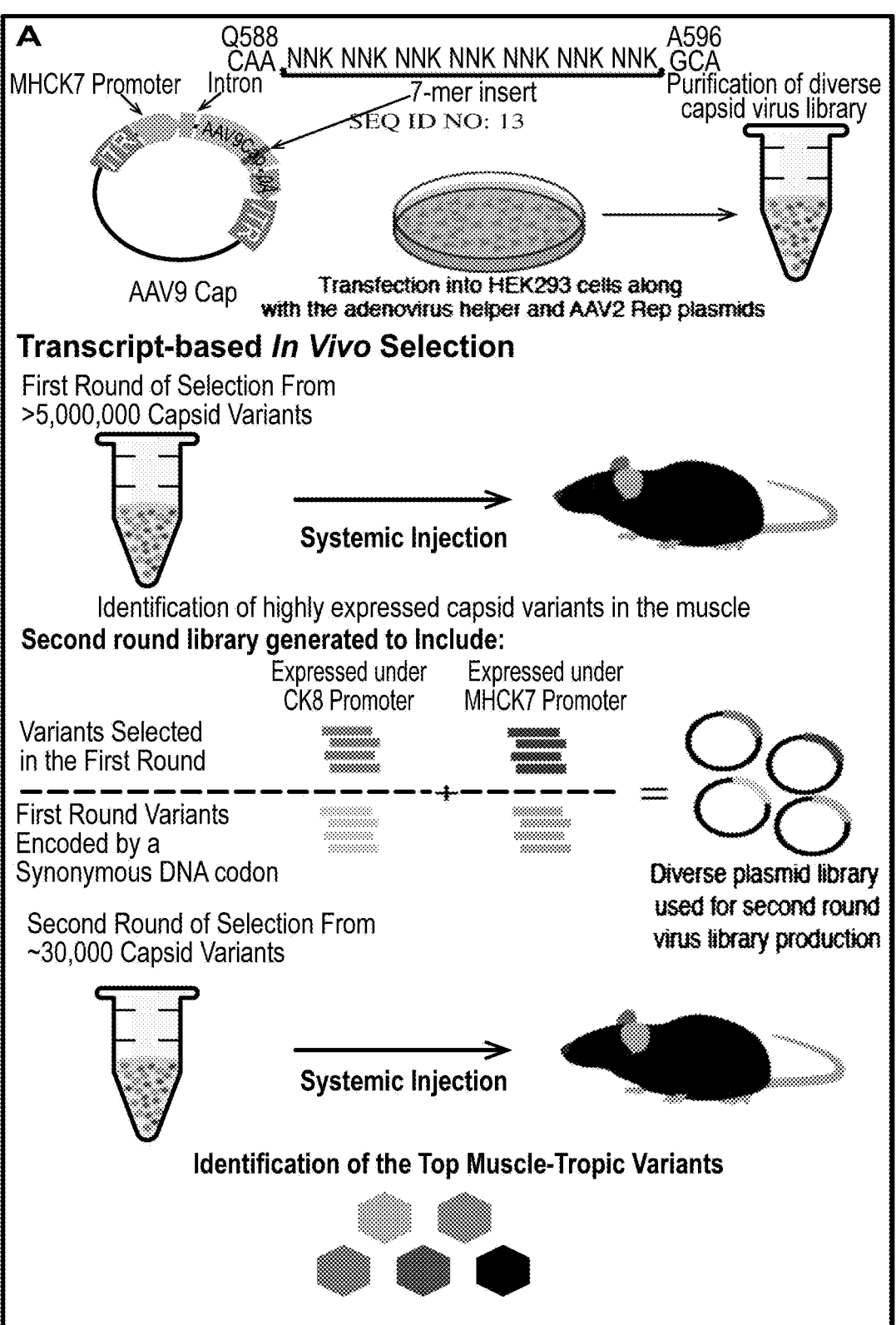

In Vivo Evolution of AAV9 Capsid Using DELIVER Identifies a Class of Muscle-Tropic Variants Library design is an important determinant of success for any screening campaign. The AAV9-based capsid libraries designed for this study included several key features to facilitate identification of muscle-directed vectors with high potency for in vivo use. First, each variant included a random 7-mer peptide inserted between amino acids 588 and 589 in the hypervariable region VIII of the AAV9 capsid, a design that ensures exposure of the variable peptide sequence on the capsid surface ((DiMattia et al., 2012), FIG. 14A). Each variant also encapsulated a transgene encoding its own capsid sequence under the control of either a ubiquitous or a cell type-specific mammalian promoter, which allowed for expression of the transgene (capsid variant) in both the HEK293 cells used for virus library production (FIG. 14B) and the animal tissues transduced with the virus after in vivo delivery (FIGS. 14C-14D).

Figures 21D, 21E, 21F, 21G, 21H, 21I:
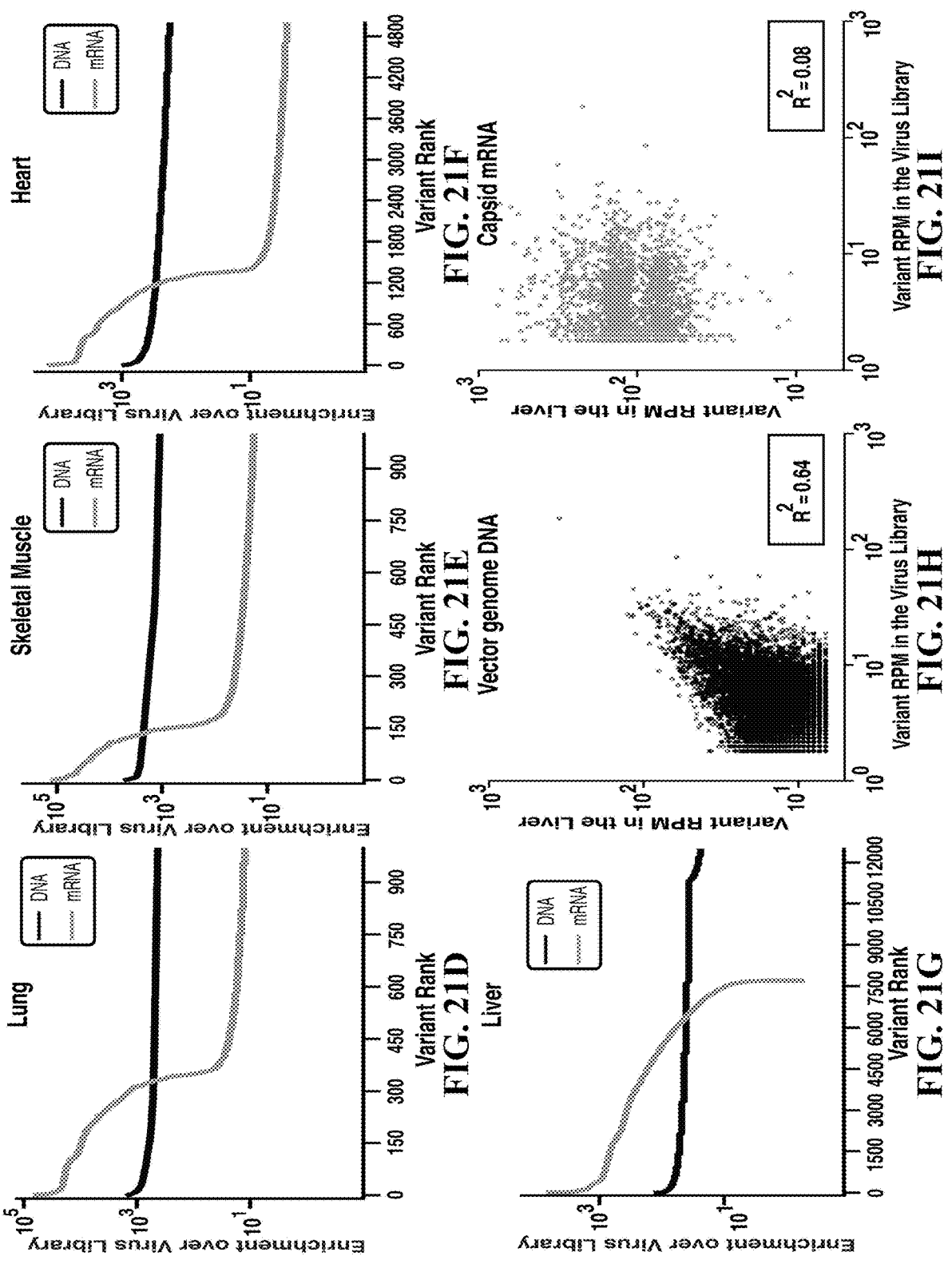

DELIVER's stringency for selecting capsid variants that functionally transduce discrete mouse tissues were evaluated in C57BL/6J mice, using a virus library in which capsid variants were expressed under the ubiquitous CMV promoter. Variants were identified that were enriched relative to the virus library at the DNA and mRNA levels in various tissues. Selection of variants based on mRNA expression yielded a select few functional capsids compared to selection based on the presence of vector genome DNA (FIGS. 21B-21G), suggesting that only a small fraction of capsid variants that physically enter target cells can functionally transduce these cells to express their encoded transgene. In line with this finding, while capsid variants with higher abundance in the injected virus library were more highly present in the liver of injected animals at the vector genome DNA level, there was almost no correlation between abundance of each variant in the virus library and the level of transgene mRNA from the same variant in the liver (FIGS. 21H-21I).

The feasibility of using muscle-specific promoters to enhance selection for potent muscle-tropic capsid variants was next evaluated. Skeletal and cardiac muscle contain several different cell types, but AAV capsids capable of effective transgene delivery to two cell types in particular—muscle fibers and cardiomyocytes—are most desired for therapeutic gene delivery for genetic myopathies. To enable selection of variants specifically expressed in these cell types in vivo, we generated AAV capsid libraries in HEK293 cells using ITR-containing constructs in which expression of capsid coding sequences was controlled by the muscle-specific CK8 or MHCK7 promoters. These constructs produced similar titers of rAAV as those produced using a construct expressing the capsid under the ubiquitous CMV promoter (FIG. 14B). Furthermore, within the skeletal and cardiac muscles of injected mice, virus libraries expressed under CK8 or MHCK7 promoters yielded even higher transgene mRNA expression compared to those expressed under CMV, greatly facilitating identification of functional variants that transduce muscle fibers and cardiomyocytes (FIGS. 14C-14D).

Two rounds of in vivo selection with directed evolution were performed and variants expressed from the MHCK7 promoter in multiple different muscles of C57BL/6J mice were screened. The process started with a diverse library of more than 5,000,000 capsid variants and the top 30,000 variants that were highly expressed in seven muscles (Quadriceps, Tibialis Anterior, Gastrocnemius, Triceps, Abdominal, Diaphragm, and Heart) were selected (FIGS. 14A and 14E). For the second round of in vivo selection, two controls were incorporated. The first was a synonymous codon control in which the same 7-mer inserted peptides identified for each selected variant from the primary screen were encoded using synonymous DNA codons. The second was an expression control in which duplicate virus libraries were generated to express the variants under either of two skeletal muscle specific promoters, CK8 or MHCK7 (FIG. 14A). FIG. 14F shows the sequence of the 7-mer insertion in the top highly expressed capsid variants in mouse muscles after the second round of transcript-based selection. Variants with the same color in each group are encoded by synonymous DNA codons.

Strikingly, in the second round of selection, all 12 of the top capsid variants highly expressed in muscles from either the CK8 or MHCK7 libraries contained the same arginine-glycine-aspartic acid (RGD) motif in the first 3 amino acid positions of the 7-mer insert. Further implicating the specific peptide sequences included in these capsid variants in their superior transduction of muscle, 10 of the top 12 hits in the CK8 group and 8 of the top 12 hits in the MHCK7 group were from synonymous pairs (i.e., the corresponding variant encoded by synonymous DNA codons was also within the top 12 muscle-expressed variants) (FIG. 14F).

Figures 22A, 22B, 22C:
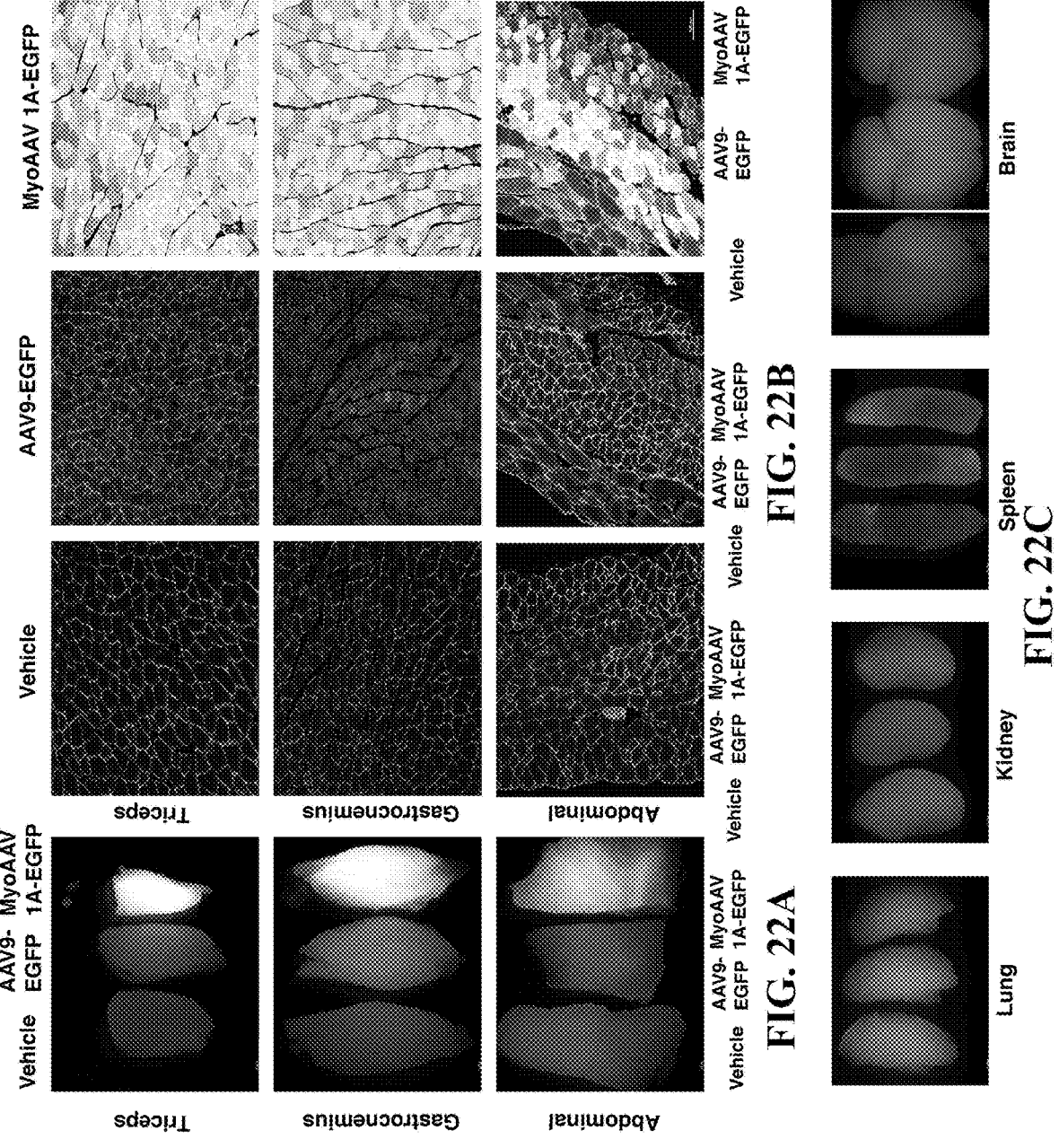
FIGS. 22A-22K—MyoAAV produces recombinant AAV with similar titers compared to AAV9 and transduces muscle stem cells more effectively than AAV8 and AAV9 after systemic delivery to adult mdx-Ai9 mice.
Figure 22D:
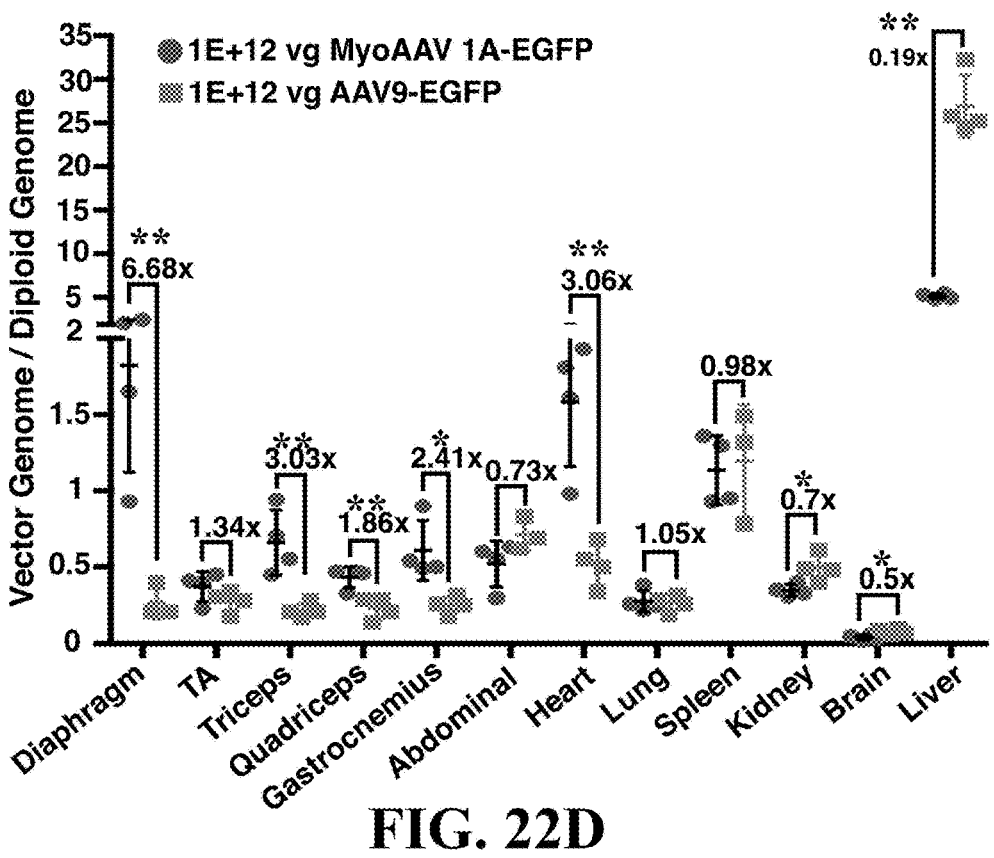
Figure 22E:
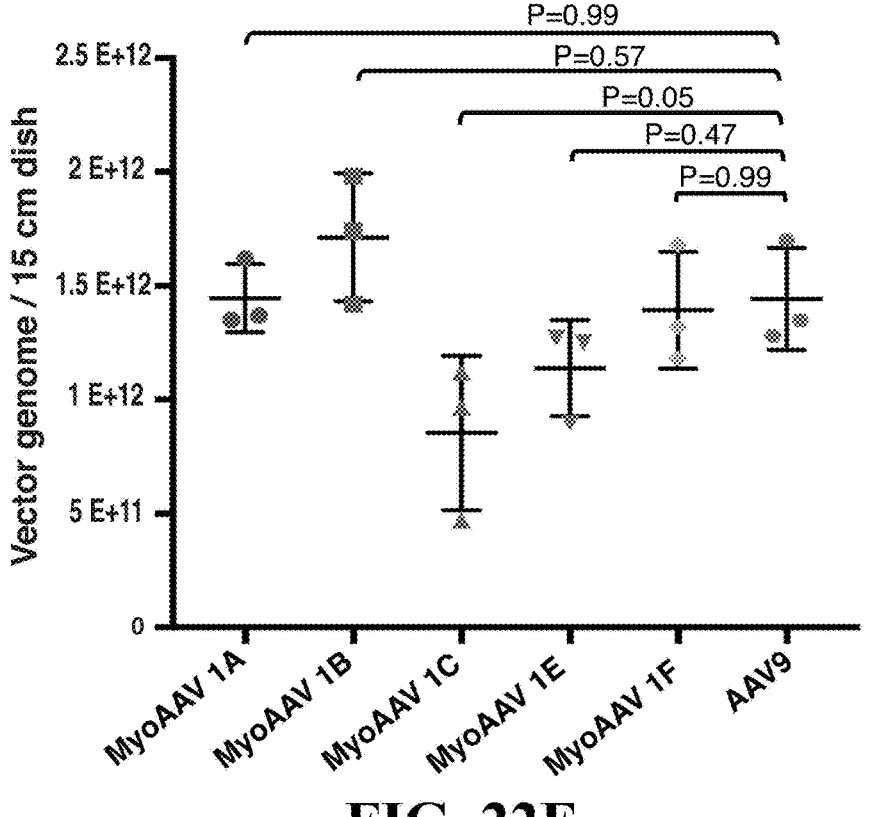

Titers of rAAVs produced using the top 5 unique RGD-containing capsid variants were quantified to assess the feasibility of using these engineered capsids for in vivo studies. Comparison of rAAV titers showed no significant difference between the top 5 RGD-containing capsid variants and the parental AAV9 capsid (FIG. 22E). The variant containing the RGDLTTP peptide insertion was selected, which also matches the consensus amino acids at each position from the top 12 RGD-containing hits, for further characterization and named this variant "MyoAAV".

Figures 15A, 15B:
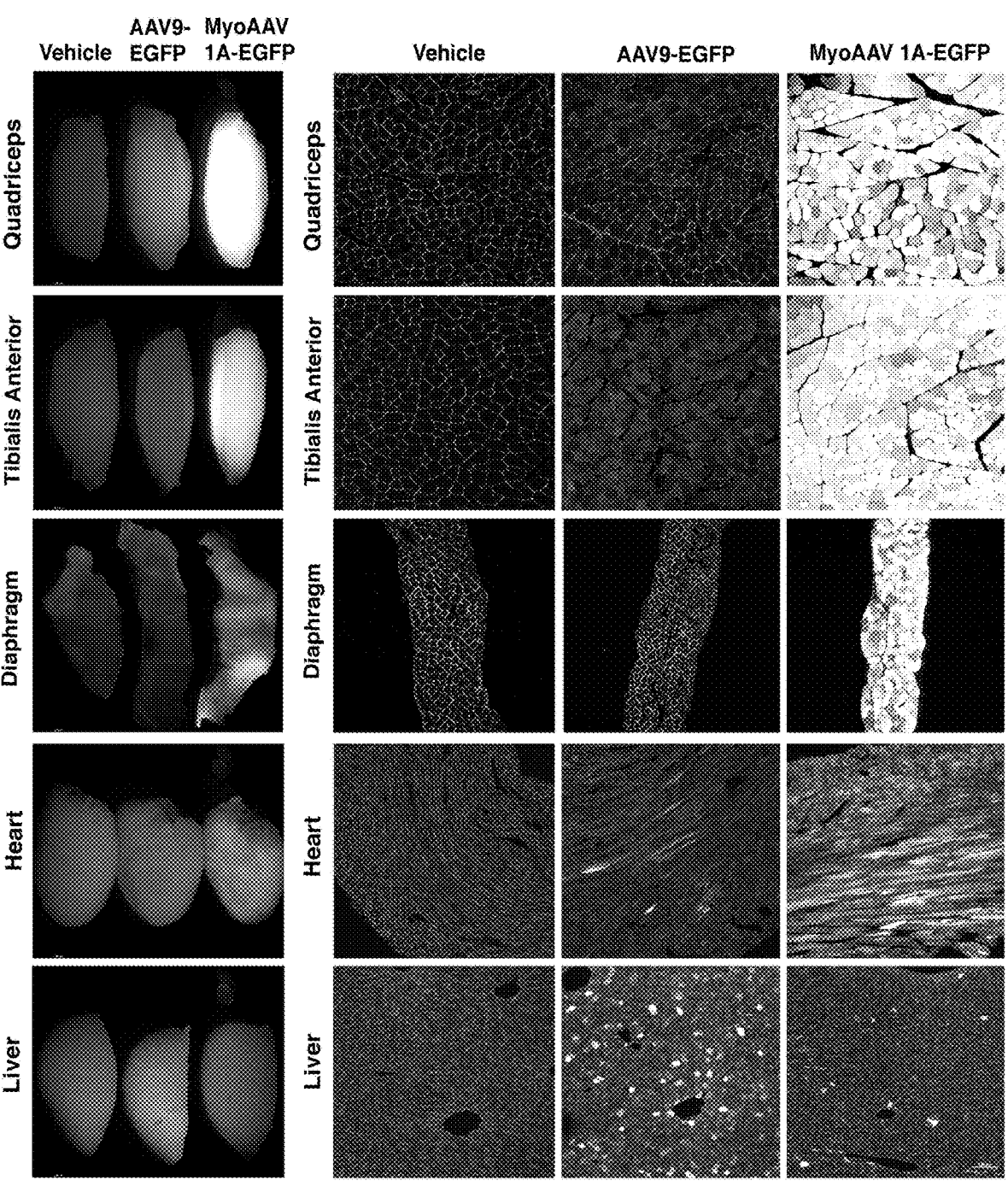
FIGS. 15A-15D—MyoAAV transduces mouse skeletal muscles with high efficiency after systemic injection.

MyoAAV Transduces Mouse Muscles with Unprecedented Efficiency after Systemic Administration To investigate the transduction profile and biodistribution of the rAAVs generated using MyoAAV in different mouse tissues after systemic delivery, adult C57BL/6J mice were injected with 1E+12 vg (~4E+13 vg/kg) AAV9- or Myo-AAV-CMV-EGFP and analyzed transgene expression and vector genome abundance in different tissues two weeks after injection. Whole mount fluorescent imaging of the harvested tissues revealed far greater fluorescence intensity in muscles of mice injected with MyoAAV as compared to AAV9-injected mice (FIGS. 15A and 22A). Importantly, MyoAAV transduced the heart, a key affected organ in many genetic myopathies, more effectively than AAV9. Strong transgene expression in muscle fibers and cardiomyocytes of MyoAAV injected mice was further confirmed by immuno-fluorescence analysis (FIGS. 15B and 22B). Remarkably, MyoAAV showed relatively diminished transduction of liver after systemic delivery in C57BL/6J mice, suggesting a liver-detargeted transduction profile for this variant compared to AAV9 (FIGS. 15A-15C).

Figures 15C, 15D:
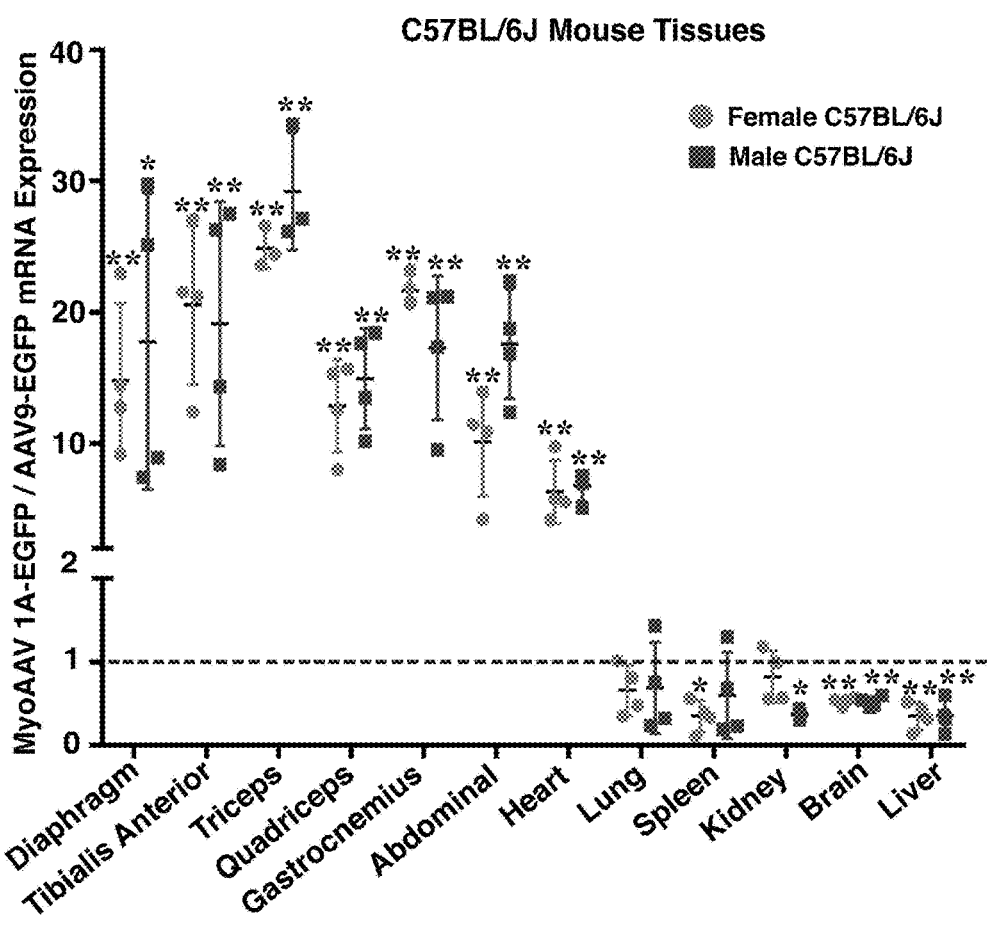

Quantification of EGFP mRNA in different skeletal muscles revealed 10 to 25 times higher transgene expression in muscles of MyoAAV-compared to AAV9-injected mice (FIG. 15C). EGFP mRNA expression was 6.3 times higher in the heart and 2.8 times lower in the liver of MyoAAV injected animals (FIG. 15C). Notably, improved transduction efficiency by MyoAAV was restricted to striated muscle tissues, and this engineered capsid variant transduced the lung, kidney, spleen, and brain of injected animals with similar or lower efficiency compared to AAV9 (FIGS. 15C and 22C). Biodistribution analysis demonstrated that Myo-AAV delivered vector genomes to all muscles of C57BL/6J mice more effectively than AAV9, with the exception of abdominal muscles, and resulted in a significantly lower number of vector genomes in the liver after systemic administration (FIG. 22D).

MyoAAV's efficiency in transducing human skeletal muscle was next analyzed. Human primary myotubes from 4 different donors (2 males and 2 females) were transduced in vitro with AAV9- or MyoAAV-CK8-Nanoluciferase (Nluc). MyoAAV transduced myotubes from different donors 35 to 52 times more effectively than AAV9 (FIG. 15D). MyoAAV also transduced mouse primary myotubes from C57BL/6J mice with 23 times higher efficiency compared to AAV9 (FIG. 15D).

Additionally, the efficiency of muscle stem cell (satellite cell) transduction by MyoAAV was evaluated after intravenous administration in 6 month old mdx-Ai9 mice. These dystrophin-deficient mice are a genetic model for human DMD, and additionally carry a Cre-activatable tdTomato transgene, which serves as a reporter for transduction by Cre-encoding AAVs. Fluorescence activated cell sorting (FACS) of satellite cells from the muscle of mice injected with AAV8-, AAV9- or MyoAAV-CMV-Cre showed transduction of a significantly greater percentage of satellite cells in animals receiving MyoAAV (FIG. 22F-22I).

Figure 16A:
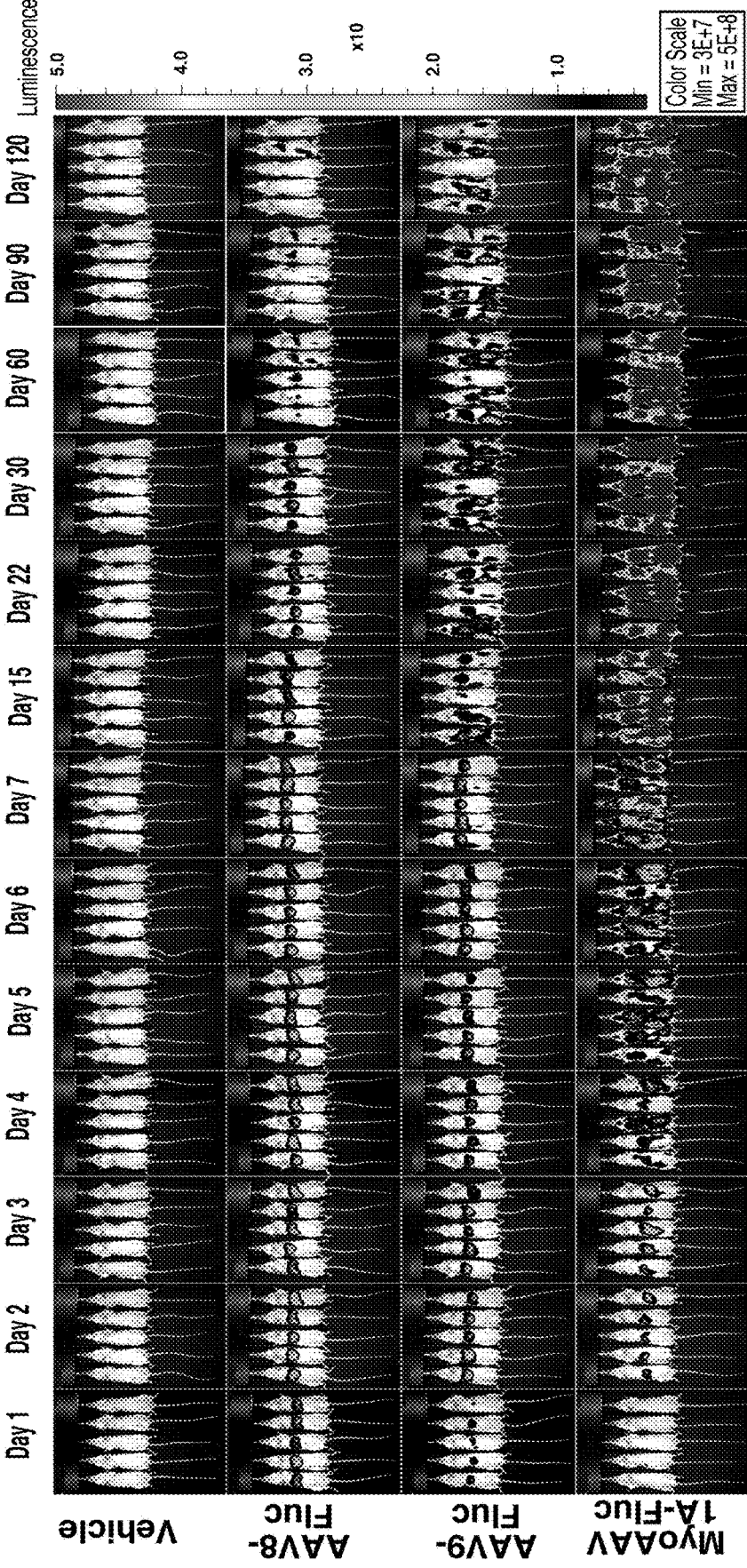
FIGS. 16A-16D—Systemic injection of MyoAAV results in fast and sustained high levels of reporter transgene expression in muscles throughout the body.
Figure 16B:
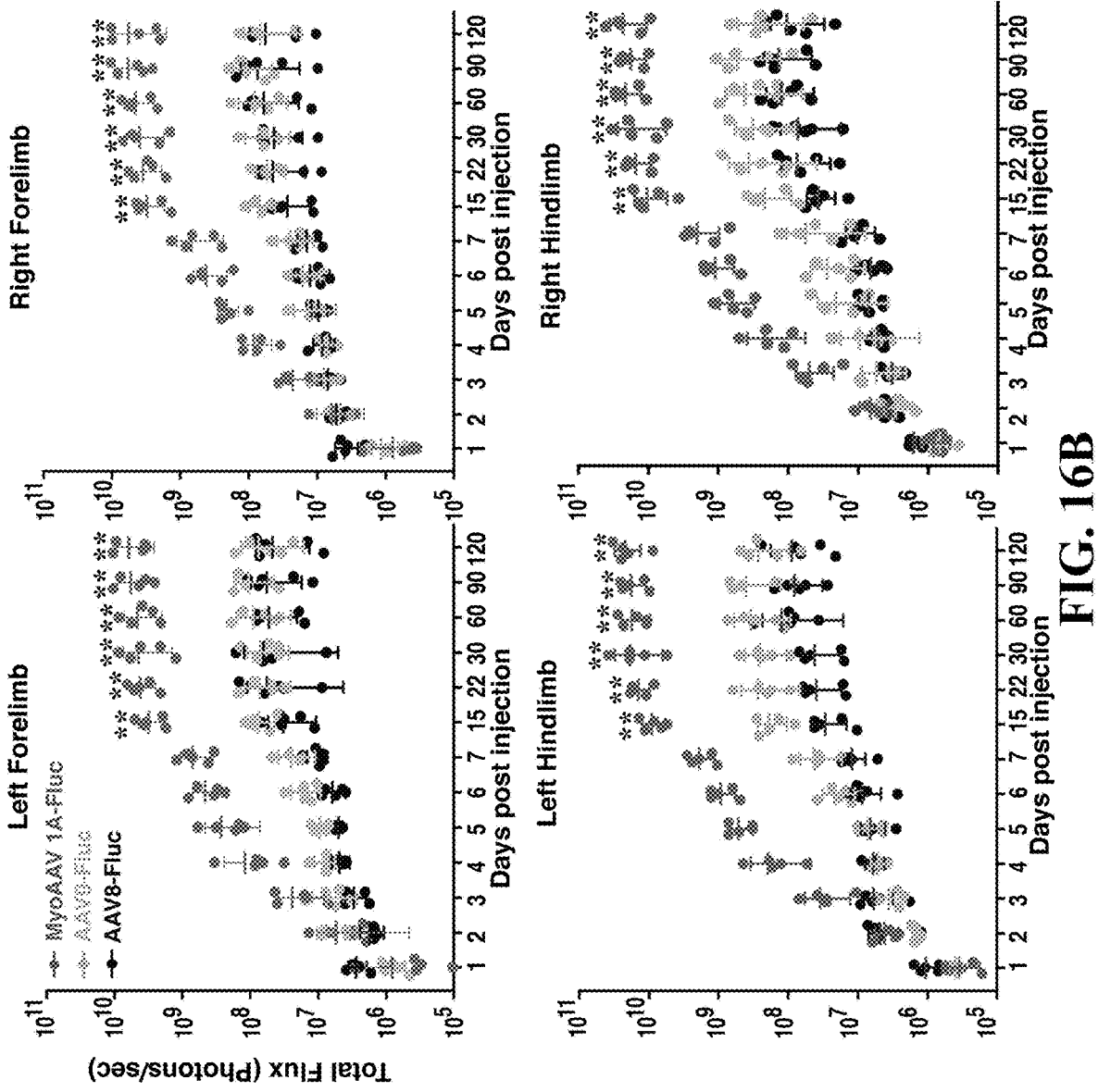
Figure 16C:
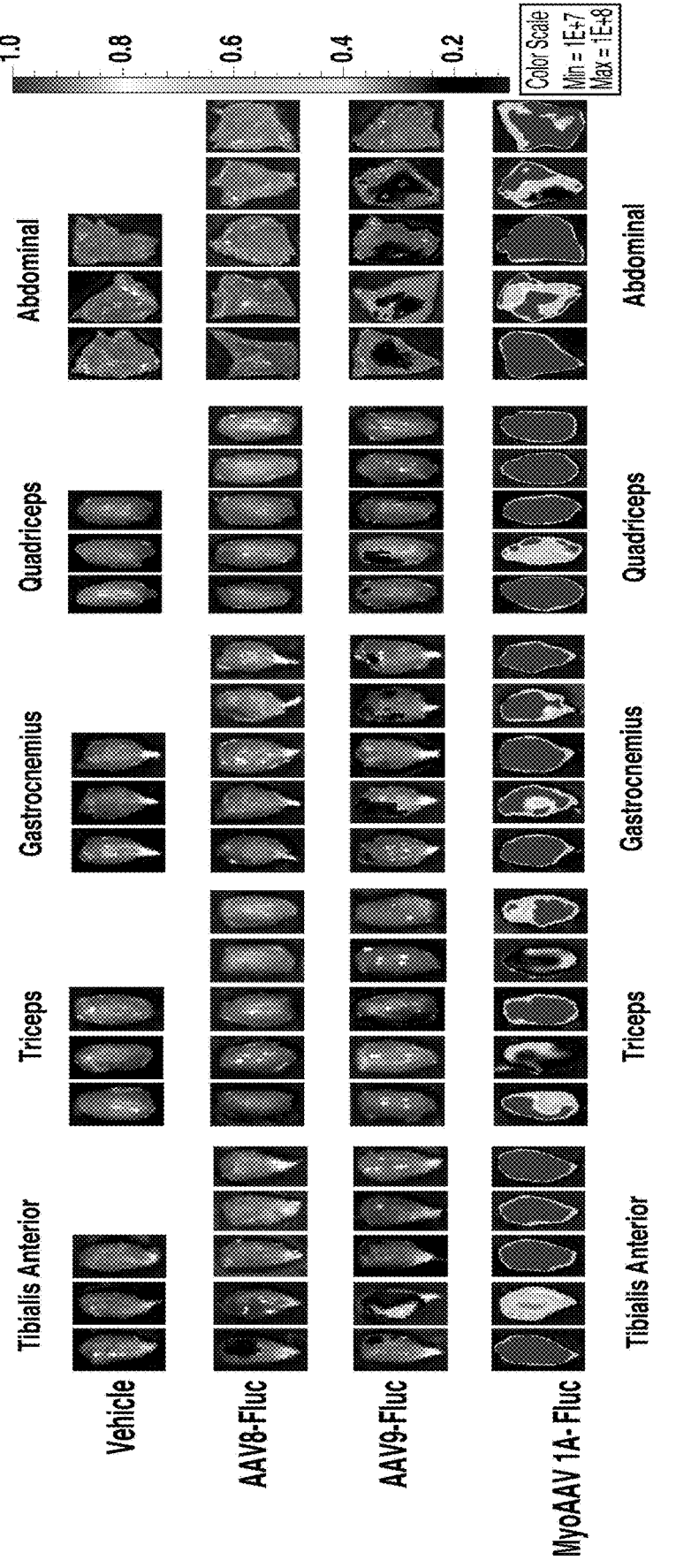
Figure 16D:
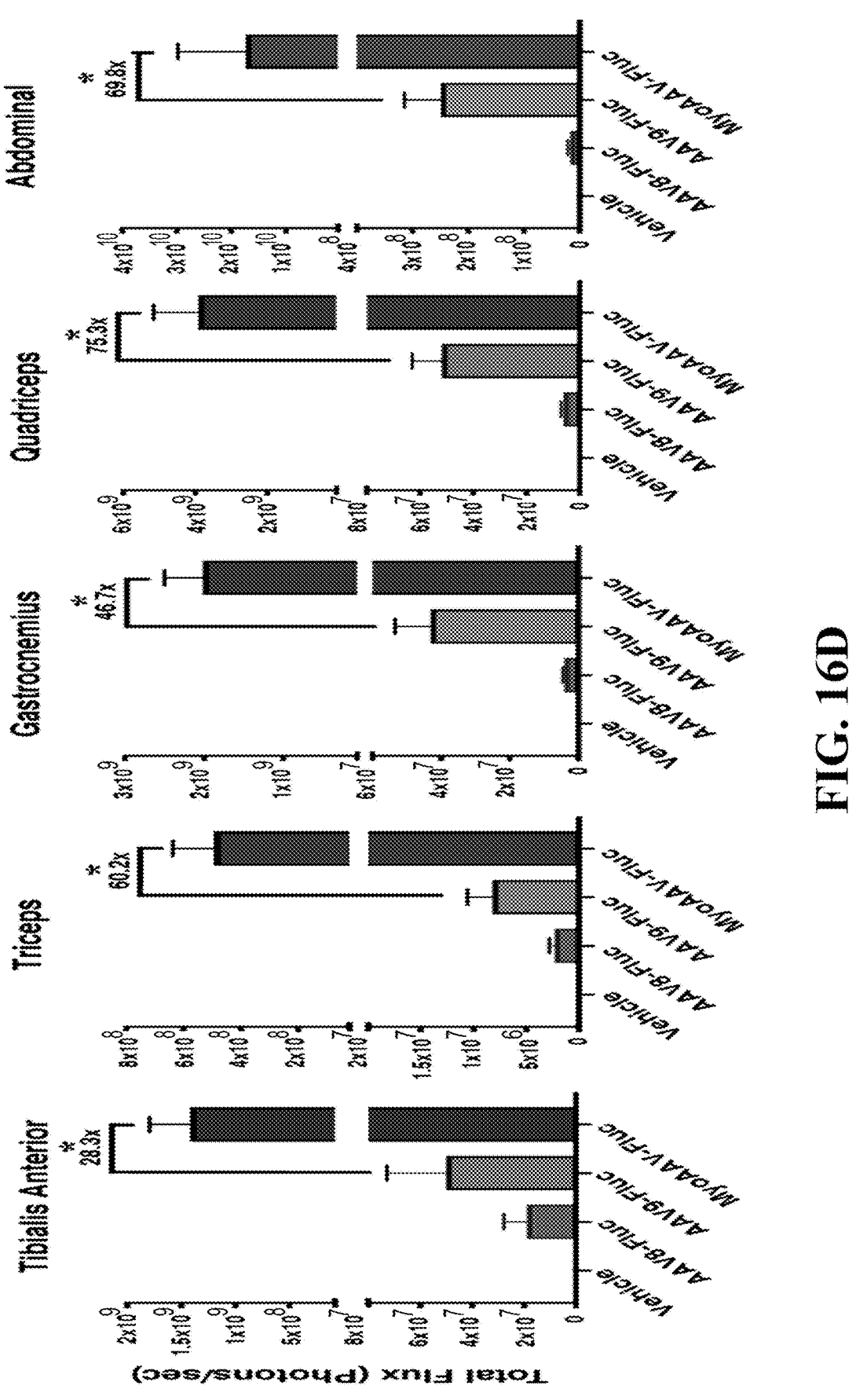
Figure 23A:
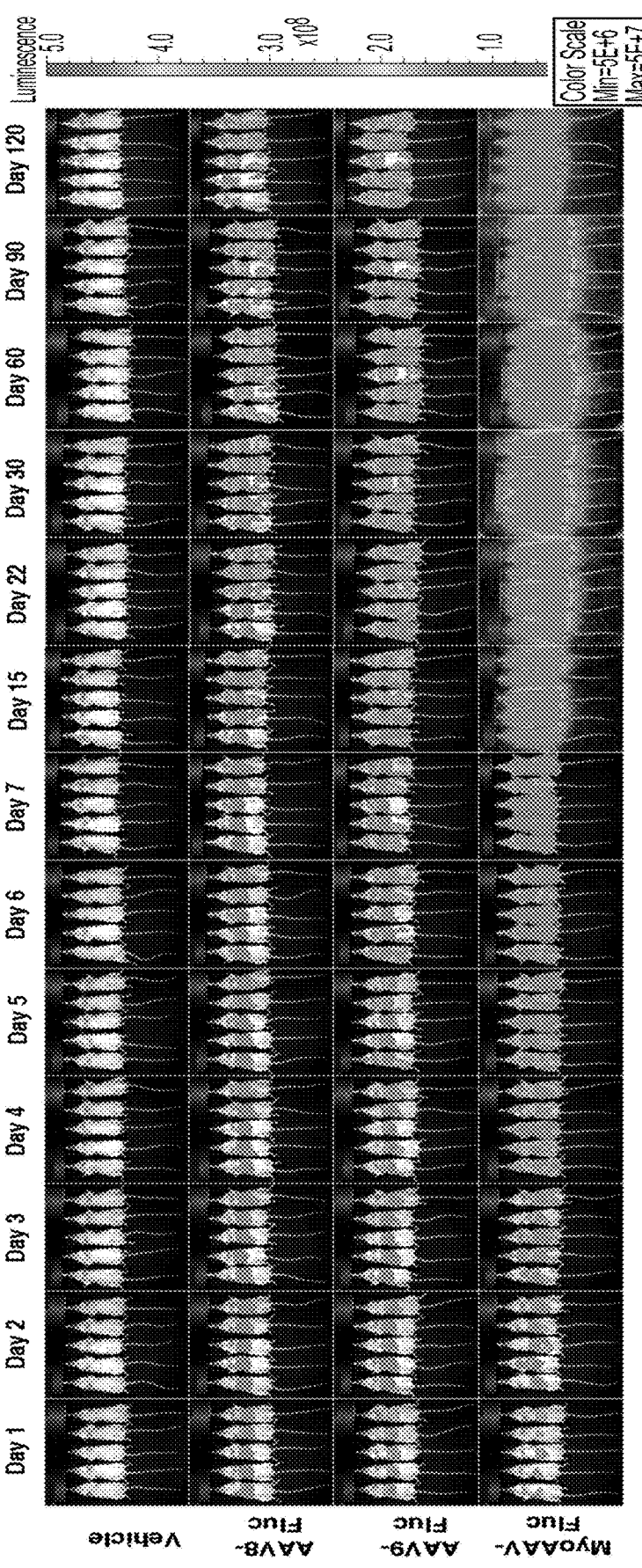
FIGS. 23A-23B—Systemic administration of MyoAAV results in long term high levels of transgene expression in BALB/cJ mouse muscles.
Figure 23B:
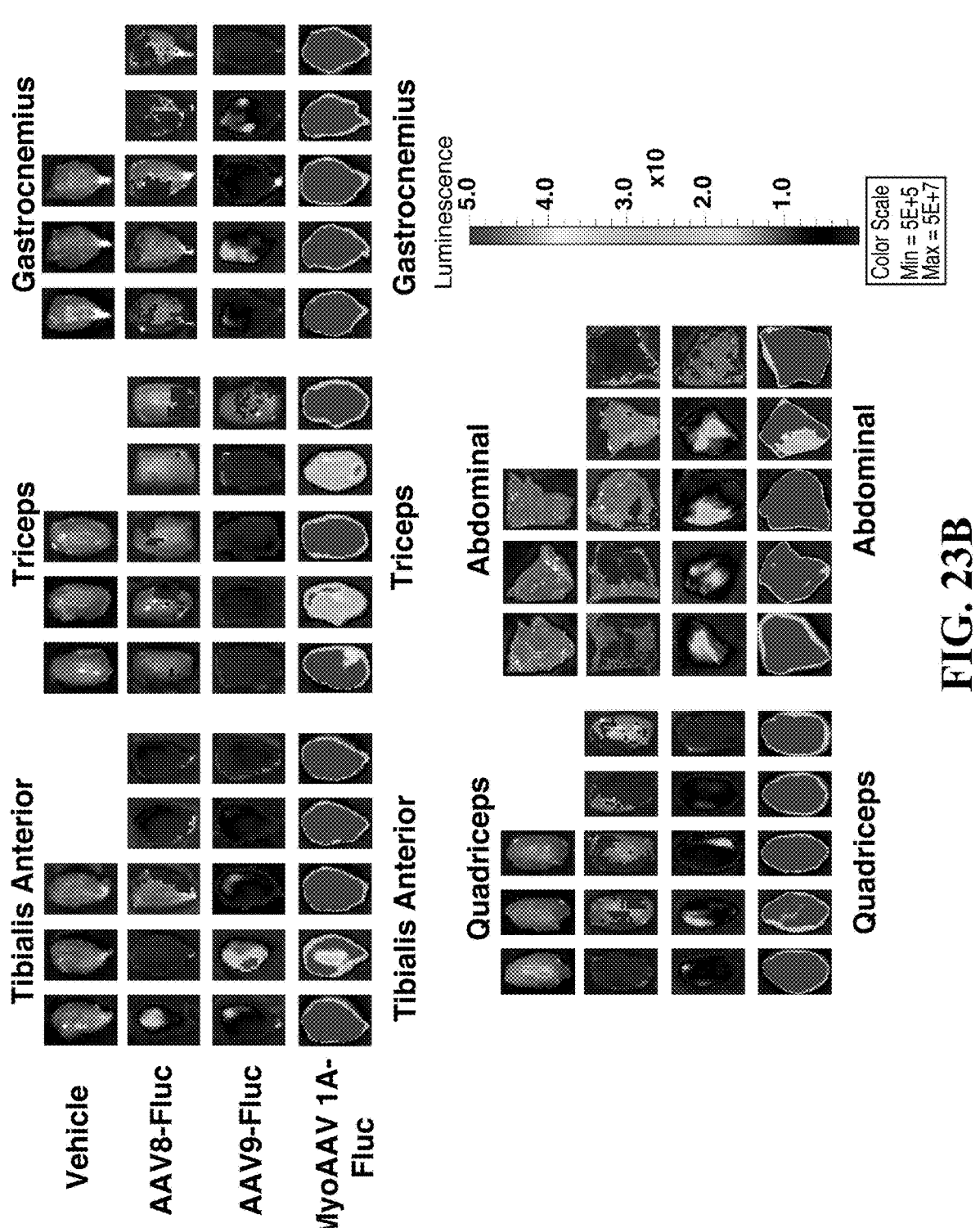

To investigate the kinetics of in vivo gene expression after systemic delivery of MyoAAV, we injected adult BALB/cJ mice with 4E+11 vg (~1.6E+13 vg/kg) AAV8-, AAV9-, or MyoAAV-CMV-Firefly luciferase (Fluc) and performed whole body bioluminescence imaging at different time points over 120 days after injection. Mice receiving Myo-AAV showed faster kinetics and significantly higher overall levels of transgene expression in their limbs and throughout their bodies compared to mice injected with AAV8 or AAV9 (FIGS. 16A-16B and 23A). Whole organ bioluminescence imaging from muscles of mice harvested four months after injection confirmed dramatically higher luciferase expression in the muscles of MyoAAV injected animals (FIGS. 16C-16D and 23B). These data, obtained in Balb/cJ as opposed to C57BL/6J, additionally demonstrate that potent muscle transduction by MyoAAV after systemic delivery is conserved across different mouse strains.

Figures 24A, 24B:
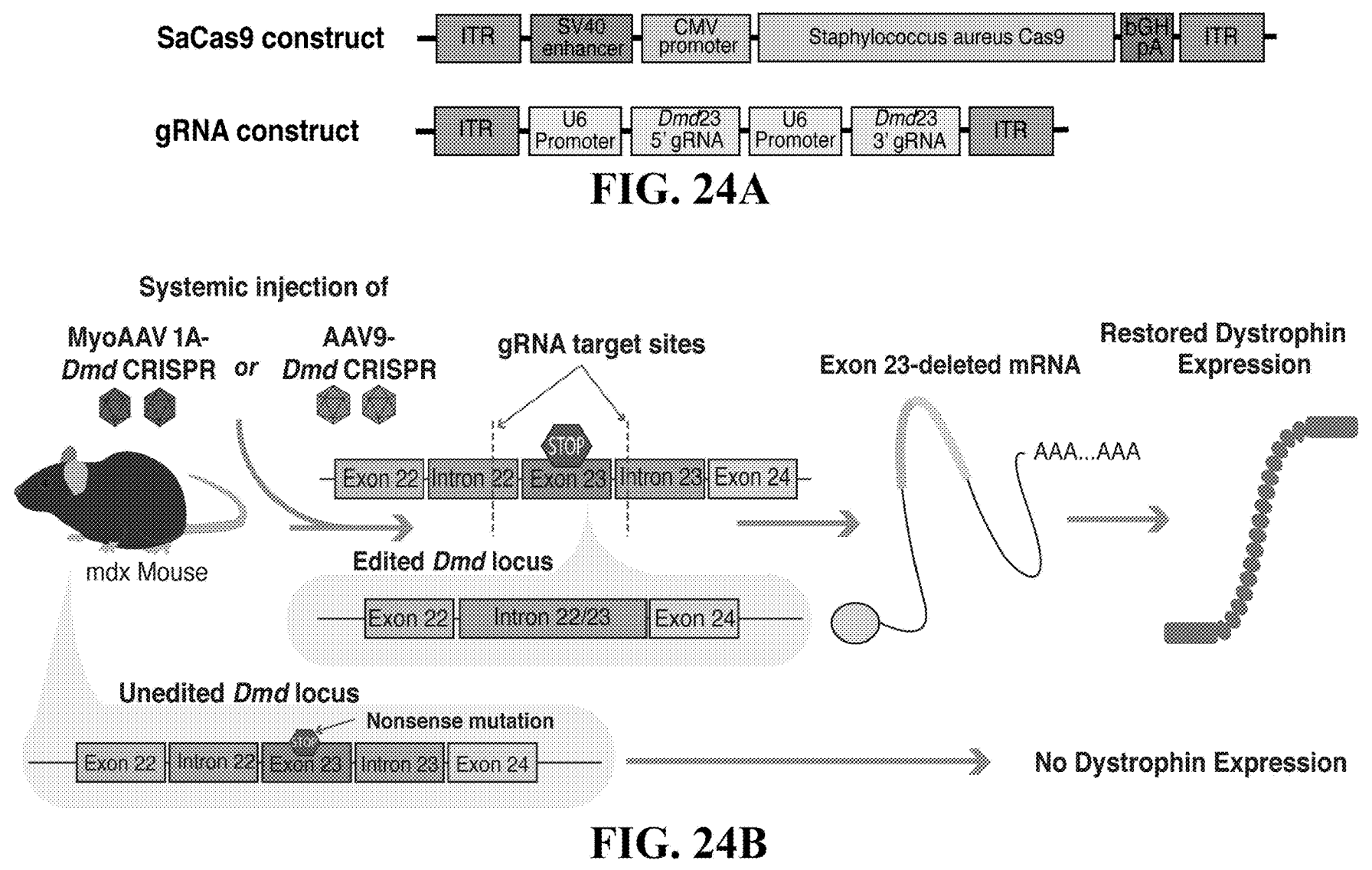

Systemic Administration of Therapeutic Transgenes using-MYoAAV Leads to Functional Improvement in Mouse Models of DMD and XLMTM To investigate the feasibility of using MyoAAV for in vivo delivery of therapeutic transgenes, adult mdx mice (a mouse model of DMD carrying a nonsense mutation in Dmd exon 23) were injected with AAV9 or MyoAAV carrying constructs encoding SaCas9 together with guide RNAs (gRNAs) targeting 5' and 3' of the mdx mutation (FIGS. 24A-24B). It has been previously shown that this CRISPR-Cas9-mediated approach results in excision of exon 23 from the genome of mdx cells and expression of a truncated but still functional version of dystrophin protein in muscle (Nelson et al., 2016; Tabebordbar et al., 2016). While producing a truncated variant, this in-frame deletion still makes a functional protein, thereby providing therapeutic benefit in DMD.

Figure 17A:
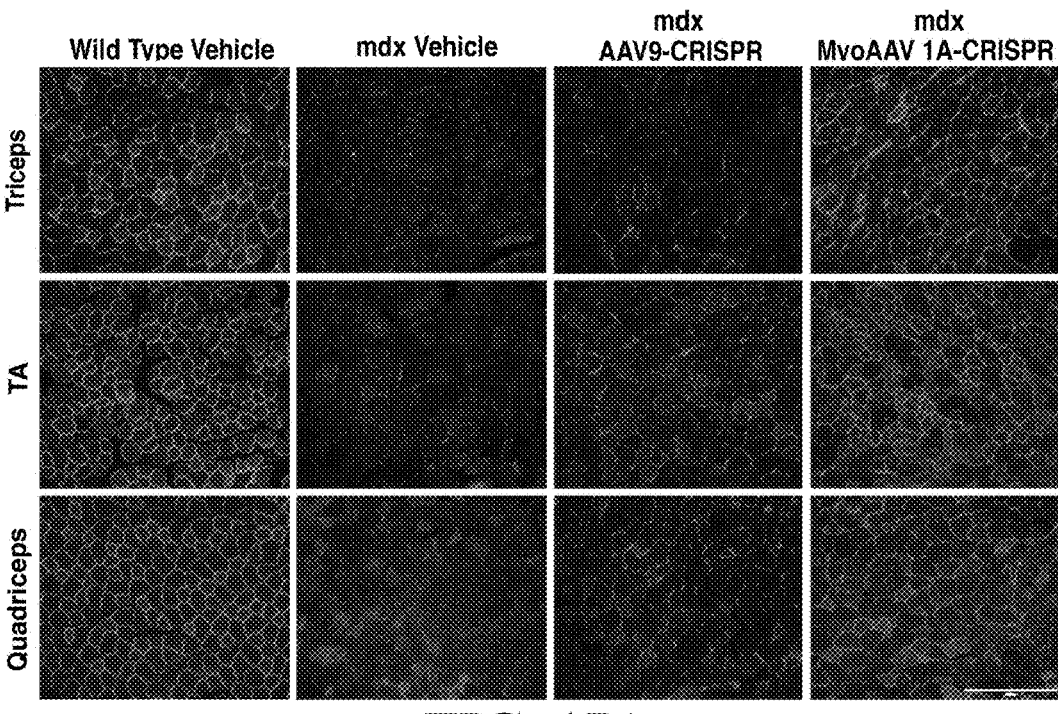
FIGS. 17A-17O—Systemic administration of MyoAAV-Dmd CRISPR and MyoAAV-human MTM1 results in therapeutic benefit in mouse models of DMD and XLMTM, respectively.
Figure 17B:
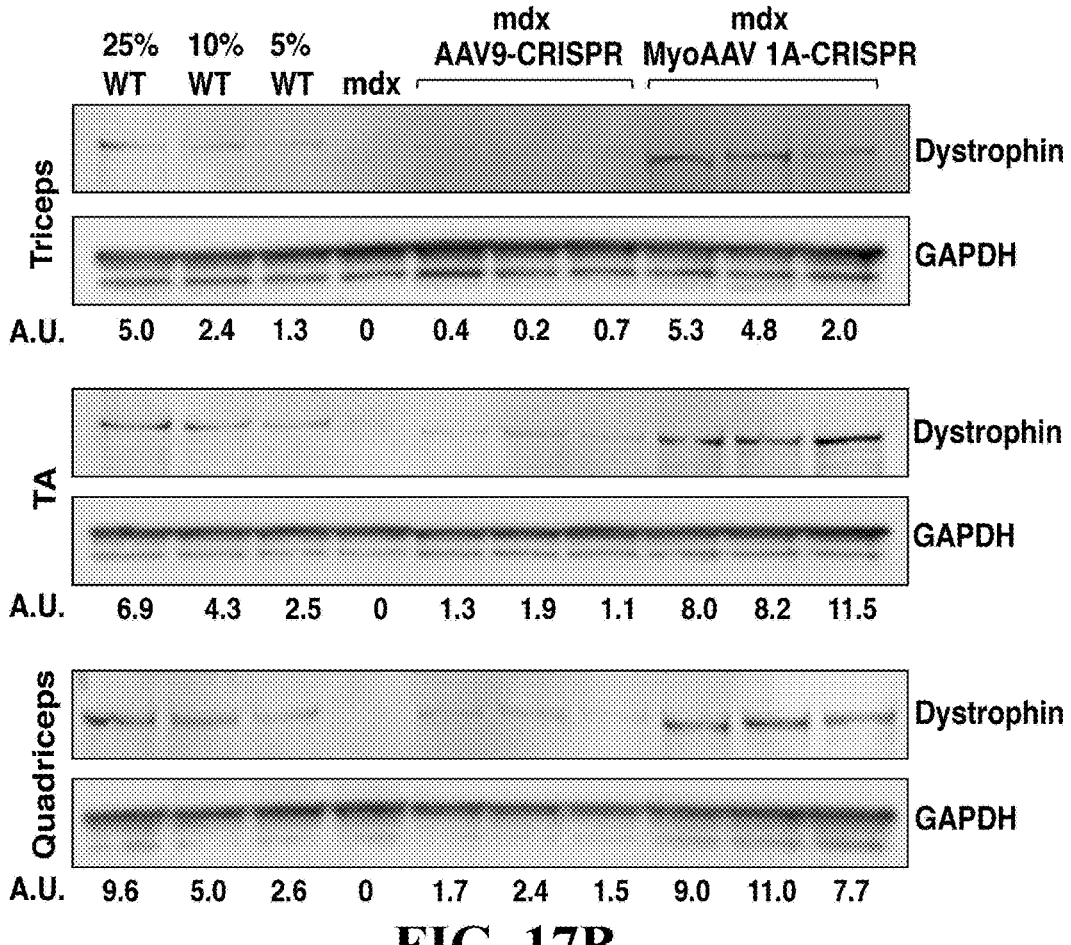
FIG. 17B) Western blots detecting dystrophin and GAPDH in muscles of mice injected with AAV9- or MyoAAV 1A-Dmd CRISPR, with relative signal intensity determined by densitometry at the bottom. A.U.: arbitrary unit, normalized to GAPDH.
Figures 17C, 17D, 17E:
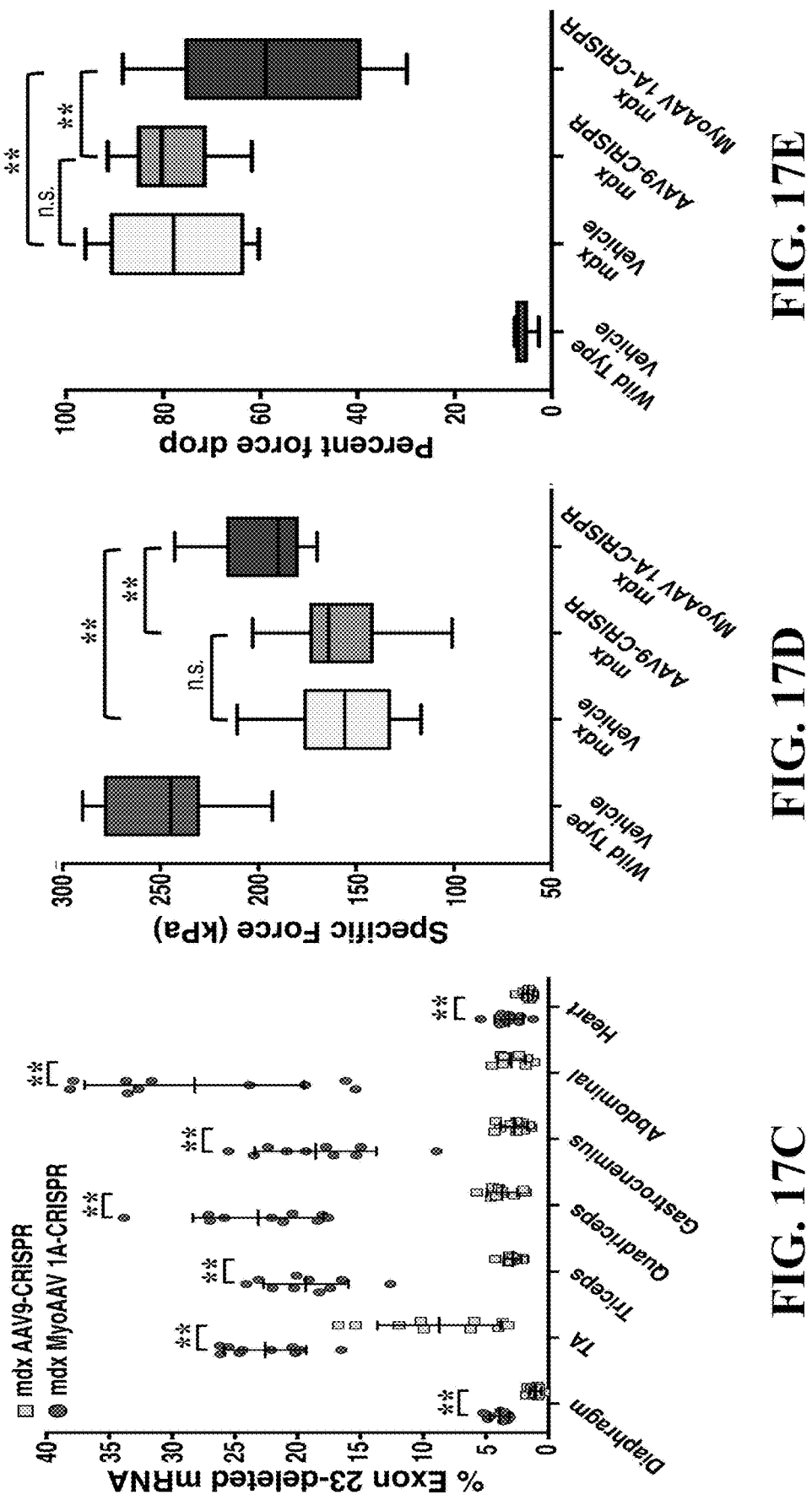
FIG. 17C) Taqman-based quantification of exon 23-deleted mRNA in different muscles of adult mdx mice injected with AAV9- or MyoAAV 1A-Dmd CRISPR. Data are presented as mean±SD (n=9-10); : P<0.01 (Student t test).
FIGS. 17D-17E) Tibialis anterior muscle specific force (FIG. 17D) and decrease in force after 6 eccentric contractions (FIG. 17E) for wild-type C57BL/6J mice injected with vehicle (n=11), and mdx muscle injected with vehicle (n=15), AAV9-Dmd CRISPR (n=15), or MyoAAV 1A-Dmd CRISPR (n=17). : P<0.01 (ANOVA with Tukey's MCT). F) Schematic of the experiment to investigate the efficacy of 2E+12 vg/kg of AAV9- or MyoAAV 1A-MHCK7-human MTM1 (hMTM1) systemically delivered to 4 weeks old Mtm1 knockout (KO) mice.
Figures 24C, 24D, 24E:
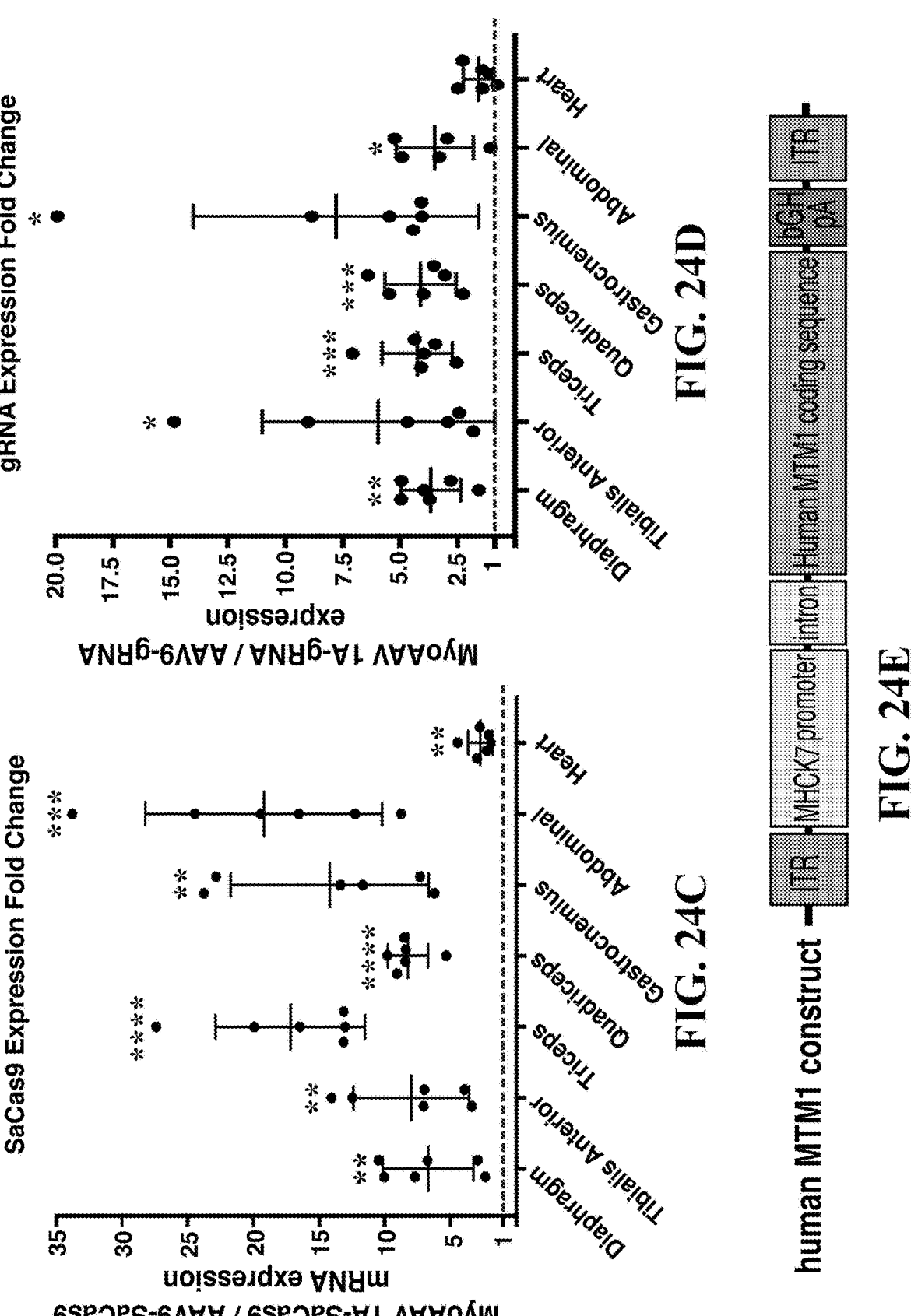

MyoAAV-Dmd CRISPR resulted in production of exon 23-deleted Dmd mRNA with efficiencies ranging from 3.4% to 25% of total Dmd mRNA in different mdx muscles. In contrast, the efficiency of production of exon 23-deleted mRNA in muscles of mdx mice injected with the same dose of AAV9-Dmd CRISPR ranged from only 1.3% to 8.7% (FIG. 17C). Quantification of SaCas9 and gRNA expression indicated 6.7 to 19 times higher SaCas9 expression and 3.5 to 7.8 times higher gRNA expression in the muscles of MyoAAV injected mice compared to AAV9 injected animals (FIGS. 24C-24D).

Several findings point to the superior rescue of dystrophin expression with MyoAAV-Dmd CRISPR compared to AAV9-Dmd CRISPR. Immunofluorescence and western blot analysis confirmed greater and more widespread dystrophin restoration in muscles of mice injected with Myo-AAV-Dmd CRISPR as compared to AAV9-Dmd CRISPR (FIGS. 17A-17B). Physiological assessment of the Tibialis Anterior (TA) muscles of AAV-CRISPR treated animals demonstrated significantly higher specific force (FIG. 17D) and decreased percent force drop after eccentric contraction (FIG. 17E) in MyoAAV-Dmd CRISPR injected mdx mice when compared to either vehicle or AAV9-Dmd CRISPR injected controls. Thus, MyoAAV exhibits markedly enhanced potency for delivery of therapeutic gene editing complexes to muscle compared to conventional and widely utilized AAV9.

Figure 17F:
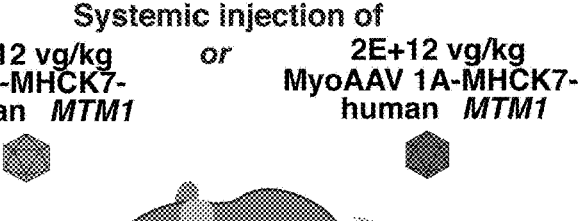
FIG. 17G) Total body weight of Mtm1 KO mice injected with vehicle or 2E+12 vg/kg of AAV9- or MyoAAV 1A-MHCK7-hMTM1, and wild type littermate controls injected with vehicle. Data are presented as mean±SD (n=6 for KO AAV9, n=6 for KO MyoAAV 1A, n=3 for wild type vehicle, n=3 for KO vehicle). P-value calculated between MyoAAV 1A and AAV9 groups; : P<0.01 (Multiple t tests with Holm-Sidak MCT).
FIG. 17H) Pictures of Mtm1 KO mice injected with 2E+12 vg/kg of either MyoAAV 1A-hMTM1 or AAV9-hMTM1 16 weeks after injection of the virus.
FIG. 17K) Survival curve for Mtm1 KO animals injected with vehicle, AAV9-hMTM1, or MyoAAV-hMTM1, as well as wild type littermates injected with vehicle. Data points for the Mtm1 KO mice injected with vehicle are from a previous experiment.
FIG. 17. I) Mean hourly passive activity assessed by in-cage running wheel rotation from wild type mice injected with vehicle, or Mtm1 KO mice injected with vehicle, AAV9-hMTM1, or MyoAAV 1A-hMTM1, both at 2E+12 vg/kg. Data are presented as mean±SD (n=6 for KO AAV9, n=6 for KO MyoAAV 1A, n=3 for wild type vehicle, n=3 for KO vehicle) for weekly measurements averaged across three-week time periods. P-value calculated between MyoAAV 1A and AAV9 groups; : P<0.01 (Multiple t tests with Holm-Sidak MCT).
FIG. 17J) Number of rearing events over 5 minutes in an activity monitor by wild type mice injected with vehicle, or Mtm1 KO mice injected with AAV9-hMTM1, or MyoAAV-hMTM1, both at 2E+12 vg/kg. Data are presented as mean±SEM (n=5 for KO AAV9, n=6 for KO MyoAAV, n=3 for wild type vehicle) for weekly measurements averaged across three-week time periods. P-value calculated between MyoAAV and AAV9 groups; *: P<0.05, : P<0.01 (two-stage Benjamini, Krieger, & Yekutieli test).
FIG. 17L) Quantification of fold difference in hMTM1 mRNA expression in gastrocnemius, quadriceps, heart, and liver of Mtm1 KO mice injected with AAV9- or MyoAAV 1A-hMTM1 analyzed 4 weeks after injection. Dashed red line indicates relative expression from AAV9-hMTM1. Data are presented as mean±SD (n=4); *: P<0.05, : P<0.01 (Student t test between AAV9 and MyoAAV 1A injected groups for each tissue).
FIG. 17N) Western blots detecting hMTM1 and GAPDH in muscles of Mtm1 KO mice injected with vehicle, AAV9- or MyoAAV 1A-hMTM1, with relative signal intensity determined by densitometry at the bottom. A.U.: arbitrary unit, normalized to GAPDH.
Figure 17G:
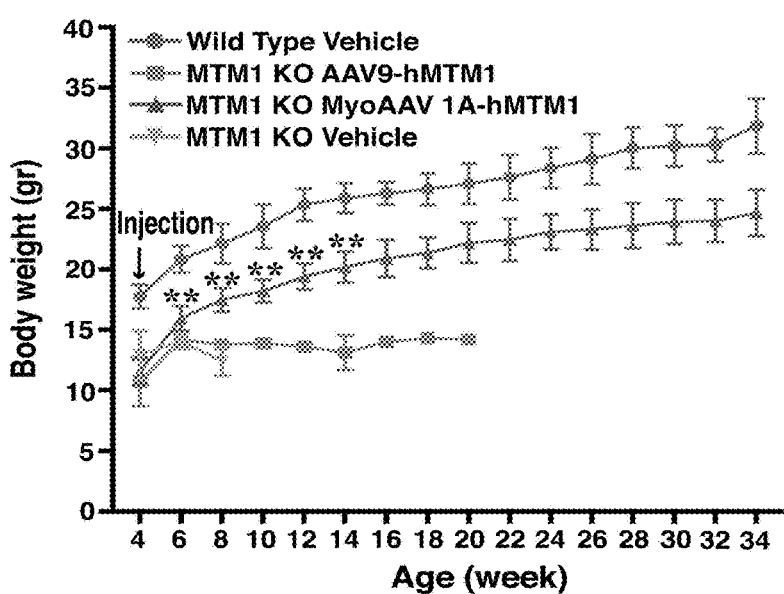
Figure 17H:
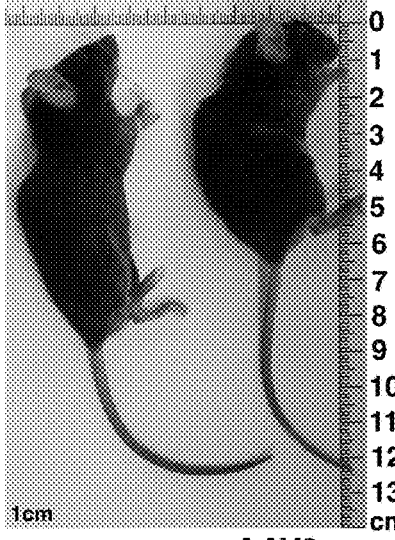

MyoAAV's performance for gene replacement after low-dose systemic administration was assessed in a mouse model of X-linked myotubular myopathy (XLMTM). Mtm1 knockout (KO) mice provide an excellent genetic and phenotypic model of XLMTM; they show marked muscle wasting, loss of mobility and dramatically shortened lifespans. 4 week old Mtm1 KO mice were injected with 2E+12 vg/kg of AAV9 or MyoAAV encoding the human MTM1 (hMTM1) expressed under the control of the MHCK7 promoter (MHCK7-hMTM1). We measured body weight, activity, and survival for each group for over a 7 month period (FIGS. 17F and 24E). The dose of virus that was used in this experiment was 50-150 times lower than the dose being used in an ongoing human clinical trial for XLMTM (clinical trials.gov identifier: NCT03199469) and 15-250 times lower than the doses used in previously published preclinical studies for XLMTM gene therapy (Childers et al., 2014; Elverman et al., 2017; Mack et al., 2017).

MyoAAV-MHCK7-hMTM1 injected mice manifested striking improvements in function and survival. All of the mice injected with 2E+12 vg/kg of AAV9-MHCK7-hMTM1 were minimally active and reached the humane endpoint for euthanasia between 11-21 weeks after the injection. In contrast, all of the mice injected with the same dose of MyoAAV-MHCK7-hMTM1 survived with a similar trajectory to wildtype mice, and also gained weight and were noticeably more active compared to the AAV9-injected mice throughout the study (FIGS. 17G-17K).

Figures 18A, 18B, 18C, 18D, 18E:
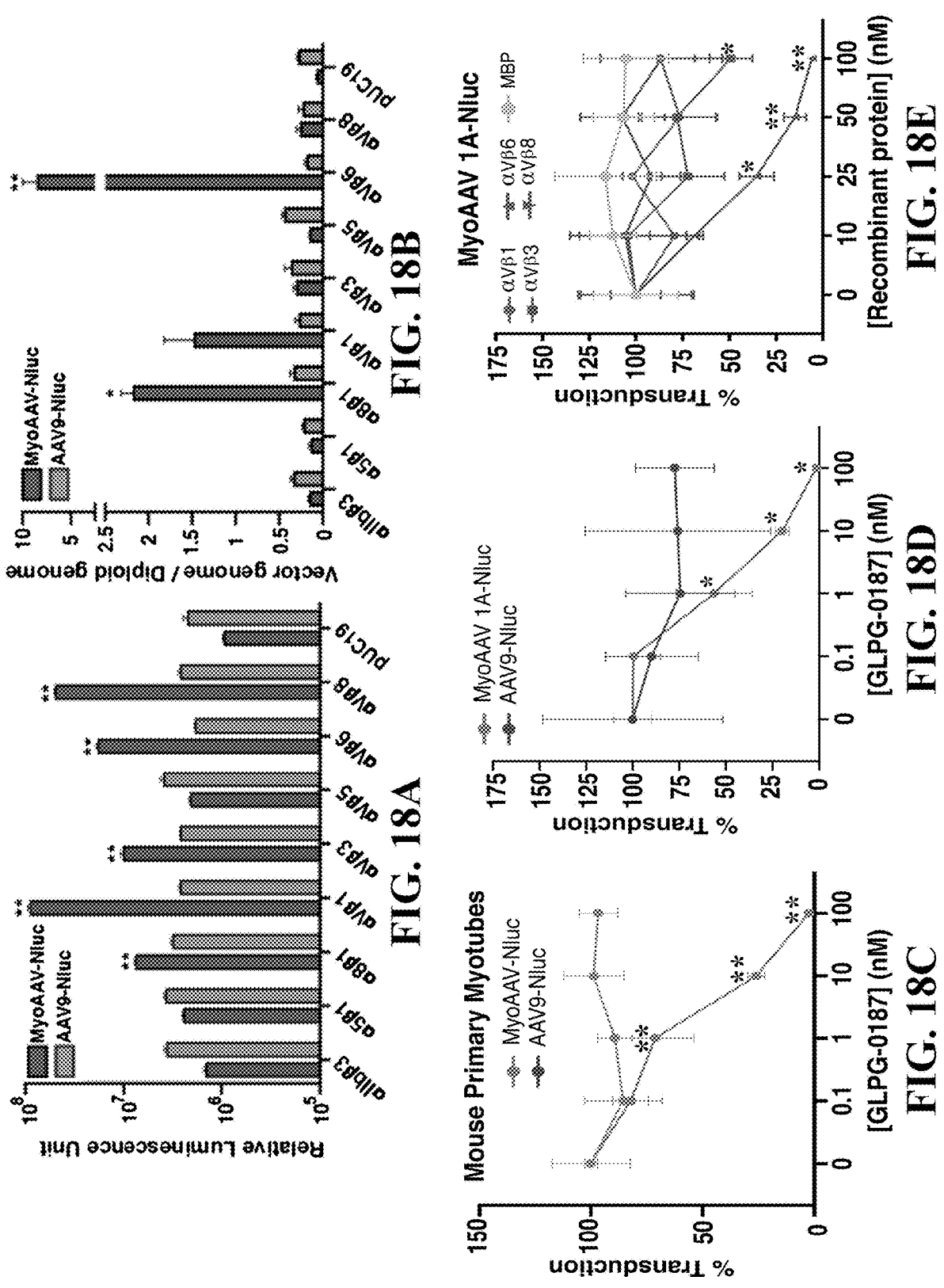

MyoAAV is Dependent on Integrin Heterodimers for Transducing Mouse and Human Primary Myotubes Given the presence of an RGD motif in MyoAAV and all of the other top variants from our selection, the role of RGD-binding integrin heterodimers in MyoAAV transduction was assessed. The RGD motif was first recognized in 1984 as the minimal sequence in fibronectin that facilitates binding to its receptor, later identified as the integrin heterodimer α5β1 (Pierschbacher and Ruoslahti, 1984; Pytela et al., 1985). RGD has since been identified as a recognition motif for several different integrin heterodimers; specifically, αIIbβ3, α5β1, α8β1, αVβ1, αVβ3, αVβ5, αVβ6, and αVβ8 (Ruoslahti, 1996). The transduction efficiency of AAV9- and MyoAAV-CMV-Nluc was compared in HEK293 cells overexpressing each of these eight human RGD-binding integrin heterodimers (FIGS. 25A-25I). Overexpression of a8β1, αVβ1, αVβ3, αVβ6, or αVβ8 increased the transduction efficiency of MyoAAV in the transfected HEK293 cells compared to PUC19-transfected controls, whereas AAV9 transduction was not enhanced by overexpression of any of these integrin heterodimers (FIG. 18A).

Next, the effect of different integrin heterodimers on the binding efficiency of MyoAAV and AAV9 to the cell surface was evaluated through overexpression experiments. The vector genomes bound to the surface of HEK293 cells transfected with each of the eight RGD-binding integrin heterodimers or a PUC19 control plasmid was quantified and it was found that α8β1, αVβ6, and to a lesser extent αV31 increased binding of MyoAAV, but not of AAV9, to integrin-transfected cells compared to PUC19-transfected controls (FIG. 18B). The impact of two different pan-αV integrin antagonists (CWHM-12 and GLPG-0187) on MyoAAV transduction efficiency in primary cells was also investigated. Both inhibitors impeded MyoAAV transduction in a dose-dependent manner in both mouse (FIGS. 18C and 26A) and human (FIGS. 18D and 26B-26H) primary skeletal muscle myotubes, while neither inhibitor had a dose-dependent effect on AAV9 transduction efficiency. These results demonstrate that inhibiting αV-containing integrin heterodimers almost completely eliminates the ability of MyoAAV to transduce both mouse and human primary myotubes.

To further elucidate the impact of individual αV-containing integrin heterodimers on MyoAAV's binding affinity, human primary myotubes were transduced with MyoAAV or AAV9 after pre-incubation of these viruses with αVβ1, αVβ3, αVβ6, αVβ8, or maltose binding protein (MBP) recombinant proteins. Remarkably, pre-incubation of MyoAAV with increasing concentrations of αVβ6 resulted in a dose-dependent inhibition of transduction of human primary myotubes, while none of the other recombinant proteins that we tested had a dose-dependent effect on transduction of the cells by either MyoAAV or AAV9 (FIGS. 18E-18F). Conversely, pre-incubation of human myotubes with increasing concentrations of anti-αVβ6 antibody decreased transduction efficiency by MyoAAV in a dose-dependent manner and did not affect transduction of myotubes by AAV9 (FIG. 18G). These data suggest that among the αV-containing integrin heterodimers that have the capability to facilitate MyoAAV transduction, αVβ6 has the highest affinity to bind to this capsid variant. Additionally, αVβ6 must be available on the surfaces of human muscle cells to enable their optimal transduction by MyoAAV.

The dependency of MyoAAV transduction on the previously identified AAV receptor (AAVR) was evaluated, The previously identified AAV receptor is a rapidly endocytosed plasma membrane protein required for effective transduction of most known AAV serotypes except AAV4 and AAVrh32.33 (Dudek et al., 2018; Pillay et al., 2016). HEK293FT AAVR knockout (KO) and the parental HEK293FT wild type (WT) cells were transduced with AAV4-, AAV2-, AAV9-, or MyoAAV-CMV-Nluc and found that, similar to AAV2 and AAV9, MyoAAV transduction requires AAVR expression (FIG. 18H).

Figure 26I:
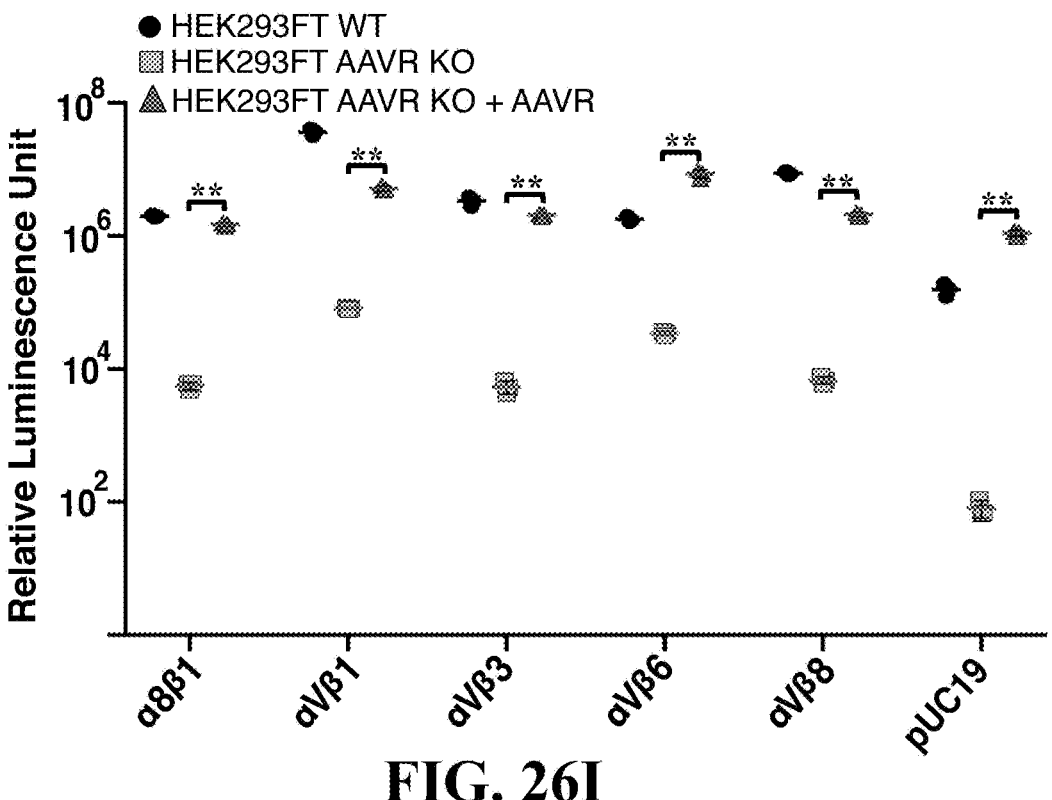
FIG. 26I) Quantification of in vitro transduction in HEK293FT cells, HEK293FT AAVR KO cells, and HEK293FT AAVR KO cells overexpressing AAVR, transfected with plasmids encoding for RGD-binding integrin heterodimers or with pUC19, and transduced with AAV9- or MyoAAV 1A-CMV-Nluc. Data are presented as mean±SD (n=3). : P<0.0001 (Student t test using the log transformed data).

To investigate if integrin heterodimers and AAVR play redundant roles in MyoAAV transduction, α8β1, αVβ1, αVβ3, αVβ6, or αVβ8 were overexpressed in the HEK293FT AAVR KO cells in the presence or absence of AAVR overexpression and then transduced the cells with MyoAAV-CMV-Nluc. These results demonstrated that while overexpression of integrin heterodimers increased MyoAAV transduction efficiency in AAVR KO cells compared to the mock transfected controls, integrin overexpression was not sufficient to rescue transduction to levels observed in AAVR KO cells overexpressing AAVR or in WT HEK293FT cells (FIG. 26I). These data suggest that integrin heterodimers and AAVR play distinct roles in and are likely utilized at different stages of MyoAAV transduction.

Figures 19A, 19B, 19C, 19D, 19E:
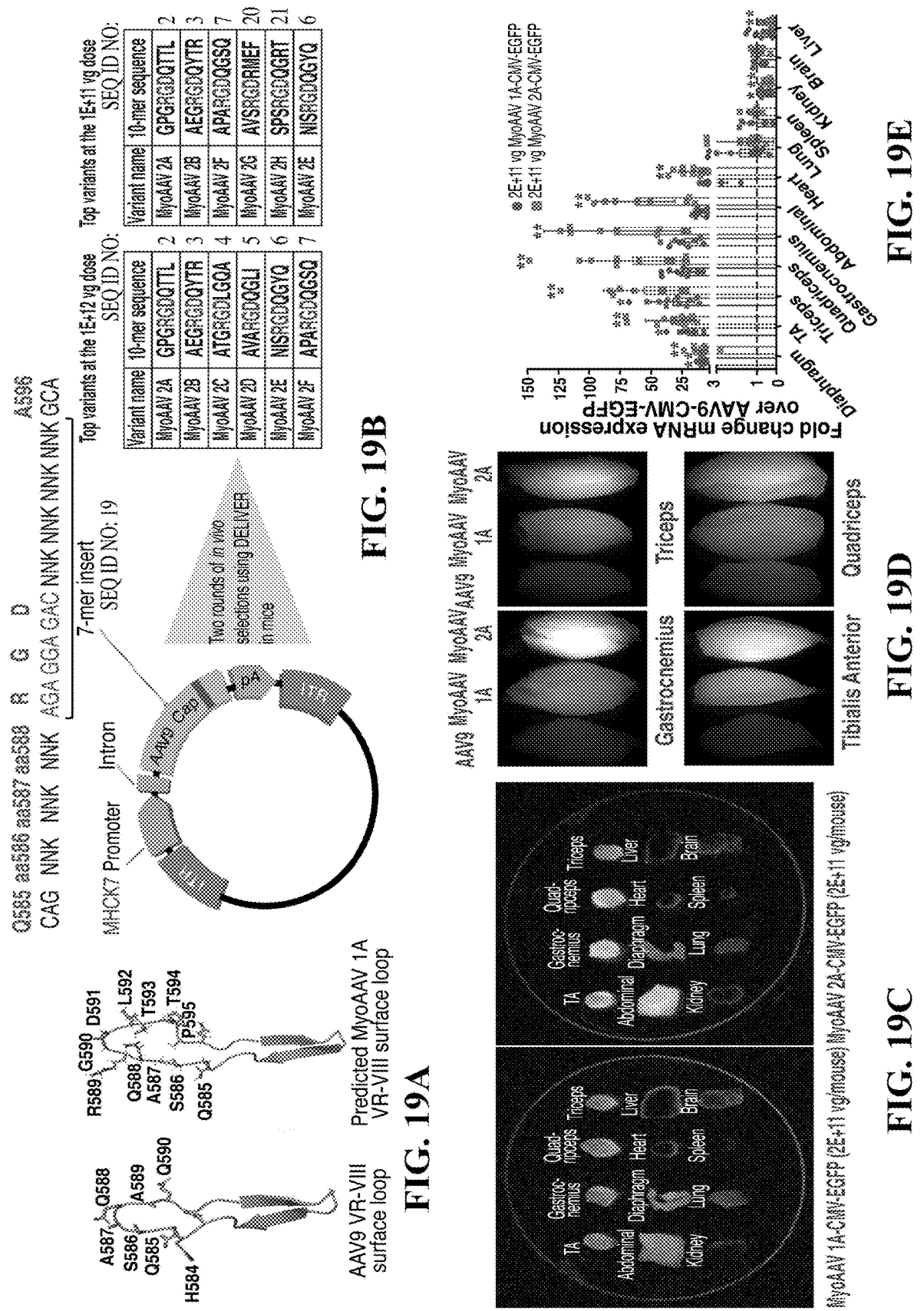

Additional Rounds of In Vivo Evolution Using DELIVER Generates Second-Generation RGD-Containing Muscle-Tropic Variants Given the importance of the RGD motif's interaction with integrin heterodimers for transduction of myotubes by MyoAAV and without being bound by theory, it was believed that modifying amino acids adjacent to the motif could improve this interaction, generating even more potent muscle-tropic capsid variants. Based on a predicted structure for the MyoAAV hypervariable region VIII surface loop, amino acids in positions 586, 587, and 588 upstream and positions 592, 593, 594, and 595 downstream of the RGD motif were identified as likely to be located in the surface loop of MyoAAV (FIG. 19A). A diverse library of capsids were generated, each with the RGD motif fixed at positions 589, 590, and 591 and varying amino acids in the above-mentioned flanking positions (FIG. 19B).

Two rounds of in vivo selection for muscle-tropic variants using DELIVER were performed in C57BL/6J and mdx mice. The second-round virus library was injected at two different doses (1E+12 vg and 1E+11 vg per mouse) to identify variants that effectively transduce muscle tissue both at high and low dose (FIG. 19B). We found that among our top hits from these selections, glycine and alanine were enriched at position 588 and glutamine was enriched at position 592. A variant containing the GPGRGDQTTL (SEQ ID NO: 2) sequence emerged as the most highly selected muscle-tropic capsid at both the 1E+12 and 1E+11 dose from the second round of selection (FIG. 19B). This second-generation variant was named "enhanced MyoAAV" (EMyoAAV) and it was used for further characterization.

Figure 27A:
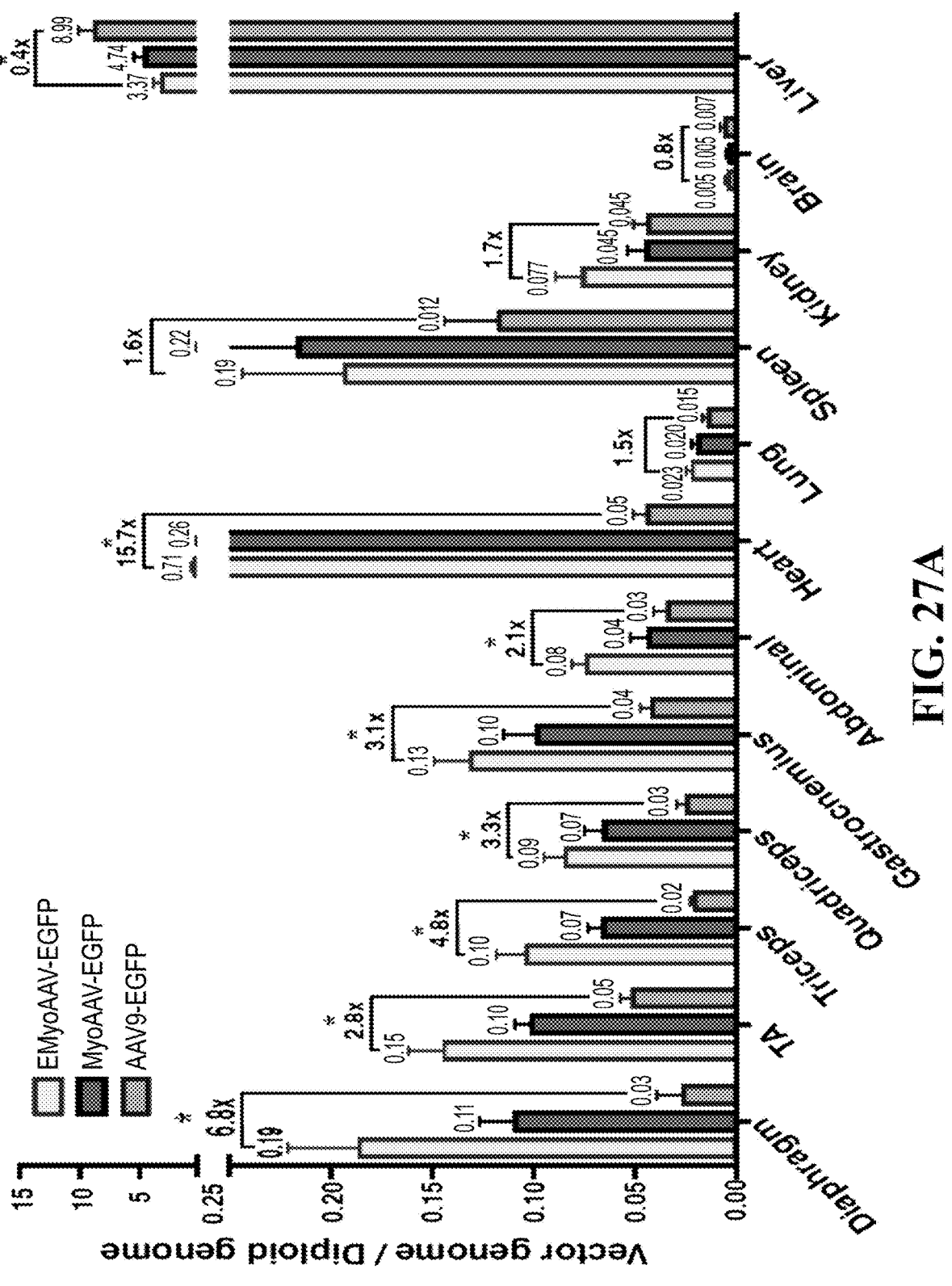
FIGS. 27A-27B—Second-generation RGD-containing capsid variants are less dependent on αVβ6 for transducing human primary myotubes compared to the first-generation variants.

The transduction efficiency of EMyoAAV was evaluated in different mouse tissues after systemic delivery of a low dose of the virus in comparison to AAV9 and MyoAAV. C57BL/6J mice were injected with 2E+11 vg (~8E+12 vg/kg) of AAV9-, MyoAAV-, or EMyoAAV-CMV-EGFP and analyzed transgene expression and vector genome biodistribution in various tissues. Whole tissue fluorescent imaging demonstrated that systemic gene delivery by EMyoAAV results in higher levels of transgene expression compared to MyoAAV or AAV9 across different skeletal muscles (FIGS. 19C-19D). Quantification of EGFP mRNA revealed that EMyoAAV transduces mouse skeletal muscles 10-80 times more efficiently, and heart 17 times more efficiently than AAV9. Furthermore, transgene mRNA expression was 2.5 times lower in the liver of EMyoAAV-injected animals compared to AAV9-injected mice (FIG. 19E). Similarly, vector genome biodistribution analysis showed that EMyoAAV-injected mice had significantly higher vector genomes per diploid genome in skeletal muscle and heart, and significantly lower vector genomes per diploid genome in the liver compared to AAV9-injected animals (FIG. 27A).

The efficiency and integrin dependency of EMyoAAV for transducing human primary myotubes was analyzed next. Remarkably, EMyoAAV transduced human primary myotubes 128 times more efficiently compared to AAV9 and 4.1 times higher than MyoAAV (FIG. 19F). Increasing concentrations of pan-αV integrin antagonist GLPG-0187 resulted in a dose-dependent decrease in the transduction efficiency of EMyoAAV (FIG. 19G), confirming that EMyoAAV infectivity remains dependent on αV-containing integrin heterodimers expressed on target cells.

To evaluate the binding affinity of EMyoAAV for different individual αV integrin heterodimers, EMyoAAV or AAV9 was pre-incubated with αVβ1, αVβ3, αVβ6, αVβ8, or maltose binding protein (MBP) recombinant proteins before transducing human primary myotubes. Interestingly, and in contrast to results obtained in these same assays with MyoAAV (FIG. 18E), all four αV-containing integrin heterodimers tested inhibited transduction of human myotubes by EMyoAAV in a dose-dependent manner (FIGS. 19H-19I), while there was no dose-dependent effect on AAV9 transduction. This result suggests that amino acid substitutions included in EMyoAAV enable higher affinity binding to a broader class of αV integrin heterodimers when compared to MyoAAV, which depends mainly on αVβ6 .

Figure 27B:
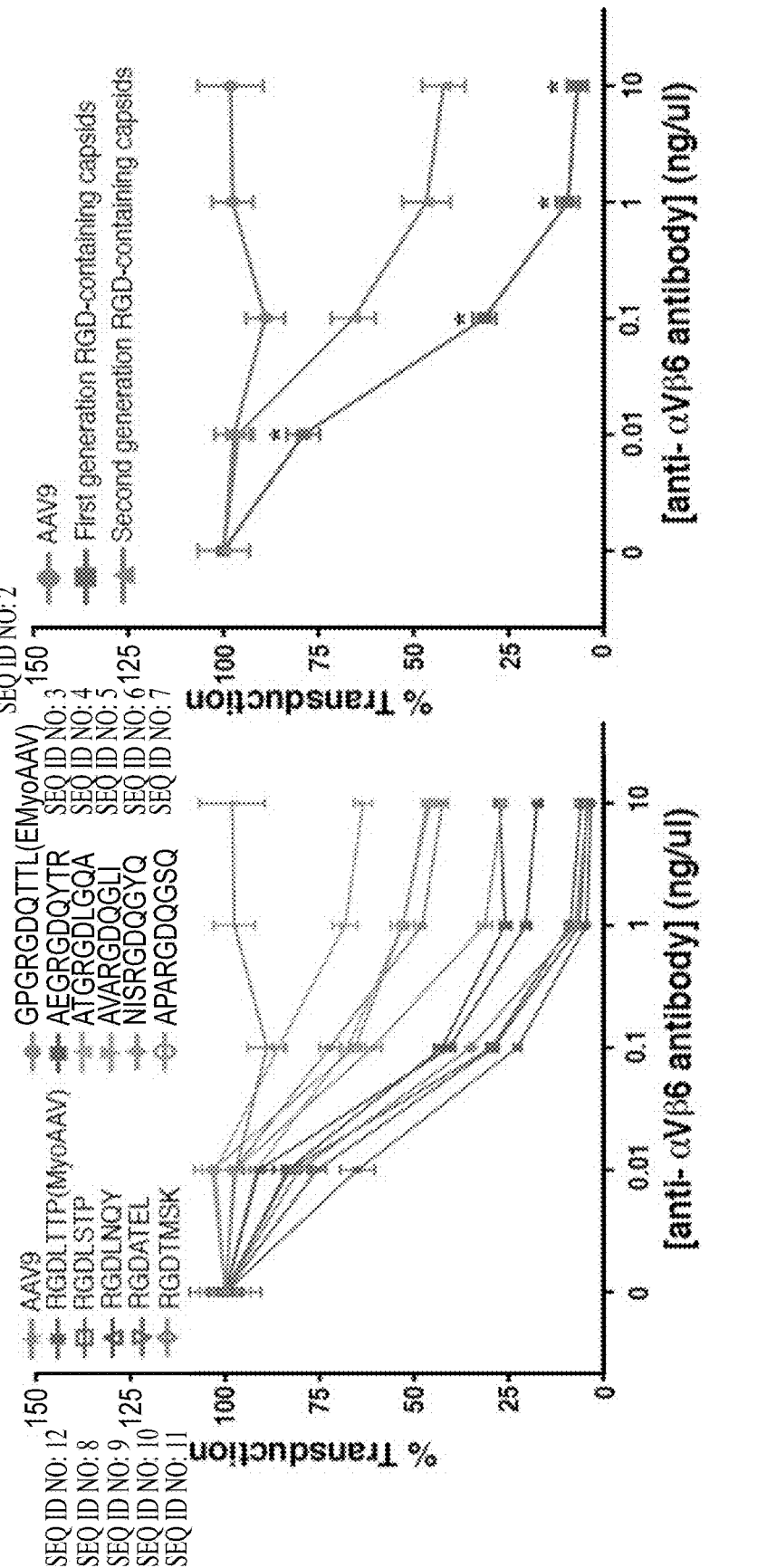

The dependency on αVβ6 heterodimers of the top first-generation and second-generation capsid variants that were evolved using DELIVER was evaluated. Human primary myotubes were pre-incubated with anti-αVβ6 antibody before transducing the cells with the top first-generation (RGDLTTP (SEQ ID NO: 12), RGDLSTP (SEQ ID NO: 8), RGDLNQY (SEQ ID NO: 9), RGDATEL (SEQ ID NO: 10), RGDTMSK (SEQ ID NO: 11)) and second-generation (GPGRGDQTTL (SEQ ID NO: 2), AEGRGDQYTR (SEQ ID NO: 3), ATGRGDLGQA (SEQ ID NO: 4), AVA-RGDQGLI (SEQ ID NO: 5), NISRGDQGYQ (SEQ ID NO: 6), APARGDQGSQ (SEQ ID NO: 7)) variants. While antibody binding inhibited transduction of human myotubes to some degree by all of these variants, the first-generation capsids were significantly more dependent on αVβ6 for myotube transduction (FIG. 27B).

EMyoAAV Shows Great Therapeutic Potential after Injection of a Low Dose of Virus Finally, the therapeutic relevance of EMyoAAV in comparison with capsids currently in clinical testing for human neuromuscular disease was examined. Specifically, for DMD, both AAV9 and AAVrh74 are being investigated in ongoing clinical trials (clinical trials.gov identifiers: NCT03362502, NCT03368742, and NCT03769116). Systemic administration of a function-complementing dystrophin mini-gene (termed microdystrophin), expressed from the muscle-specific MHCK7 promoter and delivered using the AAVrh74 vector, has shown promising results in a recently reported human clinical trial involving four DMD patients. In this trial, administering a high viral dose of 2E+14 vg/kg resulted in transgene expression in the muscle and functional improvement in disease phenotype (Mendell et al., 2020).

Figure 19J:
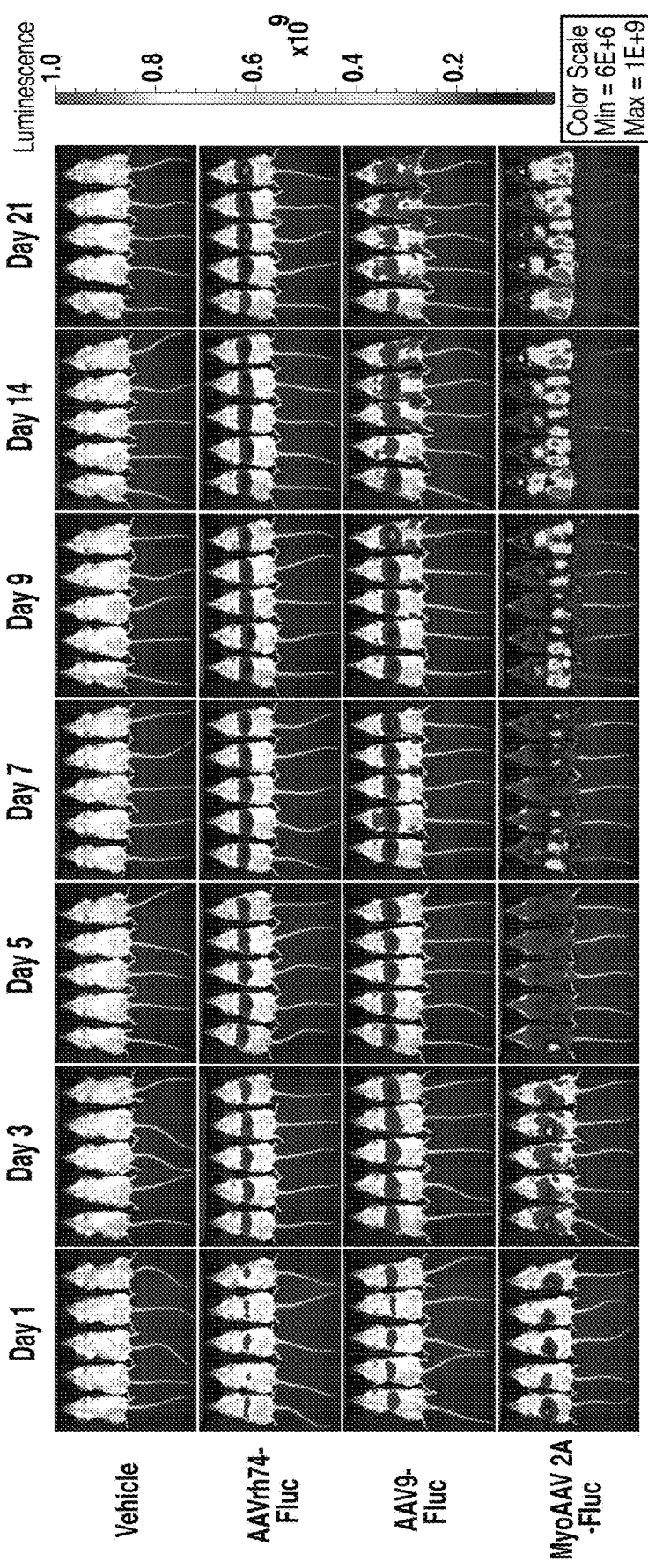
Figure 19K:
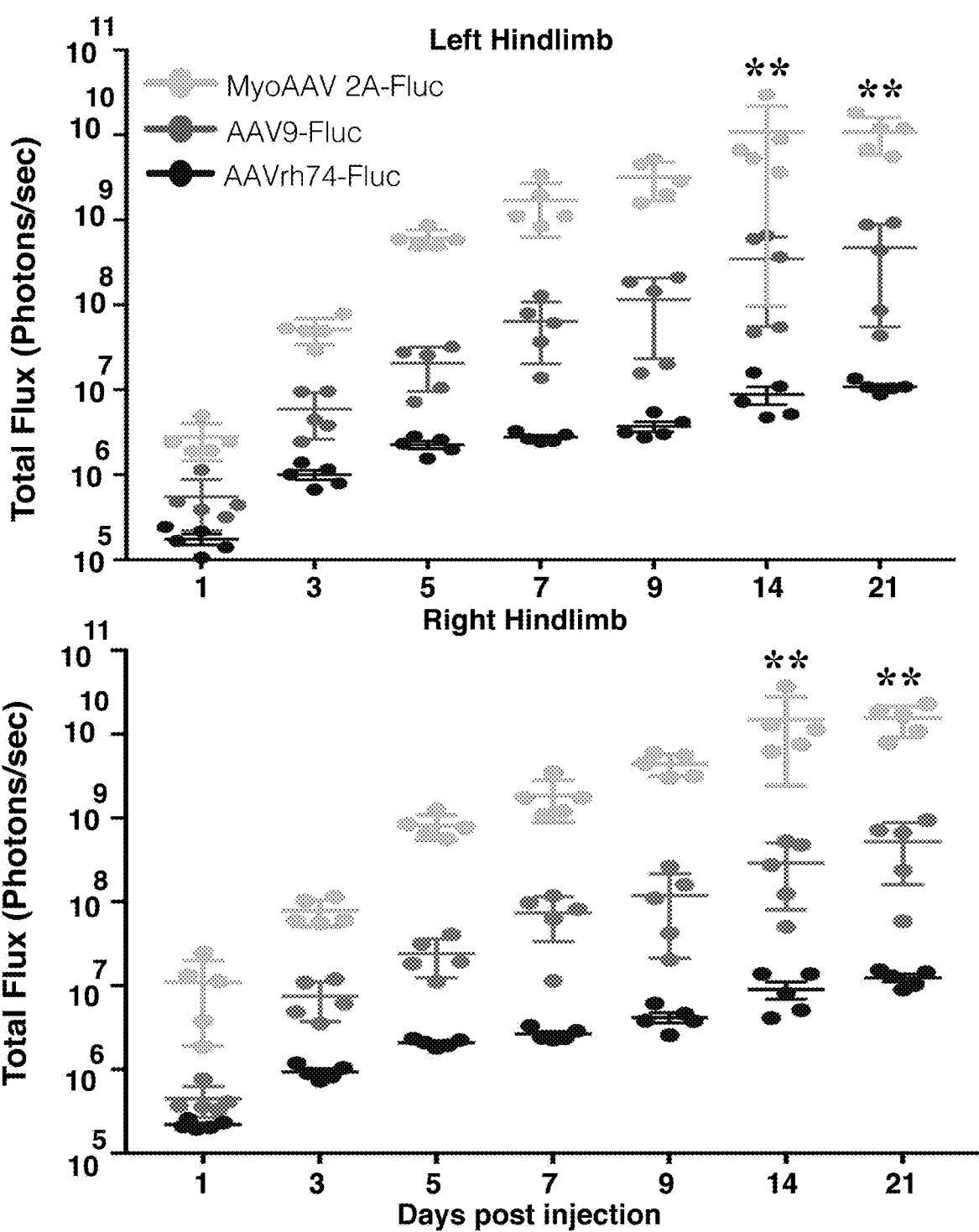
Figures 20A, 20B:
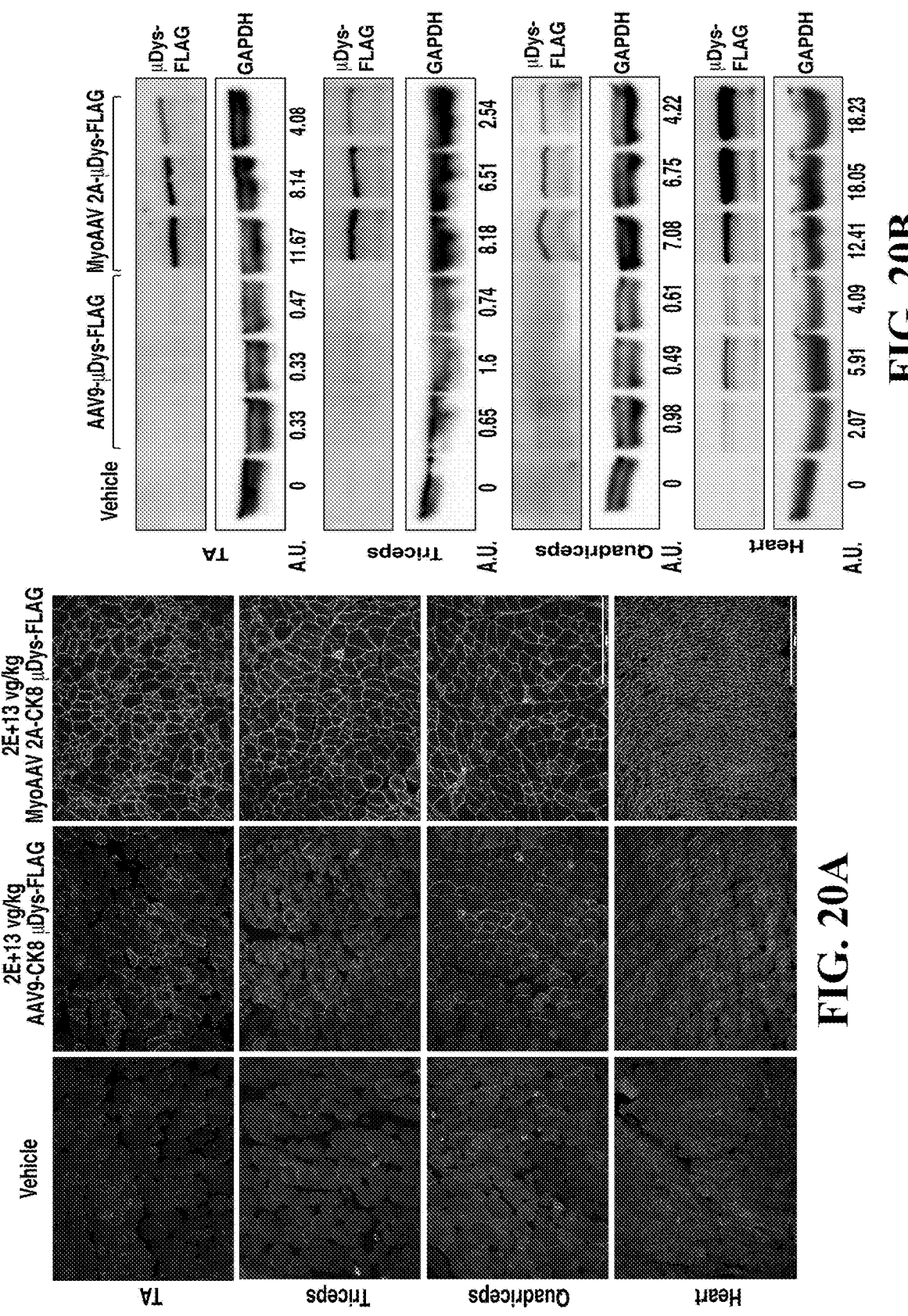
FIGS. 20A-20F—Systemic injection of EMyoAAV-CK8-microdystrophin at the low dose of 2E+13 vg/kg results in widespread microdystrophin expression and effective restoration of muscle function in adult DBA 2J-mdx mice.
Figures 20C, 20D, 20E, 20F:
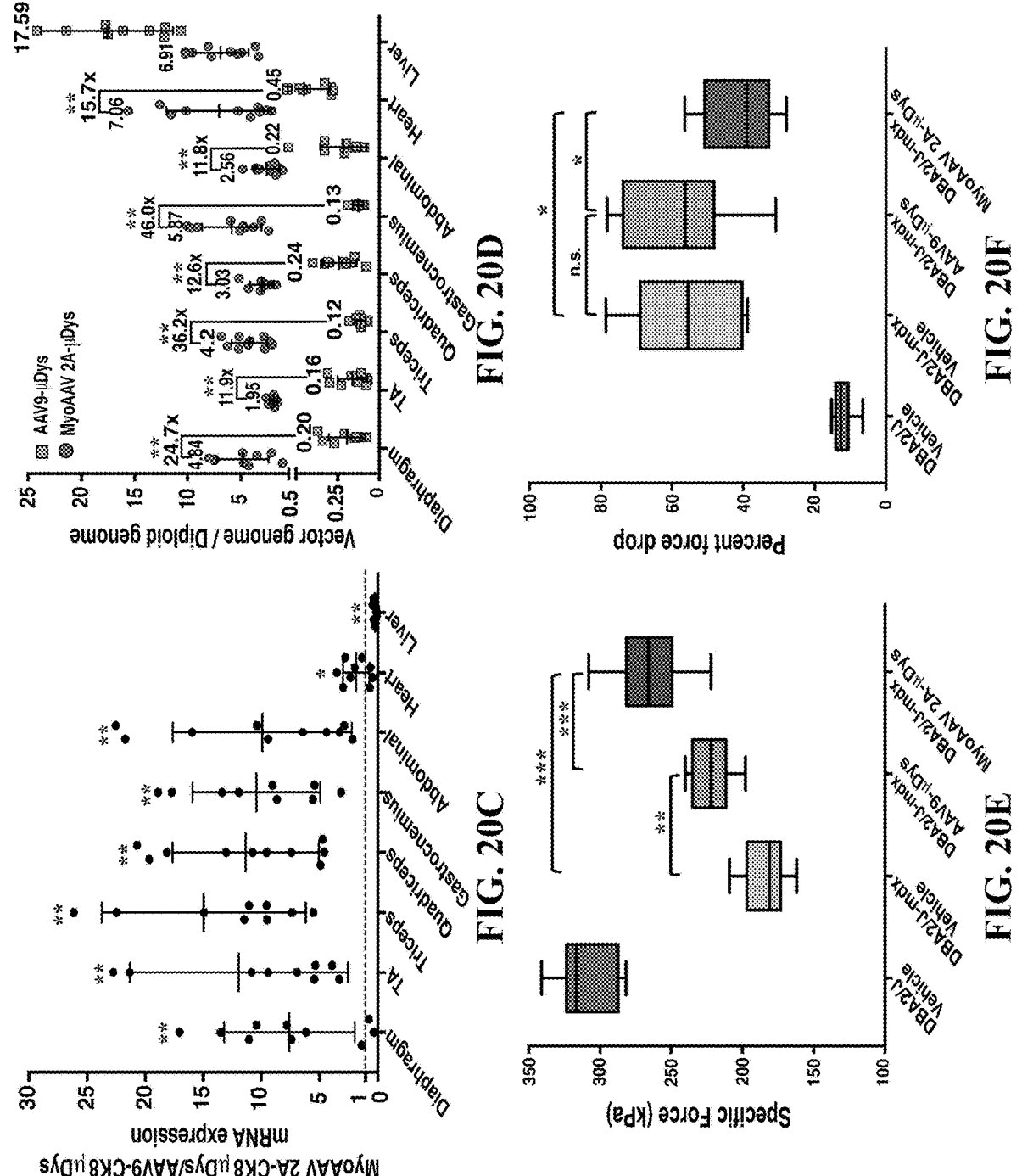

EMyoAAV-mediated gene delivery was compared to that of both AAVrh74 and AAV9 vectors, and further investigated performance in a DBA-mdx mouse model of DMD. In a longitudinal in vivo imaging experiment, we injected adult BABL/cJ mice with a low dose (2E+11 vg, representing ~8E+12 vg/kg) of AAVrh74, AAV9, or EMyoAAV encoding the CMV-Fluc reporter gene. EMyoAAV-injected mice demonstrated dramatically higher bioluminescence signal in the limbs and throughout the body as compared to those receiving AAVrh74 or AAV9 at all time points analyzed (FIGS. 19J-19K). We then tested systemic delivery of EMyoAAV or AAV9 carrying a microdystrophin transgene (CK8-microdystrophin-FLAG) into the DBA-mdx mouse model of DMD using an equivalent, low dose (2E+13 vg/kg) of each AAV. EMyoAAV-injected animals demonstrated relatively greater and more widespread expression of microdystrophin, localized at the sarcolemma, in multiple muscle groups as compared to AAV9-injected animals (FIG. 20A). Western blot confirmed higher levels of microdystrophin protein in muscles of mice injected with EMyoAAV, compared to AAV9 injected animals (FIG. 20B). Quantitative RT-PCR indicated 7.6-15 times higher levels of microdystrophin mRNA in skeletal muscles of mice injected with EMyoAAV-CK8-microdystrophin-FLAG as compared to AAV9-CK8-microdystrophin-FLAG (FIG. 20C).

Lastly, abundance of vector genomes and muscle function in the EMyoAAV-injected mice was assessed as compared to AAV9-injected animals. EMyoAAV delivered 12-46 times higher numbers of vector genomes per diploid genome in skeletal muscles of DBA-mdx mice and 2.5 times lower vector genomes per diploid genome in the liver, as compared to AAV9 (FIG. 20D). Strikingly, while AAV9-injected animals had more than 40 times higher numbers of vector genomes per diploid genome in their liver compared to their muscles, the EMyoAAV-injected mice had similar levels in their liver and muscles. Quantification of muscle specific force and percent force drop after eccentric damage demonstrated that TA muscles of EMyoAAV injected DBA-mdx mice recovered significantly greater specific force and were more protected from damage compared to muscles from mice receiving equal doses of AAV9 and to vehicle-injected animals (FIGS. 20E-20F).

Method Details

Constructs

Plasmid used for generating AAV-CMV-EGFP was generated by cloning the Cytomegalovirus (CMV) promoter, EGFP coding sequencing, and the bovine growth hormone polyadenylation signal (bGH pA) into the pZac2.1 AAV plasmid backbone using Gibson assembly. Constructs used for generating AAV-CMV-Nluc and AAV-CMV-Fluc were produced by replacing the EGFP coding sequence in the pZac2.1-CMV-EGFP-bGH pA with the Nluc and Fluc coding sequences, respectively. The pZac2.1 construct was purchased from the University of Pennsylvania vector core. Plasmids used for generating the AAV-CMV-Cre and AAV-CRISPR viruses were described previously (Goldstein et al., 2019; Tabebordbar et al., 2016). The plasmid library recipient plasmid was generated by cloning the CMV, MHCK7 (Salva et al., 2007), or CK8 (Bengtsson et al., 2017) promoters, splicing sequences of the AAV2 rep (modified from the sequence described in (Deverman et al., 2016) to include a conserved splice donor (Farris and Pintel, 2008)), AAV9 capsid coding sequence containing BsmBI restriction sites immediately after Q486 and Q588, and a SV40 polyadenylation signal, into the pZac2.1 backbone using Gibson assembly. For generating constructs encoding for integrin proteins and AAVR, coding sequences of human integrin $\alpha V$, $\beta 5$, $\beta 8$, $\alpha IIb$, $\beta 1$, $\beta 3$, $\beta 5$, $\beta 6$, $\beta 8$, and AAVR were amplified from human skeletal muscle cDNA. The amplicons were inserted into a pUC57 backbone downstream of a human elongation factor 1 alpha (EF1$\alpha$) promoter and upstream of the SV40 late polyadenylation signal sequence using Gibson assembly. Plasmid used for generating AAV-MHCK7-human MTM1 was generated by cloning the MHCK7 promoter, the chimeric intron from the pCI-neo mammalian expression vector (Promega), human MTM1 coding sequence, and the bGH pA into the pZac2.1 AAV plasmid backbone using Gibson assembly. The pZac2.1-CK8-microdystrophin-FLAG was cloned by incorporating the CK8 promoter, coding sequence of a five repeat microdystrophin (Hakim et al., 2017), a FLAG tag, and a synthetic polyadenylation signal (Levitt et al., 1989) between the ITRs of the pZac2.1 backbone.

Capsid Library Generation

For preparing capsid libraries for the first round of selection, we digested the AAV library recipient plasmid containing the CMV or MHCK7 promoter with BsmBI. We amplified a fragment encoding for the random 7-mer using the lib-F (5'-GCAACATGGCTGTCCAGGGAAGAAAC-TACATACCTG-3' (SEQ ID NO: 769)) and NNK-R (5'-GTTTT-GAACCCAGCCGGTCTGCGCCTGTGCMNNMNNM NMNMNMN NTTGGGCACTCTGGTGGTTTGTGGCC-3' (SEQ ID NO: 770)) primers using the AAV9 capsid coding sequence as the template and incorporated this fragment into the digested library recipient plasmid using Gibson assembly. For generating the second-round plasmid library, we used pools of oligonucleotides encoding for the variants selected in the first round, as well as the synonymous DNA codon replicates, synthesized by Agilent. The oligonucleotide library pools were used instead of the NNK-R primer to generate the amplicon for Gibson assembly into the digested library recipient plasmid. HEK293 cells were seeded in 15 cm dishes at a density of $2\times10^7$ cells/dish 1 day before transfection. Each plate was transfected with 16 g of the pALDX-80 helper plasmid (Aldevron), 8 g of the Rep-AAP plasmid (a generous gift from Ben Deverman (Deverman et al., 2016)), 8 g pUC19 and 10 ng of the plasmid library using PEI MAX (Polysciences). Capsid library was harvested from cells and media, and purified by ultracentrifuge using a iodixanol gradient as previously described (Rosemary C Challis, 2018).

Recombinant AAV Production and Purification

HEK293 cells were plated in 15 cm dishes at a density of $2\times10^7$ cells/dish. The next day, each plate was transfected with 16 g of the pALDX-80 helper plasmid (Aldevron), 8 g of the Rep/Cap plasmid, and 8 g of the ITR-containing plasmid using PEI MAX (Polysciences). Recombinant virus was harvested from the cells and media, and purified by ultracentrifuge using a iodixanol gradient as previously described (Rosemary C Challis, 2018). AAV titers were quantified by taqman-based qPCR.

In Vivo Selection

C57BL/6J mice were injected with 1E+12 vg of the capsid library. Two weeks after injection, mice were perfused with PBS and multiple skeletal muscles (tibialis anterior, quadriceps, gastrocnemius, triceps, abdominal, and diaphragm) and heart were harvested. Total RNA and DNA was extracted from the tissues using the TRIzol reagent (Thermo Fisher). mRNA was enriched from the total RNA samples using oligo dT beads (NEB) and cDNA synthesis was performed using SuperScript IV reverse transcriptase (Thermo Fisher) and a capsid-specific primer (5'-GAAAGTTGCCGTCCGTGTGAGG-3' (SEQ ID NO: 771)). Capsid variants DNA and expressed mRNA were amplified from the DNA and cDNA samples, respectively, with primers binding to the upstream (5'-ACAAGTGGC-CACAAACCACCA-3' (SEQ ID NO: 772)) and downstream (5'-GGTTTTGAACCCAGCCGGTC-3' (SEQ ID NO: 773)) of the 7-mer insert using the Q5 High Fidelity 2× master mix. Amplicons containing the Illumina adapters and unique indices (NEB E7600S) were quantified using qubit, pooled at equimolar ratio, and sequenced on a Nextseq.

Next Generation Sequencing Data Analysis and Virus Library Design

Illumina sequencing reads were demultiplexed using bcl2fastq2-v2.17.1. The resulting FASTQ sequences were filtered to keep only those which were directly matched to corresponding construct sequences surrounding the variable region, from which the 21 bp variant was extracted. For paired end sequencing runs, the variant was further filtered to keep only variants that were consistent in both the forward and reverse reads. Variants were counted for each sample and normalized by the sequencing depth as reads per million (RPM). Additional normalization was also performed as necessary by dividing the RPM of variants by the RPM of the same variant in the matched virus library sample. To simplify further analysis, sample variants with fewer than 10 reads were discarded for future analysis. Variants were ranked using the RPM ratio of sample RPM divided by the virus library RPM, and the highest scoring variants were identified to be used in a second round of selection. For each selected amino acid variant, a variant encoding for the same amino acids with a synonymous DNA codon was included in the design of the second-round library as a control. For variants with synonymous variants already observed in the sequenced samples, the highest scoring synonymous variant was included in the second-round design. For variants with no synonymous version among the sequenced samples, a synonymous variant was computationally generated by randomizing each possible codon of the original amino acid sequence to a different codon, if possible, thus maximally scrambling the original DNA sequence. Additionally, we designed 5% of the oligos to be random variants containing a stop codon to control for cross-packaging during the virus library production. Sequencing data from the second-round selection using designed variants was processed and counted as above, with the additional restriction that variants not matching the oligo design pool were filtered out.

Exon Skipping Transgene Expression, and Vector Genome Quantification

For the AAV-CRISPR and AAV-CMV-EGFP experiments, RNA was extracted from tissue samples using TRIzol (Thermo Fisher). For samples from the AAV-CRISPR and microdystrophin experiments, extracted RNA was treated with Turbo DNase (Thermo Fisher), and cDNA was made using the SuperScript IV VILO Master Mix (Thermo Fisher). A taqman assay against exon 4-5 junction was used for quantification of total Dmd transcripts, and another assay against exon 22-24 junction was used for quantification of exon23-deleted transcripts. For each of the exon 4-5 and exon 22-24 amplicons, a standard curve was generated by amplifying a gblock containing the taqman assay target sequences in each run. Total amount of Dmd transcripts and exon 23-deleted transcripts were quantified based on the standard curves. SaCas9 and gRNA expression in these tissue samples were quantified using taqman assays. Mouse GAPDH mRNA was used as the housekeeping control for quantification of SaCas9 and gRNA expression. For samples from the AAV-CMV-EGFP experiment, extracted RNA was treated with Turbo DNase (Thermo Fisher), and cDNA was generated using SuperScript IV reverse transcriptase (Thermo Fisher) with an oligo dT primer. Mouse beta actin mRNA was used as the housekeeping control for quantification of microdystrophin expression. Mouse GAPDH and beta actin mRNA (housekeeping controls) was quantified using predesigned taqman assays Mm.PT.39a.1 and Mm.PT.39a.22214843.g from IDT, respectively. For the vector genome quantification experiments, total DNA was extracted from tissue samples using the quick DNA extract solution (Lucigen). Number of vector genomes per diploid genome was quantified based on qPCR using taqman assays designed to amplify the transgene (EGFP or microdustrophin) or mouse GAPDH DNA. Absolute number of transgene and GAPDH molecules in each sample was quantified using standard curves generated by amplifying different amounts of the taqman assay target sequences in each run.

In Vitro AAV Transduction and Binding Experiments

Human and mouse primary myotubes were differentiated from human myoblasts and mouse satellite cells, respectively. Primary human skeletal muscle myoblasts (Lonza) were maintained in SkGM-2 media (Lonza) at 37° C. with 5% $CO_2$. Primary mouse satellite cells were isolated from C57BL/6J mice as previously described (Cerletti et al., 2008) and were expanded in the mouse muscle stem cell growth media (20% donor horse serum (Atlanta Biologics) in F10 (Gibco) containing 1% Glutamax (LifeTech), 1% penicillin-Streptomycin (LifeTech), and 5 ng/ml bFGF (Sigma)) for 6 days. Human and mouse myoblasts were seeded into 96-well plates (Corning) coated with collagen and laminin (Thermo Fisher) at a density of 15,000 cells/well. 24 hours following plating, media was changed to DMEM (Gibco) containing 2% horse serum (Gibco) and myoblasts were differentiated to myotubes for 4-6 days before they were transduced with AAV9-, or MyoAAV-Ck8-Nluc at 5E+3 vg/cell. For the integrin overexpression experiments, HEK293 cells were seeded at 35,000 cells/well in 96-well plates (Corning) in DMEM (Gibco) containing 5% fetal bovine serum (Gibco). For the integrin overexpression experiments, cells were transfected with different pairs of integrin constructs at a total of 100 ng plasmid/well using PEI MAX (Polysciences) the next day. 72 hours after transfection, cells were transduced with 1E+4 vg/cell of AAV9- or MyoAAV-CMV-Nluc. For the integrin overexpression and transduction analysis experiments, Nano-Glo Luciferase Assay Reagent (Promega) was added equal to the volume of media in the plate and luminescence was measured on the SpectraMax L microplate reader 24 hours post transduction. For the integrin overexpression and binding analysis experiments, cells were chilled on ice to inhibit endocytosis and AAV9-, or MyoAAV-Nluc were added to the cells at 1E+4 vg/cell 72 hours after transfection. Cells were kept on ice for 30 min and they were washed 3 times with PBS before they were lysed in the quick DNA extract solution (Lucigen). Vector genomes and diploid genomes were quantified by taqman qPCR using assays targeting the Nluc coding sequence and human GAPDH genomic locus. For the AAVR dependency experiments, HEK293FT AAVR KO, and HEK293FT AAVR WT cells were seeded at 35,000 cells/well in 96 well plates (Corning). The next day, cells were transduced with AAV2-, AAV4-, AAV9-, or MyoAAV-CMV-NLuc at 1E+3 vg/cell. For the AAVR rescue experiment, HEK293FT AAVR KO and HEK293FT WT cells were transfected with 33.3 ng of each integrin construct or pUC19 and 33.3 ng of AAVR construct or pUC19. A total of 100 ng plasmid DNA was used per transfection. 48 after transfection, cells were transduced with MyoAAV-CMV-Nluc at 1E+3 vg/cell. Nano-Glo Luciferase Assay Reagent (Promega) was added 24 hours after transduction at a volume equal to the volume of media in the plate and luminescence was measured using a SpectraMax L microplate reader.

Small Molecule and Antibody Inhibition Experiments

Pan-alpha V integrin antagonists CWHM-12 and GLPG0187 (MedChem Express), or anti-αVβ6 antibody (ab77906, abcam) were diluted in DMEM containing 2% horse serum at the specified concentrations. Media was removed from differentiated myotubes and replaced with the diluted inhibitors, after which the myotubes were incubated on ice for 30 minutes to inhibit endocytosis. Following this incubation, AAV9-, MyoAAV-, or EMyoAAV-CK8-Nluc were added to the cells at 5E+3 vg/cell and the plates were transferred back to the tissue culture incubators. 24 hours after transduction, luciferase intensity was measured with the Nano-Glo Luciferase Assay (Promega).

Recombinant Protein Inhibition Experiments

Human primary skeletal muscle myoblasts (Lonza) were differentiated into myotubes in DMEM with 2% horse serum (Gibco) on 96-well poly-D-lysine coated plates that were additionally coated with collagen and laminin. MyoAAV-, AAV9-, or EMyoAAV-CMV-Nluc were pre-incubated with recombinant soluble human integrin heterodimers αV31, αVβ3, αVβ6, αVβ8 (R&D Systems), or maltose-binding protein (Novus Biologicals) at 37° C. for 30 minutes. Virus and protein was then added to cells at 1E+4 vg/cell. Cells were returned to 37° C. for 24 hours before luciferase intensity was measured with the Nano-Glo Luciferase Assay (Promega).

Mice and AAV Injections

All animal care and experimental procedures were in accordance with the Broad Institute Institutional Animal Care and Use Committee (IACUC), as well as, the Harvard University and Boston Children's hospital IACUC. The following mice were purchased from the Jackson laboratories: mdx (JAX, #001801), C57BL/6J (JAX, #000664), DBA/2J (JAX, 000671), DBA/2J-mdx (JAX, 013141), and BALB/cJ mice (JAX, #000651). For the AAV-CMV-EGFP experiments, 8 weeks old C57BL/6J mice were either injected with 1E+12 vg of AAV9- or MyoAAV-CMV-EGFP, or with 2E+11 vg of AAV9-, MyoAAV-, or EMyoAAV-CMV-EGFP. For the AAV-CRISPR experiments, 8 weeks old mdx mice were injected with 4.5E+12 vg of AAV9- or MyoAAV-CMV-SaCas9 and 9E+12 vg of AAV9- or MyoAAV-gRNA. For the in vivo imaging experiments, we injected 8 weeks old BALB/cJ mice either with 4E+11 vg of AAV8-, AAV9-, or MyoAAV-CMV-Fluc, or with 2E+11 vg of AAVrh74-, AAV9-, or EMyoAAV-CMV-Fluc. For the satellite cell transduction experiment, 6 months old mdx;Ai9 mice were injected with 4E+11 vg of AAV8-, AAV9-, or MyoAAV-CMV-Cre. The MTM1 KO mice were injected with 2E+12 vg/kg of AAV9-, or MyoAAV-MHCK7-hMTM1. We injected the DBA 2J-mdx mice with 2E+13 vg/kg of AAV9-, or EMyoAAV-CK8-microdystrophin-FLAG. All the injections were performed retro-orbitally.

Mouse Activity Measurement

An actimeter (Harvard Apparatus) was used to measure the number of rearing events for each mouse every two weeks. Each animal was placed in the actimeter cage for 5 minutes and the number of rearing events were quantified for that period of time using the Actitrack software. For measuring the spontaneous running wheel rotation, mice were housed individually at 5 weeks of age and throughout their lives in cages equipped with low-profile wireless running wheels (Med Associates). Animals had free access to their running wheels and could voluntary run on them. The rotation of each wheel was continuously recorded, and the data was downloaded once a week when the running wheels were cleaned and inspected for proper operation. To normalize the data, the total activity of each week was expressed as mean of total wheel rotation per hour.

Immunofluorescence

For tissues harvested from C67BL/6J mice injected with AAV-CMV-EGFP, samples were fixed with 4% paraformaldehyde (PFA) for 1 h at room temperature (RT) and washed 3 times with DPBS. Fixed tissues were immersed in 30% sucrose at 4C until submersion, embedded in O.C.T compound (Tissue-Tek), and frozen in liquid nitrogen-cold isopentane. Muscles harvested from mdx mice injected with AAV-CRIPSR were frozen in liquid nitrogen-cold isopentane immediately after dissection. Tissues were sectioned using CM1860 cryostat (Leica Biosciences) at the thickness of 12 m. Laminin and DYSTROPHIN immunostaining of tissue sections was performed as previously described (Tabebordbar et al., 2016). For the microdystrophin-FLAG immunostaining, tissue sections were stained with a rabbit anti-FLAG antibody (Sigma) using the same protocol as DYSTROPHIN immunostaining. For the Lectin staining of the liver samples, tissue sections were washed 3×5 min with PBST (PBS+0.1% Tween-20), incubated with *Lycopersicon Esculentum* (Tomato) Lectin labeled with Dylight 594 (Vector laboratories) at 10 g/ml for 10 min at RT, washed 3×5 min with PBST, stained with Hoechst 33342 (Thermo Fisher) at 10 g/ml for 5 min, washed 2×5 min with PBST and mounted with Vectashield antifade mounting medium without DAPI (Vector Laboratories). In vitro differentiated myotubes were immunostained for Myosin Heavy Chain (MHC) as previously described (Tabebordbar et al., 2016).

Western Blot

For dystrophin western blots, protein was extracted from the muscle samples using RIPA buffer (Cell signaling). Total proteins (25 g) were separated by electrophoresis using Tris-Acetate 3-8% stain free polyacrylamide gels (Bio-Rad) and transferred to polyvinylidene difluoride (PVDF) membranes (Biorad). For the first three lanes on each gel, different percentages of wild-type muscle proteins were diluted in mdx proteins from the same muscle type so that the total protein amount for all the lanes were the same (25 g). The membranes were blocked with 5% Non-Fat Milk (Biorad) in TBST (TBS+0.1% Tween-20) for 1 hour at RT. dystrophin and GAPDH (loading control) were detected by primary antibodies against dystrophin (1:100, Abcam, ab15277) and GAPDH (1:25000, Santa-Cruz Biotechnology sc-32233) followed by goat anti-rabbit IgG HRP-linked (1:5000, abcam ab97051) or horse anti-mouse IgG HRP-linked (1:5000, Cell Signaling 7076P2) secondary antibodies, respectively. Due to the large difference in size of dystrophin and GAPDH and the requirement for different electrophoresis time, the same protein samples were run on two Tris-Acetate 3-8% gels for the generating the DYSTROPHIN and GAPDH blots. FluorChem E imaging system (Protein Simple) was used to detect chemiluminescence after using Supersignal west Dura ECL kit (Thermo Fisher). The relative abundance of DYSTROPHIN in total protein was evaluated semi-quantitatively by the ratio of DYSTROPHIN and GAPDH signals calculated using Image J and is presented in Arbitrary Units (A.U.). For the microdystrophin-FLAG western blots, protein content in tissue lysates from the tibialis anterior, quadricep, tricep, and heart of AAV9 and EMyoAAV injected mice was measured using the Pierce 660 nm protein assay reagent (Thermo Fisher). 20 μg of total protein from each sample was fractionated by SDS-PAGE on a 4-20% Criterion TGX gel (Bio-Rad) and transferred to a PVDF membrane in a wet transfer tank according to the manufacturer's instructions (Bio-Rad). The membrane was blocked for 1 hour in 5% w/v nonfat dry milk in TBST (10 mM Tris, pH 8.0, 150 mM NaCl, 1% Tween-20), washed 3 times for 10 minutes each with TBST, and incubated with primary antibodies against the FLAG tag (Millipore F7425, 1:400) or GAPDH (Santa Cruz sc-32233, 1:25,000) at 4° C. for 16 hours. The membranes were then washed 3 times for 10 minutes each with TBST and incubated in horseradish peroxidase-conjugated anti-rabbit (Abcam ab97051, 1:5000) or anti-mouse (Cell Signaling 7076P2, 1:5000) secondary antibodies for 1 hour at room temperature. Blots were washed three times with TBST, developed with SuperSignal West Pico PLUS chemiluminescent substrate (Thermo Fisher), and imaged using a CCD imager.

For integrin α8 and αIIb western blots, whole cell extracts were prepared from HEK293 cells overexpressing pUC19, α8, or αIIb integrin single chains by lysis in NP-40 lysis buffer (150 mM NaCl, 50 mM Tris-HCl pH 7.5, 1% NP-40) and centrifugation to remove cell debris. 2 μg of total protein from each sample was electrophoresed on a 4-20% Mini-PROTEAN TGX gel (Bio-Rad) and transferred to a PVDF membrane. The membrane was blocked for 1 hour in 5% w/v nonfat dry milk in TBST, and incubated with primary antibodies against integrin α8 (1:1000, Invitrogen MA5-31449), integrin αIIb (1:5000, abcam ab134131), or α-tubulin (1:5000, abcam ab7291) at 4° C. for 16 hours. The membranes were then washed 3 times for 10 minutes each with TBST and incubated in a 1:10,000 dilution of horseradish peroxidase-conjugated anti-mouse or anti-rabbit secondary antibodies for 1 hour at room temperature. Blots were washed three times with TBST and developed with SuperSignal West Pico PLUS chemiluminescent substrate (Thermo Fisher). The α8 blots were imaged using a CCD imager (ProteinSimple) and the αIIb blots were imaged on X-ray film with exposure times of 20 seconds and 15 minutes for the α-tubulin and αIIb sections, respectively.

Flow Cytometry

HEK293 cells overexpressing pUC19 or integrin single chains were harvested in PBS containing 5 mM EDTA and washed 3 times with staining buffer (2% FBS in PBS). The cells were then stained for 1 hour at 4° C. in primary antibody diluted in staining buffer. Cells were washed 3 times with staining buffer. For samples stained with the integrin β8 antibody, cells were incubated for 30 minutes at 4° C. with a PE-conjugated goat anti-mouse IgG secondary antibody (Invitrogen, 12-4010-82) diluted in staining buffer. Cells were washed 3 times, resuspended in staining buffer, and analyzed using a CytoFLEX S flow cytometer (Beckman). The flow cytometery data was analyzed with Flow Jo.

Mouse Satellite Cell Isolation, Culture, and Differentiation

Satellite cell isolation from mdx-Ai9 mice injected with AAV-CMV-Cre was performed as previously described (Goldstein et al., 2019). Satellite cells isolated from the injected animals were seeded on collagen/laminin-coated plates in satellite cell growth media (20% donor horse serum (Atlanta Biologics) in F10 (Gibco) containing 1% Glutamax (LifeTech), 1% penicillin-Streptomycin (LifeTech), and 5 ng/ml bFGF (Sigma)). Growth media was changed every other day. After 6 days, satellite cells were harvested, cell numbers were counted, and cells were re-plated in multiple wells of a 96 well plate at a density of 10,000 cells/well for differentiation. The next day, growth media was changed to differentiation media (DMEM (GIBCO) containing 2% donor horse serum (Atlanta Biologics)). Myotubes were fixed with 4% PFA 60 hours after start of the differentiation.

Muscle Physiology Analysis

Mice were prepared for in situ evaluation of the tibialis anterior as previously described (Tabebordbar et al., 2016). Force was recorded at nine different stimulation frequencies ranging from 20 to 200 Hz. The resulting data were fit by a sigmoidal curve of the form $P=P_{min}+((P_{max}-P_{min})/(1+(K/f)^H))$, where P is force at stimulation frequency f, $P_{min}$ is the minimum force, $P_{max}$ is the maximum force, K is the stimulation frequency at the inflection point of the curve, and H is the Hill coefficient or slope (Chan et al., 2007). The parameter K was used to calculate the force at the inflection point, which was termed intermediate force or $P_{int}$. The TA was then subjected to a series of 5 isometric-eccentric contractions to assess its susceptibility to injury (100 ms fixed-end contraction followed immediately by active lengthening at 4 fiber lengths/s to a final length of 1.2 fiber length). The series was bracketed by isometric contractions so that the loss of isometric force could be quantified as the relative difference between the pre- and post-protocol forces. Fiber length and TA cross-sectional area were calculated as previously described (Tabebordbar et al., 2016).

Bioluminescence Imaging

Mice were injected with 150 mg/kg of D-luciferin (Goldbio) and anesthetized with isoflurane before imaging. The bioluminescence images were acquired 5 min after D-luciferin injection with a rate of one image per 2 minutes for 25 minutes. Total and average radiance was measured from the same size of the region of interest (ROI) using Living Image 4.7.3 software (PerkinElmer). The highest captured radiance over imaging time was determined as the peak of the kinetic curve and picked for analysis. To measure the radiance from the dissected muscles, the mice were euthanized 12 minutes after D-luciferin injection. The dissected muscles were placed in a petri dish followed by bioluminescence imaging using IVIS Spectrum.

References

Asokan, A., Hamra, J. B., Govindasamy, L., Agbandje-McKenna, M., and Samulski, R. J. (2006). Adeno-associated virus type 2 contains an integrin alpha5beta1 binding domain essential for viral cell entry. J Virol 80, 8961-8969.

Bengtsson, N. E., Hall, J. K., Odom, G. L., Phelps, M. P., Andrus, C. R., Hawkins, R. D., Hauschka, S. D., Chamberlain, J. R., and Chamberlain, J. S. (2017). Muscle-specific CRISPR/Cas9 dystrophin gene editing ameliorates pathophysiology in a mouse model for Duchenne muscular dystrophy. Nat Commun 8, 14454.

Berry, G. E., and Asokan, A. (2016). Cellular transduction mechanisms of adeno-associated viral vectors. Curr Opin Virol 21, 54-60.

Cerletti, M., Jurga, S., Witczak, C. A., Hirshman, M. F., Shadrach, J. L., Goodyear, L. J., and Wagers, A. J. (2008). Highly efficient, functional engraftment of skeletal muscle stem cells in dystrophic muscles. Cell 134, 37-47.

Chan, K. Y., Jang, M. J., Yoo, B. B., Greenbaum, A., Ravi, N., Wu, W. L., Sanchez-Guardado, L., Lois, C., Mazmanian, S. K., Deverman, B. E., et al. (2017). Engineered AAVs for efficient noninvasive gene delivery to the central and peripheral nervous systems. Nat Neurosci 20, 1172-1179.

Chan, S., Head, S. I., and Morley, J. W. (2007). Branched fibers in dystrophic mdx muscle are associated with a loss of force following lengthening contractions. Am J Physiol Cell Physiol 293, C985-992.

Childers, M. K., Joubert, R., Poulard, K., Moal, C., Grange, R. W., Doering, J. A., Lawlor, M. W., Rider, B. E., Jamet, T., Daniele, N., et al. (2014). Gene therapy prolongs survival and restores function in murine and canine models of myotubular myopathy. Sci Transl Med 6, 220ra210.

Dalkara, D., Byrne, L. C., Klimczak, R. R., Visel, M., Yin, L., Merigan, W. H., Flannery, J. G., and Schaffer, D. V. (2013). In vivo-directed evolution of a new adeno-associated virus for therapeutic outer retinal gene delivery from the vitreous. Sci Transl Med 5, 189ra176.

Davidsson, M., Wang, G., Aldrin-Kirk, P., Cardoso, T., Nolbrant, S., Hartnor, M., Mudannayake, J., Parmar, M., and Bjorklund, T. (2019). A systematic capsid evolution approach performed in vivo for the design of AAV vectors with tailored properties and tropism. Proc Natl Acad Sci USA.

Deverman, B. E., Pravdo, P. L., Simpson, B. P., Kumar, S. R., Chan, K. Y., Banerjee, A., Wu, W. L., Yang, B., Huber, N., Pasca, S. P., et al. (2016). Cre-dependent selection yields AAV variants for widespread gene transfer to the adult brain. Nat Biotechnol 34, 204-209.

DiMattia, M. A., Nam, H. J., Van Vliet, K., Mitchell, M., Bennett, A., Gurda, B. L., McKenna, R., Olson, N. H., Sinkovits, R. S., Potter, M., et al. (2012). Structural insight into the unique properties of adeno-associated virus serotype 9. J Virol 86, 6947-6958.

Ding, W., Zhang, L., Yan, Z., and Engelhardt, J. F. (2005). Intracellular trafficking of adeno-associated viral vectors. Gene Ther 12, 873-880.

Duan, D. (2018a). Micro-Dystrophin Gene Therapy Goes Systemic in Duchenne Muscular Dystrophy Patients. Hum Gene Ther 29, 733-736.

Duan, D. (2018b). Systemic AAV Micro-dystrophin Gene Therapy for Duchenne Muscular Dystrophy. Mol Ther 26, 2337-2356.

Dudek, A. M., Pillay, S., Puschnik, A. S., Nagamine, C. M., Cheng, F., Qiu, J., Carette, J. E., and Vandenberghe, L. H. (2018). An Alternate Route for Adeno-associated Virus (AAV) Entry Independent of AAV Receptor. J Virol 92.

Elverman, M., Goddard, M. A., Mack, D., Snyder, J. M., Lawlor, M. W., Meng, H., Beggs, A. H., Buj-Bello, A., Poulard, K., Marsh, A. P., et al. (2017). Long-term effects of systemic gene therapy in a canine model of myotubular myopathy. Muscle Nerve 56, 943-953.

Farris, K. D., and Pintel, D. J. (2008). Improved splicing of adeno-associated viral (AAV) capsid protein-supplying pre-mRNAs leads to increased recombinant AAV vector production. Hum Gene Ther 19, 1421-1427.

Gao, G., Lu, Y., Calcedo, R., Grant, R. L., Bell, P., Wang, L., Figueredo, J., Lock, M., and Wilson, J. M. (2006). Biology of AAV serotype vectors in liver-directed gene transfer to nonhuman primates. Mol Ther 13, 77-87.

Goldstein, J. M., Tabebordbar, M., Zhu, K., Wang, L. D., Messemer, K. A., Peacker, B., Ashrafi Kakhki, S., Gonzalez-Celeiro, M., Shwartz, Y., Cheng, J. K. W., et al. (2019). In Situ Modification of Tissue Stem and Progenitor Cell Genomes. Cell Rep 27, 1254-1264 e1257.

Hakim, C. H., Wasala, N. B., Pan, X., Kodippili, K., Yue, Y., Zhang, K., Yao, G., Haffner, B., Duan, S. X., Ramos, J., et al. (2017). A Five-Repeat Micro-Dystrophin Gene Ameliorated Dystrophic Phenotype in the Severe DBA/2J-mdx Model of Duchenne Muscular Dystrophy. Mol Ther Methods Clin Dev 6, 216-230.

Hanlon, K. S., Meltzer, J. C., Buzhdygan, T., Cheng, M. J., Sena-Esteves, M., Bennett, R. E., Sullivan, T. P., Razmpour, R., Gong, Y., Ng, C., et al. (2019). Selection of an Efficient AAV Vector for Robust CNS Transgene Expression. Mol Ther Methods Clin Dev 15, 320-332.

Hinderer, C., Katz, N., Buza, E. L., Dyer, C., Goode, T., Bell, P., Richman, L. K., and Wilson, J. M. (2018). Severe Toxicity in Nonhuman Primates and Piglets Following High-Dose Intravenous Administration of an Adeno-Associated Virus Vector Expressing Human SMN. Hum Gene Ther 29, 285-298.

Hordeaux, J., Wang, Q., Katz, N., Buza, E. L., Bell, P., and Wilson, J. M. (2018). The Neurotropic Properties of AAV-PHP.B Are Limited to C57BL/6J Mice. Mol Ther 26, 664-668.

Levitt, N., Briggs, D., Gil, A., and Proudfoot, N. J. (1989). Definition of an efficient synthetic poly(A) site. Genes Dev 3, 1019-1025.

Li, C., and Samulski, R. J. (2020). Engineering adeno-associated virus vectors for gene therapy. Nat Rev Genet 21, 255-272.

Mack, D. L., Poulard, K., Goddard, M. A., Latournerie, V., Snyder, J. M., Grange, R. W., Elverman, M. R., Denard, J., Veron, P., Buscara, L., et al. (2017). Systemic AAV8-Mediated Gene Therapy Drives Whole-Body Correction of Myotubular Myopathy in Dogs. Mol Ther 25, 839-854.

Mendell, J. R., Sahenk, Z., Lehman, K., Nease, C., Lowes, L. P., Miller, N. F., Iammarino, M. A., Alfano, L. N., Nicholl, A., Al-Zaidy, S., et al. (2020). Assessment of Systemic Delivery of rAAVrh74. MHCK7.micro-dystrophin in Children With Duchenne Muscular Dystrophy: A Nonrandomized Controlled Trial. JAMA Neurol.

Morales, L., Gambhir, Y., Bennett, J., and Stedman, H. H. (2020). Broader Implications of Progressive Liver Dysfunction and Lethal Sepsis in Two Boys following Systemic High-Dose AAV. Mol Ther 28, 1753-1755.

Murrey, D. A., Naughton, B. J., Duncan, F. J., Meadows, A. S., Ware, T. A., Campbell, K. J., Bremer, W. G., Walker, C. M., Goodchild, L., Bolon, B., et al. (2014). Feasibility and safety of systemic rAAV9-hNAGLU delivery for treating mucopolysaccharidosis IIIB: toxicology, biodistribution, and immunological assessments in primates. Hum Gene Ther Clin Dev 25, 72-84.

Nelson, C. E., Hakim, C. H., Ousterout, D. G., Thakore, P. I., Moreb, E. A., Castellanos Rivera, R. M., Madhavan, S., Pan, X., Ran, F. A., Yan, W. X., et al. (2016). In vivo genome editing improves muscle function in a mouse model of Duchenne muscular dystrophy. Science 351, 403-407.

Pierschbacher, M. D., and Ruoslahti, E. (1984). Cell attachment activity of fibronectin can be duplicated by small synthetic fragments of the molecule. Nature 309, 30-33.

Pillay, S., Meyer, N. L., Puschnik, A. S., Davulcu, O., Diep, J., Ishikawa, Y., Jae, L. T., Wosen, J. E., Nagamine, C. M., Chapman, M. S., et al. (2016). An essential receptor for adeno-associated virus infection. Nature 530, 108-112.

Pulicherla, N., Shen, S., Yadav, S., Debbink, K., Govindasamy, L., Agbandje-McKenna, M., and Asokan, A. (2011). Engineering liver-detargeted AAV9 vectors for cardiac and musculoskeletal gene transfer. Mol Ther 19, 1070-1078.

Pytela, R., Pierschbacher, M. D., and Ruoslahti, E. (1985). Identification and isolation of a 140 kd cell surface glycoprotein with properties expected of a fibronectin receptor. Cell 40, 191-198.

Rosemary C Challis, S. R. K., Ken Y Chan, Collin Challis, Min J Jang, Pradeep S Rajendran, John D Tompkins, Kalyanam Shivkumar, Benjamin E Deverman, Viviana Gradinaru (2018). Widespread and targeted gene expression by systemic AAV vectors: Production, purification, and administration. bioRxiv.

Ruoslahti, E. (1996). RGD and other recognition sequences for integrins. Annu Rev Cell Dev Biol 12, 697-715.

Salva, M. Z., Himeda, C. L., Tai, P. W., Nishiuchi, E., Gregorevic, P., Allen, J. M., Finn, E. E., Nguyen, Q. G., Blankinship, M. J., Meuse, L., et al. (2007). Design of tissue-specific regulatory cassettes for high-level rAAV-mediated expression in skeletal and cardiac muscle. Mol Ther 15, 320-329.

Summerford, C., Bartlett, J. S., and Samulski, R. J. (1999). AlphaVbeta5 integrin: a co-receptor for adeno-associated virus type 2 infection. Nat Med 5, 78-82.

Tabebordbar, M., Zhu, K., Cheng, J. K. W., Chew, W. L., Widrick, J. J., Yan, W. X., Maesner, C., Wu, E. Y., Xiao, R., Ran, F. A., et al. (2016). In vivo gene editing in dystrophic mouse muscle and muscle stem cells. Science 351, 407-411.

Wu, Z., Asokan, A., Grieger, J. C., Govindasamy, L., Agbandje-McKenna, M., and Samulski, R. J. (2006). Single amino acid changes can influence titer, heparin binding, and tissue tropism in different adeno-associated virus serotypes. J Virol 80, 11393-11397.

Zincarelli, C., Soltys, S., Rengo, G., and Rabinowitz, J. E. (2008). Analysis of AAV serotypes 1-9 mediated gene expression and tropism in mice after systemic injection. Mol Ther 16, 1073-1080.

Example 7—Directed Evolution of a Class of Engineered AAV Capsid Variants Enabling Potent Muscle-Directed Gene Delivery Across Species Recombinant adeno-associated viruses (rAAVs) are the most commonly used vehicles for in vivo gene replacement therapy and gene editing in preclinical and clinical studies, yet selective transduction of specific tissues after systemic delivery remains a challenge. Recombinant AAVs generated using naturally-occurring capsids are predominantly sequestered in the liver after systemic injection. This sequestration limits the efficiency of transduction in other organs ((Gao et al., 2006; Murrey et al., 2014; Zincarelli et al., 2008) and poses a particular challenge for gene delivery to skeletal muscle. Because muscle comprises up to 40% of total body mass, achieving therapeutic thresholds in muscle with natural capsid variants requires extremely high virus doses (~2E+14 vg/kg) (Duan, 2018), which creates a formidable hurdle for vector manufacturing and can result in therapy-limiting toxicity, as observed in some recent clinical trials (Morales et al., 2020).

AAV capsid protein engineering coupled with in vivo selection is a promising approach to enable potent gene delivery to a variety of tissues. AAV capsid directed evolution strategies typically involve generating diverse capsid libraries, by various methods, followed by selection of variants with desired tropism in animal models. This approach has generated optimized vectors for delivery to a number of tissues (Choudhury et al., 2016; Dalkara et al., 2013; Deverman et al., 2016; Korbelin et al., 2016; Li et al., 2016; Michelfelder et al., 2009; Tse et al., 2017; Yang et al., 2009; Yang and Xiao, 2013).

AAV transduction is a multi-step process including binding to receptors on the cell surface, intracellular trafficking, endosomal escape, nuclear entry, vector genome second strand DNA synthesis, and transgene expression ((Berry and Asokan, 2016; Ding et al., 2005), Figure S1A), and inefficiency in any of these steps can limit vector potency. Therefore, successful identification of potent capsids requires selecting variants that proceed effectively through all stages of transduction. However, the majority of in vivo capsid directed evolution strategies select the successful capsid variants based on the presence of the vector genome DNA, and not the transgene mRNA, in the tissue of interest (Li and Samulski, 2020). Species- and strain-specific differences in the coding sequence and expression of genes involved in AAV transduction presents yet another challenge, as capsid variants selected in specific mouse strains may not yield potent transduction in other strains or other species (Hordeaux et al., 2018). Thus, a directed evolution approach that enables stringent selection of functional capsid variants across different strains and species is highly applicable and needed.

This Example describes and demonstrates at least the DELIVER (Directed Evolution of AAV capsids Leveraging In Vivo Expression of transgene RNA) strategy to combine diverse capsid library generation with stringent transcript-based in vivo selection and to enable directed evolution followed by identification of functional capsid variants in any tissue of interest and any animal model. This Example demonstrates DELIVER's utility for developing muscle-tropic capsids in mice and non-human primates and compare our results to AAV9 and AAVrh74, naturally-occurring AAV capsids currently used clinically in gene replacement trials for Duchenne Muscular Dystrophy (DMD) (clinical trials-.gov identifiers: NCT03362502, NCT03368742, NCT03375164, and NCT03769116). Overall, this muscle-directed vectors demonstrate superior potency and selectivity for transduction of both skeletal muscle and cardiac tissue, providing therapeutic efficacy at substantially reduced dosage when compared to AAV9, and with conserved transduction potency across mice, NHPs, and human muscle cells. Cross-comparison of muscle-enriched variant capsid sequences in mice and NHPs identified a common RGD motif among the top variants, and additional analyses uncovered a strong interaction with, and dependence on, target cell expression of RGD-binding integrin heterodimers. Taken together, this work provides a class of AAV capsid variants with particular utility for therapeutics development and testing in striated muscle, as well as an experimental framework for future evolution of additional families of AAVs with alternative tissue tropism.

Results

In Vivo Evolution of AAV9 Capsid Using DELIVER Identifies a Class of Muscle-Tropic Variants The AAV9-based capsid libraries that were designed for this study included several key features to facilitate identification of muscle-directed vectors with high potency for in vivo use. First, each variant included a random 7-mer peptide inserted between amino acids 588 and 589 in the hypervariable region VIII of the AAV9 capsid, a design that ensures exposure of the variable peptide sequence on the capsid surface ((Borner et al., 2020; DiMattia et al., 2012)), FIG. 14A). Each variant also encapsulated a transgene encoding its own capsid sequence under the control of either a ubiquitous or a cell type-specific mammalian promoter, which allowed for expression of the transgene (capsid variant) in both the HEK293 cells used for virus library production (FIG. 14B) and the animal tissues transduced with the virus after in vivo delivery (FIGS. 14C-14D).

DELIVER's stringency for selecting capsid variants that functionally transduce discrete mouse tissues were initially evaluated in C57BL/6J mice, using a virus library in which capsid variants were expressed under the ubiquitous CMV promoter. Variants were identified that were enriched relative to the virus library at the DNA and mRNA levels in various tissues. Selection of variants based on mRNA expression yielded a select few functional capsids compared to selection based on the presence of vector genome DNA (FIGS. 21A-21G), suggesting that only a small fraction of capsid variants that physically enter target cells can functionally transduce these cells to express their encoded transgene. In line with this finding, while capsid variants with higher abundance in the injected virus library were more highly present in the liver of injected animals at the vector genome DNA level, there was almost no correlation between abundance of each variant in the virus library and the level of transgene mRNA from the same variant in the liver (FIGS. 21H-21I).

Next, the feasibility of using muscle-specific promoters to enhance selection for potent muscle-tropic capsid variants was evaluated. Skeletal and cardiac muscle contain several different cell types, but AAV capsids capable of effective transgene delivery to two cell types in particular—muscle fibers and cardiomyocytes—are most desired for therapeutic gene delivery for genetic myopathies. To enable selection of variants specifically expressed in these cell types in vivo, we generated AAV capsid libraries in HEK293 cells using ITR-containing constructs in which expression of capsid coding sequences was controlled by the muscle-specific CK8 or MHCK7 promoters. These constructs produced similar titers of rAAV as those produced using a construct expressing the capsid under the ubiquitous CMV promoter (FIG. 14B). Furthermore, within the skeletal and cardiac muscles of injected mice, virus libraries expressed under CK8 or MHCK7 promoters yielded similar or higher transgene mRNA expression compared to those expressed under CMV, greatly facilitating identification of functional variants that transduce muscle fibers and cardiomyocytes (FIGS. 14C-14D).

Two rounds of in vivo selection was performed with directed evolution, screening capsid variants expressed from the MHCK7 promoter in multiple different muscles of C57BL/6J mice. Sequencing the first-round virus library identified more than 5,000,000 unique capsid variants. After the first round of selection, we selected the top 30,000 variants that were highly expressed in seven muscles (Quadriceps, Tibialis Anterior, Gastrocnemius, Triceps, Abdominal, Diaphragm, and Heart) (FIGS. 14A and 14E). For the second round of in vivo selectio two controls were incorporated. The first was a synonymous codon control in which the same 7-mer inserted peptides identified for each selected variant from the primary screen were encoded using synonymous DNA codons. The second was an expression control in which duplicate virus libraries were generated to express the variants under either of two skeletal muscle specific promoters, CK8 or MHCK7 (FIG. 14A).

Strikingly, in the second round of selection, all 12 of the top capsid variants highly expressed in muscles from either the CK8 or MHCK7 libraries contained the same arginine-glycine-aspartic acid (RGD) motif in the first 3 amino acid positions of the 7-mer insert. Further implicating the specific peptide sequences included in these capsid variants in their superior transduction of muscle, 10 of the top 12 hits in the CK8 group and 8 of the top 12 hits in the MHCK7 group were from synonymous pairs (i.e., the corresponding variant encoded by synonymous DNA codons was also within the top 12 muscle-expressed variants) (FIG. 14F).

Titers of rAAVs produced using the top 5 unique RGD-containing capsid variants were quantified to assess the feasibility of using these engineered capsids for in vivo studies. Comparison of rAAV titers showed no significant difference between the top 5 RGD-containing capsid variants and the parental AAV9 capsid (FIG. 22E). The variant containing the RGDLTTP (SEQ ID NO: 12) peptide insertion was selected, which also matches the consensus amino acids at each position from the top 12 RGD-containing hits, for further characterization and named this variant "MyoAAV 1A" (which is also referred to elsewhere herein as MyoAAV.

MyoAAV 1A Transduces Mouse Muscles with High Efficiency after Systemic Administration To investigate the transduction profile and biodistribution of the rAAVs generated using MyoAAV 1A in different mouse tissues after systemic delivery, adult C57BL/6J mice were injected with 1E+12 vg (~4E+13 vg/kg) AAV9- or MyoAAV 1A-CMV-EGFP and transgene expression and vector genome abundance was analyzed in different tissues two weeks after injection. Whole mount fluorescent imaging of the harvested tissues revealed far greater fluorescence intensity in muscles of mice injected with MyoAAV 1A as compared to AAV9-injected mice (FIGS. 15A and 22A). Importantly, MyoAAV 1A transduced the heart, a key affected organ in many genetic myopathies, more effectively than AAV9. Strong transgene expression in muscle fibers and cardiomyocytes of MyoAAV 1A injected mice was further confirmed by immunofluorescence analysis (FIGS. 15B and 22B). Remarkably, MyoAAV 1A showed relatively diminished transduction of liver after systemic delivery in C57BL/6J mice, suggesting a liver-detargeted transduction profile for this variant compared to AAV9 (FIGS. 15A-15C).

Figures 22F, 22G, 22H:
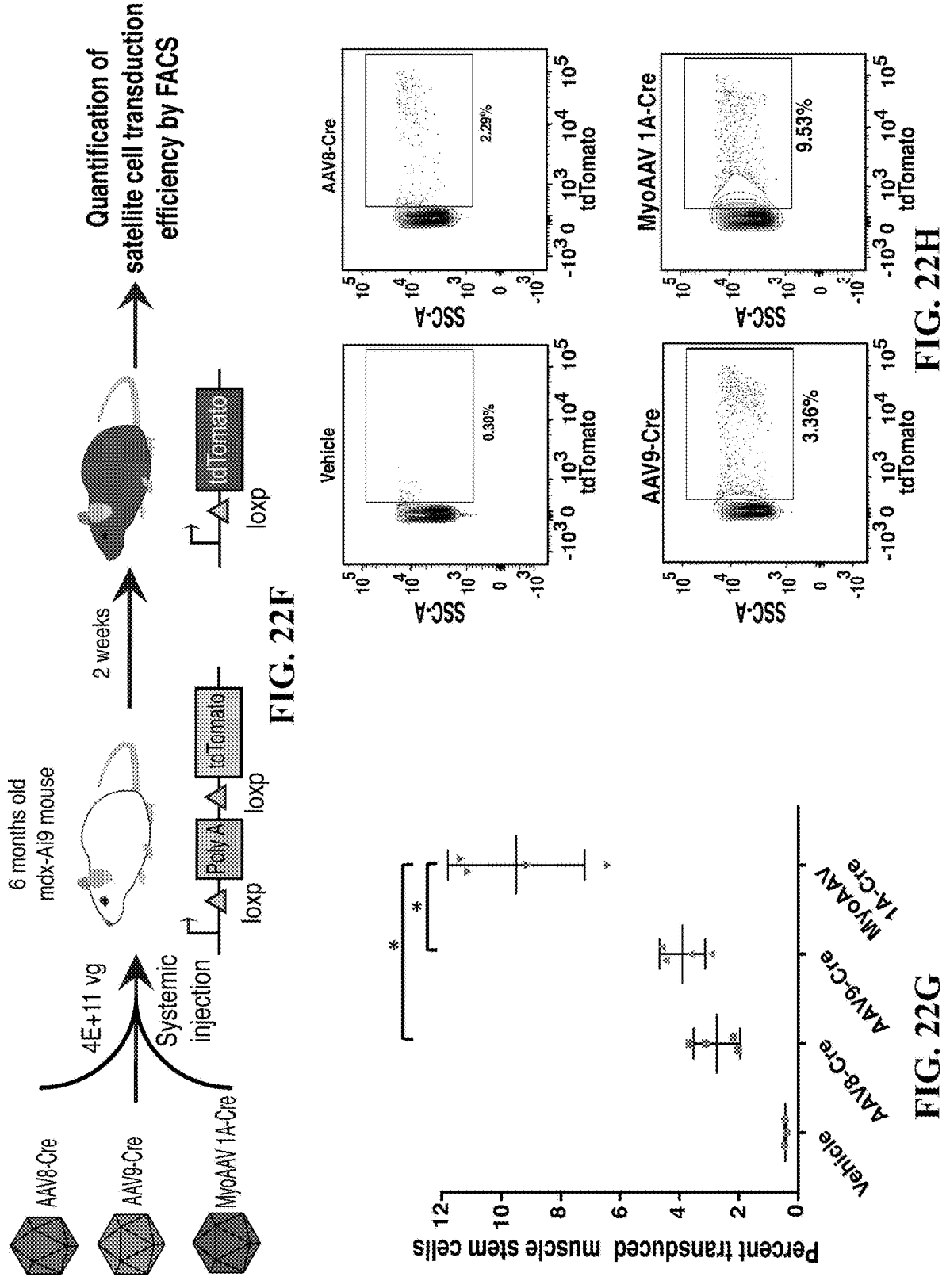
Figures 22I, 22J, 22K:
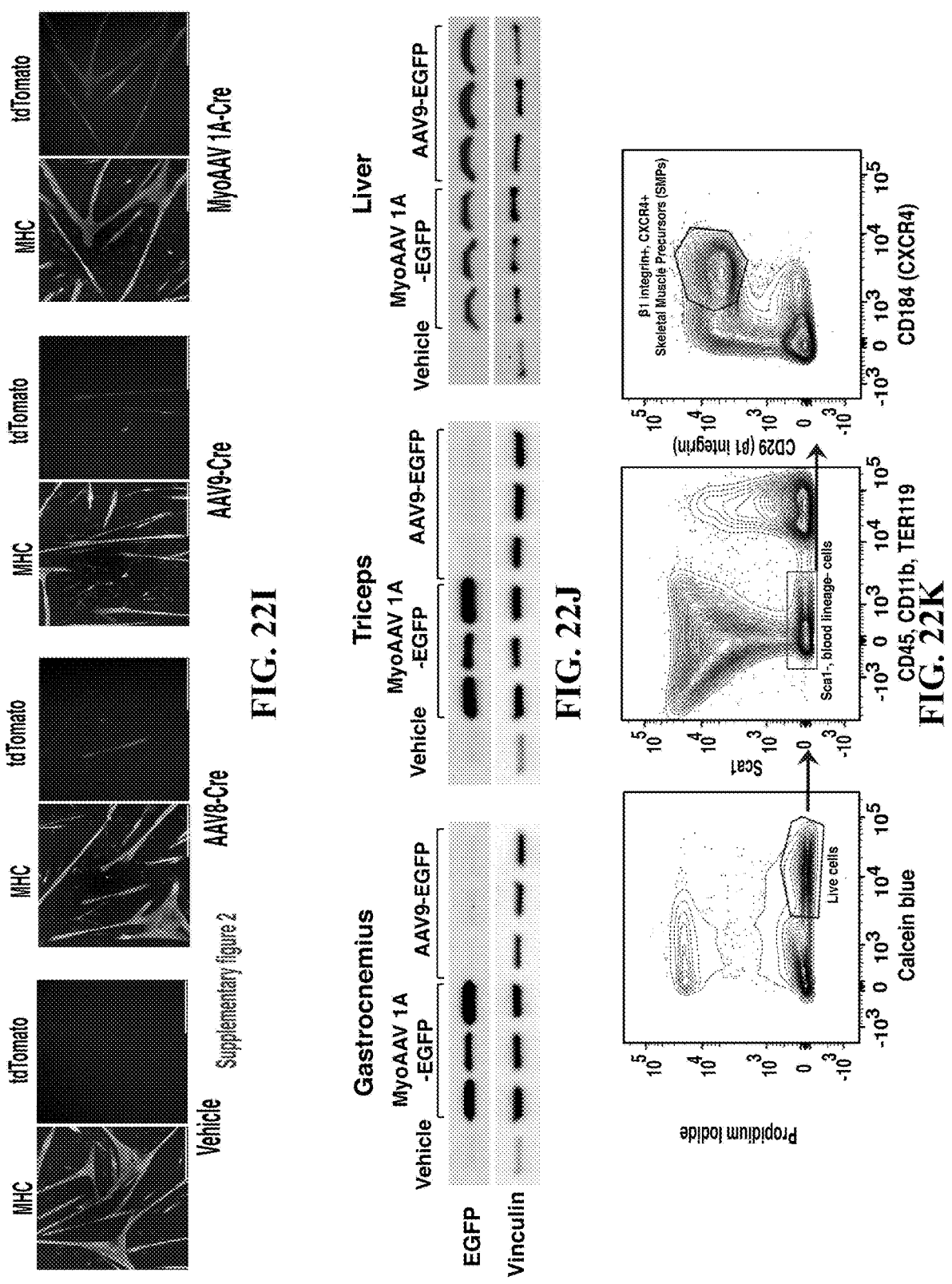

Quantification of EGFP mRNA in different skeletal muscles of male and female C57BL/6J mice revealed 10 to 29 times higher transgene expression in muscles of MyoAAV 1A-compared to AAV9-injected mice (FIG. 15C). EGFP mRNA expression was 6.3 times higher in the heart and 2.8 times lower in the liver of MyoAAV 1A injected animals (FIG. 15C). Notably, improved transduction efficiency by MyoAAV 1A was restricted to striated muscle tissues, and this engineered capsid variant transduced the lung, kidney, spleen, and brain of injected animals with similar or lower efficiency compared to AAV9 (FIGS. 15C and 22C). Western blot analysis confirmed dramatically higher expression of EGFP protein in the gastrocnemius and triceps muscles and lower EGFP expression in the liver of MyoAAV 1A injected animals compared to AAV9 injected mice (FIG. 22J). Biodistribution analysis demonstrated that MyoAAV 1A delivered vector genomes to all muscles of C57BL/6J mice more effectively than AAV9, with the exception of abdominal muscles, and resulted in a significantly lower number of vector genomes in the liver after systemic administration (FIG. 22D).

To evaluate the efficiency of muscle transduction after systemic administration of MyoAAV 1A in different mouse strains, male and female mice from the BALB/cJ and DBA/2J backgrounds were injected with 1E+12 vg (~4E+13 vg/kg) of AAV9- or MyoAAV 1A-CMV-EGFP and transgene expression in different tissues of the injected mice was compared. Whole organ imaging and EGFP mRNA quantification showed that potent muscle transduction and liver detargeting characteristics of MyoAAV 1A extend to BALB/cJ and DBA/2J mice as well (FIGS. 29A-29E).

The efficiency of muscle transduction after intramuscular delivery of MyoAAV 1A compared to AAV9 was also assessed. Intramuscular administration of 2E+10 vg of AAV9- or MyoAAV 1A-CMV-EGFP to the TA muscle in C57BL/6J mice resulted in 14 times higher EGFP mRNA expression, as well as dramatically higher EGFP protein expression, analyzed by western blot and immunofluorescence, in the MyoAAV 1A injected muscles relative to the muscles of AAV9-injected mice (FIGS. 22E-22F and 22K).

To investigate the possibility of liver damage following systemic MyoAAV 1A administration, we measured levels of Alanine Aminotransferase (ALT) and Aspartate Aminotransferase (AST) enzymes in the serum of C57BL/6J mice injected with vehicle (Saline), or 1E+12 vg (~4E+13 vg/kg) of AAV9-, or MyoAAV 1A-CMV-EGFP, before injection, as well as 14 and 28 days after injection. Levels of ALT and AST enzymes in the serum of AAV9 or MyoAAV 1A injected mice were not significantly different compared to the vehicle injected animals, suggesting lack of liver damage at the dose that we injected (FIGS. 22G, 22H). Analyzing inhibition of AAV9 and MyoAAV 1A transduction by serum isolated from mice injected with AAV9- or MyoAAV 1A-EGFP demonstrated that antibodies produced against AAV9 cross react with MyoAAV 1A and vice versa (FIGS. 29K-29L).

Next, MyoAAV 1A's efficiency in transducing human skeletal muscle was analyzed. Human primary myotubes from 4 different donors (2 males and 2 females) were transduced in vitro with AAV9- or MyoAAV 1A-CK8-Nanoluciferase (Nluc). MyoAAV 1A transduced myotubes from different donors 35 to 52 times more effectively than AAV9 (FIG. 15D). MyoAAV 1A also transduced mouse primary myotubes from C57BL/6J mice with 23 times higher efficiency compared to AAV9 (FIG. 15D).

Additionally, the efficiency of muscle stem cell (satellite cell) transduction by MyoAAV 1A after intravenous administration was evaluated in 6 months-old mdx-Ai9 mice. These dystrophin-deficient mice are a genetic model for human DMD, and additionally carry a Cre-activatable tdTomato transgene, which serves as a reporter for transduction by Cre-encoding AAVs. Fluorescence activated cell sorting (FACS) of satellite cells from the muscle of mice injected with AAV8-, AAV9- or MyoAAV 1A-CMV-Cre showed transduction of a significantly greater percentage of satellite cells in animals receiving MyoAAV 1A (FIGS. 22I-22K).

To investigate the kinetics of in vivo gene expression after systemic delivery of MyoAAV 1A, adult BALB/cJ mice were injected with 4E+11 vg (~1.6E+13 vg/kg) AAV8-, AAV9-, or MyoAAV 1A-CMV-Firefly luciferase (Fluc) and whole body bioluminescence imaging was performed at different time points over 120 days after injection. Mice receiving MyoAAV 1A showed faster kinetics and significantly higher overall levels of transgene expression in their limbs and throughout their bodies compared to mice injected with AAV8 or AAV9 (FIGS. 16A-16B). Whole organ bioluminescence imaging from muscles of mice harvested four months after injection confirmed dramatically higher luciferase expression in the muscles of MyoAAV 1A injected animals (FIGS. 29M-29O).

Additional results that further support that MyoAAV 1A effectively transduces different skeletal muscles after systemic administration in mice from DBA/2J and BALB/cJ backgrounds, and is highly potent in muscle transduction after intramuscular delivery are shown in FIGS. 29F-29L.

Systemic Administration of Therapeutic Transgenes Using MyoAAV 1A Leads to Functional Improvement in Mouse Models of DMD and X-Linked Myotubular Myopathy (XLMTM)

To investigate the feasibility of using MyoAAV 1A for in vivo delivery of therapeutic transgenes, adult mdx mice (a mouse model of DMD carrying a nonsense mutation in Dmd exon 23) were injected with AAV9 or MyoAAV 1A carrying constructs encoding SaCas9 together with guide RNAs (gRNAs) targeting 5' and 3' of the mdx mutation (FIGS. 24A-24B). Applicant and others have previously shown that this CRISPR-Cas9-mediated approach results in excision of exon 23 from the genome of mdx cells and expression of a truncated but still functional version of dystrophin protein in muscle. (Nelson et al., 2016; Tabebordbar et al., 2016). While producing a truncated variant, this in-frame deletion still makes a functional protein, thereby providing therapeutic benefit in DMD.

Figures 4A, 4B, 4C, 4D, 4E, 4F:
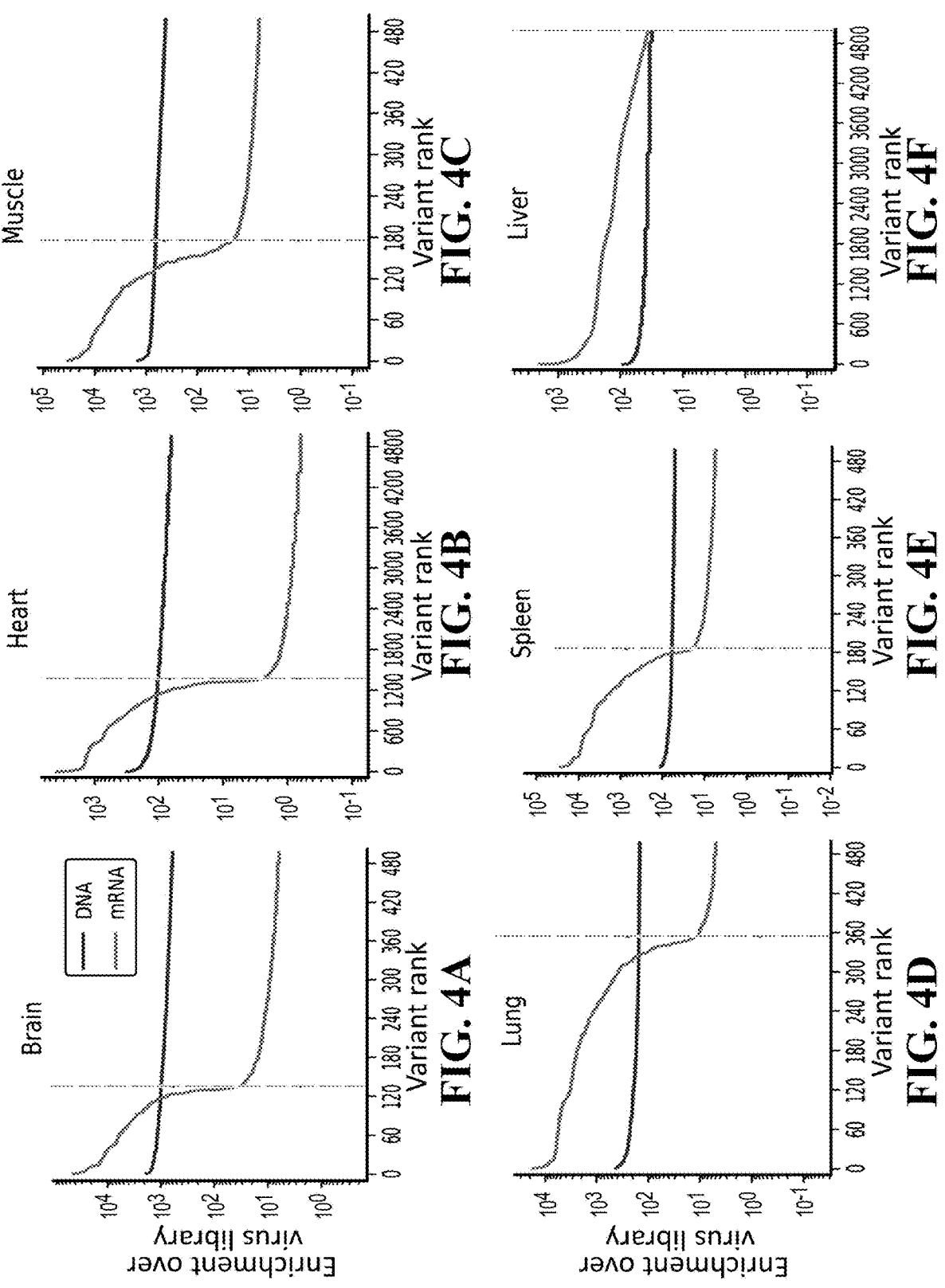
FIGS. 4A-4F—Capsid variants present at the DNA level and expressed at the mRNA level identified in different tissues. For this experiment, the virus library was expressed under the control of a CMV promoter.
Figure 24F:
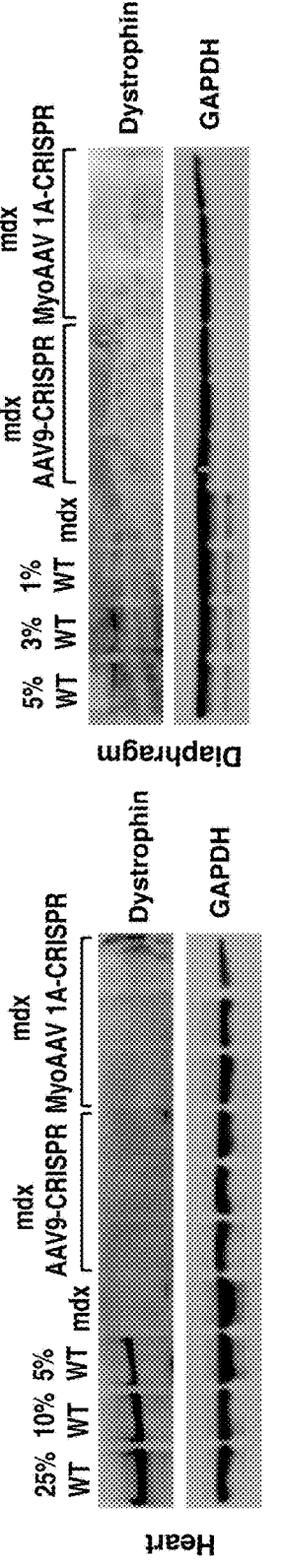
Figure 24G:
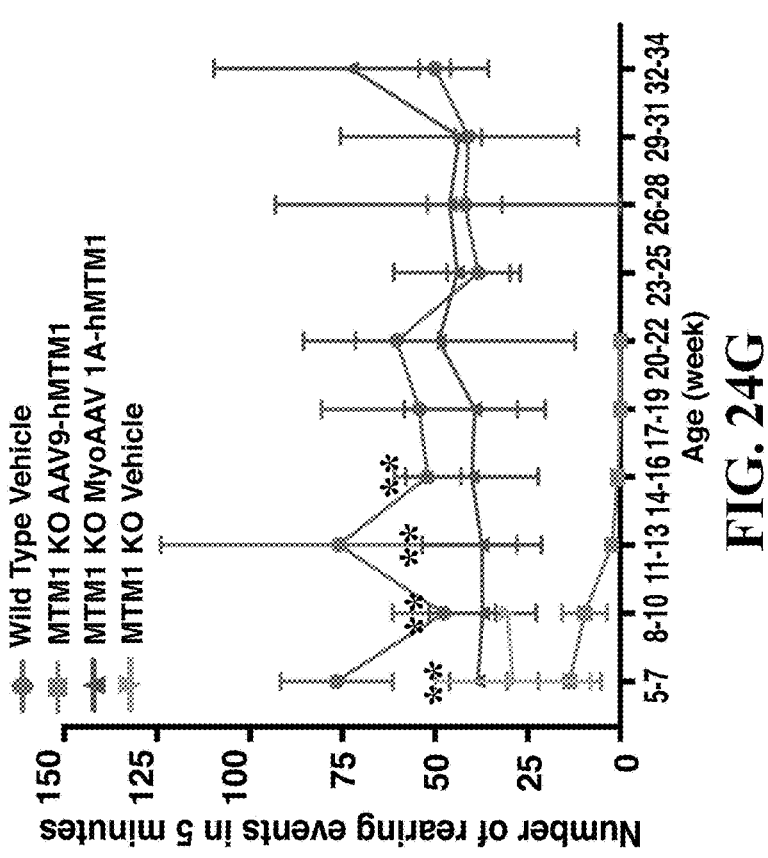
Figures 25A, 25B, 25C, 25D:
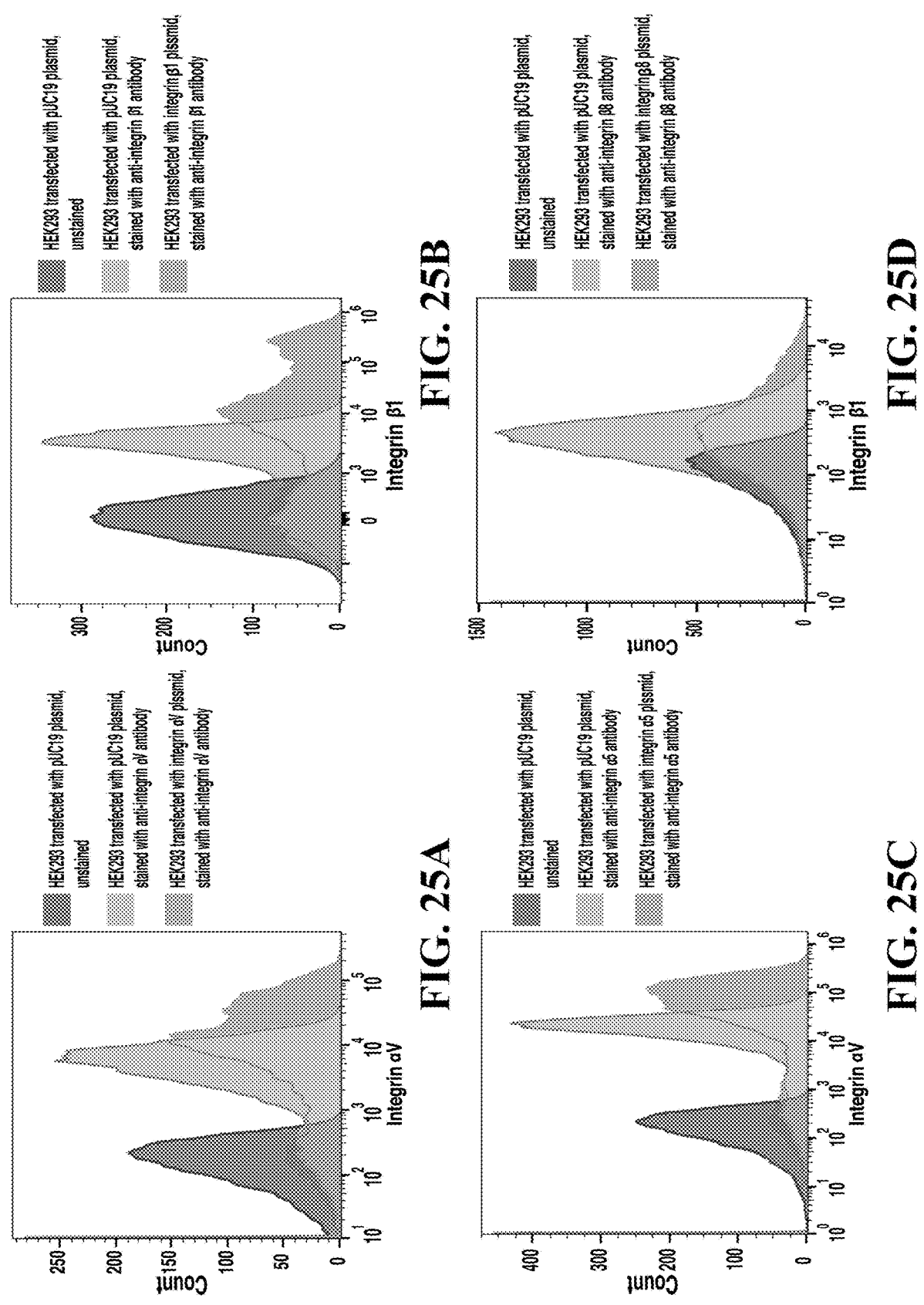
Figures 25E, 25F:
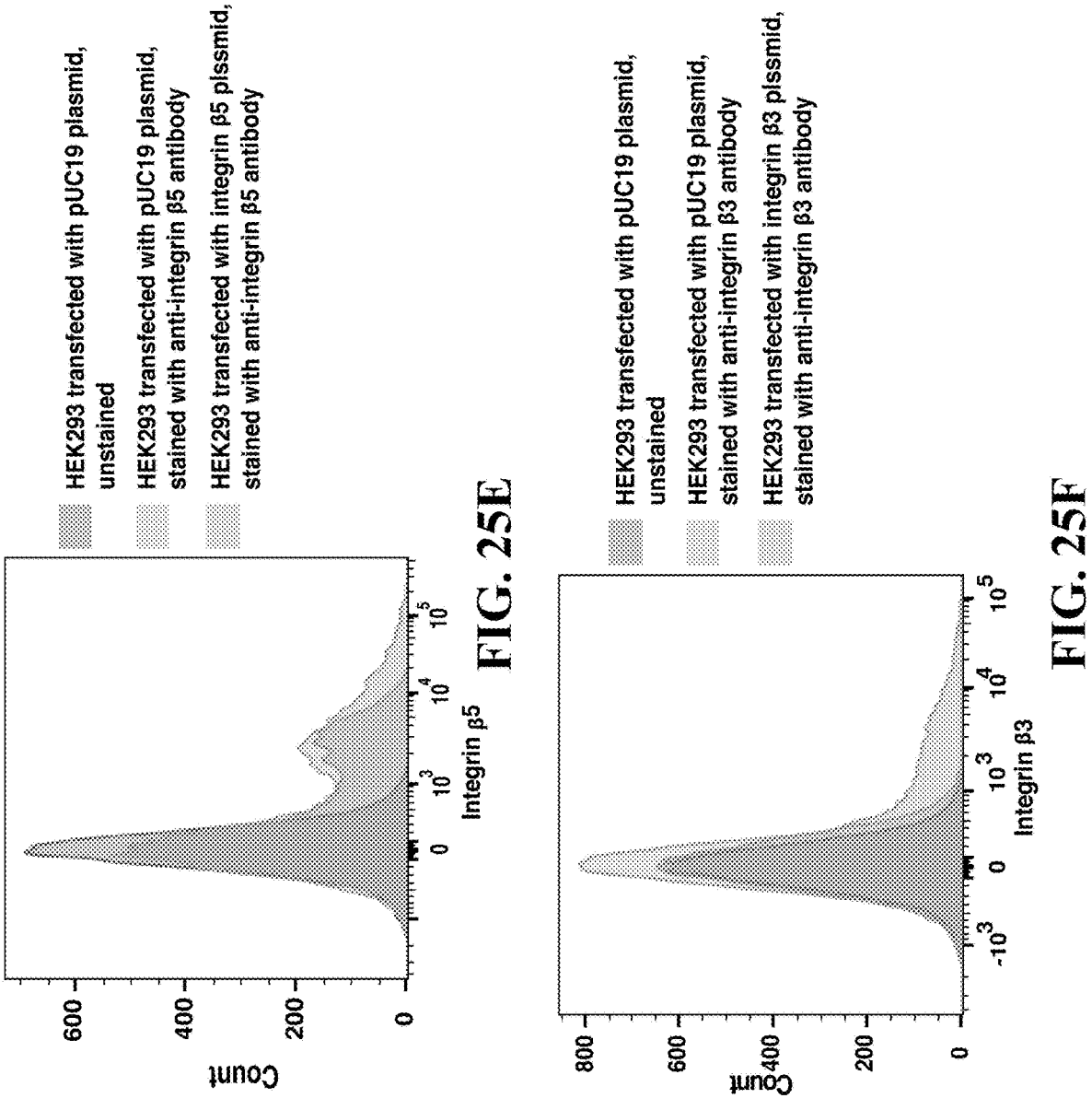

MyoAAV 1A-Dmd CRISPR resulted in production of exon 23-deleted Dmd mRNA with efficiencies ranging from 3.4% to 25% of total Dmd mRNA in different mdx muscles. In contrast, the efficiency of production of exon 23-deleted mRNA in muscles of mdx mice injected with the same dose of AAV9-Dmd CRISPR ranged from only 1.3% to 8.7% (FIG. 4C). Quantification of SaCas9 and gRNA expression indicated 6.7 to 19 times higher SaCas9 expression and 3.5 to 7.8 times higher gRNA expression in the muscles of MyoAAV 1A injected mice compared to AAV9 injected animals (FIGS. 24F, 24C).

Figures 18I, 18J, 18K, 18L:
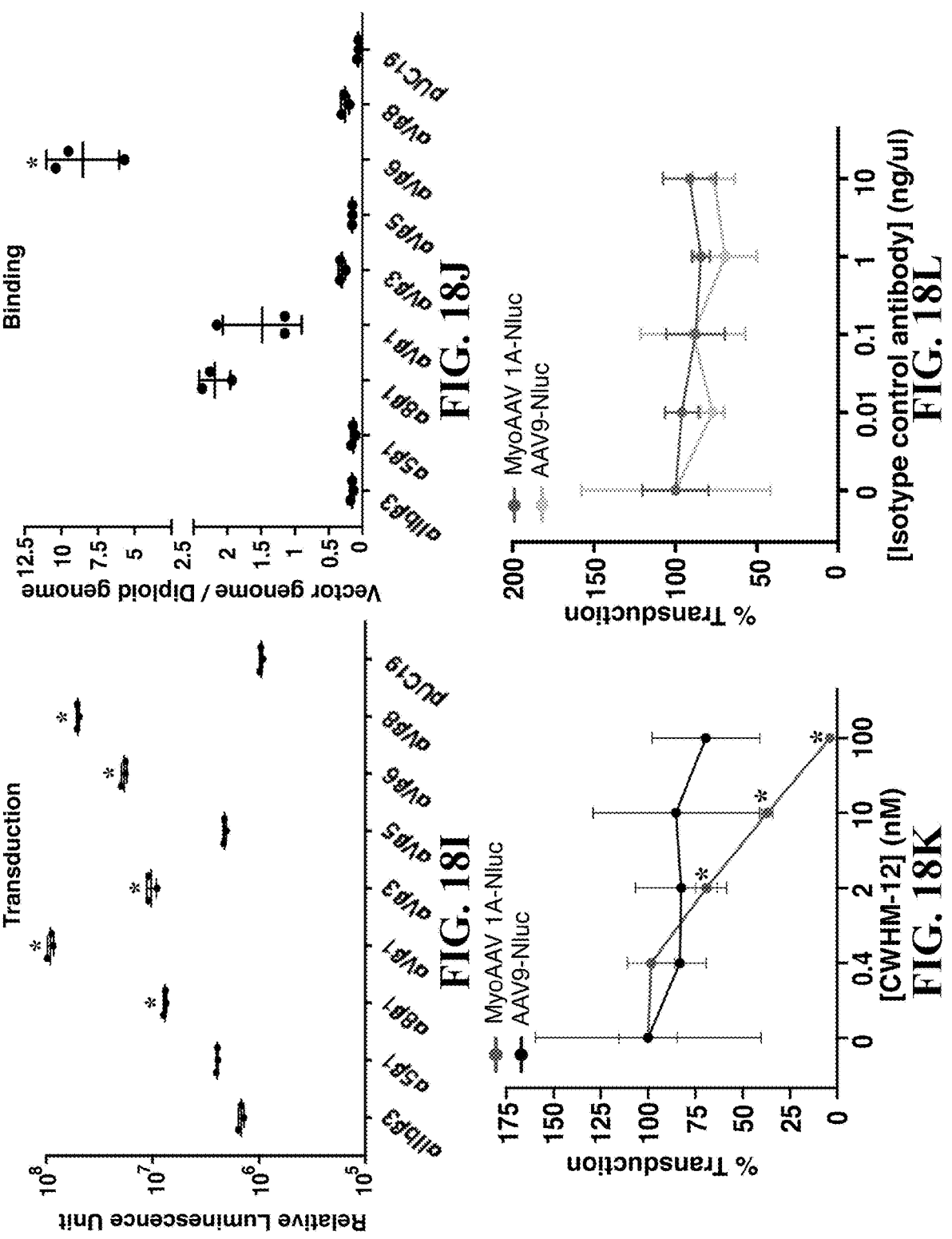

Several findings point to the superior rescue of dystrophin expression with MyoAAV 1A-Dmd CRISPR compared to AAV9-Dmd CRISPR. Immunofluorescence and western blot analysis confirmed greater and more widespread dystrophin restoration in muscles of mice injected with Myo-AAV 1A-Dmd CRISPR as compared to AAV9-Dmd CRISPR (FIGS. 18I-18J and 24F). Physiological assessment of the Tibialis Anterior (TA) muscles of AAV-CRISPR treated animals demonstrated significantly higher specific force (FIG. 4D) and decreased percent force drop after eccentric contraction (FIG. 18E) in MyoAAV 1A-Dmd CRISPR injected mdx mice when compared to either vehicle or AAV9-Dmd CRISPR injected controls. Thus, MyoAAV 1A exhibits markedly enhanced potency for delivery of therapeutic gene editing complexes to muscle compared to conventional and widely utilized AAV9.

MyoAAV 1A's performance for gene replacement after low-dose systemic administration was further assessed in a mouse model of XLMTM. Mtm1 knockout (KO) mice provide an excellent genetic and phenotypic model of XLMTM; they show marked muscle wasting, loss of mobility and dramatically shortened lifespans. 4 weeks-old Mtm1 KO mice were injected with 2E+12 vg/kg of AAV9 or MyoAAV 1A encoding the human MTM1 (hMTM1) expressed under the control of the MHCK7 promoter (FIG. 24E). We measured body weight, activity, and survival for each group over an 8 month period (FIG. 18F). The dose of virus that we used in this experiment was 50-150 times lower than the dose being used in an ongoing human clinical trial for XLMTM (clinical trials.gov identifier: NCT03199469) and 15-250 times lower than the doses used in previously published preclinical studies for XLMTM gene therapy (Childers et al., 2014; Elverman et al., 2017; Mack et al., 2017).

MyoAAV 1A-MHCK7-hMTM1 injected mice manifested striking improvements in function and survival. All of the mice injected with 2E+12 vg/kg of AAV9-MHCK7-hMTM1 were minimally active and reached the humane endpoint for euthanasia between 11-21 weeks after the injection. In contrast, all of the mice injected with the same dose of MyoAAV 1A-MHCK7-hMTM1 survived with a similar trajectory to wildtype mice, and also gained weight and were noticeably more active compared to the AAV9-injected mice throughout the study (FIGS. 29G-29J and 24G). Quantification of hMTM1 mRNA expression and vector genome biodistribution in the gastrocnemius, quadriceps, heart, and liver of the injected mice 4 weeks after AAV administration showed significantly higher transgene expression and vg/dg in the muscles of the MyoAAV 1A-MHCK7-hMTM1 injected mice compared to the AAV9-MHCK7-hMTM1 injected animals, while expression of hMTM1 and number of vg/dg in the liver of mice injected with MyoAAV 1A-MHCK7-hMTM1 was lower than animals injected with AAV9-MHCK7-hMTM1 (FIGS. 17L and 17M). Western blot analysis confirmed higher hMTM1 protein expression in the gastrocnemius and quadriceps of mice injected with MyoAAV 1A-MHCK7-hMTM1 (FIG. 17N) and physiological analysis of the Extensor digitorum longus (EDL) muscle demonstrated significantly higher specific force in MyoAAV 1A-MHCK7-hMTM1 injected mice when compared to either vehicle or AAV9-MHCK7-hMTM1 injected controls (FIG. 17O).

Additional results from systemic administration of Myo-AAV-Dmd CRISPR and MyoAAV-human MTM1 in mouse models of DMD and XLMTM, respectively are shown in FIGS. 17A-17I and 17K. MyoAAV 1A is dependent on integrin heterodimers for transducing mouse and human primary myotubes Given the presence of an RGD motif in MyoAAV and all of the other top variants from the selection, the role of RGD-binding integrin heterodimers in MyoAAV 1A transduction was assessed. The RGD motif was first recognized in 1984 as the minimal sequence in fibronectin that facilitates binding to its receptor, later identified as the integrin heterodimer $\alpha 5\beta 1$ (Pierschbacher and Ruoslahti, 1984; Pytela et al., 1985). RGD has since been identified as a recognition motif for several different integrin heterodimers; specifically, $\alpha IIb\beta 3$, $\alpha 5\beta 1$, $a8\beta 1$, $\alpha V\beta 1$, $\alpha V\beta 3$, $\alpha V\beta 5$, $\alpha V\beta 6$, and $\alpha V\beta 8$ (Ruoslahti, 1996). The transduction efficiency of MyoAAV 1A-CMV-Nluc in HEK293 cells transfected with plasmids encoding for each of these eight human RGD-binding integrin heterodimers or the pUC19 plasmid as a control was compared. Overexpression of $\alpha 8\beta 1$, $\alpha V\beta 1$, $\alpha V\beta 3$, $\alpha V\beta 6$, or $\alpha V\beta 8$ increased the transduction efficiency of MyoAAV 1A in the transfected HEK293 cells compared to pUC19-transfected controls (FIGS. 18I and 25A-25K).

Figure 26J:
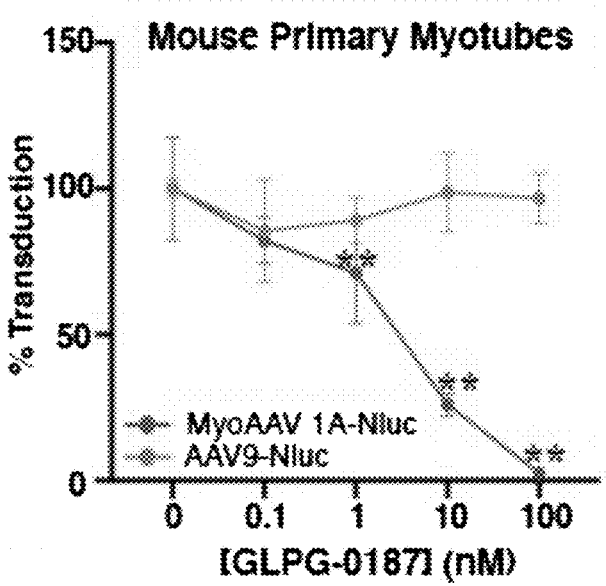

Next, the effect of different integrin heterodimers on the binding efficiency of MyoAAV 1A to the cell surface was analyzed through overexpression experiments. The vector genomes bound to the surface of HEK293 cells transfected with each of the eight RGD-binding integrin heterodimers or a pUC19 control plasmid was quantified, and it was found that $\alpha V\beta 6$, and to a lesser extent $\alpha 8\beta 1$ and $\alpha V\beta 1$ increased binding of MyoAAV 1A to integrin-transfected cells compared to pUC19-transfected controls (FIG. 18J). The impact of two different pan-$\alpha V$ integrin antagonists (CWHM-12 and GLPG-0187) on MyoAAV 1A transduction efficiency in primary cells was also investigated. Both inhibitors impeded MyoAAV 1A transduction in a dose-dependent manner in both mouse (FIGS. 26A and 26J) and human (FIGS. 18K, 18D and 26C-26H) primary skeletal muscle myotubes, while neither inhibitor had a dose-dependent effect on AAV9 transduction efficiency. These results demonstrate that inhibiting $\alpha V$-containing integrin heterodimers almost completely eliminates the ability of MyoAAV 1A to transduce both mouse and human primary myotubes.

To further elucidate the impact of individual $\alpha V$-containing integrin heterodimers on MyoAAV 1A's binding affinity, we transduced human primary myotubes with MyoAAV 1A or AAV9 after pre-incubation of these viruses with $\alpha V\beta 1$, $\alpha V\beta 3$, $\alpha V\beta 6$, $\alpha V\beta 8$, or maltose binding protein (MBP) recombinant proteins. Remarkably, pre-incubation of Myo-AAV 1A with increasing concentrations of $\alpha V\beta 6$ resulted in a dose-dependent inhibition of transduction of human primary myotubes, while none of the other recombinant proteins that we tested had a dose-dependent effect on transduction of the cells by either MyoAAV 1A or AAV9 (FIGS. 18E, 18F). Conversely, pre-incubation of human myotubes with increasing concentrations of anti-αVβ6 antibody decreased transduction efficiency by MyoAAV 1A in a dose-dependent manner and did not affect transduction of myotubes by AAV9 (FIGS. 18G, 18L). These data suggest that among the αV-containing integrin heterodimers that have the capability to facilitate MyoAAV 1A transduction, αVβ6 has the highest affinity to bind to this capsid variant. Additionally, αVβ6 must be available on the surfaces of human muscle cells to enable their optimal transduction by MyoAAV 1A.

Given the importance of glycans with terminal sialic acid on transduction and binding of AAV9 to the cells (Bell et al., 2011), next the role of glycans and sialic acid on MyoAAV 1A transduction and binding was assessed. Treatment of HEK293 cells with neuraminidase (NA), which cleaves the sialic acid linkages to glycans on the cell surface, resulted in 172 times higher transduction and 4 times more effective binding by MyoAAV 1A to the treated cells compared to untreated controls (FIGS. 26K, 26L). It was further tested if the terminal galactose is important in transduction and binding of MyoAAV 1A. Addition of *Erythrina cristagalli* lectin (ECL), which binds to terminal galactose on the cell surface, to NA-treated HEK293 cells significantly inhibited binding and transduction by both AAV9 and MyoAAV 1A, while it didn't have an effect on AAV2 binding and transduction (FIGS. 26M, 26N). These results demonstrated that similar to AAV9, MyoAAV 1A transduction and binding to the cells is enhanced by removal of sialic acid and exposing galactose on the cell surface.

The dependency of MyoAAV 1A transduction on the previously identified AAV receptor (AAVR) was evaluated. AAVR is a rapidly endocytosed plasma membrane protein required for effective transduction of most known AAV serotypes except AAV4 and AAVrh32.33 (Dudek et al., 2018; Pillay et al., 2016). HEK293FT AAVR knockout (KO) and the parental HEK293FT wild type (WT) cells were transduced with AAV4-, AAV2-, AAV9-, or MyoAAV 1A-CMV-Nluc and found that, similar to AAV2 and AAV9, MyoAAV transduction requires AAVR expression (FIG. 26O).

To investigate if integrin heterodimers and AAVR play redundant roles in MyoAAV 1A transduction, we overexpressed α8β1, αVβ1, αVβ3, αVβ6, or αVβ8 in the HEK293FT AAVR KO cells in the presence or absence of AAVR overexpression and then transduced the cells with MyoAAV 1A-CMV-Nluc. These results demonstrated that while overexpression of integrin heterodimers increased MyoAAV 1A transduction efficiency in AAVR KO cells compared to the mock transfected controls, integrin overexpression was not sufficient to rescue transduction to levels observed in AAVR KO cells overexpressing AAVR or in WT HEK293FT cells (FIG. 26I). This data suggests that integrin heterodimers and AAVR play distinct roles in and are likely utilized at different stages of MyoAAV 1A transduction.

Additional Rounds of In Vivo Evolution Using DELIVER Generates Second-Generation RGD-Containing Muscle-Tropic Variants in Mice Given the importance of the RGD motif's interaction with integrin heterodimers for transduction of myotubes by MyoAAV 1A, it was hypothesized that modifying amino acids adjacent to the motif could improve this interaction, generating even more potent muscle-tropic capsid variants. Based on a predicted structure for the MyoAAV 1A hypervariable region VIII surface loop, we identified amino acids in positions 586, 587, and 588 upstream and positions 592, 593, 594, and 595 downstream of the RGD motif as likely to be located in the surface loop of MyoAAV 1A (FIG. 19A). A diverse library of capsids was then generated, each with the RGD motif fixed at positions 589, 590, and 591 and varying amino acids in the above-mentioned flanking positions (FIG. 19B).

Two rounds of in vivo selection for muscle-tropic variants using DELIVER was performed in C57BL/6J and mdx mice. The second-round RGD-fixed virus library was injected at two different doses (1E+12 vg and 1E+11 vg per mouse) to identify variants that effectively transduce muscle tissue both at high and low dose (FIG. 19B). It was found that among our top hits from these selections, glycine and alanine were enriched at position 588 and glutamine was enriched at position 592. A variant containing the GPGRGDQTTL (SEQ ID NO: 2) sequence emerged as the most highly selected muscle-tropic capsid at both the 1E+12 and 1E+11 dose from the second round of selection (FIG. 19B). This was named this second-generation variant MyoAAV 2A (also referred to in this document as EMyoAAV or enhanced MyoAAV), and used it for further characterization.

Figure 19L:
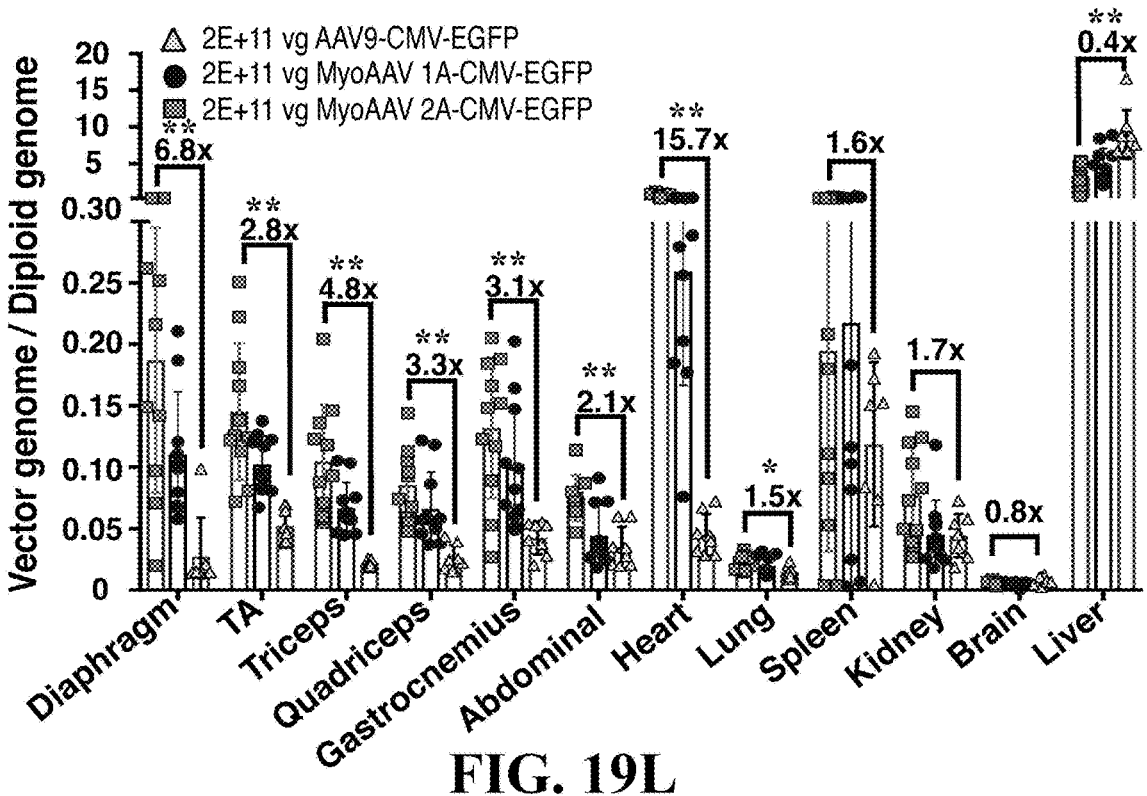

Transducation efficiency of MyoAAV 2A in different mouse tissues was examined after systemic delivery of a low dose of the virus. C57BL/6J mice were injected with 2E+11 vg (~8E+12 vg/kg) of AAV9-, MyoAAV 1A-, or MyoAAV 2A-CMV-EGFP and transgene expression and vector genome biodistribution in various tissues was analyzed. Whole tissue fluorescent imaging demonstrated that systemic gene delivery by MyoAAV 2A results in higher levels of transgene expression compared to MyoAAV 1A or AAV9 across different skeletal muscles (FIGS. 19C-19D). Quantification of EGFP mRNA revealed that MyoAAV 2A transduces mouse skeletal muscles 10-80 times more efficiently, and heart 17 times more efficiently than AAV9. Furthermore, transgene mRNA expression was 2.5 times lower in the liver of MyoAAV 2A-injected animals compared to AAV9-injected mice (FIG. 19E). Similarly, vector genome biodistribution analysis showed that MyoAAV 2A-injected mice had significantly higher vg/dg in skeletal muscle and heart, and significantly lower vg/dg in the liver compared to AAV9-injected animals (FIG. 19L).

Next, the efficiency and integrin dependency of MyoAAV 2A for transducing human primary myotubes. Remarkably, MyoAAV 2A transduced human primary myotubes 128 times more efficiently compared to AAV9 and 4.1 times higher than MyoAAV 1A (FIG. 19F). Increasing concentrations of pan-αV integrin antagonist GLPG-0187 resulted in a dose-dependent decrease in the transduction efficiency of MyoAAV 2A (FIG. 19G), confirming that MyoAAV 2A infectivity remains dependent on αV-containing integrin heterodimers expressed on target cells.

To evaluate the binding affinity of MyoAAV 2A for different individual αV integrin heterodimers, we pre-incubated MyoAAV 2A or AAV9 with αVol, αVβ3, αVβ6, αVβ8, or maltose binding protein (MBP) recombinant proteins before transducing human primary myotubes. Interestingly, and in contrast to results obtained in these same assays with MyoAAV 1A (FIG. 18E), all four αV-containing integrin heterodimers tested inhibited transduction of human myotubes by MyoAAV 2A in a dose-dependent manner (FIG. 19I1), while there was no dose-dependent effect on AAV9 transduction (FIG. 19I). This result suggests that amino acid substitutions included in MyoAAV 2A enable higher affinity binding to a broader class of αV integrin heterodimers when compared to MyoAAV 1A, which depends mainly on αVβ6 .

Figure 19M:
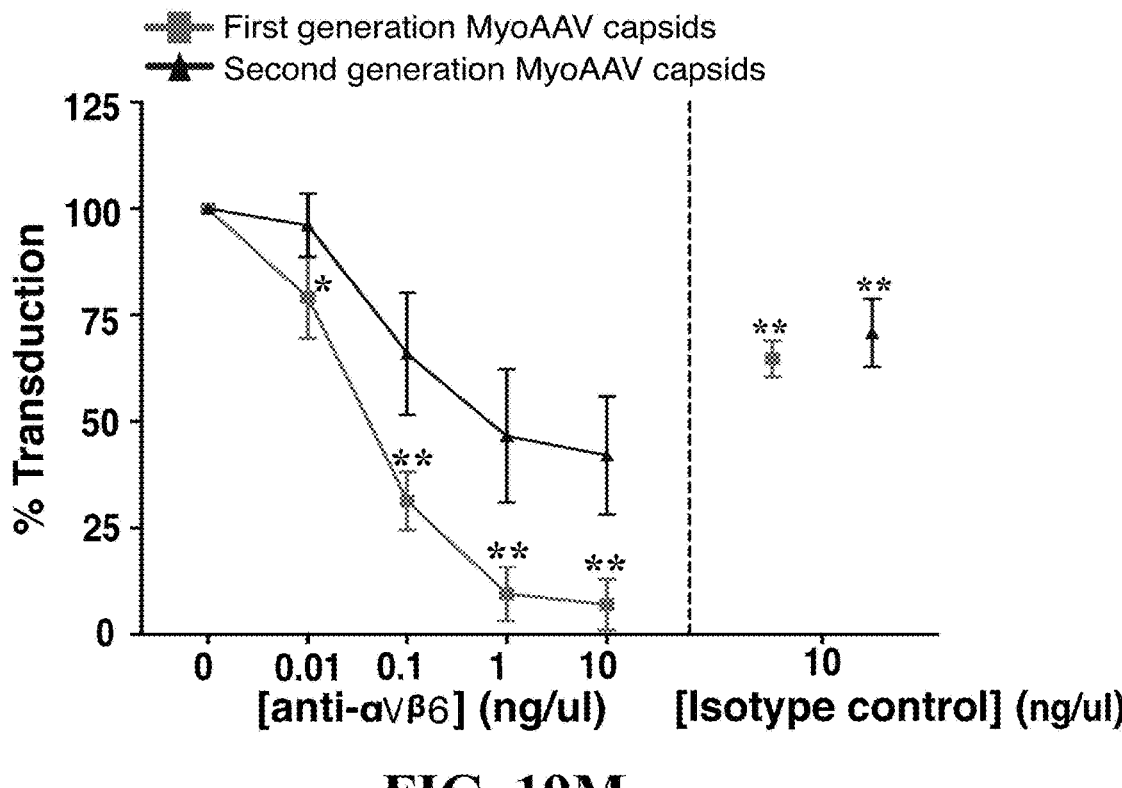

The dependency of the top first-generation and second-generation capsid variants that were evolved using DELIVER in mice were examined on αVβ6 heterodimer. Human primary myotubes were pre-incubated with anti-αVβ6 antibody before transducing the cells with the top first-generation (MyoAAV 1A, MyoAAV 1B, MyoAAV 1C, MyoAAV 1E, MyoAAV 1F) and second-generation (Myo-AAV 2A, MyoAAV 2B, MyoAAV 2C, MyoAAV 2D, Myo-AAV 2E, MyoAAV 2F) mouse variants. While antibody binding inhibited transduction of human myotubes to some degree by all of these variants, the first-generation capsids were significantly more dependent on αVβ6 for myotube transduction (FIG. 19M). MyoAAV 2A shows great therapeutic potential after injection of a low dose of virus In order to assess the potential future therapeutic relevance of MyoAAV 2A in comparison with capsids currently in clinical testing for human neuromuscular disease, the transduction efficiency of MyoAAV 2A was compared to both AAV9 and AAVrh74, which are being investigated in ongoing clinical trials for DMD (clinical trials.gov identifiers: NCT03362502, NCT03368742, and NCT03769116). Systemic administration of a function-complementing dystrophin mini-gene (termed microdystrophin), expressed from the muscle-specific MHCK7 promoter and delivered using the AAVrh74 vector, has shown promising results in a recently reported human clinical trial involving four DMD patients. In this trial, administering a high viral dose of 2E+14 vg/kg resulted in transgene expression in the muscle and functional improvement in disease phenotype (Mendell et al., 2020).

MyoAAV 2A-mediated gene delivery was compared to that of both AAVrh74 and AAV9 vectors, and further investigated performance in a DBA/2J-mdx mouse model of DMD. In a longitudinal in vivo imaging experiment, we injected adult BABL/cJ mice with a low dose (2E+11 vg, representing ~8E+12 vg/kg) of AAVrh74, AAV9, or Myo-AAV 2A encoding the CMV-Fluc reporter gene. MyoAAV 2A-injected mice demonstrated dramatically higher bioluminescence signal in the limbs and throughout the body as compared to those receiving AAVrh74 or AAV9 (FIGS. 19J-19K). Systemic delivery of MyoAAV 2A or AAV9 carrying a microdystrophin transgene (CK8-microdystro-phin-FLAG) into the DBA/2J-mdx mouse model of DMD using an equivalent, low dose (2E+13 vg/kg) of each AAV was then tested. MyoAAV 2A-injected animals demonstrated relatively greater and more widespread expression of microdystrophin, localized at the sarcolemma, in multiple muscle groups as compared to AAV9-injected animals (FIG. 20A). Western blot confirmed higher levels of microdystrophin protein in muscles of mice injected with MyoAAV 2A, compared to AAV9 injected animals (FIG. 20B). Quantitative RT-PCR indicated 7.6-15 times higher levels of microdystrophin mRNA in skeletal muscles of mice injected with MyoAAV 2A-CK8-microdystrophin-FLAG as compared to AAV9-CK8-microdystrophin-FLAG (FIG. 20C).

Lastly, the abundance of vector genomes and muscle function in the MyoAAV 2A-injected mice as compared to AAV9-injected animals was assessed. MyoAAV 2A delivered 12-46 times higher numbers of vg/dg in skeletal muscles of DBA/2J-mdx mice and 2.5 times lower vg/dg in the liver, as compared to AAV9 (FIG. 20D). Strikingly, while AAV9-injected animals had more than 40 times higher numbers of vg/dg in their liver compared to their muscles, the MyoAAV 2A-injected mice had similar levels in their liver and muscles. Quantification of muscle specific force and percent force drop after eccentric damage demonstrated that TA muscles of MyoAAV 2A injected DBA/2J-mdx mice recovered significantly greater specific force and were more protected from damage compared to muscles from mice receiving equal doses of AAV9 and to vehicle-injected animals (FIGS. 20E-20F).

In Vivo Directed Evolution Identifies MyoAAV Class of Capsid Variants as the Top Hits in Cynomolgus Macaques To identify capsid variants that enable potent muscle-directed gene delivery after systemic administration in NHPs, in vivo directed evolution of AAV9 was performed using DELIVER in cynomolgus macaques. Two rounds of in vivo selections starting from a random 7-mer peptide insertion at the 588 site identified 6 variants containing the RGD motif as the top hits (FIG. 28A). These results provided evidence for high muscle tropism of MyoAAV class of capsids in primates after systemic administration. In order to select for further evolved MyoAAV class of variants that enable potent muscle transduction across species, a round of in vivo selection in NHPs using the top 120,000 variants identified from the first round of our RGD-fixed selection in mice was performed (FIG. 28B). Interestingly, it was found that Tyrosine was enriched at the first position after the RGD motif in the top hits that we identified in NHPs.

The transduction efficiency of the most highly muscle-tropic variants that were identified in NHPs (MyoAAV 3A-F and MyoAAV 4A-E), as well as 4 muscle-tropic variants identified in mice that transduced human primary myotubes with high efficiency (MyoAAV 1C, MyoAAV 1E, MyoAAV 2A, and MyoAAV 2E) (FIG. 28C) were benchmarked with AAVrh74 and AAV9 in mice and NHPs. rAAVs were generated using each of the capsid variants, as well as AAVrh74 and AAV9, to encode for the human Frataxin (hFXN) transgene under the control of the CBh promoter. Recombinant AAVs produced with each of the capsids contained a unique set of barcodes at the 3' untranslated region (3' UTR) of the transgene (FIG. 28D). A pool of the rAAVs containing equal titer of all the 17 viruses was prepared and the pool was then administered to both Cynomolgus Macaques and mice. Quantification of transgene mRNA expression in different tissues of NHPs identified MyoAAV 4A, MyoAAV 4E, MyoAAV 3A, and MyoAAV 4C as the most potent variants in transducing different skeletal muscles compared to AAVrh74 and AAV9 in macaques (FIGS. 28D-28E and 30B). These 4 variants also transduce different mouse skeletal muscles very effectively and are detargeted from the liver compared to AAVrh74 and AAV9 in both mice and NHPs (FIGS. 30A and 28E).

To evaluate the production yield for the top 4 capsids, we produced rAAVs with the top 4 variants as well as AAVrh74 and AAV9 using 6 different transgenes. AAV9 was the best producer among the capsids that we tested and all the MyoAAV variants produced similar or higher titers of virus compared to AAVrh74 (FIG. 28F).

The transduction dependency and affinity of the top 4 capsid variants was next assessed on αV integrin heterodimers. Increasing concentrations of GLPG-0187 resulted in a dose-dependent decrease in transduction for all the 4 variants in human primary myotubes (FIG. 28G). Pre-incubation of the capsid variants with αVβ1, αVβ3, αVβ6, αVβ8, or MBP demonstrated that all the 4 top variants have the highest affinity for αVβ6, followed by αVβ8 and αVβ3 (FIGS. 28H-28I). Consistent with these results, treating human primary myotubes with increasing concentrations of the αVβ6 antibody resulted in a dose dependent decrease in transduction by all the 4 variants (FIG. 28J). Furthermore, analyzing transduction efficiency of the top 4 variants in AAVR KO and wild type cells revealed that all these variants are dependent on AAVR for transduction (FIG. 28K).

Lastly, given the high dependency and affinity of the MyoAAV class of capsid variants for αVβ6, we analyzed expression of integrin β6, which only forms a heterodimer with αV (Hynes, 2002), in mouse, NHP and human muscles. Immunofluorescence analysis demonstrated expression of integrin β6 in the muscles from all three species (FIG. 30C).

Discussion

This example at least describes and demonstrates a strategy for engineering and selecting effective AAV capsid variants for potent gene delivery into any tissue and/or cell type of interest. DELIVER combines three critical features required for a stringent and widely applicable AAV capsid engineering strategy: (i) DELIVER enables selection of capsid variants that not only physically bind or enter the cells in vivo, but also functionally transduce the tissue and express their transgenes in specific cell types. (ii) DELIVER can be applied in any mammalian species, in vivo or in vitro, enabling the identification of vector systems that can be translated directly from preclinical animal models to human applications. (iii) DELIVER supports the screening of extremely diverse capsid libraries and is fully compatible with directed evolution approaches.

Ultimately, the interest in developing the DELIVER system was rooted in its potential benefits for advancing genomic medicine through the creation of more potent and selective viral vectors, and the muscle-directed AAV capsid variants identified in this study serve as an important proof-of-concept for this application. However, equally important to increasing muscle potency of the capsid was ensuring decreased transduction of the liver. The liver is a major site of transduction by naturally-occurring AAV capsids and a target of toxicity associated with high-dose administration of AAV vectors in large animal models (Hinderer et al., 2018) and in human patients (Morales et al., 2020). In particular, two gene therapy trials (clinical trial identifiers NCT03368742 and NCT03199469) were put on clinical hold by the FDA due to severe adverse effects associated with liver toxicity. These recent setbacks in the clinical application of AAV-based gene therapy for genetic myopathies (Morales et al., 2020) highlight the exceptional challenges for delivery to the muscle and illustrate the clear need for potent-muscle directed AAV variants such as those described in this Example.

DELIVER was applied to develop novel AAV capsids that, when administered systemically, could transport genetic cargo to skeletal muscles throughout the body with greater efficiency and selectivity, and potentially a more favorable safety profile, than capsids currently used in clinical trials and preclinical discovery efforts. Two rounds of stringent, transcript-based selection uncovered a novel class of RGD-containing capsid variants, including Myo-AAV 1A, which exhibited more than 10 times greater efficiency for muscle transduction than capsids in broad use. Furthermore, the muscle-directed AAVs selected using DELIVER showed notably reduced targeting of the liver. These two attributes suggest that this new class of AAV capsids could lower the dose of virus needed to achieve therapeutic levels of target cell transduction and mitigate potentially detrimental consequences of transduction in liver cells, where it is unnecessary for therapeutic benefit.

DELIVER identified numerous variants harboring a critical RGD motif, which is known to bind to integrin heterodimers, and further work suggested this motif's functional importance for transducing mouse and human primary myotubes. The screen of muscle-targeting capsids in mice and NHPs identified a striking enrichment of variants containing RGD as the first three amino acids of the inserted 7-mer peptide. The top variants from the in vivo selections showed interaction with integrin heterodimers and could be blocked from target cell transduction by soluble integrin heterodimers, anti-integrin antibodies, and small molecule antagonists. This observed integrin dependency was conserved across mouse and human primary myotubes, suggesting a common mechanism of action for MyoAAV class of capsids transduction. MyoAAV class of capsids' interaction with integrins appears to act in parallel with the previously identified AAV binding protein AAVR, which was also necessary for target cell transduction by these variants. Among the RGD-binding integrin heterodimers, αVβ6 showed the highest affinity for binding and was specifically required on the surfaces of human muscle cells to enable their transduction by the top variants that we identified. These observations are particularly interesting in light of prior studies of AAV2, which lacks the RGD motif but still utilizes integrin heterodimers, including a531 and αVβ5 as co-receptors for virus internalization, apparently via a related NGR motif (Asokan et al., 2006; Summerford et al., 1999).

While more work is needed to understand the molecular basis underlying the RGD-integrin heterodimer interaction for AAV-mediated gene delivery to muscle, its importance for our discovered class of muscle-directed vectors enabled us to further evolve these capsids by systematically varying the flanking residues around the essential RGD motif. This second round of evolution identified additional variants capable of binding a broader subset of integrin heterodimers with even greater affinity than MyoAAV 1A. The top second-generation variant in mice, MyoAAV 2A, showed dramatically increased potency for muscle transduction (up to 128 times that of AAV9) in both in vivo and in vitro assays, while maintaining low liver transduction, and its success provides a framework for the iterative development of ultra-high potency vectors for other target tissues of interest.

With our goal of advancing genomic medicine, we applied MyoAAV 1A and MyoAAV 2A as delivery vectors for gene editing and gene therapy approaches that are currently under development and testing for human genetic myopathies. These studies employed well established mouse models of DMD and XLMTM, in which targeted DNA excision and transcript "re-framing" (Nelson et al., 2016; Tabebordbar et al., 2016) or genetic complementation with a full-length or miniaturized therapeutic transgene (Childers et al., 2014; Hakim et al., 2017) previously have shown functional benefit. In both models, notable therapeutic effects were observed, including rescue of expression of the disease-targeted proteins, significant increases in muscle strength and performance and, in the case of XLMTM, a striking rescue from disease-induced mortality that drastically extended the observed lifespan of MyoAAV 1A-treated animals beyond the average lifespan of untreated and AAV9-treated controls.

The therapeutic results are all the more notable given that they were achieved after injecting 10-250 times lower doses of therapeutic vector than those used in previously published preclinical studies based on the same gene therapy approaches (Childers et al., 2014; Elverman et al., 2017; Hakim et al., 2017; Mack et al., 2017) or in currently ongoing human clinical trials (clinical trials.gov identifiers: NCT03362502, NCT03368742, NCT03769116, and NCT03199469). The lower dosage requirements for achieving therapeutic efficacy with these new AAV variants can have substantial benefits in clinical applications, including improved expression and safety profile and reduced manufacturing costs.

Finally, variants from MyoAAV class of capsids were identified as the most highly muscle-tropic variants after in vivo directed evolution in NHPs. These results suggest direct applicability of the MyoAAV class of capsid variants across mice, NHPs, and humans as these variants showed broad activity for muscle transduction in multiple inbred mouse strains, including C57BL/6J, BALB/cJ, DBA/2J, mdx, and DBA/2J-mdx, as well as in Cynomolgus Macaques, and cultures of human primary myoblasts obtained from multiple donors. Furthermore, the necessity of integrin heterodimers for MyoAAV class of capsids' infectivity in both mouse and human muscle cells strongly suggests a conserved mode of transduction in mouse and human muscle that could accelerate the timeline for developing and implementing new gene therapy approaches for a wide range of genetic myopathies.

A recent publication by Weinmann et al (Weinmann et al., 2020) reported identification of a muscle-tropic capsid variant after testing transduction efficiency of 183 wild type and modified AAV capsids following systemic administration in mice. Interestingly, the muscle-tropic variant that Weinmann et al identified from their screen contains an RGD motif presented on the capsid surface and could serve as an independent validation of our findings. However, the authors didn't characterize the mechanism of transduction and efficiency of transduction by their variant in NHPs and human cells. The findings in this Example from in vivo directed evolution of capsids in mice and NHPs demonstrate that the sequence of amino acids around the RGD motif in the inserted peptide plays a crucial role in defining transduction efficiency of capsids in different species. Although the most highly muscle-tropic variants that were identified from in vivo directed evolution in mice and NHPs all contain the RGD motif, as demonstrated in this Example, sequence of amino acids around the motif for individual variants identified as the top hits in each species is different. For example, MyoAAV 2A is the top second-generation variant that we identified in mice and it's highly potent in transducing mouse muscles, but it doesn't transduce NHP muscles with high efficiency after systemic administration. In fact, all the variants that were identified from these NHP selections herein outperformed the variants identified in mice when tested for muscle transduction after systemic delivery as recombinant AAVs in NHPs. Fortunately, the top capsid variants from our NHP selections are highly potent in transducing mouse muscles as well, making them highly applicable for therapeutic development. These results highlight the importance of using in vivo directed evolution with a stringent selection strategy to select the most potent capsid variants in primates.

In summary, this Example describes and demonstrates the evolution, engineering, and mechanistic characterization of a family of highly potent muscle-directed AAV capsid variants across species. Also demonstrated herein is these vectors' therapeutic efficacy, even at low dosage, in multiple mouse models of genetic muscle disease. These vectors have the potential to advance muscle-directed therapeutic gene delivery for a large number of musculoskeletal disorders. More broadly, the DELIVER system described here provides a highly adaptable platform for identifying precise AAV capsid variants for any tissue or cell type in the body, an innovation that could greatly expand the clinical and experimental applications of this vector system across fields and disciplines. Adoption of DELIVER to additional tissue and organ systems will have a far-reaching impact in accelerating the development and translation of novel gene therapy and other genomic medicine approaches for a variety of human diseases.

References For Example 7

Asokan, A., Hamra, J. B., Govindasamy, L., Agbandje-McKenna, M., and Samulski, R. J. (2006). Adeno-associated virus type 2 contains an integrin alpha5beta1 binding domain essential for viral cell entry. J Virol 80, 8961-8969.

Bell, C. L., Vandenberghe, L. H., Bell, P., Limberis, M. P., Gao, G. P., Van Vliet, K., Agbandje-McKenna, M., and Wilson, J. M. (2011). The AAV9 receptor and its modification to improve in vivo lung gene transfer in mice. J Clin Invest 121, 2427-2435.

Berry, G. E., and Asokan, A. (2016). Cellular transduction mechanisms of adeno-associated viral vectors. Curr Opin Virol 21, 54-60.

Borner, K., Kienle, E., Huang, L. Y., Weinmann, J., Sacher, A., Bayer, P., Stullein, C., Fakhiri, J., Zimmermann, L., Westhaus, A., et al. (2020). Pre-arrayed Pan-AAV Peptide Display Libraries for Rapid Single-Round Screening. Mol Ther 28, 1016-1032.

Childers, M. K., Joubert, R., Poulard, K., Moal, C., Grange, R. W., Doering, J. A., Lawlor, M. W., Rider, B. E., Jamet, T., Daniele, N., et al. (2014). Gene therapy prolongs survival and restores function in murine and canine models of myotubular myopathy. Sci Transl Med 6, 220ra210.

Choudhury, S. R., Fitzpatrick, Z., Harris, A. F., Maitland, S. A., Ferreira, J. S., Zhang, Y., Ma, S., Sharma, R. B., Gray-Edwards, H. L., Johnson, J. A., et al. (2016). In Vivo Selection Yields AAV-B1 Capsid for Central Nervous System and Muscle Gene Therapy. Mol Ther 24, 1247-1257.

Dalkara, D., Byrne, L. C., Klimczak, R. R., Visel, M., Yin, L., Merigan, W. H., Flannery, J. G., and Schaffer, D. V. (2013). In vivo-directed evolution of a new adeno-associated virus for therapeutic outer retinal gene delivery from the vitreous. Sci Transl Med 5, 189ra176.

Deverman, B. E., Pravdo, P. L., Simpson, B. P., Kumar, S. R., Chan, K. Y., Banerjee, A., Wu, W. L., Yang, B., Huber, N., Pasca, S. P., et al. (2016). Cre-dependent selection yields AAV variants for widespread gene transfer to the adult brain. Nat Biotechnol 34, 204-209.

DiMattia, M. A., Nam, H. J., Van Vliet, K., Mitchell, M., Bennett, A., Gurda, B. L., McKenna, R., Olson, N. H., Sinkovits, R. S., Potter, M., et al. (2012). Structural insight into the unique properties of adeno-associated virus serotype 9. J Virol 86, 6947-6958.

Ding, W., Zhang, L., Yan, Z., and Engelhardt, J. F. (2005). Intracellular trafficking of adeno-associated viral vectors. Gene Ther 12, 873-880.

Duan, D. (2018). Systemic AAV Micro-dystrophin Gene Therapy for Duchenne Muscular Dystrophy. Mol Ther 26, 2337-2356.

Dudek, A. M., Pillay, S., Puschnik, A. S., Nagamine, C. M., Cheng, F., Qiu, J., Carette, J. E., and Vandenberghe, L. H. (2018). An Alternate Route for Adeno-associated Virus (AAV) Entry Independent of AAV Receptor. J Virol 92.

Elverman, M., Goddard, M. A., Mack, D., Snyder, J. M., Lawlor, M. W., Meng, H., Beggs, A. H., Buj-Bello, A., Poulard, K., Marsh, A. P., et al. (2017). Long-term effects of systemic gene therapy in a canine model of myotubular myopathy. Muscle Nerve 56, 943-953.

Gao, G., Lu, Y., Calcedo, R., Grant, R. L., Bell, P., Wang, L., Figueredo, J., Lock, M., and Wilson, J. M. (2006). Biology of AAV serotype vectors in liver-directed gene transfer to nonhuman primates. Mol Ther 13, 77-87.

Hakim, C. H., Wasala, N. B., Pan, X., Kodippili, K., Yue, Y., Zhang, K., Yao, G., Haffner, B., Duan, S. X., Ramos, J., et al. (2017). A Five-Repeat Micro-Dystrophin Gene Ameliorated Dystrophic Phenotype in the Severe DBA/2J-mdx Model of Duchenne Muscular Dystrophy. Mol Ther Methods Clin Dev 6, 216-230.

Hinderer, C., Katz, N., Buza, E. L., Dyer, C., Goode, T., Bell, P., Richman, L. K., and Wilson, J. M. (2018). Severe Toxicity in Nonhuman Primates and Piglets Following High-Dose Intravenous Administration of an Adeno-Associated Virus Vector Expressing Human SMN. Hum Gene Ther 29, 285-298.

Hordeaux, J., Wang, Q., Katz, N., Buza, E. L., Bell, P., and Wilson, J. M. (2018). The Neurotropic Properties of AAV-PHP.B Are Limited to C57BL/6J Mice. Mol Ther 26, 664-668.

Hynes, R. O. (2002). Integrins: bidirectional, allosteric signaling machines. Cell 110, 673-687.

Korbelin, J., Sieber, T., Michelfelder, S., Lunding, L., Spies, E., Hunger, A., Alawi, M., Rapti, K., Indenbirken, D., Muller, O. J., et al. (2016). Pulmonary Targeting of Adeno-associated Viral Vectors by Next-generation Sequencing-guided Screening of Random Capsid Displayed Peptide Libraries. Mol Ther 24, 1050-1061.

Li, C., and Samulski, R. J. (2020). Engineering adeno-associated virus vectors for gene therapy. Nat Rev Genet 21, 255-272.

Li, C., Wu, S., Albright, B., Hirsch, M., Li, W., Tseng, Y. S., Agbandje-McKenna, M., McPhee, S., Asokan, A., and Samulski, R. J. (2016). Development of Patient-specific AAV Vectors After Neutralizing Antibody Selection for Enhanced Muscle Gene Transfer. Mol Ther 24, 53-65.

Mack, D. L., Poulard, K., Goddard, M. A., Latournerie, V., Snyder, J. M., Grange, R. W., Elverman, M. R., Denard, J., Veron, P., Buscara, L., et al. (2017). Systemic AAV8-Mediated Gene Therapy Drives Whole-Body Correction of Myotubular Myopathy in Dogs. Mol Ther 25, 839-854.

Mendell, J. R., Sahenk, Z., Lehman, K., Nease, C., Lowes, L. P., Miller, N. F., Iammarino, M. A., Alfano, L. N., Nicholl, A., Al-Zaidy, S., et al. (2020). Assessment of Systemic Delivery of rAAVrh74.MHCK7.micro-dystrophin in Children With Duchenne Muscular Dystrophy: A Nonrandomized Controlled Trial. JAMA Neurol.

Michelfelder, S., Kohlschutter, J., Skorupa, A., Pfennings, S., Muller, O., Kleinschmidt, J. A., and Trepel, M. (2009). Successful expansion but not complete restriction of tropism of adeno-associated virus by in vivo biopanning of random virus display peptide libraries. PLoS One 4, e5122.

Morales, L., Gambhir, Y., Bennett, J., and Stedman, H. H. (2020). Broader Implications of Progressive Liver Dysfunction and Lethal Sepsis in Two Boys following Systemic High-Dose AAV. Mol Ther 28, 1753-1755.

Murrey, D. A., Naughton, B. J., Duncan, F. J., Meadows, A. S., Ware, T. A., Campbell, K. J., Bremer, W. G., Walker, C. M., Goodchild, L., Bolon, B., et al. (2014). Feasibility and safety of systemic rAAV9-hNAGLU delivery for treating mucopolysaccharidosis IIIB: toxicology, biodistribution, and immunological assessments in primates. Hum Gene Ther Clin Dev 25, 72-84.

Nelson, C. E., Hakim, C. H., Ousterout, D. G., Thakore, P. I., Moreb, E. A., Castellanos Rivera, R. M., Madhavan, S., Pan, X., Ran, F. A., Yan, W. X., et al. (2016). In vivo genome editing improves muscle function in a mouse model of Duchenne muscular dystrophy. Science 351, 403-407.

Pierschbacher, M. D., and Ruoslahti, E. (1984). Cell attachment activity of fibronectin can be duplicated by small synthetic fragments of the molecule. Nature 309, 30-33.

Pillay, S., Meyer, N. L., Puschnik, A. S., Davulcu, O., Diep, J., Ishikawa, Y., Jae, L. T., Wosen, J. E., Nagamine, C. M., Chapman, M. S., et al. (2016). An essential receptor for adeno-associated virus infection. Nature 530, 108-112.

Pytela, R., Pierschbacher, M. D., and Ruoslahti, E. (1985). Identification and isolation of a 140 kd cell surface glycoprotein with properties expected of a fibronectin receptor. Cell 40, 191-198.

Ruoslahti, E. (1996). RGD and other recognition sequences for integrins. Annu Rev Cell Dev Biol 12, 697-715.

Summerford, C., Bartlett, J. S., and Samulski, R. J. (1999). AlphaVbeta5 integrin: a co-receptor for adeno-associated virus type 2 infection. Nat Med 5, 78-82.

Tabebordbar, M., Zhu, K., Cheng, J. K. W., Chew, W. L., Widrick, J. J., Yan, W. X., Maesner, C., Wu, E. Y., Xiao, R., Ran, F. A., et al. (2016). In vivo gene editing in dystrophic mouse muscle and muscle stem cells. Science 351, 407-411.

Tse, L. V., Klinc, K. A., Madigan, V. J., Castellanos Rivera, R. M., Wells, L. F., Havlik, L. P., Smith, J. K., Agbandje-McKenna, M., and Asokan, A. (2017). Structure-guided evolution of antigenically distinct adeno-associated virus variants for immune evasion. Proc Natl Acad Sci USA 114, E4812-E4821.

Weinmann, J., Weis, S., Sippel, J., Tulalamba, W., Remes, A., El Andari, J., Herrmann, A. K., Pham, Q. H., Borowski, C., Hille, S., et al. (2020). Identification of a myotropic AAV by massively parallel in vivo evaluation of barcoded capsid variants. Nat Commun 11, 5432.

Yang, L., Jiang, J., Drouin, L. M., Agbandje-McKenna, M., Chen, C., Qiao, C., Pu, D., Hu, X., Wang, D. Z., Li, J., et al. (2009). A myocardium tropic adeno-associated virus (AAV) evolved by DNA shuffling and in vivo selection. Proc Natl Acad Sci USA 106, 3946-3951.

Yang, L., and Xiao, X. (2013). Creation of a cardiotropic adeno-associated virus: the story of viral directed evolution. Virol J 10, 50.

Zincarelli, C., Soltys, S., Rengo, G., and Rabinowitz, J. E. (2008). Analysis of AAV serotypes 1-9 mediated gene expression and tropism in mice after systemic injection. Mol Ther 16, 1073-1080.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A composition comprising:
a modified AAV capsid polypeptide comprising a targeting moiety capable of conferring a muscle tropism to a capsid or a viral particle
wherein the targeting moiety comprises one or more n-mer motifs inserted after amino acids 453, 587, and 588 of a wild-type AAV-9 capsid polypeptide, or an equivalent position in a wild-type AAV capsid polypeptide of a different serotype,
wherein each of the one or more n-mer motifs comprises an amino acid sequence of
$X_{m3} X_{m2} X_{m1}$ RGD $X_1 X_2 X_3 X_4$,
wherein $X_{m3}$, $X_{m2}$, and $X_{m1}$ are each independently selected from any one of amino acids A, D, E, G, K, N, R, S, L, and T,
wherein $X_1$, $X_2$, and $X_3$ are independently selected from any amino acid, and
wherein $X_4$ is L.

2. The composition of claim 1, wherein $X_1$ is selected from any one of amino acids F, H, L, Q, and Y.

3. The composition of claim 1, wherein $X_2$ is selected from any one of amino acids A, D, E, G, I, K, N, Q, R, S, and T.

4. The composition of claim 1, wherein $X_3$ is selected from any one of amino acids A, D, E, G, K, L, N, R, S, and T.

5. The composition of claim 1, further comprising a cargo, wherein the cargo is coupled to or is otherwise associated with the modified AAV capsid polypeptide.

6. The composition of claim 5, wherein the cargo is capable of treating or preventing a muscle disease or disorder, wherein the muscle disease or disorder comprises
a. an autoimmune disease;
b. a cancer;
c. a muscular dystrophy;
d. a neuro-muscular disease;
e. a sugar or glycogen storage disease;
f. an expanded repeat disease;
g. a dominant negative disease;
h. a cardiomyopathy;
i. a viral disease;
j. a progeroid disease; or
k. any combination thereof.

7. The composition of claim 6, wherein
(a) the expanded repeat disease comprises Huntington's disease, Myotonic Dystrophy, or Facioscapulohumeral muscular dystrophy (FSHD),
(b) wherein the muscular dystrophy comprises Duchenne muscular dystrophy, Becker Muscular dystrophy, a Limb-Girdle muscular dystrophy, an Emery Dreifuss muscular dystrophy, a myotonic dystrophy, or FSHD, optionally wherein the myotonic dystrophy is Type 1 or Type 2, (c) wherein the cardiomyopathy comprises dilated cardiomyopathy, hypertrophic cardiomyopathy, DMD-associated cardiomyopathy, or Dannon disease, (d) wherein the sugar or glycogen storage disease comprises a MPS type III disease or Pompe disease, optionally wherein the MPS type III disease comprises MPS Type IIIA, IIIB, IIIC, or HID, (e) wherein the neuro-muscular disease comprises Charcot-Marie-Tooth disease or Friedreich's Ataxia, or (f) any combination of (a)-(e).

8. The composition of claim 5, wherein the cargo is a morpholino, a peptide-linked morpholino, an antisense oligonucleotide, a PMO, a therapeutic transgene, a polynucleotide encoding a therapeutic polypeptide or peptide, a PPMO, one or more peptides, one or more polynucleotides encoding a CRISPR-Cas protein, a guide RNA, or both, a ribonucleoprotein, wherein the ribonucleoprotein comprises a CRISPR-Cas system molecule, a therapeutic transgene RNA, or other gene modifying or therapeutic RNA and/or protein, or any combination thereof.

9. The composition of claim 5, wherein the cargo is (a) capable of inducing exon skipping in a gene, optionally a dystrophin gene, or (b) a mini- or micro-dystrophin gene, optionally wherein the mini- or micro-dystrophin gene comprises spectrin-like repeats 1, 2, 3, and 24, and optionally an nNOS domain.

10. The composition of claim 1, wherein the wild-type AAV capsid polypeptide of a different serotype is selected from the group consisting of a wild-type AAV1, AAV2, AAV3, AAV4, AAV5, AAV6, AAV7, AAV8, AAV9, AAV rh.74, and AAV rh.10 VP1 capsid polypeptide.

11. The composition of claim 1, wherein the modified AAV capsid polypeptide comprises one or more mutations at positions 267, 269, 504, 505, or 590, or any combination thereof, of a wild-type AAV9 VP1 capsid polypeptide, or an equivalent position in a wild-type AAV capsid polypeptide of a different serotype, and wherein the modified AAV capsid polypeptide is capable of conferring on a capsid or a viral particle, a reduced tropism for non-muscle cells, as compared to a corresponding wild-type AAV capsid polypeptide.

12. The composition of claim 11, wherein the one or more mutations of the wild-type AAV9 VP1 capsid polypeptide in position 267, or an equivalent position in a wild-type AAV capsid polypeptide of a different serotype, is a G or X to A mutation, wherein X is any amino acid, or in position 269, or an equivalent position in a wild-type AAV capsid polypeptide of a different serotype, is an S or X to T mutation, wherein X is any amino acid, or in position 504, or an equivalent position in a wild-type AAV capsid polypeptide of a different serotype, is a G or X to A mutation, wherein X is any amino acid, or in position 505, or an equivalent position in a wild-type AAV capsid polypeptide of a different serotype, is a P or X to A mutation, wherein X is any amino acid, or in position 590, or an equivalent position in a wild-type AAV capsid polypeptide of a different serotype, is a Q or X to A mutation, wherein X is any amino acid, or in position 267, or an equivalent position in a wild-type AAV capsid polypeptide of a different serotype, is a G to A mutation, or in position 269, or an equivalent position in a wild-type AAV capsid polypeptide of a different serotype, is an S to T mutation, or in position 509, or an equivalent position in a wild-type AAV capsid polypeptide of a different serotype, is a Q to A mutation, or in position 504, or an equivalent position in a wild-type AAV capsid polypeptide of a different serotype, is a G to A mutation, or in position 505, or an equivalent position in a wild-type AAV capsid polypeptide of a different serotype, is a P to A mutation, or any combination of the mutations in positions 267, 269, 504, 505, or 590, or equivalent positions in a wild-type AAV capsid polypeptide of a different serotype.

13. The composition of claim 11, wherein the non-muscle cell comprises a liver cell.

\*   \*   \*   \*   \*

SEQUENCE LISTING

<160> NUMBER OF SEQ ID NOS: 773

<210> SEQ ID NO 1
<211> LENGTH: 736
<212> TYPE: PRT
<213> ORGANISM: Artificial Sequence
<220> FEATURE:
<223> OTHER INFORMATION: Synthetic

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro

-continued

```
                355                  360                  365

Ala Asp Val Phe Met Ile Pro Gln Tyr Gly Tyr Leu Thr Leu Asn Asp
    370                  375                  380

Gly Ser Gln Ala Val Gly Arg Ser Ser Phe Tyr Cys Leu Glu Tyr Phe
385                  390                  395                  400

Pro Ser Gln Met Leu Arg Thr Gly Asn Asn Phe Gln Phe Ser Tyr Glu
                405                  410                  415

Phe Glu Asn Val Pro Phe His Ser Ser Tyr Ala His Ser Gln Ser Leu
                420                  425                  430

Asp Arg Leu Met Asn Pro Leu Ile Asp Gln Tyr Leu Tyr Tyr Leu Ser
                435                  440                  445

Lys Thr Ile Asn Gly Ser Gly Gln Asn Gln Gln Thr Leu Lys Phe Ser
    450                  455                  460

Val Ala Gly Pro Ser Asn Met Ala Val Gln Gly Arg Asn Tyr Ile Pro
465                  470                  475                  480

Gly Pro Ser Tyr Arg Gln Gln Arg Val Ser Thr Thr Val Thr Gln Asn
                485                  490                  495

Asn Asn Ser Glu Phe Ala Trp Pro Gly Ala Ser Ser Trp Ala Leu Asn
                500                  505                  510

Gly Arg Asn Ser Leu Met Asn Pro Gly Pro Ala Met Ala Ser His Lys
                515                  520                  525

Glu Gly Glu Asp Arg Phe Phe Pro Leu Ser Gly Ser Leu Ile Phe Gly
    530                  535                  540

Lys Gln Gly Thr Gly Arg Asp Asn Val Asp Ala Asp Lys Val Met Ile
545                  550                  555                  560

Thr Asn Glu Glu Glu Ile Lys Thr Thr Asn Pro Val Ala Thr Glu Ser
                565                  570                  575

Tyr Gly Gln Val Ala Thr Asn His Gln Ser Ala Gln Ala Gln Ala Gln
                580                  585                  590

Thr Gly Trp Val Gln Asn Gln Gly Ile Leu Pro Gly Met Val Trp Gln
    595                  600                  605

Asp Arg Asp Val Tyr Leu Gln Gly Pro Ile Trp Ala Lys Ile Pro His
    610                  615                  620

Thr Asp Gly Asn Phe His Pro Ser Pro Leu Met Gly Gly Phe Gly Met
625                  630                  635                  640

Lys His Pro Pro Pro Gln Ile Leu Ile Lys Asn Thr Pro Val Pro Ala
                645                  650                  655

Asp Pro Pro Thr Ala Phe Asn Lys Asp Lys Leu Asn Ser Phe Ile Thr
                660                  665                  670

Gln Tyr Ser Thr Gly Gln Val Ser Val Glu Ile Glu Trp Glu Leu Gln
                675                  680                  685

Lys Glu Asn Ser Lys Arg Trp Asn Pro Glu Ile Gln Tyr Thr Ser Asn
    690                  695                  700

Tyr Tyr Lys Ser Asn Asn Val Glu Phe Ala Val Asn Thr Glu Gly Val
705                  710                  715                  720

Tyr Ser Glu Pro Arg Pro Ile Gly Thr Arg Tyr Leu Thr Arg Asn Leu
                725                  730                  735
```

<210> SEQ ID NO 2
<211> LENGTH: 10
<212> TYPE: PRT
<213> ORGANISM: Artificial Sequence
<220> FEATURE:
<223> OTHER INFORMATION: Synthetic: n-mer motif

```
<400> SEQUENCE: 2

Gly Pro Gly Arg Gly Asp Gln Thr Thr Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 3

Ala Glu Gly Arg Gly Asp Gln Tyr Thr Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 4

Ala Thr Gly Arg Gly Asp Leu Gly Gln Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 5

Ala Val Ala Arg Gly Asp Gln Gly Leu Ile
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 6

Asn Ile Ser Arg Gly Asp Gln Gly Tyr Gln
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 7

Ala Pro Ala Arg Gly Asp Gln Gly Ser Gln
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8
```

Arg Gly Asp Leu Ser Thr Pro
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Arg Gly Asp Leu Asn Gln Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Arg Gly Asp Ala Thr Glu Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Arg Gly Asp Thr Met Ser Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Arg Gly Asp Leu Thr Thr Pro
1               5

<210> SEQ ID NO 13
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is a, t, c, or g
<220> FEATURE:
<221> NAME/KEY: misc_feature
<222> LOCATION: (6)..(6)
<223> OTHER INFORMATION: n  is g or t
<220> FEATURE:
<221> NAME/KEY: misc_feature
<222> LOCATION: (7)..(8)
<223> OTHER INFORMATION: n is a, t, c, or g
<220> FEATURE:
<221> NAME/KEY: misc_feature
<222> LOCATION: (9)..(9)
<223> OTHER INFORMATION: n is g or t

```
<220> FEATURE:
<221> NAME/KEY: misc_feature
<222> LOCATION: (10)..(11)
<223> OTHER INFORMATION: n is a, t, c, or g
<220> FEATURE:
<221> NAME/KEY: misc_feature
<222> LOCATION: (12)..(12)
<223> OTHER INFORMATION: n is g or t
<220> FEATURE:
<221> NAME/KEY: misc_feature
<222> LOCATION: (13)..(14)
<223> OTHER INFORMATION: n is a, t, c, or g
<220> FEATURE:
<221> NAME/KEY: misc_feature
<222> LOCATION: (15)..(15)
<223> OTHER INFORMATION: n is g or t
<220> FEATURE:
<221> NAME/KEY: misc_feature
<222> LOCATION: (16)..(17)
<223> OTHER INFORMATION: n is a, t, c, or g
<220> FEATURE:
<221> NAME/KEY: misc_feature
<222> LOCATION: (18)..(18)
<223> OTHER INFORMATION: n is g or t
<220> FEATURE:
<221> NAME/KEY: misc_feature
<222> LOCATION: (19)..(20)
<223> OTHER INFORMATION: n is a, t, c, or g
<220> FEATURE:
<221> NAME/KEY: misc_feature
<222> LOCATION: (21)..(21)
<223> OTHER INFORMATION: n is g or t
<220> FEATURE:
<221> NAME/KEY: misc_feature
<222> LOCATION: (22)..(23)
<223> OTHER INFORMATION: n is a, t, c, or g
<220> FEATURE:
<221> NAME/KEY: misc_feature
<222> LOCATION: (24)..(24)
<223> OTHER INFORMATION: n is g or t

<400> SEQUENCE: 13
caannnnnnn nnnnnnnnn nnnngca                                              27

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Arg Gly Asp Gln Leu Tyr His
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Arg Gly Asp Val Ala Ala Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic
```

-continued

```
<400> SEQUENCE: 16

Arg Gly Asp Met Ile Asn Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Arg Gly Asp Leu Asn Asp Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Arg Gly Asp Thr Met Asn Tyr
1               5

<210> SEQ ID NO 19
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is a, t, c, or g
<220> FEATURE:
<221> NAME/KEY: misc_feature
<222> LOCATION: (6)..(6)
<223> OTHER INFORMATION: n is g or t
<220> FEATURE:
<221> NAME/KEY: misc_feature
<222> LOCATION: (7)..(8)
<223> OTHER INFORMATION: n is a, t, c, or g
<220> FEATURE:
<221> NAME/KEY: misc_feature
<222> LOCATION: (9)..(9)
<223> OTHER INFORMATION: n is g or t
<220> FEATURE:
<221> NAME/KEY: misc_feature
<222> LOCATION: (10)..(11)
<223> OTHER INFORMATION: n is a, t, c, or g
<220> FEATURE:
<221> NAME/KEY: misc_feature
<222> LOCATION: (12)..(12)
<223> OTHER INFORMATION: n is g or t
<220> FEATURE:
<221> NAME/KEY: misc_feature
<222> LOCATION: (22)..(23)
<223> OTHER INFORMATION: n is a, t, c, or g
<220> FEATURE:
<221> NAME/KEY: misc_feature
<222> LOCATION: (24)..(24)
<223> OTHER INFORMATION: n is g or t
<220> FEATURE:
<221> NAME/KEY: misc_feature
<222> LOCATION: (25)..(26)
<223> OTHER INFORMATION: n is a, t, c, or g
<220> FEATURE:
<221> NAME/KEY: misc_feature
<222> LOCATION: (27)..(27)
<223> OTHER INFORMATION: n is g or t
<220> FEATURE:
```

```
<221> NAME/KEY: misc_feature
<222> LOCATION: (28)..(29)
<223> OTHER INFORMATION: n is a, t, c, or g
<220> FEATURE:
<221> NAME/KEY: misc_feature
<222> LOCATION: (30)..(30)
<223> OTHER INFORMATION: n is g or t
<220> FEATURE:
<221> NAME/KEY: misc_feature
<222> LOCATION: (31)..(32)
<223> OTHER INFORMATION: n is a,, t, c, or g
<220> FEATURE:
<221> NAME/KEY: misc_feature
<222> LOCATION: (33)..(33)
<223> OTHER INFORMATION: n is g or t

<400> SEQUENCE: 19
cagnnnnnnn nnagaggaga cnnnnnnnnn nnngca                                36

<210> SEQ ID NO 20
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 20

Ala Val Ser Arg Gly Asp Arg Met Glu Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 21

Ser Pro Ser Arg Gly Asp Gln Gly Arg Thr
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Arg Gly Asp Tyr Val Gly Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Arg Gly Asp Tyr Ser Gly Leu
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic
```

-continued

<400> SEQUENCE: 24

Arg Gly Asp Tyr Ser Ser Val
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Arg Gly Asp Tyr Arg Glu Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Arg Gly Asp His Gly Val Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Arg Gly Asp His Ala Ser Trp
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 28

Ser Asn Ser Arg Gly Asp Tyr Asn Ser Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Ser Thr Val Arg Gly Asp Tyr Thr Ser Met
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic:  n-mer motif -continued

<400> SEQUENCE: 30

Gln Glu Arg Arg Gly Asp Tyr Thr Ser Met
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 31

Ala Ser Thr Arg Gly Asp His Gly Val Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 32

Glu Asn Arg Arg Gly Asp Phe Asn Asn Thr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

Ser Ala Gln Arg Gly Asp Tyr Val Gly Leu
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Gly Gly Gly Gly Gly Gly Gly Gly Gly Gly Gly Gly Gly Gly Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 12
<212> TYPE: DNA
<213> ORGANISM: Artificial Sequence
<220> FEATURE:
<223> OTHER INFORMATION: Synthetic

<400> SEQUENCE: 36

```
acttgtttaa gt                                                                  12

<210> SEQ ID NO 37
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n represents any set of nucleotides that are
      complementary to and together with base pair to nucleotides 9-12,
      where n is a, c, g, t, or u
<220> FEATURE:
<221> NAME/KEY: misc_feature
<222> LOCATION: (9)..(12)
<223> OTHER INFORMATION: n represents any set of nucleotides that are
      complementary to and together with base pair to nucleotides 1-4,
      where n is a, c, g, t, or u

<400> SEQUENCE: 37
nnnngtttnn nn                                                                  12

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
ggcaccgagt cggtgc                                                              16

<210> SEQ ID NO 39
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: n represents any set of nucleotides that are
      completementary to and together with base pair to nucleotides
      11-17, where n is a, c, g, t, or u
<220> FEATURE:
<221> NAME/KEY: misc_feature
<222> LOCATION: (11)..(17)
<223> OTHER INFORMATION: n represents any set of nucleotides that are
      completementary to and together with base pair to nucleotides 1-7,
      where n is a, c, g, t, or u

<400> SEQUENCE: 39
nnnnnnnagt nnnnnnn                                                             17

<210> SEQ ID NO 40
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n represents part of the bulge of the duplex,
      where n is a, c, g, t, or u
<220> FEATURE:
<221> NAME/KEY: misc_feature
<222> LOCATION: (9)..(12)
<223> OTHER INFORMATION: n represents any set of nucelotides that are
```

-continued

```
         complementary to and together will base pair to nucleotides 17-20,
         where n is a, c, g, t, or u
<220> FEATURE:
<221> NAME/KEY: misc_feature
<222> LOCATION: (13)..(16)
<223> OTHER INFORMATION: n represents a linker of any length and any
         base composition so long as it does not alter the overall
         structure of the duplex
<220> FEATURE:
<221> NAME/KEY: misc_feature
<222> LOCATION: (17)..(220)
<223> OTHER INFORMATION: n represents any set of nucelotides that are
         complementary to and together will base pair to nucleotides 9-12,
         where n is a, c, g, t, or u
<220> FEATURE:
<221> NAME/KEY: misc_feature
<222> LOCATION: (21)..(23)
<223> OTHER INFORMATION: part of the bulge in the duplex

<400> SEQUENCE: 40
gyyyyagnnn nnnnnnnnnn aanuurrrru                                         30

<210> SEQ ID NO 41
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 41
gctgagggta gaggagacca gtatactcgt                                        30

<210> SEQ ID NO 42
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 42
gggccgggta gaggagacca gactacgttg                                        30

<210> SEQ ID NO 43
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 43
gcggaaggca gaggagacca atacacaagg                                        30

<210> SEQ ID NO 44
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 44
gcgactggta gaggagacct gggtcaggct                                        30

<210> SEQ ID NO 45
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

<400> SEQUENCE: 45
gcggtggcga gaggagacca gggtcttatt                                          30

<210> SEQ ID NO 46
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 46
aacatctcca gaggagacca aggttaccaa                                          30

<210> SEQ ID NO 47
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 47
gcgccggcta gaggagacca ggggagtcag                                          30

<210> SEQ ID NO 48
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 48
gccgttagca gaggagaccg gatggaattc                                          30

<210> SEQ ID NO 49
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 49

Gln Met Gly Arg Gly Asp Met Gly Ile Lys
1               5                   10

<210> SEQ ID NO 50
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 50
cagatgggta gaggagacat ggggattaag                                          30

<210> SEQ ID NO 51
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 51

Glu Tyr Arg Arg Gly Asp Lys Ala Asp Ile
1               5                   10

<210> SEQ ID NO 52
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 52
gagtatcgga gaggagacaa ggcggatatt                                      30

<210> SEQ ID NO 53
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 53

Glu Ser Arg Arg Gly Asp Lys Glu Pro Leu
1               5                   10

<210> SEQ ID NO 54
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 54
gagagtcgga gaggagacaa ggagccgctg                                      30

<210> SEQ ID NO 55
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 55

Ala His Met Arg Gly Asp Leu Gly Gly Thr
1               5                   10

<210> SEQ ID NO 56
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 56
gcacacatga gaggagacct aggcggcacg                                      30

<210> SEQ ID NO 57
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 57

Val Trp Gln Arg Gly Asp Lys Met Asp Met
1               5                   10

<210> SEQ ID NO 58
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 58
gtgtggcaaa gaggagacaa aatggacatg                                          30

<210> SEQ ID NO 59
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 59

Ser Ile Gly Arg Gly Asp Thr Gly His Met
1               5                   10

<210> SEQ ID NO 60
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 60
tctattggga gaggagacac gggtcatatg                                          30

<210> SEQ ID NO 61
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 61

Asn Ile Ala Arg Gly Asp Ala Gly Gln Tyr
1               5                   10

<210> SEQ ID NO 62
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 62
aatattgcta gaggagacgc tggtcagtat                                          30

<210> SEQ ID NO 63
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 63
gcagtagcaa gaggagacca aggcttaatc                                          30

<210> SEQ ID NO 64
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 64

-continued

```
Ser Val Ser Arg Gly Asp Gln Gly Leu His
1               5               10

<210> SEQ ID NO 65
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 65
tcggtctcga gaggagacca aggattgcac                                    30

<210> SEQ ID NO 66
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 66
gaatacagga gaggagacaa agcagacatc                                    30

<210> SEQ ID NO 67
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 67
gcgcatatga gaggagactt gggggggact                                    30

<210> SEQ ID NO 68
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 68

Gln Ile Gly Arg Gly Asp Ile Thr His Gly
1               5               10

<210> SEQ ID NO 69
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 69
cagattggta gaggagacat tactcatggg                                    30

<210> SEQ ID NO 70
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 70

Glu Val Arg Arg Gly Asp Leu His Gly Thr
1               5               10

<210> SEQ ID NO 71
```

<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 71
gaagtcagaa gaggagactt gcacgggaca                                           30

<210> SEQ ID NO 72
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 72

Ser Val Ser Arg Gly Asp Val His Thr Met
1               5                   10

<210> SEQ ID NO 73
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 73
agtgtctcaa gaggagacgt gcacacgatg                                           30

<210> SEQ ID NO 74
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 74

Met Val Thr Arg Gly Asp Leu Gly Thr Arg
1               5                   10

<210> SEQ ID NO 75
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 75
atggtgacta gaggagacct tggtacgcgg                                           30

<210> SEQ ID NO 76
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 76

Asn Gly Gly Arg Gly Asp Thr Thr His Phe
1               5                   10

<210> SEQ ID NO 77
<211> LENGTH: 30
<212> TYPE: DNA
<213> ORGANISM: Artificial Sequence
<220> FEATURE:

<223> OTHER INFORMATION: Synthetic: n-mer encoding polynucleotide

<400> SEQUENCE: 77
aacggcggga gaggagacac gacgcacttc                                    30

<210> SEQ ID NO 78
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 78

Thr Met Gly Arg Gly Asp Met Asn Ser Leu
1               5                   10

<210> SEQ ID NO 79
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 79
acgatgggga gaggagacat gaattcgctt                                    30

<210> SEQ ID NO 80
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 80

Ala Ile Ser Arg Gly Asp Gln Gly Leu Ser
1               5                   10

<210> SEQ ID NO 81
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 81
gcgattagta gaggagacca gggtctttct                                    30

<210> SEQ ID NO 82
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 82

Asn Asp Ala Arg Gly Asp Lys Ser Thr Tyr
1               5                   10

<210> SEQ ID NO 83
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 83
aacgacgcaa gaggagacaa atccacatac                                    30

<210> SEQ ID NO 84
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 84

Val Gly Leu Arg Gly Asp Leu Thr Gly Ser
1               5                   10

<210> SEQ ID NO 85
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 85
gtggggctga gaggagactt gacgggttcg                                    30

<210> SEQ ID NO 86
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 86

Glu Met Arg Arg Gly Asp Leu Gly Thr Ser
1               5                   10

<210> SEQ ID NO 87
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 87
gagatgagga gaggagacct ggggacgagt                                    30

<210> SEQ ID NO 88
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 88

Ala Met Ser Arg Gly Asp Met Gly Met Ala
1               5                   10

<210> SEQ ID NO 89
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 89
gcgatgagta gaggagacat ggggatggcg                                    30

<210> SEQ ID NO 90

-continued

```
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 90
gcaacgggca gaggagactt aggccaagca                                              30

<210> SEQ ID NO 91
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 91

Asn Val Ala Arg Gly Asp Gln Val Asn Tyr
1               5                   10

<210> SEQ ID NO 92
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 92
aacgtagcaa gaggagacca agttaactac                                             30

<210> SEQ ID NO 93
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 93
agcatcggaa gaggagacac cggccacatg                                             30

<210> SEQ ID NO 94
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 94

Ala Ser Val Arg Gly Asp Leu Ser Gly Ser
1               5                   10

<210> SEQ ID NO 95
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 95
gcatccgtaa gaggagacct atcaggctca                                             30

<210> SEQ ID NO 96
<211> LENGTH: 10
<212> TYPE: PRT
<213> ORGANISM: Artificial Sequence
<220> FEATURE:
<223> OTHER INFORMATION: Synthetic:  n-mer motif
```

-continued

```
<400> SEQUENCE: 96

Ser Ala Ala Arg Gly Asp Thr Glu Arg Leu
1               5                   10

<210> SEQ ID NO 97
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 97
agcgccgcga gaggagacac tgaacggcta                               30

<210> SEQ ID NO 98
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 98
gccatgtcaa gaggagacat gggtatggct                               30

<210> SEQ ID NO 99
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 99
agtccatcga gaggagacca aggacgcact                               30

<210> SEQ ID NO 100
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 100

Val Pro Gly Arg Gly Asp Leu Asn Thr Met
1               5                   10

<210> SEQ ID NO 101
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 101
gtgcctggga gaggagacct taatactatg                               30

<210> SEQ ID NO 102
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 102
ggtcctggga gaggagacca aacgaccctt                               30
```

<210> SEQ ID NO 103
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 103

Thr Ser Val Arg Gly Asp His Gly Thr Leu
1               5                   10

<210> SEQ ID NO 104
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 104
acatcggtca gaggagacca cggaacattg                                        30

<210> SEQ ID NO 105
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 105

Thr Pro Ser Arg Gly Asp Leu Gly Gln Thr
1               5                   10

<210> SEQ ID NO 106
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 106
acgccttcga gaggagacct tgggcagact                                        30

<210> SEQ ID NO 107
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 107

Ala Gly His Arg Gly Asp Thr Gly Val Ile
1               5                   10

<210> SEQ ID NO 108
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 108
gctggacaca gaggagacac aggagtcatc                                        30

<210> SEQ ID NO 109
<211> LENGTH: 10
<212> TYPE: PRT

-continued

<213> ORGANISM: Artificial Sequence
<220> FEATURE:
<223> OTHER INFORMATION: Synthetic: n-mer motif

<400> SEQUENCE: 109

Ala Pro Ala Arg Gly Asp Gln Gly Ser Met
1               5                   10

<210> SEQ ID NO 110
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 110
gcgccggcga gaggagacca gggtagtatg                                      30

<210> SEQ ID NO 111
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 111

Met Ser Leu Arg Gly Asp Leu Asn Gly Ser
1               5                   10

<210> SEQ ID NO 112
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 112
atgtcgttga gaggagactt gaatgggtcg                                      30

<210> SEQ ID NO 113
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 113

Glu Ala Lys Arg Gly Asp Val His Ser Ile
1               5                   10

<210> SEQ ID NO 114
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 114
gaggctaaga gaggagacgt gcattctatt                                      30

<210> SEQ ID NO 115
<211> LENGTH: 10
<212> TYPE: PRT
<213> ORGANISM: Artificial Sequence
<220> FEATURE:
<223> OTHER INFORMATION: Synthetic: n-mer motif -continued

```
<400> SEQUENCE: 115

Ser Ala Gln Arg Gly Asp Val Gln Ala Val
1               5                   10

<210> SEQ ID NO 116
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 116
agtgctcaga gaggagacgt gcaggcggtg                                     30

<210> SEQ ID NO 117
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 117

Ser Thr Ala Arg Gly Asp Gln Gly Asp Arg
1               5                   10

<210> SEQ ID NO 118
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 118
agtacggcga gaggagacca gggggatagg                                     30

<210> SEQ ID NO 119
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 119

Gln Ile Ser Arg Gly Asp Leu Gly Ile Asn
1               5                   10

<210> SEQ ID NO 120
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 120
cagattagta gaggagacct ggggattaat                                     30

<210> SEQ ID NO 121
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 121

Thr Phe Thr Arg Gly Asp Met Thr Met Asn
1               5                   10
```

```
<210> SEQ ID NO 122
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 122
acgttcacaa gaggagacat gacgatgaac                                          30

<210> SEQ ID NO 123
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 123

Gln Glu Gly Arg Gly Asp Leu Asn Met Arg
1               5                   10

<210> SEQ ID NO 124
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 124
caagaaggaa gaggagacct gaacatgagg                                          30

<210> SEQ ID NO 125
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 125

Ala His Ala Arg Gly Asp Thr Ser Ser Leu
1               5                   10

<210> SEQ ID NO 126
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 126
gcacacgcaa gaggagacac cagctccctg                                          30

<210> SEQ ID NO 127
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 127

Thr Asn Gly Arg Gly Asp Ala Gly Thr Leu
1               5                   10

<210> SEQ ID NO 128
<211> LENGTH: 30
```

-continued

```
<212> TYPE: DNA
<213> ORGANISM: Artificial Sequence
<220> FEATURE:
<223> OTHER INFORMATION: Synthetic:  n-mer encoding polynucleotide

<400> SEQUENCE: 128
acgaatggga gaggagacgc tgggactctg                                          30

<210> SEQ ID NO 129
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 129

Ala Phe Gly Arg Gly Asp Gln Gly Gln Leu
1               5                   10

<210> SEQ ID NO 130
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 130
gctttcggca gaggagacca agggcaacta                                          30

<210> SEQ ID NO 131
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 131

Ala Asp Gly Arg Gly Asp Arg Ser Ser Leu
1               5                   10

<210> SEQ ID NO 132
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 132
gctgatggga gaggagaccg ttcgtctctg                                          30

<210> SEQ ID NO 133
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 133

Asp Gly Arg Arg Gly Asp Gly His Ser Leu
1               5                   10

<210> SEQ ID NO 134
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

<400> SEQUENCE: 134
gacggacgca gaggagacgg acacagcctt                                              30

<210> SEQ ID NO 135
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 135

Glu Lys Leu Arg Gly Asp Leu His Ser Thr
1               5                   10

<210> SEQ ID NO 136
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 136
gagaagttga gaggagacct tcattcgact                                              30

<210> SEQ ID NO 137
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 137

Glu Ala Arg Arg Gly Asp Ala Ser Ala Met
1               5                   10

<210> SEQ ID NO 138
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 138
gaggcgcgta gaggagacgc ttcggcgatg                                              30

<210> SEQ ID NO 139
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 139

Met Gly Thr Arg Gly Asp Lys Met Asp Phe
1               5                   10

<210> SEQ ID NO 140
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 140
atgggaacga gaggagacaa aatggacttc                                              30

```
<210> SEQ ID NO 141
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 141

Ser Thr Ser Arg Gly Asp Arg Glu Ser Tyr
1               5                   10

<210> SEQ ID NO 142
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 142
tcgacttcga gaggagaccg ggagtcgtat                                        30

<210> SEQ ID NO 143
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 143

Cys Gln Pro Arg Gly Asp Thr Thr Arg Cys
1               5                   10

<210> SEQ ID NO 144
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 144
tgtcagccga gaggagacac gactcggtgt                                        30

<210> SEQ ID NO 145
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 145

Met His Thr Arg Gly Asp Lys Met Asp Phe
1               5                   10

<210> SEQ ID NO 146
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 146
atgcacacga gaggagacaa aatggacttc                                        30

<210> SEQ ID NO 147
<211> LENGTH: 10
```

<212> TYPE: PRT
<213> ORGANISM: Artificial Sequence
<220> FEATURE:
<223> OTHER INFORMATION: Synthetic: n-mer motif

<400> SEQUENCE: 147

Tyr Ser Ala Arg Gly Asp Thr Ser Gly Leu
1               5                   10

<210> SEQ ID NO 148
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 148
tacagtgcca gaggagacac aagtggcctg                                30

<210> SEQ ID NO 149
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 149

Ser Thr Met Arg Gly Asp His Glu Lys Leu
1               5                   10

<210> SEQ ID NO 150
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 150
tcgacgatga gaggagacca tgagaagttg                                30

<210> SEQ ID NO 151
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 151

Thr Gln Met Arg Gly Asp Gly Val Thr Leu
1               5                   10

<210> SEQ ID NO 152
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 152
acccaaatga gaggagacgg ggtcacacta                                30

<210> SEQ ID NO 153
<211> LENGTH: 10
<212> TYPE: PRT
<213> ORGANISM: Artificial Sequence
<220> FEATURE:
<223> OTHER INFORMATION: Synthetic: n-mer motif -continued

<400> SEQUENCE: 153

Thr Thr Arg Arg Gly Asp Met Gly Asp Asn
1               5                   10

<210> SEQ ID NO 154
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 154
actactcgta gaggagacat gggggataat                                    30

<210> SEQ ID NO 155
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 155

Ala Asn Gly Arg Gly Asp Arg Leu Glu Leu
1               5                   10

<210> SEQ ID NO 156
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 156
gcgaatggta gaggagacag gctggagttg                                    30

<210> SEQ ID NO 157
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 157
gctgtgtcta gaggagacag gatggagttt                                    30

<210> SEQ ID NO 158
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 158

Glu Asn Gln Arg Gly Asp Leu Ser Gly Arg
1               5                   10

<210> SEQ ID NO 159
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 159
gagaatcaga gaggagactt gtcgggtcgg                                    30

```
<210> SEQ ID NO 160
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 160

Ser Thr Gly Arg Gly Asp Leu Gly Gln Ala
1               5                   10

<210> SEQ ID NO 161
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 161
tcgactggta gaggagacct ggggcaggct                              30

<210> SEQ ID NO 162
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 162
atgcatacta gaggagacaa gatggatttt                              30

<210> SEQ ID NO 163
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 163

Ser Ser Ala Arg Gly Asp Tyr Ser Glu Val
1               5                   10

<210> SEQ ID NO 164
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 164
agtagtgcga gaggagacta tagtgaggtg                              30

<210> SEQ ID NO 165
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 165
gcgtttggga gaggagacca gggtcagctt                              30

<210> SEQ ID NO 166
<211> LENGTH: 10
<212> TYPE: PRT
```

-continued

```
<213> ORGANISM: Artificial Sequence
<220> FEATURE:
<223> OTHER INFORMATION: Synthetic: n-mer motif

<400> SEQUENCE: 166

Ser Thr Ala Arg Gly Asp Ala Ala Thr Tyr
1               5               10

<210> SEQ ID NO 167
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 167
agtacggcga gaggagacgc ggcgacttat                                    30

<210> SEQ ID NO 168
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 168

Val Asn Thr Arg Gly Asp Thr Gln Lys Leu
1               5               10

<210> SEQ ID NO 169
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 169
gtcaacacaa gaggagacac tcaaaaactt                                    30

<210> SEQ ID NO 170
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 170

Ala Met Ser Arg Gly Asp His Ala Ser Leu
1               5               10

<210> SEQ ID NO 171
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 171
gcgatgagta gaggagacca tgcgtcgctt                                    30

<210> SEQ ID NO 172
<211> LENGTH: 10
<212> TYPE: PRT
<213> ORGANISM: Artificial Sequence
<220> FEATURE:
<223> OTHER INFORMATION: Synthetic: n-mer motif
```

<400> SEQUENCE: 172

Gln Ala Ala Arg Gly Asp Val Asn Lys Leu
1               5                   10

<210> SEQ ID NO 173
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 173
caggctgcta gaggagacgt taataagctg                                    30

<210> SEQ ID NO 174
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 174

Arg Gly Thr Arg Gly Asp Thr Val Glu Leu
1               5                   10

<210> SEQ ID NO 175
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 175
aggggtacga gaggagacac ggttgagttg                                    30

<210> SEQ ID NO 176
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 176
accacccgga gaggagacat gggagacaac                                    30

<210> SEQ ID NO 177
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 177

Ala Ser Thr Arg Gly Asp Tyr Ala Gly Val
1               5                   10

<210> SEQ ID NO 178
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 178
gctagtacga gaggagacta tgcgggtgtt                                    30

```
<210> SEQ ID NO 179
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 179

Asp Asp Arg Arg Gly Asp Lys Leu Pro Leu
1               5               10

<210> SEQ ID NO 180
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 180
gacgacagga gaggagacaa actgcccctt                                      30

<210> SEQ ID NO 181
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 181

Ser Gly Ser Arg Gly Asp Leu Asn Ala Val
1               5               10

<210> SEQ ID NO 182
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 182
tcggggtcga gaggagacct gaatgcggtg                                      30

<210> SEQ ID NO 183
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 183

Glu Tyr Arg Arg Gly Asp Gln Gln Ile Gln
1               5               10

<210> SEQ ID NO 184
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 184
gagtatagga gaggagacca gcagattcag                                      30

<210> SEQ ID NO 185
<211> LENGTH: 10
<212> TYPE: PRT
```

-continued

```
<213> ORGANISM: Artificial Sequence
<220> FEATURE:
<223> OTHER INFORMATION: Synthetic: n-mer motif

<400> SEQUENCE: 185

Thr Tyr Val Arg Gly Asp Arg Ala Glu Val
1               5                   10

<210> SEQ ID NO 186
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 186
acgtacgtca gaggagacag agcagaagtg                                        30

<210> SEQ ID NO 187
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 187

Gln Ser Leu Arg Gly Asp Leu Asn Gly Ser
1               5                   10

<210> SEQ ID NO 188
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 188
caatcactaa gaggagactt gaacggatcc                                        30

<210> SEQ ID NO 189
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 189

Glu Gly Arg Arg Gly Asp Thr Thr Ser Leu
1               5                   10

<210> SEQ ID NO 190
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 190
gagggtcgga gaggagacac gacgtcgttg                                        30

<210> SEQ ID NO 191
<211> LENGTH: 10
<212> TYPE: PRT
<213> ORGANISM: Artificial Sequence
<220> FEATURE:
<223> OTHER INFORMATION: Synthetic: n-mer motif
```

```
<400> SEQUENCE: 191

Ala Glu Asn Arg Gly Asp Arg Ser Ser Leu
1               5                   10

<210> SEQ ID NO 192
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 192
gcggagaata gaggagaccg gtcgagtttg                                  30

<210> SEQ ID NO 193
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 193

Val Ala Gly Arg Gly Asp Arg Ser Glu Leu
1               5                   10

<210> SEQ ID NO 194
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 194
gtggctggga gaggagaccg tagtgagctg                                  30

<210> SEQ ID NO 195
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 195

Asp Pro Ala Arg Gly Asp Ile Gly Ala Arg
1               5                   10

<210> SEQ ID NO 196
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 196
gatccggcga gaggagacat tggtgcgcgt                                  30

<210> SEQ ID NO 197
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 197
gaaatgcgca gaggagactt gggaacttca                                  30
```

<210> SEQ ID NO 198
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 198
gtttggcaga gaggagacaa gatggatatg                                    30

<210> SEQ ID NO 199
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 199

Val Ile Gly Arg Gly Asp Lys Ala Leu Gln
1               5                   10

<210> SEQ ID NO 200
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 200
gtgattggga gaggagacaa ggcgcttcag                                    30

<210> SEQ ID NO 201
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 201

Ser Phe Glu Arg Gly Asp Lys Asn Ser Leu
1               5                   10

<210> SEQ ID NO 202
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 202
agcttcgaaa gaggagacaa aaactctctt                                    30

<210> SEQ ID NO 203
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 203

Gln Ile Ala Arg Gly Asp Ile Ala Ser Val
1               5                   10

<210> SEQ ID NO 204
<211> LENGTH: 30
<212> TYPE: DNA

-continued

```
<213> ORGANISM: Artificial Sequence
<220> FEATURE:
<223> OTHER INFORMATION: Synthetic: n-mer encoding polynucleotide

<400> SEQUENCE: 204
cagattgcta gaggagacat tgctagtgtg                                    30

<210> SEQ ID NO 205
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 205

Thr Ile Ser Arg Gly Asp Leu Gly Gly Ala
1               5                   10

<210> SEQ ID NO 206
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 206
acgattagta gaggagacct gggtggggct                                    30

<210> SEQ ID NO 207
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 207

Ala Met Ile Arg Gly Asp Met Thr His Ser
1               5                   10

<210> SEQ ID NO 208
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 208
gcgatgatta gaggagacat gacgcatagt                                    30

<210> SEQ ID NO 209
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 209
acgagtgtga gaggagacca tgggacgctg                                    30

<210> SEQ ID NO 210
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 210
```

-continued

Thr Met Arg Arg Gly Asp Leu Asn Asp Ser
1               5                   10

<210> SEQ ID NO 211
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 211
acgatgcgga gaggagacct gaatgatagt                              30

<210> SEQ ID NO 212
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 212

Ala Tyr Ser Arg Gly Asp Leu Gly Asn His
1               5                   10

<210> SEQ ID NO 213
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 213
gcctactcca gaggagacct aggcaaccac                              30

<210> SEQ ID NO 214
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 214

Glu Glu Arg Arg Gly Asp Thr His Arg Leu
1               5                   10

<210> SEQ ID NO 215
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 215
gaggagcgga gaggagacac tcatcggctg                              30

<210> SEQ ID NO 216
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 216

Ser Gln Leu Arg Gly Asp Ala Gly Thr Ile
1               5                   10

<210> SEQ ID NO 217
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 217
tcacaactaa gaggagacgc ggggacaatc                                          30

<210> SEQ ID NO 218
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 218

Ala Met Val Arg Gly Asp Ala His Gln Leu
1               5                   10

<210> SEQ ID NO 219
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 219
gcgatggtga gaggagacgc gcatcagctg                                          30

<210> SEQ ID NO 220
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 220

Thr Thr Ser Arg Gly Asp Leu Asn Ser Val
1               5                   10

<210> SEQ ID NO 221
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 221
acgactagta gaggagactt gaattcggtt                                          30

<210> SEQ ID NO 222
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 222

Trp Glu Gln Arg Gly Asp Met Ile Gly Lys
1               5                   10

<210> SEQ ID NO 223
<211> LENGTH: 30
<212> TYPE: DNA

<213> ORGANISM: Artificial Sequence
<220> FEATURE:
<223> OTHER INFORMATION: Synthetic: n-mer encoding polynucleotide

<400> SEQUENCE: 223
tgggagcaga gaggagacat gattgggaag                                     30

<210> SEQ ID NO 224
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 224

Tyr Thr Thr Arg Gly Asp Leu Gln Ser Asn
1               5                   10

<210> SEQ ID NO 225
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 225
tacaccacca gaggagacct ccaatcaaac                                     30

<210> SEQ ID NO 226
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 226

Met Ser Gln Arg Gly Asp Leu Ser His Gln
1               5                   10

<210> SEQ ID NO 227
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 227
atgtcgcaga gaggagacct ttcgcatcag                                     30

<210> SEQ ID NO 228
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 228

Ala Ser Thr Arg Gly Asp Thr Thr His Met
1               5                   10

<210> SEQ ID NO 229
<211> LENGTH: 30
<212> TYPE: DNA
<213> ORGANISM: Artificial Sequence
<220> FEATURE:
<223> OTHER INFORMATION: Synthetic: n-mer encoding polynucleotide -continued

```
<400> SEQUENCE: 229
gcgagtacta gaggagacac gacgcatatg                                        30

<210> SEQ ID NO 230
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 230

Ser Asp Thr Arg Gly Asp Thr His Arg Leu
1               5                   10

<210> SEQ ID NO 231
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 231
tcagacacca gaggagacac ccacagactg                                        30

<210> SEQ ID NO 232
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 232

Thr Leu Gly Arg Gly Asp Gln Tyr Thr Ser
1               5                   10

<210> SEQ ID NO 233
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 233
acgctgggta gaggagacca gtatacgagt                                        30

<210> SEQ ID NO 234
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 234

Ser Tyr Ala Arg Gly Asp Val Arg Glu Val
1               5                   10

<210> SEQ ID NO 235
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 235
tcgtatgcga gaggagacgt tagggaggtt                                        30
```

```
<210> SEQ ID NO 236
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 236

Glu Thr Arg Arg Gly Asp Leu Ser Gln Asn
1               5                   10

<210> SEQ ID NO 237
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 237
gagactcgta gaggagacct gagtcagaat                                          30

<210> SEQ ID NO 238
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 238

Thr Ile Gly Arg Gly Asp Leu Met Asp Lys
1               5                   10

<210> SEQ ID NO 239
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 239
acaatcggga gaggagacct gatggacaaa                                          30

<210> SEQ ID NO 240
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 240

Ser Tyr Thr Arg Gly Asp Leu Ser Gln Asn
1               5                   10

<210> SEQ ID NO 241
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 241
agttacacca gaggagacct tagccaaaac                                          30

<210> SEQ ID NO 242
<211> LENGTH: 10
<212> TYPE: PRT
```

<213> ORGANISM: Artificial Sequence
<220> FEATURE:
<223> OTHER INFORMATION: Synthetic: n-mer motif

<400> SEQUENCE: 242

Ser Lys Leu Arg Gly Asp Ala Ser Glu Ile
1               5                   10

<210> SEQ ID NO 243
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 243
tcgaagctga gaggagacgc tagtgagatt                                   30

<210> SEQ ID NO 244
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 244

Ser Met Ala Arg Gly Asp Lys Ala Glu Ile
1               5                   10

<210> SEQ ID NO 245
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 245
tcgatggcga gaggagacaa ggcggagatt                                   30

<210> SEQ ID NO 246
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 246

Gly Ala Val Arg Gly Asp His Ser Ser Leu
1               5                   10

<210> SEQ ID NO 247
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 247
ggagccgtca gaggagacca ctcatcgtta                                   30

<210> SEQ ID NO 248
<211> LENGTH: 10
<212> TYPE: PRT
<213> ORGANISM: Artificial Sequence
<220> FEATURE:
<223> OTHER INFORMATION: Synthetic: n-mer motif

```
<400> SEQUENCE: 248

Met Glu Thr Arg Gly Asp Met Ser Asn Arg
1               5                   10

<210> SEQ ID NO 249
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 249
atggagacga gaggagacat gagtaatcgt                                      30

<210> SEQ ID NO 250
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 250

Ala Tyr Thr Arg Gly Asp Lys Asp Ala Leu
1               5                   10

<210> SEQ ID NO 251
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 251
gcgtacacaa gaggagacaa agacgcacta                                      30

<210> SEQ ID NO 252
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 252

Glu Asn Arg Arg Gly Asp Ile Thr Gln Ser
1               5                   10

<210> SEQ ID NO 253
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 253
gagaatcgga gaggagacat tacgcagtcg                                      30

<210> SEQ ID NO 254
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 254
tccacgggca gaggagacct tggacaagca                                      30
```

<210> SEQ ID NO 255
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 255
ggtgctgtta gaggagacca tagtagtctt                                30

<210> SEQ ID NO 256
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 256
tctcagctta gaggagacgc tggtacgatt                                30

<210> SEQ ID NO 257
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 257

Met Leu Leu Arg Gly Asp Lys Asn Asp Phe
1               5                   10

<210> SEQ ID NO 258
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 258
atgctcctaa gaggagacaa aaacgacttc                                30

<210> SEQ ID NO 259
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 259

Lys Val Gln Arg Gly Asp Ala Ser Asp Trp
1               5                   10

<210> SEQ ID NO 260
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 260
aaggtgcaga gaggagacgc gagtgattgg                                30

<210> SEQ ID NO 261
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 261

Ala Phe Thr Arg Gly Asp Met Gln Thr Ala
1               5                   10

<210> SEQ ID NO 262
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 262
gcgtttacga gaggagacat gcagactgct                                              30

<210> SEQ ID NO 263
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 263

Gln Pro Lys Arg Gly Asp Val Gln Ala Gln
1               5                   10

<210> SEQ ID NO 264
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 264
cagcctaaga gaggagacgt tcaggctcag                                              30

<210> SEQ ID NO 265
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 265

Ala Ser Leu Arg Gly Asp Met Gly Val Ser
1               5                   10

<210> SEQ ID NO 266
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 266
gctagtctga gaggagacat gggggtgagt                                              30

<210> SEQ ID NO 267
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 267

-continued

```
Ala Tyr Ser Arg Gly Asp Lys Glu Ser Phe
1               5                   10

<210> SEQ ID NO 268
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 268
gcctactcca gaggagacaa agaatcgttc                                          30

<210> SEQ ID NO 269
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 269

Arg Phe Gln Arg Gly Asp Leu Thr Asp Ala
1               5                   10

<210> SEQ ID NO 270
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 270
cggttccaaa gaggagactt gaccgacgct                                          30

<210> SEQ ID NO 271
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 271

Ser Asp Ala Arg Gly Asp Thr Met Lys Leu
1               5                   10

<210> SEQ ID NO 272
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 272
tctgatgcta gaggagacac gatgaagctg                                          30

<210> SEQ ID NO 273
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 273

Ser Gly Ala Arg Gly Asp Thr Val Ser Leu
1               5                   10
```

<210> SEQ ID NO 274
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 274
agcggggcca gaggagacac agtaagtctc                                                    30

<210> SEQ ID NO 275
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 275

Asp Glu Lys Arg Gly Asp Gln Lys His Leu
1               5                   10

<210> SEQ ID NO 276
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 276
gatgagaaga gaggagacca gaagcatctt                                                    30

<210> SEQ ID NO 277
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 277

Asn Gly Val Arg Gly Asp Val Gln Asn Phe
1               5                   10

<210> SEQ ID NO 278
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 278
aacggagtaa gaggagacgt ccaaaacttc                                                    30

<210> SEQ ID NO 279
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 279

Met Thr Leu Arg Gly Asp Leu Gly Gly Ser
1               5                   10

<210> SEQ ID NO 280
<211> LENGTH: 30
<212> TYPE: DNA

<213> ORGANISM: Artificial Sequence
<220> FEATURE:
<223> OTHER INFORMATION: Synthetic: n-mer encoding polynucleotide

<400> SEQUENCE: 280
atgacgttga gaggagacct gggtgggtcg                                           30

<210> SEQ ID NO 281
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 281
gaggctagga gaggagacgc tagtgcgatg                                           30

<210> SEQ ID NO 282
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 282

Gly Gln Glu Arg Gly Asp Leu Gly Thr Arg
1               5                   10

<210> SEQ ID NO 283
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 283
gggcaggaga gaggagacct ggggactcgg                                           30

<210> SEQ ID NO 284
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 284

Arg Gly Ala Arg Gly Asp Leu Val Asp Ala
1               5                   10

<210> SEQ ID NO 285
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 285
agaggcgcca gaggagacct agtcgacgct                                           30

<210> SEQ ID NO 286
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 286

-continued

```
Gln Tyr Ser Arg Gly Asp His Thr Asp Leu
1               5                   10

<210> SEQ ID NO 287
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 287
caatactcca gaggagacca caccgacctt                                    30

<210> SEQ ID NO 288
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 288

Met Asn Thr Arg Gly Asp Val His Ala Met
1               5                   10

<210> SEQ ID NO 289
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 289
atgaacacca gaggagacgt gcacgctatg                                    30

<210> SEQ ID NO 290
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 290

Thr Val Arg Arg Gly Asp Leu Ala Thr Glu
1               5                   10

<210> SEQ ID NO 291
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 291
acggtacgga gaggagacct agcaaccgaa                                    30

<210> SEQ ID NO 292
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 292
aatattgcga gaggagacgc tggtcagtat                                    30
```

-continued

```
<210> SEQ ID NO 293
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 293

Ser Val Gly Arg Gly Asp Lys Ala Asp Ile
1               5                   10

<210> SEQ ID NO 294
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 294
tctgttggga gaggagacaa ggctgatatt                                    30

<210> SEQ ID NO 295
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 295

Ser His Asn Arg Gly Asp Thr Gly Thr Met
1               5                   10

<210> SEQ ID NO 296
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 296
tcacacaaca gaggagacac cggaaccatg                                    30

<210> SEQ ID NO 297
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 297

Thr Asn Thr Arg Gly Asp Lys Glu Ser Val
1               5                   10

<210> SEQ ID NO 298
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 298
acgaacacca gaggagacaa agaatcagta                                    30

<210> SEQ ID NO 299
<211> LENGTH: 10
<212> TYPE: PRT
<213> ORGANISM: Artificial Sequence
```

```
<220> FEATURE:
<223> OTHER INFORMATION: Synthetic:  n-mer motif

<400> SEQUENCE: 299

Ser Ile Gly Arg Gly Asp Gln Tyr Thr Ile
1               5                   10

<210> SEQ ID NO 300
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 300
tcgattggta gaggagacca gtatacgatt                                30

<210> SEQ ID NO 301
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 301

Gln Thr Ser Arg Gly Asp Ala Gly Ser Trp
1               5                   10

<210> SEQ ID NO 302
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 302
cagacgagta gaggagacgc ggggtcttgg                                30

<210> SEQ ID NO 303
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 303
gctgaaaaca gaggagaccg aagcagccta                                30

<210> SEQ ID NO 304
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 304

Ala Ile Ser Arg Gly Asp Val Gln Ser Leu
1               5                   10

<210> SEQ ID NO 305
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 305
```

-continued gcgatttcga gaggagacgt tcagtcgttg                                        30

<210> SEQ ID NO 306
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 306

Asn Ala Gln Arg Gly Asp His Gly Gln Leu
1               5                   10

<210> SEQ ID NO 307
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 307
aacgcacaaa gaggagacca cgggcaactg                                        30

<210> SEQ ID NO 308
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 308

Leu Asn Ser Arg Gly Asp Gln Ala Ser Val
1               5                   10

<210> SEQ ID NO 309
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 309
ctcaactcga gaggagacca agcctccgtc                                        30

<210> SEQ ID NO 310
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 310

Ser Gly Asn Arg Gly Asp Ile Gly Thr Phe
1               5                   10

<210> SEQ ID NO 311
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 311
tcgggaaaca gaggagacat aggtacattc                                        30

<210> SEQ ID NO 312
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 312

Asn Val Gly Arg Gly Asp Gln Ala Thr Met
1               5                   10

<210> SEQ ID NO 313
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 313
aacgtgggaa gaggagacca agccacaatg                                    30

<210> SEQ ID NO 314
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 314

Ser Tyr Ser Arg Gly Asp Thr Gly Arg Leu
1               5                   10

<210> SEQ ID NO 315
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 315
tcgtattcta gaggagacac tggtcggctt                                    30

<210> SEQ ID NO 316
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 316

Ser His Leu Arg Gly Asp Gln Ala Leu Ala
1               5                   10

<210> SEQ ID NO 317
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 317
agccacttaa gaggagacca agcgttggcc                                    30

<210> SEQ ID NO 318
<211> LENGTH: 10
<212> TYPE: PRT
<213> ORGANISM: Artificial Sequence -continued

```
<220> FEATURE:
<223> OTHER INFORMATION: Synthetic: n-mer motif

<400> SEQUENCE: 318

Tyr Phe Ala Arg Gly Asp Met Thr Met Asn
1               5                   10

<210> SEQ ID NO 319
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 319
tacttcgcca gaggagacat gactatgaac                                    30

<210> SEQ ID NO 320
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 320

Gln Ser Gln Arg Gly Asp Leu Asn Pro Met
1               5                   10

<210> SEQ ID NO 321
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 321
cagtcgcaga gaggagacct taatcctatg                                    30

<210> SEQ ID NO 322
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 322

Glu Gln Arg Arg Gly Asp Lys Thr Glu Leu
1               5                   10

<210> SEQ ID NO 323
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 323
gagcagagga gaggagacaa gacggagctg                                    30

<210> SEQ ID NO 324
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 324
```

Val Ser Ala Arg Gly Asp Ala Gly Gln Leu
1               5                   10

<210> SEQ ID NO 325
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 325
gtgtctgcga gaggagacgc gggtcagttg                                    30

<210> SEQ ID NO 326
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 326
tctccgtcta gaggagacca ggggcggacg                                    30

<210> SEQ ID NO 327
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 327

Glu Ala Ser Arg Gly Asp Lys Gly Thr His
1               5                   10

<210> SEQ ID NO 328
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 328
gaggctagta gaggagacaa gggtacgcat                                    30

<210> SEQ ID NO 329
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 329

Leu Ser Thr Arg Gly Asp Met Gly Met Gln
1               5                   10

<210> SEQ ID NO 330
<211> LENGTH: 736
<212> TYPE: PRT
<213> ORGANISM: Artificial Sequence
<220> FEATURE:
<223> OTHER INFORMATION: Synthetic

<400> SEQUENCE: 330

Met Ala Ala Asp Gly Tyr Leu Pro Asp Trp Leu Glu Asp Asn Leu Ser
1               5                   10                  15

-continued

```
Glu Gly Ile Arg Glu Trp Trp Ala Leu Lys Pro Gly Ala Pro Gln Pro
            20              25              30

Lys Ala Asn Gln Gln His Gln Asp Asn Ala Arg Gly Leu Val Leu Pro
        35              40              45

Gly Tyr Lys Val Leu Gly Pro Gly Asn Gly Leu Asp Lys Gly Glu Pro
    50              55              60

Val Asn Ala Ala Asp Ala Ala Ala Leu Glu His Asp Lys Ala Tyr Asp
65              70              75              80

Gln Gln Leu Lys Ala Gly Asp Asn Pro Tyr Leu Lys Tyr Asn His Ala
            85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Leu Leu Glu Pro
        115             120             125

Leu Gly Leu Val Glu Glu Ala Ala Lys Thr Ala Pro Gly Lys Lys Arg
    130             135             140

Pro Val Glu Gln Ser Pro Gln Glu Pro Asp Ser Ser Ala Gly Ile Gly
145             150             155             160

Lys Ser Gly Ala Gln Pro Ala Lys Lys Arg Leu Asn Phe Gly Gln Thr
            165             170             175

Gly Asp Thr Glu Ser Val Pro Asp Pro Gln Pro Ile Gly Glu Pro Pro
            180             185             190

Ala Ala Pro Ser Gly Val Gly Ser Leu Thr Met Ala Ser Gly Gly Gly
            195             200             205

Ala Pro Val Ala Asp Asn Asn Glu Gly Ala Asp Gly Val Gly Ser Ser
    210             215             220

Ser Gly Asn Trp His Cys Asp Ser Gln Trp Leu Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Asn Ser Thr Ser Gly Ala Ser Ser Asn Asp Asn
            260             265             270

Ala Tyr Phe Gly Tyr Ser Thr Pro Trp Gly Tyr Phe Asp Phe Asn Arg
    275             280             285

Phe His Cys His Phe Ser Pro Arg Asp Trp Gln Arg Leu Ile Asn Asn
    290             295             300

Asn Trp Gly Phe Arg Pro Lys Arg Leu Asn Phe Lys Leu Phe Asn Ile
305             310             315             320

Gln Val Lys Glu Val Thr Asp Asn Asn Gly Val Lys Thr Ile Ala Asn
            325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
    370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
```

-continued

```
          435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

```
<210> SEQ ID NO 331
<211> LENGTH: 736
<212> TYPE: PRT
<213> ORGANISM: Artificial Sequence
<220> FEATURE:
<223> OTHER INFORMATION: Synthetic

<400> SEQUENCE: 331

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Val Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
```

```
     65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
                115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ala Ser Thr Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

-continued

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

```
<210> SEQ ID NO 332
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 332
ctgtctacta gaggagacat gggtatgcag                                              30
```

```
<210> SEQ ID NO 333
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 333

Ala Asn Met Arg Gly Asp Gln Leu His Thr
1               5                   10
```

```
<210> SEQ ID NO 334
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

```
<400> SEQUENCE: 334
gcgaatatga gaggagacca gctgcatact                                    30

<210> SEQ ID NO 335
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 335

Glu Asn Thr Arg Gly Asp Leu Thr His Ala
1               5                   10

<210> SEQ ID NO 336
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 336
gagaatacga gaggagacct tactcatgcg                                    30

<210> SEQ ID NO 337
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 337

Ile Glu Arg Arg Gly Asp Ser Ala Gly Leu
1               5                   10

<210> SEQ ID NO 338
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 338
attgagcgta gaggagactc ggcggggctg                                    30

<210> SEQ ID NO 339
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 339

Ser Ala Met Arg Gly Asp Gly Val Ser Leu
1               5                   10

<210> SEQ ID NO 340
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 340
agtgcgatga gaggagacgg agtgagcttg                                    30
```

-continued

```
<210> SEQ ID NO 341
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 341

Thr Val Ser Arg Gly Asp Gln Gly Leu Ser
1               5                   10

<210> SEQ ID NO 342
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 342
acggtttcga gaggagacca ggggttgtct                                    30

<210> SEQ ID NO 343
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 343

Ser Ile Val Arg Gly Asp Leu Asn Ser Thr
1               5                   10

<210> SEQ ID NO 344
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 344
tcgatcgtca gaggagacct gaactccacg                                    30

<210> SEQ ID NO 345
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 345

Asp Val Ala Arg Gly Asp Lys Thr Asn Phe
1               5                   10

<210> SEQ ID NO 346
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 346
gacgtagcga gaggagacaa aacaaacttc                                    30

<210> SEQ ID NO 347
<211> LENGTH: 10
<212> TYPE: PRT
```

<213> ORGANISM: Artificial Sequence
<220> FEATURE:
<223> OTHER INFORMATION: Synthetic: n-mer motif

<400> SEQUENCE: 347

Trp Ser Gln Arg Gly Asp Leu Ser Gly Thr
1               5                   10

<210> SEQ ID NO 348
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 348
tggagccaaa gaggagacct gagtggaacc                                         30

<210> SEQ ID NO 349
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 349

Leu Asn Gln Arg Gly Asp Val Ser Asn Met
1               5                   10

<210> SEQ ID NO 350
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 350
ctgaaccaaa gaggagacgt ttccaacatg                                         30

<210> SEQ ID NO 351
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 351

Ala Ala Leu Arg Gly Asp Leu Ser Gly Ser
1               5                   10

<210> SEQ ID NO 352
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 352
gccgccctaa gaggagacct atccggctca                                         30

<210> SEQ ID NO 353
<211> LENGTH: 10
<212> TYPE: PRT
<213> ORGANISM: Artificial Sequence
<220> FEATURE:
<223> OTHER INFORMATION: Synthetic: n-mer motif -continued

```
<400> SEQUENCE: 353

Arg Val Ala Arg Gly Asp Ile Thr Asp Ile
1               5               10

<210> SEQ ID NO 354
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 354
agggttgcga gaggagacat tacggatatt                                   30

<210> SEQ ID NO 355
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 355

Ser Thr Asn Arg Gly Asp Leu Asn Gln Val
1               5               10

<210> SEQ ID NO 356
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 356
tcgacgaaca gaggagacct caaccaagtt                                   30

<210> SEQ ID NO 357
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 357

Asp Ser Arg Arg Gly Asp Ser Val Ser Leu
1               5               10

<210> SEQ ID NO 358
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 358
gattcgcgga gaggagactc tgtgagtctt                                   30

<210> SEQ ID NO 359
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 359

Ser Val Gly Arg Gly Asp Gln Ser Gln Met
1               5               10
```

```
<210> SEQ ID NO 360
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 360
agtgttggga gaggagacca gtctcagatg                                            30

<210> SEQ ID NO 361
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 361

Ser Asn Thr Arg Gly Asp Thr Asn Ser Leu
1               5                   10

<210> SEQ ID NO 362
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 362
tccaacacga gaggagacac aaactcccta                                            30

<210> SEQ ID NO 363
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 363

Asp Asn Arg Arg Gly Asp Gly Thr Thr Met
1               5                   10

<210> SEQ ID NO 364
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 364
gataatcgga gaggagacgg tacgactatg                                            30

<210> SEQ ID NO 365
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 365

Thr Pro Ser Arg Gly Asp Gln Gly Arg Leu
1               5                   10

<210> SEQ ID NO 366
<211> LENGTH: 30
```

-continued

```
<212> TYPE: DNA
<213> ORGANISM: Artificial Sequence
<220> FEATURE:
<223> OTHER INFORMATION: Synthetic:  n-mer encoding polynucleotide

<400> SEQUENCE: 366
acgccttcga gaggagacca aggaagacta                                    30

<210> SEQ ID NO 367
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 367

Asn Tyr Ser Arg Gly Asp Ser Met Thr Leu
1               5                   10

<210> SEQ ID NO 368
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 368
aactacagca gaggagactc aatgacgctt                                    30

<210> SEQ ID NO 369
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 369

Met Gln Ala Arg Gly Asp Ala Gly Thr Leu
1               5                   10

<210> SEQ ID NO 370
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 370
atgcaggcta gaggagacgc tgggactctg                                    30

<210> SEQ ID NO 371
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 371

Thr Gln Ser Arg Gly Asp Leu Ser Gly Ala
1               5                   10

<210> SEQ ID NO 372
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

<400> SEQUENCE: 372
acgcagtcga gaggagactt gtctggtgcg                                    30

<210> SEQ ID NO 373
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 373

Phe Ala Gln Arg Gly Asp Leu Thr Gly Val
1               5                   10

<210> SEQ ID NO 374
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 374
tttgcgcaga gaggagactt gactggggtt                                    30

<210> SEQ ID NO 375
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 375

Ala Pro Val Arg Gly Asp Leu Ile Gly Thr
1               5                   10

<210> SEQ ID NO 376
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 376
gcgccggtga gaggagacct gattggtacg                                    30

<210> SEQ ID NO 377
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 377
tcgaatacta gaggagacac gaatagtttg                                    30

<210> SEQ ID NO 378
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 378

Glu Pro Lys Arg Gly Asp Leu Ser Asn Thr
1               5                   10

<210> SEQ ID NO 379
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 379
gagccgaaga gaggagactt gagtaatacg                                      30

<210> SEQ ID NO 380
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 380

Ser Val Gly Arg Gly Asp Thr Tyr Pro Leu
1               5                   10

<210> SEQ ID NO 381
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 381
tcggttggga gaggagacac ttatcctctg                                      30

<210> SEQ ID NO 382
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 382

Gln Thr Ala Arg Gly Asp Met Thr Gly His
1               5                   10

<210> SEQ ID NO 383
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 383
caaacagcca gaggagacat gactggccac                                      30

<210> SEQ ID NO 384
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 384

Ala Gly Ala Arg Gly Asp Leu Glu Asn Arg
1               5                   10

<210> SEQ ID NO 385
<211> LENGTH: 30

-continued

```
<212> TYPE: DNA
<213> ORGANISM: Artificial Sequence
<220> FEATURE:
<223> OTHER INFORMATION: Synthetic:  n-mer encoding polynucleotide

<400> SEQUENCE: 385
gctggtgcga gaggagactt ggagaatcgg                                        30

<210> SEQ ID NO 386
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 386

Met Ser Thr Arg Gly Asp Leu Asn Asn Val
1               5                   10

<210> SEQ ID NO 387
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 387
atgagcacta gaggagacct aaacaacgtc                                        30

<210> SEQ ID NO 388
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 388

Glu Lys Gln Arg Gly Asp Leu Asn Ser Met
1               5                   10

<210> SEQ ID NO 389
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 389
gaaaaacaaa gaggagacct caacagcatg                                        30

<210> SEQ ID NO 390
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 390

Ile Lys Thr Arg Gly Asp Leu Gly His Glu
1               5                   10

<210> SEQ ID NO 391
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

<400> SEQUENCE: 391
attaagacga gaggagacct tggtcatgag                                            30

<210> SEQ ID NO 392
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 392

Ile Gly Arg Arg Gly Asp Met Glu Leu Ser
1               5                   10

<210> SEQ ID NO 393
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 393
attgggagga gaggagacat ggagttgtct                                            30

<210> SEQ ID NO 394
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 394

Thr Thr Gly Arg Gly Asp Leu Lys Glu Val
1               5                   10

<210> SEQ ID NO 395
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 395
actacgggta gaggagactt gaaggaggtt                                            30

<210> SEQ ID NO 396
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 396

Thr Asp Lys Arg Gly Asp Gln Asn Thr Val
1               5                   10

<210> SEQ ID NO 397
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 397
acggataaga gaggagacca gaatactgtg                                            30

-continued

```
<210> SEQ ID NO 398
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 398

Ser Asn Val Arg Gly Asp Arg Glu Ala Val
1               5                   10

<210> SEQ ID NO 399
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 399
tcgaatgtta gaggagaccg ggaggcggtt                                    30

<210> SEQ ID NO 400
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 400
tcagtcggca gaggagacca aagtcaaatg                                    30

<210> SEQ ID NO 401
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 401

Tyr Ala Asn Arg Gly Asp Leu Ser His Gln
1               5                   10

<210> SEQ ID NO 402
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 402
tacgccaaca gaggagacct gagtcaccaa                                    30

<210> SEQ ID NO 403
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 403
caaatatcga gaggagacct aggtatcaac                                    30

<210> SEQ ID NO 404
<211> LENGTH: 10
<212> TYPE: PRT
```

-continued

```
<213> ORGANISM: Artificial Sequence
<220> FEATURE:
<223> OTHER INFORMATION: Synthetic: n-mer motif

<400> SEQUENCE: 404

Ser Met Met Arg Gly Asp Ala Gly Gln Leu
1               5                   10

<210> SEQ ID NO 405
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 405
tcgatgatga gaggagacgc tgggcagttg                                   30

<210> SEQ ID NO 406
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 406

Glu Ala Arg Arg Gly Asp Ser Gln Gly Leu
1               5                   10

<210> SEQ ID NO 407
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 407
gaggcgcgga gaggagacag tcaggggctg                                   30

<210> SEQ ID NO 408
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 408

Met Pro Thr Arg Gly Asp Gln Thr Lys Phe
1               5                   10

<210> SEQ ID NO 409
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 409
atgcccacaa gaggagacca aaccaaattc                                   30

<210> SEQ ID NO 410
<211> LENGTH: 30
<212> TYPE: DNA
<213> ORGANISM: Artificial Sequence
<220> FEATURE:
<223> OTHER INFORMATION: Synthetic: n-mer encoding polynucleotide
```

```
<400> SEQUENCE: 410
tcaaactcca gaggagacta caactccttg                                    30

<210> SEQ ID NO 411
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 411

Ser Ser Ala Arg Gly Asp Arg Asp Tyr Leu
1               5                   10

<210> SEQ ID NO 412
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 412
tcgtcggcta gaggagaccg tgattatctg                                    30

<210> SEQ ID NO 413
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 413

Ser Thr Val Arg Gly Asp Tyr Thr Ser Val
1               5                   10

<210> SEQ ID NO 414
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 414
agcacggtca gaggagacta cacgtccgtg                                    30

<210> SEQ ID NO 415
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 415
caggagcgga gaggagacta tacgagtatg                                    30

<210> SEQ ID NO 416
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 416
aacggcggga gaggagacac gacgcacttc                                    30
```

<210> SEQ ID NO 417
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 417
gcgagtacta gaggagacca tggtgtgttg                                        30

<210> SEQ ID NO 418
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 418

Ser Tyr Gln Arg Gly Asp Gln His Asn Met
1               5                   10

<210> SEQ ID NO 419
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 419
tcgtaccaaa gaggagacca acacaacatg                                        30

<210> SEQ ID NO 420
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 420

Asn Asp Thr Arg Gly Asp Arg Ser Tyr Met
1               5                   10

<210> SEQ ID NO 421
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 421
aacgacacaa gaggagaccg atcttacatg                                        30

<210> SEQ ID NO 422
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 422
gaaaacagga gaggagactt caacaacact                                        30

<210> SEQ ID NO 423
<211> LENGTH: 10
<212> TYPE: PRT
<213> ORGANISM: Artificial Sequence
<220> FEATURE:

-continued

```
<223> OTHER INFORMATION: Synthetic:  n-mer motif

<400> SEQUENCE: 423

Ser Gly Ser Arg Gly Asp Leu Ser Gly His
1               5                   10

<210> SEQ ID NO 424
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 424
tccggctcga gaggagactt gtcaggacac                                    30

<210> SEQ ID NO 425
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 425
gagaatcgga gaggagacat tacgcagtcg                                    30

<210> SEQ ID NO 426
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 426

Asp Lys Pro Arg Gly Asp Arg Gln Leu Leu
1               5                   10

<210> SEQ ID NO 427
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 427
gataagccga gaggagaccg gcagttgttg                                    30

<210> SEQ ID NO 428
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 428
gaggagcgga gaggagacac tcatcggctg                                    30

<210> SEQ ID NO 429
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 429
gcgatgatta gaggagacat gacgcatagt                                    30
```

```
<210> SEQ ID NO 430
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 430

Ser Asn Asn Arg Gly Asp Tyr Thr Thr Met
1               5               10

<210> SEQ ID NO 431
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 431
tcaaacaaca gaggagacta cacgacaatg                                      30

<210> SEQ ID NO 432
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 432

Gln Gly Gly Arg Gly Asp Leu Ser Thr Leu
1               5               10

<210> SEQ ID NO 433
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 433
cagggtggga gaggagactt gtcgacgttg                                      30

<210> SEQ ID NO 434
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 434

Ser Lys Asp Arg Gly Asp Tyr Gln Thr Leu
1               5               10

<210> SEQ ID NO 435
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 435
tcgaaggata gaggagacta tcagactctt                                      30

<210> SEQ ID NO 436
<211> LENGTH: 10
```

```
<212> TYPE: PRT
<213> ORGANISM: Artificial Sequence
<220> FEATURE:
<223> OTHER INFORMATION: Synthetic:  n-mer motif

<400> SEQUENCE: 436

Ala Thr Ala Arg Gly Asp Gln Met Lys Leu
1               5                   10

<210> SEQ ID NO 437
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 437
gctacggcga gaggagacca gatgaagctg                                    30

<210> SEQ ID NO 438
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 438

Gln His Met Arg Gly Asp Leu Thr Gly Ala
1               5                   10

<210> SEQ ID NO 439
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 439
cagcatatga gaggagactt gactggtgcg                                    30

<210> SEQ ID NO 440
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 440

Asp Gly Thr Arg Gly Asp Leu Gly Arg Tyr
1               5                   10

<210> SEQ ID NO 441
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 441
gacggcacga gaggagacct tggaaggtac                                    30

<210> SEQ ID NO 442
<211> LENGTH: 10
<212> TYPE: PRT
<213> ORGANISM: Artificial Sequence
<220> FEATURE:
<223> OTHER INFORMATION: Synthetic:  n-mer motif
```

-continued

<400> SEQUENCE: 442

Asp Ser Arg Arg Gly Asp Tyr Ala Asn Leu
1               5                   10

<210> SEQ ID NO 443
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 443
gactctcgga gaggagacta cgcaaacctc                                    30

<210> SEQ ID NO 444
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 444

Ser Ala Met Arg Gly Asp Tyr Thr Ser Thr
1               5                   10

<210> SEQ ID NO 445
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 445
tcggcgatga gaggagacta tactagtact                                    30

<210> SEQ ID NO 446
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 446

Glu Asn Arg Arg Gly Asp Ala Gln Leu Leu
1               5                   10

<210> SEQ ID NO 447
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 447
gagaatcgga gaggagacgc gcagctgctg                                    30

<210> SEQ ID NO 448
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 448

Thr Thr Leu Arg Gly Asp His Ser Gln Leu 1              5              10

<210> SEQ ID NO 449
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 449
acgacgctga gaggagacca tagtcagctt                                    30

<210> SEQ ID NO 450
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 450

Asp Ala Gly Arg Gly Asp Met His Arg Met
1              5              10

<210> SEQ ID NO 451
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 451
gacgcaggga gaggagacat gcaccgtatg                                    30

<210> SEQ ID NO 452
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 452

Gln His Thr Arg Gly Asp Leu Ser Ser Thr
1              5              10

<210> SEQ ID NO 453
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 453
cagcatacga gaggagactt gagttctact                                    30

<210> SEQ ID NO 454
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 454

Gln Val Tyr Arg Gly Asp Arg Glu Ser Val
1              5              10

<210> SEQ ID NO 455

-continued

```
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 455
caagtttaca gaggagacag ggaatccgtg                                         30

<210> SEQ ID NO 456
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 456

Ser Ser Gln Arg Gly Asp Leu Ala Gly Thr
1               5                   10

<210> SEQ ID NO 457
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 457
tcgagtcaga gaggagactt ggctggtact                                         30

<210> SEQ ID NO 458
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 458

Thr Asp Val Arg Gly Asp Arg Gly Thr Phe
1               5                   10

<210> SEQ ID NO 459
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 459
acggatgtta gaggagacag ggggacgttt                                         30

<210> SEQ ID NO 460
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 460

Ser Ser Val Arg Gly Asp Arg Glu Val Thr
1               5                   10

<210> SEQ ID NO 461
<211> LENGTH: 30
<212> TYPE: DNA
<213> ORGANISM: Artificial Sequence
<220> FEATURE:
```

<223> OTHER INFORMATION: Synthetic:  n-mer encoding polynucleotide

<400> SEQUENCE: 461
tcgtctgtga gaggagaccg ggaggtgacg                                              30

<210> SEQ ID NO 462
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 462

Glu Asn Arg Arg Gly Asp Leu Thr Asn Ala
1               5                   10

<210> SEQ ID NO 463
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 463
gagaatagga gaggagacct gactaatgcg                                              30

<210> SEQ ID NO 464
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 464

Ser Tyr Ala Arg Gly Asp Val His Ser Ile
1               5                   10

<210> SEQ ID NO 465
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 465
tcgtatgcga gaggagacgt tcattctatt                                              30

<210> SEQ ID NO 466
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 466

Asp Ser Ser Arg Gly Asp Leu Asn Leu Arg
1               5                   10

<210> SEQ ID NO 467
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 467

-continued

```
gacagctcaa gaggagacct caacctccgg                                   30

<210> SEQ ID NO 468
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 468

Ser Asn Ala Arg Gly Asp Tyr Ser Asn Met
1               5                   10

<210> SEQ ID NO 469
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 469
tcgaacgcga gaggagacta ctcaaacatg                                   30

<210> SEQ ID NO 470
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 470

Ser Ser Val Arg Gly Asp His Ser Val Leu
1               5                   10

<210> SEQ ID NO 471
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 471
tcgtctgtga gaggagacca ttcggtgctt                                   30

<210> SEQ ID NO 472
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 472

Ser Ala Phe Arg Gly Asp Leu His Ala Thr
1               5                   10

<210> SEQ ID NO 473
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 473
tcggctttta gaggagacct gcatgctact                                   30

<210> SEQ ID NO 474
```

```
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 474
tccgccatga gaggagacta cacaagcacg                                30

<210> SEQ ID NO 475
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 475
aacgcacaaa gaggagacca cgggcaactg                                30

<210> SEQ ID NO 476
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 476

Ser Asp Arg Arg Gly Asp Gln Leu Leu Tyr
1               5                   10

<210> SEQ ID NO 477
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 477
tcggatcgga gaggagacca gctgttgtat                                30

<210> SEQ ID NO 478
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 478

Ser Gly Val Arg Gly Asp Arg Leu Ala Val
1               5                   10

<210> SEQ ID NO 479
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 479
agcggcgtaa gaggagaccg cctagccgta                                30

<210> SEQ ID NO 480
<211> LENGTH: 10
<212> TYPE: PRT
<213> ORGANISM: Artificial Sequence
<220> FEATURE:
<223> OTHER INFORMATION: Synthetic:  n-mer motif
```

-continued

<400> SEQUENCE: 480

Ala Ser Leu Arg Gly Asp Leu Ser Ser Thr
1               5                   10

<210> SEQ ID NO 481
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 481
gccagcctaa gaggagacct cagctcaacg                                    30

<210> SEQ ID NO 482
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 482

Thr Asn Gly Arg Gly Asp Leu His Gly Met
1               5                   10

<210> SEQ ID NO 483
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 483
acgaacggaa gaggagacct tcacggaatg                                    30

<210> SEQ ID NO 484
<211> LENGTH: 10
<212> TYPE: PRT
<213> ORGANISM: Artificial Sequence
<220> FEATURE:
<223> OTHER INFORMATION: Synthetic:   n-mer motif

<400> SEQUENCE: 484

Thr Asn Thr Arg Gly Asp His Gly Met Leu
1               5                   10

<210> SEQ ID NO 485
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 485
acgaatacga gaggagacca tgggatgctg                                    30

<210> SEQ ID NO 486
<211> LENGTH: 30
<212> TYPE: DNA
<213> ORGANISM: Artificial Sequence
<220> FEATURE:
<223> OTHER INFORMATION: Synthetic:   n-mer encoding polynucleotide

<400> SEQUENCE: 486
agttccgcca gaggagaccg ggactacctc                                    30

```
<210> SEQ ID NO 487
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 487

Glu Asp Arg Arg Gly Asp Leu Leu Arg Thr
1               5                   10

<210> SEQ ID NO 488
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 488
gaggatcgga gaggagacct tttgaggact                                    30

<210> SEQ ID NO 489
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 489

Ser Ser Leu Arg Gly Asp Leu Leu His Ser
1               5                   10

<210> SEQ ID NO 490
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 490
tcgtcgctga gaggagacct gttgcattct                                    30

<210> SEQ ID NO 491
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 491
gaaaaccgta gaggagacct cacgaacgct                                    30

<210> SEQ ID NO 492
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 492

Asp Gly Arg Arg Gly Asp Arg Glu Ser Ile
1               5                   10

<210> SEQ ID NO 493
<211> LENGTH: 30
```

-continued

```
<212> TYPE: DNA
<213> ORGANISM: Artificial Sequence
<220> FEATURE:
<223> OTHER INFORMATION: Synthetic: n-mer encoding polynucleotide

<400> SEQUENCE: 493
gacggcagga gaggagaccg ggaatcgatc                                     30

<210> SEQ ID NO 494
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 494

Thr Gly Thr Arg Gly Asp Thr Met Thr Trp
1               5                   10

<210> SEQ ID NO 495
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 495
actggaacca gaggagacac aatgacatgg                                     30

<210> SEQ ID NO 496
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 496
tcgactgtta gaggagacta tacttctgtt                                     30

<210> SEQ ID NO 497
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 497

Ser Ala Thr Arg Gly Asp His Asn Val Leu
1               5                   10

<210> SEQ ID NO 498
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 498
tcggcaacga gaggagacca caacgtactg                                     30

<210> SEQ ID NO 499
<211> LENGTH: 10
<212> TYPE: PRT
<213> ORGANISM: Artificial Sequence
<220> FEATURE:
<223> OTHER INFORMATION: Synthetic: n-mer motif
```

```
<400> SEQUENCE: 499

Thr Asp Arg Arg Gly Asp Ser Gly Thr Leu
1               5                   10

<210> SEQ ID NO 500
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 500
acggatcgga gaggagacag tggtactctg                                    30

<210> SEQ ID NO 501
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 501

Thr Ser Ala Arg Gly Asp Leu Ile His Thr
1               5                   10

<210> SEQ ID NO 502
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 502
acgagtgcta gaggagacct gattcatacg                                    30

<210> SEQ ID NO 503
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 503
agtggggtga gaggagaccg gctggcggtg                                    30

<210> SEQ ID NO 504
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 504

Ala Val Glu Arg Gly Asp Arg Leu Met Leu
1               5                   10

<210> SEQ ID NO 505
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 505
gcggttgaga gaggagaccg tcttatgctg                                    30
```

```
<210> SEQ ID NO 506
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 506

Asp Arg Ser Arg Gly Asp Thr His Val Leu
1               5                   10

<210> SEQ ID NO 507
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 507
gacaggtcga gaggagacac gcacgtactc                                        30

<210> SEQ ID NO 508
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 508

Glu Ser Thr Arg Gly Asp Leu Arg Val Val
1               5                   10

<210> SEQ ID NO 509
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 509
gagtcgacga gaggagacct tcgtgttgtg                                        30

<210> SEQ ID NO 510
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 510

Thr Thr Ile Arg Gly Asp Tyr Arg Glu Leu
1               5                   10

<210> SEQ ID NO 511
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 511
acgacgatta gaggagacta tcgtgagttg                                        30

<210> SEQ ID NO 512
<211> LENGTH: 10
<212> TYPE: PRT
```

```
<213> ORGANISM: Artificial Sequence
<220> FEATURE:
<223> OTHER INFORMATION: Synthetic:  n-mer motif

<400> SEQUENCE: 512

Thr Phe Ile Arg Gly Asp Leu Ala Gly Ala
1               5                   10

<210> SEQ ID NO 513
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 513
acgttcatca gaggagacct ggcaggtgcg                                      30

<210> SEQ ID NO 514
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 514

Met Thr Ser Arg Gly Asp Leu Thr Thr Tyr
1               5                   10

<210> SEQ ID NO 515
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 515
atgacgagca gaggagactt gacaacatac                                      30

<210> SEQ ID NO 516
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 516

Ala Asp Arg Arg Gly Asp Gln Leu Tyr Ser
1               5                   10

<210> SEQ ID NO 517
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 517
gcggatcgta gaggagacca gctttattcg                                      30

<210> SEQ ID NO 518
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

```
<400> SEQUENCE: 518
gcacacatga gaggagacct aggcggcacg                                      30

<210> SEQ ID NO 519
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 519

Gly Tyr Val Arg Gly Asp Leu Gly Gln His
1               5                   10

<210> SEQ ID NO 520
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 520
gggtacgtca gaggagacct ggggcaacac                                      30

<210> SEQ ID NO 521
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 521

Asp Ala Ser Arg Gly Asp Arg Thr Ser Leu
1               5                   10

<210> SEQ ID NO 522
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 522
gatgcgagta gaggagacag gactagtttg                                      30

<210> SEQ ID NO 523
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 523

Thr Glu Val Arg Gly Asp Arg Ser Gln Val
1               5                   10

<210> SEQ ID NO 524
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 524
acggaggtga gaggagacag gtcgcaggtt                                      30
```

<210> SEQ ID NO 525
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 525
tcgcatctga gaggagacca ggctcttgcg                                                                  30

<210> SEQ ID NO 526
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 526

Ser Glu Val Arg Gly Asp Arg Leu Ser Ile
1               5                   10

<210> SEQ ID NO 527
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 527
tcggaggtga gaggagaccg gttgagtatt                                                                  30

<210> SEQ ID NO 528
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 528
agcgccgcga gaggagacac tgaacggcta                                                                  30

<210> SEQ ID NO 529
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 529

Ser Asp Arg Arg Gly Asp Leu Ser Gly Ala
1               5                   10

<210> SEQ ID NO 530
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 530
tcagaccgta gaggagacct gtcgggcgct                                                                  30

<210> SEQ ID NO 531
<211> LENGTH: 10
<212> TYPE: PRT
<213> ORGANISM: Artificial Sequence -continued
<220> FEATURE:
<223> OTHER INFORMATION: Synthetic: n-mer motif

<400> SEQUENCE: 531

Ser Val Thr Arg Gly Asp Arg Val Val Ile
1               5               10

<210> SEQ ID NO 532
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 532
agcgtcacaa gaggagacag agtagtcatc                                      30

<210> SEQ ID NO 533
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 533

Ser Glu Gly Arg Gly Asp Arg Met Ala Leu
1               5               10

<210> SEQ ID NO 534
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 534
tcggagggga gaggagacag gatggctctt                                      30

<210> SEQ ID NO 535
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 535

Ser Ser Thr Arg Gly Asp His Leu Ser Leu
1               5               10

<210> SEQ ID NO 536
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 536
tcgtctacta gaggagacca tctttcgctg                                      30

<210> SEQ ID NO 537
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 537

-continued gctatgatca gaggagacat gacccactcc                                      30

<210> SEQ ID NO 538
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 538

Ser Ser Thr Arg Gly Asp Gln Ile Tyr Val
1               5                   10

<210> SEQ ID NO 539
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 539
tcgtcgacga gaggagacca gatttatgtg                                      30

<210> SEQ ID NO 540
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 540
gaggagcgga gaggagacac tcatcggttg                                      30

<210> SEQ ID NO 541
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 541
tcgaattcga gaggagacta taatagtctt                                      30

<210> SEQ ID NO 542
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 542

Ser Ala Gln Arg Asp Arg Met Gly Ser Pro
1               5                   10

<210> SEQ ID NO 543
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 543
tccgcacaaa gggatcgtat gggttctccg                                      30

<210> SEQ ID NO 544

-continued

```
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 544

Thr Gly Thr Arg Gly Asp Ile Ala Thr Phe
1               5                   10

<210> SEQ ID NO 545
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 545
acgggtacga gaggagacat tgcgactttt                                     30

<210> SEQ ID NO 546
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 546

Ser Met Gln Arg Gly Asp Leu Leu Ser Thr
1               5                   10

<210> SEQ ID NO 547
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 547
tcgatgcaga gaggagacct gctttctact                                     30

<210> SEQ ID NO 548
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 548

Glu Asp Val Arg Gly Asp Arg Ser Lys Leu
1               5                   10

<210> SEQ ID NO 549
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 549
gaggatgtga gaggagacag gagtaagctt                                     30

<210> SEQ ID NO 550
<211> LENGTH: 30
<212> TYPE: DNA
<213> ORGANISM: Artificial Sequence
<220> FEATURE:
```

-continued

<223> OTHER INFORMATION: Synthetic:  n-mer encoding polynucleotide

<400> SEQUENCE: 550
gcgcatatga gaggagactt ggggggggact                                              30

<210> SEQ ID NO 551
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 551

Thr Ser Val Arg Gly Asp Gln Ser Gln Tyr
1               5                   10

<210> SEQ ID NO 552
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 552
acgagtgtga gaggagacca gagtcagtat                                              30

<210> SEQ ID NO 553
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 553

Ala Asp Arg Arg Gly Asp Thr Gly Leu Phe
1               5                   10

<210> SEQ ID NO 554
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 554
gcggatcgga gaggagacac ggggttgttt                                              30

<210> SEQ ID NO 555
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 555

Asn Thr Tyr Arg Gly Asp Arg Asp Ser Leu
1               5                   10

<210> SEQ ID NO 556
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 556

-continued aacacttaca gaggagaccg agacagcctg                                           30

<210> SEQ ID NO 557
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 557
acggatgtta gaggagaccg ggggacgttt                                           30

<210> SEQ ID NO 558
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 558

Ser Arg Gly Arg Gly Asp Leu Asn Asp Leu
1               5                   10

<210> SEQ ID NO 559
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 559
tctcgtggga gaggagacct gaatgatttg                                           30

<210> SEQ ID NO 560
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 560
agcaacgtaa gaggagacag ggaagccgtc                                           30

<210> SEQ ID NO 561
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 561

Met Asp Arg Arg Gly Asp Ala Ser Ile Leu
1               5                   10

<210> SEQ ID NO 562
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 562
atggacagga gaggagacgc ctccatactg                                           30

<210> SEQ ID NO 563
<211> LENGTH: 10

-continued

```
<212> TYPE: PRT
<213> ORGANISM: Artificial Sequence
<220> FEATURE:
<223> OTHER INFORMATION: Synthetic:  n-mer motif

<400> SEQUENCE: 563

Ser Ile Trp Arg Gly Asp Arg Thr Glu Val
1               5                   10

<210> SEQ ID NO 564
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 564
tcgatatgga gaggagaccg tacagaagtc                                    30

<210> SEQ ID NO 565
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 565

Asn Ser Gln Arg Gly Asp Tyr Ser Gly Met
1               5                   10

<210> SEQ ID NO 566
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 566
aactcacaaa gaggagacta cagtggaatg                                    30

<210> SEQ ID NO 567
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 567

Ser Ser Val Arg Gly Asp Ile Gly Gly Ile
1               5                   10

<210> SEQ ID NO 568
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 568
tctagcgtaa gaggagacat cggggggatc                                    30

<210> SEQ ID NO 569
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

<400> SEQUENCE: 569
gagaatcaga gaggagactt gtcgggtcgg                                        30

<210> SEQ ID NO 570
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 570

Glu Ile Arg Arg Gly Asp Leu Leu Ala Gln
1               5                   10

<210> SEQ ID NO 571
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 571
gagattcgga gaggagacct tctggctcag                                        30

<210> SEQ ID NO 572
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 572

Ser Asn Ile Arg Gly Asp His Ala Val Met
1               5                   10

<210> SEQ ID NO 573
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 573
tcgaacatca gaggagacca cgcagtcatg                                        30

<210> SEQ ID NO 574
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 574

Leu Asp Thr Arg Gly Asp Arg Ser Gln Val
1               5                   10

<210> SEQ ID NO 575
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 575
ctggatacga gaggagaccg gagtcaggtt                                        30

```
<210> SEQ ID NO 576
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 576

Ala Asn Thr Arg Gly Asp His Gln Asn Phe
1               5                   10

<210> SEQ ID NO 577
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 577
gcgaatacga gaggagacca tcagaatttt                                    30

<210> SEQ ID NO 578
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 578
caggtgtata gaggagaccg tgagtctgtt                                    30

<210> SEQ ID NO 579
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 579

Thr Ser Val Arg Gly Asp Leu Ser Met Asn
1               5                   10

<210> SEQ ID NO 580
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 580
acgtcggtga gaggagacct ttcgatgaat                                    30

<210> SEQ ID NO 581
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 581
gcctcaacga gaggagacca cggagttctc                                    30

<210> SEQ ID NO 582
<211> LENGTH: 10
<212> TYPE: PRT
```

```
<213> ORGANISM: Artificial Sequence
<220> FEATURE:
<223> OTHER INFORMATION: Synthetic:  n-mer motif

<400> SEQUENCE: 582

Thr Thr Thr Arg Gly Asp Tyr Leu Asn Thr
1               5                   10

<210> SEQ ID NO 583
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 583
acgacgacga gaggagacta tcttaatacg                                    30

<210> SEQ ID NO 584
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 584

Ala Glu Arg Arg Gly Asp Ile Lys Glu Tyr
1               5                   10

<210> SEQ ID NO 585
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 585
gcggagagga gaggagacat taaggagtat                                    30

<210> SEQ ID NO 586
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 586

Ser His Ala Arg Gly Asp Leu Gly Ser Thr
1               5                   10

<210> SEQ ID NO 587
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 587
tcgcatgcta gaggagactt gggttcgact                                    30

<210> SEQ ID NO 588
<211> LENGTH: 10
<212> TYPE: PRT
<213> ORGANISM: Artificial Sequence
<220> FEATURE:
<223> OTHER INFORMATION: Synthetic:  n-mer motif
```

```
<400> SEQUENCE: 588

Thr Ser Gln Arg Gly Asp Tyr Val Ser Leu
1               5               10

<210> SEQ ID NO 589
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 589
acgtctcaga gaggagacta tgtttctctt                                    30

<210> SEQ ID NO 590
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 590
gggccgggta gaggagacca gactacgttg                                    30

<210> SEQ ID NO 591
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 591

Val Asn Val Arg Gly Asp Arg Gly Glu Val
1               5               10

<210> SEQ ID NO 592
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 592
gtgaatgtga gaggagaccg tggtgaggtg                                    30

<210> SEQ ID NO 593
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 593

Ser Tyr Arg Arg Gly Asp His Asp Gln Leu
1               5               10

<210> SEQ ID NO 594
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 594
tcgtatcgta gaggagacca tgatcagctt                                    30
```

-continued

```
<210> SEQ ID NO 595
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 595

Ser Gly Thr Arg Gly Asp Arg Val Asp Leu
1               5                   10

<210> SEQ ID NO 596
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 596
agcggcacaa gaggagacag ggtagacctc                              30

<210> SEQ ID NO 597
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 597

Ser His Phe Arg Gly Asp Leu His Thr Ser
1               5                   10

<210> SEQ ID NO 598
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 598
tcccacttca gaggagactt gcacacgtcc                              30

<210> SEQ ID NO 599
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 599

Ser Asp Arg Arg Gly Asp Leu Ser Val Pro
1               5                   10

<210> SEQ ID NO 600
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 600
tcggatcgta gaggagacct ttcggtgcct                              30

<210> SEQ ID NO 601
<211> LENGTH: 10
<212> TYPE: PRT
```

-continued

```
<213> ORGANISM: Artificial Sequence
<220> FEATURE:
<223> OTHER INFORMATION: Synthetic: n-mer motif

<400> SEQUENCE: 601

Ser Gly Thr Arg Gly Asp Thr Leu Ile Leu
1               5                   10

<210> SEQ ID NO 602
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 602
agcggcacca gaggagacac ccttatactc                                        30

<210> SEQ ID NO 603
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 603

Glu Asn Thr Arg Gly Asp Leu His Gly Lys
1               5                   10

<210> SEQ ID NO 604
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 604
gaaaacacca gaggagacct ccacggcaaa                                        30

<210> SEQ ID NO 605
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 605

Asp Arg Ala Arg Gly Asp Thr His Val Leu
1               5                   10

<210> SEQ ID NO 606
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 606
gatcgggcga gaggagacac gcatgtgctg                                        30

<210> SEQ ID NO 607
<211> LENGTH: 10
<212> TYPE: PRT
<213> ORGANISM: Artificial Sequence
<220> FEATURE:
<223> OTHER INFORMATION: Synthetic: n-mer motif
```

```
<400> SEQUENCE: 607

Ala Ser Gly Arg Gly Asp Ile Ala Gly Leu
1               5                   10

<210> SEQ ID NO 608
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 608
gcgtctggta gaggagacat tgcggggctt                                30

<210> SEQ ID NO 609
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 609

Glu Gly Arg Arg Gly Asp Leu Phe Gln Ala
1               5                   10

<210> SEQ ID NO 610
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 610
gagggtcgta gaggagacct gtttcaggcg                                30

<210> SEQ ID NO 611
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 611

Arg Ser Glu Arg Gly Asp Arg Leu Glu Ile
1               5                   10

<210> SEQ ID NO 612
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 612
agatccgaaa gaggagacag gctagaaatc                                30

<210> SEQ ID NO 613
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 613

Ala Ala Tyr Arg Gly Asp Ala His Val Leu
1               5                   10
```

```
<210> SEQ ID NO 614
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 614
gcggcctaca gaggagacgc acacgtgctc                                        30

<210> SEQ ID NO 615
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 615

Asn Asp Ser Arg Gly Asp Gln His Arg Leu
1               5                   10

<210> SEQ ID NO 616
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 616
aacgactcga gaggagacca acaccgattg                                        30

<210> SEQ ID NO 617
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 617

Ser Ser Ala Arg Gly Asp His Ser Gln Leu
1               5                   10

<210> SEQ ID NO 618
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 618
tcatcggcaa gaggagacca ctctcaactg                                        30

<210> SEQ ID NO 619
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 619

Thr Asn Glu Arg Gly Asp Arg Leu Ser Ile
1               5                   10

<210> SEQ ID NO 620
<211> LENGTH: 30
```

<212> TYPE: DNA
<213> ORGANISM: Artificial Sequence
<220> FEATURE:
<223> OTHER INFORMATION: Synthetic: n-mer encoding polynucleotide

<400> SEQUENCE: 620
acgaatgaga gaggagaccg tctttcgatt                                    30

<210> SEQ ID NO 621
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 621

Ser Asn Ser Arg Gly Asp Tyr Thr Ser Val
1               5                   10

<210> SEQ ID NO 622
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 622
agcaactcca gaggagacta caccagtgtc                                    30

<210> SEQ ID NO 623
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 623

Asn Val Thr Arg Gly Asp His Thr Val Met
1               5                   10

<210> SEQ ID NO 624
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 624
aacgtcacaa gaggagacca caccgttatg                                    30

<210> SEQ ID NO 625
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 625

Thr Met Val Arg Gly Asp Val Lys Gly Leu
1               5                   10

<210> SEQ ID NO 626
<211> LENGTH: 30
<212> TYPE: DNA
<213> ORGANISM: Artificial Sequence
<220> FEATURE:
<223> OTHER INFORMATION: Synthetic: n-mer encoding polynucleotide -continued

```
<400> SEQUENCE: 626
acgatggtga gaggagacgt taaggggctt                                    30

<210> SEQ ID NO 627
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 627
accgggacaa gaggagacat agccacgttc                                    30

<210> SEQ ID NO 628
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 628

Val Gln Leu Arg Gly Asp Leu Ala Ser Thr
1               5                   10

<210> SEQ ID NO 629
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 629
gtgcagctga gaggagactt ggcttctact                                    30

<210> SEQ ID NO 630
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 630

Met Asn Arg Arg Gly Asp Tyr Ser Glu Gln
1               5                   10

<210> SEQ ID NO 631
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 631
atgaaccgga gaggagacta ctcggaacaa                                    30

<210> SEQ ID NO 632
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 632

Ala Asn Thr Arg Gly Asp Leu Ser Pro Val
1               5                   10
```

-continued

<210> SEQ ID NO 633
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 633
gcgaatacta gaggagacct gagtccggtt                                                      30

<210> SEQ ID NO 634
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 634

Thr Gly Met Arg Gly Asp Ala Gly Ser Leu
1               5                   10

<210> SEQ ID NO 635
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 635
acgggtatga gaggagacgc tgggagtctt                                                      30

<210> SEQ ID NO 636
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 636

Leu Asp Arg Arg Gly Asp Phe Ser Ser Ala
1               5                   10

<210> SEQ ID NO 637
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 637
ctagaccgca gaggagactt cagctccgcg                                                      30

<210> SEQ ID NO 638
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 638

Met Tyr His Arg Gly Asp Met Thr Ser Val
1               5                   10

<210> SEQ ID NO 639
<211> LENGTH: 30

<212> TYPE: DNA
<213> ORGANISM: Artificial Sequence
<220> FEATURE:
<223> OTHER INFORMATION: Synthetic:  n-mer encoding polynucleotide

<400> SEQUENCE: 639
atgtaccaca gaggagacat gacttcggtg                                          30

<210> SEQ ID NO 640
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 640

Gly Ser Met Arg Gly Asp Leu His Ser Thr
1               5                   10

<210> SEQ ID NO 641
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 641
gggtcgatga gaggagactt gcattcgacg                                          30

<210> SEQ ID NO 642
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 642

Ser Ser Ser Arg Gly Asp Phe Ser Ser Val
1               5                   10

<210> SEQ ID NO 643
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 643
tcgtcgtcca gaggagactt cagctctgtt                                          30

<210> SEQ ID NO 644
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 644

Thr Gly Thr Arg Gly Asp Leu His Thr Tyr
1               5                   10

<210> SEQ ID NO 645
<211> LENGTH: 30
<212> TYPE: DNA
<213> ORGANISM: Artificial Sequence
<220> FEATURE:
<223> OTHER INFORMATION: Synthetic:  n-mer encoding polynucleotide -continued

```
<400> SEQUENCE: 645
acgggtacga gaggagactt gcatacttat                                      30

<210> SEQ ID NO 646
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 646

Tyr Thr Gln Arg Gly Asp Leu Ala Thr Val
1               5                   10

<210> SEQ ID NO 647
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 647
tacacccaaa gaggagacct tgccaccgtc                                      30

<210> SEQ ID NO 648
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 648

Thr Asp Val Arg Gly Asp Arg Met Tyr Val
1               5                   10

<210> SEQ ID NO 649
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 649
acggatgtta gaggagaccg gatgtatgtg                                      30

<210> SEQ ID NO 650
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 650
acatcggtca gaggagacca cggaacattg                                      30

<210> SEQ ID NO 651
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 651

Ser Asn Ser Arg Gly Asp Leu Ser Val Asn
1               5                   10
```

```
<210> SEQ ID NO 652
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 652
tcgaactcca gaggagacct atcggtaaac                                    30

<210> SEQ ID NO 653
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 653

Gln Ser Gly Arg Gly Asp Gln Met Thr Leu
1               5                   10

<210> SEQ ID NO 654
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 654
cagtctggga gaggagacca gatgacgttg                                    30

<210> SEQ ID NO 655
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 655

Met Asn Thr Arg Gly Asp Leu Gln Gln Ser
1               5                   10

<210> SEQ ID NO 656
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 656
atgaacacca gaggagactt gcaacaatcg                                    30

<210> SEQ ID NO 657
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 657

Ala Gly Ser Arg Gly Asp Leu Gln Thr Val
1               5                   10

<210> SEQ ID NO 658
<211> LENGTH: 30
```

-continued

```
<212> TYPE: DNA
<213> ORGANISM: Artificial Sequence
<220> FEATURE:
<223> OTHER INFORMATION: Synthetic:  n-mer encoding polynucleotide

<400> SEQUENCE: 658
gcgggatcaa gaggagacct acaaacggtg                                        30

<210> SEQ ID NO 659
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 659

Ser Asn Met Arg Gly Asp Gln Thr Tyr Val
1               5                   10

<210> SEQ ID NO 660
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 660
tcgaacatga gaggagacca aacttacgtc                                        30

<210> SEQ ID NO 661
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 661

Thr Pro Ser Arg Gly Asp Met Ser Asn Val
1               5                   10

<210> SEQ ID NO 662
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 662
acgccaagta gaggagacat gtccaacgtc                                        30

<210> SEQ ID NO 663
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 663

Asn Ser Thr Arg Gly Asp Leu His Met Ala
1               5                   10

<210> SEQ ID NO 664
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

<400> SEQUENCE: 664
aacagcacaa gaggagacct acacatggca                                    30

<210> SEQ ID NO 665
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 665

Ala Asn Thr Arg Gly Asp Leu Ser Val Ser
1               5                   10

<210> SEQ ID NO 666
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 666
gctaacacca gaggagacct ctcagtcagt                                    30

<210> SEQ ID NO 667
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 667

Thr Asp Arg Arg Gly Asp Thr Gly Leu Leu
1               5                   10

<210> SEQ ID NO 668
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 668
accgaccgaa gaggagacac cggcttactg                                    30

<210> SEQ ID NO 669
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 669

Asp Gly Val Arg Gly Asp Arg Ala Thr Trp
1               5                   10

<210> SEQ ID NO 670
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 670
gacggcgtaa gaggagaccg tgcaacatgg                                    30

```
<210> SEQ ID NO 671
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 671
gagaatcgta gaggagactt taataatacg                                           30

<210> SEQ ID NO 672
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 672

Glu Pro Ser Arg Gly Asp Arg Met Val Leu
1               5                   10

<210> SEQ ID NO 673
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 673
gagcctagta gaggagacag gatggtgttg                                           30

<210> SEQ ID NO 674
<211> LENGTH: 10
<212> TYPE: PRT
<213> ORGANISM: artificial Sequence
<220> FEATURE:
<223> OTHER INFORMATION: Synthetic:  n-mer motif

<400> SEQUENCE: 674

Ser Gly Val Arg Gly Asp Arg Ile Ile Ile
1               5                   10

<210> SEQ ID NO 675
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 675
agcggcgtta gaggagaccg gatcataatc                                           30

<210> SEQ ID NO 676
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 676

Thr Ser Met Arg Gly Asp Tyr Thr His Val
1               5                   10

<210> SEQ ID NO 677
<211> LENGTH: 30
```

<212> TYPE: DNA
<213> ORGANISM: Artificial Sequence
<220> FEATURE:
<223> OTHER INFORMATION: Synthetic: n-mer encoding polynucleotide

<400> SEQUENCE: 677
acgtcgatga gaggagacta tacgcatgtt                                                30

<210> SEQ ID NO 678
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 678

Ala Ser Ser Arg Gly Asp Leu Thr Val Ile
1               5                   10

<210> SEQ ID NO 679
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 679
gcgtcgagta gaggagactt gactgttatt                                                30

<210> SEQ ID NO 680
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 680

Glu Thr Arg Arg Gly Asp Leu Ser Leu Gln
1               5                   10

<210> SEQ ID NO 681
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 681
gagacgcgta gaggagacct gtcgcttcag                                                30

<210> SEQ ID NO 682
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 682

Asn Asn Ala Arg Gly Asp Gln Ser Met His
1               5                   10

<210> SEQ ID NO 683
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 683
aacaacgcaa gaggagacca atcaatgcac                                    30

<210> SEQ ID NO 684
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 684

Thr Asp Arg Arg Gly Asp Ser Ser Ala Leu
1               5                   10

<210> SEQ ID NO 685
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 685
acggatagga gaggagactc tagtgcgctt                                    30

<210> SEQ ID NO 686
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 686

Ser Ser Gln Arg Gly Asp Leu Thr Gly Val
1               5                   10

<210> SEQ ID NO 687
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 687
tcaagccaaa gaggagactt gacaggtgtg                                    30

<210> SEQ ID NO 688
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 688

Gln Thr Ala Arg Gly Asp Val Met Val His
1               5                   10

<210> SEQ ID NO 689
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 689
cagacggcta gaggagacgt tatggttcat                                    30

```
<210> SEQ ID NO 690
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 690

Val Ser Gln Arg Gly Asp Leu Asn Ala Val
1               5                   10

<210> SEQ ID NO 691
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 691
gtgtcgcaga gaggagacct gaatgctgtt                                      30

<210> SEQ ID NO 692
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 692

Thr Met Thr Arg Gly Asp Leu Ala Ala Asn
1               5                   10

<210> SEQ ID NO 693
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 693
acgatgacca gaggagacct cgctgctaac                                      30

<210> SEQ ID NO 694
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 694

Asn Ala Ser Arg Gly Asp His Ser Ser Leu
1               5                   10

<210> SEQ ID NO 695
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 695
aatgcttcga gaggagacca ttcgtcgttg                                      30

<210> SEQ ID NO 696
<211> LENGTH: 10
```

```
<212> TYPE: PRT
<213> ORGANISM: Artificial Sequence
<220> FEATURE:
<223> OTHER INFORMATION: Synthetic:  n-mer motif

<400> SEQUENCE: 696

Ser Asn Thr Arg Gly Asp Met Gly Leu Thr
1               5                   10

<210> SEQ ID NO 697
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 697
tcaaacacca gaggagacat gggcctcacg                                          30

<210> SEQ ID NO 698
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 698

Met Tyr Ser Arg Gly Asp Thr His Ser Leu
1               5                   10

<210> SEQ ID NO 699
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 699
atgtattcga gaggagacac tcatagtctg                                          30

<210> SEQ ID NO 700
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 700

Ala Asp Gln Arg Gly Asp Arg Ala Pro Leu
1               5                   10

<210> SEQ ID NO 701
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 701
gcggatcaga gaggagacag ggctccgctt                                          30

<210> SEQ ID NO 702
<211> LENGTH: 30
<212> TYPE: DNA
<213> ORGANISM: Artificial Sequence
<220> FEATURE:
<223> OTHER INFORMATION: Synthetic:  n-mer encoding polynucleotide
```

-continued

<400> SEQUENCE: 702
caagaaagga gaggagacta cacctctatg                                30

<210> SEQ ID NO 703
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 703

Ser Gln Asn Arg Gly Asp Leu Ala Asn Thr
1               5                   10

<210> SEQ ID NO 704
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 704
tcccaaaaca gaggagacct agccaacacg                                30

<210> SEQ ID NO 705
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 705
gagaagttga gaggagacct tcattcgact                                30

<210> SEQ ID NO 706
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 706
caaggcggaa gaggagacct gagtacactg                                30

<210> SEQ ID NO 707
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 707

Ser Asn Arg Arg Gly Asp Thr Glu Met Gln
1               5                   10

<210> SEQ ID NO 708
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 708
tcgaatagga gaggagacac tgagatgcag                                30

<210> SEQ ID NO 709
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 709

Ser Gly Ser Arg Gly Asp Val Ser Ala Leu
1               5                   10

<210> SEQ ID NO 710
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 710
tcgggtagta gaggagacgt gagtgctttg                                          30

<210> SEQ ID NO 711
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 711

Glu Ser Thr Arg Gly Asp Arg Gly Thr Leu
1               5                   10

<210> SEQ ID NO 712
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 712
gagtcgacga gaggagaccg tggtacgctg                                          30

<210> SEQ ID NO 713
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 713

Ser Ala Val Arg Gly Asp Ala Ala Leu His
1               5                   10

<210> SEQ ID NO 714
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 714
tcggcggtga gaggagacgc ggcgcttcat                                          30

<210> SEQ ID NO 715
<211> LENGTH: 10
<212> TYPE: PRT

```
<213> ORGANISM: Artificial Sequence
<220> FEATURE:
<223> OTHER INFORMATION: Synthetic: n-mer motif

<400> SEQUENCE: 715

Leu Ser Ser Arg Gly Asp Val Asn Arg Leu
1               5                   10

<210> SEQ ID NO 716
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 716
ctgagcagca gaggagacgt taaccgcctt                                    30

<210> SEQ ID NO 717
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 717

Glu Gln Arg Arg Gly Asp Ile Gln Thr Ile
1               5                   10

<210> SEQ ID NO 718
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 718
gagcagagga gaggagacat tcagactatt                                    30

<210> SEQ ID NO 719
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 719
gctgcgtata gaggagacgc gcatgttctt                                    30

<210> SEQ ID NO 720
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 720

Ser Pro Val Arg Gly Asp His Gly Ala Leu
1               5                   10

<210> SEQ ID NO 721
<211> LENGTH: 30
<212> TYPE: DNA
<213> ORGANISM: Artificial Sequence
<220> FEATURE:
<223> OTHER INFORMATION: Synthetic: n-mer encoding polynucleotide
```

-continued

```
<400> SEQUENCE: 721
tcgccggtga gaggagacca tggggctttg                                   30

<210> SEQ ID NO 722
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 722
gattcgagga gaggagacta tgcgaatctg                                   30

<210> SEQ ID NO 723
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 723

Leu Ser Arg Arg Gly Asp Tyr Gln Glu Leu
1               5                   10

<210> SEQ ID NO 724
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 724
ttgagtcgga gaggagacta tcaggagttg                                   30

<210> SEQ ID NO 725
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 725
tcctacgcaa gaggagacgt ccactccatc                                   30

<210> SEQ ID NO 726
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 726

Asp Ser Arg Arg Gly Asp Ala Ser Tyr His
1               5                   10

<210> SEQ ID NO 727
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 727
gactcacgca gaggagacgc gtcgtaccac                                   30
```

```
<210> SEQ ID NO 728
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 728

Asn His Gln Arg Gly Asp Leu Ser Ser Ser
1               5                   10

<210> SEQ ID NO 729
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 729
aaccaccaaa gaggagacct gagctcgagt                                       30

<210> SEQ ID NO 730
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 730
tcctcaacga gaggagacca cctgtctttg                                       30

<210> SEQ ID NO 731
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 731

Ser Trp Asn Arg Gly Asp Ile Ser Gly Leu
1               5                   10

<210> SEQ ID NO 732
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 732
tcgtggaaca gaggagacat atctggcctt                                       30

<210> SEQ ID NO 733
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 733

Thr Gly Thr Arg Gly Asp Leu Gly Thr Met
1               5                   10

<210> SEQ ID NO 734
<211> LENGTH: 30
<212> TYPE: DNA
<213> ORGANISM: Artificial Sequence
```

<220> FEATURE:
<223> OTHER INFORMATION: Synthetic: n-mer encoding polynucleotide

<400> SEQUENCE: 734
acgggtacta gaggagacct ggggacgatg                                    30

<210> SEQ ID NO 735
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 735

Gln Gln Leu Arg Gly Asp Thr His Thr Leu
1               5               10

<210> SEQ ID NO 736
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 736
cagcagctta gaggagacac gcatactctt                                    30

<210> SEQ ID NO 737
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 737

Ala Gly Leu Arg Gly Asp Arg Asp Ser Leu
1               5               10

<210> SEQ ID NO 738
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 738
gcggggttga gaggagaccg tgattcgctt                                    30

<210> SEQ ID NO 739
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 739

Gln Val Tyr Arg Gly Asp Arg Asp Gln Leu
1               5               10

<210> SEQ ID NO 740
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 740

```
caggtttata gaggagaccg ggatcagttg                                    30

<210> SEQ ID NO 741
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 741

Ala Gly Val Arg Gly Asp Arg Val Thr Ile
1               5                   10

<210> SEQ ID NO 742
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 742
gcaggagtaa gaggagacag agtgaccatc                                    30

<210> SEQ ID NO 743
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 743

Asn Ser Ala Arg Gly Asp Leu Leu His Ser
1               5                   10

<210> SEQ ID NO 744
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 744
aactcagcca gaggagacct tctgcactcc                                    30

<210> SEQ ID NO 745
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 745

Asn His Ser Arg Gly Asp Leu Thr Gly Val
1               5                   10

<210> SEQ ID NO 746
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 746
aaccacagta gaggagacct gacaggcgtt                                    30
```

-continued

```
<210> SEQ ID NO 747
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 747

Asn Ala Tyr Arg Gly Asp Thr Ser Ala Phe
1               5                   10

<210> SEQ ID NO 748
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 748
aacgcttaca gaggagacac atccgcgttc                                  30

<210> SEQ ID NO 749
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 749

Ser Ala Asn Arg Gly Asp Ile Met His Thr
1               5                   10

<210> SEQ ID NO 750
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 750
tcggctaaca gaggagacat aatgcacacg                                  30

<210> SEQ ID NO 751
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 751

Gln Ser Ala Arg Gly Asp Leu Val Ser Tyr
1               5                   10

<210> SEQ ID NO 752
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 752
caatccgcca gaggagacct cgtcagttac                                  30

<210> SEQ ID NO 753
<211> LENGTH: 30
<212> TYPE: DNA
<213> ORGANISM: Artificial Sequence
```

```
<220> FEATURE:
<223> OTHER INFORMATION: Synthetic:  n-mer encoding polynucleotide

<400> SEQUENCE: 753
gatagtagga gaggagacgc tagttatcat                                      30

<210> SEQ ID NO 754
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 754

Ser Phe Val Arg Gly Asp Val Arg Thr Leu
1               5                   10

<210> SEQ ID NO 755
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 755
tcgtttgtga gaggagacgt tcgtacgctg                                      30

<210> SEQ ID NO 756
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 756

Ser Asp Met Arg Gly Asp Arg Ser Val Tyr
1               5                   10

<210> SEQ ID NO 757
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 757
agcgacatga gaggagaccg atctgtgtac                                      30

<210> SEQ ID NO 758
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 758

Ser Gly Ile Arg Gly Asp Arg Tyr Pro Ile
1               5                   10

<210> SEQ ID NO 759
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 759
```
tccggaatca gaggagaccg ctacccaata                                                    30

<210> SEQ ID NO 760
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 760

Ser Asn Val Arg Gly Asp Met Ala His Ser
1               5                   10

<210> SEQ ID NO 761
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 761
tccaacgtca gaggagacat ggctcacagc                                                    30

<210> SEQ ID NO 762
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 762
actgaggtta gaggagaccg ttcgcaggtt                                                    30

<210> SEQ ID NO 763
<211> LENGTH: 10
<212> TYPE: PRT
<213> ORGANISM: Artificial Sequence
<220> FEATURE:
<223> OTHER INFORMATION: Synthetic: n-mer motif

<400> SEQUENCE: 763

Ala Ser Ser Arg Gly Asp Leu Gln Gln Thr
1               5                   10

<210> SEQ ID NO 764
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 764
gcgagcagca gaggagacct gcaacaaacg                                                    30

<210> SEQ ID NO 765
<211> LENGTH: 30
<212> TYPE: DNA
<213> ORGANISM: Artificial Sequence
<220> FEATURE:
<223> OTHER INFORMATION: Synthetic: n-mer encoding polynucleotide

<400> SEQUENCE: 765
cagtctgcta gaggagacct tgtgtcttat                                                    30

<210> SEQ ID NO 766

-continued

```
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 766
gacgcatcta gaggagaccg aacatccctc                                         30

<210> SEQ ID NO 767
<211> LENGTH: 10
<212> TYPE: PRT
<213> ORGANISM: Artificial Sequence
<220> FEATURE:
<223> OTHER INFORMATION: Synthetic:  n-mer motif

<400> SEQUENCE: 767

Asn Ser Val Arg Gly Asp Leu Asn Gln Thr
1               5                   10

<210> SEQ ID NO 768
<211> LENGTH: 30
<212> TYPE: DNA
<213> ORGANISM: Artificial Sequence
<220> FEATURE:
<223> OTHER INFORMATION: Synthetic:  n-mer encoding polynucleotide

<400> SEQUENCE: 768
aacagtgtca gaggagacct caaccaaact                                         30

<210> SEQ ID NO 769
<211> LENGTH: 36
<212> TYPE: DNA
<213> ORGANISM: Artificial Sequence
<220> FEATURE:
<223> OTHER INFORMATION: Synthetic

<400> SEQUENCE: 769
gcaacatggc tgtccaggga agaaactaca tacctg                                  36

<210> SEQ ID NO 770
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
```

-continued

```
<221> NAME/KEY: misc_feature
<222> LOCATION: (50)..(51)
<223> OTHER INFORMATION: n is a, c, g, or t

<400> SEQUENCE: 770
gttttgaacc cagccggtct gcgcctgtgc mnnmnnmnnm nnmnnmnnmn nttgggcact        60
ctggtggttt gtggcc                                                       76

<210> SEQ ID NO 771
<211> LENGTH: 22
<212> TYPE: DNA
<213> ORGANISM: Artificial Sequence
<220> FEATURE:
<223> OTHER INFORMATION: Synthetic

<400> SEQUENCE: 771
gaaagttgcc gtccgtgtga gg                                                22

<210> SEQ ID NO 772
<211> LENGTH: 21
<212> TYPE: DNA
<213> ORGANISM: Artificial Sequence
<220> FEATURE:
<223> OTHER INFORMATION: Synthetic

<400> SEQUENCE: 772
acaagtggcc acaaaccacc a                                                 21

<210> SEQ ID NO 773
<211> LENGTH: 20
<212> TYPE: DNA
<213> ORGANISM: Artificial Sequence
<220> FEATURE:
<223> OTHER INFORMATION: Synthetic

<400> SEQUENCE: 773
ggttttgaac ccagccggtc                                                   20
```